US010207988B2

(12) United States Patent
Mills et al.

(10) Patent No.: US 10,207,988 B2
(45) Date of Patent: Feb. 19, 2019

(54) METHODS AND COMPOSITIONS FOR TREATMENT OF CANCER AND AUTOIMMUNE DISEASE

(71) Applicant: THE JACKSON LABORATORY, Bar Harbor, ME (US)

(72) Inventors: Kevin David Mills, Bar Harbor, ME (US); Muneer Gulamhusien Hasham, Ellsworth, ME (US); Caroline Gardner McPhee, Seal Cove, ME (US)

(73) Assignee: THE JACKSON LABORATORY, Bar Harbor, ME (US)

(*) Notice: Subject to any disclaimer, the term of this patent is extended or adjusted under 35 U.S.C. 154(b) by 50 days.

(21) Appl. No.: 13/799,963

(22) Filed: Mar. 13, 2013

(65) Prior Publication Data
US 2013/0184342 A1 Jul. 18, 2013

Related U.S. Application Data

(63) Continuation-in-part of application No. PCT/US2012/043074, filed on Jun. 19, 2012.

(60) Provisional application No. 61/501,522, filed on Jun. 27, 2011.

(51) Int. Cl.
C07C 331/30 (2006.01)
C07C 307/10 (2006.01)
C07C 311/08 (2006.01)
C07C 311/14 (2006.01)
G01N 33/50 (2006.01)
A61K 31/145 (2006.01)
C07C 309/51 (2006.01)
C07C 335/20 (2006.01)

(52) U.S. Cl.
CPC .......... C07C 331/30 (2013.01); A61K 31/145 (2013.01); C07C 309/51 (2013.01); C07C 311/08 (2013.01); C07C 311/14 (2013.01); C07C 335/20 (2013.01); G01N 33/5008 (2013.01); C07C 2601/02 (2017.05); G01N 2500/10 (2013.01); G01N 2800/52 (2013.01)

(58) Field of Classification Search
None
See application file for complete search history.

(56) References Cited

U.S. PATENT DOCUMENTS

| 3,828,060 | A | 8/1974 | Lyness et al. |
| 5,569,786 | A | 10/1996 | Pettit et al. |
| 6,048,903 | A | 4/2000 | Toppo et al. |
| 6,361,815 | B1 | 3/2002 | Zheng et al. |
| 6,552,213 | B1 | 4/2003 | Deshpande et al. |
| 6,844,471 | B2 | 1/2005 | Despande et al. |
| 7,803,790 | B2 | 9/2010 | Chong et al. |
| 2002/0058708 | A1 | 5/2002 | Inman et al. |
| 2004/0015020 | A1 | 1/2004 | Deshpande et al. |
| 2004/0147788 | A1 | 7/2004 | Savouret et al. |
| 2004/0152629 | A1 | 8/2004 | Hadfield et al. |
| 2009/0182003 | A1* | 7/2009 | Sinclair .................. A61K 31/05 514/291 |
| 2013/0184342 | A1 | 7/2013 | Mills et al. |

FOREIGN PATENT DOCUMENTS

| EP | 0331983 B1 | 12/1994 |
| WO | 2003/039557 | 5/2003 |
| WO | 2003/039557 A1 | 5/2003 |
| WO | 2004/021987 | 3/2004 |

OTHER PUBLICATIONS

Gundrum et al. (Investigational New Drugs, 2005, 23, 3-9).*
Johnson et al., (British J. of Cancer 2001, p. 1424-1431).*
Cecil Textbook of Medicine, 20th Edition, vol. 1, 1996.*
Gura et al. (Science 1997, Nov. 7, 278).*
Silverman (Prodrugs and Drug Delivery Systems, The Organic Chemistry of Drug Design and Drug Action, pp. 352-401, 1992.*
Bundgaard, Design of Prodrugs, 1985, chapter 1.*
Dorwald, Side Reactions in Organic Synthesis: A Guide to Successful Synthesis Design 2005.*
Greeve et al. (Blood, 101, 9, 1, May 2003, p. 3574-3580).*
Jiang et al. (European J of Pharmacology, 488, 2004, 27-34).*
Weise et al. (Molecular Cell, 28, 482-490, Nov. 9, 2007).*
Klein et al. (DNA repair, 2008, 686-693).*
(Cancercompass, https://www.cancercompass.com/leukemia-information.htm, 2016).*
Lockwood (WWW. Rn.org, Leukemia: AML, CML, ALL and CLL).*
Feldhahn (The J of Experimental Medicine, 2007, 204, 5, 1157-1166).*
Wieder et al. (Leukemia, 2001, p. 1735-1742).*
Horvat et al. (Eur J Cancer, vol. 29 A, 132-137, 1993).*
Badger et al., Journal of Pharmacology and Experimental Therapeutics, 291(3):1380-1386 (1999). "Idoxifene, a novel selective estrogen receptor modulator, is effective in a rat model of adjuvant-induced arthritis."
Hasham et al., Nature Immunology, 11(9):820-826 (2010). "Widespread genomic breaks generated by activation-induced cytidine deaminase are prevented by homologous recombination."
Horvat et al., European Journal of Cancer, 29(1):132-137 (1993). "Tumour cell proflieration is abolished by inhibitors Na+H+ and HC03-CL—exchange."
Hwang et al., Molecular and Cellular Biochemistry, 327(1-2):135-144 (2009). "Reduction of anion exchanger 2 expression induces apoptosis of human hepatocellular carcinoma cells."
Ishida et al., Nucleic Acids Research, 37(10):3367-3376 (2009). "DIDS, a chemical compound that inhibits RAD51-mediated homologous pairing and strand exchange."

(Continued)

Primary Examiner — Umamaheswari Ramachandran
(74) Attorney, Agent, or Firm — Nixon Peabody LLP; David S. Resnick; Nicole D. King

(57) ABSTRACT

The technology described herein relates to methods of inducing cell death. The technology described herein further relates to treating conditions including cancers and autoimmune diseases comprising administering inhibitors of double strand break repair. Also described herein are inhibitors of double strand break repair and methods of screening for such inhibitors.

1 Claim, 27 Drawing Sheets
Specification includes a Sequence Listing.

(56) References Cited

OTHER PUBLICATIONS

Kim et al., International Immunopharmacology, 8(12):1695-1702 (2008). "Piceatannol, a stilbene present in grapes, attenuates dextran sulfate sodium-induced colitis."
Leuenberger et al., Modern Pathology, 23(2):177-186 (2010). "AID protein expression in chronic lymphocytic leukeia/small lymphocytic lymphoma is associated with poor prognosis and complex genetic alterations."
Li et al., British Journal of Pharmacology, 160(6):1352-1361 (2010). "2,3', 4, 4', 5'-Pentamethoxy-trans-stilbene, a resveratrol derivative, inhibits colitis-associated colorectal carcinogenesis in mice."
Liu et al., Molecular and Cellular Biochemistry, 308(1-2):117-125 (2007). "Anion exchanger inhibitor DIDS induces human poorly-differentiated malignant hepatocellular carcinoma HA22T cell apoptosis."
Palacios, F. et al. "High expression of AID and active class switch recombination might account for a more aggressive disease in unmutated CLL patients: link with an activated microenvironment in CLL disease," Blood, 115(22):4488-4496 (Jun. 3, 2010). doi: 10.1182/blood-2009-12-257758. Epub Mar. 16, 2010.
Roberti et al., "Synthesis and biological evaluation of resveratrol and analogues as apoptosis-inducing agents." J. Med. Chem. 46(16):3546-54 (2003).
Yu et al., "Convenient preparation of trans-arylalkenes via palladium(IO)-catalyzed isomerization of cis-arylalkenes. Meier et al., Bis(stilbenyl)squaraines-Novel Pigments with Extended Conjugation." Tetrahedron Lett., 37(8):1191-1194 (1996). J. Org. Chem. 67(13):4627-29 (2002).
Solladie et al., "A re-investigation of resveratrol synthesis by Perkins reaction. Application to the synthesis of aryl cinnamic acids." Tetrahedron 59:3315-3321 (2003).
Eddarir et al., "Fluorinated resveratrol and pterostilbene." Tetrahedron Lett., 42:9127-9130 (2001).
Thomas et al., "Manganese triacetate oxidative lactonisation of electron-rich stilbenes possessing catechol and resorcinol substitution (resveratrol analogues)." Tetrahedron Lett. 43:3151-3155 (2002).
Lao et al., "Autophagy Pathway of Raji Cell Death Induced by Resveratrol", Chinese Journal of Biologicals, 22(7): 654-658 (2009).
Li et al., "2,3',4,4',5'-Pentamethoxy-trans-stilbene, a resveratrol derivatve, inhibits colitis-associated colorectal carcinogenesis in mice", British Journal of Pharmacology, 160: 1352-1361 (2010).
Roman et al., "Analysis of resveratrol-induced apoptosis in human B-cell chronic leukemia", British Journal of Haematology, 117: 842-851 (2002).
Wang et al., "The study of resveratrol by modulating SATA3 on acute myeloblastic leukemia", Chinese Pharmacological Bulletin, 26(3): 346-352 (2010).
Li et al., "Crystal Struture of an Archaeal Rad51 Homologue in Complex with a Metatungstate Inhibitor", Biochemistry 48(29):6805-6810 (2009).
Froeyen et al., "RNA as a target for drug design, the example of Tat-TAR interaction." Current Topics in Medicinal chemistry 2(10):1123-1145 (2002).
Gunosewoyo et al. ,"Molecular probes for P2X7 receptor studies." Current Medicinal Chemistry 14(14):1505-1523 (2007).
Soo et al. "Visible light-induced hole injection into rectifying molecular wires anchored on Co3O4 and SiO2 nanoparticles." Journal of the American Chemical Society 134(41):17104-17116 (2012).
Thompson et al., "Inhibitors of the glutamate vesicular transporter (VGLUT)." Current Medicinal Chemistry 12(18):2041-2056 (2005).
Wrobel et al. "Synthesis of (bis) sulfonic acid,(bis) benzamides as follicle-stimulating hormone (FSH) antagonists." Bioorganic & Medicinal Chemistry 10(3):639-656 (2002).
Eckermann et al., "Stilbenecarboxylate biosynthesis: a new function in the family of chalcone synthase-related proteins." Phytochemistry 62(3):271-286 (2003).

* cited by examiner

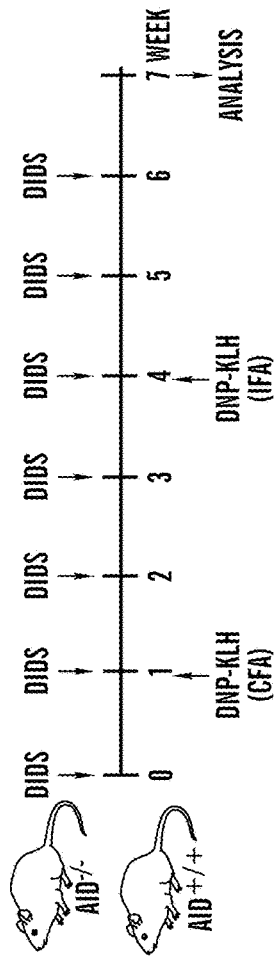
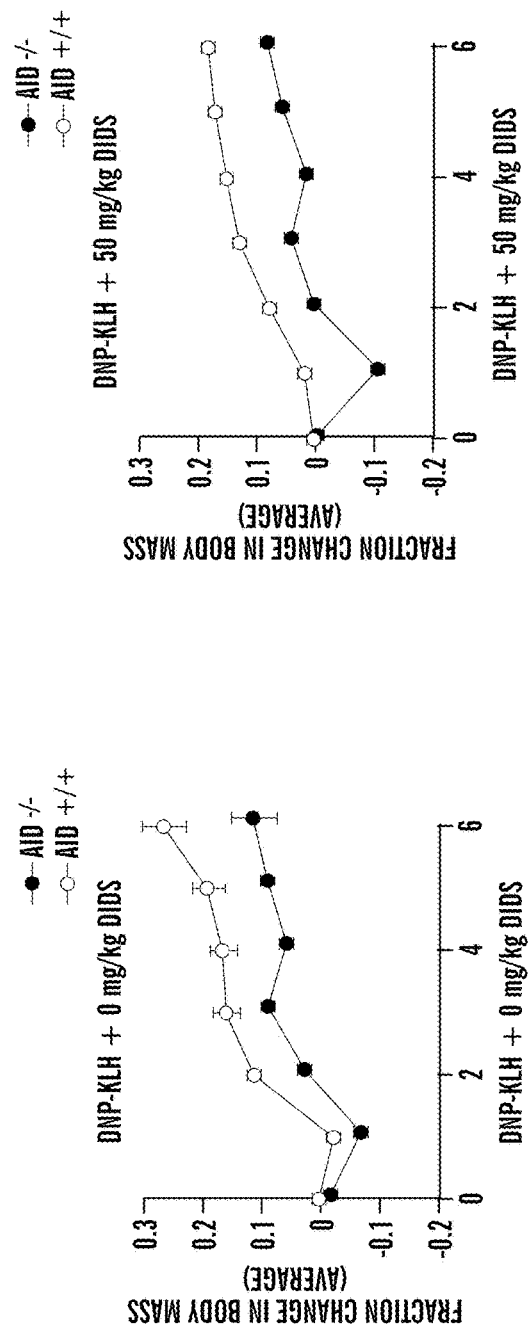
FIG. 25A
FIG. 25B
FIG. 25C

METHODS AND COMPOSITIONS FOR TREATMENT OF CANCER AND AUTOIMMUNE DISEASE

CROSS-REFERENCE TO RELATED APPLICATIONS

This application is a continuation-in-part application of International Patent Application No. PCT/US12/43074 filed Jun. 19, 2012, which designates the United States and which claims benefit under 35 U.S.C. § 119(e) of U.S. Provisional Application No. 61/501,522 filed Jun. 27, 2011, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 7, 2013, is named 060636069472CIP.txt and is 547,092 bytes in size.

TECHNICAL FIELD

The technology described herein relates to methods of treating cancers and autoimmune diseases expressing activation-induced cytidine deaminase (AID) by inhibiting DNA double strand break repair mechanisms.

BACKGROUND

In 2010, there were an estimated 137,000 new cases of leukemia, lymphoma and multiple myeloma, and more than 54,000 deaths from these cancers in the United States alone. The current standard of care in leukemia/lymphoma treatment often involves intensive, long-term chemotherapy, which can be physically taxing for the patient. Common side effects of conventional chemotherapy include immune system disruption, myelosuppression, bone marrow destruction, nausea, fatigue, liver toxicity, weight loss, hair loss, long-term cognitive impairment and therapy-related secondary tumors. A major problem with standard chemotherapy is the damage done to otherwise healthy cells and tissues in the cancer patient. Current treatment often fails to achieve long-term remission, and patients who do survive routinely experience long-lasting chemotherapy-related health concerns that prevent them from ever being truly well.

Selective targeting of the therapy specifically to the cancer cells could ameliorate most of these devastating side effects. Unfortunately, with few exceptions, selective targeting is technically difficult or impossible. Additional or alternative approaches to selectively target cancer cells, while minimizing off-target side effects, are therefore desperately needed.

SUMMARY

The technology described herein is directed to treating cells having an active DNA editing enzyme with an inhibitor of DNA repair. As used herein, "DNA editing enzyme" refers to an enzyme which normally catalyzes the mutation, exchange or excision of DNA segments, particularly enzymes which can generate or promote the generation of point mutations, DNA single strand breaks, DNA double-strand breaks or protein-DNA adducts. A DNA editing enzyme, as referred to herein, is not necessarily site-specific in its action. Similarly, it is not necessarily cell specific. In some embodiments, the cell is a B cell expressing a detectable amount of such an enzyme. Non-limiting examples of DNA editing enzymes include, but are not limited to Recombination Activating Gene 1 (RAG1; NCBI Gene ID: 5896, e.g. SEQ ID NO: 0157; NCBI Ref: NM_000448 (mRNA) and SEQ ID NO 0158; NCBI Ref: NP_000439 (polypeptide)), Recombination Activating Gene 2 (RAG2; NCBI Gene ID: 5897, e.g. SEQ ID NO: 0159; NCBI Ref: NM_001243785 (mRNA) and SEQ ID NO: 160; NCBI Ref: NP_001230714 (polypeptide)), Sporulation-specific protein 11 (SPO11; NCBI Gene ID: 23626, e.g. SEQ ID NO: 0161; NCBI Ref: NM_012444 (mRNA) and SEQ ID NO 0162; NCBI Ref: NP_036576 (polypeptide)), APOBEC family members and/or AID. In some embodiments, the DNA editing enzyme can be AID.

In some embodiments, the DNA editing enzyme can be a member of the APOBEC (apolipoprotein B mRNA editing enzyme, catalytic polypeptide-like) family. As used herein "APOBEC family" refers to a family of cytidine deaminase enzymes having an N-terminal zinc-dependent cytidine deaminase catalytic domain comprising and a C-terminal pseudocatalytic domain. Non-limiting examples of APOBEC family members include AID, APOBEC1, APOBEC2, APOBEC3A, APOBEC3C, APOBEC3E, APOBEC3F, APOBEC3G, APOBEC3H, and APOBEC4.

Embodiments of the technology described herein utilize a DNA editing enzyme such as activation-induced cytidine deaminase (AID, or AICDA), a B-cell recombinase, which causes widespread genomic breaks when expressed in cells. Further, the inventors have discovered that when DNA homologous recombination ability (double strand break repair) is diminished and/or inhibited, this activity of a DNA editing enzyme, such as AID will cause cell death. Specifically, as demonstrated herein, inhibition of DNA double-strand break (DSB) repair in a cell expressing AID results in cytotoxicity due to the uncorrected off-target double strand breaks generated by AID.

Provided herein, in one aspect, is a cancer treatment paradigm that selectively induces self-destruction of cells expressing AID, e.g. cancerous B-cells or B-cells of an autoimmune disease, or other cancerous cells such as intestine cancer cells, colon cancer cells, lung cancer cells, liver cancer cells, epithelial cancer cells, breast cancer cells, esophageal cancer cells, thyroid cancer cells, prostate cancer cells, renal cancer, melanoma etc. In some embodiments, the method selectively treats, e.g. cancer cells (while sparing normal cells), by exploiting DNA recombination systems to induce tumor cell self-destruction. This approach takes advantage of the finding that AID induces widespread genomic breaks and cell death in cells that have diminished DNA homologous recombination ability. As described herein, the inventors have determined that when a population of cells characterized by elevated expression of AID is treated with an inhibitor of double strand break repair (DSB), cell death occurs. Accordingly, methods for treating patients with cancers or autoimmune diseases having elevated AID expression with an inhibitor of double strand break repair are provided.

The inhibitor of DSB repair can be an inhibitor which reduces the expression or activity of any gene or protein necessary for DSB repair. In certain embodiments provided herein, the inhibitor of DSB repair is an inhibitor which reduces or inhibits the expression or activity of Rad51; Rad51AP1; Rad51B; Rad51C; Rad51D; XRCC2; XRCC3; RAD54; RAD52; BRCA1; BRCA2; ATM; ATR; MRE11; RAD50; NBS1; WRN; BLM; RECQ4; LIG4 (DNA Ligase 4); XRCC4; PRKDC (DNA-PKcs7 XRCC7); DCLRE1C; XRCC6 (Ku70); XRCC5 (Ku80) and/or XLF (NHEJ1; XRCC4-like factor). In certain embodiments provided herein, the inhibitor of DSB repair is an inhibitor which reduces the expression or activity of Rad51; Rad51AP1; Rad51B; Rad51C; Rad51D; XRCC3; RAD54; RAD52; BRCA1; BRCA2; ATM; ATR; MRE11; RAD50; NBS1; WRN; BLM; RECQ4; LIG4 (DNA Ligase 4); XRCC4; PRKDC (DNA-PKcs7 XRCC7); DCLRE1C; XRCC6 (Ku70); XRCC5 (Ku80) and/or XLF (NHEJ1; XRCC4-like factor). In some embodiments, the inhibitor of double strand break repair can inhibit a Rad51 family member (e.g. Rad51; Rad51AP1; Rad51B; Rad51C; Rad51D; XRCC2; XRCC3). In some embodiments, the inhibitor of double strand break repair can inhibit a Non-homologous end joining (NHEJ) protein member (e.g. LIG4; XRCC4; PRKDC; DCLRE1C; XRCC6; XRCC5; XLF).

In certain embodiments provided herein the DSB repair inhibitor, is a RAD51-mediated strand exchange repair inhibitor and is a stilbene derivative. Stilbene derivatives can include, but are not limited to, stilbene ((E)-1,2-Diphenylethene), trans-stilbene, ((E)-stilbene, trans-1,2-diphenylethylene), cis-stilbene derivatives, combretastatin (5-[(2R)-2-hydroxy-2-(3,4,5-trimethoxyphenyl)ethyl]-2-methoxyphenol), resveratrol (trans-3,5,4'-Trihydroxystilbene; (E)-5-(4-hydroxystyryl)benzene-1,3-diol), diethylstilboestrol (4,4'-(3E)-hex-3-ene-3,4-diyldiphenol), colchicine, and ((S) N-(5,6,7,9-tetrahydro-1,2,3, IO-tetramethoxy-9-oxobenzo[alpha]heptaien-7-yl) acetamide). In one embodiment, the inhibitor of RAD51-mediated strand exchange repair is 4,4'diisothiocyanostilbene-2,2'-disulfonic acid (DIDS). It has been reported that DIDS disrupts Rad51 complexes and inhibits heteroduplex formation (Ishida, T., et al., Nucleic Acids Res, 2009, 37(10): p. 3367-76).

In some embodiments provided herein, the DSB repair inhibitor is salazinic acid or a derivative thereof. In certain embodiments provided herein, the DSB repair inhibitor is stictic acid or a derivative thereof. In some embodiments provided herein, the DSB repair inhibitor is STK856883 or a derivative thereof. In some embodiments provided herein, the DSB repair inhibitor is 4'-Bromo-3' nitropropiophenone (NS-123) or a derivative thereof (Lally et al, Cancer Res 2007, 67; 8791).

Any cancer with an elevated level of a DNA editing enzyme can be treated according to the methods and compositions described herein. For example, the cancer may be breast, prostate, ovarian, brain, skin, colorectal (colon; large intestine), liver, lymphoma, lung, oral, head and neck, spleen, lymph node, small intestine, blood cells, stomach, kidney, pancreatic, endometrium, testicle, skin, esophagus, bone marrow, blood, cervical, bladder, Ewing's sarcoma, thyroid, a glioma, and/or gastrointestinal. The invention is applicable to other cancers discussed herein, including precancers. In certain embodiments the cancer to be treated is a cancer of B cell, e.g. chronic lymphocytic leukemia (CLL).

Any cancer expressing AID can be treated. In certain embodiments, the cancer to be treated is a lymphoma or leukemia. In certain embodiments, the lymphoma to be treated is a Non-Hodgkin's lymphoma, e.g. including but not limited to Burkitt's lymphoma, follicular lymphoma, chronic lymphocytic leukemia (CLL), B-cell acute lymphocytic leukemia (B-ALL), acute lymphoblastic leukemia, hairy cell leukemia, splenic marginal zone lymphoma, Diffuse large B-cell lymphoma (DLBCL, DLBL, DLCL) and/or plasmacytoma. In certain embodiments the cancer to be treated is a leukemia, e.g. including but not limited to Hodgkin's disease, acute myelogenous leukemia (AML), chronic myelogenous leukemia (CML), MALT lymphoma and/or T-cell leukemia and lymphoma. In certain embodiments the cancer to be treated is a sarcoma, a carcinoma, colon cancer, liver cancer, gastric cancer, intestinal cancer, lung cancer, breast cancer, prostate cancer, renal cancer, melanoma, thyroid cancer, esophageal cancer, and/or cholangiocarcinoma.

Any autoimmune disease with an elevated level of a DNA editing enzyme can be treated. In certain embodiments the DNA editing enzyme is AID. In certain embodiments, the autoimmune disease to be treated is lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis, subacute cutaneous lupus erythematosus, cutaneous lupus erythematosus including chilblain lupus erythematosus, chronic arthritis, Sjogren's syndrome, autoimmune nephritis, autoimmune vasculitis, autoimmune hepatitis, autoimmune carditis, autoimmune encephalitis, autoimmune mediated hematological disease, inflammatory chronic rhinosinusitis, colitis, celiac disease, inflammatory bowel disease, Barrett's esophagus, and/or inflammatory gastritis.

In certain embodiments the DSB repair inhibitor is contained in a composition comprising the inhibitor and a pharmaceutically acceptable carrier. In further embodiments the DSB repair inhibitor can be contained in a composition comprising a pharmaceutically acceptable carrier and another chemotherapeutic compound. In certain embodiments a composition comprising a DSB repair inhibitor can be administered to a patient who is also receiving another treatment for cancer. In certain embodiments a composition comprising a DSB repair inhibitor can be administered to a patient who is also receiving another treatment for an autoimmune disease.

In certain embodiments, treating a patient having a cancer with high AID expression with a DSB repair inhibitor decreases an indicator, a marker, a symptom, the severity, the rate of metastasis, recurrence and/or tumor size of the cancer by at least 10%, e.g., by at least 20%, at least 30%, at least 50%, at least 75%, at least 80%, at least 90% or more as compared to the indicator, marker, symptom, severity, metastasis, recurrence and/or tumor size prior to treatment with the DSB repair inhibitor or as compared to patients not receiving treatment with a DSB repair inhibitor.

In certain embodiments, treating a patient having an autoimmune disease with high AID expression with a DSB repair inhibitor decreases an indicator, a marker, a symptom, and/or the severity, of the autoimmune disease by at least 10%, e.g., by at least 20%, at least 30%, at least 50%, at least 75%, at least 80%, at least 90% or more as compared to the indicator, marker, symptom, severity, metastasis, recurrence and/or tumor size prior to treatment with the DSB repair inhibitor or as compared to patients not receiving treatment with a DSB repair inhibitor.

Also provided herein are methods for determining if a cancer or autoimmune disease in a patient would be responsive to treatment by a DSB repair inhibitor by determining the level of protein or mRNA of AID in cells of that patient. In some embodiments, the level of AID mRNA and/or protein in cancerous cells obtained from the subject is determined. In some embodiments, the level of AID mRNA and/or protein is determined in autoreactive cells obtained from the subject. A high level of an AID expression product, i.e. mRNA or protein, indicates the disease is treatable by a DSB repair inhibitor. For example, a subject having cells that express elevated levels of AID may be identified by measuring the level of AID protein or mRNA in a test sample of cells obtained from a subject suspected of having elevated levels and comparing that level to the level of AID found in a sample of the same type of cells obtained from a healthy subject, wherein an increased amount of AID in the test sample is indicative of a subject in need of treatment with an inhibitor of double strand break repair.

In certain embodiments the determining of the level of AID protein involves the use of one or more of the following assays; Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; gel diffusion precipitation reaction; immunodiffusion assay; in situ immunoassay; precipitation reaction; agglutination assay; complement fixation assay; immunofluorescence assay; protein A assay; mass spectroscopy and/or immunoelectrophoresis assay. In certain embodiments the determining of the level of AID protein involves the use of an antibody, an antibody fragment, a polypeptide comprising an epitope-binding fragment of an antibody, a monoclonal antibody, a monoclonal antibody fragment, a protein binding protein, and/or a AID-binding peptide.

In certain embodiments, the determining of the level of AID mRNA involves the use of one or more of the following assays; RT-PCR, quantitative RT-PCR, RNA-seq, Northern blot, microarray based expression analysis, transcription amplification and/or self-sustained sequence replication. In certain embodiments the determining of the level of AID mRNA involves the use of an antibody, an antibody fragment, a monoclonal antibody, and/or a monoclonal antibody fragment and/or a protein binding protein. In certain embodiments AID primers for RT-PCR include, but are not limited to SEQ ID NO:101 and SEQ ID NO:102.

In certain embodiments the level of AID is determined by its activity and can be determined by sequence analysis, PCR or FISH analysis of its target genes and/or the transcripts encoded by the target genes. AID target genes can include, but are not limited to IGH (NCBI Gene ID 3492), BCL6 (NCBI Gene ID 604; SEQ ID NO:001), MYC (NCBI Gene ID 4609; SEQ ID NO:002), BCL11A (NCBI Gene ID 53335; SEQ ID NO:003), CD93 (NCBI Gene ID 22918; SEQ ID NO:004), PIM1 (NCBI Gene ID 5292; SEQ ID NO:005) and/or PAX5 (NCBI Gene ID 5079; SEQ ID NO:006).

The detection of hypermutations in the gene loci is indicative of AID activity. In certain embodiments the activity of AID is determined by using whole genome sequencing or full genome sequencing and determine the level of hypermutations over the whole genome or in the specific target genes including IGH, BCL6, MYC, BCL11a, CD93, PIM1 and/or PAX5.

In certain embodiments the activity of AID is determined by using FISH analysis to detect double strand break, e.g. DNA breakage detection fish (DBD-FISH) (Volpi and Bridger, BioTechniques, Vol. 45, No. 4, 385-409).

In certain embodiments the activity of AID is determined by using a phospho-H2AX assay (Rakiman et al., Advance Biotech 2008, 39-42).

In certain embodiments, the antibody, antibody fragment, monoclonal antibody, monoclonal antibody fragment, protein binding protein, and/or AID-binding peptide used to determine the level of AID mRNA or protein is labeled with a detectable label.

In certain embodiments, the effective dose of a DSB repair inhibitor can be administered to a patient once. In certain embodiments, the effective dose of a DSB repair inhibitor can be administered to a patient repeatedly.

In one aspect, the technology described herein relates to a method of causing cell death comprising: (a) administering to a cell an effective amount of a DNA editing enzyme; and (b) thereafter contacting the cell of step (a) with an inhibitor of double strand break repair, thereby causing cell death. In one aspect, the technology described herein relates to a method of sensitizing a cell to cell death comprising: (a) administering to a subject, a therapeutically effective amount of a DNA editing enzyme to sensitize a cell to cell death by use of an inhibitor of double strand break repair: and (b) thereafter administering to the subject an inhibitor of double strand break repair. In some embodiments, the DNA editing enzyme is administered in a form selected from the group consisting of: a polypeptide; a nucleic acid encoding a DNA editing enzyme; and a vector comprising a nucleic acid encoding a DNA editing enzyme. In some embodiments, the DNA editing enzyme can be a member of the APOBEC family. In some embodiments, the DNA editing enzyme can be activation-induced cytidine deaminase (AID).

The details of various embodiments are set forth in the description below. Other features, objects, and advantages of the technology described herein will be apparent from the description and the drawings, and from the claims.

DESCRIPTION OF THE DRAWINGS

FIG. 8A shows expression data from a collection of 59 cancer-derived human cell lines. FIG. 8B shows expression data from primary human tissues and cancers.

FIG. 23A depicts the results of treatment with a 0 μM DIDS control and FIG. 23B depicts the results of treatment with 30 μM DIDS. Error bars represent the standard error of the mean (S.E.M.) for 4 independent cultures of the AID−/− (open bars) samples and 5 independent cultures of the AID+ samples (filled bars).

FIG. 25A shows the experimental design to test the effect of systemic DIDS treatment in a mouse model. FIG. 25B shows the fraction change in body mass of control mice. FIG. 25C shows the fraction change in body mass of mice treated with DIDS.

DETAILED DESCRIPTION

Definitions

Figure 1:
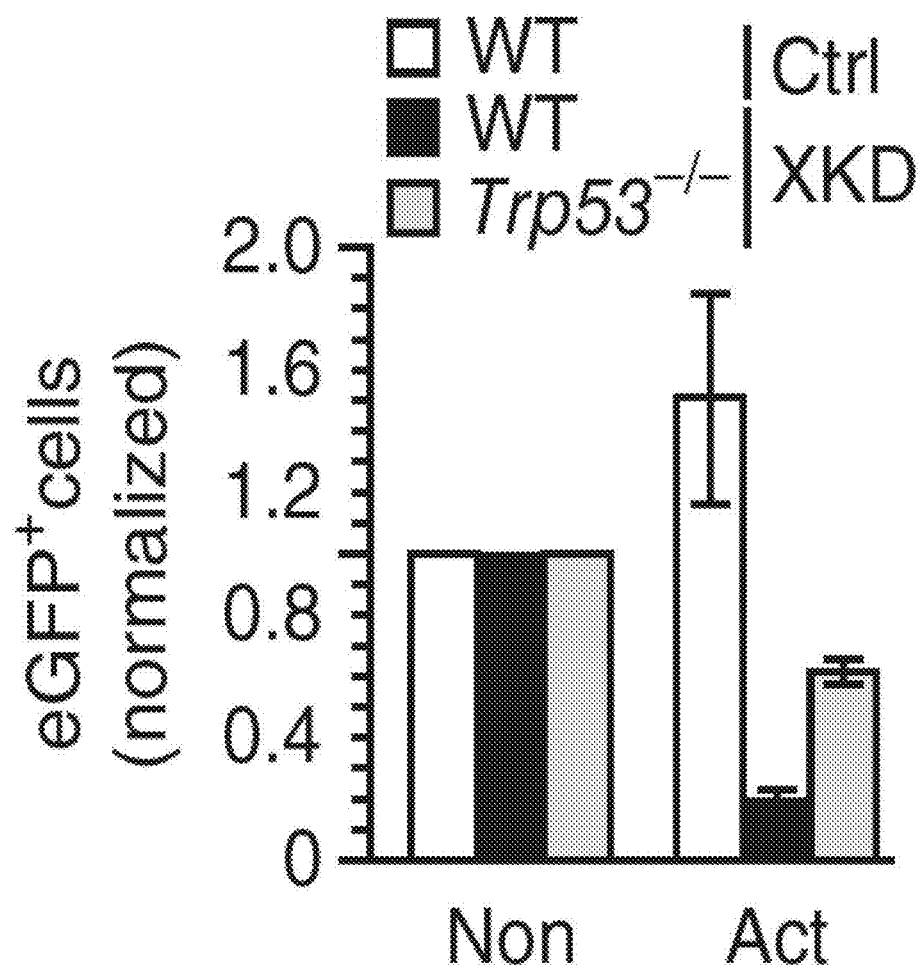
FIG. 1 shows a flow cytometry data graph indicating that XRCC2 knockdown leads to activation induced cytotoxicity. Flow cytometry analysis of eGFP$^+$ cells from wild-type and Trp53$^{-/-}$ mouse splenocytes transduced with constructs expressing Xrcc2-specific shRNA (XKD) or control shRNA (Ctrl), was performed 3 days after stimulation. Shown are wild-type (WT) cells transduced with Ctrl (white bars), wild-type cells transduced with XKD (black bars) and Trp53$^{-/-}$ cells transduced with XKD (grey bars). Data are representative of two experiments with three replicates, experiments (mean and s.e.m.).

For convenience, the meaning of certain terms and phrases used in the specification, examples, and appended claims, are provided below. If there is an apparent discrepancy between the usage of a term in the art and its definition provided herein, the definition provided within the specification shall prevail.

Definitions of common terms in cell biology and molecular biology can be found in "The Merck Manual of Diagnosis and Therapy", 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology are also be found in Benjamin Lewin, Genes IX, published by Jones & Bartlett Publishing, 2007 (ISBN-13: 9780763740634); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the technology described herein was performed using standard procedures, as described, for example in Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (3 ed.), Cold Spring Harbor Laboratory Press, Cold Spring Harbor, N.Y., USA (2000); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

The singular terms "a", "an" and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example".

Other than in the operating examples, or where otherwise indicated, all numbers expressing quantities of ingredients or reaction conditions used herein should be understood as modified in all instances by the term "about". The term "about" when used in connection with percentages can mean±1%.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral, enteral or parenteral routes, including intravenous, intramuscular, subcutaneous, transdermal, airway (aerosol), pulmonary, nasal, intranasal, rectal, and topical (including buccal and sublingual) administration. Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. In preferred embodiments, the compositions are administered by intravenous infusion or injection.

As used herein, the terms "autoimmune disease" or "autoimmune disorder" refer to a condition that is immune-mediated due to an attack on self-tissues, such as when a subject's own antibodies react with host tissue, but can also involve an immune response to a microorganism. Such conditions include, but are not limited to, lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis, discoid lupus, subacute cutaneous lupus erythematosus, cutaneous lupus erythematosus including chilblain lupus erythematosus, chronic arthritis, Sjogren's syndrome, inflammatory chronic rhinosinusitis, colitis, celiac disease, inflammatory bowel disease, Barrett's esophagus, inflammatory gastritis, autoimmune nephritis, autoimmune vasculitis, autoimmune hepatitis, autoimmune carditis, autoimmune encephalitis, and autoimmune mediated hematological disease.

The terms "decrease", "reduce", "reduction", "inhibit" or "inhibition" are all used herein generally to mean a decrease by a statistically significant amount. However, for avoidance of doubt, "decrease", "reduced", "reduction", "inhibit" or "inhibition" means a decrease by at least 5% as compared to a reference level, for example a decrease by at least about 10%, or at least about 20%, or at least about 30%, or at least about 40%, or at least about 50%, or at least about 60%, or at least about 70%, or at least about 80%, or at least about 90% or at least about 95%, or at least about 98% or at least about 99%, or more as compared to a reference level.

The terms "increased", "increase" or "enhance" or "activate" or "elevated" are all used herein to generally mean an increase by a statically significant amount; for the avoidance of any doubt, the terms "increased", "increase" or "enhance" or "activate" or "elevated" means a statistically significant increase, such as an increase of at least 5% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 5-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below or above normal, or lower, or higher concentration of the marker. The term refers to statistical evidence that there is a difference. It is defined as the probability of making a decision to reject the null hypothesis when the null hypothesis is actually true. The decision is often made using the p-value.

As used herein, the terms "compound" or "agent" are used interchangeably and refer to molecules and/or compositions that inhibit DSB repair. The compounds/agents include, but are not limited to, chemical compounds and mixtures of chemical compounds, e.g., small organic or inorganic molecules; saccharide; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or mammalian cells or tissues; naturally occurring or synthetic compositions; peptides; aptamers; and antibodies, or fragments thereof.

As used herein, the terms "test compound" or "test agent" refer to a compound or agent and/or compositions thereof that are to be screened for their ability to inhibit the expression and/or activity of a gene or protein involved in DSB repair, as identified herein.

As used herein, the term "DSB repair inhibitor" is any compound or agent that inhibits the repair of double-strand DNA breaks. In certain embodiments, such inhibitors can include inhibiting homologous recombination and non-homologous end joining (NHEJ). In certain embodiments, such inhibitors can include inhibitors of RAD51-mediated strand exchange. In some embodiments, such inhibitors can include inhibitors of, e.g. Rad51; Rad51AP1; Rad51B; Rad51C; Rad51D; XRCC2; XRCC3; RAD54; RAD52; BRCA1; BRCA2; ATM; ATR; MRE11; RAD50; NBS1; WRN; BLM; RECQ4; LIG4; XRCC4; PRKDC; DCLRE1C; XRCC6; XRCC5; and XLF.

As used herein, the term "antibody" refers to immunoglobulin molecules and immunologically active portions of immunoglobulin molecules, i.e., molecules that contain an antigen binding site that specifically bind an antigen comprising one or more epitopes. The terms also refers to antibodies comprised of two immunoglobulin heavy chains and two immunoglobulin light chains as well as a variety of forms besides antibodies; including, for example, Fv, Fab, and F(ab)'2 as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference) and single domain antibodies (sdAb) including for example nanobodies, camelids (VHH fragments) and immunoglobulin new antigen receptor (IgNAR) (Harmsen et al. 2007, Appl. Microbiol. Biotechnol. 77 (1): 13-22; Holt et al. 2003, Trends in Biotechnology 21 (11): 484-490; which are incorporated by reference herein in their entireties). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). The term also includes intrabodies, i.e. antibodies that work within the cell and bind to intracellular protein. Intrabodies can include whole antibodies or antibody binding fragments thereof, e.g. single Fv, Fab and F(ab)'2, etc. As used herein, the term "epitope" refers to a fragment of a polypeptide or protein or a non-protein molecule having antigenic or immunogenic activity in an animal, preferably in a mammal, and most preferably in a human. An epitope having immunogenic activity is a fragment of a polypeptide or protein that elicits an antibody response in an animal. An epitope to which an antibody immunospecifically binds can be determined by any method well-known to one of skill in the art, for example by immunoassays. Antigenic epitopes need not necessarily be immunogenic.

The term "protein binding protein" refers to a non-immunoglobulin binding protein and is selected from the group consisting of antibody substructure (e.g. Fc fragment), minibody, adnectin, anticalin, affibody, affilin, ankyrin repeat proteins, DARPin, knottin, glubody, C-type lectin-like domain protein, tetranectin, kringle domain (KD), kunitz domain protein, thioredoxin, cytochrome b562, zinc finger scaffold, Staphylococcal nuclease scaffold, fibronectin or fibronectin dimer, tenascin, N-cadherin, E-cadherin, ICAM, titin, GCSF-receptor, cytokine receptor, glycosidase inhibitor, antibiotic chromoprotein, myelin membrane adhesion molecule PO, CD8, CD4, CD2, class I MHC, T-cell antigen receptor, CD1, C2 and I-set domains of VCAM-1, 1-set immunoglobulin domain of myosin-binding protein C, 1-set immunoglobulin domain of myosin-binding protein H, I-set immunoglobulin domain of telokin, NCAM, twitchin, neuroglian, growth hormone receptor, erythropoietin receptor, prolactin receptor, interferon-gamma receptor, β-galactosidase/glucuronidase, β-glucuronidase, transglutaminase, T-cell antigen receptor, superoxide dismutase, tissue factor domain, cytochrome F, green fluorescent protein, GroEL, and thaumatin. Methods for preparation of such non-immunoglobulin binding proteins are well-known in the art (Binz et al. 2005, Nat Biotechnol 1257-6; Lee et al. 2010, Proc Natl Acad Sci USA 107(21):9567-71; Gebauer and Skerra 2009, Curr Opin Chem. Biol. 13(3):245-255).

The term "expression" refers to the cellular processes involved in producing RNA and proteins and as appropriate, secreting proteins, including where applicable, but not limited to, for example, transcription, translation, folding, modification and processing. The terms "expression product" or "expression products" include RNA transcribed from a gene, and polypeptides obtained by translation of mRNA transcribed from a gene. In some embodiments, an expression product is transcribed from a sequence that does not encode a polypeptide, such as a microRNA or RNAi.

As used herein, the term "complementary" or "complementary base pair" refers to A:T and G:C in DNA and A:U in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U).

The term "nucleic acids" or "nucleic acid sequence" used herein refers to any molecule, preferably a polymeric molecule, incorporating units of ribonucleic acid, deoxyribonucleic acid or an analog thereof, polynucleotides such as deoxyribonucleic acid (DNA), and, where appropriate, ribonucleic acid (RNA), polymers thereof in either single- or double-stranded form. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, i.e., prepared based up human action, or may be a combination of the two. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985), and Rossolini, et al., Mol. Cell. Probes 8:91-98 (1994)). The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety. The term "nucleic acid" should also be understood to include, as equivalents, derivatives, variants and analogs of either RNA or DNA made from nucleotide analogs, and, single (sense or antisense) and double-stranded polynucleotides.

The term "gene" means the nucleic acid sequence (DNA) which is transcribed to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the terms "protein" and "polypeptide and "peptide" are used interchangeably herein to designate a series of amino acid residues connected the other by peptide bonds between the alpha-amino and carboxy groups of adjacent residues. The terms "protein", and "polypeptide and "peptide", which are used interchangeably herein, refer to a polymer of amino acids, including modified amino acids (e.g., phosphorylated, glycated, glycosylated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "polypeptide" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

The term "vector", as used herein, refers to a nucleic acid construct designed for delivery to a host cell or transfer between different host cells. As used herein, a vector can be viral or non-viral. A vector can include, but is not limited to, a cloning vector, an expression vector, a plasmid, a phage, a transposon, a cosmid, a bacterial artificial chromosome (BAC), a yeast artificial chromosome (YAC), a virus, a virion, a retrovirus etc. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the term "expression vector" refers to a vector that has the ability to incorporate and express heterologous nucleic acid fragments in a cell. An expression vector may comprise additional elements, for example, the expression vector may have two replication systems, thus allowing it to be maintained in two organisms, for example in human cells for expression and in a prokaryotic host for cloning and amplification. An expression vector may direct expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the target gene in place of non-essential viral genes. The vector and/or particle may be utilized for the purpose of transferring any nucleic acids into cells either in vitro or in vivo. Numerous forms of viral vectors are known in the art, including but not limited to cytomegalovirus, adenovirus, lentivirus, pox virus, herpes virus, retrovirus (e.g. MMLV, HIV-1 or ALV). Viral can be used as carriers of a nucleic acid modulatory compound into the cell. For example, constructs containing the modulatory compound may be integrated and packaged into non-replicating, defective viral genomes like Adenovirus, Adeno-associated virus (AAV), or Herpes simplex virus (HSV) or others, including retroviral and lentiviral vectors, for infection or transduction into cells. Alternatively, the construct may be incorporated into vectors capable of episomal replication, e.g. EPV and EBV vectors. The nucleic acid incorporated into the vector can be operatively linked to an expression control sequence when the expression control sequence controls and regulates the transcription and translation of that polynucleotide sequence.

The term "operatively linked" or "operably linked" as used herein refers to a nucleic acid in functional relationship with a second nucleic acid. The term "operably linked" encompasses functional connection of two or more nucleic acid molecules, such as an oligonucleotide or polynucleotide to be transcribed and a regulatory element such as a promoter or an enhancer element, which allows transcription of the oligonucleotide or polynucleotide to be transcribed. In some examples, transcription of a nucleic acid modulatory compound is under the control of a promoter sequence (or other transcriptional regulatory sequence) which controls the expression of the nucleic acid in a cell-type in which expression is intended. It will also be understood that the modulatory nucleic acid can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene. The promoter sequence may be a "tissue-specific promoter", which means a nucleic acid sequence that serves as a promoter, i.e., regulates expression of a selected nucleic acid sequence operably linked to the promoter, and which affects expression of the selected nucleic acid sequence in specific cells, e.g. lymphocytes or epithelial cells. The term also covers so-called "leaky" promoters, which regulate expression of a selected nucleic acid primarily in one tissue, but cause expression in other tissues as well.

As used herein, the term "heterologous nucleic acid fragments" refers to nucleic acid sequences that are not naturally occurring in that cell. For example, when a heterologous gene, such as DNA editing enzyme (e.g. AID) is inserted into the genome of a bacteria or virus, that gene is heterologous to that recipient bacteria or virus because the bacteria and viral genome do not naturally have the DNA editing enzyme gene.

The term "replication incompetent" as used herein means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins from packaging the virus) and viral particles cannot be formed in the patient's cells.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

As used herein in the context of disease, the terms "treat", "treatment", "treating" and the like, refer to a decrease in severity of indicators, symptoms, markers, physical parameters, tumor size or recurrence of a cancer as described herein. In the context of the technology described herein insofar as it relates to any of the conditions recited herein, the terms "treat", "treatment", "treating" and the like mean to relieve, alleviate, ameliorate, inhibit, slow down, delay, reverse, or stop the progression, aggravation, deterioration, progression, anticipated progression or severity of at least one symptom or complication associated with such cancer or autoimmune disorder or delaying the onset of the disease or disorder. In one embodiment, the symptoms of a cancer or an autoimmune disorder are alleviated by at least 5%, at least 10%, at least 20%, at least 30%, at least 40%, or at least 50%.

By "lower" in the context of a disease or disorder marker or symptom is meant a statistically significant decrease in such level. The decrease can be, for example, at least 10%, at least 20%, at least 30%, at least 40% or more, and is preferably down to a level accepted as within the range of normal for an individual without such disease or disorder.

By "higher" in the context of a disease or disorder marker or symptom is meant a statistically significant increase in such level. The increase can be, for example, at least 10%, at least 20%, at least 30%, at least 40%, at least 50% or more, and is preferably up from a level accepted as within the range of normal for an individual without such disease or disorder.

As used herein, the phrase "therapeutically effective amount", "effective amount" or "effective dose" refers to an amount that provides a therapeutic benefit in the treatment, prevention, or management of a condition described herein, (e.g. cancer or an autoimmune disease), e.g. an amount that provides a statistically significant decrease in at least one symptom of such a condition. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "pharmaceutical composition" refers to the active agent in combination with a pharmaceutically acceptable carrier commonly used in the pharmaceutical industry.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein means any pharmaceutically acceptable material, composition, media, or vehicle, such as a liquid or solid filler, diluent, excipient (e.g., dyes, flavors, binders, emollients, fillers, lubricants, preservatives, cornstarch, lactose, talc, magnesium stearate, sucrose, gelatin, calcium stearate, silicon dioxide, shellac and glaze), solvent or encapsulating material, coating, surfactant, absorption delaying agents, manufacturing aid (e.g., lubricant, talc magnesium, calcium or zinc stearate, or steric acid), or solvent encapsulating material, salts, preservative, stabilizers, gels, disintegration agents, sweetening agents, such like materials and combinations thereof, as would be known to one of ordinary skill in the art (see, for example, Remington's Pharmaceutical Sciences, 18$^{th}$ Ed. Mack Printing Company, 1990, pp. 1289-1329). Except insofar as any conventional carrier is incompatible with the active ingredient, its use in the therapeutic or pharmaceutical compositions is contemplated. Each carrier must be "acceptable" in the sense of being compatible with the other ingredients of the formulation and not injurious to the patient. For example, the carrier does not decrease the impact of the agent on the treatment. In other words, a carrier is pharmaceutically inert. Some examples of materials which can serve as pharmaceutically-acceptable carriers include, but are not limited to: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other nontoxic compatible substances employed in pharmaceutical formulations. Wetting agents, binding agents, fillers, lubricants, coloring agents, disintegrants, release agents, coating agents, sweetening agents, flavoring agents, perfuming agents, preservative, water, salt solutions, alcohols, antioxidants, polyethylene glycols, gelatin, lactose, amylose, magnesium stearate, talc, silicic acid, viscous paraffin, hydroxymethylcellulose, polyvinylpyrrolidone and the like can also be present in the formulation. The terms such as "excipient", "carrier", "pharmaceutically acceptable carrier" or the like are used interchangeably herein.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, a "subject" means a human or an animal. In one embodiment, the animal is a vertebrate such as a primate, rodent, domestic animal, avian species, fish or game animal. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of cancer, an autoimmune disease, or an inflammatory disease. In addition, the methods described herein can be used to treat domesticated animals and/or pets. A subject can be male or female. A subject can be one who has been previously diagnosed with cancer or an autoimmune disease, or a subject identified as having one or more complications related to cancer or an autoimmune disease, and optionally, but need not have already undergone treatment for the cancer or an autoimmune disease or the one or more complications related to the cancer or an autoimmune disease. A subject can also be one who is not suffering from cancer or an autoimmune disease. For example, a subject can be one who exhibits one or more risk factors for cancer or an autoimmune disease or one or more complications related to cancer or an autoimmune disease. A subject can be asymptomatic for cancer or an autoimmune disease or one or more complications related to cancer or an autoimmune disease. In one embodiment, the subject is selected for having, or being at risk for having, cancer or an autoimmune disease. A subject can also be one who has been diagnosed with or identified as having one or more complications related to cancer or an autoimmune disease, or alternatively, a subject can be one who has not been previously diagnosed with or identified as having one or more complications related to cancer or an autoimmune disease.

As used herein, the term "alkyl" refers to saturated straight-chain, branched-chain, or cyclyl hydrocarbon radicals. The term "alkyl" includes cycloalkyl or cyclic alkyl. In addition, backbone of the alkyl can comprise one or more heteroatoms, such as O, N, or S. Examples of alkyl radicals include, but are not limited to, methyl, ethyl, propyl, isopropyl, n-butyl, tert-butyl, neopentyl, n-hexyl, and n-octyl radicals.

As used herein, the term "alkenyl" refers to unsaturated straight-chain, branched-chain, or cyclyl hydrocarbon radicals having at least one carbon-carbon double bond. The term "alkenyl" includes cycloalkyl or cyclic alkenyl. In addition, backbone of the alkenyl can comprise one or more heteroatoms, such as O, N, or S. Examples of alkenyl radicals include, but are not limited to, allyl, butenyl, and hexenyl radicals.

As used herein, the term "alkynyl" refers to unsaturated hydrocarbon radicals having at least one carbon-carbon triple bond. In addition, backbone of the alkynyl can comprise one or more heteroatoms, such as O, N, or S. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

As used herein, the term "halogen" refers to an atom selected from fluorine, chlorine, bromine and iodine. The term "halogen radioisotope" refers to a radionuclide of an atom selected from fluorine, chlorine, bromine and iodine.

As used herein, the term "cyclyl" refers to a saturated and partially unsaturated cyclic hydrocarbon group having 3 to 12 carbons, preferably 3 to 8 carbons, and more preferably 3 to 6 carbons, wherein the cyclyl group may be optionally substituted. Examples of cyclyl groups include, without limitation, cyclopropyl, cyclobutyl, cyclopentyl, cyclopentenyl, cyclohexyl, cyclohexenyl, cycloheptyl, and cyclooctyl.

As used herein, the term "heterocyclyl" refers to a non-aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, sAICD heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring can be substituted by a substituent. Examples of heterocyclyl groups include piperazinyl, pyrrolidinyl, dioxanyl, morpholinyl, tetrahydrofuranyl, and the like.

As used herein, the term "aryl" refers to a 6-carbon monocyclic, 10-carbonbicyclic, 14-carbon tricyclic aromatic ring system wherein each ring can have 1 to 4 substituents. Examples of aryl groups include, but are not limited to, phenyl, methylphenyl, naphthyl, and anthracenyl.

As used herein, the term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, sAICD heteroatoms selected from O, N, or S (e.g., carbon atoms and 1-3, 1-6, or 1-9 heteroatoms of N, O, or S if monocyclic, bicyclic, or tricyclic, respectively), wherein each ring may have 1 to 5 substituents. Examples of heteroaryl groups include pyridyl, furyl or furanyl, imidazolyl, benzimidazolyl, pyrimidinyl, pyrrolyl, pyrazinyl, thiophenyl or thienyl, quinolinyl, indolyl, thiazolyl, and the like.

As used herein, the term "substituted" refers to independent replacement of one or more of the hydrogen atoms on the substituted moiety with substituents independently selected from, but not limited to, alkyl, alkenyl, heterocycloalkyl, alkoxy, aryloxy, hydroxy, amino, amido, alkylamino, arylamino, cyano, halo, mercapto, nitro, carbonyl, acyl, aryl and heteroaryl groups.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The term "racemic mixture", "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); or (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction $F_{(+)}$ and $F_{(−)}$ (where the sum of $F_{(+)}$ and $F_{(−)}=1$). The enantiomeric excess is defined as $*F_{(+)}−F_{(−)}*$ and the percent enantiomeric excess by $100\times *F_{(+)}−F_{(−)}*$. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer", "substantially resolved enantiomer" "substantially purified enantiomer preparation" are meant to indicate a preparation (e.g. derived from non-optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer", "resolved enantiomer" and "purified enantiomer preparation" are meant to indicate a preparation (e.g. derived from non-optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity", also called the enantiomeric ratio indicated by the symbol "E", refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

Compounds of the present invention may exist in prodrug form. As used herein, "prodrug" is intended to include any carriers which release the active parent drug or compounds that are metabolized in vivo to an active drug or other compounds employed in the methods of the invention in vivo when such prodrug is administered to a subject. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a free hydroxyl, free amino, or carboxylic acid, respectively. Other examples include, but are not limited to, acetate, formate, and benzoate derivatives of alcohol and amine functional groups; and alkyl, carbocyclic, aryl, and alkyl aryl esters such as methyl, ethyl, propyl, iso-propyl, butyl, isobutyl, sec-butyl, tertbutyl, cyclopropyl, phenyl, benzyl, and phenethyl esters, and the like.

As used herein, the term "pharmaceutically-acceptable salts" refers to the inorganic and organic salts, conventional nontoxic salts or quaternary ammonium salts of a therapeutic agent or compound or prodrug, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, adipic, aspartic, carbonic, gluconic, glucuronic, malonic, oleic, pamoic and the like. See, for example, Berge et al., "Pharmaceutical Salts", *J. Pharm. Sci.* 66:1-19 (1977) or P. H. Stahl and C. G. Wermuth, editors, Handbook of Pharmaceutical Salts: Properties, Selection and Use, Weinheim/Zürich:Wiley-VCH/VHCA, 2002, content of which is herein incorporated by reference in its entirety. The terms "salt" or "salts" is used interchangeably with "pharmaceutically acceptable salts".

In some embodiments of the aspects described herein, representative salts include hydrobromide, hydrochloride, sulfate, bisulfate, phosphate, nitrate, acetate, succinate, valerate, oleate, palmitate, stearate, laurate, benzoate, lactate, tosylate, citrate, maleate, fumarate, succinate, tartrate, napthylate, mesylate, monohydrogenphosphate, glucoheptonate, lactobionate, laurylsulphonate, pyrophosphate, pyrosulfate, and sodium salts and the like.

All patents and other publications identified are expressly incorporated herein by reference in their entirety for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

DNA-Editing Enzymes and Double Strand DNA Break Repair

Embodiments of the technology described herein are based on the discovery that activation-induced cytidine deaminase (AID, or AICDA, also known as ARP2, CDA2 or HIGM2), a DNA-editing enzyme that is a member of the apolipoprotein B mRNA editing enzymes, catalytic polypeptide-like (APOBEC), will cause widespread genomic breaks and cell death in cells with diminished homologous recombination ability (e.g. cells with diminished DNA double strand break repair abilities). Accordingly, provided herein is a method of causing cell death comprising detecting increased expression of a DNA-editing enzyme (e.g. AID) in a cell and thereafter contacting the cell with an inhibitor of double strand break repair; thereby resulting in cell death. Accordingly, provided herein is a method of causing cell death comprising increasing expression of a DNA-editing enzyme (e.g. AID) in a cell and thereafter contacting the cell with an inhibitor of double strand break repair; thereby resulting in cell death. Accordingly, provided herein is a method of causing cell death comprising administering to a cell a therapeutically effective amount of a DNA editing enzyme (e.g. AID) and thereafter contacting the cell with an inhibitor of double strand break repair; thereby resulting in cell death.

AID, encoded by the AICDA gene (NCBI Gene ID: 57379), is required for proper B-cell function and is most prominently expressed in centroblast B-cells. The protein is involved in somatic hypermutation, gene conversion, and class-switch recombination of immunoglobulin genes. AID is normally expressed almost exclusively in antigen-activated germinal center B-cells, where it initiates immunoglobulin isotype class switching (Manis et al. 2002, Trends Immunol, 23, 31-39; Chaudhuri and Alt, Nat Rev Immunol, 2004, 4, 541-552; Longerich et al., Curr Opin Immunol, 2006, 18, 164-174; Chaudhuri et al., Adv Immunol 2007, 94, 157-214). AID is required for somatic hypermutation and immunoglobulin class switching in activated B cells. AID expression is regulated by CD40 ligand, B-cell receptor, IL4R, or Toll-like receptor stimulation (Crouch et al., J Exp Med 2007 204:1145-1156; Muramatsu et al., J Biol Chem 1999 274:18470-6). After activation, AID is transiently upregulated, induces point mutations or DNA double strand breaks in a sequence non-specific manner within immunoglobulin genes, and is then down-regulated (Longerich et al., Curr Opin Immunol, 2006, 18, 164-176; Chaudhuri et al., Adv Immunol 2007, 94, 157-214). Overall, AID is active in only a tiny population of normal cells (antigen-activated B-cells) at any given time. The genomic rearrangements and mutations controlled by AID lead to the development of antigen-recognition diversity, receptor editing and lymphoid effector function required for functional adaptive immunity (Mills, et al. Immunol Rev 2003 194:77-95). Recently it has been reported that AID has off-target point mutation activities (Liu, M. et al., Nature 2008, 451, 841-845; Liu and Schatz, Trends Immunol. 2009, 30, 173-181; Pérez-Dúran et al., Carcinogenesis. 2007, 28(12):2427-33). Robbiani et al. has reported off-target activities of AID in B-cells, especially c-myc/IgH translocations (Robbiani et al., Mol Cell 2009, 36(4):631-41). AID expression accelerates the rate of tumor development in Bcl6 transgenic mice (Pasqualucci et al., 2008, Nat. Genet. 40, 108-112). However, deregulated AID does not necessarily cause malignancy or translocation-associated cancer on its own in B cells (Muto et al., 2006, Proc. Natl. Acad. Sci. USA 103, 2752-2757; Okazaki et al., 2003, J. Exp. Med. 197, 1173-1181; Shen et al., 2008, Mol. Immunol. 45, 1883-1892). In addition, despite its obligate role in c-myc/IgH translocation, AID is not required for the development of plasmacytosis or plasmacytoma in IL-6 transgenic or pristane-treated mice, respectively (Kovalchuk et al., 2007, J. Exp. Med. 204, 2989-3001; Ramiro et al., 2004, J. Exp. Med. 200, 1103-1110). However, most human B cell lymphoma-associated translocations do not involve c-myc, and many do not involve Ig genes (Kuppers, 2005, Oncogene 20, 5580-5594).

Overexpression of AID has been reported in chronic lymphocytic leukemia (CLL) (Hancer et al. Leuk Lymphoma. 2011 January; 52(1):79-84; Heintel et al., Leukemia. 2004 April; 18(4):756-62). Further, AID expression has been shown to be correlated with blast crisis B lineage leukemia and therapy resistance in myeloid leukemia and to be associated with generally poor prognosis in chronic B lymphocytic leukemia (Mao et al., Br J Dermatol 2001, 145: 117-122; Chaudhuri et al., Nature 2004, 430:992-8). Further expression of AID in tumor cells from a variety of cancers has been reported including but not limited to lung, breast, gastric, colon, intestinal, liver cancer and choriangiocarcinoma (Greeve et al., Blood 2003, 1010, 3574-3580; Feldhahn et al., J Exp Med 2007, 204, 1157-1166; Kotani et al., PNAS USA 2007, 104, 1616-1620; Engels et al., 2008, Appl Immunohistochem Mol Morphol 16, 521-529; Klemm et al., 2009, Cancer Cell 6, 232-245; Palacios et al., 2010, Blood 115(22), 4488-4496; Leuenberger et al., 2009, Mod Pathol 32, 177-186; Gruber et al., 2010, Cancer Res 70, 7411-7420; inflammatory cancer (Marusawa 2008, Int J Biochem Cell Biol. 40, 399-402); follicular lymphoma (Hardianti et al., 2004, Leukemia 18, 826-831; Shikata et al., 2012, Cancer Sci. 103(3):415-21); thyroid cancer (Qiu et al. 2012, Mod Pathol 25(1), 36-45); breast cancer (Borchert et al. 2011, BMC Cancer 11:347); Marusawa, et al., 2011, Adv Immunol 111:109-41; Zhang et al. 2012, Hum Pathol 43(3):423-34; Komori et al., 2008, Hepatology 47(3):888-896; Hockley 2010, Leukemia 24(5):1084-6; adult T-cell leukemia (Nakamura et al., 2011, Br J. Dermatol. 165(2):437-9). All of the references in the foregoing paragraph are incorporated by reference herein in their entireties.

Elevated levels of AID have been reported in arthritis (Xu et al. Scand. J. Immunol. 2009, 296, 2033-6) and in the MRL/Fas(lpr/lpr) mouse lupus model (White et al. 2011, Autoimmunity 44(8), 585-98). All of the references in the foregoing paragraph are incorporated by reference herein in their entireties.

It is demonstrated herein that when DSB repair is inhibited, the extent of the DSBs generated by AID is much higher than previously suspected and the extent of genomic damage is so severe as to result in cell death. Accordingly, in one embodiment of the technology described herein, there is provided a method of treatment comprising; (a) selecting a subject having cells that express elevated levels of activation-induced cytidine deaminase (AID); and (b) administering a therapeutically effective amount of an inhibitor of double strand break repair to the subject; wherein an elevated level of AID is a level of AID that is higher than the level of AID in cells of the same type from a healthy individual. In some embodiments, the cells expressing elevated levels of AID are B cells. In some embodiments, the B cell expressing elevated levels of AID is a cancerous B cells or a B cell associated with autoimmune disease. In some embodiments, the subject can be a human subject.

Methods provided herein treat cancers and/or autoimmune disorders by inhibiting DNA double strand break repair. This inhibition proves lethal to cells expressing AID, as AID generates widespread genomic breaks, and the treatment with a double strand break repair inhibitor prevents the repair of these lesions which are being generated by the cell itself. This results in cell death in the subject which is specific to the cells expressing AID, e.g. cancerous B cells and/or autoimmune cells. Accordingly, as described herein, in one embodiment there is provided a treatment paradigm that selectively induces self-destruction of certain diseased cells, while reducing the unintended side effects in healthy tissues.

RAD51-mediated strand exchange repair is a component of homologous recombination, which is used to repair DNA double strand breaks (DSBs) generated by irradiation, cross-linking drugs or as a consequence of the activity of enzymes such as AID (Klein 2008, DNA Repair, 7:686-93).

RAD51 (NCBI Gene ID: 5888) is a eukaryotic recombinase with ATP-dependent DNA binding activity and plays a role in meiotic recombination and DNA repair in mammals. RAD51 binds to the 3'-tailed single strands of the DSB and promotes pairing with homologous sequences. Further steps involve strand invasion and repair (see San Filippo et al., Annual Review of Biochemistry 2008, 77:229-257). Further RAD51 has been shown to have a function in class switch recombination during antibody maturation (Li et al., PNAS 1996, 93:10222-7). In certain embodiments, the DSB repair inhibitor inhibits the expression or activity of RAD51.

In certain embodiments, the DSB repair inhibitor inhibits the expression or activity of one or more of the following proteins and/or transcripts including, but not limited to: Rad51AP1 (NCBI Gene ID: 10635; e.g. SEQ ID NO:007 (mRNA) and SEQ ID NO:114 (protein)); Rad51B (NCBI Gene ID: 5890; e.g. SEQ ID NO:008 (mRNA) and SEQ ID NO:115 (protein)); Rad51C (NCBI Gene ID: 5889 e.g. SEQ ID NO: 0163 (mRNA; NM_058216) and SEQ ID NO: 0164 (protein; NP_478123) or SEQ ID NO:0165 (mRNA; NM_002876) and SEQ ID NO:0166 (protein; NP_002867); Rad51D (NCBI Gene ID: 5892; e.g. SEQ ID NO:009 (mRNA) and SEQ ID NO:116 (protein)); XRCC2 (NCBI Gene ID: 7516; e.g. SEQ ID NO:010 (mRNA) and SEQ ID NO:117 (protein)); XRCC3 (NCBI Gene ID: 7517; e.g. SEQ ID NO:011 (mRNA) and SEQ ID NO:118 (protein)); RAD54 (NCBI Gene ID: 546; e.g. SEQ ID NO:012 (mRNA) and SEQ ID NO:119 (protein)); RAD52 (NCBI Gene ID: 5893; e.g. SEQ ID NO:013 (mRNA) and SEQ ID NO:120 (protein)); BRCA1 (NCBI Gene ID: 672; e.g. SEQ ID NO:014 (mRNA) and SEQ ID NO:121 (protein)); BRCA2 (NCBI Gene ID: 675; e.g. SEQ ID NO:015 (mRNA) and SEQ ID NO:122 (protein)); ATM (NCBI Gene ID: 472; e.g. SEQ ID NO:016 (mRNA) and SEQ ID NO:123 (protein)); ATR (NCBI Gene ID: 545; e.g. SEQ ID NO:017 (mRNA) and SEQ ID NO:124 (protein)); MRE11 (NCBI Gene ID: 4361; e.g. SEQ ID NO:018 (mRNA) and SEQ ID NO:125 (protein)); RAD50 (NCBI Gene ID: 10111: e.g. SEQ ID NO:019 (mRNA) and SEQ ID NO:126 (protein)); NBS1 (NCBI Gene ID: 4683; e.g. SEQ ID NO:020 (mRNA) and SEQ ID NO:127 (protein)); WRN(NCBI Gene ID: 7486; e.g. SEQ ID NO:021 (mRNA) and SEQ ID NO:128 (protein)); BLM (NCBI Gene ID: 641; e.g. SEQ ID NO:022 (mRNA) and SEQ ID NO:129)); RECQ4 (NCBI Gene ID: 9401; e.g. SEQ ID NO:023 (mRNA) and SEQ ID NO:130 (protein)); LIG4 (DNA Ligase 4; NCBI Gene ID: 3981; e.g. SEQ ID NO:024 (mRNA) and SEQ ID NO:131 (protein)); XRCC4 (NCBI Gene ID: 7518; e.g. SEQ ID NO:025 (mRNA) and SEQ ID NO:132 (protein)); PRKDC (DNA-PKcs7; XRCC7; NCBI Gene ID: 5591; e.g. SEQ ID NO:026 (mRNA) and SEQ ID NO:133 (protein)); DCLRE1C (NCBI Gene ID: 64421; e.g. SEQ ID NO:027 (mRNA) and SEQ ID NO:134 (protein)); XRCC6 (Ku70; NCBI Gene ID: 2547; e.g. SEQ ID NO:028 (mRNA) and SEQ ID NO:135 (protein)); XRCC5 (Ku80; NCBI Gene ID: 7520; e.g. SEQ ID NO:029 (mRNA) and SEQ ID NO:136 (protein)) and/or XLF (NHEJ1; XRCC4-like factor; NCBI Gene ID: 79840; e.g. SEQ ID NO:030 (mRNA) and SEQ ID NO:137 (protein)).

In certain embodiments, the DSB repair inhibitor inhibits the expression or activity of one or more proteins and/or transcripts encoded by a gene selected from the group consisting of: Rad51AP1; Rad51B; Rad51C; Rad51D; XRCC3; RAD54; RAD52; BRCA1; BRCA2; ATM; ATR;

MRE11; RAD50; NBS1; WRN; BLM; RECQ4; LIG4; XRCC4; PRKDC; DCLRE1C; XRCC6; XRCC5; and XLF.

In certain embodiments, the DSB repair inhibitor inhibits the expression or activity of one or more proteins and/or transcripts encoded by a gene selected from the group consisting of: Rad51AP1; Rad51B; Rad51C; Rad51D; RAD54; RAD52; BRCA1; BRCA2; ATM; ATR; MRE11; RAD50; NBS1; WRN; BLM; RECQ4; LIG4; and PRKDC.

In certain embodiments, the DSB repair inhibitor binds to one or more of the following proteins and/or transcripts including, but not limited to: Rad51AP1; Rad51B; Rad51C; and/or Rad51D.

In some embodiments, the inhibitor of double strand break repair can inhibit the expression or activity of a Rad51 family member (e.g. Rad51; Rad51AP1; Rad51B; Rad51C; Rad51D; XRCC2; XRCC3). In some embodiments, the inhibitor of double strand break repair can inhibit a Non-homologous end joining (NHEJ) protein member (e.g. LIG4; XRCC4; PRKDC; DCLRE1C; XRCC6; XRCC5; XLF).

In yeast Rad52 has been shown to mediate binding of Rad51 to ssDNA. BRCA2 also appears to function as a recombination mediator; promoting the binding of RAD51 to ssDNA and possibly mediating the translocation of RAD51 to the nucleus. RAD51B, Rad51C, RAD51D, XRCC2 and XRCC3 are paralogs of RAD51 and are all functioning in HR of DSBR pathway (Yokoyama et al. J Biol Chem. 2003, 278(4):2767-72; Thacker, Trends Genet. 1999, 15:166-168; Schild D, et al., J. Biol. Chem. 2000, 275:16443-16449). Rad51AP1 is a RAD51 associated protein that promotes binding to branched DNA molecules (Modesti et al., Mol Cell 2007, 28:468-481; Dunlop et al., 2012, J Biol Chem 6, 287, 12343-7). RAD54 is a protein with dsDNA-dependent ATPase activity and this activity is enhanced by the presence of RAD51. In yeast, Rad54 promotes the search for DNA homology, remodeling of chromatin, formation of the invasion complex, and eventual removal of Rad51 from the dsDNA. In humans it has been shown to function in branch migration of the Holliday junction, a key intermediate in DNA repair and recombination (San Filippo et al., Annual Review of Biochemistry 2008, 77:229-257; Mazina et al., 2012, J Biol Chem 6, 287(15):11820-32). BRCA1 promotes RAD51-mediated repair of DSBs and suppresses crossover type repair (Cousineau et al., Cancer Res 2005 65:11384-91). ATM and ATR are protein kinases. ATM phosphorylates targets when DSBs are detected, halting the cell cycle. MRE11, RAD50 and NBS1 form the MRN complex which recruits ATM to DSBs. In contrast, ATR is activated by ssDNA. WRN, BLM, and RECQ4 are members of the RECQ helicase family. WRN is a helicase and exonuclease which is believed to unwind the Holliday junctions formed during HR, thus decreasing inappropriate recombination (Yang et al., J Biol Chem 2002, 277, 31980-7). BLM and RECQ4 are both helicases which are activated by interaction with RAD51 (Brosh et al., 2000, J Biol Chem, 275:23500-8; Rossi et al., 2010, DNA Repair 9:796-804).

XRCC2 is a key member of the RAD51 family of mammalian homologous-recombination factors (Thacker, Biochimie 1999, 81: 77-85; Braybrooke et al., J Biol Chem 2000, 275:29110-6; Deans et al., EMBO J 2000, 19:6675-6685), and is known for its DSB repair functions (Johnson et al., Nature 1999, 401:397-9). In the human genome, XRCC2 is located on cytoband q36 of chromosome 7 (7q36), a region frequently rearranged in various cancers (Dohner et al., Blood 1998, 92:4031-5; Simmons et al., Leukemia 2002, 16:2408-2416; Mao et al., Br J Dermatol 2001, 145:117-122). XRCC2-deficient cells show proliferation defects, hypersensitivity to ionizing radiation and other DNA-damaging agents, and spontaneous chromosomal instability (Deans et al., EMBO J 2000, 19:6675-6685; Liu et al., J Biomed Biotechnol 2002, 2:106-113; Deans et al., Cancer Res 2003, 63:8181-7). XRCC2 is required for successful proliferation and genomic integrity in early developing B cells (Caddle, et al., 2008, Mol. Cell. Biol. 28, 2295-2303). Mice with homozygous deletion of Xrcc2 die during mid-gestation, associated with widespread cellular apoptosis (Deans et al., EMBO J 2000, 19:6675-6685; Orii et al., PNAS 2006, 103:10017-10022; Adam et al., DNA Repair (Amst.) 2007, 6:224-234). As described herein and in Hasham et al. (Nature Immunology, 2010, 11 (9), 820-826), the inventors have found that AID expression in XRCC2-defective mature B cells lead to widespread, highly cytotoxic DSBs.

XRCC3 is a member of the RecA/Rad51-related protein family that participates in homologous recombination to maintain chromosome stability and repair DNA damage. XRCC4 is a DNA double strand break repair gene and important for genome stability. It is known to interact with DNA ligase IV.

Inhibitors of DSB Repair

In certain embodiments, the DSB repair inhibitor, e.g. is an inhibitor of RAD51-mediated strand exchange repair, can be a stilbene derivative. Stilbene derivatives can include, but are not limited to, stilbene, trans-stilbene derivatives, cis-stilbene derivatives, cis-stilbene oxide, trans-stilbene oxide, 4,4'-bis(2-benzoxazolyl)stilbene, 4-nitro-4'-(octadecylamino)stilbene, α,β-bis(phenylazo)stilbene, meso-1,2-dibromo-1,2-diphenylethane, (Z)-1,2-diphenyl-1,2-ethylenediboronic acid bis(pinacol) ester, 2,4-dinitro-3',4'-(methylenedioxy)-stilbene, polymethoxystilbenes, dihydrostilbenes, combretastatin, combretastatin A-4, 3,5,4'-trimethoxy-trans-stilbene, 3,4,5,4'-tetramethoxystilbene, resveratrol, diethylstilboestrol, 2,4,6-trihydrophenanthrene-2-O-glucoside, resveratrol-2-C-glucosides, cis-ε-viniferin diglucoside, trans-ε-viniferin diglucoside, pallidol glucoside, pallidol diglucoside, cis-3,4',5-trimethyoxy-3'-aminostilbene, cis-3,4',5-trimethoxy-3'-hydroxystilbene, cholchicine, combretastatin A4-phosphate, desoxyrhapontigenin, dimethylaminonitrostilbene, rhapontigenin, piceatannol, 4-hydroxystilbene, 4,4'-dihydroxystilbene, 3,5-dihydroxystilbene, trimethylresveratrol, silbamidine, diethylstilbestrol, parthenocissine, pallidol, quadrangularin A, quadrangularin B, quadrangularin C, ZD6126. Non-limiting examples of stilbene derivatives include those structures disclosed in U.S. Pat. Nos. 4,723,034, 4,326,055, 4,723,028, 4,892,949, 6,562,834, 5,589,506, 7,655,696, 4,996,237, 5,561,122, 5,525,632, 5,430,062, 5,731,353, 7,781,580, US patent Publications US2004/0147788, US2008/071364, Japanese Patent Kokai Publications JP-A-7-225558, JP-A-8-301831 and JP-A-10-81673, Roberti et al., J. Med. Chem. 2003 46:3546-54; Baderschneider and Winterhalter J of Agricultural and Food Chem 2000 48:2681-6; Hillis and Ishikura, Journal of Chromatography A 1968 32:323-336; Kim et al., J Med Chem 2002 45:160-4; Young et al., J Am Chem Soc 1972 94:3976-81; Iliya et al., Phytochemistry 2003 62:601-6; Aguamah et al., Phytochemistry 1981 20:1381-3; and Kim et al., J Biol Chem 2002 277:16340-4; which are incorporated by reference herein in their entireties. Known compounds, as well as stilbene compounds which will be found in the future, are included in the stilbene derivatives in the technology described herein provided that such newly found compounds are classed as stilbene derivatives. The stilbene derivatives of the technology described herein also include bioprecursors or compounds which may be converted in a subject body into a stilbene derivative. The manufacture of stilbene derivatives, which can be in the form of pharmaceutically acceptable salts, esters, hydrates and solvates, and the manufacture of pharmaceutical compositions comprising a stilbene derivative, its inert pharmaceutically acceptable carrier(s) and/or diluent(s), are disclosed in U.S. Pat. No. 5,525,632 and in the publications listed above. Certain stilbene derivatives are also available commercially, for example; cis-stilbene (#S2259 Sigma-Aldrich, St. Louis Mo.), trans-stilbene (#S6382 Sigma-Aldrich, St. Louis Mo.), resveratrol (#R5010 Sigma-Aldrich, St. Louis Mo.), or 4,4'diisothiocyanostilbene-2,2'-disulfonic acid (#D3514 Sigma-Aldrich, St. Louis Mo.).

In certain embodiments, the inhibitor of DSB repair can be the RAD51-mediated strand exchange repair inhibitor 4,4'diisothiocyanostilbene-2,2'-disulfonic acid (DIDS; Formula XXVI).

Formula XXVI

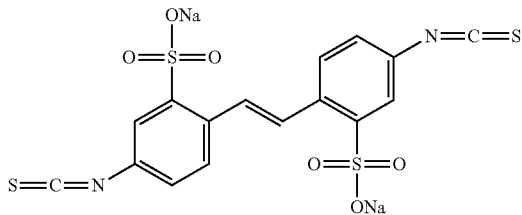

In some embodiments, described herein is a stilbene or derivative thereof of formula (V):

Formula V

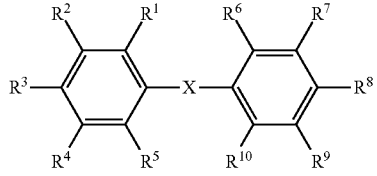

$R^1$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^1$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1$-$C_4$ alkyl. In some embodiments, $R^1$ is hydrogen, OH, $OCH_3$, $NO_2$, $NH_2$, $OP(O)(OH)_2$. In some embodiments, $R^1$ is $C_1$-$C_4$ alkyl. In some embodiments, $R^1$ is methyl, ethyl, n-propyl, i-propyl, n-butyl, i-butyl or t-butyl. In some embodiments, $R^1$ is $SO_3H$, or $SO_3^-Y^+$, wherein Y can be sodium, potassium, aluminum, calcium, lithium, magnesium, barium, or zinc. In some embodiments, $R^1$ is $CO_2H$, or $CO_2^-Y^+$, wherein Y can be sodium, potassium, aluminum, calcium, lithium, magnesium, barium, or zinc. In some embodiments, $R^1$ is optionally substituted aryl. In some embodiments, aryl is cylcopentadiene, or phenyl. In some embodiments, $R^1$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^2$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^2$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1$-$C_4$ alkyl. In some embodiments, $R^2$ is hydrogen, OH, $OCH_3$, $NO_2$, $NH_2$, $OP(O)(OH)_2$. In some embodiments, $R^2$ is $C_1$-$C_4$ alkyl. In some embodiments, $R^2$ is methyl, ethyl, n-propyl, i-propyl, n-butyl, i-butyl or t-butyl. In some embodiments, $R^2$ is $SO_3H$, or $SO_3^-Y^+$, wherein Y can be sodium, potassium, aluminum, calcium, lithium, magnesium, barium, or zinc. In some embodiments, $R^2$ is $CO_2H$, or $CO_2^-Y^+$, wherein Y can be sodium, potassium, aluminum, calcium, lithium, magnesium, barium, or zinc. In some embodiments, $R^2$ is optionally substituted aryl. In some embodiments, aryl is cylcopentadiene, or phenyl. In some embodiments, $R^2$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^3$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^3$ is hydrogen, heterocyclyl, $OR^{21}$, $NO_2$, $N(R^{22})_2$, N=C=S, $NHC(O)R^{21}$, $NHSO_2R^{21}$, $N(R^{22})_2$, $NHC(O)N(R^{22})_2$, $NHC(S)N(R^{22})_2$, or $NHSO_2N(R^{22})_2$, wherein $R^{21}$ and $R^{22}$ are independently H or $C_1$-$C_4$ alkyl. In some embodiments, $R^3$ is hydrogen, OH, $OCH_3$, N=C=S, $NH_2$, $NHCH_3$, $NO_2$, NH-octadecane, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, $NHC(S)NH$-cyclopropane, $NHC(O)NHCH_3$, $NHC(O)NHCH(CH_3)_2$, benzoxazolyl, or $NHC(O)NH$-cyclopropane. In some embodiments, $R^3$ is $C_1$-$C_4$ alkyl. In some embodiments, $R^3$ is methyl, ethyl, n-propyl, i-propyl, n-butyl, i-butyl or t-butyl. In some embodiments, $R^3$ is $SO_3H$, or $SO_3^-Y^+$, wherein Y can be sodium, potassium, aluminum, calcium, lithium, magnesium, barium, or zinc. In some embodiments, $R^3$ is $CO_2H$, or $CO_2^-Y^+$, wherein Y can be sodium, potassium, aluminum, calcium, lithium, magnesium, barium, or zinc. In some embodiments, $R^3$ is optionally substituted aryl. In some embodiments, aryl is cylcopentadiene, or phenyl. In some embodiments, $R^3$ is optionally substituted heteroaryl. In some embodiments, $R^4$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1-C_{10}$ alkyl, optionally substituted linear or branched $C_2-C_{10}$ alkenyl, optionally substituted linear or branched $C_2-C_{10}$ alkynyl, optionally substituted cyclyl, optionally substituted heterocyclyl, optionally substituted aryl, and optionally substituted heteroaryl. Preferably, $R^4$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1-C_4$ alkyl. In some embodiments, $R^4$ is hydrogen, OH, $OCH_3$, $NO_2$, $NH_2$, $OP(O)(OH)_2$. In some embodiments, $R^4$ is $C_1-C_4$ alkyl. In some embodiments, $R^4$ is methyl, ethyl, n-propyl, i-propyl, n-butyl, i-butyl or t-butyl. In some embodiments, $R^4$ is $SO_3H$, or $SO_3^-Y^+$, wherein Y can be sodium, potassium, aluminum, calcium, lithium, magnesium, barium, or zinc. In some embodiments, $R^4$ is $CO_2H$, or $CO_2^-Y^+$, wherein Y can be sodium, potassium, aluminum, calcium, lithium, magnesium, barium, or zinc. In some embodiments, $R^4$ is optionally substituted aryl. In some embodiments, aryl is cylcopentadiene, or phenyl. In some embodiments, $R^4$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^5$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1-C_{10}$ alkyl, optionally substituted linear or branched $C_2-C_{10}$ alkenyl, optionally substituted linear or branched $C_2-C_{10}$ alkynyl, optionally substituted cyclyl, optionally substituted heterocyclyl, optionally substituted aryl, and optionally substituted heteroaryl. Preferably, $R^5$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1-C_4$ alkyl. In some embodiments, $R^5$ is hydrogen, OH, $OCH_3$, $NO_2$, $NH_2$, $OP(O)(OH)_2$. In some embodiments, $R^5$ is $C_1-C_4$ alkyl. In some embodiments, $R^5$ is methyl, ethyl, n-propyl, i-propyl, n-butyl, i-butyl or t-butyl. In some embodiments, $R^5$ is $SO_3H$, or $SO_3^-Y^+$, wherein Y can be sodium, potassium, aluminum, calcium, lithium, magnesium, barium, or zinc. In some embodiments, $R^5$ is $CO_2H$, or $CO_2^-Y^+$, wherein Y can be sodium, potassium, aluminum, calcium, lithium, magnesium, barium, or zinc. In some embodiments, $R^5$ is optionally substituted aryl. In some embodiments, aryl is cylcopentadiene, or phenyl. In some embodiments, $R^5$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^6$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1-C_{10}$ alkyl, optionally substituted linear or branched $C_2-C_{10}$ alkenyl, optionally substituted linear or branched $C_2-C_{10}$ alkynyl, optionally substituted cyclyl, optionally substituted heterocyclyl, optionally substituted aryl, and optionally substituted heteroaryl. Preferably, $R^6$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1-C_4$ alkyl. In some embodiments, $R^6$ is hydrogen, OH, $OCH_3$, $NO_2$, $NH_2$, $OP(O)(OH)_2$. In some embodiments, $R^6$ is $C_1-C_4$ alkyl. In some embodiments, $R^6$ is methyl, ethyl, n-propyl, i-propyl, n-butyl, i-butyl or t-butyl. In some embodiments, $R^6$ is $SO_3H$, or $SO_3^-Y^+$, wherein Y can be sodium, potassium, aluminum, calcium, lithium, magnesium, barium, or zinc. In some embodiments, $R^6$ is $CO_2H$, or $CO_2^-Y^+$, wherein Y can be sodium, potassium, aluminum, calcium, lithium, magnesium, barium, or zinc. In some embodiments, $R^6$ is optionally substituted aryl. In some embodiments, aryl is cylcopentadiene, or phenyl. In some embodiments, $R^6$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^7$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1-C_{10}$ alkyl, optionally substituted linear or branched $C_2-C_{10}$ alkenyl, optionally substituted linear or branched $C_2-C_{10}$ alkynyl, optionally substituted cyclyl, optionally substituted heterocyclyl, optionally substituted aryl, and optionally substituted heteroaryl. Preferably, $R^7$ is hydrogen, $OR^{21}$, $NO_2$, $N(R^{22})_2$, $OP(O)(OH)_2$, or $SO_3R^{21}$, wherein $R^{21}$ and $R^{22}$ are independently H or $C_1-C_4$ alkyl. In some embodiments, $R^7$ is hydrogen, OH, $OCH_3$, $NO_2$, $NH_2$, $OP(O)(OH)_2$. In some embodiments, $R^7$ is $C_1-C_4$ alkyl. In some embodiments, $R^7$ is methyl, ethyl, n-propyl, i-propyl, n-butyl, i-butyl or t-butyl. In some embodiments, $R^7$ is $SO_3H$, or $SO_3^-Y^+$, wherein Y can be sodium, potassium, aluminum, calcium, lithium, magnesium, barium, or zinc. In some embodiments, $R^7$ is $CO_2H$, or $CO_2^-Y^+$, wherein Y can be sodium, potassium, aluminum, calcium, lithium, magnesium, barium, or zinc. In some embodiments, $R^7$ is optionally substituted aryl. In some embodiments, aryl is cylcopentadiene, or phenyl. In some embodiments, $R^7$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^8$ can be selected from the group consisting of hydrogen, halogen, $CF_3$, CN, $C(O)R^{21}$, $CO_2R^{21}$, $CO_2^-Y^+$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $SO_3^-Y^+$, $OP(O)(OH)_2$, optionally substituted linear or branched $C_1-C_{10}$ alkyl, optionally substituted linear or branched $C_2-C_{10}$ alkenyl, optionally substituted linear or branched $C_2-C_{10}$ alkynyl, optionally substituted cyclyl, optionally substituted heterocyclyl, optionally substituted aryl, and optionally substituted heteroaryl. Preferably, $R^8$ is hydrogen, heterocyclyl, $OR^{21}$, $NO_2$, $N(R^{22})_2$, N=C=S, $NHC(O)R^{21}$, $NHSO_2R^{21}$, $N(R^{22})_2$, $NHC(O)N(R^{22})_2$, $NHC(S)N(R^{22})_2$, or $NHSO_2N(R^{22})_2$, wherein $R^{21}$ and $R^{22}$ are independently H or $C_1$-$C_4$ alkyl. In some embodiments, $R^8$ is hydrogen, OH, $OCH_3$, N=C=S, $NH_2$, $NHCH_3$, $NO_2$, NH-octadecane, NHC(O)$CH_3$, NHC(O)CH($CH_3$)$_2$, NHC(O)$CH_2OCH_3$, $NHSO_2CH_3$, $NHSO_2$-cyclopropane, $NHSO_2$CH($CH_3$)$_2$, $NHSO_2$N($CH_3$)$_2$, NHC(S)$NHCH_3$, NHC(S)NHCH($CH_3$)$_2$, NHC(S)NH-cyclopropane, NHCH$_3$, NHC(O)NHCH($CH_3$)$_2$, benzoxazolyl, or NHC(O)NH-cyclopropane. In some embodiments, $R^8$ is $C_1$-$C_4$ alkyl. In some embodiments, $R^8$ is methyl, ethyl, n-propyl, i-propyl, n-butyl, i-butyl or t-butyl. In some embodiments, $R^1$ is $SO_3H$, or $SO_3^-Y^+$, wherein Y can be sodium, potassium, aluminum, calcium, lithium, magnesium, barium, or zinc. In some embodiments, $R^8$ is $CO_2H$, or $CO_2^-Y^+$, wherein Y can be sodium, potassium, aluminum, calcium, lithium, magnesium, barium, or zinc. In some embodiments, $R^8$ is optionally substituted aryl. In some embodiments, aryl is cylcopentadiene, or phenyl. In some embodiments, $R^8$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^9$ can be selected from the group consisting of hydrogen, halogen, $CF_3$, CN, C(O)$R^{21}$, $CO_2R^{21}$, $CO_2^-Y^+$, C(O)N($R^{22}$)$_2$, OH, $OR^{21}$, N($R^{22}$)$_2$, N=C=S, NHC(O)$R^{21}$, NHC(O)$OR^{21}$, NHC(S)$R^{21}$, NHC(S)N($R^{22}$)$_2$, $NHSO_2R^{21}$, $NHSO_2$N($R^{22}$)$_2$, $NO_2$, $N_2$—$R^{22}$, $SOR^{21}$, $SO_2R^{21}$, $SO_3R^{21}$, $SO_3^-Y^+$, OP(O)(OH)$_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^9$ is hydrogen, $OR^{21}$, $NO_2$, N($R^{22}$)$_2$, OP(O)(OH)$_2$, or $SO_3R^{21}$, wherein $R^{21}$ and $R^{22}$ are independently H or $C_1$-$C_4$ alkyl. In some embodiments, $R^9$ is hydrogen, OH, $OCH_3$, $NO_2$, $NH_2$, OP(O)(OH)$_2$. In some embodiments, $R^9$ is $C_1$-$C_4$ alkyl. In some embodiments, $R^9$ is methyl, ethyl, n-propyl, i-propyl, n-butyl, i-butyl or t-butyl. In some embodiments, $R^1$ is $SO_3H$, or $SO_3^-Y^+$, wherein Y can be sodium, potassium, aluminum, calcium, lithium, magnesium, barium, or zinc. In some embodiments, $R^9$ is $CO_2H$, or $CO_2^-Y^+$, wherein Y can be sodium, potassium, aluminum, calcium, lithium, magnesium, barium, or zinc. In some embodiments, $R^9$ is optionally substituted aryl. In some embodiments, aryl is cylcopentadiene, or phenyl. In some embodiments, $R^9$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

$R^{10}$ can be selected from the group consisting of hydrogen, halogen, $CF_3$, CN, C(O)$R^{21}$, $CO_2R^{21}$, $CO_2^-Y^+$, C(O)N($R^{22}$)$_2$, OH, $OR^{21}$, N($R^{22}$)$_2$, N=C=S, NHC(O)$R^{21}$, NHC(O)$OR^{21}$, NHC(S)$R^{21}$, NHC(S)N($R^{22}$)$_2$, $NHSO_2R^{21}$, $NHSO_2$N($R^{22}$)$_2$, $NO_2$, $N_2$—$R^{22}$, $SOR^{21}$, $SO_2R^{21}$, $SO_3R^{21}$, $SO_3^-Y^+$, OP(O)(OH)$_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl. Preferably, $R^{10}$ is hydrogen, $OR^{21}$, $NO_2$, N($R^{22}$)$_2$, OP(O)(OH)$_2$, or $SO_3R^{21}$, wherein $R^{21}$ and $R^{22}$ are independently H or $C_1$-$C_4$ alkyl. In some embodiments, $R^{10}$ is hydrogen, OH, $OCH_3$, $NO_2$, $NH_2$, OP(O)(OH)$_2$. In some embodiments, $R^{10}$ is $C_1$-$C_4$ alkyl. In some embodiments, $R^{10}$ is methyl, ethyl, n-propyl, i-propyl, n-butyl, i-butyl or t-butyl. In some embodiments, $R^{10}$ is $SO_3H$, or $SO_3^-Y^+$, wherein Y can be sodium, potassium, aluminum, calcium, lithium, magnesium, barium, or zinc. In some embodiments, $R^{10}$ is $CO_2H$, or $CO_2^-Y^+$, wherein Y can be sodium, potassium, aluminum, calcium, lithium, magnesium, barium, or zinc. In some embodiments, $R^{10}$ is optionally substituted aryl. In some embodiments, aryl is cylcopentadiene, or phenyl. In some embodiments, $R^{10}$ is optionally substituted heteroaryl. In some embodiments, heteroaryl is furanyl, pyridyl, thiophenyl, pyrrolyl, oxazolyl, imidazolyl, thiazolyl, pyrazolyl, purinyl, quinolinyl, isoquinolinyl, phenanthrinyl, pyridazinyl, cinnolinyl, phthalazinyl, pyrazinyl, pyrimidinyl, quinazolinyl or triazinyl.

X can be selected from the group consisting of C($R^{21}$)$_2$, —C(O)N($R^{22}$)—, —C(O)—, —C(O)O—, —S(O)—, —SO$_2$— —CH($R^{11}$)CH($R^{12}$)—, —C($R^{11}$)=C($R^{12}$)—,

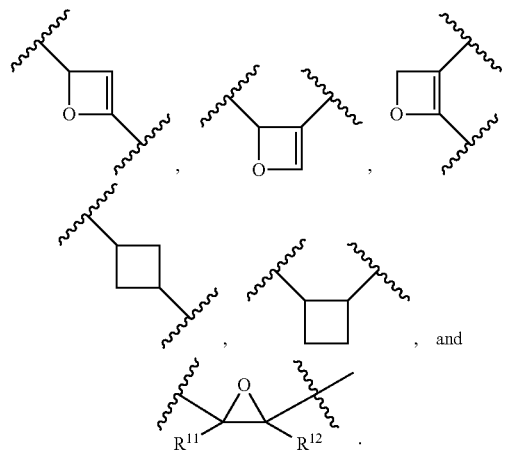

Preferably X is —C($R^{11}$)=C($R^{12}$)— or

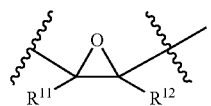

It is to be understood that when X is —C($R^{11}$)=C($R^{12}$)— or

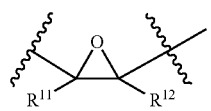

the substituents $R^{11}$ and $R^{12}$ can be present in either the cis- or the trans-conformation. Further, when X is

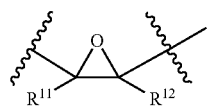

the carbons to which $R^{11}$ and $R^{12}$ are attached can independently have the R or the S configuration. Thus, X can be

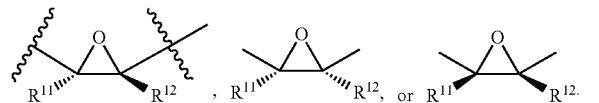

In some embodiments, X is

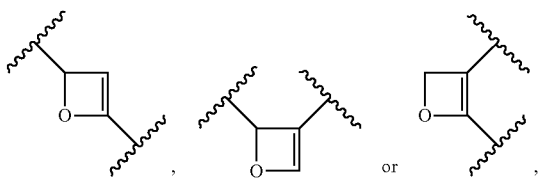 [SMILES: *C1=CC(*)O1 ; *C1=COC1* ; *C1=C(*)OC1]

In some embodiments, X is

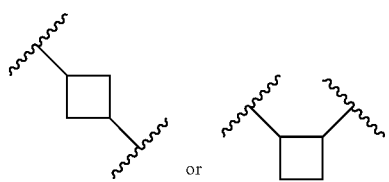

Preferably X iIn some embodiments, X is —CH=CH—. In some embodiments, X is —C(O)N(R$^{22}$)—, wherein R$^{22}$ is selected from the group consisting of hydrogen and C$_1$-C$_4$ alkyl.

R$^{11}$ can be selected from the group consisting of hydrogen, halogen, CF$_3$, CN, C(O)R$^{21}$, CO$_2$R$^{21}$, C(O)N(R$^{22}$)$_2$, OH, OR$^{21}$, N(R$^{22}$)$_2$NC(O)R$^{21}$, NC(O)OR$^{21}$, NC(S)R$^{21}$, NC(S)N(R$^{22}$)$_2$, NSO$_2$R$^{21}$, NO$_2$, N$_2$—R$^{22}$, SOR$^{21}$, SO$_2$R$^{21}$, SO$_3$R$^{21}$, OP(O)(OH)$_2$, optionally substituted linear or branched C$_1$-C$_{10}$ alkyl, optionally substituted linear or branched C$_2$-C$_{10}$ alkenyl, optionally substituted linear or branched C$_2$-C$_{10}$ alkynyl, optionally substituted cyclyl, optionally substituted heterocyclyl, optionally substituted aryl, and optionally substituted heteroaryl. Preferably, R$^{11}$ is hydrogen, C$_1$-C$_{10}$ alkyl, halogen, OR$^{21}$, cyclyl, or heterocyclyl. In some embodiments, R$^{11}$ is hydrogen, methyl, ethyl, OH, OCH$_3$, Br, N$_2$-phenyl,

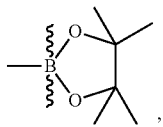

R$^{12}$ can be selected from the group consisting of hydrogen, halogen, CF$_3$, CN, C(O)R$^{21}$, CO$_2$R$^{21}$, C(O)N(R$^{22}$)$_2$, OH, OR$^{21}$, N(R$^{22}$)$_2$NC(O)R$^{21}$, NC(O)OR$^{21}$, NC(S)R$^{21}$, NC(S)N(R$^{22}$)$_2$, NSO$_2$R$^{21}$, NO$_2$, N$_2$—R$^{22}$, SOR$^{21}$, SO$_2$R$^{21}$, SO$_3$R$^{21}$, OP(O)(OH)$_2$, optionally substituted linear or branched C$_1$-C$_{10}$ alkyl, optionally substituted linear or branched C$_2$-C$_{10}$ alkenyl, optionally substituted linear or branched C$_2$-C$_{10}$ alkynyl, optionally substituted cyclyl, optionally substituted heterocyclyl, optionally substituted aryl, and optionally substituted heteroaryl. In some embodiments, R$^{12}$ is hydrogen.

Further, R$^{11}$ and R$^{12}$ both can be the same or both different. In some embodiments, R$^{11}$ and R$^{12}$ are both hydrogen. In some embodiments, X is —CH$_2$CH$_2$—, —CH=CH—,

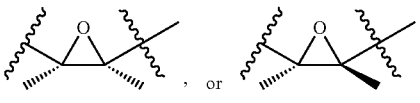

Each R$^{21}$ can be selected independently from the group consisting of hydrogen, optionally substituted linear or branched C$_1$-C$_{10}$ alkyl, optionally substituted linear or branched C$_2$-C$_{10}$ alkenyl, optionally substituted linear or branched C$_2$-C$_{10}$ alkynyl, optionally substituted cyclyl, optionally substituted heterocyclyl, optionally substituted aryl, optionally substituted heteroaryl, and any combinations thereof. Preferably, R$^{21}$ is hydrogen or a linear or branched C$_1$-C$_{10}$ alkylene. In some embodiments, R$^{21}$ can be methyl, ethyl, propyl, isopropyl, butyl, isobutyl, pentyl, t-butyl, cyclopropyl, or CH$_2$OCH$_3$.

Each R$^{22}$ can be selected independently from the group consisting of hydrogen, optionally substituted linear or branched C$_1$-C$_{10}$ alkyl, optionally substituted linear or branched C$_2$-C$_{10}$ alkenyl, optionally substituted linear or branched C$_2$-C$_{10}$ alkynyl, optionally substituted cyclyl, optionally substituted heterocyclyl, optionally substituted aryl, optionally substituted heteroaryl, and any combinations thereof. Preferably, R$^{22}$ is hydrogen or a linear or branched C$_1$-C$_{10}$ alkylene. In some embodiments, R$^{22}$ can be hydrogen, methyl, ethyl, propyl, isopropyl, butyl, isobutyl, pentyl, t-butyl, or cyclopropyl.

R$^3$ and R$^8$ can be the same or different. Accordingly, in some embodiments, R$^3$ and R$^8$ are selected independently from the group consisting of hydrogen, heterocyclyl, OR$^{21}$, NO$_2$, N(R$^{22}$)$_2$, N=C=S, NHC(O)R$^{21}$, NHSO$_2$R$^{21}$, N(R$^{22}$)$_2$, NHC(O)N(R$^{22}$)$_2$, NHC(S)N(R$^{22}$)$_2$, and NHSO$_2$N(R$^{22}$)$_2$, wherein R$^{21}$ can be H or C$_1$-C$_4$alkyl and R$^{22}$ can be H or C$_1$-C$_{10}$ alkyl. For example, R$^3$ and R$^8$ can be selected independently from the group consisting of hydrogen, OH, OCH$_3$, N=C=S, NH$_2$, NHCH$_3$, NO$_2$, NH-octadecane, NHC(O)CH$_3$, NHC(O)CH(CH$_3$)$_2$, NHC(O)CH$_2$OCH$_3$, NHSO$_2$CH$_3$, NHSO$_2$-cyclopropane, NHSO$_2$CH(CH$_3$)$_2$, NHSO$_2$N(CH$_3$)$_2$, NHC(S)NHCH$_3$, NHC(S)NHCH(CH$_3$)$_2$, NHC(S)NH-cyclopropane, NHC(O)NHCH$_3$, NHC(O)NHCH(CH$_3$)$_2$, benzoxazolyl, or NHC(O)NH-cyclopropane.

In some embodiments, at least one of R$^3$ and R$^8$ is not hydrogen. In some embodiments, both of R$^3$ and R$^8$ are not hydrogen.

In some embodiments, R$^3$ and R$^8$ are different and selected independently from the group consisting of hydrogen, OH, OCH$_3$, N=C=S, NH$_2$, NHCH$_3$, NO$_2$, NH-octadecane, NHC(O)CH$_3$, NHC(O)CH(CH$_3$)$_2$, NHC(O)CH$_2$OCH$_3$, NHSO$_2$CH$_3$, NHSO$_2$-cyclopropane, NHSO$_2$CH(CH$_3$)$_2$, NHSO$_2$N(CH$_3$)$_2$, NHC(S)NHCH$_3$, NHC(S)NHCH(CH$_3$)$_2$, NHC(S)NH-cyclopropane, NHC(O)NHCH$_3$, NHC(O)NHCH(CH$_3$)$_2$, benzoxazolyl, or NHC(O)NH-cyclopropane. For example, one of R$^3$ and R$^8$ can be H and the other can be NH$_2$, one of R$^3$ and R$^8$ can be H and the other can be NHCH$_3$, one of R$^3$ and R$^8$ can be H and the other can be N(CH$_3$)$_2$, one of R$^3$ and R$^8$ can be H and the other can be NHC(O)CH$_3$, one of R$^3$ and R$^8$ can be H and the other can be NHC(O)CH(CH$_3$)$_2$, one of R$^3$ and R$^8$ can be H and the other can be NHC(O)CH$_2$OCH$_3$, one of R$^3$ and R$^8$ can be H and the other can be NHSO$_2$—CH$_3$, one of R$^3$ and R$^8$ can be H and the other can be NHSO$_2$—CH(CH$_3$)$_2$, one of R$^3$ and R$^8$ can be H and the other can be NHSO$_2$-cyclopropane, one of R$^3$ and R$^8$ can be H and the other can be NHSO$_2$—NHCH$_3$, one of R$^3$ and R$^8$ can be H and the other can be NHSO$_2$—N(CH$_3$)$_2$, one of R$^3$ and R$^8$ can be H and the other can be NHSO$_2$—NHCH(CH$_3$)$_2$, one of R$^3$ and $R^8$ can be H and the other can be $NHSO_2$—NH-cyclopropane, one of $R^3$ and $R^8$ can be H and the other can be $NHC(S)NH$—$CH_3$, one of $R^3$ and $R^8$ can be H and the other can be $NHC(S)NH$—$CH(CH_3)_2$, one of $R^3$ and $R^8$ can be H and the other can be NHC(S)NH-cyclopropane, one of $R^3$ and $R^8$ can be H and the other can be $NHC(O)NH$—$CH_3$, one of $R^3$ and $R^8$ can be H and the other can be $NHC(O)NH$—$CH(CH_3)_2$, one of $R^3$ and $R^8$ can be H and the other can be NHC(O)NH-cyclopropane, one of $R^3$ and $R^8$ can be $NH_2$ and the other can be $NHCH_3$, one of $R^3$ and $R^8$ can be $NH_2$ and the other can be $N(CH_3)_2$, one of $R^3$ and $R^8$ can be $NH_2$ and the other can be $NHC(O)CH_3$, one of $R^3$ and $R^8$ can be $NH_2$ and the other can be $NHC(O)CH(CH_3)_2$, one of $R^3$ and $R^8$ can be $NH_2$ and the other can be $NHC(O)CH_2OCH_3$, one of $R^3$ and $R^8$ can be $NH_2$ and the other can be $NHSO_2$—$CH_3$, one of $R^3$ and $R^8$ can be $NH_2$ and the other can be $NHSO_2$—$CH(CH_3)_2$, one of $R^3$ and $R^8$ can be $NH_2$ and the other can be $NHSO_2$-cyclopropane, one of $R^3$ and $R^8$ can be $NH_2$ and the other can be $NHSO_2$—$NHCH_3$, one of $R^3$ and $R^8$ can be $NH_2$ and the other can be $NHSO_2$—$N(CH_3)_2$, one of $R^3$ and $R^8$ can be $NH_2$ and the other can be $NHSO_2$—$NHCH(CH_3)_2$, one of $R^3$ and $R^8$ can be $NH_2$ and the other can be $NHSO_2$—NH-cyclopropane, one of $R^3$ and $R^8$ can be $NH_2$ and the other can be $NHC(S)NH$—$CH_3$, one of $R^3$ and $R^8$ can be $NH_2$ and the other can be $NHC(S)NH$—$CH(CH_3)_2$, one of $R^3$ and $R^8$ can be $NH_2$ and the other can be NHC(S)NH-cyclopropane, one of $R^3$ and $R^8$ can be $NH_2$ and the other can be $NHC(O)NH$—$CH_3$, one of $R^3$ and $R^8$ can be $NH_2$ and the other can be $NHC(O)NH$—$CH(CH_3)_2$, one of $R^3$ and $R^8$ can be $NH_2$ and the other can be NHC(O)NH-cyclopropane, one of $R^3$ and $R^8$ can be $NHCH_3$ and the other can be $N(CH_3)_2$, one of $R^3$ and $R^8$ can be $NHCH_3$ and the other can be $NHC(O)CH_3$, one of $R^3$ and $R^8$ can be $NHCH_3$ and the other can be $NHC(O)CH(CH_3)_2$, one of $R^3$ and $R^8$ can be $NHCH_3$ and the other can be $NHC(O)CH_2OCH_3$, one of $R^3$ and $R^8$ can be $NHCH_3$ and the other can be $NHSO_2$—$CH_3$, one of $R^3$ and $R^8$ can be $NHCH_3$ and the other can be $NHSO_2$—$CH(CH_3)_2$, one of $R^3$ and $R^8$ can be $NHCH_3$ and the other can be $NHSO_2$-cyclopropane, one of $R^3$ and $R^8$ can be $NHCH_3$ and the other can be $NHSO_2$—$NHCH_3$, one of $R^3$ and $R^8$ can be $NHCH_3$ and the other can be $NHSO_2$—$N(CH_3)_2$, one of $R^3$ and $R^8$ can be $NHCH_3$ and the other can be $NHSO_2$—$NHCH(CH_3)_2$, one of $R^3$ and $R^8$ can be $NHCH_3$ and the other can be $NHSO_2$—NH-cyclopropane, one of $R^3$ and $R^8$ can be $NHCH_3$ and the other can be $NHC(S)NH$—$CH_3$, one of $R^3$ and $R^8$ can be $NHCH_3$ and the other can be $NHC(S)NH$—$CH(CH_3)_2$, one of $R^3$ and $R^8$ can be $NHCH_3$ and the other can be NHC(S)NH-cyclopropane, one of $R^3$ and $R^8$ can be $NHCH_3$ and the other can be $NHCO)NH$—$CH_3$, one of $R^3$ and $R^8$ can be $NHCH_3$ and the other can be $NHC(O)NH$—$CH(CH_3)_2$, one of $R^3$ and $R^8$ can be $NHCH_3$ and the other can be NHC(O)NH-cyclopropane, one of $R^3$ and $R^8$ can be $N(CH_3)_2$ and the other can be $NHC(O)CH_3$, one of $R^3$ and $R^8$ can be $N(CH_3)_2$ and the other can be $NHC(O)CH(CH_3)_2$, one of $R^3$ and $R^8$ can be $N(CH_3)_2$ and the other can be $NHC(O)CH_2OCH_3$, one of $R^3$ and $R^8$ can be $N(CH_3)_2$ and the other can be $NHSO_2$—$CH_3$, one of $R^3$ and $R^8$ can be $N(CH_3)_2$ and the other can be $NHSO_2$—$CH(CH_3)_2$, one of $R^3$ and $R^8$ can be $N(CH_3)_2$ and the other can be $NHSO_2$-cyclopropane, one of $R^3$ and $R^8$ can be $N(CH_3)_2$ and the other can be $NHSO_2$—$NHCH_3$, one of $R^3$ and $R^8$ can be $N(CH_3)_2$ and the other can be $NHSO_2$—$N(CH_3)_2$, one of $R^3$ and $R^8$ can be $N(CH_3)_2$ and the other can be $NHSO_2$—$NHCH(CH_3)_2$, one of $R^3$ and $R^8$ can be $N(CH_3)_2$ and the other can be $NHSO_2$—NH-cyclopropane, one of $R^3$ and $R^8$ can be $N(CH_3)_2$ and the other can be $NHC(S)NH$—$CH_3$, one of $R^3$ and $R^8$ can be $N(CH_3)_2$ and the other can be $NHC(S)NH$—$CH(CH_3)_2$, one of $R^3$ and $R^8$ can be $N(CH_3)_2$ and the other can be NHC(S)NH-cyclopropane, one of $R^3$ and $R^8$ can be $N(CH_3)_2$ and the other can be $NHC(O)NH$—$CH_3$, one of $R^3$ and $R^8$ can be $N(CH_3)_2$ and the other can be $NHC(O)NH$—$CH(CH_3)_2$, one of $R^3$ and $R^8$ can be $N(CH_3)_2$ and the other can be NHC(O)NH-cyclopropane, one of $R^3$ and $R^8$ can be $NHC(O)CH_3$ and the other can be $NHC(O)CH(CH_3)_2$, one of $R^3$ and $R^8$ can be $NHC(O)CH_3$ and the other can be $NHC(O)CH_2OCH_3$, one of $R^3$ and $R^8$ can be $NHC(O)CH_3$ and the other can be $NHSO_2$—$CH_3$, one of $R^3$ and $R^8$ can be $NHC(O)CH_3$ and the other can be $NHSO_2$—$CH(CH_3)_2$, one of $R^3$ and $R^8$ can be $NHC(O)CH_3$ and the other can be $NHSO_2$-cyclopropane, one of $R^3$ and $R^8$ can be $NHC(O)CH_3$ and the other can be $NHSO_2$—$NHCH_3$, one of $R^3$ and $R^8$ can be $NHC(O)CH_3$ and the other can be $NHSO_2$—$N(CH_3)_2$, one of $R^3$ and $R^8$ can be $NHC(O)CH_3$ and the other can be $NHSO_2$—$NHCH(CH_3)_2$, one of $R^3$ and $R^8$ can be $NHC(O)CH_3$ and the other can be $NHSO_2$—NH-cyclopropane, one of $R^3$ and $R^8$ can be $NHC(O)CH_3$ and the other can be $NHC(S)NH$—$CH_3$, one of $R^3$ and $R^8$ can be $NHC(O)CH_3$ and the other can be $NHC(S)NH$—$CH(CH_3)_2$, one of $R^3$ and $R^8$ can be $NHC(O)CH_3$ and the other can be NHC(S)NH-cyclopropane, one of $R^3$ and $R^8$ can be $NHC(O)CH_3$ and the other can be $NHC(O)NH$—$CH_3$, one of $R^3$ and $R^8$ can be $NHC(O)CH_3$ and the other can be $NHC(O)NH$—$CH(CH_3)_2$, one of $R^3$ and $R^8$ can be $NHC(O)CH_3$ and the other can be NHC(O)NH-cyclopropane, one of $R^3$ and $R^8$ can be $NHC(O)CH(CH_3)_2$ and the other can be $NHC(O)CH_2OCH_3$, one of $R^3$ and $R^8$ can be $NHC(O)CH(CH_3)_2$ and the other can be $NHSO_2$—$CH_3$, one of $R^3$ and $R^8$ can be $NHC(O)CH(CH_3)_2$ and the other can be $NHSO_2$—$CH(CH_3)_2$, one of $R^3$ and $R^8$ can be $NHC(O)CH(CH_3)_2$ and the other can be $NHSO_2$-cyclopropane, one of $R^3$ and $R^8$ can be $NHC(O)CH(CH_3)_2$ and the other can be $NHSO_2$—$NHCH_3$, one of $R^3$ and $R^8$ can be $NHC(O)CH(CH_3)_2$ and the other can be $NHSO_2$—$N(CH_3)_2$, one of $R^3$ and $R^8$ can be $NHC(O)CH(CH_3)_2$ and the other can be $NHSO_2$—$NHCH(CH_3)_2$, one of $R^3$ and $R^8$ can be $NHC(O)CH(CH_3)_2$ and the other can be $NHSO_2$—NH-cyclopropane, one of $R^3$ and $R^8$ can be $NHC(O)CH(CH_3)_2$ and the other can be $NHC(S)NH$—$CH_3$, one of $R^3$ and $R^8$ can be $NHC(O)CH(CH_3)_2$ and the other can be $NHC(S)NH$—$CH(CH_3)_2$, one of $R^3$ and $R^8$ can be $NHC(O)CH(CH_3)_2$ and the other can be NHC(S)NH-cyclopropane, one of $R^3$ and $R^8$ can be $NHC(O)CH(CH_3)_2$ and the other can be $NHC(O)NH$—$CH_3$, one of $R^3$ and $R^8$ can be $NHC(O)CH(CH_3)_2$ and the other can be $NHC(O)NH$—$CH(CH_3)_2$, one of $R^3$ and $R^8$ can be $NHC(O)CH(CH_3)_2$ and the other can be NHC(O)NH-cyclopropane, one of $R^3$ and $R^8$ can be $NHC(O)CH_2OCH_3$ and the other can be $NHSO_2$—$CH_3$, one of $R^3$ and $R^8$ can be $NHC(O)CH_2OCH_3$ and the other can be $NHSO_2$—$CH(CH_3)_2$, one of $R^3$ and $R^8$ can be $NHC(O)CH_2OCH_3$ and the other can be $NHSO_2$-cyclopropane, one of $R^3$ and $R^8$ can be $NHC(O)CH_2OCH_3$ and the other can be $NHSO_2$—$NHCH_3$, one of $R^3$ and $R^8$ can be $NHC(O)CH_2OCH_3$ and the other can be $NHSO_2$—$N(CH_3)_2$, one of $R^3$ and $R^8$ can be $NHC(O)CH_2OCH_3$ and the other can be $NHSO_2$—$NHCH(CH_3)_2$, one of $R^3$ and $R^8$ can be $NHC(O)CH_2OCH_3$ and the other can be $NHSO_2$—NH-cyclopropane, one of $R^3$ and $R^8$ can be $NHC(O)CH_2OCH_3$ and the other can be $NHC(S)NH$—$CH_3$, one of $R^3$ and $R^8$ can be $NHC(O)CH_2OCH_3$ and the other can be $NHC(S)NH$—$CH(CH_3)_2$, one of $R^3$ and $R^8$ can be $NHC(O)CH_2OCH_3$ and the other can be NHC(S)NH-cyclopropane, one of $R^3$ and $R^8$ can be $NHC(O)CH_2OCH_3$ and the other can be $NHC(O)NH$—$CH_3$, one of $R^3$ and $R^8$ can be $NHC(O)CH_2OCH_3$ and the other can be $NHC(O)NH$—$CH(CH_3)_2$, one of $R^3$ and $R^8$ can be $NHC(O)CH_2OCH_3$ and the other can be NHC(O)NH-cyclopropane, one of $R^3$ and $R^8$ can be $NHSO_2$—$CH_3$ and the other can be $NHSO_2$—CH$(CH_3)_2$, one of $R^3$ and $R^8$ can be $NHSO_2$—$CH_3$ and the other can be $NHSO_2$-cyclopropane, one of $R^3$ and $R^8$ can be $NHSO_2$—$CH_3$ and the other can be $NHSO_2$—$NHCH_3$, one of $R^3$ and $R^8$ can be $NHSO_2$—$CH_3$ and the other can be $NHSO_2$—$N(CH_3)_2$, one of $R^3$ and $R^8$ can be $NHSO_2$—$CH_3$ and the other can be $NHSO_2$—$NHCH(CH_3)_2$, one of $R^3$ and $R^8$ can be $NHSO_2$—$CH_3$ and the other can be $NHSO_2$—NH-cyclopropane, one of $R^3$ and $R^8$ can be $NHSO_2$—$CH_3$ and the other can be NHC(S)NH—$CH_3$, one of $R^3$ and $R^8$ can be $NHSO_2$—$CH_3$ and the other can be NHC(S)NH—CH$(CH_3)_2$, one of $R^3$ and $R^8$ can be $NHSO_2$—$CH_3$ and the other can be NHC(S)NH-cyclopropane, one of $R^3$ and $R^8$ can be $NHSO_2$—$CH_3$ and the other can be NHC(O)NH—$CH_3$, one of $R^3$ and $R^8$ can be $NHSO_2$—$CH_3$ and the other can be NHC(O)NH—CH$(CH_3)_2$, one of $R^3$ and $R^8$ can be $NHSO_2$—$CH_3$ and the other can be NHC(O)NH-cyclopropane, one of $R^3$ and $R^8$ can be $NHSO_2$—CH$(CH_3)_2$ and the other can be $NHSO_2$-cyclopropane, one of $R^3$ and $R^8$ can be $NHSO_2$—CH$(CH_3)_2$ and the other can be $NHSO_2$—$NHCH_3$, one of $R^3$ and $R^8$ can be $NHSO_2$—CH$(CH_3)_2$ and the other can be $NHSO_2$—$N(CH_3)_2$, one of $R^3$ and $R^8$ can be $NHSO_2$—CH$(CH_3)_2$ and the other can be $NHSO_2$—NHCH$(CH_3)_2$, one of $R^3$ and $R^8$ can be $NHSO_2$—CH$(CH_3)_2$ and the other can be $NHSO_2$—NH-cyclopropane, one of $R^3$ and $R^8$ can be $NHSO_2$—CH$(CH_3)_2$ and the other can be NHC(S)NH—$CH_3$, one of $R^3$ and $R^8$ can be $NHSO_2$—CH$(CH_3)_2$ and the other can be NHC(S)NH—CH$(CH_3)_2$, one of $R^3$ and $R^8$ can be $NHSO_2$—CH$(CH_3)_2$ and the other can be NHC(S)NH-cyclopropane, one of $R^3$ and $R^8$ can be $NHSO_2$—CH$(CH_3)_2$ and the other can be NHC(O)NH—$CH_3$, one of $R^3$ and $R^8$ can be $NHSO_2$—CH$(CH_3)_2$ and the other can be NHC(O)NH—CH$(CH_3)_2$, one of $R^3$ and $R^8$ can be $NHSO_2$—CH$(CH_3)_2$ and the other can be NHC(O)NH-cyclopropane, one of $R^3$ and $R^8$ can be $NHSO_2$-cyclopropane and the other can be $NHSO_2$—$NHCH_3$, one of $R^3$ and $R^8$ can be $NHSO_2$-cyclopropane and the other can be $NHSO_2$—$N(CH_3)_2$, one of $R^3$ and $R^8$ can be $NHSO_2$-cyclopropane and the other can be $NHSO_2$—NHCH$(CH_3)_2$, one of $R^3$ and $R^8$ can be $NHSO_2$-cyclopropane and the other can be $NHSO_2$—NH-cyclopropane, one of $R^3$ and $R^8$ can be $NHSO_2$-cyclopropane and the other can be NHC(S)NH—$CH_3$, one of $R^3$ and $R^8$ can be $NHSO_2$-cyclopropane and the other can be NHC(S)NH—CH$(CH_3)_2$, one of $R^3$ and $R^8$ can be $NHSO_2$-cyclopropane and the other can be NHC(S)NH-cyclopropane, one of $R^3$ and $R^8$ can be $NHSO_2$-cyclopropane and the other can be NHC(O)NH—$CH_3$, one of $R^3$ and $R^8$ can be $NHSO_2$-cyclopropane and the other can be NHC(O)NH—CH$(CH_3)_2$, one of $R^3$ and $R^8$ can be $NHSO_2$-cyclopropane and the other can be NHC(O)NH-cyclopropane, one of $R^3$ and $R^8$ can be $NHSO_2$—$NHCH_3$ and the other can be $NHSO_2$—$N(CH_3)_2$, one of $R^3$ and $R^8$ can be $NHSO_2$—$NHCH_3$ and the other can be $NHSO_2$—NHCH$(CH_3)_2$, one of $R^3$ and $R^8$ can be $NHSO_2$—$NHCH_3$ and the other can be $NHSO_2$—NH-cyclopropane, one of $R^3$ and $R^8$ can be $NHSO_2$—$NHCH_3$ and the other can be NHC(S)NH—$CH_3$, one of $R^3$ and $R^8$ can be $NHSO_2$—$NHCH_3$ and the other can be NHC(S)NH—CH$(CH_3)_2$, one of $R^3$ and $R^8$ can be $NHSO_2$—$NHCH_3$ and the other can be NHC(S)NH-cyclopropane, one of $R^3$ and $R^8$ can be $NHSO_2$—$NHCH_3$ and the other can be NHC(O)NH—$CH_3$, one of $R^3$ and $R^8$ can be $NHSO_2$—$NHCH_3$ and the other can be NHC(O)NH—CH$(CH_3)_2$, one of $R^3$ and $R^8$ can be $NHSO_2$—$NHCH_3$ and the other can be NHC(O)NH-cyclopropane, one of $R^3$ and $R^8$ can be $NHSO_2$—$N(CH_3)_2$ and the other can be $NHSO_2$—NHCH$(CH_3)_2$, one of $R^3$ and $R^8$ can be $NHSO_2$—

$N(CH_3)_2$ and the other can be $NHSO_2$—NH-cyclopropane, one of $R^3$ and $R^8$ can be $NHSO_2$—$N(CH_3)_2$ and the other can be NHC(S)NH—$CH_3$, one of $R^3$ and $R^8$ can be $NHSO_2$—$N(CH_3)_2$ and the other can be NHC(S)NH—CH$(CH_3)_2$, one of $R^3$ and $R^8$ can be $NHSO_2$—$N(CH_3)_2$ and the other can be NHC(S)NH-cyclopropane, one of $R^3$ and $R^8$ can be $NHSO_2$—$N(CH_3)_2$ and the other can be NHC(O)NH—$CH_3$, one of $R^3$ and $R^8$ can be $NHSO_2$—$N(CH_3)_2$ and the other can be NHC(O)NH—CH$(CH_3)_2$, one of $R^3$ and $R^8$ can be $NHSO_2$—$N(CH_3)_2$ and the other can be NHC(O)NH-cyclopropane, one of $R^3$ and $R^8$ can be $NHSO_2$—NHCH$(CH_3)_2$ and the other can be $NHSO_2$—NH-cyclopropane, one of $R^3$ and $R^8$ can be $NHSO_2$—NHCH$(CH_3)_2$ and the other can be NHC(S)NH—$CH_3$, one of $R^3$ and $R^8$ can be $NHSO_2$—NHCH$(CH_3)_2$ and the other can be NHC(S)NH—CH$(CH_3)_2$, one of $R^3$ and $R^8$ can be $NHSO_2$—NHCH$(CH_3)_2$ and the other can be NHC(S)NH-cyclopropane, one of $R^3$ and $R^8$ can be $NHSO_2$—NHCH$(CH_3)_2$ and the other can be NHC(O)NH—$CH_3$, one of $R^3$ and $R^8$ can be $NHSO_2$—NHCH$(CH_3)_2$ and the other can be NHC(O)NH—CH$(CH_3)_2$, one of $R^3$ and $R^8$ can be $NHSO_2$—NHCH$(CH_3)_2$ and the other can be NHC(O)NH-cyclopropane, one of $R^3$ and $R^8$ can be $NHSO_2$—NH-cyclopropane and the other can be NHC(S)NH—$CH_3$, one of $R^3$ and $R^8$ can be $NHSO_2$—NH-cyclopropane and the other can be NHC(S)NH—CH$(CH_3)_2$, one of $R^3$ and $R^8$ can be $NHSO_2$—NH-cyclopropane and the other can be NHC(S)NH-cyclopropane, one of $R^3$ and $R^8$ can be $NHSO_2$—NH-cyclopropane and the other can be NHC(O)NH—$CH_3$, one of $R^3$ and $R^8$ can be $NHSO_2$—NH-cyclopropane and the other can be NHC(O)NH—CH$(CH_3)_2$, one of $R^3$ and $R^8$ can be $NHSO_2$—NH-cyclopropane and the other can be NHC(O)NH-cyclopropane, one of $R^3$ and $R^8$ can be NHC(S)$NHCH_3$ and the other can be NHC(S)NH—CH$(CH_3)_2$, one of $R^3$ and $R^8$ can be NHC(S)$NHCH_3$ and the other can be NHC(S)NH-cyclopropane, one of $R^3$ and $R^8$ can be NHC(S)$NHCH_3$ and the other can be NHC(O)NH—$CH_3$, one of $R^3$ and $R^8$ can be NHC(S)$NHCH_3$ and the other can be NHC(O)NH—CH$(CH_3)_2$, one of $R^3$ and $R^8$ can be NHC(S)$NHCH_3$ and the other can be NHC(O)NH-cyclopropane, one of $R^3$ and $R^8$ can be NHC(S)NH—CH$(CH_3)_2$ and the other can be NHC(S)NH-cyclopropane, one of $R^3$ and $R^8$ can be NHC(S)NH—CH$(CH_3)_2$ and the other can be NHC(O)NH—$CH_3$, one of $R^3$ and $R^8$ can be NHC(S)NH—CH$(CH_3)_2$ and the other can be NHC(O)NH—CH$(CH_3)_2$, one of $R^3$ and $R^8$ can be NHC(S)NH—CH$(CH_3)_2$ and the other can be NHC(O)NH-cyclopropane, one of $R^3$ and $R^8$ can be NHC(S)NH—CH$(CH_3)_2$ and the other can be NHC(O)NH—$CH_3$ and the other can be NHC(O)NH—CH$(CH_3)_2$, one of $R^3$ and $R^8$ can be NHC(O)NH—$CH_3$ and the other can be NHC(O)NH-cyclopropane, or one of $R^3$ and $R^8$ can be NHC(O)NH—CH$(CH_3)_2$ and the other can be NHC(O)NH—CH$(CH_3)_2$.

In some embodiments, $R^3$ and $R^8$ are both N=C=S, $NH_2$, NHC(O)$CH_3$, NHC(O)CH$(CH_3)_2$, NHC(O)CH$_2$OCH$_3$, $NHSO_2CH_3$, $NHSO_2$-cyclopropane, $NHSO_2$CH$(CH_3)_2$, $NHSO_2N(CH_3)_2$, NHC(S)$NHCH_3$, NHC(S)NHCH$(CH_3)_2$, NHC(S)NH-cyclopropane, NHC(O)$NHCH_3$, NHC(O)NHCH$(CH_3)_2$, or NHC(O)NH-cyclopropane.

In some embodiments, at least one of $R^1$ and $R^6$ (e.g., one or both) is $SO_3R^{21}$. For example, at least one (e.g., one or both) of $R^1$ and $R^6$ is $SO_3H$ or a salt thereof.

In some embodiments, at least one of $R^1$ and $R^6$ (e.g., one or both) can be $SO_3R^{21}$ and $R^3$ and $R^8$ can be selected independently from the group consisting of hydrogen, heterocyclyl, $OR^{21}$, $NO_2$, $N(R^{22})_2$, N=C=S, NHC(O)$R^{21}$, $NHSO_2R^{21}$, $N(R^{22})_2$, NHC(O)N$(R^{22})_2$, NHC(S)N$(R^{22})_2$, and $NHSO_2N(R^{22})_2$, wherein $R^{21}$ and $R^{22}$ are independently H or $C_1$-$C_4$ alkyl. For example, at least one (e.g., one or both) of $R^1$ and $R^6$ can be $SO_3H$ and $R^3$ and $R^8$ can be selected independently from the group consisting of hydrogen, OH, $OCH_3$, N=C=S, $NH_2$, $NHCH_3$, $NO_2$, NH-octadecane, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, NHC(S)NH-cyclopropane, $NHC(O)NHCH_3$, $NHC(O)NHCH(CH_3)_2$, benzoxazolyl, or NHC(O)NH-cyclopropane.

In some embodiments, at least one of $R^1$ and $R^6$ (e.g., one or both) can be $SO_3R^{21}$ and $R^3$ and $R^8$ are both same and selected from the group consisting of hydrogen, N=C=S, $NHC(O)R^{21}$, $NHSO_2R^{21}$, $N(R^{22})_2$, $NHC(O)N(R^{22})_2$, $NHC(S)N(R^{22})_2$, and $NHSO_2N(R^{22})_2$. For example, at least one (e.g., one or both) of $R^1$ and $R^6$ can be $SO_3H$ and $R^3$ and $R^8$ are the same and can be selected from the group consisting of hydrogen, N=C=S, $NH_2$, $NHC(O)CH_3$, $NHC(O)CH(CH_3)_2$, $NHC(O)CH_2OCH_3$, $NHSO_2CH_3$, $NHSO_2$-cyclopropane, $NHSO_2CH(CH_3)_2$, $NHSO_2N(CH_3)_2$, $NHC(S)NHCH_3$, $NHC(S)NHCH(CH_3)_2$, NHC(S)NH-cyclopropane, $NHC(O)NHCH_3$, $NHC(O)NHCH(CH_3)_2$, and NHC(O)NH-cyclopropane.

In some embodiments, 1, 2, 3, 4, 5, or 6 of $R^1$-$R^{10}$ are OH or $OCH_3$.

The compounds of formula (V) include pharmaceutically acceptable salts, stereoisomer mixtures, and enantiomers thereof. The compounds of the technology described herein can also include physiologically acceptable salts of the compounds of formula (V). The compounds of formula (V) can be present as a racemic mixture or as a substantially pure stereoisomer or enantiomer.

Methods of making stilbenes are well known in the art and are described, for example in U.S. Pat. Nos. 7,321,050; 6,022,998; 6,177,220; 5,068,300; 3,387,050; 5,563,298; 7,820,848; 8,101,804; 6,218,108; and 7,714,161; U.S. Patent Publications 2007/0276172 and 2004/0143023; Likhtenstein, Gertz I. "Stilbenes Synthesis and Applications" in Kirk-Othmer Encyclopedia of Chemical Technology. 2000, John Wiley & Sons, Inc.; Likhtenshtein, G. "Stilbenes Preparation and Analysis" in "Applications in Chemistry, Life Sciences and Materials Science" 2010, Wiley-VCH; which are incorporated by reference herein in their entireties. Synthesis of stilbenes and stilbene derivatives is also available as a commercial service (e.g. Mercachem, Nijmegen, Netherlands; Proteros, Martinsried, Germany; AMRI, Albany, N.Y.; WuXi Apptec, Shanghai, China; and Richman Chemical Inc., Gwynedd, Pa.). In some embodiments, a stilbene may be further functionalized to amide and sulfonamide derivatives.

Some exemplary compounds of formula (V) are (E)-N,N'-(ethene-1,2-diylbis(4,1-phenylene))diacetamide; (E)-N,N'-(ethene-1,2-diylbis(4,1-phenylene)bis(2-methylpropanamide); (E)-N,N'-(ethene-1,2-diylbis(4,1-phenylene))bis(2-methoxyacetamide); (E)-N,N'-(ethene-1,2-diylbis(4,1-phenylene))dimethanesulfonamide; (E)-N,N'-(ethene-1,2-diylbis(4,1-phenylene))dicyclopropanesulfonamide; (E)-N,N'-(ethene-1,2-diylbis(4,1-phenylene))bis(propane-2-sulfonamide); (E)-N,N'-(ethene-1,2-diylbis(4,1-phenylene))bis(dimethylamino-sulfonamide); (E)-N-(4-(4-aminostyryl)phenyl)propane-2-sulfonamide; (E)-1,1'-(ethene-1,2-diylbis(4,1-phenylene))bis(3-methylthiourea); (E)-1,1'-(ethene-1,2-diylbis(4,1-phenylene))bis(3-isopropylthiourea); (E)-N-(4-(4-(dimethylamino)styryl)phenyl)acetamide; (E)-N-(4-(4-(dimethylamino)styryl)phenyl)isobutyramide; (E)-N-(4-(4-(dimethylamino)styryl)phenyl)-2-methoxyacetamide; (E)-N-(4-(4-(dimethylamino)styryl)phenyl)methanesulfonamide; (E)-N-(4-(4-(dimethylamino)styryl)phenyl)cyclopropanesulfonamide; (E)-N-(4-(4-(dimethylamino)styryl)phenyl)propane-2-sulfonamide; N'-(4-{(E)-2-[4-(dimethylamino)phenyl]-1-ethenyl}phenyl)-N,N-dimethylsulfamide; (E)-1-(4-(4-(dimethylamino)styryl)phenyl)-3-methylthiourea; (E)-1-(4-(4-(dimethylamino)styryl)phenyl)-3-isopropylthiourea; (E)-1-cyclopropyl-3-(4-(4-(dimethylamino)styryl)phenyl)thiourea; (E)-1-(4-(4-(dimethylamino)styryl)phenyl)-3-methylurea; (E)-1-(4-(4-(dimethylamino)styryl)phenyl)-3-isopropylurea; (E)-1-cyclopropyl-3-(4-(4-(dimethylamino)styryl)phenyl)urea; sodium (E)-6,6'-(ethene-1,2-diyl)bis(3-acetamidobenzenesulfonate); sodium (E)-6,6'-(ethene-1,2-diyl)bis(3-isobutyramidobenzenesulfonate); sodium (E)-6,6'-(ethene-1,2-diyl)bis(3-(2-methoxyacetamido)benzenesulfonate); sodium (E)-6,6'-(ethene-1,2-diyl)bis(3-(cyclopropanesulfonamido)benzenesulfonate); sodium (E)-6,6'-(ethene-1,2-diyl)bis(3-(1-methylethylsulfonamido)benzenesulfonate); sodium (E)-6,6'-(ethene-1,2-diyl)bis(3-((N,N-dimethylsulfamoyl)amino)benzenesulfonate); sodium 6,6'-(ethane-1,2-diyl)bis(3-acetamidobenzenesulfonate); sodium 6,6'-(ethane-1,2-diyl)bis(3-isobutyramidobenzenesulfonate); sodium 6,6'-(ethane-1,2-diyl)bis(3-(2-methoxyacetamido)benzenesulfonate); sodium 6,6'-(ethane-1,2-diyl)bis(3-(methylsulfonamido)benzenesulfonate); sodium 6,6'-(ethane-1,2-diyl)bis(3-(cyclopropanesulfonamido)benzenesulfonate); sodium 6,6'-(ethane-1,2-diyl)bis(3-(1-methylethylsulfonamido)benzenesulfonate); sodium 6,6'-(ethane-1,2-diyl)bis(3-((N,N-dimethylsulfamoyl)amino)benzenesulfonate); sodium 6,6'-(ethane-1,2-diyl)bis(3-(3-cyclopropylthioureido)benzenesulfonate); sodium 6,6'-(ethane-1,2-diyl)bis(3-(3-ethylureido)benzenesulfonate); sodium 6,6'-(ethane-1,2-diyl)bis(3-(3-isopropylureido)benzenesulfonate); sodium (E)-5-acetamido-2-(4-isobutyramido-2-sulfonatostyryl)benzenesulfonate; sodium (E)-5-acetamido-2-(4-(2-methoxyacetamido)-2-sulfonatostyryl)benzenesulfonate; sodium (E)-5-acetamido-2-(4-(cyclopropanesulfonamido)-2-sulfonatostyryl)benzenesulfonate; sodium (E)-5-acetamido-2-(4-(1-methylethylsulfonamido)-2-sulfonatostyryl)benzenesulfonate; sodium (E)-5-acetamido-2-(4-((N,N-dimethylsulfamoyl)amino)-2-sulfonatostyryl)benzenesulfonate; sodium (E)-5-isobutyramido-2-(4-(2-methoxyacetamido)-2-sulfonatostyryl)benzenesulfonate; sodium (E)-5-isobutyramido-2-(4-(methylsulfonamido)-2-sulfonatostyryl)benzenesulfonate; sodium (E)-5-(cyclopropanesulfonamido)-2-(4-isobutyramido-2-sulfonatostyryl)benzenesulfonate; sodium (E)-5-isobutyramido-2-(4-(1-methylethylsulfonamido)-2-sulfonatostyryl)benzenesulfonate; sodium (E)-5-((N,N-dimethylsulfamoyl)amino)-2-(4-isobutyramido-2-sulfonatostyryl)benzenesulfonate; sodium (E)-5-(cyclopropanesulfonamido)-2-(4-(2-methoxyacetamido)-2-sulfonatostyryl)benzenesulfonate; sodium (E)-5-(2-methoxyacetamido)-2-(4-(1-methylethylsulfonamido)-2-sulfonatostyryl)benzenesulfonate; sodium (E)-5-((N,N-dimethylsulfamoyl)amino)-2-(4-(2-methoxyacetamido)-2-sulfonatostyryl)benzenesulfonate; sodium (E)-5-(cyclopropanesulfonamido)-2-(4-(methylsulfonamido)-2-sulfonatostyryl)benzenesulfonate; sodium (E)-5-(1-methylethylsulfonamido)-2-(4-(methylsulfonamido)-2-sulfonatostyryl)benzenesulfonate; sodium (E)-5-((N,N-dimethylsulfamoyl)amino)-2-(4-(methylsulfonamido)-2-sulfonatostyryl)benzenesulfonate; sodium (E)-5-(cyclopropanesulfonamido)-2-(4-(1-methylethylsulfonamido)-2-sulfonatostyryl)benzenesulfonate; sodium (E)-5-(cyclopropanesulfonamido)-2-(4-((N,N-dimethylsulfamoyl)amino)-2-sulfonatostyryl)benzenesulfonate; sodium (E)-5-((N,N-dimethylsulfamoyl)amino)-2-(4-(1-methylethylsulfonamido)-2-sulfonatostyryl)benzenesulfonate; sodium (E)-5-acetamido-2-(4-(3-methylthioureido)-2-sulfonatostyryl)benzenesulfonate; sodium (E)-5-acetamido-2-(4-(3-isopropylthioureido)-2-sulfonatostyryl)benzenesulfonate; sodium (E)-5-acetamido- 2-(4-(3-cyclopropylthioureido)-2-sulfonatostyryl)benzenesulfonate; sodium (E)-5-isobutyramido-2-(4-(3-methylthioureido)-2-sulfonatostyryl)benzenesulfonate; sodium (E)-5-isobutyramido-2-(4-(3-isopropylthioureido)-2-sulfonatostyryl)benzenesulfonate; sodium (E)-5-(2-methoxyacetamido)-2-(4-(3-methylthioureido)-2-sulfonatostyryl)benzenesulfonate; sodium (E)-5-(3-isopropylthioureido)-2-(4-(2-methoxyacetamido)-2-sulfonatostyryl)benzenesulfonate; sodium (E)-5-(3-cyclopropylthioureido)-2-(4-(2-methoxyacetamido)-2-sulfonatostyryl)benzenesulfonate; sodium (E)-5-(methylsulfonamido)-2-(4-(3-methylthioureido)-2-sulfonatostyryl)benzenesulfonate; sodium (E)-5-(3-isopropylthioureido)-2-(4-(methylsulfonamido)-2-sulfonatostyryl)benzenesulfonate; sodium (E)-5-(3-cyclopropylthioureido)-2-(4-(methylsulfonamido)-2-sulfonatostyryl)benzenesulfonate; sodium (E)-5-(cyclopropanesulfonamido)-2-(4-(3-methylthioureido)-2-sulfonatostyryl)benzenesulfonate; sodium (E)-5-(cyclopropanesulfonamido)-2-(4-(3-cyclopropylthioureido)-2-sulfonatostyryl)benzenesulfonate; sodium (E)-5-(1-methylethylsulfonamido)-2-(4-(3-methylthioureido)-2-sulfonatostyryl)benzenesulfonate; sodium (E)-5-(3-isopropylthioureido)-2-(4-(1-methylethylsulfonamido)-2-sulfonatostyryl)benzenesulfonate; sodium (E)-5-(3-cyclopropylthioureido)-2-(4-(1-methylethylsulfonamido)-2-sulfonatostyryl)benzenesulfonate; sodium (E)-5-((N,N-dimethylsulfamoyl)amino)-2-(4-(3-methylthioureido)-2-sulfonatostyryl)benzenesulfonate; sodium (E)-5-((N,N-dimethylsulfamoyl)amino)-2-(4-(3-isopropylthioureido)-2-sulfonatostyryl)benzenesulfonate; sodium (E)-5-(3-cyclopropylthioureido)-2-(4-((N,N-dimethylsulfamoyl)amino)-2-sulfonatostyryl)benzenesulfonate; sodium (E)-5-acetamido-2-(4-(3-ethylureido)-2-sulfonatostyryl)benzenesulfonate; sodium (E)-5-acetamido-2-(4-(3-isopropylureido)-2-sulfonatostyryl)benzenesulfonate; sodium (E)-5-(3-ethylureido)-2-(4-isobutyramido-2-sulfonatostyryl)benzenesulfonate; sodium (E)-5-isobutyramido-2-(4-(3-isopropylureido)-2-sulfonatostyryl)benzenesulfonate; sodium (E)-5-(3-ethylureido)-2-(4-(2-methoxyacetamido)-2-sulfonatostyryl)benzenesulfonate; sodium (E)-5-(3-isopropylureido)-2-(4-(2-methoxyacetamido)-2-sulfonatostyryl)benzenesulfonate; sodium (E)-5-(3-ethylureido)-2-(4-(methylsulfonamido)-2-sulfonatostyryl)benzenesulfonate; sodium (E)-5-(3-isopropylureido)-2-(4-(methylsulfonamido)-2-sulfonatostyryl)benzenesulfonate; sodium (E)-5-(cyclopropanesulfonamido)-2-(4-(3-isopropylureido)-2-sulfonatostyryl)benzenesulfonate; sodium (E)-5-(3-ethylureido)-2-(4-(1-methylethylsulfonamido)-2-sulfonatostyryl)benzenesulfonate; sodium (E)-5-(3-isopropylureido)-2-(4-(1-methylethylsulfonamido)-2-sulfonatostyryl)benzenesulfonate; sodium (E)-5-((N,N-dimethylsulfamoyl)amino)-2-(4-(3-ethylureido)-2-sulfonatostyryl)benzenesulfonate; sodium (E)-5-((N,N-dimethylsulfamoyl)amino)-2-(4-(3-isopropylureido)-2-sulfonatostyryl)benzenesulfonate; sodium (E)-5-isobutyramido-2-(2-sulfonatostyryl)benzenesulfonate; sodium (E)-5-(2-methoxyacetamido)-2-(2-sulfonatostyryl)benzenesulfonate; sodium (E)-5-(cyclopropanesulfonamido)-2-(2-sulfonatostyryl)benzenesulfonate; sodium (E)-5-(3-methylthioureido)-2-(2-sulfonatostyryl)benzenesulfonate; sodium (E)-5-(3-isopropylthioureido)-2-(2-sulfonatostyryl)benzenesulfonate; sodium (E)-5-(3-cyclopropylthioureido)-2-(2-sulfonatostyryl)benzenesulfonate; sodium (E)-5-(3-isopropylureido)-2-(2-sulfonatostyryl)benzenesulfonate; sodium (E)-6,6'-(ethene-1,2-diyl)bis(3-(3-methylthioureido)benzenesulfonate); sodium (E)-6,6'-(ethene-1,2-diyl)bis(3-(3-isopropylthioureido)benzenesulfonate); sodium (E)-6,6'-(ethene-1,2-diyl)bis(3-(3-ethylureido)benzenesulfonate); sodium (E)-6,6'-(ethene-1,2-diyl)bis(3-(3-isopropylureido)benzenesulfonate); (E)-4,4'-(ethene-1,2-diyl)bis(N-methylbenzamide); (E)-4,4'-(ethene-1,2-diyl)bis(N-isopropylbenzamide); (E)-4,4'-(ethene-1,2-diyl)bis(N,N-dimethylbenzamide); (E)-(ethene-1,2-diylbis(4,1-phenylene))bis(morpholinomethanone); and (E)-5-(4-hydroxystyryl)benzene-1,3diol(3,5,4'-trihydroxy-trans-stilbene).

In some embodiments, the stilbene derivative can be selected from the group consisting of (E)-5-acetamido-2-(4-(cyclopropanesulfonamido)-2-sulfonatostyryl)benzenesulfonate; sodium (E)-5-acetamido-2-(4-(cyclopropanesulfonamido)-2-sulfonatostyryl)benzenesulfonate (Formula VI, also referred to herein as BB5-4); (E)-N-(4-(4-(dimethylamino)styryl)phenyl)cyclopropanesulfonamide (Formula VII, also referred to herein as BB2-5); (E)-N,N'-(ethene-1,2-diylbis(4,1-phenylene))bis(propane-2-sulfonamide) (Formula VIII, also referred to herein as BB1-6); (E)-N,N'-(ethene-1,2-diylbis(4,1-phenylene))bis(dimethylaminosulfonamide) (Formula IX, also referred to herein as BB1-7); (E)-N-(4-(4-(dimethylamino)styryl)phenyl)propane-2-sulfonamide (Formula X, also referred to herein as BB2-6); (E)-5-(3-cyclopropylthioureido)-2-(4-(1-methylethylsulfonamido)-2-sulfonatostyryl)benzenesulfonate; sodium (E)-5-(3-cyclopropylthioureido)-2-(4-(1-methylethylsulfonamido)-2-sulfonatostyryl)benzenesulfonate (Formula XI, also referred to herein as BB5-39); 6,6'-(ethane-1,2-diyl)bis(3-(3-isopropylureido)benzenesulfonate); sodium 6,6'-(ethane-1,2-diyl)bis(3-(3-isopropylureido)benzenesulfonate) (Formula XII, also referred to herein as BB4B-2); (E)-5-(3-ethylureido)-2-(4-(2-methoxyacetamido)-2-sulfonatostyryl)benzenesulfonate; sodium (E)-5-(3-ethylureido)-2-(4-(2-methoxyacetamido)-2-sulfonatostyryl)benzenesulfonate (Formula XIII, also referred to herein as BB5-47); (E)-4,4'-(ethene-1,2-diyl)bis(N-methylbenzamide) (Formula XIV, also referred to herein as BB8-1); (E)-5-acetamido-2-(4-((N,N-dimethylsulfamoyl)amino)-2-sulfonatostyryl)benzenesulfonate; sodium (E)-5-acetamido-2-(4-((N,N-dimethylsulfamoyl)amino)-2-sulfonatostyryl)benzenesulfonate (Formula XXIII, also referred to herein as BB5-6); sodium (E)-5-acetamido-2-(4-(3-cyclopropylthioureido)-2-sulfonatostyryl)benzenesulfonate (Formula XXVII); sodium (E)-5-(cyclopropanesulfonamido)-2-(4-(3-isopropylureido)-2-sulfonatostyryl)benzenesulfonate (Formula XXVIII); sodium (E)-5-((N,N-dimethylsulfamoyl)amino)-2-(4-(3-methylthioureido)-2-sulfonatostyryl)benzenesulfonate (Formula XXIX); and sodium (E)-5-acetamido-2-(4-(3-isopropylthioureido)-2-sulfonatostyryl)benzenesulfonate (Formula XXX).

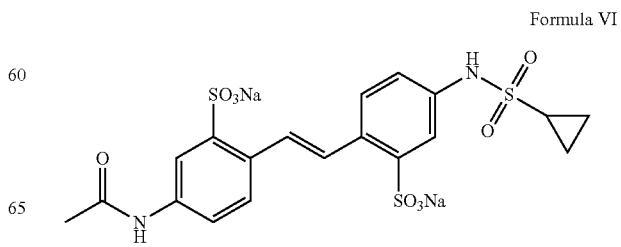

Formula VI

Formula VII
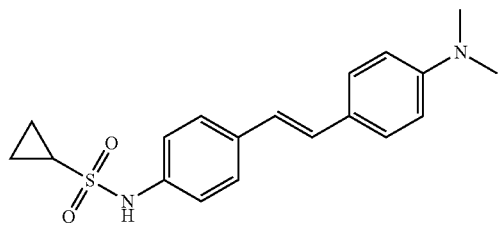

Formula VIII
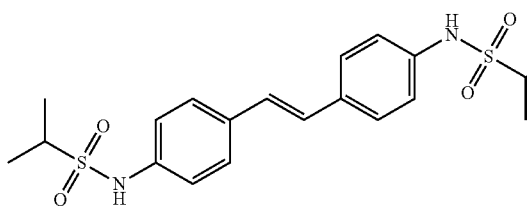

Formula IX
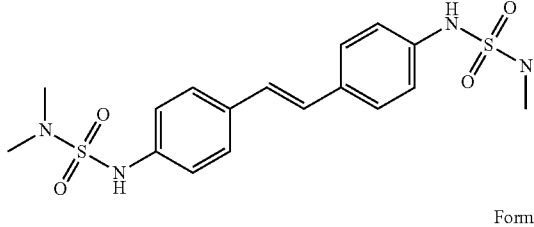

Formula X
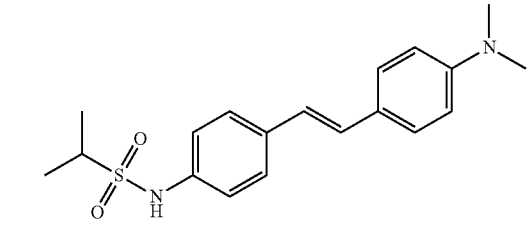

Formula XI
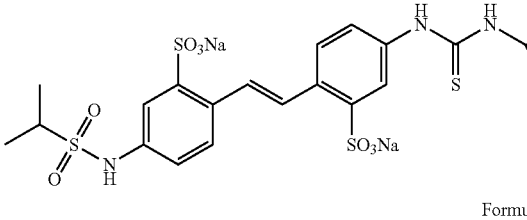

Formula XII
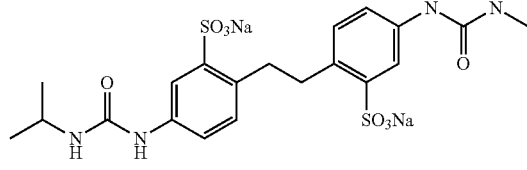

Formula XIII
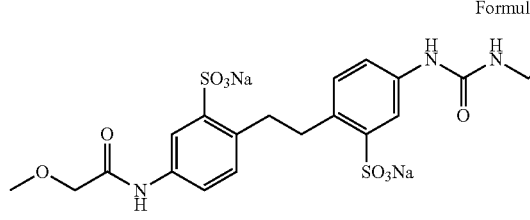

Formula XIV
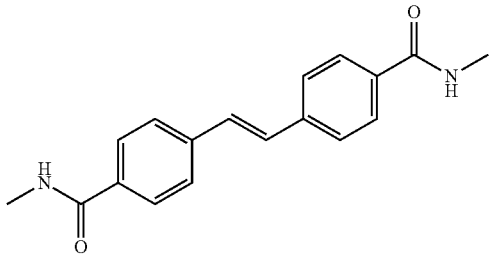

Formula XXIII
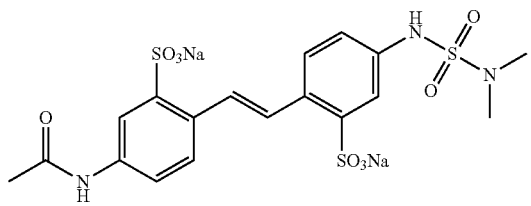

Formula XXVII
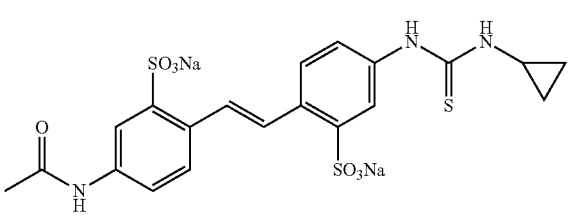

Formula XXVIII
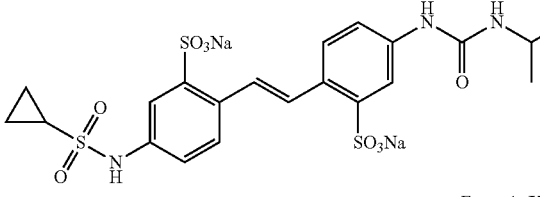

Formula XXIX
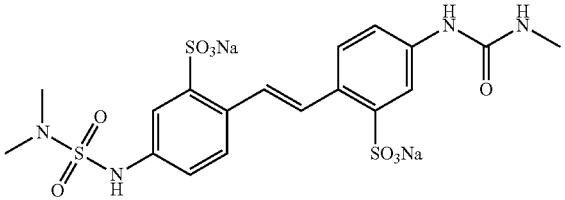

Formula XXX
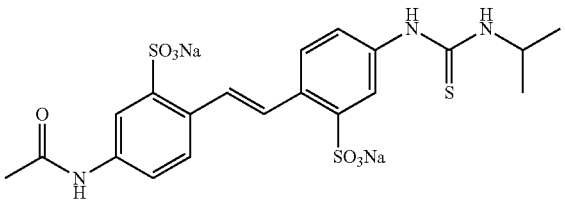

In certain embodiments, the stilbene derivative can be selected from the group consisting of sodium (E)-5-acetamido-2-(4-(cyclopropanesulfonamido)-2-sulfonatostyryl) benzenesulfonate (Formula VI); sodium (E)-5-acetamido-2-(4-(3-cyclopropylthioureido)-2-sulfonatostyryl) benzenesulfonate (Formula XXVII); sodium (E)-5-((N,N-dimethylsulfamoyl)amino)-2-(4-(3-methylthioureido)-2-sulfonatostyryl)benzenesulfonate (Formula XXIX); sodium (E)-5-(cyclopropanesulfonamido)-2-(4-(3-isopropylureido)-2-sulfonatostyryl)benzenesulfonate (Formula XXVIII); and sodium 6,6'-(ethane-1,2-diyl)bis(3-(3-isopropylureido)benzenesulfonate (Formula XII, also referred to herein as BB4B-2).

In some embodiments, the stilbene derivative can be (E)-5-acetamido-2-(4-(cyclopropanesulfonamido)-2-sulfonatostyryl)benzenesulfonate. In some embodiments, the stilbene derivative can have the structure of Formula XXIV:

Formula XXIV

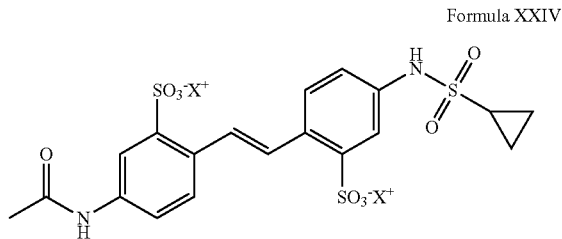

wherein X can be any pharmaceutically acceptable salt cation. By way of non-limiting example, X can be sodium, potassium, aluminum, calcium, lithium, magnesium, barium, or zinc.

In some embodiments, the stilbene derivative can be (E)-5-acetamido-2-(4-((N,N-dimethylsulfamoyl)amino)-2-sulfonatostyryl)benzenesulfonate. In some embodiments, the stilbene derivative can have the structure of Formula XXV:

Formula XXV

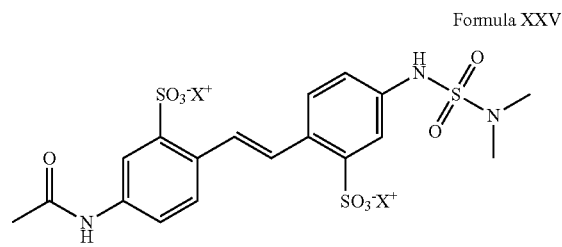

wherein X can be any pharmaceutically acceptable salt cation. By way of non-limiting example, X can be sodium, potassium, aluminum, calcium, lithium, magnesium, barium, or zinc.

In some embodiments, the stilbene derivative can be (E)-5-acetamido-2-(4-(3-cyclopropylthioureido)-2-sulfonatostyryl)benzenesulfonate. In some embodiments, the stilbene derivative can have the structure of Formula XXXI:

Formula XXXI

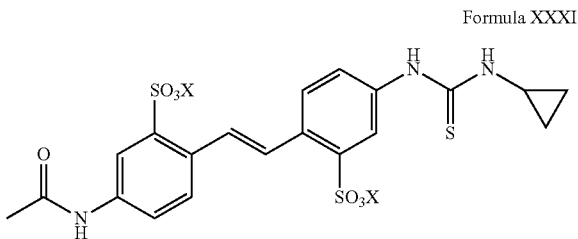

wherein X can be any pharmaceutically acceptable salt cation. By way of non-limiting example, X can be sodium, potassium, aluminum, calcium, lithium, magnesium, barium, or zinc.

In some embodiments, the stilbene derivative can be (E)-5-(cyclopropanesulfonamido)-2-(4-(3-isopropylureido)-2-sulfonatostyryl)benzenesulfonate. In some embodiments, the stilbene derivative can have the structure of Formula XXXII:

Formula XXXII

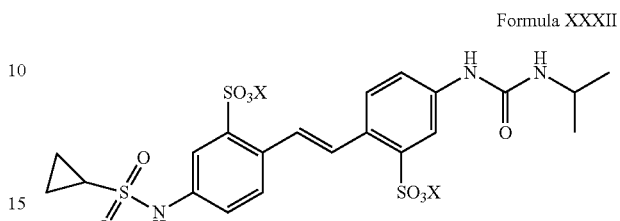

wherein X can be any pharmaceutically acceptable salt cation. By way of non-limiting example, X can be sodium, potassium, aluminum, calcium, lithium, magnesium, barium, or zinc.

In some embodiments, the stilbene derivative can be (E)-5-((N,N-dimethylsulfamoyl)amino)-2-(4-(3-methylthioureido)-2-sulfonatostyryl)benzenesulfonate. In some embodiments, the stilbene derivative can have the structure of Formula XXXIII:

Formula XXXIII

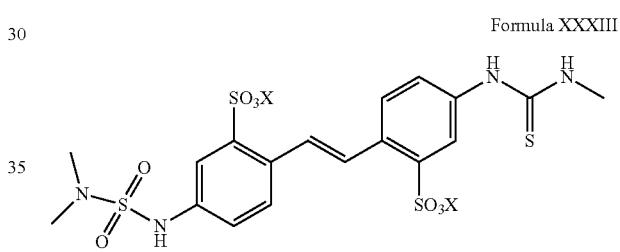

wherein X can be any pharmaceutically acceptable salt cation. By way of non-limiting example, X can be sodium, potassium, aluminum, calcium, lithium, magnesium, barium, or zinc.

In some embodiments, the stilbene derivative can be 6,6'-(ethane-1,2-diyl)bis(3-(3-isopropylureido)benzenesulfonate). In some embodiments, the stilbene derivative can have the structure of Formula XXXIV:

Formula XXXIV

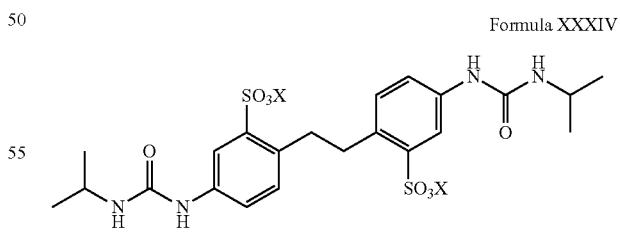

wherein X can be any pharmaceutically acceptable salt cation. By way of non-limiting example, X can be sodium, potassium, aluminum, calcium, lithium, magnesium, barium, or zinc.

In some embodiments, the stilbene derivative can be (E)-5-acetamido-2-(4-(3-isopropylthioureido)-2-sulfonatostyryl)benzenesulfonate. In some embodiments, the stilbene derivative can have the structure of Formula XXXV:

Formula XXXV

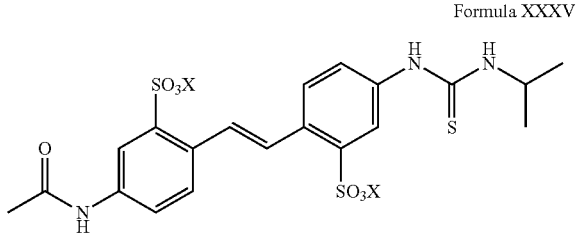

wherein X can be any pharmaceutically acceptable salt cation. By way of non-limiting example, X can be sodium, potassium, aluminum, calcium, lithium, magnesium, barium, or zinc.

In some embodiments, described herein is a stilbene or derivative thereof of formula (Va):

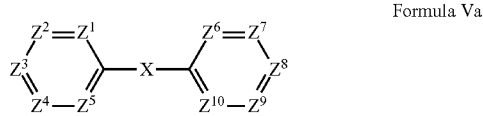
Formula Va $Z^1$ is $CR^1$ or N;
$Z^2$ is $CR^2$ or N;
$Z^3$ is $CR^3$ or N;
$Z^4$ is $CR^4$ or N;
$Z^5$ is $CR^5$ or N;
$Z^6$ is $CR^6$ or N;
$Z^7$ is $CR^7$ or N;
$Z^8$ is $CR^8$ or N;
$Z^9$ is $CR^9$ or N;
$Z^{10}$ is $CR^{10}$ or N; and
X, $R^1$-$R^{10}$ are as described for Formula (V).

In some embodiments, at least one of $Z^1$-$Z^5$ is N. In some embodiments, at least one of $Z^6$-$Z^{10}$ is N.

In some embodiments, $Z^1$ is $CR^1$. In some embodiments, $Z^6$ is $CR^6$. In some embodiments, $Z^3$ is $CR^3$. In some embodiments, $Z^8$ is $CR^8$.

In some embodiments, $Z^1$ is $CR^1$, $Z^6$ is $CR^6$, and at least one of $Z^2$-$Z^5$ or $Z^7$-$Z^{10}$ is N. In some embodiments, $Z^3$ is $CR^3$, $Z^8$ is $CR^8$, and at least one of $Z^1$-$Z^2$, $Z^4$-$Z^5$, $Z^6$, $Z^7$-$Z^9$-$Z^{10}$ is N. In some embodiments, $Z^3$ is $CR^3$, $Z^6$ is $CR^6$, and at least one of $Z^1$-$Z^2$, $Z^4$-$Z^5$, $Z^7$-$Z^{10}$ is N.

In some embodiments, the invention provides a compound of formula Va is of structure:

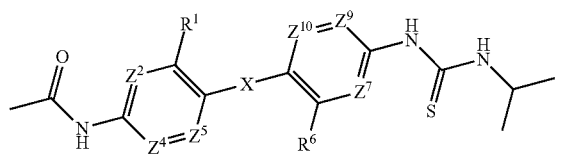

wherein:
$R^1$ and $R^6$ are $SO_3Y$, $CO_2H$ or a $C_5$-$C_8$ aryl;
Y is sodium, potassium, aluminum, calcium, lithium, magnesium, barium, or zinc; and
X is —CH=CH—, —C(O)NH—, a 1,3-disubstituted cyclobutane, or an oxetane.

In some embodiments, a compound of formula V is of structure:

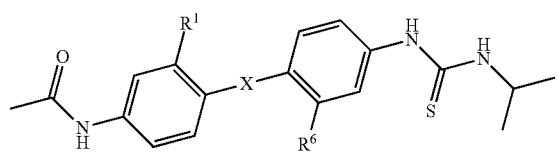

wherein:
$R^1$ and $R^6$ are $SO_3Y$, $CO_2H$ or a $C_5$-$C_8$ aryl;
Y is sodium, potassium, aluminum, calcium, lithium, magnesium, barium, or zinc; and
X is —CH=CH—, —C(O)NH—, a 1,3-disubstituted cyclobutane, or an oxetane.

In some embodiments, the stilbene and stilbene derivatives described above herein can be inhibitors of double strand break repair. In some embodiments, the stilbenes and stilbene derivatives described above can be used in the methods described herein.

In some embodiments, the inhibitor of double strand break repair can be a stilbenoid. As used herein, a "stilbenoid" is a hydroxylated stilbene derivative. Non-limiting examples of stilbenoids include, but are not limited to, resveratrol; aglycones; picetannol; pinosylvin; pterostilbene; alpha-viniferin; ampelopsin A; ampelopsin E; diptoindonesin C; diptoindonesin F; epsilon-viniferin; flexuosol A; gnetin H; hemsleyanol D; hopeaphenol; trans-diptoindonesin B; vaticanol B; astringin; piceid; diptoindonesin A.

In certain embodiments provided herein, the inhibitor can be salazinic acid (Formula I) (Pubchem Substance ID: 24840333; Compound A03). Salazinic acid can also be referred to as 1,4,10-trihydroxy-5-(hydroxymethyl)-8-methyl-3,7-dioxo-1,3-dihydro-7H-2,6,12-trioxabenzo[5,6]cyclohepta[1,2-e]indene-11-carbaldehyde.

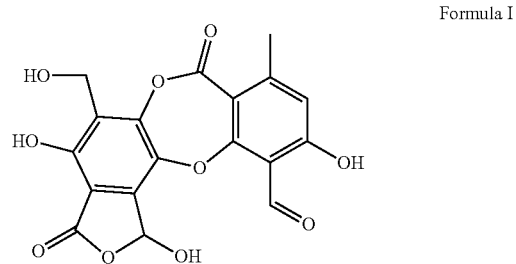 [SMILES: Cc1cc(O)c(C=O)c2c1C(=O)Oc1c(CO)c(O)c3c(c1O2)C(O)OC3=O]
Formula I

In certain embodiments provided herein, the inhibitor can be stictic acid (Formula II) (Pubchem Substance ID: 24840609; Compound A10). This compound is also known as NSC-87511, scopularic acid, sterocaulonic acid; and 1,3-dihydro-1,4-dihydroxy-10-methoxy-5,8-dimethyl-3,7-dioxo-7H-isobenzofuro[4,5-b][1,4]benzodioxepin-11-carbaldehyde.

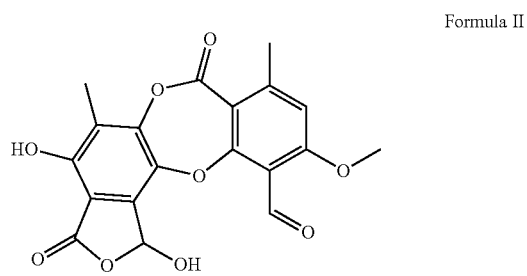 [SMILES: COc1cc(C)c2c(c1C=O)Oc1c(c(C)c(O)c3c1C(O)OC3=O)OC2=O]
Formula II

In certain embodiments provided herein, the inhibitor can be STK856883 (Formula III) (Pubchem Substance ID: 24787209; Compound B02). This compound can also be referred to as 3-benzyl-2-[(E)-2-pyridin-3-ylethenyl]quinazolin-4-one. STK856883 has been identified as a RAD51 inhibitor (Huang et al. ACS Chem. Biol. 2011 Mar. 23).

Formula III

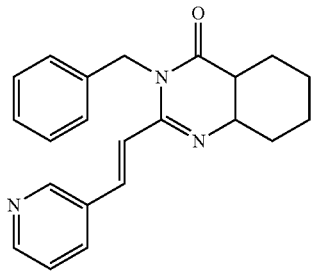

In certain embodiments provided herein, the inhibitor can be 4'-bromo-3' nitropropiophenone (Formula IV) (Calbiochem Cat: No. 323115). 4'-Bromo-3'-nitropropiophenone, also known as NS-123 or 1-(4-bromo-3-nitrophenyl)propan-1-one, is a cell-permeable nitro-ropiophenone compound as described in WO2009036297 that preferentially enhances tumor growth-inhibitory effects of ionizing radiation (~5 µM in U251, HT-29 and A549 tumor cells and in U251 xenograft mouse model, 50 mg/kg, i.p.) with no apparent effect on normal human glial cells, Zebrafish embryos and nude mice. It has been shown to increase the accumulation of unrepaired double-strand DNA breaks and prolong the damage-dependent signaling.

Formula IV

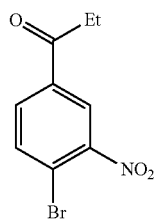

In some embodiments, the inhibitor can be selected from the group consisting of 4-methylquinazoline-2-carboxamide (Formula XV); benz[h]isoquinolin-6-amine (Formula XVI); 5,6-dimethyl-2-mercaptomethylbenzimidazole (Formula XVII); (E)-1-(2-hydroxyphenyl)-3-(pyridine-3-yl)prop-2-en-1-one (Formula XVIII); N4-butyl-6-chloropyrimidine-2,4-diamine (Formula XIX); 1-thermopsine (Formula XX); 6-amino-5-nitroso-2-phenylpyrimidin-4(1H)-one (Formula XXI); and 4-(2-amino-4-nitrophenylamino)phenyl (Formula XXII).

Formula XV

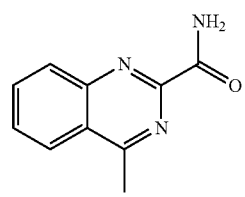

Formula XVI

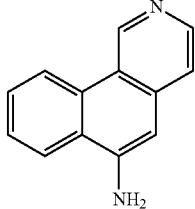

Formula XVII

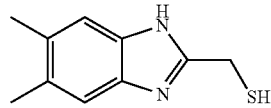

Formula XVIII

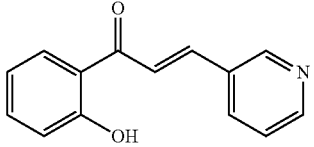

Formula XIX

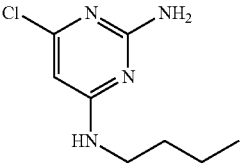

Formula XX

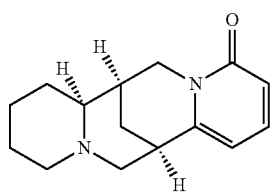

Formula XXI

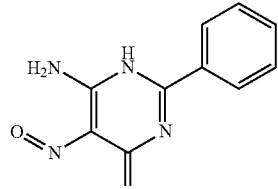

Formula XXII

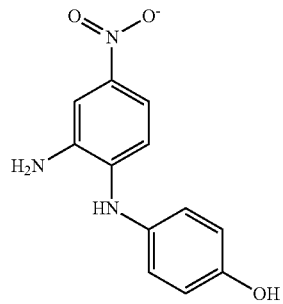

In some embodiments, the inhibitor can be selected from the group consisting of 7-Aazaindole-3-carboxaldehyde (CAS4649-09-6); 2-Amino-4-phenylphenol (CAS1134-36-7); 3-(1-methyl-3-pyrrolidinyl)indole (CAS3671-00-9); 1-methyl-[1,2,4]Triazolo[4,3-a]quinolone (CAS35359-22-9); 2-amino-5-nitro-1H-benzimidazole (CAS6232-92-4); 2-(5-nitro-2-furfurylidene)aminoethanol-N-oxide (CAS19561-70-7; Nifuratrone); alpha-mercapto-N,2-naphthylacetamide (CAS93-42-5; Thionalide); (CAS486-90-8;

1-thermospine); N4-butyl-6-chloro-2,4-Pyrimidinediamine (CAS5457-91-0); 2-(2-hydroxy-6-propan-2-yloxy-cyclohexyl)acetic acid (CAS7248-04-6); 6-amino-5-nitroso-2-phenyl-1H-pyrimidin-4-one (CAS5466-66-0); 4-amino-2-hydroxyphenyl)arsonic acid (CAS6318-57-6); spiro[1,2-dihydroindene-3,5'-imidazolidine]-2',4'-dione (CAS6252-98-8); N~-4~-(4-methoxyphenyl)-6-methylpyrimidine-2,4-diamine (CAS93001-35-5); 2-amino-9-pentyl-3H-purine-6-thione (CAS24397-98-6); 2-(4-methoxyphenyl)-3-(pyridin-3-yl)prop-2-enenitrile (CAS92437-25-7); 2-chloropyrimidine-4,6-dicarboxamide (CAS7150-30-3); 2-amino-3H-Phenoxazin-3-one (CAS1916-59-2); 2-methyl-N-benzyl-7H-pyrrolo[2,3-d]pyrimidine-4-amine; 4-(benzylamino)-2-methyl-7H-pyrrolo[2,3-d]pyrimidine; NSC-106570 (CAS1866-43-9; Rolodine); 2-amino-1-naphthalenesulfonic acid (CAS81-16-3); N-sec-butyl-3-methylbenzamide (NSC 34983); benz[h]isoquinolin-6-amine; and 2-(2-methylcyclohexylidene)hydrazinecarboxamide.

In certain embodiments, the DSB repair inhibitor can be an ATM inhibitor. In some embodiments the inhibitor is 2-morpholin-4-yl-6-thianthren-1-yl-pyran-4-one (KU-55933, 51092 Selleck Chemicals LLC: Houston, Tex.; WO/03070726) or 2-((2R,6S)-2,6-Dimethyl-morpholin-4-yl)-N-[5-(6-morpholin-4-yl-4-oxo-4H-pyran-2-yl)-9H-thioxanthen-2-yl]-acetamide (KU-60019 or KU60019; WO/2007/026157; 51570 Selleck Chemicals LLC; Houston Tex.; Mol Cancer Ther 2009, 8(10): 2894-2902). Also by way of a non-limiting example, the DSB repair inhibitor can be compounds such as those disclosed in European Patent EP1946757 and WO 03/070726 and WO 2005/016919.

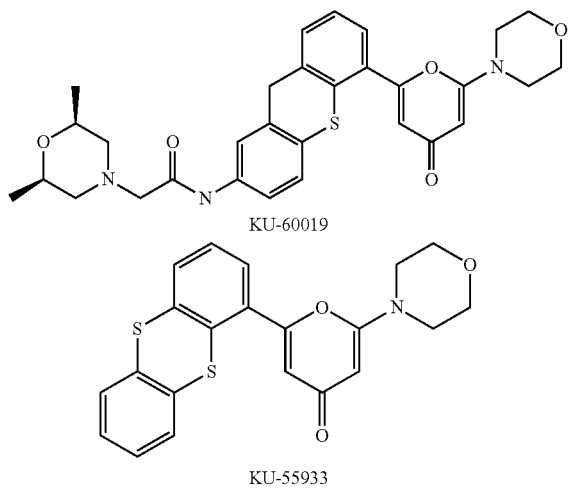

KU-60019

KU-55933

In certain embodiments provided herein, the DSB repair inhibitor is an inhibitor which reduces the expression or activity of any gene or protein which promotes DSB repair. These genes or proteins may be enzymes that participate in DSB repair, in RAD51-mediated strand exchange or regulatory or scaffolding genes or proteins that control the activity of enzymes which participate in DSB repair. A gene or protein is considered to be a gene or protein which promotes DSB repair if a decrease in the expression or activity of that gene or protein results in a decrease in DSB repair. The reduction in DSB repair can be by about 5%, about 10%, about 20%, about 30%, about 40%, about 50%, about 60%, about 70%, about 80%, about 90%, about 100%, about 125%, about 150% or more compared to a control with normal expression or activity of the gene or protein being tested. DSB repair can be measured by methods well known to those skilled in the art. By way of non-limiting example, DSB repair can be measured by colorimetric or immunofluorescence detection of H2AX-S139PO4 (γ-H2AX, a phosphorylated histone 2A) foci (Rogakou et al., J Biol Chem 1998, 273:5858-5868; Rothkamm and Löbrich, Proc Natl Acad Sci USA, 2003, 100(9): 5057-5062; Redon et al., Aging 2011, 3(2):168-74; Rakiman et al. 2008, Advanced Biotech 39). By way of non-limiting example, DSB repair can be measured by detection of gamma-H2AX phosphorylation. By way of non-limiting example, DSB repair can be measured by the COMET assay (Orlow et al. 2008, J. Clin. Oncol. 26, 3560-3566; Muller et al 1994, International Journal of Radiation Biology 65, 315-319; Fairbairn et al. 1995, Mutation Research/Reviews in Genetic Toxicology 339, 37-59). By way of non-limiting example, DSB repair can be assessed by measuring RAD51-mediated strand exchange, a component of DSB repair. RAD51-mediated strand exchange can be measured by the in vitro strand-exchange assay described in Ishida et al., Nucleic Acids Res 2009 37:3367-3376. All of the references in the foregoing paragraph are incorporated by reference herein in their entireties.

In certain embodiments provided herein, the DSB repair inhibitor is an inhibitor which reduces the expression or activity of one or more of the following proteins; including, but not limited to: Rad51AP1 (NCBI Gene ID: 10635; SEQ ID NO:007); Rad51B (NCBI Gene ID: 5890; SEQ ID NO:008); Rad51D (NCBI Gene ID: 5892; SEQ ID NO; 009); Rad51C (NCBI Gene ID: 5889 e.g. SEQ ID NO:0163 (mRNA; NM_058216) and SEQ ID NO:0164 (protein; NP_478123) or SEQ ID NO:0165 (mRNA; NM_002876) and SEQ ID NO:0166 (protein; NP_002867); XRCC2 (NCBI Gene ID: 7516; SEQ ID NO:010); XRCC3 (NCBI Gene ID: 7517; SEQ ID NO:011); RAD54 (NCBI Gene ID: 546; SEQ ID NO:012); RAD52 (NCBI Gene ID: 5893; SEQ ID NO:013); BRCA1 (NCBI Gene ID: 672; SEQ ID NO:014); BRCA2 (NCBI Gene ID: 675; SEQ ID NO:015); ATM (NCBI Gene ID: 472; SEQ ID NO:016); ATR (NCBI Gene ID: 545; SEQ ID NO:017); MRE11 (NCBI Gene ID: 4361; SEQ ID NO:018); RAD50 (NCBI Gene ID: 10111: SEQ ID NO:019); NBS1 (NCBI Gene ID: 4683; SEQ ID NO:020); WRN (NCBI Gene ID: 7486; SEQ ID NO:021); BLM (NCBI Gene ID: 641; SEQ ID NO:022); RECQ4 (NCBI Gene ID: 9401; SEQ ID NO:023); LIG4 (DNA Ligase 4; NCBI Gene ID: 3981; SEQ ID NO:024; XRCC4 (NCBI Gene ID: 7518; SEQ ID NO:025); PRKDC (DNA-PKcs7; XRCC7; NCBI Gene ID: 5591; SEQ ID NO:026); DCLRE1C (NCBI Gene ID: 64421; SEQ ID NO:027); XRCC6 (Ku70; NCBI Gene ID: 2547; SEQ ID NO:028); XRCC5 (Ku80; NCBI Gene ID: 7520; SEQ ID NO:029) and/or XLF (NHEJ1; XRCC4-like factor; NCBI Gene ID: 79840; SEQ ID NO:030).

An inhibitor of DSB repair can be a nucleic acid (DNA or RNA), a small molecule, an aptamer, a protein, a peptide, an antibody, a polypeptide comprising an epitope-binding fragment of an antibody, an antibody fragment, a peptide-nucleic acid (PNA), a locked nucleic acid (LNA) or a ribozyme. In some embodiments, an inhibitor of DSB repair can be selected from the group consisting of a small molecule, an aptamer, a protein, a peptide, an antibody, a polypeptide comprising an epitope-binding fragment of an antibody, an antibody fragment, and a peptide-nucleic acid (PNA).

LNA bases are ribonucleotide analogs containing a methylene linkage between the 2' oxygen and the 4' carbon of the ribose ring (Koshkin A. A., 1998, Tetrahedron, 54:3607-

3630; Obika S., 1998, Tetrahedron Lett., 39:5401-5404). The constraint on the sugar moiety results in a locked 3'-endo conformation that preorganizes the base for hybridization and increases melting temperature (Tm) values as much as 10° C. per base (Wengel J., 1999, Acc. Chem. Res., 32:301-310; Braasch D. A. and Corey, D. R., 2001, Chem. Biol., 8:1-7). LNA bases can be incorporated into oligonucleotides using standard protocols for DNA synthesis. Introduction of LNA bases also confers resistance to nucleases when incorporated at the 5' and 3' ends of oligomers (Crinelli R., et. al., 2002, Nucleic Acids Res., 30:2435-2443). In some embodiments, the gene silencing agent is an LNA-DNA chimera. The syntheses of LNA-containing oligomers are known in the art, for examples, those described in U.S. Pat. Nos. 6,316,198, 6,670,461, 6,794,499, 6,977,295, 6,998,484, 7,053,195, and U.S Patent Publication No. US 2004/0014959, and all of which are hereby incorporated by reference in their entirety.

In some embodiments, the DSB inhibitor comprises an RNA interfering sequence selected from the group consisting of: SEQ ID NO:050, SEQ ID NO:051, SEQ ID NO:052, SEQ ID NO:053, SEQ ID NO:054, SEQ ID NO:055, SEQ ID NO:056, SEQ ID NO:057, SEQ ID NO:058, SEQ ID NO:059, SEQ ID NO:060, SEQ ID NO:061, SEQ ID NO:062, SEQ ID NO:063, SEQ ID NO:064, SEQ ID NO:065, SEQ ID NO:066, SEQ ID NO:067, SEQ ID NO:068, SEQ ID NO:069, SEQ ID NO:070, SEQ ID NO:071, SEQ ID NO:072, SEQ ID NO:073, SEQ ID NO:074, SEQ ID NO:075, SEQ ID NO:076, SEQ ID NO:077, SEQ ID NO:078, SEQ ID NO:079, SEQ ID NO:080, SEQ ID NO:081, SEQ ID NO:082, SEQ ID NO:083, SEQ ID NO:084, SEQ ID NO:085, SEQ ID NO:086, SEQ ID NO:087, SEQ ID NO:088, SEQ ID NO:089, SEQ ID NO:090, SEQ ID NO:091, SEQ ID NO:092, SEQ ID NO:093, SEQ ID NO:094, SEQ ID NO:095, SEQ ID NO:096, SEQ ID NO:097, and SEQ ID NO:098.

Inhibitors of DSB repair can be produced recombinantly using methods well known to those of skill in the art (see Sambrook et al., Molecular Cloning: A Laboratory Manual (2 ed.), Cold Spring Harbor Laboratory Press, Cold Spring Harbor, N.Y., USA (1989)). Alternatively, DSB repair can be obtained commercially e.g. DIDS (#38440 Sigma-Aldrich; St. Louis, Mo.); 4'-Bromo-3' nitropropiophenone (Calbiochem Cat: No. 323115) or chemically synthesized.

Test compounds and agents can be screened for their ability to inhibit DSB repair. The inhibition of DSB repair can be monitored in vivo or in vitro. In one embodiment, the disruption of DSB repair is monitored by assessing the level of double strand breaks (DSBs) present in cells expressing a DNA editing enzyme, e.g. AID in the presence and absence of a test compound, e.g. by karyotyping as described herein. In one embodiment DSB are measured by γ-H2AX foci formation. In one embodiment DSB repair is measured by 53BP1 or Rad50 foci formation. In one embodiment, the ability of a test compound to disrupt DSB repair is monitored in vivo, e.g. by determining the ability to prevent or reduce tumor growth, symptoms, or markers of a cancer wherein the cancerous cells express AID. DSB repair can also be measured in vitro by the strand-exchange assay described in Ishida et al., Nucleic Acids Res 2009 37:3367-3376.

In one embodiment, an in vitro strand exchange assay is performed that monitors the production of joined nucleic acid molecules. For example, the φX174 circular ssDNA (20 μM) is incubated with RAD51 (6 μM) in the presence of a test agent at 37° C. for 10 min, in 10 μl of 26 mM HEPES buffer (pH 7.5), containing 45 mM NaCl, 0.03 mM EDTA, 0.6 mM 2-mercaptoethanol, 3% glycerol, 1 mM $MgCl_2$, 1 mM DTT, 1 mM ATP, 0.1 mg/ml bovine serum albumin, 2 mM $CaCl_2$, 20 mM creatine phosphate and 75 μg/ml creatine kinase. After this incubation, 2 μM RPA is added to the reaction mixture, and the mixture is incubated at 37° C. for a further 10 min. The reactions are then initiated by the addition of 20 μM φX174 linear dsDNA, and are continued for 60 min. The reactions are stopped by the addition of 0.1% SDS and 1.97 mg/ml proteinase K (Roche Applied Science, Basel, Switzerland), and are further incubated at 37° C. for 20 min. After adding 6-fold loading dye, the deproteinized reaction products are separated by 1% agarose gel electrophoresis in 1×TAE buffer at 3.3 V/cm for 4 h. The products are visualized by SYBR Gold (Invitrogen, Carlsbad, Calif., USA) staining.

In another embodiment of the assay, the reactions can be performed with $^{32}$P-labeled dsDNA. Visualization is performed by drying the gels, exposing them to an imaging plate and visualizing the plate using an FLA-7000 imaging analyzer (Fujifilm, Tokyo, Japan).

When the reactions are visualized, the ssDNA and dsDNA molecules provided in excess will be visible. If DSB repair occurred, a larger, joint molecule will be detected. Inhibitors of DSB repair will cause a reduction in the amount of joint molecule visible.

Test agents are typically first screened for their ability to inhibit gene expression or protein activity in vitro and those test agents with inhibitory effect on gene expression or protein activity are identified. Positive inhibitory agents are then tested for efficacy with respect to inhibition of DSB repair by in vitro or in vivo assays.

Generally, compounds can be tested at any concentration that can modulate expression or protein activity relative to a control over an appropriate time period. In some embodiments, compounds are tested at concentration in the range of about 0.1 nM to about 1000 mM. In one embodiment, the compound is tested in the range of about 0.1 μM to about 20 μM, about 0.1 μM to about 10 μM, or about 0.1 μM to about 5 μM. In one embodiment, compounds are tested at 1 μM.

Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

To screen test agents, an in vitro assay system and/or a cell-based assay system can be used. For example, test agents can be screened for binding to a gene or protein encoded by a gene, screened for altering the expression level of a gene, or screened for modulating activity/function of a protein encoded by a gene.

In one embodiment, protein/peptide test agents (including antibodies, or fragments thereof) can be assessed for their ability to bind an encoded protein in vitro. Examples direct binding assays include, but are not limited to, labeled in vitro protein-protein binding assays, electrophoretic mobility shift assays, immunoassays for protein binding, ELISA assays, co-immunoprecipitation assays, competition assays (e.g. with a known binder), and the like. See, e.g., U.S. Pat. Nos. 4,366,241; 4,376,110; 4,517,288; and 4,837,168; and also Bevan et al., Trends in Biotechnology 13:115-122, 1995; Ecker and Crooke, 1995, Biotechnology (NY) 13:351-360; and Hodgson, Biotechnology (NY) 10:973-980, 1992. The test agent can also be identified by detecting a signal that indicates that the agent binds to a protein of interest e.g., fluorescence quenching or FRET. Test agent polypeptides can also be monitored for their ability to bind nucleic acid in vitro, e.g. ELISA-format assays can be a convenient alternative to gel mobility shift assays (EMSA) for analysis of protein binding to nucleic acid. Binding of a test agent to an encoded protein provides an indication the agent may be an inhibitor of protein activity.

In one embodiment, the test agent is assayed for the ability to downregulate the biological activity or function of a protein encoded by a gene. The assay used will be dependent on the function of the protein and can be readily determined by a skilled artisan, for example monitoring inhibition of RAD51-mediated repair in vitro.

In one embodiment the test agent is assayed for the ability to inhibit transcription of a gene. Transcriptional assays are well known to those of skill in the art (see e.g. U.S. Pat. Nos. 7,319,933 and 6,913,880). For example, modulation of expression of a gene can be examined in a cell-based system by transient or stable transfection of a reporter expression vector into cultured cell lines. Test compounds can be assayed for ability to inhibit or increase expression of a reporter gene (e.g., luciferase gene) under the control of a transcription regulatory element (e.g., promoter sequence) of a gene. An assay vector bearing the transcription regulatory element that is operably linked to the reporter gene can be transfected into any mammalian cell line for assays of promoter activity. Reporter genes typically encode polypeptides with an easily assayed enzymatic activity that is naturally absent from the host cell. Typical reporter polypeptides for eukaryotic promoters include, e.g., chloramphenicol acetyltransferase (CAT), firefly or *Renilla luciferase*, beta-galactosidase, beta-glucuronidase, alkaline phosphatase, Dendra2, mCherry, mRaspberry, mPlum, tdTomato, green fluorescent protein (GFP), yellow fluorescent protein (YFP), enhanced green fluorescent protein (eGFP), red fluorescent protein (RFP), cyan fluorescent protein (CFP), etc. Vectors expressing a reporter gene under the control of a transcription regulatory element of a gene can be prepared using routinely practiced techniques and methods of molecular biology (see, e.g., e.g., Sambrook et al., supra; Brent et al., supra).

In addition to a reporter gene, the vector can also comprise elements necessary for propagation or maintenance in the host cell, and elements such as polyadenylation sequences and transcriptional terminators. Exemplary assay vectors include pGL3 series of vectors (Promega, Madison, Wis.; U.S. Pat. No. 5,670,356), which include a polylinker sequence 5' of a luciferase gene. General methods of cell culture, transfection, and reporter gene assay have been described in the art, e.g., Sambrook et al., supra; and Transfection Guide, Promega Corporation, Madison, Wis. (1998). Any readily transfectable mammalian cell line may be used to assay expression of the reporter gene from the vector, e.g., 3T3, Caco-2, CCRF-CEM, CHO, COS-7, HCT 116, HEK 293, CH12-F3, MCF-7, HepG2, Jurkat, Mo-B, KG-1, K-562, MOLT-4 and HL-60 cells.

Alternatively, determining mRNA levels can be assessed using, e.g., biochemical and molecular biology techniques such as Northern blotting or other hybridization assays, nuclease protection assay, reverse transcription (quantitative RT-PCR) techniques, RNA-Seq, high throughput sequencing and the like. Such assays are well known to those in the art. In one embodiment, nuclear "run-on" (or "run-off") transcription assays are used (see e.g. Methods in Molecular Biology, Volume: 49, Sep. 27, 1995, Page Range: 229-238). Arrays can also be used; arrays, and methods of analyzing mRNA using such arrays have been described previously, e.g. in EP0834575, EP0834576, WO96/31622, U.S. Pat. No. 5,837,832 or WO98/30883. WO97/10365 provides methods for monitoring of expression levels of a multiplicity of genes using high density oligonucleotide arrays.

In one embodiment, one or more cells from the subject to be tested are obtained and RNA is isolated from the cells. When obtaining the cells, it is preferable to obtain a sample containing predominantly cells of the desired type, e.g., a sample of cells in which at least about 50%, preferably at least about 60%, even more preferably at least about 70%, 80% and even more preferably, at least about 90% of the cells are of the desired type. Tissue samples can be obtained according to methods known in the art.

It is also possible to obtain a cell sample from a subject, and then to enrich it in the desired cell type. For example, cells can be isolated from other cells using a variety of techniques, such as isolation with an antibody binding to an epitope on the cell surface of the desired cell type. Where the desired cells are in a solid tissue, particular cells can be dissected out, e.g., by microdissection, or laser capture microdissection (LCM).

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly-become degraded. Accordingly, in a preferred embodiment, the tissue or cells obtained from a subject is snap frozen or treated with RNAlater as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190: 199. Care to avoid RNA degradation must be taken, e.g., by inclusion of RNAsin.

The RNA sample can then be enriched in a particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the QuickExtract® kit (Epicentre Biotechnologies, Madison, Wis.; Oligotex Direct mRNA kit, Qiagen, Valencia, Calif.).

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize mRNA transcripts of a regulatable protein, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the gene encoding the protein to be assayed. As herein used, the term "stringent conditions" means hybridization will occur only if there is at least 95% identity in nucleotide sequences. In another embodiment, hybridization under "stringent conditions" occurs when there is at least 97% identity between the sequences.

In one embodiment the test agent is assayed for the ability to inhibit translation of a gene. Gene translation can be measured by quantitation of protein expressed from a gene, for example by Western blotting, by an immunological detection of the protein, ELISA (enzyme-linked immunosorbent assay), radioimmunoassay (RIA) or other immunoassays and fluorescence-activated cell analysis (FACS), mass spectrometry, or protein sequencing to detect protein.

Methods for developing small molecule, polymeric and genome based libraries are described, for example, in Ding, et al., J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International, Selleck Chemicals and Oxford Chemicals Limited. These libraries can be screened for ability to inhibit DSB repair using methods described herein.

In certain embodiments, the DSB repair inhibitor is a nucleic acid which is able to inhibit the expression of a gene encoding a protein which promotes DSB repair. By way of non-limiting example, the DSB repair inhibitor can be an antisense inhibitor of DSB repair, for example an antisense inhibitor of RAD51 as disclosed in US Patent Publication 2002/0137698. Gene silencing or RNAi can be used. In certain embodiments, contacting a cell with the inhibitor of DSB repair results in a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one embodiment, the mRNA levels are decreased by at least about 70%, about 80%, about 90%, about 95%, about 99%, about 100%. In certain embodiments, the inhibitor of DSB repair comprises an expression vector or viral vector comprising the RNAi molecule.

As used herein, the term "RNAi" refers to any type of interfering RNA, including but are not limited to RNAi, siRNA, shRNA, endogenous microRNA and artificial microRNA. For instance, it includes sequences previously identified as siRNA, regardless of the mechanism of downstream processing of the RNA (i.e. although siRNAs are believed to have a specific method of in vivo processing resulting in the cleavage of mRNA, such sequences can be incorporated into the vectors in the context of the flanking sequences described herein). The term "RNAi" and "RNA interfering" with respect to an agent of the technology described herein, are used interchangeably herein.

As used herein an "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

RNAi may be delivered with the help of nanoparticles as described for example in Schiffelers and Storm, Expert Opin Drug Deliv. 2006 May; 3(3):445-54 or liposomes (e.g. Hughes et al., Methods Mol. Biol. 2010; 605:445-59).

In certain embodiments, the DSB repair inhibitor which is a nucleic acid can be an antisense RNA.

In certain embodiments, the DSB repair inhibitor which is a nucleic acid can be a ribozyme. Ribozyme molecules designed to catalytically cleave cellular mRNA transcripts can also be used to prevent translation of cellular mRNAs and expression of cellular polypeptides, or both (See, e.g., PCT International Publication WO90111364; Sarver et al. 1990, Science 247, 1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach 1988, Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in Tetrahymena thermophil a (known as the IVS, or L-19 IVS RNA) and which has been extensively described by Cech and collaborators (Zaug, et al. 1984, Science 224:574-578; Zaug, et al. 1986, Science 231:470-475; Zaug, et al. 1986 Nature 324:429-433; published International patent application No. WO88/04300; Been, et al. 1986, Cell 47:207-216). The Cech-type ribozymes have an eight base pair active site which hybridizes to a target RNA sequence whereafter cleavage of the target RNA takes place. The methods and compositions of this invention includes those Cech-type ribozymes which target eight base-pair active site sequences that are present in cellular genes.

As in the antisense approach, the ribozymes can be composed of modified oligonucleotides (e.g., for improved stability, targeting, etc.) and should be delivered to cells which express DNA editing enzyme genes in vivo. A preferred method of delivery involves using a DNA construct encoding the ribozyme under the control of a strong constitutive pol HI or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003); Lim et al., Science 299, 1540 (2003); Lee and Ambros, Science, 294, 862 (2001); Lau et al., Science 294, 858-861 (2001); Lagos-Quintana et al., Current Biology, 12, 735-739 (2002); Lagos Quintana et al., Science 294, 853-857 (2001); and Lagos-Quintana et al., RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al., 2004, Cell 116:281-297), comprises a dsRNA molecule.

Means for selecting nucleotide sequences (e.g. RNAi, siRNA, shRNA) that can serve as inhibitors or activators of target gene expression are well known and practiced by those of skill in the art. Many computer programs are available to design RNAi agents against a particular nucleic acid sequence. The targeted region of RNAi (e.g. siRNA etc.) can be selected from a given target gene sequence, e.g., RAD51), beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule of the technology described herein involves identifying the 23 nucleotide sequence motif AA(N19)TT (where N can be any nucleotide) (SEQ ID NO: 156), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense RNAi molecule can then be synthesized as the complement to nucleotide positions 1 to 21 of the 23 nucleotide sequence motif. The use of symmetric 3' TT overhangs can be advantageous to ensure e.g. that the small interfering ribonucleoprotein particles (siRNPs) are formed with approximately equal ratios of sense and antisense target RNA-cleaving siRNPs (Elbashir et al. 2001 supra).

In some embodiments, the RNAi agent targets at least 5 contiguous nucleotides in the identified target gene sequence. In one embodiment, the RNAi agent targets at least 6, 7, 8, 9 or 10 contiguous nucleotides in the identified target sequence. In some embodiments, the RNAi agent targets at least 11, 12, 13, 14, 15, 16, 17, 18 or 19 contiguous nucleotides in the identified target sequence.

In some embodiments, in order to increase nuclease resistance in an RNAi agent as disclosed herein, one can incorporate non-phosphodiester backbone linkages, as for example methylphosphonate, phosphorothioate or phosphorodithioate linkages or mixtures thereof, into one or more non-RNASE H-activating regions of the RNAi agents. Such nonactivating regions may additionally include 2'-substituents and can also include chirally selected backbone linkages in order to increase binding affinity and duplex stability. Other functional groups may also be joined to the oligonucleoside sequence to instill a variety of desirable properties, such as to enhance uptake of the oligonucleoside sequence through cellular membranes, to enhance stability or to enhance the formation of hybrids with the target nucleic acid, or to promote cross-linking with the target (as with a psoralen photo-cross-linking substituent). See, for example, PCT Publication No. WO 92/02532 which is incorporated herein in by reference.

In certain embodiments, the inhibitor of DSB repair is an antibody, monoclonal antibody, or antibody fragment (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Antibodies are prepared using methods well known to those of skill in the art. Typically, spleen cells from an animal immunized with a desired antigen are immortalized, commonly by fusion with a myeloma cell (see, Kohler and Milstein (1976) Eur, J. Immunol. 6:511-519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or an antibody fragment or a binding fragment thereof by screening a DNA library from human B cells according, e.g., to the general protocol outlined by Huse, et al. (1989), Science 246:1275-1281, or by screening phage display libraries (See e.g. WO 91/17271 and WO 92/01047). In certain embodiments, the inhibitor of RAD51-mediated strand exchange repair is an intrabody. Methods for intrabody production are well known to those of skill in the art, e.g. as described in WO 2002/086096. Antibodies will usually bind with at least a KD of about 1 mM, e.g. 1 mM or lower, 300 µM or lower, 30 µM or lower, 10 µM or lower, 3 µM or lower, 1 µM or lower, 100 nM or lower, or 10 nM or lower.

In certain embodiments, the inhibitor of DSB repair is a protein or peptide. A peptide agent can be a fragment of a naturally occurring protein, or a mimic or pepetidomimetic of a protein of RAD51-mediated exchange repair. Agents in the form of a protein and/or peptide or fragment thereof can be designed to modulate a gene or protein involved in DSB repair described herein, i.e. modulate gene expression or encoded protein activity. Such agents are intended to encompass proteins which are normally absent as well as proteins normally endogenously expressed within a cell, e.g. expressed at low levels. Examples of useful proteins are mutated proteins, genetically engineered proteins, peptides, synthetic peptides, recombinant proteins, chimeric proteins, humanized proteins, modified proteins and fragments thereof. Modulation of gene expression or protein activity can be direct or indirect. In one embodiment, a protein/peptide agent directly binds to a protein encoded by a gene identified herein, or directly binds to a nucleic acid of a gene identified herein.

Peptides can be screened for inhibitory activity. Peptide libraries, e.g. combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be naturally occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the test agents are polypeptides, peptides or proteins. The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

Libraries of test agents to be screened can also be generated based on structural studies of the proteins, or their fragments, encoded by the genes identified herein. Such structural studies allow the identification of test agents that are more likely to bind to the proteins and modulate their activity. The three-dimensional structures of the proteins can be studied in a number of ways, e.g., crystal structure and molecular modeling. Methods of studying protein structures using X-ray crystallography are well known in the literature. See Physical Bio-chemistry, Van Holde, K. E. (Prentice-Hall, New Jersey 1971), pp. 221-239, and Physical Chemistry with Applications to the Life Sciences, D. Eisenberg & D. C. Crothers (Benjamin Cummings, Menlo Park 1979). Computer modeling of structures provides another means for designing test agents to screen for modulators. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR). See, e.g., Physical Chemistry, 4th Ed. Moore, W. J. (Prentice-Hall, New Jersey 1972), and NMR of Proteins and Nucleic Acids, K. Wuthrich (Wiley-Interscience, New York 1986).

In some embodiments, the test compound that is screened and identified to inhibit expression of a gene identified herein, or identified to inhibit the activity of a protein encoded by a gene identified herein can inhibit DSB repair by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control.

The DSB repair inhibitory compounds or agents may function directly in the form in which it is administered. Alternatively, the agent can be modified or utilized intracellularly to produce something which modulates the gene, e.g. introduction of a nucleic acid sequence into the cell and its transcription resulting in the production of an inhibitor or activator of gene expression or protein activity.

Treatment

In some embodiments, the technology described herein relates to a method of treatment comprising (a) selecting a subject having cells that express an elevated level of a DNA editing enzyme; and (b) administering a therapeutically effective amount of an inhibitor of double strand break repair to the subject; wherein an elevated level is a level of AID that is higher than the level of a DNA editing enzyme in cells of the same type from a healthy individual. In some embodiments, the technology described herein relates to a method of treatment comprising (a) selecting a subject having B cells that express an elevated level of a DNA editing enzyme; and (b) administering a therapeutically effective amount of an inhibitor of double strand break repair to the subject, wherein an elevated level is a level of a DNA editing enzyme that is higher than the level of a DNA editing enzyme in B cells of from a healthy individual. In some embodiments the DNA editing enzyme expression is not detectable in the healthy subject. In some embodiments, the subject can be a human subject.

In some embodiments, the subject having cells expressing elevated levels of a DNA editing enzyme as compared to the level of a DNA editing enzyme in cells of the same type from a healthy individual is identified by determining the level of a DNA editing enzyme protein and/or mRNA in a sample of cells obtained from the subject. In some embodiments, the levels of a DNA editing enzyme in the cells expressing an elevated level of a DNA editing enzyme are significantly higher than normal cells from a healthy subject. In some embodiments, the levels of a DNA editing enzyme in the cells expressing an elevated level of a DNA editing enzyme are significantly higher than the levels of a DNA editing enzyme expressed in unactivated B cells from a healthy subject. In some embodiments, the levels of a DNA editing enzyme in the B cells expressing an elevated level of a DNA editing enzyme are significantly higher than the levels of AID expressed in unactivated B cells from a healthy subject.

In some embodiments, the technology described herein relates to a method of treatment comprising (a) selecting a subject having cells that express an elevated level of activation-induced cytidine deaminase (AID); and (b) administering a therapeutically effective amount of an inhibitor of double strand break repair to the subject; wherein an elevated level is a level of AID that is higher than the level of AID in cells of the same type from a healthy individual. In some embodiments, the technology described herein relates to a method of treatment comprising (a) selecting a subject having B cells that express an elevated level of AID; and (b) administering a therapeutically effective amount of an inhibitor of double strand break repair to the subject, wherein an elevated level is a level of AID that is higher than the level of AID in B cells of from a healthy individual. In some embodiments the AID expression is not detectable in the healthy subject.

In some embodiments, the subject having cells expressing elevated levels of AID as compared to the level of AID in cells of the same type from a healthy individual is identified by determining the level of AID protein and/or mRNA in a sample of cells obtained from the subject. In some embodiments, the levels of AID in the cells expressing an elevated level of AID are significantly higher than normal cells from a healthy subject. In some embodiments, the levels of AID in the cells expressing an elevated level of AID are significantly higher than the levels of AID expressed in unactivated B cells from a healthy subject. In some embodiments, the levels of AID in the B cells expressing an elevated level of AID are significantly higher than the levels of AID expressed in unactivated B cells from a healthy subject.

Also provided herein are methods for determining if a condition in a subject, e.g. a cancer or autoimmune disease, will be responsive to treatment by an inhibitor of DSB repair by determining the level of a DNA editing enzyme (e.g. AID) protein, mRNA and/or activity in the cells of that subject. The presence of high levels of a DNA editing enzyme in the subject's cells (test sample) can be indicative that the subject will be responsive to treatment by an inhibitor of DSB repair. The level of a DNA editing enzyme can be determined by assessing the level in a biological sample obtained from a subject and comparing the observed levels to the levels of a DNA editing enzyme found in a control reference sample. In some embodiments the DNA editing enzyme is AID.

In one embodiment, the condition (e.g. cancer or autoimmune disease) to be treated is already known to those of skill in the art to have high levels of a DNA editing enzyme, and thus treatment with an inhibitor of DSB repair is indicated without the need to measure levels of a DNA editing enzyme protein, mRNA, and/or expression in a biological sample obtained from the patient. In certain embodiments the DNA editing enzyme is AID. As used herein, a "biological sample" refers to a sample of biological material obtained from a patient, preferably a human patient, including a tissue sample (e.g., a tissue biopsy, such as, an aspiration biopsy, a brush biopsy, a surface biopsy, a needle biopsy, a punch biopsy, an excision biopsy, an open biopsy, an incision biopsy or an endoscopic biopsy) or cell samples (e.g. epithelial cells or lymphocytes). Biological samples can also be biological fluid samples e.g. semen, urine, blood, serum, saliva, cerebrospinal fluid, and supernatant from cell lysate, e.g. lymphocyte fraction. Some embodiments of the technology described herein also encompass the use of isolates of a biological sample in the methods described herein.

The control reference sample can be a biological sample (of the same type) that is obtained from a healthy individual, i.e. an individual that does not have cancer or an autoimmune disease. The control reference sample can also be a standard sample that contains the same concentration of a DNA editing enzyme that is normally found in a biological sample of the same type and that is obtained from a healthy individual. For example, there can be a standard reference control sample for the amounts of a DNA editing enzyme normally found in biological samples such as particular cell fractions (e.g. lymphocytes), semen, urine, blood, cerebral spinal fluid, or tissue. In one embodiment, the control reference sample is a standard reference sample that contains a mean or median concentration of a DNA editing enzyme mRNA or a DNA editing enzyme protein found in cells from a population of healthy individuals that do not have cancer or an autoimmune disease. In one embodiment, e.g., when the cells are B cells, the reference level is the level of a DNA editing enzyme protein or mRNA found in a population of unactivated B-lymphocytes from a healthy individual. In one embodiment, the control reference sample is a biological sample of the patient from healthy cells or tissue from the patient, e.g. if the patient has lymphoma, a cheek swab or skin biopsy can be used as a reference sample. In some embodiments, the levels of a DNA editing enzyme mRNA, protein, and/or activity found in a population of B-cells undergoing class switching are not suitable control reference samples.

Cells obtained from a subject are characterized as having increased, or elevated levels of a DNA editing enzyme protein and/or mRNA if the level of a DNA editing enzyme protein, a DNA editing enzyme mRNA, and/or a DNA editing enzyme activity detected in the subject's cells (e.g. a biological sample comprising cancerous or autoimmune cells), is higher by a statistically significant amount, than the level of a DNA editing enzyme protein, mRNA and/or activity found in a reference control sample representative of the level of a DNA editing enzyme in cells of the same type from a healthy subject. The levels of a DNA editing enzyme can be represented by arbitrary units, for example as units obtained from a densitometer, luminometer, or an ELISA plate reader etc. In a certain embodiment the DNA editing enzyme is AID.

As used herein, the terms, a "high level" an "elevated level", and/or "increased level" of a DNA editing enzyme protein, mRNA, and/or activity are used interchangeably and refer to amounts of a DNA editing enzyme protein, mRNA, and/or activity that are significantly greater than the amounts of a DNA editing enzyme protein, mRNA, and/or activity present in a control reference sample representative of the levels of a DNA editing enzyme in cells of the same type from a healthy individual. In a certain embodiment the DNA editing enzyme is AID.

In some embodiments, the control reference sample can comprise healthy cells of the same type as the cells for which a DNA editing enzyme levels are to be determined. In some embodiments, the cells of the control reference sample can be of similar age, developmental status, sex, and/or cell type as the cells for which the level of a DNA editing enzyme expression is to be determined. In some embodiments, the control reference sample can be obtained from a healthy organism of similar age, developmental status, and/or sex as the subject organism for which the level of a DNA editing enzyme expression is to be determined. In some embodiments, the test sample and control reference sample are of the same type, that is, obtained from the same biological source, and comprising the same composition, e.g. the same number and type of cells. In a certain embodiment the DNA editing enzyme is AID.

In some embodiments, the control reference sample can comprise healthy, unactivated and/or non-transformed B cells. In some embodiments, an elevated level of a DNA editing enzyme is a level significantly greater than that in a healthy, unactivated and/or non-transformed B cell. In some embodiments, B-cells undergoing class-switching are not considered to be useful reference samples. In a certain embodiment the DNA editing enzyme is AID.

In most normal cells AID protein/mRNA are not detectable, therefore in some embodiments, mere detection of AID can be considered to be an increased level as compared to there being no detectable levels in cells from a healthy individual. In some embodiments, an elevated level of AID can be the level of AID which is detectable using an RT-PCR assay using the primers SEQ ID NO:101 and SEQ ID NO:102, e.g. as described further in Example 11 herein.

In some embodiments, a detectable level of AID can be 1 pg of AID mRNA per 1 mL of blood or more, e.g. 10 pg/mL, 100 pg/mL, 1 ng/mL, 10 ng/mL or more. In some embodiments, a detectable level of AID can be 10 pg of AID mRNA per 1 mL of blood or more. In some embodiments, a detectable level of AID can be 100 pg of AID mRNA per 1 mL of blood or more. In some embodiments, a detectable level of AID can be 1 ng of AID mRNA per 1 mL of blood or more. In some embodiments, a detectable level of AID can be 10 ng of AID mRNA per 1 mL of blood or more. In some embodiments, a detectable level of AID can be 100 ng of AID mRNA per 1 mL of blood or more.

In some embodiments, a detectable level of AID can be 5 copies (e.g. transcripts) of AID mRNA per cell or more, e.g. 10 copies, 100 copies, 1,000 copies or more per cell.

In some embodiments, a detectable level of AID can be, as measured by immunohistochemistry, 1 AID polypeptide per 20 square microns in a tissue section or more e.g. 1 polypeptide, 10 polypeptides, 100 polypeptides, 1,000 polypeptides or more per 20 square microns in a tissue section In some embodiments, a detectable level of AID can be 0.1 pg of AID polypeptide per mL of blood or serum or more, e.g. 0.1 pg, 1 pg, 10 pg, 100 pg, 1 ng, 10 ng, or more per mL of blood. In some embodiments, a detectable level of AID can be 0.1 pg or more of AID polypeptide per mL of blood or serum. In some embodiments, a detectable level of AID can be 10 pg or more of AID polypeptide per mL of blood. In some embodiments, a detectable level of AID can be 100 pg or more of AID polypeptide per mL of blood. In some embodiments, a detectable level of AID can be 1 ng or more of AID polypeptide per mL of blood. In some embodiments, a detectable level of AID can be 10 ng or more of AID polypeptide per mL of blood. In some embodiments, a detectable level of AID can be 100 ng or more of AID polypeptide per mL of blood.

In some embodiments, a sample comprising serum can first be depleted of serum albumin to increase sensitivity. In some embodiments, a sample comprising blood can be enriched for B-cells or for cancerous cells before detecting the level of a DNA editing enzyme. In some embodiments, numeric expression values can be quantified and analyzed with software (e.g., Microsoft EXCEL® spreadsheet and Affymetrix GENECHIP® software).

In some embodiments, a subject is a candidate for treatment according to the methods described herein if the levels of AID in the cells of a subject are significantly greater than the levels of AID present in the control reference sample. In some embodiments, a subject is a candidate for treatment according to the methods described herein if the levels of AID in the cells of a subject are at least 1.5-fold, 2-fold, 5-fold, 10-fold greater than the levels of AID present in the control reference sample, e.g. 1.5-fold or greater, 2-fold or greater, 3-fold or greater, 4-fold or greater, 5-fold or greater, or 6-fold or greater.

In some embodiments, a healthy subject and/or a subject not in need of treatment according to the methods described herein can be one whose cells do not express a detectable level of a DNA editing enzyme. In some embodiments, the DNA editing enzyme can be AID.

The levels of AID, as described herein, can be measured by any means known to those skilled in the art. In certain embodiments the determining of the level of AID protein involves the use of one or more of the following assays; Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; gel diffusion precipitation reaction; immunodiffusion assay; in situ immunoassay; precipitation reaction; agglutination assay; complement fixation assay; immunofluorescence assay; protein A assay; mass spectroscopy and/or immunoelectrophoresis assay. In certain embodiments the determining of the level of AID protein involves the use of an antibody, an antibody fragment, a monoclonal antibody, a monoclonal antibody fragment, a protein binding protein, and/or an AID-binding peptide.

In certain embodiments, the determining of the level of AID mRNA involves the use of one or more of the following assays; RT-PCR, quantitative RT-PCR, hybridization assays, RNA-Seq, Northern blot, high-throughput sequencing, microarray based expression analysis, transcription amplification and/or self-sustained sequence replication. In certain embodiments the determining of the level of AID mRNA involves the use of an antibody, an antibody fragment, a monoclonal antibody, and/or a monoclonal antibody fragment.

Methods for assessing levels of mRNA are well known to those skilled in the art. Preferred embodiments are herein described. Laser Capture Microdissection Laser Capture Microdissection (LCM) is known to those of skill in the art, see, for example, Simon et al. (1998) Trends in Genetics 14:272 and Emmert-Buck et al. (1996) Science 274:998-1001. In one embodiment of the technology described herein a tumor sample or biopsy is obtained and LCM is used to obtain genetic material, such as, mRNA, for analysis. Nucleic acid molecules can be isolated from a particular biological sample using any of a number of procedures, which are well known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994).

Real time PCR is an amplification technique that can be used to determine levels of mRNA expression. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For mRNA levels, mRNA is extracted from a biological sample, e.g. a tumor and normal tissue, and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.).

To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-106 copies of the gene of interest are generally sufficient. In addition, a standard curve is generated for the control sequence. This permits standardization of initial content of the nucleic acid of interest in a tissue sample to the amount of control for comparison purposes. Methods of real-time quantitative PCR using TaqMan probes are well known in the art. Detailed protocols for real-time quantitative PCR are provided, for example, for RNA in: Gibson et al., 1996 Genome Res., 10:995-1001; and for DNA in: Heid et al., 1996 Genome Res., 10:986-994.

A TaqMan-based assay also can be used to quantify the expression level. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification.

In another embodiment, for example, detection of RNA transcripts may be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

To monitor mRNA levels, for example, mRNA is extracted from the biological sample to be tested, reverse transcribed, and fluorescently-labeled cDNA probes are generated. The microarrays capable of hybridizing to cDNA generated from transcripts encoding a regulatable protein are then probed with the labeled cDNA probes, the slides scanned and fluorescence intensity measured. This intensity correlates with the hybridization intensity and expression levels.

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Detection of RNA transcripts can further be accomplished using known amplification methods. For example, it is within the scope of the technology described herein to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by asymmetric gap lipase chain reaction (RT-AGLCR) as described by R. L. Marshall, et al., PCR Methods and Applications 4: 80-84 (1994). Real time PCR may also be used. Other suitable methods are isothermal detection methods including but not limited to ligase chain reaction (LCR) (see, e.g., Wu and Wallace 1989, Genomics 4, 560 Landegren et al. 1988, Science 241, 1077); self-sustained sequence replication (SSR) (see, e.g., Guatelli et al. 1990, PNAS USA, 87, 1874); transcription amplification (see, e.g., Kwoh et al. 1989, PNAS USA 86, 1173); strand displacement amplification (G. T. Walker et al., 1996, Clin. Chem. 42: 9-13 and European Patent Application No. 684315); rolling circle amplification; loop-mediated isothermal amplification; isothermal chimeric primer-initiated amplification of nucleic acids; Q-beta amplification systems (European Patent Application (EPA) No. 4544610); or OneCutEventAmplificatioN (OCEAN; Clinical Chemistry 52, 1855-1863 (2006)). The isothermal detection methods may further utilize Nuclease Chain Reaction (NCR), RNAse-mediated Nucleases Chain Reaction (RNCR), Polymerase Nuclease Chain Reaction (PNCR), RNAse-Mediated Detection (RMD), Tandem Repeat Restriction Enzyme Facilitated (TR-REF) Chain Reaction or Inverted reverse Complement Restriction Enzyme Facilitated (IRC-REF) Chain Reaction. Other known amplification methods which can be utilized herein include but are not limited to the so-called "NASBA" (nucleic acid sequence based amplification) or "3SR" (self-sustained sequence replication) technique described in PNAS USA 87: 1874-1878 (1990) and also described in Nature 350 (No. 6313): 91-92 (1991) and Mollasalehi et al., 2012, Anal Biochem, 425, 91-95; and target mediated amplification, as described by PCT Publication WO9322461 and PCT Publication WO2010/019898A1.

In some embodiments, AID nucleic acids can be detected using sequencing methods, e.g. high throughput sequencing, whole transcriptome shotgun sequencing or RNA-seq. RNA-seq can utilize any of a number of next-generation, commercially available sequencing technologies (e.g. 454 SEQUENCING™ or ILLUMINA™) to generate high-throughput sequencing of the entire transcriptome or portions thereof. RNA-seq is described, for example in Ryan et al. (2008). BioTechniques 45 (1): 81-94; Wang Z, et al. (2009). Nature Reviews Genetics 10 (1): 57-63; Maher C A, et al. (2009). Nature 458 (7234): 97-101; which are incorporated by reference herein in their entireties.

In another embodiment, AID nucleic acids can be detected using "self-sustained sequence replication." This is a method of nucleic acid amplification using target nucleic acid sequences which are amplified (replicated) exponentially in vitro under isothermal conditions by using three enzymatic activities essential to retroviral replication: (1) reverse transcriptase, (2) RNase H, and (3) a DNA-dependent RNA polymerase (Guatelli, et al. 1990, Proc. Natl. Acad. Sci. USA 87:1874). By mimicking the retroviral strategy of RNA replication by means of cDNA intermediates, this reaction accumulates cDNA and RNA copies of the original target. Substantially isothermal means that the temperature may be varied over the course of an approximately one hour reaction time within the temperature range of about 37° C. to 50° C. Alternatively, one temperature may be selected to carry out the entire reaction. Self-sustained sequence replication at 45° C. is preferred.

In another embodiment, AID nucleic acids can be detected using "transcription amplification". In this method of nucleic acid amplification, each cycle is composed of two steps. In the first step, a cDNA copy of a RNA or DNA target is made and in the second step, multiple RNA transcripts of each cDNA copy are generated (see, e.g., Kwoh (1989) Proc. Natl. Acad. Sci. USA 86: 1173).

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Nucleic acids corresponding to a DNA editing enzyme are immobilized on a chip which is then hybridized with labeled nucleic acids of a test sample obtained from a patient. Positive hybridization signal is obtained with the sample containing a DNA editing enzyme transcript. Methods of preparing DNA arrays and their use are well known in the art. (See, for example U.S. Pat. Nos. 6,618,6796; 6,379,897; 6,664,377; 6,451,536; 548, 257; U.S. 20030157485 and Schena et al. 1995, Science 20:467-470; Gerhold et al. 1999, Trends in Biochem. Sci. 24, 168-173; and Lennon et al. 2000, Drug discovery Today 5: 59-65, which are herein incorporated by reference in their entirety). Serial Analysis of Gene Expression (SAGE) can also be performed (See for example U.S. Patent Application 20030215858). To monitor mRNA levels, for example, mRNA is extracted from the biological sample to be tested, reverse transcribed, and fluorescent-labeled cDNA probes are generated. The microarrays capable of hybridizing to a DNA editing enzyme cDNA are then probed with the labeled cDNA probes, the slides scanned and fluorescence intensity measured. This intensity correlates with the hybridization intensity and expression levels. Quantitative PCR methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided, for example, in Innis et al. (1990), PCR Protocols, A Guide to Methods and Applications, Academic Press, Inc. N.Y.

DNA editing enzyme protein levels or DNA editing enzyme activity, can also be measured, in particular, when the biological sample is a fluid sample such as cell lysate. In one embodiment, levels of DNA editing enzyme protein can be measured by contacting the biological sample with an antibody moiety or protein-binding protein that specifically binds to a DNA editing enzyme, or to a fragment of a DNA editing enzyme. Formation of the antibody-DNA editing enzyme complex can then be detected as a measure of DNA editing enzyme levels. Antibodies which recognize a DNA editing enzyme (e.g. AID) can be obtained commercially or prepared according to the methods described elsewhere herein.

AID protein levels or AID activity can also be measured. In one embodiment, levels of AID protein are measured by contacting the biological sample with an antibody moiety or a protein-binding protein that specifically binds to AID, or to a fragment of AID. Formation of the antibody-AID complex is then detected as a measure of AID levels. Antibodies which recognize AID can be obtained commercially (ab59361, ab93596 or ab77401; AbCam Cambridge, Mass.) or prepared according to the methods described elsewhere herein. Tissues samples can be prepared as sections, for example as frozen or fixed sections and stained with an antibody. Liquid samples, can be analyzed for example in an ELISA or a flow cytometry analysis.

In one embodiment, the antibody moiety is detectably labeled. "Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. In the diagnostic and prognostic methods described herein that use antibody based binding moieties for the detection of AID, the level of AID present in the biological samples correlate to the intensity of the signal emitted from the detectably labeled antibody. In one preferred embodiment, the antibody-based binding moiety is detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes which can be used to detectably label the antibodies of the technology described herein include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection may also be accomplished using any of a variety of other immunoassays. For example, by radioactively labeling an antibody, it is possible to detect the antibody through the use of radioimmunology assays. The radioactive isotope can be detected by such means as the use of a gamma counter or a scintillation counter or by autoradiography. Isotopes which are particularly useful for the purpose of the technology described herein are $^{3}H$, $^{131}I$, $^{35}S$, $^{14}C$, and preferably $^{125}I$. It is also possible to label an antibody with a fluorescent compound. When the fluorescently labeled antibody is exposed to light of the proper wavelength, its presence can then be detected due to fluorescence. Among the most commonly used fluorescent labeling compounds are CYE dyes, fluorescein isothiocyanate, rhodamine, phycoerythrin, phycocyanin, allophycocyanin, o-phthaldehyde and fluorescamine. An antibody can also be detectably labeled using fluorescence emitting metals such as $^{152}Eu$, or others of the lanthanide series. These metals can be attached to the antibody using such metal chelating groups as diethylenetriaminepentaacetic acid (DTPA) or ethylenediaminetetraacetic acid (EDTA). An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, therometric acridinium ester, imidazole, acridinium salt and oxalate ester.

In one embodiment, the levels of AID protein is detected by immunoassays, such as enzyme linked immunoabsorbant assay (ELISA), Western blotting, immunocytochemistry or flow cytometry. Immunoassays such as ELISA, flow cytometry or RIA, which can be extremely rapid. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

The most common enzyme immunoassay is the Enzyme-Linked Immunosorbent Assay (ELISA). ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g. anti-AID) is linked to a solid phase (i.e. a microtiter plate) and exposed to a biological sample containing antigen (e.g. AID). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme-linked antibody reacts with a substrate to generate a colored reaction product that can be measured.

In a "competitive ELISA", antibody is incubated with a sample containing antigen (i.e. AID). The antigen-antibody mixture is then contacted with a solid phase (e.g. a microtiter plate) that is coated with antigen (i.e., AID). The more antigen present in the sample, the less free antibody that will be available to bind to the solid phase. A labeled (e.g., enzyme linked) secondary antibody is then added to the solid phase to determine the amount of primary antibody bound to the solid phase. In an "immunohistochemistry assay" a section of tissue or cells is tested for specific proteins by exposing the tissue to antibodies that are specific for the protein that is being assayed. An immunohistochemistry assay can include, but is not limited to, in situ immunofluorescence, or widefield epifluorescence microscopy, and immunofluorescence microscopy.

A "precipitation assay" or a "gel diffusion precipitation reaction" may also be used to detect AID protein. An antibody is incubated with a sample containing antigen (i.e. AID). A precipitate will form when the point of equivalence is reached. In a gel diffusion precipitation reaction, the antigen and antibody are introduced into an agar gel, typically at different points, and freely diffuse into the gel. When reactants are in contact at optimal proportions, a precipitate will form. Variations of the precipitation assay include but are not limited to, radial immunodiffusion, double diffusion gel precipitation and Ouchterlony double immunodiffusion. Quantitative precipitation assays are known to those skilled in the art (Basic Techniques in Biochemistry and Molecular Biology, Sharma and Sangha (Eds), I.K. International Publishers Pvt. Lt, New Delhi, India (2009); Essentials of Immunology and Serology, Stanley, J. Thomson, Albany, N.Y., (2002)).

The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). Alternatively, "radioimmunoassays" may be employed. A radioimmunoassay is a technique for detecting and measuring the concentration of an antigen using a labeled (e.g. radioactively or fluorescently labeled) form of the antigen or epitope. Examples of radioactive labels for antigens include $^3H$, $^{14}C$, and $^{125}I$. The concentration of antigen in a biological sample is measured by having the antigen or epitope in the biological sample compete with the labeled (e.g. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In some embodiments, the level of a DNA editing enzyme can be measured by using protein in situ array (PISA). Briefly, PISA involves an array surface comprising free or immobilized PCR DNA to template protein synthesis in a cell-free system, (e.g. rabbit reticulocyte extract) and the proteins undergo simultaneous immobilization through a tag sequence which combines with a capture reagent which is already pre-coated on the array surface. PISA is described, for example, in patent publication WO 02/14860, which is incorporated by reference herein in its entirety. In certain embodiments the DNA editing enzyme is AID.

In some embodiments, the level of a DNA editing enzyme can be measured by using quantitative in situ protein analyses, for example, AQUA™. AQUA™ is described, for example in Stemmann O., Zou H., Gerber S. A., Gygi S. P., Kirschner M. W.; Dual inhibition of sister chromatid separation at metaphase, Cell 2001 Dec. 14, 107: 715-726 and Keshishian, et al. 2007, Molecular & Cellular Proteomics 6.12, 2212-2229; which are incorporated by reference herein in their entireties. In certain embodiments the DNA editing enzyme is AID.

Other techniques may be used to detect a DNA editing enzyme, according to a practitioner's preference, based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Detectably labeled anti-DNA editing enzyme antibodies can then be used to assess a DNA editing enzyme levels, where the intensity of the signal from the detectable label corresponds to the amount of a DNA editing enzyme present. Levels can be quantitated, for example by densitometry. In certain embodiments the DNA editing enzyme is AID.

In addition, a DNA editing enzyme may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, and 20030077616, which are herein incorporated by reference. Mass spectrometry methods are well known in the art and have been used to quantify and/or identify biomolecules, such as proteins (see, e.g., Li et al. (2000), Tibtech 18:151-160; Rowley et al. (2000), Methods 20: 383-397; and Kuster and Mann (1998), Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000). In certain embodiments, a gas phase ion spectrophotometer is used. In certain embodiments the DNA editing enzyme is AID.

In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait). In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094. Detection of the presence of a DNA editing enzyme mRNA or protein will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to analyzing mass spectra. The mass spectrometers and their techniques are well known to those of skill in the art.

In some embodiments, the activity of a DNA editing enzyme can be measured by determined the overall mutation status in all or a portion of the genome of a cell. An overall mutation status at least 2% greater, e.g. 2% greater or more, 3% greater or more, 5% greater or more, 10% greater or more, or 20% greater or more than the overall mutation status in a reference cell can be indicative of an increased, elevated, and/or significant level of a DNA editing enzyme activity. In some embodiments, the level of hyper mutations can be determined. In some embodiments, the overall mutation status in the whole genome or a portion thereof can be determined using FISH, whole genome sequencing, high throughput sequencing, exome sequencing, hybridization, and/or PCR. In some embodiments the activity of a DNA editing enzyme can be measured by determining the level of hypermutations in the specific target genes including, but not limited to IGH, BCL6, MYC, BCL11A, CD93, PIM1 and/or PAX5. In certain embodiments the DNA editing enzyme is AID. The detection of hypermutations in the gene loci is indicative of AID activity. In some embodiments, a level of mutation in specific target genes including IGH, BCL6, MYC, BCL11A, CD93, PIM1 and/or PAX5 which is at least 2% greater, e.g. 2% greater or more, 3% greater or more, 5% greater or more, 10% greater or more, or 20% greater or more than the level of mutation in IGH, BCL6, MYC, BCL11A, CD93, PIM1 and/or PAX5 in a reference cell can be indicative of an increased, elevated, and/or significant level of AID activity.

In some embodiments the activity of a DNA editing enzyme is determined by using FISH analysis to detect DNA double strand breaks, e.g. DNA breakage detection fish (DBD-FISH) (Volpi and Bridger, BioTechniques, Vol. 45, No. 4, October 2008, pp. 385-409). In certain embodiments the DNA editing enzyme is AID.

In some embodiments the activity of a DNA editing enzyme is determined by using a phospho-H2AX assay (e.g. Rakiman et al., Advance Biotech 2008, 39-42; which is incorporated by reference herein in its entirety), 53BP1 assay (e.g. Schultz et al., Journal of Cell Biology 2000, 151:1381-1390; which is incorporated by reference herein in its entirety), or a RAD51 assay (e.g. Hochegger and Takeda (2006), Subcell Biochem., 40, 313-325; which is incorporated by reference herein in its entirety). In certain embodiments the DNA editing enzyme is AID.

As used herein, the phrase "subject in need of at least one inhibitor of DSB repair" can refer to a subject who is diagnosed with or identified as suffering from a cancer, the cells of which cancer have an increased level of a DNA editing enzyme protein or a DNA editing enzyme mRNA or a DNA editing enzyme activity. As used herein, the phrase "subject in need of at least one inhibitor of DSB repair" can also refer to a subject who is diagnosed with or identified as suffering from an autoimmune disease, the cells of which autoimmune disease have an increased level of a DNA editing enzyme protein or a DNA editing enzyme mRNA or a DNA editing enzyme activity. A subject in need of at least one inhibitor of DSB repair can be identified using any method used for determining the level of a mRNA or protein or a DNA editing enzyme activity present in a biological sample as described herein. Alternatively, the phrase "subject in need of at least one inhibitor of DSB repair" can refer to a subject who is diagnosed with or identified as suffering from a B-cell disease or autoimmune disorder or cancer. The cancer cells or B-cells of the subject can have an increased level of a DNA editing enzyme protein or a DNA editing enzyme mRNA or a DNA editing enzyme activity. Non-limiting examples of B-cell diseases include B cell cancers (e.g. lymphomas and leukemias), autoimmune diseases characterized by aberrant B cell proliferation, class switching, and/or activation. In some embodiments the autoimmune diseases are characterized by aberrant a DNA editing enzyme activity in cells. Autoimmune diseases with aberrant a DNA editing enzyme activity include, but are not limited to lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis, subacute cutaneous lupus erythematosus, cutaneous lupus erythematosus including chilblain lupus erythematosus, chronic arthritis, Sjogren's syndrome, autoimmune nephritis, autoimmune vasculitis, autoimmune hepatitis, autoimmune carditis, autoimmune encephalitis, inflammatory chronic rhinosinusitis, colitis, celiac disease, inflammatory bowel disease, Barrett's esophagus, inflammatory gastritis and autoimmune mediated hematological disease. In certain embodiments the DNA editing enzyme is AID.

In some embodiments, the methods described herein further comprise selecting a subject identified as being in need of an inhibitor of DSB repair. A subject in need of a DSB repair inhibitor can be selected based on the level of a DNA editing enzyme mRNA, or a DNA editing enzyme protein or a DNA editing enzyme activity. In certain embodiments the DNA editing enzyme is AID.

In some embodiments, a subject identified as being in need of an inhibitor of DSB repair may in addition to the increased level of or a DNA editing enzyme protein or a DNA editing enzyme mRNA or a DNA editing enzyme activity display hypermutations in IGH. In certain embodiments the DNA editing enzyme is AID.

Combination Therapies

It is contemplated that the therapeutic agents of the technology described herein can be administered together with any other therapy effective against one of the cancers or autoimmune disorders described herein. It is contemplated that the therapeutic agents of the technology described herein can be administered together with any other therapy effective against one of the cancers or autoimmune disorders described herein. When two or more therapeutic agents are administered together, they can be administered simultaneously or with some delay between administrations thereof (i.e., according to an optimized delivery schedule). In further embodiments, the pharmaceutical compositions of the technology described herein can comprise at least one DSB repair inhibitor and at least one additional pharmaceutical agent.

In some embodiments the pharmaceutical compositions of the technology described herein can comprise at least one DSB repair inhibitor and at least one Bruton's Tyrosine Kinase (BTK) inhibitor agent. BTK has been shown to be an inhibitor of the Fas/APO-1 (CD-95) death inducing signaling complex (DISC) in B-lineage lymphoid cells (Vassilev et al., J. Biol. Chem. 1998, 274, 1646-1656). BTK inhibitors result in reduction of lymph node tumor burden, but elevate circulating tumor burden. Genetic chemotherapy is effective in treating circulating tumor cells, and thus may be effective in combination with BTK inhibitors in controlling both lymph node and circulating disease It has also been discovered that BTK inhibitors are useful as chemosensitizing agents, and, thus, are useful in combination with genetic chemotherapy. Exemplary BTK inhibitor agents include ibrutinib (PCI-32765; 1-[(3R)-3-[4-amino-3-(4-phenoxyphenyl)pyrazolo[3,4-d]pyrimidin-1-yl]piperidin-1-yl]prop-2-en-1-one); AVL-291; AVL-292; PCI-45292; 6-phenyl-imidazo[1,2-a]pyridine; 6-phenyl-imidazo[1,2-b]pyridazine derivatives as described in U.S. Pat. No. 8,324,211; pyridinone and pyridazinone derivatives as described in U.S. Pat. No. 8,318,719; 3-amino-5-phenyl-1H-pyridin-2-one derivatives as described in U.S. Pat. No. 8,299,077; 1H-pyrazolo (3,4-d)pyrimidin-4-ylamine substitutes as described in U.S. Pat. No. 8,232,280; 3-phenyl-1H-pyrazolo-pyrimidin-4-ylamine substitutes as described in U.S. Pat. No. 8,236,812; compounds as described in U.S. Pat. No. 7,393,848; U.S. Pat. No. 7,405,295; U.S. Pat. No. 7,514,444; U.S. Pat. No. 7,625,880; U.S. Pat. No. 7,683,064; U.S. Pat. No. 7,732,454; U.S. Pat. No. 7,741,330; U.S. Pat. No. 7,825,118; U.S. Pat. No. 7,902,194; U.S. Pat. No. 7,906,509; U.S. Pat. No. 7,943,618; U.S. Pat. No. 7,960,396; U.S. Pat. No. 8,008,309; U.S. Pat. No. 8,067,395; U.S. Pat. No. 8,088,781; U.S. Pat. No. 8,124,604; US20130018032; US20130018060, and US20130035334, the disclosures of which are incorporated herein by reference thereto.

In some embodiments the pharmaceutical compositions of the technology described herein can comprise at least one DSB repair inhibitor and at least one Bcl-2 inhibitor agent. Bcl-2 inhibitors are pro-apoptotic and, when administered in combination with a DSB repair inhibitor, may further enhance the cancer apoptotic effect. Exemplary Bcl-2 inhibitor agents include ABT-199 (GDC-0199), navitoclax (ABT-263; (R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3-((trifluoromethyl)sulfonyl)phenyl)sulfonyl)benzamide), ABT-737 (Benzamide, 4-[4-[(4'-chloro[1,1'-biphenyl]-2-yl) methyl]-1-piperazinyl]-N-[[4-[[(1R)-3-(dimethylamino)-1-[(phenylthio)methyl]propyl]amino]-3-nitrophenyl]sulfonyl]-), obatoclax (GX15-070; 2-(2-((3,5-Dimethyl-1H-pyrrol-2-yl)methylene)-3-methoxy-2H-pyrrol-5-yl)-1H-indole), and TW-37 (5-(2-isopropylbenzyl)-N-(4-(2-tert-butylphenylsulfonyl)phenyl)-2,3,4-trihydroxybenzamide).

In some embodiments the pharmaceutical compositions of the technology described herein can comprise at least one DSB repair inhibitor and at least one Chk1 inhibitor agent. Chk1 is an ATP-dependent serine-threonine kinase and a key component in the DNA replication-monitoring checkpoint system activated by double-stranded breaks (DSBs). Chk1 contributes to all currently defined cell cycle checkpoints, including G1/S, intra-5-phase, G2/M, and the mitotic spindle checkpoint. As used herein, Chk1 inhibitors are compounds that are capable of at least partially abrogating at least one cell cycle checkpoint activity of the Chk1 protein. Combination treatment with a DNA repair inhibitor and Chk1 inhibitor could result in synergistic cell arrest or killing. Exemplary Chk1 inhibitor agents include AZD7762 (1-(2-((S)-piperidin-3-ylcarbamoyl)-5-(3-fluorophenyl) thiophen-3-yl)urea), LY2603618 (IC-83; (S)-1-(5-bromo-4-methyl-2-(morpholin-2-ylmethoxy)phenyl)-3-(5-methyl-pyrazin-2-yl)urea), CHIR-124 ((S)-3-(1H-benzo[d] imidazol-2-yl)-6-chloro-4-(quinuclidin-3-ylamino)quinolin-2(1H)-one), SCH900776 (6-bromo-3-(1-methyl-1H-pyrazol-4-yl)-5-((R)-piperidin-3-yl)pyrazolo[1,5-a] pyrimidin-7-amine), and PF 477736 (Cyclohexaneacetamide, α-amino-N-[5,6-dihydro-2-(1-methyl-1H-pyrazol-4-yl)-6-oxo-1H-pyrrolo[4,3,2-ef][2,3] benzodiazepin-8-yl]-, (αR)-), UCN-01 (KW-24101; 7-Hydroxystaurosporine; from Kyowa Hakko Kogyo Co., Ltd., Tokyo, Japan and Keryx Biopharmaceuticals, Inc., New York, N.Y.), Lilly/ICOS IC83/LY2603618 (from Eli Lilly, Indianapolis, Ind.), XL-844 (EXEL-9844 from Exelixis), PF-394691 (from Pfizer), PF-473336 (from Pfizer) and compounds as described in U.S. Pat. No. 8,093,244; U.S. Pat. No. 7,560,462; U.S. Pat. No. 7,550,477; U.S. Pat. No. 7,501,435, U.S. Pat. No. 7,485,649, US 2007/0083044, US 2007/0082900, US 2007/0105864 and US 2007/0117804, the disclosures of which are incorporated herein by reference thereto.

In some embodiments the pharmaceutical compositions of the technology described herein can comprise at least one DSB repair inhibitor and at least one MDM2 inhibitor agent. The term "a MDM2 inhibitor", as used herein, relates to a compound which targets, decreases or inhibits the interaction of MDM2 and the p53 tumor suppressor. An example of a MDM2 inhibitor includes, but is not limited to, trans-4-iodo, 4'-boranyl-chalcone; Nutlin-3 (4-(4,5-bis(4-chlorophenyl)-2-(2-isopropoxy-4-methoxyphenyl)-4,5-dihydro-1H-imidazole-1-carbonyl)piperazin-2-one); NSC-207895 (XI-006; 2,1,3-Benzoxadiazole, 4-(4-methyl-1-piperazinyl)-7-nitro-, 3-oxide); RG7112 (nutlin-3a); cis-imidazoline analogs known as nutlins (nutlin-1, nutlin-2, nutlin-3) and compounds as described in U.S. Pat. No. 7,737,174; U.S. Pat. No. 8,288,377; U.S. Pat. No. 8,222,288; U.S. Pat. No. 7,834,016; US20110319378; and WO2012121662, the disclosures of which are incorporated herein by reference thereto.

In some embodiments the pharmaceutical compositions of the technology described herein can comprise at least one DSB repair inhibitor and at least one WEE1 inhibitor agent. A Wee1 kinase is a tyrosine kinase that participates in the G2 checkpoint of a cell cycle. Wee1 phosphorylates Cdc2 (Cdk1) tyrosine 15 that takes part in the progress to the M stage from the G2 stage in a cell cycle, thereby inactivating Cdc2 and temporarily stopping the cell cycle at the G2 stage (McGowan and Russell 1993 The EMBO Journal, 12, 75-85). It has been reported that the Wee1 expression reduction by RNA interference or the Wee1 inhibition by compounds may increase the sensitivity of cancer cells to adriamycin, X ray and gamma ray (Wang et al. 2004, Cancer Biology & Therapy, 3, 305-313; Wang et al. 2001, Cancer Research, 61, 8211-8217). The treatment with a DNA repair inhibitor combined with a Chk1 inhibitor could result in enhanced sensitivity of cancer cell to the treatment. It is considered that a Wee1 inhibitor may inhibit the G2 checkpoint function of p53-depleted cancer cells, thereby enhancing the sensitivity of the cells to a DSB repair inhibitor. Exemplary WEE1 inhibitor agents include MK-1775 (2-allyl-1-(6-(2-hydroxypropan-2-yl)pyridin-2-yl)-6-(4-(4-methylpiperazin-1-yl)phenylamino)-1,2-dihydropyrazolo[3,4-d]pyrimidin-3-one); PD0166285 (6-(2,6-Dichlorophenyl)-2-[[4-[2-(diethylamino)ethoxy]phenyl]amino]-8-methylpyrido[2,3-d]pyrimidin-7(8H)-one dihydrochloride), and compounds as described in US Application 2005/0250836, WO2003/091255, each of which is herein incorporated by reference in its entirety.

In some embodiments the pharmaceutical compositions of the technology described herein can comprise at least one DSB repair inhibitor and at least one poly ADP ribose polymerase (PARP) inhibitor agent. Poly(ADP-ribose)polymerase (PARP) or poly(ADP-ribose)synthase (PARS) has an essential role in facilitating DNA repair, controlling RNA transcription, mediating cell death, and regulating immune response. PARP inhibitors effectively target cells with reduced capacity for homologous recombination repair, such as BRCA1 or BRCA2-defective breast or ovarian cancer. Treatment with a DSB repair inhibitor may render cells with intact homologous recombination susceptible to PARP inhibitors, may enhance the efficacy of PARP inhibitors in homologous recombination deficient cancers, and may circumvent cases of acquired resistance to PARP inhibitors. An example of a PARP inhibitor includes, but is not limited to Iniparib (BSI 201; 4-iodo-3-nitrobenzamide), Olaparib (AZD-2281; KU-59436; 4-[(3-[(4-cyclopropylcarbonyl)piperazin-4-yl]carbonyl)-4-fluorophenyl]methyl(2H) phthalazin-1-one), Rucaparib (AG014699, PF-01367338; 2-{4-[(methylamino)methyl]phenyl}-1,3,4,5-tetrahydro-6H-azepino[5,4,3-cd]indol-6-one), Veliparib (ABT-888; 2-((R)-2-Methylpyrrolidin-2-yl)-1H-benzimidazole-4-carboxamide); CEP-8983; CEP-9722; MK-4827 (Niraparib; 2-{4-[(3S)-Piperidin-3-yl]phenyl}-2H-indazole-7-carboxamide); BMN-673 (LT-673; (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one); LT-674; LT-628; 3-aminobenzamide (INO-1001; 3-AB); PD128763 (3,4-dihydro-5-methyl-1(2H)-isoquinolinone); NU1025 (8-Hydroxy-2-methyl-4(3H)-quinazolinone); DR 2313 (1,5,7,8-Tetrahydro-2-methyl-4H-thiopyrano[4,3-d]pyrimidin-4-one); UPF 1069 (5-(2-Oxo-2-phenylethoxy)-3,4-dihydroisoquinolin-1(2H)-one); EB 47 (5'-Deoxy-5'-[4-[2-[(2,3-Dihydro-1-oxo-1H-isoindol-4-yl)amino]-2-oxoethyl]-1-piperazinyl]-5'-oxoadenosine dihydrochloride); E7016 (Benzopyrano[4,3,2-de]phthalazin-3(2H)-one, 10-[(4-hydroxy-1-piperidinyl)methyl]-); 4-HQN (4-(1H)-Quinazolinone); ABT-767 and compounds as described in Griffin et al 1998, J. Med. Chem. 41, 5247; Skalitzky et al. 2003, J. Med. Chem. 46:210-213; Zaremba et al. 2007, Anti-Cancer Agents in Medicinal Chemistry 7, 515; Lewis et al. 2007, Curr Opin. Investigational Drugs 8, 1061; Guha 2011, Nature Biotechnology 29, 373-374; Rouleau et al. 2010, Nature Reviews Cancer 10, 293-301; Miknyoczki et al., 2007 Mol Cancer Ther, 6 (8), 2290-2302; Pellicciari et al. 2008, Chem. Med. Chem 3, 91; Jones et al., 2009, J Med Chem, 52(22), 7170-7185; Mason et al. 2008, Invest New Drugs, 26(1), 1-5; Ferraris et al., 2010, J. Med. Chem. 53 4561; US patent applications: US2006/0229289; US20070259937; US20120309717; US20130011365; US patents: U.S. Pat. No. 8,372,987; U.S. Pat. No. 8,362,030; U.S. Pat. No. 8,236,802; U.S. Pat. No. 8,217,070; U.S. Pat. No. 8,183,250; U.S. Pat. No. 8,088,760; international patent applications: WO 01/85686; WO 00/42040; WO 00/39070; WO 00/39104; WO 99/11623; WO 99/11628; WO 99/11622; WO 99/59975; WO 99/11644; WO 99/11945; WO 99/11649; and WO 99/59973, each of which is herein incorporated by reference in its entirety.

It is contemplated that the therapeutic agents of the technology described herein can be administered together with any other therapy effective against one of the autoimmune disorder described herein. It is contemplated that the therapeutic agents of the technology described herein can be administered together with any other therapy effective against any of the autoimmune disorders described herein. When two or more therapeutic agents are administered together, they can be administered simultaneously or with some delay between administrations thereof (i.e., according to an optimized delivery schedule). In further embodiments, the pharmaceutical compositions of the technology described herein can comprise at least one DSB repair inhibitor and at least one additional pharmaceutical agent.

In some embodiments the pharmaceutical compositions of the technology described herein can comprise at least one DSB repair inhibitor and at least one interleukin-1 receptor-associated kinase 4 (IRAK-4) inhibitor agent. An example of an IRAK-4 inhibitor includes, but is not limited to ND-346, ND-2110 and ND-2158 (Nimbus Discovery), and compounds as described in Kim et al., J. Exp. Med. 2007 204(5), 1025-1036; Lebakken et al., J. Biomol. Screen. 2007, 12(6), 828-841; Maschera et al., Biochem. J. 1999, 339, 227-231; Song et al., Mol. Immunol. 2009, 46, 1458-1466; US Application US20120283238; U.S. Pat. No. 8,293,923, each of which is herein incorporated by reference in its entirety.

Methods of Treating Cancers Characterized by Abnormal Expression of DNA Editing Enzymes As described above herein, some embodiments of the invention relate to methods of treatment comprising (a) selecting a subject having cells that express a DNA editing enzyme, e.g. activation-induced cytidine deaminase (AID); and (b) administering a therapeutically effective amount of an inhibitor of double strand break repair to the subject.

Some embodiments of the invention relate to methods of treatment comprising (a) selecting a subject having cells that express an elevated level of DNA editing enzyme, e.g. activation-induced cytidine deaminase (AID); and (b) administering a therapeutically effective amount of an inhibitor of double strand break repair to the subject wherein an elevated level of a DNA editing enzyme is a level of a DNA editing enzyme that is higher than the level of a DNA editing enzyme in cells of the same type from a healthy individual. In some embodiments, the methods of treatment comprise (a) selecting a subject having B cells that express a DNA editing enzyme; and (b) administering a therapeutically effective amount of an inhibitor of double strand break repair to the subject. In some embodiments, the methods of treatment comprise (a) selecting a subject having B cells that express an elevated level of a DNA editing enzyme; and (b) administering a therapeutically effective amount of an inhibitor of double strand break repair to the subject; wherein an elevated level of a DNA editing enzyme is a level of a DNA editing enzyme that is higher than the level of a DNA editing enzyme in B cells from a healthy individual. In some embodiments, the cells that express a DNA editing enzyme are cancerous cells. In some embodiments, the B cells that express a DNA editing enzyme are cancerous cells. In some embodiments the DNA editing enzyme is AID. As used herein, the term "cancerous cell" refers to cells that proliferate in an unregulated manner. In some embodiments, a subject having cancerous B cells that express elevated levels of a DNA editing enzyme can be a subject having or diagnosed as having a B-cell cancer (e.g. B cell lymphoma or leukemia), as described below herein. In some embodiments the DNA editing enzyme is AID. In some embodiments the high level of a DNA editing enzyme is detected in blood, serum or a biopsy sample.

In certain embodiments, the methods described herein selectively treat B-cell neoplasms, lymphomas, and leukemias by exploiting recombination and DNA repair systems to induce tumor cell self-destruction. This approach takes advantage of the finding that the DNA editing enzyme induces widespread genomic breaks and cell death in primary B-cells with diminished homologous recombination ability. As described herein, the inventors have determined that where a population of cells characterized by increased expression of AID is treated with an inhibitor of DSB repair, cell death results. Accordingly, provided herein are methods for treating patients with cancers having high DNA editing enzyme, e.g. AID, expression with an inhibitor of DSB repair.

In certain embodiments, the cancer to be treated is a type with high expression of a DNA editing enzyme. In certain embodiments, the cancer to be treated is a B-cell neoplasm. In certain embodiments, the cancer to be treated is a lymphoma. In certain embodiments, the cancer to be treated is Burkitt's lymphoma, follicular lymphoma, MALT lymphoma, multiple myeloma, small lymphocytic lymphoma, lymphoplasmacytic lymphoma, plasma cell myeloma, large B-cell lymphoma and/or T-cell lymphoma. Lymphoma is a malignancy in the lymphatic cells of the immune system (e.g. B cells, T cells, or natural killer (NK) cells). Lymphomas often originate in the lymph nodes and present as solid tumors. They can metastasize to other organs such as the brain, bone, or skin. Extranodal sites are often located in the abdomen. Lymphomas are closely related to the lymphoid leukemias and in some cases a particular form of cancer is categorized as both a lymphoma and a leukemia.

Several classification systems exist for lymphomas with the most recent being the World Health Organization classification developed in 2001 and updated in 2008 (Jaffe, E. S., et al., (Eds.) World Health Organization Classification of Tumors, Pathology and Genetics of tumors of hematopoietic and lymphoid tissues IARC Press: Lyon, France 2001). The WHO system divides lymphomas into three primary categories; mature B-cell lymphomas, mature T-cell lymphomas and mature NK cell lymphomas. Included in separate categories are Hodgkin lymphomas (comprised of abnormal B cells) and a number of other less common lymphomas.

Lymphoma can be diagnosed by a biopsy. Tissue obtained from the biopsy is subjected to histological examination to determine the presence, type, and arrangement of malignant cells. The cells are also tested to determine if they are lymphocytes and if so, what type of lymphocyte. Additional tests to determine the scope of the lymphoma and where it is located in the body can include additional biopsies, nuclear medicine, X-rays, CT scans or MRI (see US Patent Publication US2003/0129665). Hodgkin's lymphoma can be diagnosed by the presence of Reed-Sternberg cells in addition to other abnormal cell patterns characteristic of the disease. Markers and histological signs that differentiate each type of lymphoma are known to those skilled in the art (Jaffe, E. S., et al. (Eds.) World Health Organization Classification of Tumors, Pathology and Genetics of tumors of hematopoietic and lymphoid tissues IARC Press: Lyon, France 2001).

In certain embodiments the cancer to be treated is a leukemia. Leukemias are malignant neoplasms of hematopoietic tissues. Leukemias are categorized into two predominant forms: chronic and acute. Acute leukemia is characterized by the rapid increase of immature blood cells, which impairs the ability of the bone marrow to produce healthy blood cells. Chronic leukemia is characterized by the build up of relatively mature, yet abnormal, white blood cells. Abnormal cells are produced at a much higher rate than normal cells and result in the accumulation of abnormal white blood cells in the blood. Notwithstanding these classifications, however, the pathological impairment of normal hematopoiesis is the hallmark of all leukemias.

Further, leukemias are subdivided according to which blood cell is affected. For example, leukemias can be divided into lymphoblastic or lymphocytic leukemias and myeloid or myelogenous leukemias. In lymphoblastic or lymphocytic leukemias, a pre-lymphocyte cell is typically affected, which impairs the infection-fighting properties of cells derived from lymphocytes. Most lymphocytic leukemias involve B cells, a specific subtype of lymphocyte. In myeloid or myelogenous leukemias, white blood cell precursors are often affected as are some other types of red cells, and platelets. Thus, leukemias can be generally subdivided into four categories: acute lymphoblastic leukemia (ALL), chronic lymphocytic leukemia (CLL), and chronic myelogeneous leukemia (CML). Specific manifestations of each subtype can involve B cells. In some embodiments, the term leukemia includes Burkitt's leukemia; chronic lymphocytic leukemia (CLL), acute myelogenous leukemia (AML); B-cell acute lymphocytic leukemia (B-ALL) and T-cell acute lymphoblastic leukemia (T-ALL). In one embodiment, the term leukemia as described herein also encompasses hairy cell leukemia, which is often considered to be outside of the above-described classification scheme.

Leukemias can be diagnosed by any method known in the art. Typically, a complete blood count (CBC) test is initially performed. A CBC counts the number of white blood cells, red blood cells, and platelets in a blood sample. A sample of blood with high numbers of white blood cells and low levels of red blood cells or platelets can indicate leukemia, and abnormal liver and kidney function tests will indicate if the leukemia has affected those organs. Flow cytometry can also be used for a more precise diagnosis, for example, by using mature myeloid markers such as CD11b and Gr-1 to determine cell type, cell number, and/or cell morphology. Markers and histological signs that differentiate each type of cancer are known to those skilled in the art (Jaffe, E. S., et al. (Eds.) World Health Organization Classification of Tumors, Pathology and Genetics of tumors of hematopoietic and lymphoid tissues IARC Press: Lyon, France 2001). For AML, there would be a drop in red blood cells, platelets, and normal white blood cells. These symptoms include fatigue, shortness of breath, easy bruising and bleeding, and increased risk of infection. The symptoms of are caused by replacement of normal bone marrow with leukemic cells, which are mainly immature abnormal white blood cells that accumulate in the bone marrow and interfere with the production of normal blood cells.

In certain embodiments the cancer to be treated is B-cell neoplasms, B-cell leukemia, B-cell acute lymphoblastic leukemia, chronic lymphocytic leukemia, chronic myelogenous leukemia, Burkitt's leukemia, acute myelogenous leukemia and/or T-ALL. The maturation of B cells most typically ceases or substantially decreases when the foreign antigen has been neutralized. Occasionally, however, proliferation of a particular B cell will continue unabated; such proliferation can result in a cancer referred to as "B-cell lymphoma" or a "B-cell leukemia." In certain embodiments the cancer to be treated is chronic lymphocytic leukemia (CLL) or chronic myelogenous leukemia (CML).

In one embodiment, a bone marrow biopsy is used to assist in diagnosis of leukemia. A bone marrow biopsy sample can include bone marrow tissue or a mixture of bone marrow and bone. In another embodiment, cytogenetics is used to examine the chromosomes in individual cells. Cytogenetic testing uses a sample taken from a blood draw or a bone marrow or lymph node biopsy. The sample's chromosomes are microscopically examined for abnormalities that indicate damage to the cells' DNA and to support a diagnosis of leukemia. In another embodiment, a spinal tap can be used in the diagnosis of leukemia. Typically, a sample of cerebrospinal fluid is taken from the lower back (the lumbar area). The fluid sample is then checked for leukemia cells and other abnormalities. MRIs (Magnetic Resonance Imaging), CT (Computerized Axial Tomography) scans, and X-rays are imaging techniques that can be used to support a diagnosis of leukemia.

In certain embodiments the cancer to be treated is a plasma cell neoplasm. Examples for plasma cell neoplasms include multiple myeloma; plasma cell myeloma; plasma cell leukemia and plasmacytoma.

Any cancer characterized by high levels of a DNA editing enzyme expression can be treated with an inhibitor of DSB repair. For example, sarcomas, epithelial cell cancer (carcinomas), colon cancer, gastric cancer, intestinal cancer, liver cancer, hepatocellular cancer, breast cancer, thyroid cancer, esophageal cancer, lung cancer, brain cancer, head and neck cancer, melanoma, renal cancer, prostate cancer, hemangioma, rhabdomyosarcoma, chondrosarcoma, osteosarcoma, fibrosarcoma and cholangiocarcinoma may be characterized by high levels of a DNA editing enzyme expression, e.g. AID. In certain embodiments the cancer to be treated is colon cancer, liver cancer, gastric cancer, intestinal cancer, breast cancer, lung cancer, thyroid cancer and/or cholangiocarcinoma. Any of these cancers can be diagnosed by any method known in the art. Biopsies, colonoscopies, stool samples, imaging or other means known in the art can be used to detect the presence of tumors and/or polyps. Tissue obtained by these methods is subjected to histological examination to determine the presence, type, and arrangement of malignant cells. Markers and histological signs that differentiate each type of lymphoma are known to those skilled in the art (Diagnostic Histopathology of Tumors, Fletcher, C. D. M. (Ed.), $3^{rd}$ Edition, Churchill Livingstone Elsevier, China (2007); Methods of Cancer Diagnosis, Therapy and Prognosis. Hayat, M. A. (Ed), (Vol 3), Springer (2009)). Additional tests to determine the scope of the cancer and where it is located in the body can include additional biopsies, nuclear medicine, X-rays, CT scans or MRI.

In certain embodiments, treating a patient having a cancer with high DNA editing enzyme expression, e.g. AID, with a inhibitor of DSB repair decreases an indicator, marker, symptom, severity, metastasis, recurrence and/or tumor size of the cancer by at least 10%, e.g., by at least 20%, at least 30%, at least 50%, at least 75%, at least 100%, at least 200% or more as compared to the indicator, marker, symptom, severity, metastasis, recurrence and/or tumor size prior to treatment with the inhibitor of DSB repair or as compared to patients not receiving treatment with a inhibitor of DSB repair.

The technology described herein can relate to the use of at least one inhibitor of DSB repair and compositions comprising at least one such inhibitor of DSB repair for the treatment of a cancer having increased levels of AID protein or mRNA. For example, a composition containing an inhibitor of DSB repair is used to reduce the tumor size, tumor growth, cancer cell count, cancer cell expansion or metastasis of a cancer. For example, a composition containing a inhibitor of DSB repair is used to reduce the severity, duration, or number of symptoms associated with one of the following, which are offered by way of example only; a B-cell cancer, a leukemia, a lymphoma, a colon cancer, a liver cancer, a gastric cancer, an intestinal cancer, a breast cancer, a lung cancer, a thyroid cancer, a brain cancer, a renal cancer, a melanoma, a prostate cancer or a cholangiocarcinoma.

The technology described herein can also relates to the use of at least one inhibitor of RAD51-mediated strand exchange repair or a composition comprising an inhibitor of RAD51-mediated strand exchange repair to increase life expectancy or increase time to remission in patients treated with the inhibitor of DSB repair as compared to patients not treated with the inhibitor of DSB repair.

In certain embodiments the inhibitor of DSB repair is contained in a composition comprising the inhibitor of DSB repair and a pharmaceutically acceptable carrier. In further embodiments the inhibitor of DSB repair can be contained in a composition comprising a pharmaceutically acceptable carrier and another pharmaceutically effective compound.

The pharmaceutical compositions of the technology described herein can be administered alone or in combination with other therapies, including without limitation immunotherapy or immunotherapeutic agents, or other therapies which can be beneficial to patients with cancer or combinations thereof. It is contemplated that the therapeutic agents of the technology described herein can be administered together with any other therapy effective against one of the cancers described herein. When two or more therapeutic agents are administered together, they can be administered simultaneously or with some delay between administrations thereof (i.e., according to an optimized delivery schedule). In further embodiments, the pharmaceutical compositions of the technology described herein can comprise at least one DSB repair inhibitor and at least one additional pharmaceutical agent.

As used herein, the term "immunotherapy" refers to treatment of a subject with an antibody or antibody-based therapeutic. As used herein, immunotherapy can be passive or active. Passive immunotherapy, as defined herein, is the passive transfer of antibody to a subject (patient). Active immunization is the induction of antibody and/or T-cell responses in a subject (patient).

Exemplary immunotherapy agents include bevacizumab (Avastin®), Alemtuzumab (Campath®), cetuximab (Erbitux), Ibritumomab tiuxetan (Zevalin), Panitumumab (Vectibix), rituximab (Rituxan®), and tositumomab with $^{131}$I (Bexxar®, Corixia Corp.). Rituximab works by selectively depleting CD20⁺ B cells. The therapeutic effectiveness of rituximab is described in Collins-Burow et al., Rituximab and its Role as Maintenance Therapy in non-Hodgkin Lymphoma, *Expert Rev Anticancer Ther* 7(3):257-73 (2007); Marcus et al., The Therapeutic Use of Rituximab in non-Hodgkin's Lymphoma, *Eur J Haemotal Suppl* (67): 5-14 (2007); Plosker et al., Rituximab: A Review of its Use in non-Hodgkin's Lymphoma and Chronic Lymphocytic Leukaemia, *Drugs* (2003), which are hereby incorporated by reference in their entirety. Bevacizumab (Avastin®, Genentech/Roche) blocks angiogenesis, and is used to treat various cancers, Cetuximab (IMC-C225; Erbitux®) is a chimeric (mouse/human) monoclonal antibody, against epidermal growth factor receptor (EGFR) inhibitor, given by intravenous infusion for treatment of metastatic colorectal cancer and squamous cell carcinoma of the head and neck. Ibritumomab tiuxetan (Zevalin), is a monoclonal antibody radioimmunotherapy treatment for some forms of B cell non-Hodgkin's lymphoma and binds to the CD20 antigen. Panitumumab is a fully human monoclonal antibody specific to the epidermal growth factor receptor (also known as EGF receptor, EGFR, ErbB-1 and HER1) for the treatment of colorectal cancer.

A further form of therapy for some cancers described herein is stem cell transplantation.

In some embodiments, the pharmaceutical compositions of the technology described herein can be administered after or before other therapies, including without limitation, immunotherapy agents, chemotherapy agents, radiation treatments or other therapies which can be beneficial to patients with cancer or combinations thereof.

In some embodiments, a subject is administered a cycle of treatment comprising administration of a composition comprising a DSB repair inhibitor as described herein. The subject is then administered a cycle of treatment comprising administration of another chemotherapy, immunotherapy, radiation or other therapy which can be beneficial to patients with cancers or combinations thereof. Each cycle of treatment can comprised 1 or more administrations of a composition or therapeutic, i.e. 1 administration, 2 administrations, 3 administrations, 5 administrations, 10 administrations, 20 administrations or more. Each cycle of treatment can last at least 1 day, i.e. at least 1 day, at least 2 days, at least 1 week, at least 2 weeks, at least 3 weeks, at least 4 weeks, at least 6 weeks or more. In some embodiments, there is a hiatus or break between the cycles of treatment which can last at least 1 day, i.e. at least 1 day, at least 2 days, at least 1 week, at least 2 weeks, at least 3 weeks, at least 4 weeks, at least 6 weeks or more. A course of treatment comprising a cycle of treatment with a DSB repair inhibitor as described herein, optionally a break, and a cycle of treatment with another chemotherapy, immunotherapy, radiation or other therapy which can be beneficial to patients with cancers or combinations thereof, and optionally a second break can be repeated in part or in whole. In some embodiments, the cycle of treatment with a DSB repair inhibitor is the second cycle and the other anti-cancer therapy is used in the first cycle. In some embodiments, the other chemotherapy, immunotherapy, radiation or other therapy which can be beneficial to patients with cancers or combinations thereof comprises a therapy which causes damage to the subject's DNA. In some embodiments, the other chemotherapy, immunotherapy, radiation or other therapy which can be beneficial to patients with cancers or combinations thereof comprises doxorubicin. In some embodiments, the other chemotherapy, immunotherapy, radiation or other therapy which can be beneficial to patients with cancers or combinations thereof comprises fludarabine.

Other therapies include, without limitation, chemotherapies may be done before, during or after the methods described herein. In one embodiment, the chemotherapy is administered before or after, but not during, treatment with a composition or method as described herein. Non-limiting examples of chemotherapies include radiation or treatment with chemotherapy agents such as actinomycin, amsacrine (Amsidine®), anthracyclines, bleomycin (Blenoxane®), busulfan, camptothecin, carboplatin (Paraplatin®), chlorambucil (Leukeran®), cisplatin, cyclophosphamide (Cytoxan®), cladribine, cytarabine (Cytosar-U®), cytoxan, dacarbazine (DTIC-Dome®), dactinomycin, daunorubicin, dexamethasone (Decadron®), docetaxel, doxorubicin (Adriamycin®), epirubicin, etoposide (Etopophos®), fludarabine (Fludara®), hexamethylmelamineoxaliplatin, ifosfamide (Ifex®), iphosphamide, melphalan, merchlorethamine, methotrexate, mitomycin, mitoxantrone, nitrosourea, paclitaxel, plicamycin, prednisone, procarbazine, teniposide, triethylenethiophosphoramide, etoposide (VPI6), vincristine (Oncovin®), vinblastine, bendamustine (Ribomustin and Treanda), CHOP therapy, monoclonal antibodies and inhibitors of the c-myc gene, DNA methyltransferase, proteasomes and cyclin-dependent kinases.

Chemotherapeutics can include agents which induce DNA damage. Non-limiting examples of such agents can include alkylating agents, nitrosourea, anti-metabolites, plant alkaloids, plant extracts, or radioisotopes.

Also included are courses of therapy which include, but are not limited to, 1) the CODOX-M/IVAC regimen (Magrath protocol)—two cycles of CODOX-M (cyclophosphamide, vincristine, doxorubicin and high-dose methotrexate) alternating with IVAC (ifosfamide, etoposide and high-dose cytarabine), 2) three cycles of CODOX-M. Also included are modified versions of such combination therapies such as the adapted Magrath protocols of the United Kingdom Lymphoma Group and the Dana-Farber Cancer Institute.

Methods of Treating Autoimmune Disorders

As described above herein, some embodiments of the invention relate to methods of treatment comprising (a) selecting a subject having cells that express an elevated level of activation-induced cytidine deaminase (AID); and (b) administering a therapeutically effective amount of an inhibitor of double strand break repair to the subject; wherein an elevated level of AID is a level of AID that is higher than the level of AID in cells of the same type from a healthy individual. In some embodiments, the cells that express an elevated level of AID are autoimmune cells. As used herein, "autoimmune cell" or "autoreactive cell" refers to immune cells that have activity towards and/or recognize cells or biological components of the organism from which the cell is derived. Examples of cells which can be autoimmune cells include, but are not limited to, adult splenocytes, T cells, and B cells. In some embodiments, the subject can be a human subject.

In some embodiments, the methods of treatment comprise (a) selecting a subject having B cells that express an elevated level of activation-induced cytidine deaminase (AID); and (b) administering a therapeutically effective amount of an inhibitor of double strand break repair to the subject; wherein an elevated level of AID is a level of AID that is higher than the level of AID in B cells from a healthy individual. In some embodiments, the B cells that express an elevated level of AID are B cells associated with autoimmune disease. As used herein, the term "B cell associated with autoimmune disease" refers to B cells with abnormal function, behavior, and/or proliferation in a particular autoimmune disease. In some embodiments, the B cells associated with autoimmune disease can be B cells which cause the disease due to their abnormal function, behavior, and/or proliferation. In some embodiments, the B cells associated with autoimmune disease can be B cells which cause one or more symptoms of an autoimmune disease due to their abnormal function, behavior, and/or proliferation. In some embodiments, a subject having B cells associated with an autoimmune disease can be a subject having or diagnosed as having an autoimmune disease characterized or caused by B cells with abnormal function, behavior, and/or proliferation. By way of non-limiting example, in systemic lupus erythematosus, a subject's B cells abnormally produce antibodies specific for auto-antigens and in rheumatoid arthritis, a subject's B cells interact abnormally with the subject's T cells.

In certain embodiments, the methods described herein selectively treat autoimmune diseases by exploiting lymphoid recombination systems to induce self-destruction of diseased B-cells while sparing normal cells. This approach takes advantage of the finding that the B-cell recombinase AID induces widespread genomic breaks and cell death in primary B-cells with diminished homologous recombination ability. As described herein, it has been determined that where a population of cells characterized by increased expression of a DNA editing enzyme, e.g. AID is treated with an inhibitor of DSB repair, cell death results. Accordingly, provided herein are methods for treating patients with autoimmune diseases characterized by aberrant B cell proliferation, class switching, or activation. In some embodiments, the autoimmune disease can be characterized by increased B cell proliferation, class switching, or activation. In some embodiments, the autoimmune disease can be characterized by having B cells with high AID expression. In some embodiments, the method relates to treating a subject with an autoimmune disease and cells with high DNA editing enzyme expression with a DSB repair inhibitor. In some embodiments, the method relates to treating a subject with an autoimmune disease and B cells with high AID expression with a DSB repair inhibitor. In certain embodiments, the autoimmune disease to be treated is a type with B cells having high expression of AID. Autoimmune diseases known to be characterized by aberrant B cell proliferation, class switching and/or activation include, but are not limited to lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis; discoid lupus; subacute cutaneous lupus erythematosus; cutaneous lupus erythematosus including chilblain lupus erythematosus; chronic arthritis; Sjogren's syndrome; autoimmune nephritis; autoimmune vasculitis; autoimmune hepatitis; autoimmune carditis; autoimmune encephalitis; and autoimmune mediated hematological disease. In certain embodiments, autoimmune diseases are characterized by aberrant expression of a DNA editing enzyme. In certain embodiments, the autoimmune disease to be treated is Crohn's disease, ulcerative colitis, vasculitis; ankylosing spondylitis; Behçet's disease; paraneoplastic autoimmunity or dermatomyositis. In some embodiments, the autoimmune disease to be treated according to the methods described herein is an autoimmune disease characterized by aberrant B cell proliferation.

Lupus or lupus erythematosus or systemic lupus erythematosus (SLE) is an autoimmune disorder that can cause chronic inflammation in various parts of the body, especially the skin, joints, blood, and kidneys. The body's immune system normally makes proteins called antibodies to protect the body against viruses, bacteria, and other foreign materials (i.e., antigens). In an autoimmune disorder such as lupus, or lupus erythematosus or SLE, the immune system loses the ability to discriminate between antigens and its own cells and tissues and can thus make antibodies directed against its own cells and tissues to form immune complexes. These immune complexes can build up in the tissues and cause inflammation, injury to tissues and/or pain. The three most common types of lupus include systemic lupus erythematosus (SLE), cutaneous lupus erythematosus (CLE) and drug-induced lupus. Additional types of autoimmune disorders include, but are not limited to subacute cutaneous lupus erythematosus, cutaneous lupus erythematosus including chilblain lupus erythematosus, rheumatoid arthritis, chronic arthritis, Sjogren's syndrome, autoimmune nephritis, autoimmune vasculitis, autoimmune hepatitis, autoimmune carditis, autoimmune encephalitis, and autoimmune mediated hematological disease. More detailed descriptions of lupus or lupus erythematosus can be found in Wallace, 2000, *The Lupus Book; A Guide for Patients and Their Families*, Oxford University Press, Revised and Expanded Edition; Kuhn et al., 2004, *Cutaneous Lupus Erythematosus*, Springer, First Edition; and Lahita, 1999, *Systemic Lupus Erythematosus*, Academic Press, Third Edition; which are incorporated by reference herein in their entireties.

Methods of diagnosing lupus erythematosus are well known in the art. Laboratory tests for the presence of lupus include the LE Cell Test, the Anti-Nuclear Antibody Test, and the test for anti-DNA antibodies. Lupus is, however, often recognized by particular clinical manifestations including: (i) arthritis (occurring in 90-95% of persons with systemic lupus), (ii) skin changes, such as a photosensitive induced "butterfly" rash across the bridge of the nose, across the cheeks and/or beneath the eyes, and/or red, raised and scaly patches, known as discoid lupus, anywhere on the body (occurring in 75-80% of persons with lupus), (iii) hematologic abnormalities, such as anemia, leukopenia, and thrombocytopenia (occurring in about 50% of persons with lupus), (iv) kidney impairment (occurring in about 50% of persons with lupus), (v) heart or lung disease, such as an irritation of the heart or lung lining causing pericarditis or pleurisy (occurring in about 30% of persons with lupus), and (vi) neuropsychiatric changes (occurring in about 10% to 20% of persons with lupus). By way of non-limiting example, a subject can be diagnosed with systemic erythematosus lupus by having elevated levels of at least one autoantibody relative to the level of the autoantibody in a subject not diagnosed with systemic erythematosus lupus. Exemplary autoantibodies for diagnosis of systemic erythematosus lupus include, but are not limited to, antinuclear antibody (ANA), anti-double strand DNA antibody (anti-dsDNA), anti Sm nuclear antigen antibody (anti-Sm), anti-phospholipid antibody, and any combinations thereof. Such elevated levels can be at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, or at least 10-fold or higher compared to a subject not diagnosed with systemic erythematosus lupus. Alternatively, a subject can be diagnosed with systemic erythematosus lupus by having elevated levels of interferon-beta and or interferon-beta gene expression relative to levels in a subject not diagnosed with systemic erythematosus lupus. Such elevated levels can be at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, or at least 10-fold or higher compared to a subject not diagnosed with systemic erythematosus lupus.

In certain embodiments, treating a patient having an autoimmune disease or an autoimmune disorder having B cells with high AID expression with a inhibitor of DSB repair decreases an indicator, marker, symptom, and/or severity of the autoimmune disease by at least 10%, e.g., by at least 20%, at least 30%, at least 50%, at least 75%, at least 80%, at least 90%, at least 95% or more as compared to the indicator, marker, symptom, and/or severity prior to treatment with the inhibitor of DSB repair or as compared to patients not receiving treatment with a inhibitor of DSB repair.

The technology described herein can relate to the use of at least one inhibitor of DSB repair and compositions comprising at least one such inhibitor of DSB repair for the treatment of an autoimmune disease or an autoimmune disorder having B cells having increased levels of AID protein or mRNA. For example, a composition containing an inhibitor of DSB repair is used to reduce the severity, duration, or number of symptoms associated with one of the following, which are offered by way of example only; lupus erythematosus; systemic lupus erythematosus (SLE); cutaneous lupus erythematosus (CLE); drug-induced lupus; subacute cutaneous lupus erythematosus; cutaneous lupus erythematosus including chilblain lupus erythematosus; rheumatoid arthritis; Sjogren's syndrome; autoimmune nephritis; autoimmune vasculitis; autoimmune hepatitis; autoimmune carditis; autoimmune encephalitis; and autoimmune mediated hematological disease. By "reduce" in this context is meant a statistically significant decrease in such level. The decrease can be, for example, at least 10%, at least 20%, at least 50%, at least 90% or more.

In certain embodiments the inhibitor of DSB repair is contained in a composition comprising the inhibitor of DSB repair and a pharmaceutically acceptable carrier. In further embodiments the inhibitor of DSB repair can be contained in a composition comprising a pharmaceutically acceptable carrier and another pharmaceutically effective compound.

The pharmaceutical compositions of the technology described herein can be administered alone or in combination with other therapies, including without limitation anti-inflammatories, or other therapies which can be beneficial to patients with autoimmune diseases or combinations thereof. It is contemplated that the therapeutic agents of the technology described herein can be administered together with any other therapy effective against one of the autoimmune diseases described herein. When two or more therapeutic agents are administered together, they can be administered simultaneously or with some delay between administrations thereof (i.e., according to an optimized delivery schedule). In further embodiments, the pharmaceutical compositions of the technology described herein can comprise at least one DSB repair inhibitor and at least one additional pharmaceutical agent.

Agents for treatment of lupus erythematosus include, but are not limited to, nonsteroidal anti-inflammatory drugs (NSAIDs), corticosteroids, antimalarials (e.g. chloroquinine; hydroxychloroquine; and quinacrine), immunosuppressants (e.g. azathioprine, cyclosporine A, alkylating agents, nitrogen mustards, chlorambucil or cyclophosphamide), heparin, aspirin, danazol (Danocrine), dehydroepiandrosterone (DHEA), vincristine (Oncovin), warfarin, methylprednisolone pulse therapy, dapsone, thalidomide (Synovir); methylprednisolone sodium succinate (A-Methapred, Solu-Medrol), methotrexate (Rheumatrex), hydroxychloroquine (Plaquenil), triamcinolone (Aristospan), retinoids (e.g. istretinoin and etretinate). Non-limiting examples of anti-inflammatory drugs (NSAIDs) include such as aspirin, salisylates, ibuprofen, naproxen, clinoril, oxaprozin and tolmetin.

In some embodiments, the pharmaceutical compositions of the technology described herein can be administered after or before other therapies, including without limitation, anti-inflammatories or immunosuppressants or other therapies which can be beneficial to patients with autoimmune diseases or combinations thereof.

Sensitizing Cells to Death

In some embodiments, there is provided herein a method of sensitizing cells to death and/or inducing or causing cell death. In some embodiments, there is provided herein a method of causing cell death comprising: administering to a cell an effective amount of a DNA editing enzyme; and thereafter contacting the cells with an inhibitor of double strand break repair; thereby causing cell death. In some embodiments, there is provided herein a method of sensitizing a cell to cell death comprising: administering to a subject a therapeutically effective amount of a DNA editing enzyme; and thereafter administering to the subject an inhibitor of double strand break repair; thereby sensitizing a cell in the subject to cell death. In some embodiments, the DNA editing enzyme can be a member of the APOBEC family, or AID, Rag1 or Rag2 or SPO11.

In some embodiments, the DNA editing enzyme can be a member of the APOBEC family. Non-limiting examples of APOBEC family members include APOBEC1 (e.g. SEQ ID NO:138); APOBEC2 (e.g. SEQ ID NO:139), APOBEC3A (e.g. SEQ ID NO:140); APOBEC3C (e.g. SEQ ID NO:141); APOBEC3E (e.g. SEQ ID NO:142); APOBEC3F (e.g. SEQ ID NO:143); APOBEC3G (e.g. SEQ ID NO:144); APOBEC3H (e.g. SEQ ID NO:145); and APOBEC4 (e.g. SEQ ID NO:146).

In some embodiments, the DNA editing enzyme can be administered in the form of a polypeptide, a nucleic acid encoding a DNA editing enzyme, or a vector comprising a nucleic acid encoding a DNA editing enzyme. In some embodiments, the DNA editing enzyme can be AID. In some embodiments, the DNA editing enzyme administered to the cell is a polypeptide comprising the sequence of SEQ ID NO:099 or a variant, functional fragment, or homolog thereof. In some embodiments, the DNA editing enzyme administered to the cell is a nucleic acid encoding an AID polypeptide, e.g. a nucleic acid comprising the nucleotide sequence of SEQ ID NO:100, such that AID or a variant, functional fragment, or homolog thereof will be expressed in the cell administered the nucleic acid.

Gene therapy compositions and methods are also contemplated for use with the methods described herein. Such methods allow clinicians to introduce DNA encoding a polypeptide or RNA molecule of interest directly into a patient (in vivo gene therapy) or into cells isolated from a patient or a donor (ex vivo gene therapy). Therapeutic proteins produced by transduced cells after gene therapy can be maintained at a relatively constant level in, for example, in cancerous cells, e.g. a tumor of a subject, as compared to a protein that is administered directly. Such sustained production of a therapeutic agent, such as AID and/or an inhibitor of DNA double strand break repair, is particularly appropriate in the treatment of chronic diseases, such as cancers.

Further, regulatable genetic constructs using small molecule inducers have been developed that can be included in vectors to be used in some embodiments of the present invention described herein. (Rivera et al. (1996) Nat. Med. 2:1028-32; No et al. (1996) Proc. Natl. Acad. Sci. USA, 93:3346-51; Gossen and Bujard (1992) Proc. Natl. Acad. Sci. USA 89:5547-51; the GeneSwitch® system (Valentis, Inc., Burlingame, Calif.)). These systems are based on the use of engineered transcription factors the activity of which is controlled by a small molecule drug, and a transgene, the expression of which is driven by the regulated transcription factor (Rivera et al. (1996) Nat. Med. 2:1028-32; Pollock et al. (2000) Proc. Natl. Acad. Sci. USA 97:13221-26; U.S. Pat. Nos. 6,043,082 and 6,649,595; Rivera et al. (1999) Proc. Natl. Acad. Sci. USA 96:8657-62).

Vectors useful in the methods described herein can include, but are not limited to, plasmids, retroviral vectors, adenoviral vectors, adeno-associated viral vectors, herpes virus and pox virus vectors.

The term "transduction" as used herein refers to the use of viral particles or viruses to introduce exogenous nucleic acids into a cell.

The term "transfection" as used herein in reference to methods, such as chemical methods, to introduce exogenous nucleic acids, such as the nucleic acid sequences encoding an agent which increases the activity and/or level of AID as described herein, into a cell. As used herein, the term transfection does not encompass viral-based methods of introducing exogenous nucleic acids into a cell. Methods of transfection include physical treatments (electroporation, nanoparticles, magnetofection), and chemical-based transfection methods. Chemical-based transfection methods include, but are not limited to those that use cyclodextrin, polymers, liposomes, nanoparticles, cationic lipids or mixtures thereof (e.g., DOPA, Lipofectamine and UptiFectin), and cationic polymers, such as DEAE-dextran or polyethylenimine.

An inhibitor of double strand break repair can be as described above herein, e.g. a small molecule, polypeptide, protein, RNAi agent, stilbene derivative, antibody, or polypeptide comprising an epitope-binding fragment of an antibody as described above herein.

In some embodiments, the cell can be an in vitro cell, a cell in cell culture, or a cell in a sample obtained from a subject. In some embodiments, the DNA editing enzyme, and/or the inhibitor of double strand break repair can, for example, be added to the cell culture media in which the cell is being maintained. In some embodiments, the DNA editing enzyme, and/or the inhibitor of double strand break repair can, for example, be comprised by compositions which mediate or enhance their entry into the cell. Suitable compositions for delivering agents to cells, either in vivo or in vitro are described below herein, e.g. liposomes.

In some embodiments, the cell can be a cell in vivo, e.g. a cell in a subject.

In some embodiments, it is desirable to target specific cells or tissues of interest (targeted cells or tissues), e.g. to enhance effectiveness of vectors, minimize the effective dose, and/or minimize side effects or off-target effects. Methods of targeting agents to particular cell types are well known in the art. For reviews, see Peng et al., "Viral Vector Targeting", Curr. Opin. Biotechnol. 10:454-457, 1999; Gunzburg et al., "Retroviral Vector Targeting for Gene Therapy", Cytokines Mol. Ther. 2:177-184, 1996; Wickham, "Targeting Adenovirus", Gene Ther. 7:110-114, 2000; Dachs et al., "Targeting Gene Therapy to Cancer: A Review", Oncol. Res. 9; 313-325, 1997; Curiel, "Strategies to Adapt Adenoviral Vectors for Targeted Delivery", Ann NY Acad. Sci, 886: 158171, 1999; Findeis et al., "Targeted Delivery of DNA for Gene Therapy via Receptors", Trends Biotechnol, 11:202205, 1993; all of which are incorporated by reference herein in their entirety.

Some targeting strategies make use of cellular receptors and their natural ligands in whole or in part. See, for example, Cristiano et al., "Strategies to Accomplish Gene Delivery Via the Receptor-Mediated Endocytosis Pathway", Cancer Gene Ther., Vol. 3, No. 1, pp. 49-57, January-February 1996; S. C. Philips, "Receptor-Mediated DNA Delivery Approaches to Human Gene Therapy", Biologicals, Vol. 23, No. 1, pp. 13-6, March 1995; Michael et al., "Strategies to Achieve Targeted Gene Delivery Via the Receptor-Mediated Endocytosis Pathway", Gene Ther., Vol. 1, No. 4, pp. 223-32, July 1994; Lin et al., "Antiangiogenic Gene Therapy Targeting The Endothelium-Specific Receptor Tyrosine Kinase Tie2", Proc. Natl. Acad. Sci., USA, Vol. 95, pp. 8829-8834, 1998. Sudimack et al, "Targeted Drug Delivery Via the Folate Receptor", Adv. Drug Deliv., pp. 147-62, March 2000; Fan et al., "Therapeutic Application of Anti-Growth Factor Receptor Antibodies", Curr. Opin. Oncol., Vol. 10, No. 1, pp. 67-73, January 1998; Wadhwa et al., "Receptor Mediated Glycotargeting", J. Drug Target, Vol. 3, No. 2, pp. 111-27, 1995; Perales et al, "An Evaluation of Receptor-Mediated Gene Transfer Using Synthetic DNA-Ligand Complexes", Eur. J. Biochem, Vol. 1, No 2, pp. 226, 255-66, December 1994; Smith et al., "Hepatocyte Directed Gene Delivery by Receptor-Mediated Endocytosis", Semin Liver Dis., Vol. 19, No. 1, pp, 83-92, 1999; which are all incorporated by reference herein in their entireties.

Antibodies, particularly single-chain antibodies, to surface antigens specific for a particular cell type may also be used as targeting elements. See, for example, Kuroki et al., "Specific Targeting Strategies of Cancer Gene Therapy Using a Single-Chain Variable Fragment (scFv) with a High Affinity for CEA", Anticancer Res., pp. 4067-71, 2000; U.S. Pat. No. 6,146,885, to Dornburg, entitled "Cell-Type Specific Gene Transfer Using Retroviral Vectors Containing Antibody-Envelope Fusion Proteins"; Jiang et al., "In Vivo Cell Type-Specific Gene Delivery With Retroviral Vectors That Display Single Chain Antibodies", Gene Ther. 1999, 6:1982-7; Engelstadter et al., "Targeting Human T Cells By Retroviral Vectors Displaying Antibody Domains Selected From A Phage Display library", Hum. Gene Ther. 2000, 11:293-303; Jiang et al., "Cell-Type-Specific Gene Transfer Into Human Cells With Retroviral Vectors That Display Single-Chain Antibodies", J. Virol 1998, 72:10148-56; Chu et al., "Toward Highly Efficient Cell-Type-Specific Gene Transfer With Retroviral Vectors Displaying Single-Chain Antibodies", J. Virol 1997, 71:720-5; Chu et al., Retroviral Vector Particles Displaying The Antigen-Binding Site Of An Antibody Enable Cell-Type-Specific Gene Transfer, J. Virol 1995, 69:2659-63; and Chu et al, "Cell Targeting With Retroviral Vector Particles Containing Antibody-Envelope Fusion Proteins", Gene Ther. 1994, 1:292-9; which are all incorporated by reference herein in their entireties.

Administration and Dosages

The inhibitor of DSB repair and a second pharmaceutically active agent can be administered to the subject in the same pharmaceutical composition or in different pharmaceutical compositions (at the same time or at different times). When administered at different times, the inhibitor of DSB repair and the pharmaceutically active agent can be administered within 5 minutes, 10 minutes, 20 minutes, 60 minutes, 2 hours, 3 hours, 4, hours, 8 hours, 12 hours, 24 hours, 48 hours, 72 hours, one week, two weeks, three weeks or more of administration of the other. When the DSB repair inhibitor and the pharmaceutically active agent are administered in different pharmaceutical compositions, routes of administration can be different. For example, the inhibitor of DSB repair is administered by any appropriate route known in the art including, but not limited to oral or parenteral routes, including intravenous, intramuscular, intratumor, intralesional, intradermal, intraperitoneal, subcutaneous, transdermal, airway (aerosol), pulmonary, nasal, rectal, and topical (including buccal and sublingual) administration, and pharmaceutically active agent is administration by a different route, e.g. a route commonly used in the art for administration of said pharmaceutically active agent. In a non-limiting example, an inhibitor of DSB repair can be administered orally, while a pharmaceutically active agent can be administrated subcutaneously.

The dosage ranges for the administration of a inhibitor of DSB repair depend upon the form of the compound, its potency, and the extent to which symptoms, markers, or indicators of the cancer are desired to be reduced, for example the percentage reduction desired for symptoms, nausea, tumor size, etc. In certain embodiments, the dosage should not be so large as to cause adverse side effects. Generally, the dosage will vary with the age, condition, and sex of the patient and can be determined by one of skill in the art. The dosage can also be adjusted by the individual physician in the event of any complication.

In certain embodiments, the effective dose of an inhibitor of DSB repair is administered to a patient once. In certain embodiments, the effective dose of an inhibitor of DSB repair is administered to a patient repeatedly. Patients can be administered a therapeutic amount of an inhibitor of DSB repair, such as 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg or 50 mg/kg. The inhibitor of DSB repair can be administered by intravenous infusion over a period of time, such as over a 5 minute, 10 minute, 15 minute, 20 minute, or 25 minute period. The administration is repeated, for example, on a regular basis, such as hourly for 3 hours, 6 hours, 12 hours or longer or such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the inhibitor of DSB repair can reduce levels of a marker or symptom of cancer, e.g., tumor size by at least 10%, at least 15%, at least 20%, at least 25%, at least 30%, at least 40%, at least 50%, at least 60%, at least 70%, at least 80% or at least 90% or more.

Before administration of a full dose of the inhibitor of DSB repair, patients can be administered a smaller dose, such as a 5% infusion, and monitored for adverse effects, such as an allergic reaction.

Owing to the effects on a cancer or autoimmunity, an inhibitor of DSB repair or a pharmaceutical composition prepared there from can enhance the quality of life.

Efficacy Measurement

Efficacy of treatment or prevention of disease can be assessed, for example by measuring a marker, indicator, or symptom of cancer or any other measurable parameter appropriate. It is well within the ability of one skilled in the art to monitor efficacy of treatment or prevention by measuring any one of such parameters, or any combination of parameters.

A treatment is evident when there is a statistically significant improvement in one or more parameters of cancer, or by a failure to worsen or to develop symptoms where they would otherwise be anticipated. As an example, a favorable change of at least 10% in a measurable parameter of cancer, and preferably at least 20%, 30%, 40%, 50% or more can be indicative of effective treatment. Efficacy for a given inhibitor of DSB repair or formulation of that drug can also be judged using an experimental animal model for cancer as known in the art. When using an experimental animal model, efficacy of treatment is evidenced when a statistically significant increase in a marker is observed.

The efficacy of a given RAD51-strand exchange repair inhibitor can be determined by the skilled clinician. However, a treatment is considered "effective treatment", as the term is used herein, if any one or all of the signs, symptoms or makers of a cancer are altered in a beneficial manner, other clinically accepted symptoms are improved, or even ameliorated, e.g., by at least 10% following treatment with a compound as described herein. Efficacy can also be measured by a failure of an individual to worsen as assessed by hospitalization, or need for medical interventions (i.e., progression of the disease is halted). Methods of measuring these indicators are known to those of skill in the art and/or are described herein. For example, treatment of leukemia includes any treatment of a leukemia in an individual or an animal (some non-limiting examples include a human, or a mammal) and includes: (1) inhibiting the disease, e.g., arresting, or slowing the pathogenic growth of new blood vessels; or (2) relieving the disease, e.g., causing regression of symptoms, reducing the number of leukemia initiating cells; and (3) preventing or reducing the likelihood of the development of a leukemia. An effective amount for the treatment of a disease means that amount which, when administered to a mammal in need thereof, is sufficient to result in effective treatment as that term is defined herein, for that disease. Efficacy of an agent can be determined by assessing physical indicators of, for example leukemia, such as e.g., high white blood cell count, impaired immune response to infection, presence of leukemia initiating cells, etc. Efficacy can be assessed in animal models of cancer, for example a mouse transplanted with human cancer cells, and any treatment or administration of the compositions or formulations that leads to a decrease of at least one symptom, marker, or parameter of a cancer.

Efficacy can be measured by a reduction in any of the symptoms of the cancers described herein, for example, a reduction in bruising, bleeding, petechiae, infections, dyspnea, pallor, nausea, fever, chills, night sweats, flu-like symptoms, fatigue, a feeling of fullness, and/or an increase in blood platelets, white blood cells, and/or red blood cells Efficacy can also be measured by a failure of an individual to worsen as assessed by hospitalization or need for medical interventions (i.e., progression of the disease is halted or at least slowed).

Another marker of the efficacy of treatment as described herein is survival. Statistical survival rates for specific cancers are well established—when an individual or group of individuals treated according to the methods described herein survives beyond the expected time or at a greater than expected rate, the treatment can be considered effective.

Efficacy testing can be performed during the course of treatment using the methods described herein. Measurements of the degree of severity of a number of symptoms associated with a particular ailment are noted prior to the start of a treatment and then at later specific time period after the start of the treatment. For example, leukemia is initiated in the bone marrow and can spread to other organs before it is detected, thus traditional staging of a tumor, performed routinely with other cancer types, is not useful in the staging of leukemia. Instead, physicians rely upon cytological (cellular) classification systems to identify the type and subtype of leukemia. The prognosis or outcome of specific leukemias, and also the likely response to treatment can be determined using such cell classification systems. In one embodiment, the classification method for acute leukemia is the French-American-British (FAB) system. According to FAB classification, acute leukemia is divided into eight subtypes of acute myelogenous leukemia (AML) and three subtypes of acute lymphocytic leukemia (ALL). One of skill in the art is aware of such methods for determining disease severity in a variety of different leukemias and can easily diagnose the severity of the leukemia based on such a classification scheme.

The efficacy of treatment according to the methods described herein can be evaluated by following surrogate or indirect markers of cancer. Without intending to be limiting, such markers that indicate efficacy of treatment of a cancer can include an increase in red blood cell or platelet counts, a normalization of white blood cell counts, improvements in liver and kidney function tests, a decrease in lactate dehydrogenase levels, improved scores on the follicular lymphoma international prognostic Index (FLIPI) (Lopez-Guillermo, A. et al., J Clin Oncol 1994; 12:1343-1348; Solal-Céligny et al., Blood 2004 104:1258-1265), a decrease in CD11b+ and Gr-1+ cells, improve bone marrow morphology as determined by bone marrow biopsy, decreased in cells with abnormal DNA as determined by cytogenic testing, and decreased presence of cancer cells in cerebrospinal fluid. Tests specific to each type of cancer are known to those of skill in the art. By way of non-limiting example, Burkitt's lymphoma can be diagnosed and monitored by detecting of cells with an immunophenotype that is $CD20^+$, $CD10^+$, $Bcl-6^+$, $Bcl-2^-$, $TdT^-$, and monotypic $sIg^+$, with virtually all cells $Ki67^+$ (proliferation), and a translocation involving c-myc and IgH or IgL, without rearrangements involving the bcl-2 or bcl-6 genes.

The skilled artisan will appreciate that there are many ways to use the measurements of two or more markers in order to improve the diagnostic question under investigation. In a quite simple, but nonetheless often effective approach, a positive result is assumed if a sample is positive for at least one of the markers investigated. This can e.g. be the case when diagnosing a cancer, Burkitt's lymphoma, by either detecting cells with an immunophenotype that is $CD20^+$, $CD10^+$, $Bcl-6^+$, $Bcl-2^-$, $TdT^-$, and monotypic $sIg^+$, with virtually all cells $Ki67^+$ (proliferation), and a translocation involving c-myc and IgH or IgL, without rearrangements involving the bcl-2 or bcl-6 genes. Frequently, however, the combination of markers is mathematically/statistically evaluated. Preferably the values measured for markers of a marker panel, e.g. the immunophenotype for Burkitt's lymphoma and blood panel counts, are mathematically combined and the combined value is correlated to the underlying diagnostic question. Preferably the diagnostic question is the effectiveness of an inhibitor of DSB repair in treating a cancer. Preferably the relative risk is given in comparison to controls not receiving an inhibitor of DSB repair. Preferably controls are matched for age and other covariates.

Marker values can be combined by any appropriate state of the art mathematical method. Well-known mathematical methods for correlating a marker combination to a disease or to the risk of developing a disease employ methods like, Discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination of the technology described herein. Preferably the method used in correlating the marker e.g. to the absence or presence of cancer is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., J. of Computational and Graphical Statistics, 12 (2003) 475-511; Friedman, J. H., Regularized Discriminant Analysis, JASA 84 (1989) 165-175; Hastie, T., Tibshirani, R., Friedman, J., The Elements of Statistical Learning, Springer Series in Statistics, 2001; Breiman, L., Friedman, J. H., Olshen, R. A., Stone, C. J., (1984) Classification and regression trees, California: Wadsworth; Breiman, L. Random Forests, Machine Learning, 45 (2001) 5-32; Pepe, M. S., The Statistical Evaluation of Medical Tests for Classification and Prediction, Oxford Statistical Science Series, 28 (2003) and Duda, R. O., Hart, P. E., Stork, D. G., Pattern Classification, Wiley Interscience, 2nd Edition (2001).

In some embodiments, an optimized multivariate cut-off for the underlying combination of biological markers can be used to e.g. discriminate patients with low, intermediate and high risk of developing cancer. In this type of multivariate analysis the markers are no longer independent but form a marker panel.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease, respectively.

In each case, the ROC plot depicts the overlap between the two distributions by plotting the sensitivity versus 1-specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1-specificity [defined as (number of false-positive results)/(number of true-negative+number of false-positive results)].

It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45 degree diagonal line from the lower left corner to the upper right corner. Most plots fall in between these two extremes. (If the ROC plot falls completely below the 45 degree diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always >0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Definition of Dose-Limiting Toxicity (DLT)

The determination of DLT for purposes of assessing dose escalation is defined as follows using the NCI CTC version 3.0 criteria with consideration of known and accepted toxicities of certain drugs. Toxicities reached without pre-medication are not considered DLT. Criteria for DLT include: any nausea, vomiting at or above Grade 3 with maximum anti-emetic pre-medication; all other drug-related non-hematologic toxicity at or above Grade 3; neutrophil count <500 cell/ul for >7 days; any febrile neutropenia (defined as T>101° F.) with a neutrophil count <500 cells/ul after drug administration; platelet count <10,000 cell/ul OR Grade 3 with evidence of bleeding necessitating blood product or platelet transfusion; hemoglobin at or above Grade 4 toxicity with erythropoietin co-administration. The response is measured by standard criteria. Patients are reevaluated after every two cycles of treatment. In addition to a baseline/screening scan, confirmatory scans are obtained 4 weeks following initial documentation of an objective response.

Pharmaceutical Compositions

For administration to a subject, the compounds can be provided in pharmaceutically acceptable compositions. These pharmaceutically acceptable compositions comprise a therapeutically effective amount of at least one DSB repair inhibitor as described above, formulated together with one or more pharmaceutically acceptable carriers (additives) and/or diluents. As described in detail below, the pharmaceutical compositions of the technology described herein can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, lotion, gel, ointment, or a controlled-release patch or spray applied to the skin; (4) intravaginally or intrarectally, for example, as a pessary, cream, suppository or foam; (5) sublingually; (6) ocularly; (7) transdermally; (8) transmucosally; or (9) nasally. Additionally, compounds can be implanted into a patient or injected using a drug delivery system. Coated delivery devices can also be useful. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; U.S. Pat. No. 6,747,014; and U.S. Pat. No. 3,270,960.

Many organized surfactant structures have been studied and used for the formulation of drugs. These include monolayers, micelles, bilayers and vesicles. Vesicles, such as liposomes, have attracted great interest because of their specificity and the duration of action they offer from the standpoint of drug delivery. Liposomes are unilamellar or multilamellar vesicles which have a membrane formed from a lipophilic material and an aqueous interior. The aqueous portion contains the composition to be delivered. Liposomes can be cationic (Wang et al., Biochem. Biophys. Res. Commun., 1987, 147, 980-985), anionic (Zhou et al., Journal of Controlled Release, 1992, 19, 269-274), or nonionic (Hu et al. S.T.P.Pharma. Sci., 1994, 4, 6, 466). Liposomes can comprise a number of different phospholipids, lipids, glycolipids, and/or polymers which can impart specific properties useful in certain applications and which have been described in the art (Allen et al., FEBS Letters, 1987, 223, 42; Wu et al., Cancer Research, 1993, 53, 3765; Papahadjopoulos et al., Ann. N.Y. Acad. Sci., 1987, 507, 64; Gabizon et al., PNAS, 1988, 85, 6949; Klibanov et al. FEBS Lett., 1990, 268, 235; Sunamoto et al., Bull. Chem. Soc. Jpn., 1980, 53, 2778; Illum et al., FEBS Lett., 1984, 167, 79; Blume et al., Biochimica et Biophysica Acta, 1990, 1029, 91; Hughes et al., Methods Mol. Biol. 2010; 605:445-59; U.S. Pat. Nos. 4,837,028; 5,543,152; 4,426,330; 4,534,899; 5,013,556; 5,356,633; 5,213,804; 5,225,212; 5,540,935; 5,556,948; 5,264,221; 5,665,710; European Patents EP 0 445 131 B1; EP 0 496 813 B1; and European Patent Publications WO 88/04924; WO 97/13499; WO 90/04384; WO 91/05545; WO 94/20073; WO 96/10391; WO 96/40062; WO 97/0478).

The compositions of the technology described herein can be prepared and formulated as emulsions or microemulsions. Emulsions are typically heterogeneous systems of one liquid dispersed in another in the form of droplets usually exceeding 0.1 µm in diameter and have been described in the art. Microemulsion can be defined as a system of water, oil and amphiphile which is a single optically isotropic and thermodynamically stable liquid solution and can comprise surfactants and cosurfactants. Both of these drug delivery means have been described in the art (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 199, 245, & 335; Higuchi et al., in Remington's Pharmaceutical Sciences, Mack Publishing Co., Easton, Pa., 1985, p. 301; Leung and Shah, in: Controlled Release of Drugs: Polymers and Aggregate Systems, Rosoff, M., Ed., 1989, VCH Publishers, New York, pages 185-215; Schott, in Remington's Pharmaceutical Sciences, Mack Publishing Co., Easton, Pa., 1985, p. 271; Constantinides et al., Pharmaceutical Research, 1994, 11, 1385-1390; Ritschel, Meth. Find. Exp. Clin. Pharmacol., 1993, 13, 205; Ho et al., J. Pharm. Sci., 1996, 85, 138-143; Lee et al., Critical Reviews in Therapeutic Drug Carrier Systems, 1991, p. 92; U.S. Pat. Nos. 6,191,105; 7,063,860; 7,070,802; 7,157,099).

In one embodiment, the liposome or emulsion formulation comprises a surfactant. Surfactants find wide application in formulations such as emulsions (including microemulsions) and liposomes. The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285). Suitable surfactants include fatty acids and/or esters or salts thereof, bile acids and/or salts thereof. In some embodiments, the surfactant can be anionic, cationic, or nonionic. The use of surfactants in drug products, formulations and in emulsions has been reviewed (Rieger, in Pharmaceutical Dosage Forms, Marcel Dekker, Inc., New York, N.Y., 1988, p. 285).

In one embodiment, the technology described herein employs various penetration enhancers to affect the efficient delivery of DSB repair inhibitors across cell membranes. Penetration enhancers can be classified as belonging to one of five broad categories, i.e., surfactants, fatty acids, bile salts, chelating agents, and non-chelating non-surfactants all of which have been described elsewhere (see e.g., Malmsten, M. Surfactants and polymers in drug delivery, Informa Health Care, New York, N.Y., 2002; Lee et al., Critical Reviews in Therapeutic Drug Carrier Systems, 1991, p. 92; Takahashi et al., J. Pharm. Pharmacol., 1988, 40, 252; Touitou, E., et al. Enhancement in Drug Delivery, CRC Press, Danvers, Mass., 2006; Muranishi, Critical Reviews in Therapeutic Drug Carrier Systems, 1990, 7, 1-33; El Hariri et al., J. Pharm. Pharmacol., 1992, 44, 651-654; Brunton, Chapter 38 in: Goodman & Gilman's The Pharmacological Basis of Therapeutics, 9th Ed., Hardman et al., Eds., McGraw-Hill, New York, 1996, pp. 934-935; Swinyard, Chapter 39 In: Remington's Pharmaceutical Sciences, 18th Ed., Gennaro, ed., Mack Publishing Co., Easton, Pa., 1990, pages 782-783; Yamamoto et al., J. Pharm. Exp. Ther., 1992, 263, 25; Yamashita et al., J. Pharm. Sci., 1990, 79, 579-583; Jarrett, J. Chromatogr., 1993, 618, 315-339; Katdare, A. et al., Excipient development for pharmaceutical, biotechnology, and drug delivery, CRC Press, Danvers, Mass., 2006; Buur et al., J. Control Rel., 1990, 14, 43-51)

Oral formulations and their preparation are described in detail in U.S. Pat. No. 6,887,906, US Publn. No. 20030027780, and U.S. Pat. No. 6,747,014, each of which is incorporated herein by reference. Compositions and formulations for parenteral, intraparenchymal, intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients. Aqueous suspensions can further contain substances which increase the viscosity of the suspension including, for example, sodium carboxymethylcellulose, sorbitol and/or dextran. The suspension can also contain stabilizers.

The compositions of the technology described herein can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the technology described herein, such as dyes, flavoring agents, preservatives, antioxidants, opacifiers, thickening agents and stabilizers. However, such materials, when added, should not unduly interfere with the biological activities of the components of the compositions of the technology described herein. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with DSB repair inhibitor(s) of the formulation.

Suitable emulsifiers include synthetic non-ionic emulsifiers, such as, for example, ethoxylated ethers, ethoxylated esters, polyoxypropylene-polyoxyethylene block co-polymers and phospholipids. Naturally-occurring phospholipids, such as egg or soya phospholipids, and modified or artificially manipulated phospholipids or mixtures thereof can also be used. In some embodiments, emulsifiers are egg phospholipids and soya phospholipids. Egg yolk phospholipids include phosphatidylcholine, lecithin and phosphatidylethanolamine.

The compositions of the technology described herein may also include stabilizing agents. Anionic stabilizers include, for example, phosphatidylethanolamines, conjugated with polyethylene glycol, (PEG-PE) and phosphatidylglycerols, a specific example of which is dimyristolphosphatidylgylcerol (DMPG). Additional stabilizers include, but are not limited to, oleic acid and its sodium salt, cholic acid and deoxycholic acid and respective salts thereof, cationic lipids such as stearylamine and oleylamine, and 3│3-[N—(N',N'-dimethylaminoethane)carbamoyl]cholesterol (DC-Chol).

The compositions of the technology described herein can be made isotonic with blood by the incorporation of a suitable tonicity modifier. Glycerol is most frequently used as a tonicity modifier. Alternative tonicity modifying agents include xylitol, mannitol and sorbitol. The pharmaceutical compositions are typically formulated to be at physiologically neutral pH, typically in the range 6.0-8.5. The pH can be adjusted by the addition of base, for example, NaOH or NaHCO3, or in some cases acid, such as HCl.

The compositions of the technology can be formulated with pharmaceutically safe oil-water emulsions comprising a vegetable oil, a phosphatide emulsifier, typically egg lecithin or soybean lecithin, and a tonicity modifier such as, for example, Liposyn® II and Liposyn® III (Abbott Laboratories, North Chicago, Ill.) and Intralipid® (Fresenius Kabi A B, Uppsala, Sweden) or other similar oil-water emulsions.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred. Murine genetics have generated a number of mouse models for the study of DSB repair inhibitors. Such models can be used for in vivo testing of DSB repair inhibitor, as well as for determining a therapeutically effective dose. A suitable mouse model is, for example, the AICDA$^{-/-}$ mouse described herein or model developed using patient derived tissue xenografting (PDX). In certain embodiments of this technique that would be useful in the study DSB repair inhibitors, a immunocompromised mouse strain, such as Nod-scid, NSG (NOD-scid Il2ry-null; NOD.Cg-Prkdc-scid<Il2rg>/Wjl/SzJ) or NRG (NOD-RagIl2ry-null; NOD-Rag1<null> IL2rg<null>/Wjl/SzJ) is engrafted with primary human cancer cells, such as leukemias.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized.

The therapeutically effective dose can be estimated initially from cell culture assays. A dose can be formulated in animal models to achieve a circulating plasma concentration range that includes the IC50 (i.e., the concentration of the therapeutic which achieves a half-maximal inhibition of symptoms) as determined in cell culture. Levels of a compound in plasma can be measured, for example, by high performance liquid chromatography. The effects of any particular dosage can be monitored by a suitable bioassay.

The amount of a DSB repair inhibitor which can be combined with a carrier material to produce a single dosage form will generally be that amount of the compound which produces a therapeutic effect. Generally out of one hundred percent, this amount will range from about 0.1% to 99% of compound, preferably from about 5% to about 70%, most preferably from 10% to about 30%.

The dosage can be determined by a physician and adjusted, as necessary, to suit observed effects of the treatment. Generally, the compositions are administered so that the DSB repair inhibitor is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg etc. It is to be further understood that the ranges intermediate to the given above are also within the scope of this technology described herein, for example, in the range 1 mg/kg to 10 mg/kg, dose ranges such as 2 mg/kg to 8 mg/kg, 3 mg/kg to 7 mg/kg, 4 mg/kg to 6 mg/kg etc.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the DSB repair inhibitor. The desired dose can be administered at one time or divided into subdoses, e.g., 2-4 subdoses and administered over a period of time, e.g., at appropriate intervals through the day or other appropriate schedule. Such subdoses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more. The desired dose can be administered using continuous infusion or delivery through a controlled release formulation. In that case, the Inhibitor of DSB repair contained in each sub-dose must be correspondingly smaller in order to achieve the total daily dosage. The dosage unit can also be compounded for delivery over several days, e.g., using a conventional sustained release formulation which provides sustained release of the DSB repair inhibitor over a several day period. Sustained release formulations are well known in the art and are particularly useful for delivery of agents at a particular site, such as could be used with the agents of the technology described herein. In this embodiment, the dosage unit contains a corresponding multiple of the daily dose.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the DSB repair inhibitors described herein can be made using conventional methodologies or on the basis of in vivo testing using an appropriate animal model, as described elsewhere herein.

In some embodiments, pharmaceutical compositions can include (a) one or more DSB repair inhibitor and (b) one or more pharmaceutically effective compounds as described herein.

Screening Assays

In some embodiments, the technology described herein relates to methods of determining if an agent is an inhibitor of DNA double strand break repair, e.g. screening agents to determine if one or more of them is an inhibitor of DNA double strand break repair.

In some embodiments, the method of determining if a test agent is an inhibitor of DNA double strand break repair comprises (a) contacting a cell expressing a DNA editing enzyme with a test agent; and (b) determining cell viability; wherein decreased cell viability indicates the test agent is an inhibitor of DNA double strand break repair.

In some embodiments, the method of determining if a test agent is an inhibitor of DNA double strand break repair comprises (a) contacting a cell expressing a DNA editing enzyme with a test agent; and (b) determining cell viability of the cells of step (a); (c) contacting a cell not expressing a DNA editing enzyme with the test agent; (d) determining cell viability of the cells of step c); and (e) determining the ratio by dividing the fraction of live cells of step c by the fraction of live cells in step d; wherein a ratio below 0.8 indicates the test agent is an inhibitor of DNA double strand break repair.

In the context of the screening methods described herein, "a cell expressing a DNA editing enzyme" is a cell which expresses a DNA editing enzyme at a level which is higher than the level in a control reference cell. In some embodiments, a control reference cell can be an unactivated, untransformed, healthy B cell. In some embodiments, "a cell expressing a DNA editing enzyme" can be a cell which has a higher overall mutation rate than the overall mutation rate observed in an unactivated, untransformed, healthy human B cell. In some embodiments, the cell expressing a DNA editing enzyme is a cell expressing elevated levels of AID.

In some embodiments the cells expressing a DNA editing enzyme which are contacted with a test agent can be cells expressing at least one copy of a DNA editing enzyme mRNA per cell, e.g. 1 or more copies per cell, 10 or more copies per cell, or 100 or more copies per cell. In some embodiments the cells expressing a DNA editing enzyme which are contacted with a test agent can be cells expressing at least 5 copies of a DNA editing enzyme per cell. In some embodiments the cells expressing a DNA editing enzyme which are contacted with a test agent can be cells expressing at least 10 copies of a DNA editing enzyme per cell. In some embodiments the cells expressing a DNA editing enzyme which are contacted with a test agent can be cells expressing at least 100 copies of a DNA editing enzyme per cell.

In some embodiments the cells expressing a DNA editing enzyme which are contacted with a test agent can be cells expressing at least 100 copies of a DNA editing enzyme polypeptide per cell, e.g. 100 or more copies per cell, 200 or more copies per cell, 300 or more copies per cell, 400 or more copies per cell, 500 or more copies per cell, 600 or more copies per cell, 1000 or more copies per cell, 5000 or more copies per cell, or 10,000 or more copies per cell. In some embodiments the cells expressing a DNA editing enzyme which are contacted with a test agent can be cells expressing at least 200 copies of a DNA editing enzyme polypeptide per cell. In some embodiments the cells expressing a DNA editing enzyme which are contacted with a test agent can be cells expressing at least 300 copies of a DNA editing enzyme polypeptide per cell. In some embodiments the cells expressing a DNA editing enzyme which are contacted with a test agent can be cells expressing at least 400 copies of a DNA editing enzyme polypeptide per cell. In some embodiments the cells expressing a DNA editing enzyme which are contacted with a test agent can be cells expressing at least 500 copies of a DNA editing enzyme polypeptide per cell. In some embodiments the cells expressing a DNA editing enzyme which are contacted with a test agent can be cells expressing at least 600 copies of a DNA editing enzyme polypeptide per cell. In some embodiments the cells expressing a DNA editing enzyme which are contacted with a test agent can be cells expressing at least 1,000 copies of a DNA editing enzyme polypeptide per cell. In some embodiments the cells expressing a DNA editing enzyme which are contacted with a test agent can be cells expressing at least 5,000 copies of a DNA editing enzyme polypeptide per cell. In some embodiments the cells expressing a DNA editing enzyme which are contacted with a test agent can be cells expressing at least 10,000 copies of a DNA editing enzyme polypeptide per cell.

In some embodiments, the cell contacted with a test agent can be a cell selected from the group consisting of: a stimulated B cell, a splenic B cell, a cancerous cell, or an autoimmune cell. In some embodiments, a cancerous cell can be a B cell from a subject having a disease selected from the group consisting of: lymphoma; leukemia; Burkitt's lymphoma; follicular lymphoma; diffuse large B-cell lymphoma; B-cell leukemia; B-cell acute lymphoblastic leukemia; chronic lymphocytic leukemia (CLL); acute myelogenous leukemia (AML); chronic myelogenous leukemia (CML); and Epstein-Barr virus transformed peripheral human B-lymphocytes derived cell lines GM05881, GM07323, and GM13689.

In some embodiments, the cell contacted with a test agent can be a stably transfected cell line where the cell line has been transfected with a vector encoding a DNA editing enzyme. Cell lines suitable for transfection include but are not limited to 3T3, CH12F3, Caco-2, CCRF-CEM, CHO, CH12-F3, COS-7, HCT 116, HEK 293, HL-60, HepG2, Jurkat, KG-1, K-562, MCF-7, MDCK, MG-63, Mo-B, MOLT-4, Ramos (RA 1) and U2-OS. Further cell lines established from primary cells, embryonic stem cells and induced pluripotent cells (iPS) can be useful for screening.

In some embodiments, the cell can be a cell which has been manipulated to cause it to express higher levels of a DNA editing enzyme, e.g. a B cell which has been stimulated or a cell which contains an exogenous polypeptide comprising a DNA editing enzyme and/or exogenous nucleic acid encoding a DNA editing enzyme.

In the context of the screening methods described herein, a "test agent" or "test compound" can be a nucleic acid (DNA or RNA), small molecule, aptamer, protein, peptide, antibody, polypeptide comprising an epitope-binding fragment of an antibody, antibody fragment, peptide-nucleic acid (PNA), locked nucleic acid (LNA), small organic or inorganic molecules; saccharide; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or mammalian cells or tissues; naturally occurring or synthetic compositions; peptides; aptamers; and antibodies, or fragments thereof. In some embodiments, a test agent can be a stilbene, stilbene derivative, or stilbenoid as described above herein. Examples of stilbenes, stilbene derivatives, stilbenoids, and other inhibitors of DNA double strand break repair are described above herein. Test agents and compounds are also described above herein.

In the context of the screening methods described herein, "determining cell viability" refers to measuring or detecting any aspect of cell metabolism, growth, structure, and/or propagation which is indicative of either a healthy, viable cell or a dead and/or nonviable cell. Colorimetric, luminescent, radiometric, and/or fluorometric assays known in the art can be used. In some embodiments, determining cell viability can comprise manual counting of cells using a hemacytometer. In some embodiments, determining cell viability can comprise the use of a live-dead cell stain, e.g. a stain which will stain either a live cell or a dead cell.

Colorimetric techniques for determining cell viability include, by way of non-limiting example, Trypan Blue exclusion. In brief, cells are stained with Trypan Blue and counted using a hemocytometer. Viable cells exclude the dye whereas dead and dying cells take up the blue dye and are easily distinguished under a light microscope. Neutral Red is adsorbed by viable cells and concentrates in cell lysosomes; viable cells can be determined with a light microscope, by quantitating numbers of Neutral Red stained cells.

Fluorometric techniques for determining cell viability include, by way of non-limiting example, propidium iodide, a fluorescent DNA intercalating agent. Propidium iodide is excluded from viable cells but stains the nucleus of dead cells. Flow cytometry of propidium iodide labeled cells can then be used to quantitate viable and dead cells. Release of lactate dehydrogenase (LDH) indicates structural damage and death of cells, and can be measured by a spectrophotometric enzyme assay, Bromodeoxyuridine (BrdU) is incorporated into newly synthesized DNA and can be detected with a fluorochromelabeled antibody. The fluorescent dye Hoechst 33258 labels DNA and can be used to quantitate proliferation of cells (e.g., flow cytometry). Quantitative incorporation of the fluorescent dye carboxyfluorescein diacetate succinimidyl ester (CESE CFDA-SE) can provide cell division analysis (e.g., flow cytometry). This technique can be used either in vitro or in vivo, 7-aminoactinomycin D (7-AAD) is a fluorescent intercalator that undergoes a spectral shift upon association with DNA, and can provide cell division analysis (e.g., flow cytometry).

Radiometric techniques for determining cell proliferation include, by way of non-limiting example, [3H]-Thymidine, which is incorporated into newly synthesized DNA of living cells and frequently used to determine proliferation of cells, Chromium (51Cr)-release from dead cells can be quantitated by scintillation counting in order to quantitate cell viability Luminescent techniques for determining cell viability include, by way of non-limiting example, the CellTiter-Glo luminescent cell viability assay (Promega Madison Wis.). This technique quantifies the amount of ATP present to determine the number of viable cells.

Kits for determining cell viability are commercially available, e.g. the MUTLITOX-FLOUR™ Multiplex Cytotoxicity Assay (Cat. No. G9200; Promega, Inc.; Madison, Wis.).

In some embodiments, the means of determining cell viability can comprise a high-throughput method, e.g. live-dead cell stains can be detected using a fluorescence-capable multiplate reader. In some embodiments, imaging analysis can be performed via automated image acquisition and analysis.

Some embodiments of the technology described herein can be defined as any of the following numbered paragraphs.
1. A method of treatment comprising;
   (a) obtaining a biological sample derived from a subject;
   (b) measuring a level of a DNA editing enzyme; and
   (c) administering a therapeutically effective amount of an inhibitor of DNA double strand break repair to a subject with a detectable level of a DNA editing enzyme.
2. A method of treatment comprising;
   administering a therapeutically effective amount of an inhibitor of DNA double strand break repair to a subject determined to have a detectable level of a DNA editing enzyme.
3. A method of treatment comprising;
   (a) selecting a subject having cells that express an elevated level of a DNA editing enzyme; and
   (b) administering a therapeutically effective amount of an inhibitor of DNA double strand break repair to the subject;
      wherein the elevated level of the DNA editing enzyme is a level of DNA editing enzyme that is higher than the level of DNA editing enzyme in cells of the same type from a healthy individual.
4. The method of paragraph 1, wherein the biological sample comprises blood cells.
5. The method of paragraph 1, wherein the biological sample comprises B cells.
6. The method of any of paragraphs 1-5, wherein the level of DNA editing enzyme in the cells expressing a detectable or elevated level of a DNA editing enzyme is statistically significantly higher than in normal cells from a healthy subject.
7. The method of paragraphs 1-6, wherein the DNA editing enzyme is selected from the group consisting of:
   recombination activating gene 1 (RAG1); recombination activating gene 2 (RAG2); sporulation-specific protein 11 (SPO11); apolipoprotein B mRNA editing enzyme, catalytic polypeptide-like (APOBEC) family member; and activation-induced cytidine deaminase (AID).
8. The method of paragraph 7, wherein the DNA editing enzyme is activation-induced cytidine deaminase (AID).
9. The method of paragraph 8, wherein the level of activation-induced cytidine deaminase (AID) in B cells expressing an elevated level of AID is significantly higher than the level of AID expressed in unactivated B cells from a healthy subject
10. The method of any of paragraphs 1-9, wherein the subject is a human subject.
11. The method of any of paragraphs 1-10, wherein the biological sample or cells that express a detectable or elevated level of a DNA editing enzyme are cancerous cells.
12. The method of any of paragraphs 1-11, wherein the subject has cancer.
13. The method of any of paragraphs 1-11, wherein the biological sample or cells that express detectable or elevated level of a DNA editing enzyme are autoimmune cells.
14. The method of any of paragraphs 1-13, wherein the subject has a condition selected from the group consisting of:
   lymphoma, leukemia, and a plasma cell neoplasm.
15. The method of paragraph 14, wherein the lymphoma is selected from the group consisting of:
   Non-Hodgkin's lymphoma; Burkitt's lymphoma, small lymphocytic lymphoma; lymphoplasmacytic lymphoma; MALT lymphoma; follicular lymphoma; diffuse large B-cell lymphoma; and T-cell lymphoma.
16. The method of paragraph 14, wherein the leukemia is selected from the group consisting of:
   acute lymphoblastic leukemia (ALL), Burkitt's leukemia; B-cell leukemia; B-cell acute lymphoblastic leukemia; chronic lymphocytic leukemia (CLL); acute myelogenous leukemia (AML); chronic myelogenous leukemia (CML); and T-cell acute lymphoblastic leukemia (T-ALL).
17. The method of paragraph 14, wherein the plasma cell neoplasm is selected from the group consisting of:
   multiple myeloma; plasma cell myeloma; plasma cell leukemia; and plasmacytoma.
18. The method of paragraph 12, wherein the subject has a cancer selected from the group consisting of:
   epithelial cell cancer; colon cancer, liver cancer, gastric cancer; intestinal cancer; esophageal cancer; breast cancer; lung cancer; and thyroid cancer.
19. The method of any of paragraphs 1-10 and 13, wherein the subject has an autoimmune disease.
20. The method of paragraph 19, wherein the autoimmune disease is selected from the group consisting of:
   lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis, discoid lupus, subacute cutaneous lupus erythematosus, cutaneous lupus erythematosus including chilblain lupus erythematosus, chronic arthritis, Sjogren's syndrome, inflammatory chronic rhinosinusitis, colitis, celiac disease, inflammatory bowel disease, Barrett's esophagus, inflammatory gastritis autoimmune nephritis, autoimmune vasculitis, autoimmune hepatitis, autoimmune carditis, autoimmune encephalitis, and autoimmune mediated hematological disease.

21. The method of any of paragraphs 1-20, wherein the inhibitor of DNA double strand break repair decreases the expression or activity of one or more genes selected from the group consisting of:
   Rad51; Rad51AP1; Rad51B; Rad51C; Rad51D; XRCC2; XRCC3; RAD54; RAD52; BRCA1; BRCA2; ATM; ATR; MRE11; RAD50; NBS1; WRN; BLM; RECQ4; LIG4; XRCC4; PRKDC; DCLRE1C; XRCC6; XRCC5; and XLF.

22. The method of any of paragraphs 1-21, wherein the inhibitor of DNA double strand break repair is selected from the group consisting of:
   a small molecule; a protein; a peptide; an antibody; an antibody fragment; a protein binding protein; a ribonucleic acid; a deoxyribonucleic acid; an aptamer; a peptide nucleic acid (PNA); and a locked nucleic acid (LNA).

23. The method of any of paragraphs 1-20, wherein the inhibitor of DNA double strand break repair is stilbene, a stilbenoid, or a derivative thereof.

24. The method of paragraph 23, wherein the stilbene or stilbene derivative is a compound of Formula V:

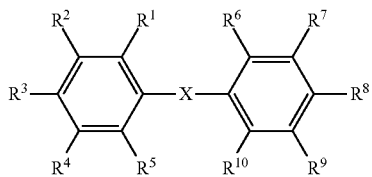

Formula V or a stereoisomer, enantiomer, prodrug, or pharmaceutically acceptable salt thereof;
wherein $R^1$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;
wherein $R^2$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;
wherein $R^3$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;
wherein $R^4$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;
wherein $R^5$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;
wherein $R^6$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;
wherein $R^7$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;
wherein $R^8$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2-R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^9$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^{10}$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein X can be selected from the group consisting of $C(R^{21})_2$, —$C(O)N(R^{22})$—, —$C(O)$—, —$C(O)O$—, —$S(O)$—, —$SO_2$— —$CH(R^{11})CH(R^{12})$—, —$C(R^{11})=C(R^{12})$—, and

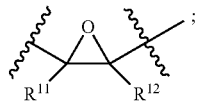

wherein $R^{11}$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2NC(O)R^{21}$, $NC(O)OR^{21}$, $NC(S)R^{21}$, $NC(S)N(R^{22})_2$, $NSO_2R^{21}$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^{12}$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2NC(O)R^{21}$, $NC(O)OR^{21}$, $NC(S)R^{21}$, $NC(S)N(R^{22})_2$, $NSO_2R^{21}$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein each $R^{21}$ can be selected independently from the group consisting of hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, and any combinations thereof;

wherein each $R^{22}$ can be selected independently from the group consisting of hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, and any combinations thereof.

25. The method of paragraph 21, wherein the stilbene derivative is 4,4'diisothiocyanostilbene-2,2'-disulfonic acid (DIDS).

26. The method of paragraph 21, wherein the stilbene or stilbene derivative is selected from the group consisting of:

(E)-N,N'-(ethene-1,2-diylbis(4,1-phenylene))diacetamide; (E)-N,N'-(ethene-1,2-diylbis(4,1-phenylene))bis(2-methylpropanamide); (E)-N,N'-(ethene-1,2-diylbis(4,1-phenylene))bis(2-methoxyacetamide); (E)-N,N'-(ethene-1,2-diylbis(4,1-phenylene))dimethanesulfonamide; (E)-N,N'-(ethene-1,2-diylbis(4,1-phenylene))dicyclopropanesulfonamide; (E)-N,N'-(ethene-1,2-diylbis(4,1-phenylene))bis(propane-2-sulfonamide); (E)-N,N'-(ethene-1,2-diylbis(4,1-phenylene))bis(propane-2-sulfonamide); (E)-N-(4-(4-aminostyryl)phenyl)propane-2-sulfonamide; (E)-1,1'-(ethene-1,2-diylbis(4,1-phenylene))bis(3-methylthiourea); (E)-1,1'-(ethene-1,2-diylbis(4,1-phenylene))bis(3-isopropylthiourea); (E)-N-(4-(4-(dimethylamino)styryl)phenyl)acetamide; (E)-N-(4-(4-(dimethylamino)styryl)phenyl)isobutyramide; (E)-N-(4-(4-(dimethylamino)styryl)phenyl)-2-methoxyacetamide; (E)-N-(4-(4-(dimethylamino)styryl)phenyl)methanesulfonamide; (E)-N-(4-(4-(dimethylamino)styryl)phenyl)cyclopropanesulfonamide; (E)-N-(4-(4-(dimethylamino)styryl)phenyl)propane-2-sulfonamide; N'-(4-{(E)-2-[4-(dimethylamino)phenyl]-1-ethenyl}phenyl)-N,N-dimethylsulfamide; (E)-1-(4-(4-(dimethylamino)styryl)phenyl)-3-methylthiourea; (E)-1-(4-(4-(dimethylamino)styryl)phenyl)-3-isopropylthiourea; (E)-1-cyclopropyl-3-(4-(4-(dimethylamino)styryl)phenyl)thiourea; (E)-1-(4-(4-(dimethylamino)styryl)phenyl)-3-methylurea; (E)-1-(4-(4-(dimethylamino)styryl)phenyl)-3-isopropylurea; (E)-1-cyclopropyl-3-(4-(4-(dimethylamino)styryl)phenyl)urea; sodium (E)-6,6'-(ethene-1,2-diyl)bis(3-acetamidobenzenesulfonate); sodium (E)-6,6'-(ethene-1,2-diyl)bis(3-isobutyramidobenzenesulfonate); sodium (E)-6,6'-(ethene-1,2-diyl)bis(3-(2-methoxyacetamido)benzenesulfonate); sodium (E)-6,6'-(ethene-1,2-diyl)bis(3-(cyclopropanesulfonamido)benzenesulfonate); sodium (E)-6,6'-(ethene-1,2-diyl)bis(3-(1-methylethylsulfonamido)benzenesulfonate); sodium (E)-6,6'-(ethene-1,2-diyl)bis(3-((N,N-dimethylsulfamoyl)amino)benzenesulfonate); sodium 6,6'-(ethane-1,2-diyl)bis(3-acetamidobenzenesulfonate); sodium 6,6'-(ethane-1,2-diyl)bis(3-isobutyramidobenzenesulfonate); sodium 6,6'-(ethane-1,2-diyl)bis(3-(2-methoxyacetamido)benzenesulfonate); sodium 6,6'-(ethane-1,2-diyl)bis(3-(methylsulfonamido)benzenesulfonate); sodium 6,6'-(ethane-1,2-diyl)bis(3-(cyclopropanesulfonamido)benzenesulfonate); sodium 6,6'-(ethane-1,2-diyl)bis(3-(1-methylethylsulfonamido)benzenesulfonate); sodium 6,6'-(ethane-1,2-diyl)bis(3-((N,N-dimethylsulfamoyl)

amino)benzenesulfonate); sodium 6,6'-(ethane-1,2-diyl)bis(3-(3-cyclopropylthioureido)benzenesulfonate); sodium 6,6'-(ethane-1,2-diyl)bis(3-(3-ethylureido)benzenesulfonate); sodium 6,6'-(ethane-1,2-diyl)bis(3-(3-isopropylureido)benzenesulfonate); sodium (E)-5-acetamido-2-(4-isobutyramido-2-sulfonatostyryl)benzenesulfonate; sodium (E)-5-acetamido-2-(4-(2-methoxyacetamido)-2-sulfonatostyryl)benzenesulfonate; sodium (E)-5-acetamido-2-(4-(cyclopropanesulfonamido)-2-sulfonatostyryl)benzenesulfonate; sodium (E)-5-acetamido-2-(4-(1-methylethylsulfonamido)-2-sulfonatostyryl)benzenesulfonate; sodium (E)-5-acetamido-2-(4-((N,N-dimethylsulfamoyl)amino)-2-sulfonatostyryl)benzenesulfonate; sodium (E)-5-isobutyramido-2-(4-(2-methoxyacetamido)-2-sulfonatostyryl)benzenesulfonate; sodium (E)-5-isobutyramido-2-(4-(methylsulfonamido)-2-sulfonatostyryl)benzenesulfonate; sodium (E)-5-(cyclopropanesulfonamido)-2-(4-isobutyramido-2-sulfonatostyryl)benzenesulfonate; sodium (E)-5-isobutyramido-2-(4-(1-methylethylsulfonamido)-2-sulfonatostyryl)benzenesulfonate; sodium (E)-5-((N,N-dimethylsulfamoyl)amino)-2-(4-isobutyramido-2-sulfonatostyryl)benzenesulfonate; sodium (E)-5-(cyclopropanesulfonamido)-2-(4-(2-methoxyacetamido)-2-sulfonatostyryl)benzenesulfonate; sodium (E)-5-(2-methoxyacetamido)-2-(4-(1-methylethylsulfonamido)-2-sulfonatostyryl)benzenesulfonate; sodium (E)-5-((N,N-dimethylsulfamoyl)amino)-2-(4-(2-methoxyacetamido)-2-sulfonatostyryl)benzenesulfonate; sodium (E)-5-(cyclopropanesulfonamido)-2-(4-(methylsulfonamido)-2-sulfonatostyryl)benzenesulfonate; sodium (E)-5-(1-methylethylsulfonamido)-2-(4-(methylsulfonamido)-2-sulfonatostyryl)benzenesulfonate; sodium (E)-5-((N,N-dimethylsulfamoyl)amino)-2-(4-(methylsulfonamido)-2-sulfonatostyryl)benzenesulfonate; sodium (E)-5-(cyclopropanesulfonamido)-2-(4-(1-methylethylsulfonamido)-2-sulfonatostyryl)benzenesulfonate; sodium (E)-5-(cyclopropanesulfonamido)-2-(4-((N,N-dimethylsulfamoyl)amino)-2-sulfonatostyryl)benzenesulfonate; sodium (E)-5-((N,N-dimethylsulfamoyl)amino)-2-(4-(1-methylethylsulfonamido)-2-sulfonatostyryl)benzenesulfonate; sodium (E)-5-acetamido-2-(4-(3-methylthioureido)-2-sulfonatostyryl)benzenesulfonate; sodium (E)-5-acetamido-2-(4-(3-isopropylthioureido)-2-sulfonatostyryl)benzenesulfonate; sodium (E)-5-acetamido-2-(4-(3-cyclopropylthioureido)-2-sulfonatostyryl)benzenesulfonate; sodium (E)-5-isobutyramido-2-(4-(3-methylthioureido)-2-sulfonatostyryl)benzenesulfonate; sodium (E)-5-isobutyramido-2-(4-(3-isopropylthioureido)-2-sulfonatostyryl)benzenesulfonate; sodium (E)-5-(2-methoxyacetamido)-2-(4-(3-methylthioureido)-2-sulfonatostyryl)benzenesulfonate; sodium (E)-5-(3-isopropylthioureido)-2-(4-(2-methoxyacetamido)-2-sulfonatostyryl)benzenesulfonate; sodium (E)-5-(3-cyclopropylthioureido)-2-(4-(2-methoxyacetamido)-2-sulfonatostyryl)benzenesulfonate; sodium (E)-5-(methylsulfonamido)-2-(4-(3-methylthioureido)-2-sulfonatostyryl)benzenesulfonate; sodium (E)-5-(3-isopropylthioureido)-2-(4-(methylsulfonamido)-2-sulfonatostyryl)benzenesulfonate; sodium (E)-5-(3-cyclopropylthioureido)-2-(4-(methylsulfonamido)-2-sulfonatostyryl)benzenesulfonate; sodium (E)-5-(cyclopropanesulfonamido)-2-(4-(3-methylthioureido)-2-sulfonatostyryl)benzenesulfonate; sodium (E)-5-(cyclopropanesulfonamido)-2-(4-(3-cyclopropylthioureido)-2-sulfonatostyryl)benzenesulfonate; sodium (E)-5-(1-methylethylsulfonamido)-2-(4-(3-methylthioureido)-2-sulfonatostyryl)benzenesulfonate; sodium (E)-5-(3-isopropylthioureido)-2-(4-(1-methylethylsulfonamido)-2-sulfonatostyryl)benzenesulfonate; sodium (E)-5-(3-cyclopropylthioureido)-2-(4-(1-methylethylsulfonamido)-2-sulfonatostyryl)benzenesulfonate; sodium (E)-5-((N,N-dimethylsulfamoyl)amino)-2-(4-(3-methylthioureido)-2-sulfonatostyryl)benzenesulfonate; sodium (E)-5-((N,N-dimethylsulfamoyl)amino)-2-(4-(3-isopropylthioureido)-2-sulfonatostyryl)benzenesulfonate; sodium (E)-5-(3-cyclopropylthioureido)-2-(4-((N,N-dimethylsulfamoyl)amino)-2-sulfonatostyryl)benzenesulfonate; sodium (E)-5-acetamido-2-(4-(3-ethylureido)-2-sulfonatostyryl)benzenesulfonate; sodium (E)-5-acetamido-2-(4-(3-isopropylureido)-2-sulfonatostyryl)benzenesulfonate; sodium (E)-5-(3-ethylureido)-2-(4-isobutyramido-2-sulfonatostyryl)benzenesulfonate; sodium (E)-5-isobutyramido-2-(4-(3-isopropylureido)-2-sulfonatostyryl)benzenesulfonate; sodium (E)-5-(3-ethylureido)-2-(4-(2-methoxyacetamido)-2-sulfonatostyryl)benzenesulfonate; sodium (E)-5-(3-isopropylureido)-2-(4-(2-methoxyacetamido)-2-sulfonatostyryl)benzenesulfonate; sodium (E)-5-(3-ethylureido)-2-(4-(methylsulfonamido)-2-sulfonatostyryl)benzenesulfonate; sodium (E)-5-(3-isopropylureido)-2-(4-(methylsulfonamido)-2-sulfonatostyryl)benzenesulfonate; sodium (E)-5-(cyclopropanesulfonamido)-2-(4-(3-isopropylureido)-2-sulfonatostyryl)benzenesulfonate; sodium (E)-5-(3-ethylureido)-2-(4-(1-methylethylsulfonamido)-2-sulfonatostyryl)benzenesulfonate; sodium (E)-5-(3-isopropylureido)-2-(4-(1-methylethylsulfonamido)-2-sulfonatostyryl)benzenesulfonate; sodium (E)-5-((N,N-dimethylsulfamoyl)amino)-2-(4-(3-ethylureido)-2-sulfonatostyryl)benzenesulfonate; sodium (E)-5-((N,N-dimethylsulfamoyl)amino)-2-(4-(3-isopropylureido)-2-sulfonatostyryl)benzenesulfonate; sodium (E)-5-isobutyramido-2-(2-sulfonatostyryl)benzenesulfonate; sodium (E)-5-(2-methoxyacetamido)-2-(2-sulfonatostyryl)benzenesulfonate; sodium (E)-5-(cyclopropanesulfonamido)-2-(2-sulfonatostyryl)benzenesulfonate; sodium (E)-5-(3-methylthioureido)-2-(2-sulfonatostyryl)benzenesulfonate; sodium (E)-5-(3-isopropylthioureido)-2-(2-sulfonatostyryl)benzenesulfonate; sodium (E)-5-(3-cyclopropylthioureido)-2-(2-sulfonatostyryl)benzenesulfonate; sodium (E)-5-(3-isopropylureido)-2-(2-sulfonatostyryl)benzenesulfonate; sodium (E)-6,6'-(ethene-1,2-diyl)bis(3-(3-methylthioureido)benzenesulfonate); sodium (E)-6,6'-(ethene-1,2-diyl)bis(3-(3-isopropylthioureido)benzenesulfonate); sodium (E)-6,6'-(ethene-1,2-diyl)bis(3-(3-ethylureido)benzenesulfonate); sodium (E)-6,6'-(ethene-1,2-diyl)bis(3-(3-isopropylureido)benzenesulfonate); (E)-4,4'-

(ethene-1,2-diyl)bis(N-methylbenzamide); (E)-4,4'-(ethene-1,2-diyl)bis(N-isopropylbenzamide); (E)-4,4'-(ethene-1,2-diyl)bis(N,N-dimethylbenzamide); (E)-(ethene-1,2-diylbis(4,1-phenylene))bis(morpholinomethanone); (E)-5-(4-hydroxystyryl)benzene-1,3-diol(3,5,4'-trihydroxy-trans-stilbene); and resveratrol.

27. The method of paragraph 21, wherein the stilbene or stilbene derivative is selected from the group consisting of:
(E)-N,N'-(ethene-1,2-diylbis(4,1-phenylene))bis(propane-2-sulfonamide); (E)-N-(4-(4-(dimethylamino)styryl)phenyl)cyclopropanesulfonamide; sodium (E)-5-acetamido-2-(4-(cyclopropanesulfonamido)-2-sulfonatostyryl)benzenesulfonate; (E)-N,N'-(ethene-1,2-diylbis(4,1-phenylene))bis(dimethylaminosulfonamide); (E)-N-(4-(4-(dimethylamino)styryl)phenyl)propane-2-sulfonamide; sodium (E)-5-(3-cyclopropylthioureido)-2-(4-(1-methylethylsulfonamido)-2-sulfonatostyryl)benzenesulfonate; sodium 6,6'-(ethane-1,2-diyl)bis(3-(3-isopropylureido)benzenesulfonate); sodium (E)-5-(3-ethylureido)-2-(4-(2-methoxyacetamido)-2-sulfonatostyryl)benzenesulfonate; (E)-4,4'-(ethene-1,2-diyl)bis(N-methylbenzamide); (E)-5-acetamido-2-(4-(3-cyclopropylthioureido)-2-sulfonatostyryl)benzenesulfonate; (E)-5-(cyclopropanesulfonamido)-2-(4-(3-isopropylureido)-2-sulfonatostyryl)benzenesulfonate; (E)-5-((N,N-dimethylsulfamoyl)amino)-2-(4-(3-methylthioureido)-2-sulfonatostyryl)benzenesulfonate; 6,6'-(ethane-1,2-diyl)bis(3-(3-isopropylureido)benzenesulfonate); (E)-5-acetamido-2-(4-(3-isopropylthioureido)-2-sulfonatostyryl)benzenesulfonate; (E)-5-acetamido-2-(4-(cyclopropanesulfonamido)-2-sulfonatostyryl)benzenesulfonate; and (E)-5-acetamido-2-(4-((N,N-dimethylsulfamoyl)amino)-2-sulfonatostyryl)benzenesulfonate.

28. The method of paragraph 20, wherein the inhibitor of DNA double strand break repair is selected from the group consisting of:
4-methylquinazoline-2-carboxamide; benz[h]isoquinolin-6-amine; 5,6-dimethyl-2-mercaptomethylbenzimidazole; (E)-1-(2-hydroxyphenyl)-3-(pyridine-3-yl)prop-2-en-1-one; N4-butyl-6-chloropyrimidine-2,4-diamine; 1-thermopsine; 6-amino-5-nitroso-2-phenylpyrimidin-4(1H)-one; and 4-(2-amino-4-nitrophenylamino)phenyl.

29. The method of paragraph 20, wherein the inhibitor of DNA double strand break repair is selected from the group consisting of:
7-azaindole-3-carboxaldehyde; 2-amino-4-phenylphenol; 3-(1-methyl-3-pyrrolidinyl)indole; 1-methyl-[1,2,4]Triazolo[4,3-a]quinolone; 2-amino-5-nitro-1H-benzimidazole; 2-(5-nitro-2-furfurylidene)aminoethanol-N-oxide; Nifuratrone; alpha-mercapto-N,2-naphthylacetamide; 1-thermopsine; N4-butyl-6-chloro-2,4-pyrimidinediamine; 2-(2-hydroxy-6-propan-2-yloxy-cyclohexyl)acetic acid; 6-amino-5-nitroso-2-phenyl-1H-pyrimidin-4-one; 4-amino-2-hydroxyphenyl)arsonic acid; spiro[1,2-dihydroindene-3,5'-imidazolidine]-2',4'-dione; N~4~-(4-methoxyphenyl)-6-methylpyrimidine-2,4-diamine; 2-amino-9-pentyl-3H-purine-6-thione; 2-(4-methoxyphenyl)-3-(pyridin-3-yl)prop-2-enenitrile; 2-chloropyrimidine-4,6-dicarboxamide; 2-amino-3H-phenoxazin-3-one; 2-methyl-N-benzyl-7H-pyrrolo[2,3-d]pyrimidine-4-amine; 4-(benzylamino)-2-methyl-7H-pyrrolo[2,3-d]pyrimidine; 2-amino-1-naphthalenesulfonic acid; N-sec-butyl-3-methylbenzamide; Benz[h]isoquinolin-6-amine; and 2-(2-methylcyclohexylidene)hydrazinecarboxamide.

30. The method of any of paragraphs 1-20, wherein the inhibitor of DNA double strand break repair is an antibody or polypeptide comprising an antigen-binding fragment of an antibody or a protein binding protein.

31. The method of any of paragraphs 1-20, wherein the inhibitor of DNA double strand break repair is an RNAi agent selected from the group consisting of:
miRNA; shRNA; siRNA; amiRNA; dsRNA, antisense RNA or ribozyme.

32. The method of any of paragraphs 1-31, wherein the inhibitor of DNA double strand break repair further comprises a pharmaceutically acceptable carrier.

33. The method of any of paragraphs 1-32, further comprising administration of a therapeutic agent.

34. The method of any of paragraphs 1-33, wherein the subject having cells that express an a detectable or elevated level of DNA editing enzyme is identified by measuring the level of DNA editing enzyme polypeptide, mRNA, or activity in a biological sample obtained from the subject suspected of having detectable or elevated levels.

35. The method of any of paragraphs 1-34, wherein the subject having cells that express a detectable or elevated level of DNA editing enzyme is identified by measuring the level of DNA editing enzyme polypeptide, mRNA, or activity in a biological sample obtained from the subject suspected of having elevated levels and comparing that level to the level of DNA editing enzyme polypeptide, mRNA, or activity found in a biological sample obtained from a healthy subject, wherein an increased amount of DNA editing enzyme polypeptide, mRNA, or activity in the test sample is indicative of a subject in need of treatment with an inhibitor of DNA double strand break repair.

36. The method of any of paragraphs 34-35, wherein measuring the level of a DNA editing enzyme polypeptide comprises using one or more assays selected from the group consisting of:
Western blot; immunoprecipitation; enzyme-linked immunosorbent assay (ELISA); radioimmunological assay (RIA); sandwich assay; protein in situ array; immunohistological staining; radioimmunometric assay; gel diffusion precipitation reaction; immunodiffusion assay; in situ immunoassay; precipitation reaction; immunofluorescence assay; quantitative in situ protein analyses (AQUA); mass spectroscopy and immunoelectrophoresis assay.

37. The method of any of paragraphs 34-36, wherein measuring the level of a DNA editing enzyme polypeptide comprises using an assay that uses an antibody, an antibody fragment, a protein binding protein, or a peptide which binds to the DNA editing enzyme polypeptide.

38. The method of any of paragraphs 34-37, wherein the antibody or antibody fragment is a monoclonal antibody.

39. The method of any of paragraphs 34-38, wherein the antibody, antibody fragment, protein binding protein or peptide which binds to the DNA editing enzyme polypeptide is labeled with a detectable label.

40. The method of any of paragraphs 34-35, wherein measuring the level of a DNA editing enzyme mRNA comprises using one or more assays selected from the group consisting of:

RT-PCR; quantitative RT-PCR; hybridization assay; Northern blot; microarray based expression analysis; transcription amplification; self-sustained sequence replication; high throughput sequencing; and RNA-Seq.

41. The method of any of paragraphs 1-40, wherein measuring the activity of a DNA editing enzyme activity comprises determining the overall mutation status of the genome or a portion thereof using one or more assays selected from the group consisting of:
    hybridization; high throughput sequencing; exome sequencing; fluorescence in situ hybridization (FISH), PCR, and genome sequencing;
    wherein a mutation status 2% or greater than the normal mutation status indicates activity of a DNA editing enzyme.

42. The method of any of paragraphs 35-36 or 41, wherein measuring the activity of activation-induced cytidine deaminase (AID) comprises determining the status of hypermutations in the target genes IGH, BCL6, MYC, BCL11A, CD93, PIM1 and/or PAX5 using one or more assays selected from the group consisting of:
    hybridization; high throughput sequencing; exome sequencing; fluorescence in situ hybridization (FISH), PCR, and genome sequencing.

43. The method of any of paragraphs 35-36, wherein measuring the activity of activation-induced cytidine deaminase (AID) comprises using a phospho-H2AX assay, a 53BP1 assay, or a RAD51 assay.

44. A method of causing cell death comprising:
    (a) administering to a cell an effective amount of a DNA editing enzyme; and
    (b) thereafter contacting the cell of step (a) with an inhibitor of DNA double strand break repair, thereby causing cell death.

45. A method of sensitizing a cell to cell death comprising:
    (c) administering to a subject, a therapeutically effective amount of a DNA editing enzyme to sensitize a cell to cell death by use of an inhibitor of DNA double strand break repair: and
    (d) thereafter administering to the subject an inhibitor of DNA double strand break repair.

46. The method of any of paragraphs 44-44, wherein the DNA editing enzyme is administered in a form selected from the group consisting of:
    a polypeptide; a nucleic acid encoding a DNA editing enzyme; and a vector comprising a nucleic acid encoding a DNA editing enzyme.

47. The method of any of paragraphs 44-46, wherein the DNA editing enzyme is selected from the group consisting of:
    recombination activating gene 1 (RAG1); recombination activating gene 1 (RAG2); sporulation-specific protein 11 (SPO11); apolipoprotein B mRNA editing enzyme, catalytic polypeptide-like (APOBEC) family member; and activation-induced cytidine deaminase (AID).

48. The method of any of paragraphs 44-47, wherein the DNA editing enzyme is activation-induced cytidine deaminase (AID).

49. A method of determining if a test agent is an inhibitor of DNA double strand break repair comprising:
    a) contacting a cell expressing a DNA editing enzyme with a test agent; and
    b) determining cell viability of the cells of step a);
    wherein decreased cell viability indicates the test agent is an inhibitor of DNA double strand break repair.

50. The method of paragraph 49, further comprising;
    c) contacting a cell not expressing a DNA editing enzyme with the test agent;
    d) determining cell viability of the cells of step c); and
    e) determining the ratio by dividing the fraction of live cells of step b) of by the fraction of live cells in step d;
    wherein a ratio below 0.8 indicates the test agent is an inhibitor of DNA double strand break repair.

51. The method of any of paragraphs 49-50, wherein the cell expressing a DNA editing enzyme is a cell expressing AID.

52. The method of paragraph 51, wherein the cell expressing AID is a stimulated B cell.

53. The method of any of paragraphs 49-52, wherein the cell is a cancerous cell.

54. The method of any of paragraphs 49-53, wherein the cells are transfected with a nucleic acid vector encoding a DNA editing enzyme.

55. The method of any of paragraphs 49-54, wherein the cell is a cell line selected from the group consisting of CH12-F3, 3T3, CH12F3, Caco-2, CCRF-CEM, CHO, CH12-F3, COS-7, HCT 116, HEK 293, HL-60, HepG2, Jurkat, KG-1, K-562, MCF-7, MDCK, MG-63, Mo-B, MOLT-4, Ramos (RA 1) and U2-OS, 56. The method of any of paragraphs 49-55, wherein the cell is an autoimmune cell.

57. A compound of Formula XXIV:

XXIV a stereoisomer or prodrug thereof;
wherein X is sodium, potassium, aluminum, calcium, lithium, magnesium, barium, or zinc.

58. The compound of paragraph 57, wherein X is sodium.

59. A compound of Formula VIII:

VIII a stereoisomer, prodrug, or pharmaceutically acceptable salt thereof.

60. A compound of Formula X;

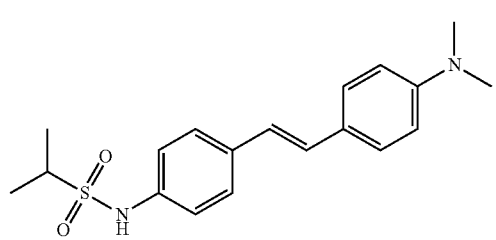

X a stereoisomer, prodrug, or pharmaceutically acceptable salt thereof.

61. A compound of Formula XXV;

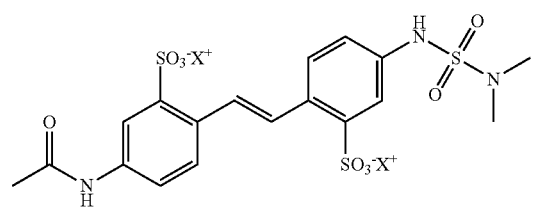

XXV a stereoisomer, or prodrug thereof;
wherein X is sodium, potassium, aluminum, calcium, lithium, magnesium, barium, or zinc.

62. The compound of paragraph 61, wherein X is sodium.

63. A compound of Formula XXXI;

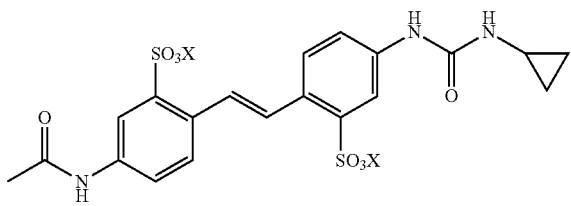

XXXI a stereoisomer, or prodrug thereof;
wherein X is sodium, potassium, aluminum, calcium, lithium, magnesium, barium, or zinc.

64. The compound of paragraph 63, wherein X is sodium.

65. A compound of Formula XXXII;

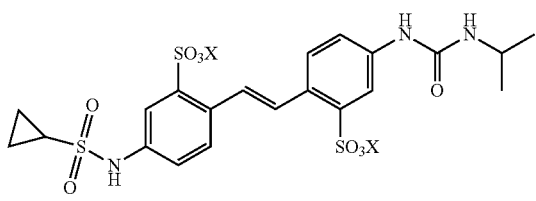

XXXII a stereoisomer, or prodrug thereof;
wherein X is sodium, potassium, aluminum, calcium, lithium, magnesium, barium, or zinc.

66. The compound of paragraph 65, wherein X is sodium.

67. A compound of Formula XXXIII;

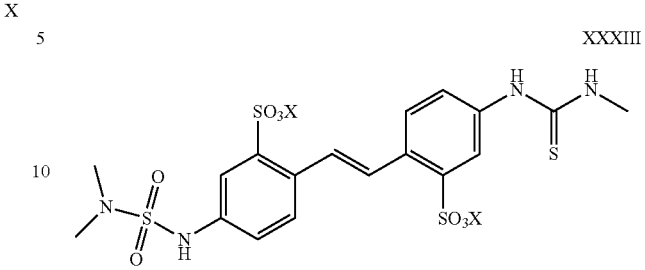

XXXIII a stereoisomer, or prodrug thereof;
wherein X is sodium, potassium, aluminum, calcium, lithium, magnesium, barium, or zinc.

68. The compound of paragraph 67, wherein X is sodium.

69. A compound of Formula XXXIV;

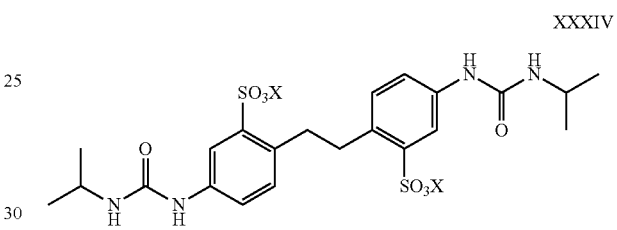

XXXIV a stereoisomer, or prodrug thereof;
wherein X is sodium, potassium, aluminum, calcium, lithium, magnesium, barium, or zinc.

70. The compound of paragraph 69, wherein X is sodium.

71. A compound of Formula XXXV;

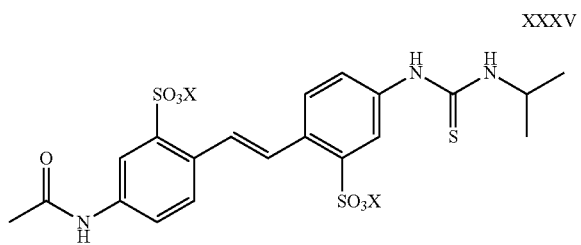

XXXV a stereoisomer, or prodrug thereof;
wherein X is sodium, potassium, aluminum, calcium, lithium, magnesium, barium, or zinc.

72. The compound of paragraph 71, wherein X is sodium.

73. The use of an inhibitor of DNA double strand break repair to treat a subject determined to have a detectable level of a DNA editing enzyme.

74. The use of paragraph 73, wherein the subject is determined to have a detectable level of DNA editing enzyme by;
   (a) obtaining a biological sample derived from a subject; and
   (b) measuring a level of a DNA editing enzyme.

75. The use of an inhibitor of DNA double strand break repair to treat a subject, the method comprising;
   (a) selecting a subject having cells that express an elevated level of a DNA editing enzyme; and (b) administering a therapeutically effective amount of an inhibitor of DNA double strand break repair to the subject;

wherein the elevated level of the DNA editing enzyme is a level of DNA editing enzyme that is higher than the level of DNA editing enzyme in cells of the same type from a healthy individual.

76. The use of paragraph 73, wherein the biological sample comprises blood cells.

77. The use of paragraph 73, wherein the biological sample comprises B cells.

78. The use of any of paragraphs 73-77, wherein the level of DNA editing enzyme in the cells expressing a detectable or elevated level of a DNA editing enzyme is statistically significantly higher than in normal cells from a healthy subject.

79. The use of paragraphs 73-78, wherein the DNA editing enzyme is selected from the group consisting of:
recombination activating gene 1 (RAG1); recombination activating gene 2 (RAG2); sporulation-specific protein 11 (SPO11); apolipoprotein B mRNA editing enzyme, catalytic polypeptide-like (APOBEC) family member; and activation-induced cytidine deaminase (AID).

80. The use of paragraph 79, wherein the DNA editing enzyme is activation-induced cytidine deaminase (AID).

81. The use of paragraph 80, wherein the level of activation-induced cytidine deaminase (AID) in B cells expressing an elevated level of AID is significantly higher than the level of AID expressed in unactivated B cells from a healthy subject 82. The use of any of paragraphs 73-81, wherein the subject is a human subject.

83. The use of any of paragraphs 73-82, wherein the biological sample or cells that express a detectable or elevated level of a DNA editing enzyme are cancerous cells.

84. The use of any of paragraphs 73-83, wherein the subject has cancer.

85. The use of any of paragraphs 73-84, wherein the biological sample or cells that express detectable or elevated level of a DNA editing enzyme are autoimmune cells.

86. The use of any of paragraphs 73-85, wherein the subject has a condition selected from the group consisting of: lymphoma, leukemia, and a plasma cell neoplasm.

87. The use of paragraph 86, wherein the lymphoma is selected from the group consisting of:
Non-Hodgkin's lymphoma; Burkitt's lymphoma, small lymphocytic lymphoma; lymphoplasmacytic lymphoma; MALT lymphoma; follicular lymphoma; diffuse large B-cell lymphoma; and T-cell lymphoma.

88. The use of paragraph 86, wherein the leukemia is selected from the group consisting of:
acute lymphoblastic leukemia (ALL), Burkitt's leukemia; B-cell leukemia; B-cell acute lymphoblastic leukemia; chronic lymphocytic leukemia (CLL); acute myelogenous leukemia (AML); chronic myelogenous leukemia (CML); and T-cell acute lymphoblastic leukemia (T-ALL).

89. The use of paragraph 86, wherein the plasma cell neoplasm is selected from the group consisting of:
multiple myeloma; plasma cell myeloma; plasma cell leukemia; and plasmacytoma.

90. The use of paragraph 86, wherein the subject has a cancer selected from the group consisting of:

epithelial cell cancer; colon cancer; liver cancer, gastric cancer; intestinal cancer; esophageal cancer; breast cancer; lung cancer; and thyroid cancer.

91. The use of any of paragraphs 73-82 and 85, wherein the subject has an autoimmune disease.

92. The use of paragraph 91, wherein the autoimmune disease is selected from the group consisting of:
lupus erythematosus; Wiskott-Aldrich syndrome; autoimmune lymphoproliferative syndrome; myasthenia gravis; rheumatoid arthritis (RA); lupus nephritis; multiple sclerosis; systemic lupus erythematosis, discoid lupus, subacute cutaneous lupus erythematosus, cutaneous lupus erythematosus including chilblain lupus erythematosus, chronic arthritis, Sjogren's syndrome, inflammatory chronic rhinosinusitis, colitis, celiac disease, inflammatory bowel disease, Barrett's esophagus, inflammatory gastritis autoimmune nephritis, autoimmune vasculitis, autoimmune hepatitis, autoimmune carditis, autoimmune encephalitis, and autoimmune mediated hematological disease.

93. The use of any of paragraphs 73-92, wherein the inhibitor of DNA double strand break repair decreases the expression or activity of one or more genes selected from the group consisting of:
Rad51; Rad51AP1; Rad51B; Rad51C; Rad51D; XRCC2; XRCC3; RAD54; RAD52; BRCA1; BRCA2; ATM; ATR; MRE11; RAD50; NBS1; WRN; BLM; RECQ4; LIG4; XRCC4; PRKDC; DCLRE1C; XRCC6; XRCC5; and XLF.

94. The use of any of paragraphs 73-93, wherein the inhibitor of DNA double strand break repair is selected from the group consisting of:
a small molecule; a protein; a peptide; an antibody; an antibody fragment; a protein binding protein; a ribonucleic acid; a deoxyribonucleic acid; an aptamer; a peptide nucleic acid (PNA); and a locked nucleic acid (LNA).

95. The use of any of paragraphs 73-93, wherein the inhibitor of DNA double strand break repair is stilbene, a stilbenoid, or a derivative thereof.

96. The use of paragraph 95, wherein the stilbene or stilbene derivative is a compound of Formula V:

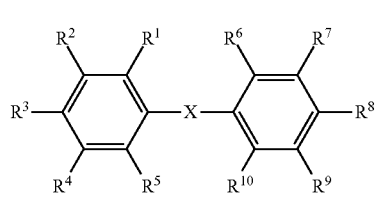

Formula V or a stereoisomer, enantiomer, prodrug, or pharmaceutically acceptable salt thereof;
wherein $R^1$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^2$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^3$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^4$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^5$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^6$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^7$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^8$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^9$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^{10}$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2$, N=C=S, $NHC(O)R^{21}$, $NHC(O)OR^{21}$, $NHC(S)R^{21}$, $NHC(S)N(R^{22})_2$, $NHSO_2R^{21}$, $NHSO_2N(R^{22})_2$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein X can be selected from the group consisting of $C(R^{21})_2$, —$C(O)N(R^{22})$—, —C(O)—, —C(O)O—, —S(O)—, —$SO_2$— —$CH(R^{11})CH(R^{12})$—, —$C(R^{11})$=$C(R^{12})$—, and wherein $R^{11}$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2NC(O)R^{21}$, $NC(O)OR^{21}$, $NC(S)R^{21}$, $NC(S)N(R^{22})_2$, $NSO_2R^{21}$, $NO_2$, $N_2$—$R^{22}$, $SOR^{21}$, $SO_2R^{21}$, $SO_3R^{21}$, $OP(O)(OH)_2$, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein $R^{12}$ can be selected from the group consisting of hydrogen, halogen, $CF_3$, CN, $C(O)R^{21}$, $CO_2R^{21}$, $C(O)N(R^{22})_2$, OH, $OR^{21}$, $N(R^{22})_2NC(O)R^{21}$, $NC(O)OR^{21}$, NC(S)R²¹, NC(S)N(R²²)₂, NSO₂R²¹, NO₂, N₂—R²², SOR²¹, SO₂R²¹, SO₃R²¹, OP(O)(OH)₂, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, and optionally substituted heteroaryl;

wherein each R²¹ can be selected independently from the group consisting of hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, and any combinations thereof;

wherein each R²² can be selected independently from the group consisting of hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, and any combinations thereof.

97. The use of paragraph 95, wherein the stilbene derivative is 4,4'diisothiocyanostilbene-2,2'-disulfonic acid (DIDS).

98. The use of paragraph 95, wherein the stilbene or stilbene derivative is selected from the group consisting of:
(E)-N,N'-(ethene-1,2-diylbis(4,1-phenylene))diacetamide; (E)-N,N'-(ethene-1,2-diylbis(4,1-phenylene))bis(2-methylpropanamide); (E)-N,N'-(ethene-1,2-diylbis(4,1-phenylene))bis(2-methoxyacetamide); (E)-N,N'-(ethene-1,2-diylbis(4,1-phenylene))dimethanesulfonamide; (E)-N,N'-(ethene-1,2-diylbis(4,1-phenylene))dicyclopropanesulfonamide; (E)-N,N'-(ethene-1,2-diylbis(4,1-phenylene))bis(propane-2-sulfonamide); (E)-N,N'-(ethene-1,2-diylbis(4,1-phenylene))bis(propane-2-sulfonamide); (E)-N-(4-(4-aminostyryl)phenyl)propane-2-sulfonamide; (E)-1,1'-(ethene-1,2-diylbis(4,1-phenylene))bis(3-methylthiourea); (E)-1,1'-(ethene-1,2-diylbis(4,1-phenylene))bis(3-isopropylthiourea); (E)-N-(4-(4-(dimethylamino)styryl)phenyl)acetamide; (E)-N-(4-(4-(dimethylamino)styryl)phenyl)isobutyramide; (E)-N-(4-(4-(dimethylamino)styryl)phenyl)-2-methoxyacetamide; (E)-N-(4-(4-(dimethylamino)styryl)phenyl) methanesulfonamide; (E)-N-(4-(4-(dimethylamino)styryl)phenyl)cyclopropanesulfonamide; (E)-N-(4-(4-(dimethylamino)styryl)phenyl)propane-2-sulfonamide; N'-(4-{(E)-2-[4-(dimethylamino)phenyl]-1-ethenyl}phenyl)-N,N-dimethylsulfamide; (E)-1-(4-(4-(dimethylamino)styryl)phenyl)-3-methylthiourea; (E)-1-(4-(4-(dimethylamino)styryl)phenyl)-3-isopropylthiourea; (E)-1-cyclopropyl-3-(4-(4-(dimethylamino)styryl)phenyl)thiourea; (E)-1-(4-(4-(dimethylamino)styryl)phenyl)-3-methylurea; (E)-1-(4-(4-(dimethylamino)styryl)phenyl)-3-isopropylurea; (E)-1-cyclopropyl-3-(4-(4-(dimethylamino)styryl)phenyl)urea; sodium (E)-6,6'-(ethene-1,2-diyl)bis(3-acetamidobenzenesulfonate); sodium (E)-6,6'-(ethene-1,2-diyl)bis(3-isobutyramidobenzenesulfonate); sodium (E)-6,6'-(ethene-1,2-diyl)bis(3-(2-methoxyacetamido)benzenesulfonate); sodium (E)-6,6'-(ethene-1,2-diyl)bis(3-(cyclopropanesulfonamido)benzenesulfonate); sodium (E)-6,6'-(ethene-1,2-diyl)bis(3-(1-methylethylsulfonamido)benzenesulfonate); sodium (E)-6,6'-(ethene-1,2-diyl)bis(3-((N,N-dimethylsulfamoyl)amino)benzenesulfonate); sodium 6,6'-(ethane-1,2-diyl)bis(3-acetamidobenzenesulfonate); sodium 6,6'-(ethane-1,2-diyl)bis(3-isobutyramidobenzenesulfonate); sodium 6,6'-(ethane-1,2-diyl)bis(3-(2-methoxyacetamido)benzenesulfonate); sodium 6,6'-(ethane-1,2-diyl)bis(3-(methylsulfonamido)benzenesulfonate); sodium 6,6'-(ethane-1,2-diyl)bis(3-(cyclopropanesulfonamido)benzenesulfonate); sodium 6,6'-(ethane-1,2-diyl)bis(3-(1-methylethylsulfonamido)benzenesulfonate); sodium 6,6'-(ethane-1,2-diyl)bis(3-((N,N-dimethylsulfamoyl)amino)benzenesulfonate); sodium 6,6'-(ethane-1,2-diyl)bis(3-(3-cyclopropylthioureido)benzenesulfonate); sodium 6,6'-(ethane-1,2-diyl)bis(3-(3-ethylureido)benzenesulfonate); sodium 6,6'-(ethane-1,2-diyl)bis(3-(3-isopropylureido)benzenesulfonate); sodium (E)-5-acetamido-2-(4-isobutyramido-2-sulfonatostyryl)benzenesulfonate; sodium (E)-5-acetamido-2-(4-(2-methoxyacetamido)-2-sulfonatostyryl)benzenesulfonate; sodium (E)-5-acetamido-2-(4-(cyclopropanesulfonamido)-2-sulfonatostyryl)benzenesulfonate; sodium (E)-5-acetamido-2-(4-(1-methylethylsulfonamido)-2-sulfonatostyryl)benzenesulfonate; sodium (E)-5-acetamido-2-(4-((N,N-dimethylsulfamoyl)amino)-2-sulfonatostyryl)benzenesulfonate; sodium (E)-5-isobutyramido-2-(4-(2-methoxyacetamido)-2-sulfonatostyryl)benzenesulfonate; sodium (E)-5-isobutyramido-2-(4-(methylsulfonamido)-2-sulfonatostyryl)benzenesulfonate; sodium (E)-5-(cyclopropanesulfonamido)-2-(4-isobutyramido-2-sulfonatostyryl)benzenesulfonate; sodium (E)-5-isobutyramido-2-(4-(1-methylethylsulfonamido)-2-sulfonatostyryl)benzenesulfonate; sodium (E)-5-((N,N-dimethylsulfamoyl)amino)-2-(4-isobutyramido-2-sulfonatostyryl)benzenesulfonate; sodium (E)-5-(cyclopropanesulfonamido)-2-(4-(2-methoxyacetamido)-2-sulfonatostyryl)benzenesulfonate; sodium (E)-5-(2-methoxyacetamido)-2-(4-(1-methylethylsulfonamido)-2-sulfonatostyryl)benzenesulfonate; sodium (E)-5-((N,N-dimethylsulfamoyl)amino)-2-(4-(2-methoxyacetamido)-2-sulfonatostyryl)benzenesulfonate; sodium (E)-5-(cyclopropanesulfonamido)-2-(4-(methylsulfonamido)-2-sulfonatostyryl)benzenesulfonate; sodium (E)-5-(1-methylethylsulfonamido)-2-(4-(methylsulfonamido)-2-sulfonatostyryl)benzenesulfonate; sodium (E)-5-((N,N-dimethylsulfamoyl)amino)-2-(4-(methylsulfonamido)-2-sulfonatostyryl)benzenesulfonate; sodium (E)-5-(cyclopropanesulfonamido)-2-(4-(1-methylethylsulfonamido)-2-sulfonatostyryl)benzenesulfonate; sodium (E)-5-(cyclopropanesulfonamido)-2-(4-((N,N-dimethylsulfamoyl)amino)-2-sulfonatostyryl)benzenesulfonate; sodium (E)-5-((N,N-dimethylsulfamoyl)amino)-2-(4-(1-methylethylsulfonamido)-2-sulfonatostyryl)benzenesulfonate; sodium (E)-5-acetamido-2-(4-(3-methylthioureido)-2-sulfonatostyryl)benzenesulfonate; sodium (E)-5-acetamido-2-(4-(3-isopropylthioureido)-2-sulfonatostyryl)benzenesulfonate; sodium (E)-5-acetamido-2-(4-(3-cyclopropylthioureido)-2-sulfonatostyryl)benzenesulfonate; sodium (E)-5-isobutyramido-2-(4-(3-methylthioureido)-2-sulfonatostyryl)benzenesulfonate; sodium (E)-5-isobutyramido-2-(4-(3-isopropylthioureido)-2-sulfonatostyryl)benzenesulfonate; sodium (E)-5-(2-methoxyacetamido)-2-(4-(3-methylthioureido)-2-sulfonatostyryl)benzenesulfonate; sodium (E)-5-(3-isopropylthioureido)-2-(4-(2-methoxyacetamido)-2-sulfonatostyryl)benzenesulfonate; sodium (E)-5-(3-cyclopropylthioureido)-2-(4-(2-methoxyacetamido)-2-sulfonatostyryl)benzenesulfonate; sodium (E)-5-(methylsulfonamido)-2-(4-(3-methylthioureido)-2-sulfonatostyryl)benzenesulfonate; sodium (E)-5-(3-isopropylthioureido)-2-(4-(methylsulfonamido)-2-sulfonatostyryl)benzenesulfonate; sodium (E)-5-(3- cyclopropylthioureido)-2-(4-(methylsulfonamido)-2-sulfonatostyryl)benzenesulfonate; sodium (E)-5-(cyclopropanesulfonamido)-2-(4-(3-methylthioureido)-2-sulfonatostyryl)benzenesulfonate; sodium (E)-5-(cyclopropanesulfonamido)-2-(4-(3-cyclopropylthioureido)-2-sulfonatostyryl)benzenesulfonate; sodium (E)-5-(1-methylethylsulfonamido)-2-(4-(3-methylthioureido)-2-sulfonatostyryl)benzenesulfonate; sodium (E)-5-(3-isopropylthioureido)-2-(4-(1-methylethylsulfonamido)-2-sulfonatostyryl)benzenesulfonate; sodium (E)-5-(3-cyclopropylthioureido)-2-(4-(1-methylethylsulfonamido)-2-sulfonatostyryl)benzenesulfonate; sodium (E)-5-((N,N-dimethylsulfamoyl)amino)-2-(4-(3-methylthioureido)-2-sulfonatostyryl)benzenesulfonate; sodium (E)-5-((N,N-dimethylsulfamoyl)amino)-2-(4-(3-isopropylthioureido)-2-sulfonatostyryl)benzenesulfonate; sodium (E)-5-(3-cyclopropylthioureido)-2-(4-((N,N-dimethylsulfamoyl)amino)-2-sulfonatostyryl)benzenesulfonate; sodium (E)-5-acetamido-2-(4-(3-ethylureido)-2-sulfonatostyryl)benzenesulfonate; sodium (E)-5-acetamido-2-(4-(3-isopropylureido)-2-sulfonatostyryl)benzenesulfonate; sodium (E)-5-(3-ethylureido)-2-(4-isobutyramido-2-sulfonatostyryl)benzenesulfonate; sodium (E)-5-isobutyramido-2-(4-(3-isopropylureido)-2-sulfonatostyryl)benzenesulfonate; sodium (E)-5-(3-ethylureido)-2-(4-(2-methoxyacetamido)-2-sulfonatostyryl)benzenesulfonate; sodium (E)-5-(3-isopropylureido)-2-(4-(2-methoxyacetamido)-2-sulfonatostyryl)benzenesulfonate; sodium (E)-5-(3-ethylureido)-2-(4-(methylsulfonamido)-2-sulfonatostyryl)benzenesulfonate; sodium (E)-5-(3-isopropylureido)-2-(4-(methylsulfonamido)-2-sulfonatostyryl)benzenesulfonate; sodium (E)-5-(cyclopropanesulfonamido)-2-(4-(3-isopropylureido)-2-sulfonatostyryl)benzenesulfonate; sodium (E)-5-(3-ethylureido)-2-(4-(1-methylethylsulfonamido)-2-sulfonatostyryl)benzenesulfonate; sodium (E)-5-(3-isopropylureido)-2-(4-(1-methylethylsulfonamido)-2-sulfonatostyryl)benzenesulfonate; sodium (E)-5-((N,N-dimethylsulfamoyl)amino)-2-(4-(3-ethylureido)-2-sulfonatostyryl)benzenesulfonate; sodium (E)-5-((N,N-dimethylsulfamoyl)amino)-2-(4-(3-isopropylureido)-2-sulfonatostyryl)benzenesulfonate; sodium (E)-5-isobutyramido-2-(2-sulfonatostyryl)benzenesulfonate; sodium (E)-5-(2-methoxyacetamido)-2-(2-sulfonatostyryl)benzenesulfonate; sodium (E)-5-(cyclopropanesulfonamido)-2-(2-sulfonatostyryl)benzenesulfonate; sodium (E)-5-(3-methylthioureido)-2-(2-sulfonatostyryl)benzenesulfonate; sodium (E)-5-(3-isopropylthioureido)-2-(2-sulfonatostyryl)benzenesulfonate; sodium (E)-5-(3-cyclopropylthioureido)-2-(2-sulfonatostyryl)benzenesulfonate; sodium (E)-5-(3-isopropylureido)-2-(2-sulfonatostyryl)benzenesulfonate; sodium (E)-6,6'-(ethene-1,2-diyl)bis(3-(3-methylthioureido)benzenesulfonate); sodium (E)-6,6'-(ethene-1,2-diyl)bis(3-(3-isopropylthioureido)benzenesulfonate); sodium (E)-6,6'-(ethene-1,2-diyl)bis(3-(3-ethylureido)benzenesulfonate); sodium (E)-6,6'-(ethene-1,2-diyl)bis(3-(3-isopropylureido)benzenesulfonate); (E)-4,4'-(ethene-1,2-diyl)bis(N-methylbenzamide); (E)-4,4'-(ethene-1,2-diyl)bis(N-isopropylbenzamide); (E)-4,4'-(ethene-1,2-diyl)bis(N,N-dimethylbenzamide); (E)-(ethene-1,2-diylbis(4,1-phenylene))bis(morpholinomethanone); (E)-5-(4-hydroxystyryl)benzene-1,3-diol(3,5,4'-trihydroxy-trans-stilbene); and resveratrol.

99. The use of paragraph 95, wherein the stilbene or stilbene derivative is selected from the group consisting of:
(E)-N,N'-(ethene-1,2-diylbis(4,1-phenylene))bis(propane-2-sulfonamide); (E)-N-(4-(4-(dimethylamino)styryl)phenyl)cyclopropanesulfonamide; sodium (E)-5-acetamido-2-(4-(cyclopropanesulfonamido)-2-sulfonatostyryl)benzenesulfonate; (E)-N,N'-(ethene-1,2-diylbis(4,1-phenylene))bis(dimethylaminosulfonamide); (E)-N-(4-(4-(dimethylamino)styryl)phenyl)propane-2-sulfonamide; sodium (E)-5-(3-cyclopropylthioureido)-2-(4-(1-methylethylsulfonamido)-2-sulfonatostyryl)benzenesulfonate; sodium 6,6'-(ethane-1,2-diyl)bis(3-(3-isopropylureido)benzenesulfonate); sodium (E)-5-(3-ethylureido)-2-(4-(2-methoxyacetamido)-2-sulfonatostyryl)benzenesulfonate; (E)-4,4'-(ethene-1,2-diyl)bis(N-methylbenzamide); (E)-5-acetamido-2-(4-(3-cyclopropylthioureido)-2-sulfonatostyryl)benzenesulfonate; (E)-5-(cyclopropanesulfonamido)-2-(4-(3-isopropylureido)-2-sulfonatostyryl)benzenesulfonate; (E)-5-((N,N-dimethylsulfamoyl)amino)-2-(4-(3-methylthioureido)-2-sulfonatostyryl)benzenesulfonate; 6,6'-(ethane-1,2-diyl)bis(3-(3-isopropylureido)benzenesulfonate); (E)-5-acetamido-2-(4-(3-isopropylthioureido)-2-sulfonatostyryl)benzenesulfonate; (E)-5-acetamido-2-(4-(cyclopropanesulfonamido)-2-sulfonatostyryl)benzenesulfonate; and (E)-5-acetamido-2-(4-((N,N-dimethylsulfamoyl)amino)-2-sulfonatostyryl)benzenesulfonate.

100. The use of paragraph 94, wherein the inhibitor of DNA double strand break repair is selected from the group consisting of:
4-methylquinazoline-2-carboxamide; benz[h]isoquinolin-6-amine; 5,6-dimethyl-2-mercaptomethylbenzimidazole; (E)-1-(2-hydroxyphenyl)-3-(pyridine-3-yl)prop-2-en-1-one; N4-butyl-6-chloropyrimidine-2,4-diamine; 1-thermopsine; 6-amino-5-nitroso-2-phenylpyrimidin-4(1H)-one; and 4-(2-amino-4-nitrophenylamino)phenyl.

101. The use of paragraph 94, wherein the inhibitor of DNA double strand break repair is selected from the group consisting of:
7-azaindole-3-carboxaldehyde; 2-amino-4-phenylphenol; 3-(1-methyl-3-pyrrolidinyl)indole; 1-methyl-[1,2,4]Triazolo[4,3-a]quinolone; 2-amino-5-nitro-1H-benzimidazole; 2-(5-nitro-2-furfurylidene)aminoethanol-N-oxide; Nifuratrone; alpha-mercapto-N,2-naphthylacetamide; 1-thermospine; N4-butyl-6-chloro-2,4-pyrimidinediamine; 2-(2-hydroxy-6-propan-2-yloxy-cyclohexyl)acetic acid; 6-amino-5-nitroso-2-phenyl-1H-pyrimidin-4-one; 4-amino-2-hydroxyphenyl)arsonic acid; spiro[1,2-dihydroindene-3,5'-imidazolidine]-2',4'-dione; N~4~-(4-methoxyphenyl)-6-methylpyrimidine-2,4-diamine; 2-amino-9-pentyl-3H-purine-6-thione; 2-(4-methoxyphenyl)-3-(pyridin-3-yl)prop-2-enenitrile; 2-chloropyrimidine-4,6-dicarboxamide; 2-amino-3H-phenoxazin-3-one; 2-methyl-N-benzyl-7H-pyrrolo[2,3-d]pyrimidine-4-amine; 4-(benzylamino)-2-methyl-7H-pyrrolo[2,3-d]pyrimidine; 2-amino-1-naphthalenesulfonic acid; N-sec-butyl-3-methylbenzamide; Benz[h]isoquinolin-6-amine; and 2-(2-methylcyclohexylidene)hydrazinecarboxamide.

102. The use of any of paragraphs 73-94, wherein the inhibitor of DNA double strand break repair is an antibody or polypeptide comprising an antigen-binding fragment of an antibody or a protein binding protein.

103. The use of any of paragraphs 73-94, wherein the inhibitor of DNA double strand break repair is an RNAi agent selected from the group consisting of:
   miRNA; shRNA; siRNA; amiRNA; dsRNA; antisense RNA or ribozyme.
104. The use of any of paragraphs 73-103, wherein the inhibitor of DNA double strand break repair further comprises a pharmaceutically acceptable carrier.
105. The use of any of paragraphs 73-104, further comprising administration of a therapeutic agent.
106. The use of any of paragraphs 73-105, wherein the subject having cells that express an a detectable or elevated level of DNA editing enzyme is identified by measuring the level of DNA editing enzyme polypeptide, mRNA, or activity in a biological sample obtained from the subject suspected of having detectable or elevated levels.
107. The use of any of paragraphs 73-106, wherein the subject having cells that express a detectable or elevated level of DNA editing enzyme is identified by measuring the level of DNA editing enzyme polypeptide, mRNA, or activity in a biological sample obtained from the subject suspected of having elevated levels and comparing that level to the level of DNA editing enzyme polypeptide, mRNA, or activity found in a biological sample obtained from a healthy subject, wherein an increased amount of DNA editing enzyme polypeptide, mRNA, or activity in the test sample is indicative of a subject in need of treatment with an inhibitor of DNA double strand break repair.
108. The use of any of paragraphs 106-107, wherein measuring the level of a DNA editing enzyme polypeptide comprises using one or more assays selected from the group consisting of:
   Western blot; immunoprecipitation; enzyme-linked immunosorbent assay (ELISA); radioimmunological assay (RIA); sandwich assay; protein in situ array; immunohistological staining; radioimmunometric assay; gel diffusion precipitation reaction; immunodiffusion assay; in situ immunoassay; precipitation reaction; immunofluorescence assay; quantitative in situ protein analyses (AQUA); mass spectroscopy and immunoelectrophoresis assay.
109. The use of any of paragraphs 106-107, wherein measuring the level of a DNA editing enzyme polypeptide comprises using an assay that uses an antibody, an antibody fragment, a protein binding protein, or a peptide which binds to the DNA editing enzyme polypeptide.
110. The use of any of paragraphs 106-109, wherein the antibody or antibody fragment is a monoclonal antibody.
111. The use of any of paragraphs 106-110, wherein the antibody, antibody fragment, protein binding protein or peptide which binds to the DNA editing enzyme polypeptide is labeled with a detectable label.
112. The use of any of paragraphs 106-107, wherein measuring the level of a DNA editing enzyme mRNA comprises using one or more assays selected from the group consisting of:
   RT-PCR; quantitative RT-PCR; hybridization assay; Northern blot; microarray based expression analysis; transcription amplification; self-sustained sequence replication; high throughput sequencing; and RNA-Seq.
113. The use of any of paragraphs 106-107, wherein measuring the activity of a DNA editing enzyme comprises determining the overall mutation status of the genome or a portion thereof using one or more assays selected from the group consisting of:
   hybridization; high throughput sequencing; exome sequencing; fluorescence in situ hybridization (FISH), PCR, and genome sequencing;
   wherein a mutation status 2% or greater than the normal mutation status indicates activity of a DNA editing enzyme.
114. The use of any of paragraphs 106-107 and 113, wherein measuring the activity of activation-induced cytidine deaminase (AID) activity comprises determining the status of hypermutations in the target genes IGH, BCL6, MYC, BCL11A, CD93, PIM1 and/or PAX5 using one or more assays selected from the group consisting of:
   hybridization; high throughput sequencing; exome sequencing; fluorescence in situ hybridization (FISH), PCR, and genome sequencing.
115. The use of any of paragraphs 106-107, wherein measuring the activity of activation-induced cytidine deaminase (AID) comprises using a phospho-H2AX assay, a 53BP1 assay, or a RAD51 assay.
116. The method or use of any of claims 1-48 and 73-115 wherein the method or use further comprises administering at least one compound selected from the group consisting of:
   a Bruton's tyrosine kinase inhibitor (BTK inhibitor); a Bcl-2 inhibitor; a Chk1 inhibitor; a MDM2 inhibitor; a WEE1 inhibitor; a poly ADP ribose polymerase (PARP) inhibitor; and an interleukin-1 receptor-associated kinase 4 (IRAK-4) inhibitor.

EXAMPLES

Example 1: Inhibition of XRCC2 in Splenocytes

Adult splenocytes were isolated from 4 to 6-month-old C57BL6/J mice. A single cell suspension was prepared by mechanical disruption, dispersing the spleens through fine, sterile mesh in RPMI-1640 medium with 2-10 mM L-glutamine (Gibco) with 10% (vol/vol) heat-inactivated fetal bovine serum (FBS, Gibco). Red blood cells were removed by hypotonic lysis using 8.3 g/L of ammonium chloride in 0.01M Tris-HCl buffer at a pH of 7.5. The remaining splenocytes were cultured in supplemented RPMI-1640 with 2-10 mM L-glutamine supplemented with 10% fetal bovine serum (FBS) in a 5% $CO_2$ humidified atmosphere at 37° C. The cells were transduced with lentiviral shRNA vectors targeting Xrcc2 (TRCN0000071023, TRCN0000071024 and TRCN0000071027; from Sigma). CH12-F3-derivative lines stably expressing Xrcc2-specific short hairpin RNA (shRNA) or control shRNA (with a scrambled sequence) were generated by direct transduction with individual shRNA vectors, followed by selection for puromycin resistance. For transduction of primary splenocytes, the original vectors were modified by replacement of the puromycin-resistance cassette with sequence encoding enhanced Green Fluorescent Protein (eGFP) (Clontech). As a control, empty pLKO.1-eGFP vector or vector expressing scrambled shRNA was used. Vectors were packaged into pseudotyped viruses and were used to transduce primary cells as described in Hasham, and Tsygankov, 2004, Virology 320, 313-329. The cells transduced with the Xrcc2-specific shRNA were called XKD cells and the controls labeled Ctrl. One subset was cultured as non-activated (Non) with 1 μg/ml antibody to CD40 (anti-CD40; HM40-3; Pharmingen) alone to induce proliferation without class switching, and the other set as activated (Act) with 1 µg/ml anti-CD40 plus 25 ng/ml interleukin 4 (IL-4; Peprotech, Cat. No. 214-14) to induce proliferation and class-switch recombination. Media and cytokines were replenished after 2 days. After 3 days of stimulation cells were assessed for viability using the expression of eGFP. FIG. 1 shows that all non-activated cells behave the same. In activated cells the knockdown of Xrcc2 results in a greatly reduced cell number. FIG. 1 further shows that the lack of p53 (Trp53−/−) can partially rescue the cytotoxicity observed in the group expressing Xrcc2 shRNA.

Example 2: Comparison of AID Expressing Cells with AID-Deficient Cells

Figure 2:
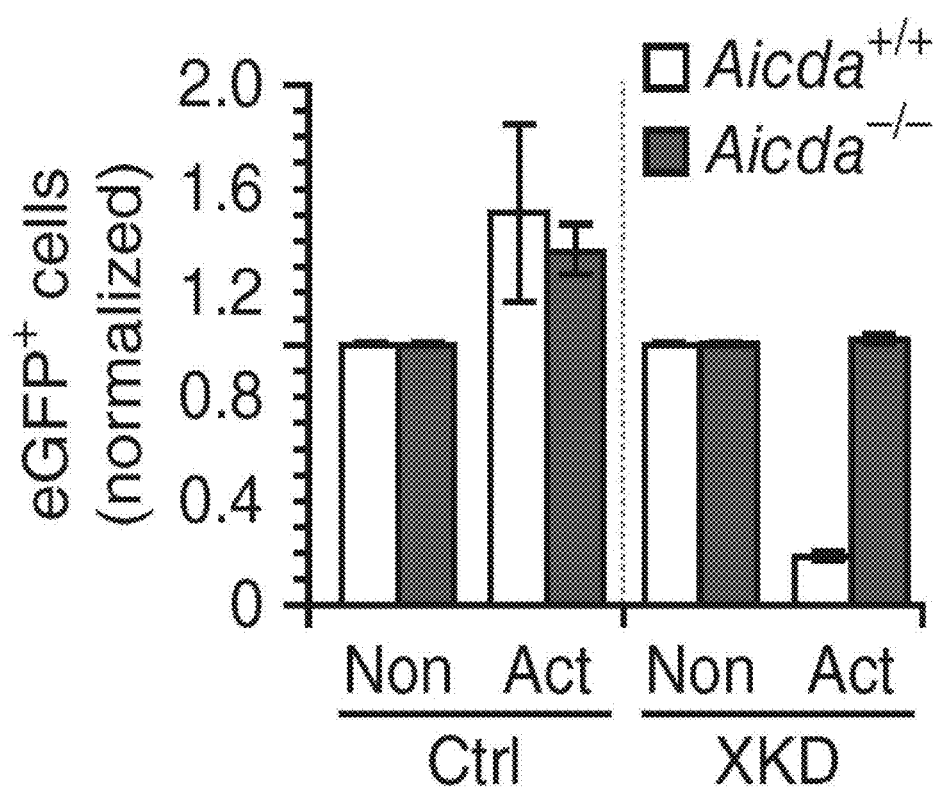
FIG. 2 shows a graph of flow cytometry data of activated (ACT) and non-activated (NON) wild-type (Aicda$^{+/+}$, open bars) or Aicda$^{-/-}$ mouse splenocytes (filled bars) transduced with Xrcc2-specific (XKD) or control shRNA (Ctrl). Flow cytometry analysis of eGFP$^+$ cells was performed 3 days after stimulation. Data are representative of two experiments with four replicates, experiments (mean and s.e.m.).
Figure 3:
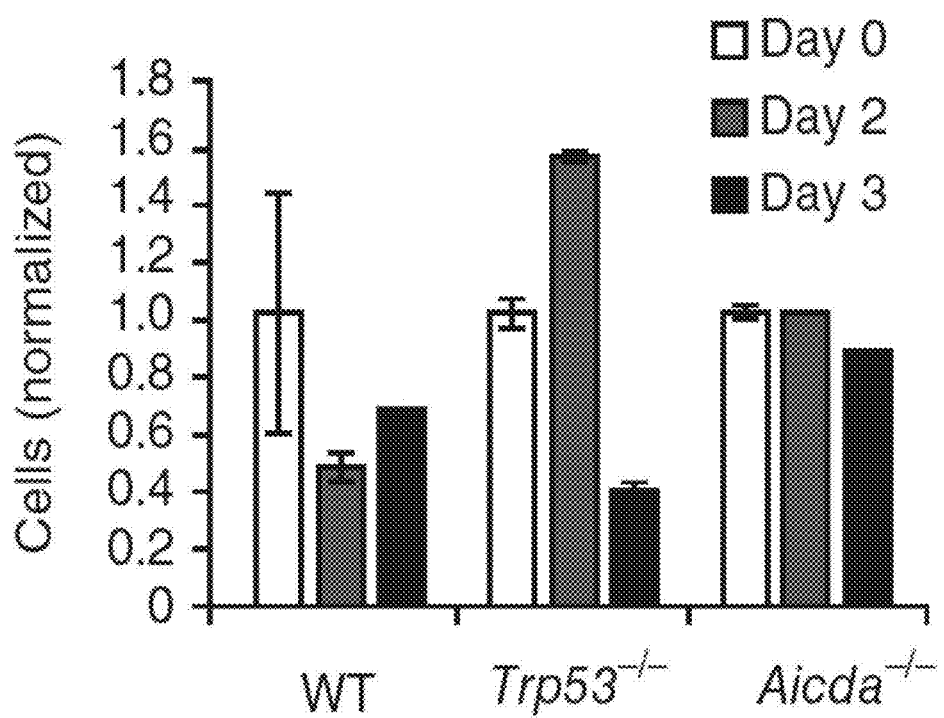
FIG. 3 shows a flow cytometry data graph from the B cells, transduced with Xrcc2-specific shRNA and stimulated for 0, 2 or 3 days with anti-CD40 plus IL-4; total counts of cells activated with anti-CD40 and IL-4 are normalized to those of cells stimulated with anti-CD40 alone. Day 0 data is shown in the white bars, Day 2 data is shown in the grey bars and Day 3 data is shown in the black bars. Data are representative of two experiments with four replicates, experiments (mean and s.e.m.). The x-axis shows the genotype of the cells.

Splenocytes were isolated and cultured as described in Example 1 from either wild type mice (AID$^{+/+}$) or AID-deficient (AID−/−) mice (Muramatsu et al. et al., 2000, Cell 102: 553-63) and transduced with Xrcc2 shRNA (XKD) or control shRNA as described in Example 1. Knockdown of XRCC2 in AID$^{+/+}$ B cells compromised survival after activation (FIG. 2). In contrast, activation of XKD B cells from AID$^{-/-}$ mice produced no detectable change in cell viability or survival. When XKD cells were enriched specifically for B220$^+$IgM$^+$ B cells by depletion of CD43-expressing cells via magnetic bead-based cell sorting (120-000-302; Miltenyi) and assayed at various time points after activation for cell viability or survival, no change was observed in AID$^{-/-}$ cells (FIG. 3). In B-cells expressing AID (WT), an increase in cell death was observed on day 2 and day 3.

Figure 4:
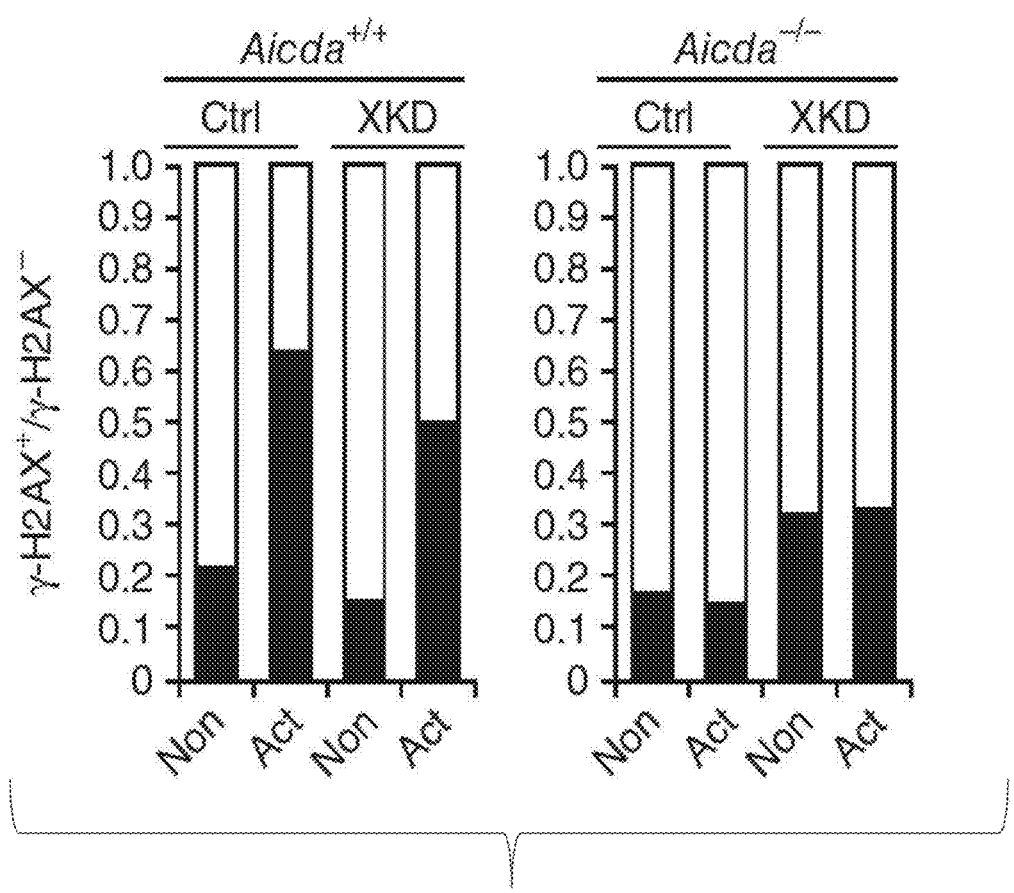
FIG. 4 shows foci of γ-H2AX in Aicda$^{+/+}$ and Aicda$^{-/-}$ XKD and control (Ctrl) splenic B cells grown in nonactivating (Non) or activating (Act) conditions, presented as the ratio of γ-H2AX$^+$ cells (one or more foci; filled bar) to γ-H2AX$^-$ cells (no foci; open bar).
Figure 5:
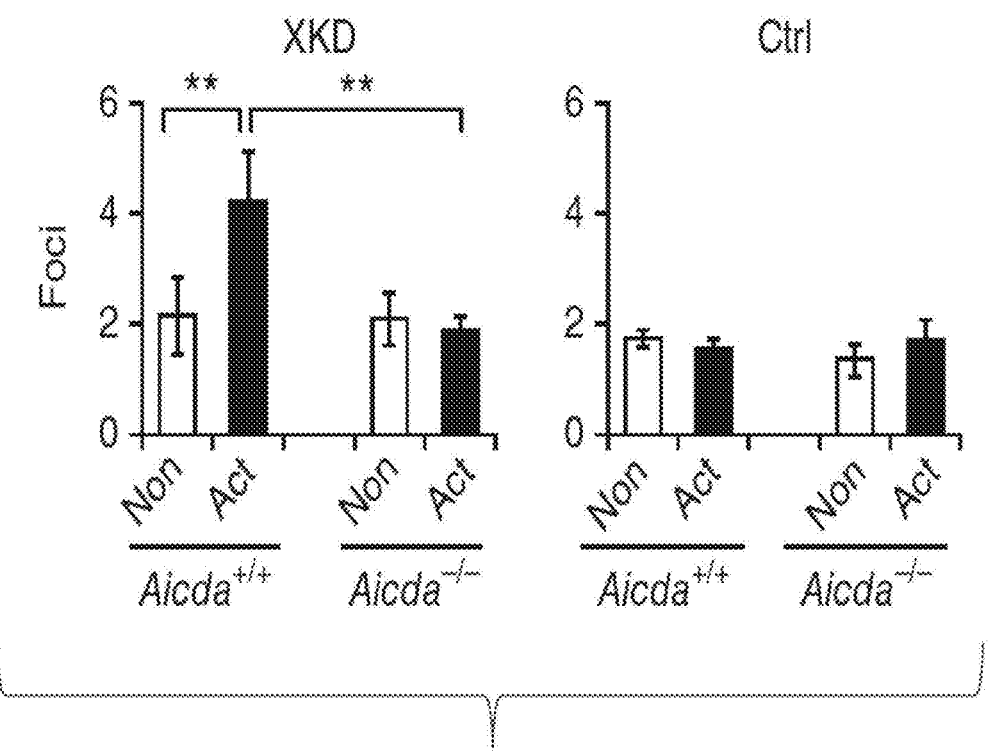
FIG. 5 shows a graph with the number of DSB repair foci in Aicda$^{+/+}$ and Aicda$^{-/-}$ XKD and control (Ctrl) splenic B cells. The y-axis represents the number of γ-H2AX foci; open bars represent the nonactivating and filled bars the activating conditions in Aicda$^{+/+}$ and Aicda$^{-/-}$ treated with XKD or control (Ctrl) shRNA splenic B cells. *P<0.05 and **P<0.01 (two-sample t-test). Data are representative of four experiments (error bars, s.e.m.).

AID$^{+/+}$ or AID$^{-/-}$ XKD B cell cultures were cultured with either 1 µg/ml anti-CD40 (nonactivated, Non) or 1 µg/ml anti-CD40 plus 25 ng/ml IL-4 (activated, Act) and the cells then stained for foci of γ-H2AX, a marker of unrepaired double strand breaks (DSBs) (Rogakou et al., J Biol Chem 1998, 273:5858-5868) using a polyclonal antibody to phosphorylated γ-H2AX (1:400 dilution; A300-018A; Bethyl Laboratories, Montgomery, Tex.). Both control and XKD B cell cultures showed an AID-dependent larger fraction of γ-H2AX$^+$ cells (cells containing one γ-H2AX focus or more γ-H2AX foci) after activation (FIG. 4). AID$^{-/-}$ cultures transduced with control shRNA or AID$^{-/-}$ XKD cultures showed no change in γ-H2AX positivity after activation (FIG. 5). However, when foci per cell were quantified in the γ-H2AX$^+$ fraction, XKD cells were found to have had a specific and significant increase in the number of γ-H2AX foci per cell (from approximately two foci per cell before activation to more than four foci per cell after activation; FIG. 5). This effect was not seen in AID$^{-/-}$ cells suggesting that it is dependent on AID.

Figure 6:
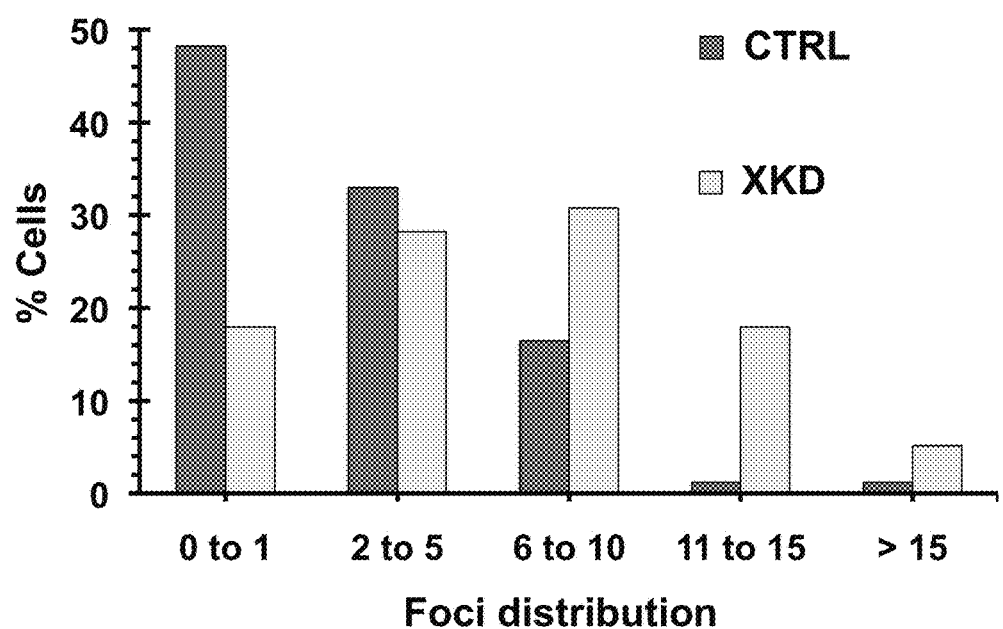
FIG. 6 shows the foci distribution of gamma-H2AX foci in activated XKD or control (Ctrl) mouse CH12-F3 cells.

A similar γ-H2AX response was observed in the class-switch-competent mouse B cell line CH12-F3 (Nakamura, M. et al. 1996, Int. Immunol. 8, 193-201) containing the same Xrcc2-knockdown construct used in primary cells (CH12-XKD cells) (FIG. 6). CH12-F3 cells were maintained in RPMI-1640 medium supplemented with 2-10 mM L-glutamine (Gibco) 10% (vol/vol) heat-inactivated fetal bovine serum (FBS) (Omega Scientific) and 5% (vol/vol) NCTC 109 media (Gibco). CH12-F3-derivative lines stably expressing Xrcc2-specific shRNA or control shRNA (with a scrambled sequence) were generated by direct transduction with individual shRNA vectors, followed by selection for puromycin resistance. Accumulation of activation-induced foci was observed specifically in XKD cells but not in control cells using the DNA damage-response factor 53BP1, another marker of DNA DSBs.

In summary, it is demonstrated herein that AID can promiscuously attack the B cell genome, producing widespread DSBs. It has been further demonstrated herein that the homologous recombination factor XRCC2 is critical in the resistance to AID-induced collateral damage, ensuring B cell viability and genome stability. Specifically, these findings indicate that the same mechanisms that introduce developmentally programmed DSBs can carry an inherent and simultaneous risk for the genome at large. This suggests that homologous recombination is important not only for normal lymphocyte development but also for the prevention of lymphoid pathologies such as immunodeficiency or cancer.

Example 3: DIDS Reduces Cell Viability of Receptive Cells

To validate DIDS as a potential agent, and to confirm its DSB repair inhibitory activity, radiosensitivity of primary wild-type mouse splenocytes was measured after exposure to DIDS. A total of 2×10$^6$ splenocytes were suspended in medium with 0, 300 µM, 600 µM or 1000 µM DIDS, or in vehicle-only control, and immediately given 2.5 Gy ionizing irradiation using a $^{137}$Cs irradiator (Shepard). Cells were then cultured in medium containing the same DIDS concentration, and cell counts were determined after 36 hours recovery time. DIDS treatment resulted in hypersensitivity to 2.5 Gy irradiation, relative to vehicle-control, in a dose-dependent manner. At 0 and 300 µM DIDS, cell counts were similar to vehicle-only. But cells cultured in 600 µM DIDS showed approximately 25% reduction in viability, and cells cultured in 1000 µM DIDS showed 87% reduction in viability. These data show that DIDS treatment confers the expected radiosensitivity on primary splenocytes, consistent with its known role in RAD51 inhibition.

Figure 7:
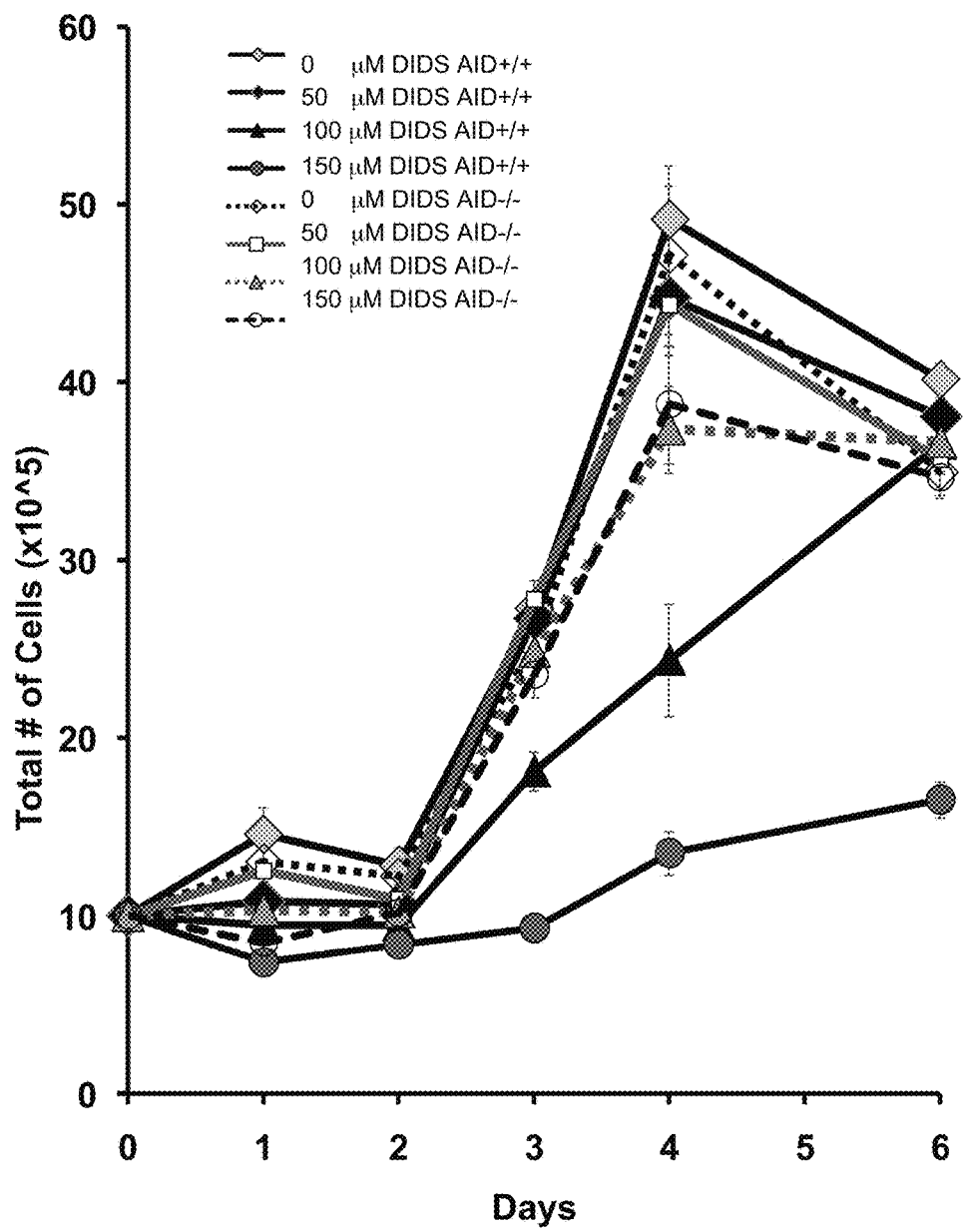
FIG. 7 shows a graph of cell counts indicating that DIDS treatment decreases survival of stimulated splenocytes. Cells isolated from the spleens of wild-type (AID+/+; filled markers) or AICDA knock-out (AID−/−, open markers) mice were stimulated with anti-CD40 antibodies and IL-4 on day 0 and day 2. DIDS was added on day 0 and day 2 at concentrations of 0 μM, 50 μM, 100 μM and 150 μM. The total number of viable cells was determined on days 1, 2, 3, 4 and 6 using Trypan blue staining.

Primary mouse B-cells were isolated from spleens of adult C57BL/6J mice (AID+/+) and from AID knockout mice (AID−/−) (see Example 1 and 2). 1×10$^{\wedge}$6 primary B-cells were seeded into tissue culture plates, stimulated with 1 µg/ml anti-CD40 antibodies (anti-CD40; BD Pharmingen; Cat. No. 553721) and 25 ng/ml IL-4 or with anti-CD40 alone on day 0 and day 2. 0, 50 µM, 100 µM or 150 µM of DIDS was added at time 0 and 2 days after culture initiation, when culture volumes were adjusted to accommodate cell growth. The cells were cultured over 6 days. The number of viable cells were counted after staining with Trypan blue using a hemacytometer on days 1, 2, 3, 4 and 6. In FIG. 7 the number of viable primary B-cells from C57BL/6J mice (AID+/+) and AID-knockout mice (AID−/−) after treatment with DIDS is shown. In AID+/+ B-cells 150 µM DIDS greatly reduces the cell viability from day 3 on. A decrease of B-cell viability is also observed at concentration of 100 µM DIDS. When AID+/+ B-cells are not stimulated with anti-CD40+IL-4, DIDS does not influence the cell viability. Further AID−/− cells are not affected by DIDS and show no significant change in cell viability.

Figure 9:
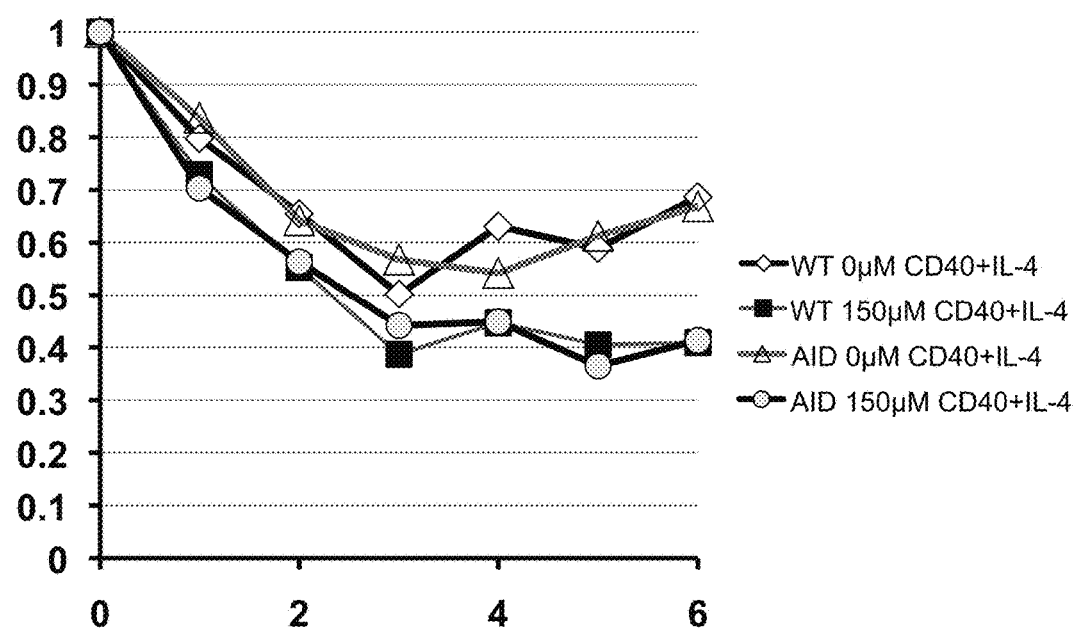
FIG. 9 shows a graph of splenocyte viability using Guava EasyCyte Flow Cytometer. Cells isolated from the spleens of wild-type (WT) or AICDA knock-out (−/−) mice were stimulated with anti-CD40 antibodies and IL-4 on day 0 and day 2. DIDS was added on day 0 and day 2 at concentrations of 0 or 150 μM. WT cells stimulated with anti-CD40 antibodies plus IL-4 and treated with DIDS are shown as filled boxes, AICDA−/− cells stimulated with anti-CD40 antibodies plus IL-4 and treated with DIDS as circle; WT cells stimulated with anti-CD40 antibodies plus IL-4 are shown as open diamonds; and AICDA−/− cells stimulated with anti-CD40 plus IL-4 antibodies as open triangles. The total number of viable cells was determined every other day. Days are shown on the x-axis and the fraction of viable cells is shown on the y-axis.

Cells were isolated from the spleens of wild type or AID knockout (−/−) mice, cultured and stimulated with anti-CD40 antibodies and IL-4 on day 0 and day 2. DIDS was added on day 0 and day 2 at concentrations of 0 or 150 µM. The total number of viable cells was determined every other day using Guava EasyCyte Flow Cytometer Assay. Stimulated cells treated with 150 µM DIDS showed lower viability (FIG. 9).

Example 4: AID Gene Expression Profiling

Figure 8A:
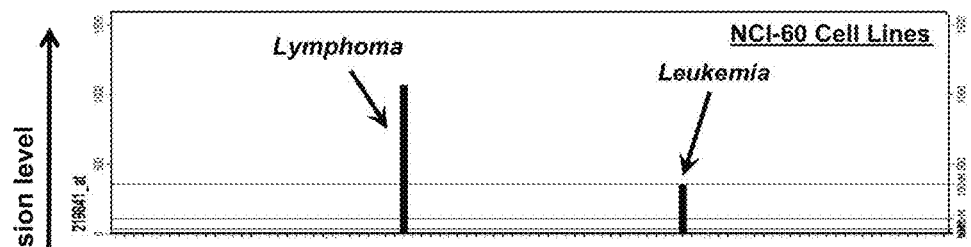
FIGS. 8A-8B show graphs indicating that cancer cells display high levels of AICDA expression. Each column/tick on the x-axis represents a different cell or tissue type while the y-axis represents the level of AICDA expression as the fold change above the dataset medial level.
Figure 8B:
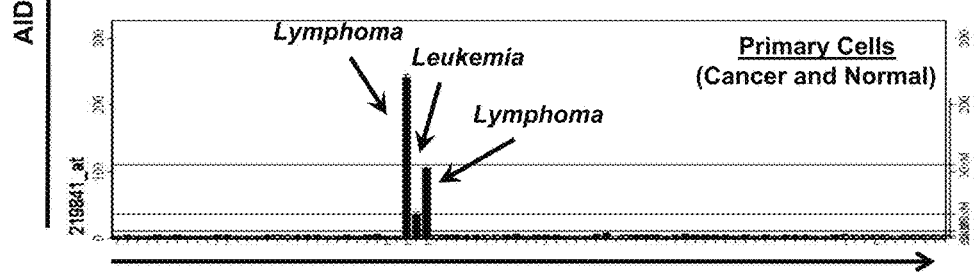

The expression of AID was profiled in the NCI-60 set of 59 human cancer cell lines derived from diverse tissues;

brain, blood and bone marrow, breast, colon, kidney, lung, ovary, prostate and skin. As shown in FIG. 8A high AID expression was detected in lymphoma and leukemia cell lines. Expression was further characterized in primary human cells/tissues and high expression was detected in leukemia and lymphoma samples (FIG. 8 B).

Example 5: Screening of New Bioactive Compounds

Figure 10:
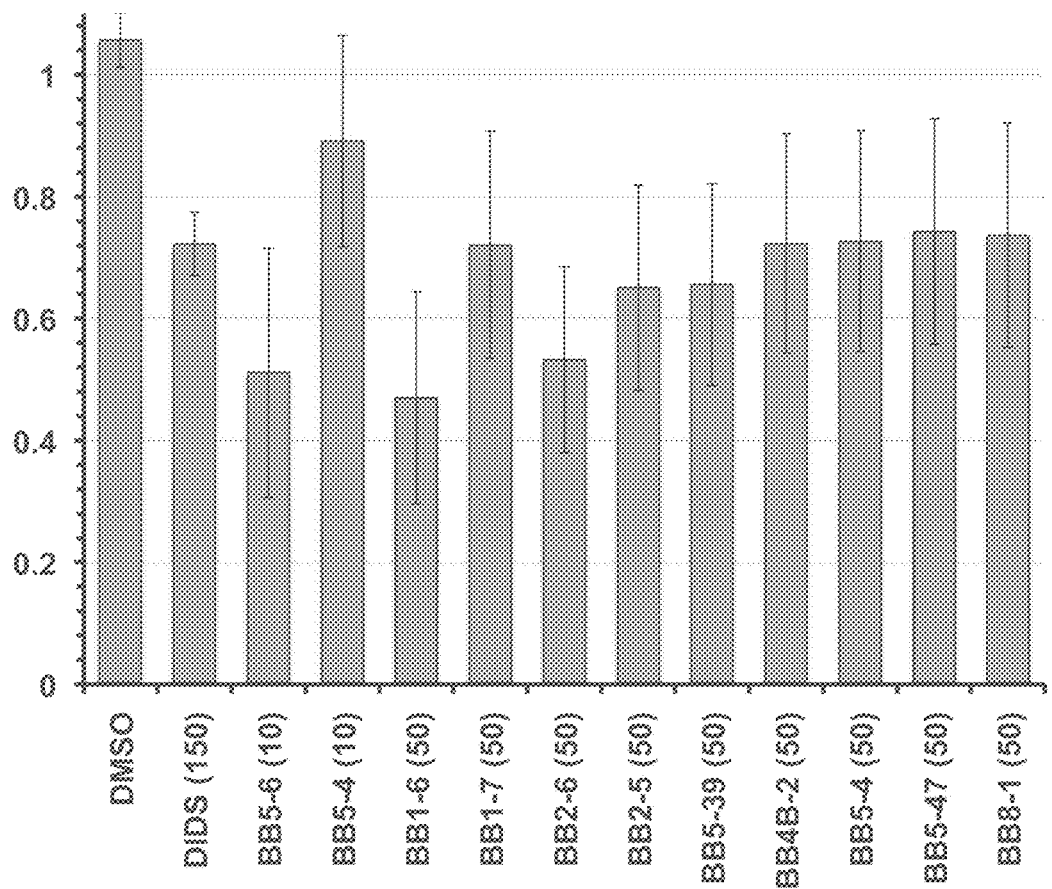
FIG. 10 shows screening results of DIDS derivatives using the MultiTox-Fluor Multiplex Cytotoxicity Assay. Compound identity is shown on the x-axis and the fraction of viable cells is shown on the y-axis.

To identify bioactive derivatives of DIDS, a library of $10^5$ chemical variants of DIDS was generated by replacing the sulfonate or isothiocyanate group with other chemical entities, or by altering the double bond joining the two rings in the stilbene backbone. All compounds were resuspended in dimethyl sulfoxide (DMSO) at a stock concentration of 100 micromolar, and used by serial dilution to generate working concentrations of 10, 50, or 150 µM. These were individually pipetted into 96-well microtiter culture dishes in duplicate, generating two plates of 10 µM, two plates of 50 µM, and two plates of 150 µM compounds. In each set, one plate was seeded with 100,000 normal C57BL/6J splenic B-cells (AID+/+) isolated by magnetic bead based sorting to enrich for B220+ IgM+ B-cells; and one plate was seeded with 100,000 splenic B-cells from AID−/− mice identically isolated. Each culture was stimulated on day 0 by addition of 1 µg/ml anti-CD40 plus 25 ng/ml IL-4 to induce proliferation and class-switch recombination. After two days, each culture was re-stimulated by an additional 1 µg/ml anti-CD40 plus 25 ng/ml IL-4. After two additional days in culture, for a total of 4 days of stimulation, viable cell counts were determined in each well of each plate using the MultiTox-Fluor Multiplex Cytotoxicity Assay (Promega, Inc.). For viability measurements, 100 microliters of the 2× MultiTox-Fluor Multiplex Cytotoxicity Reagent was added to each well and mixed before incubating at 37° C. for 30 min. Plates were then transferred to a fluorescence-capable multiplate reader and analyzed using 400 nm excitation and detection of 505 nm emission to measure the fraction of remaining live cells. As controls, wells containing either vehicle alone (DMSO) or 150 µM DIDS were included on each plate. Viability scores for each compound were determined as the fraction of live cells in the normal B-cell plate divided by the fraction of live cells in the corresponding AID knockout plate. Compounds that produce normal/AID knockout ratios at or below the level of the DIDS ratio were considered candidate compounds for further validation and testing. In the absence of DIDS compounds that result in a reduced cell viability selectively in the AID+/+ cell relative to the AID−/− cells leading to an AID+/+: AID−/− ratio of less than 1 are scored as a initial positive hit. The initial screen identified 10 derivatives, BB5-6, BB1-6, BB1-7, BB2-6, BB2-5, BB5-39, BB4B-2, BB5-4, BB5-47, and BB8-1 (FIG. 10).

Example 6: Effect of DIDS on Human CLL Cells

Figure 11:
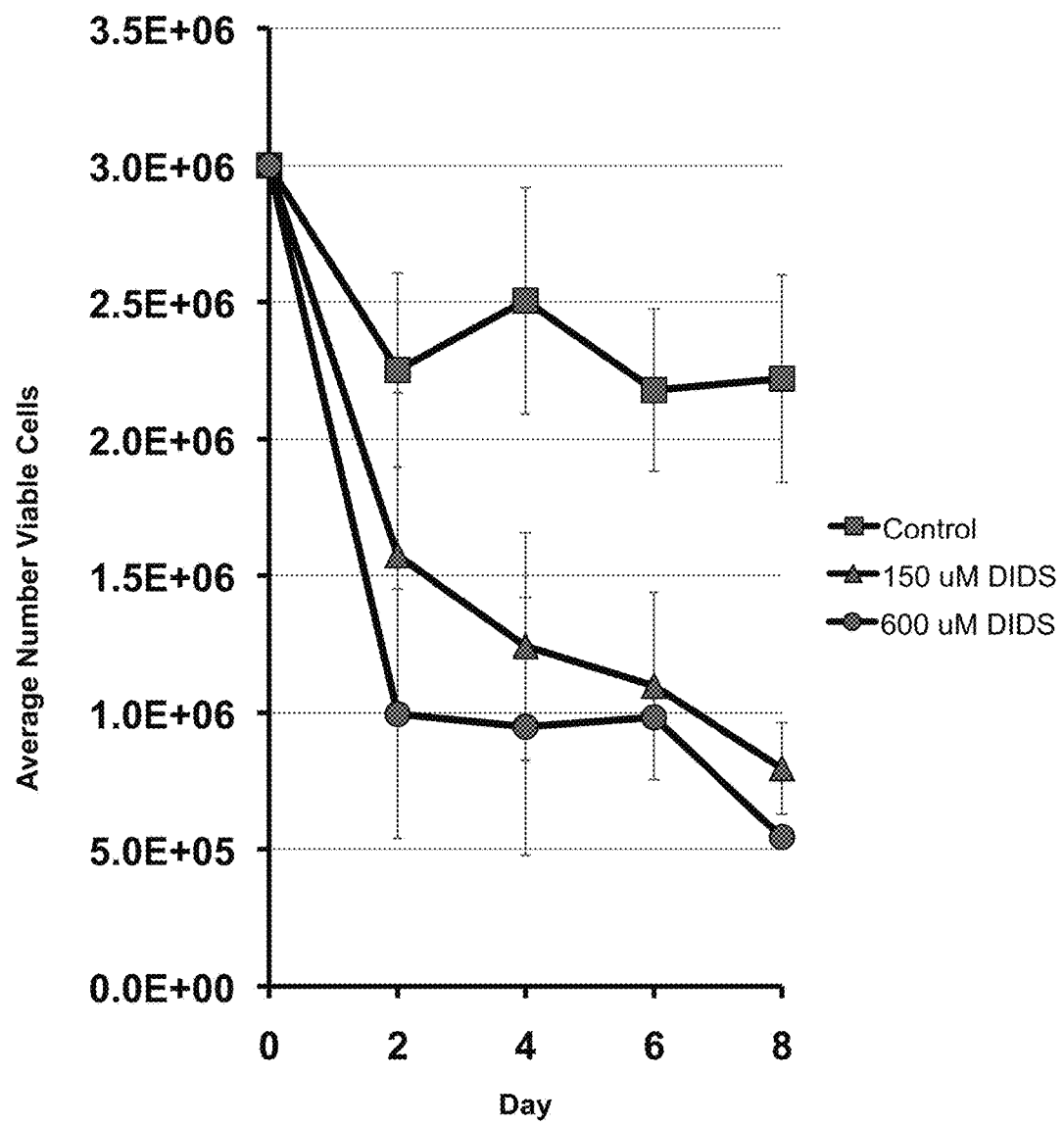
FIG. 11 shows primary human CLL cells from 14 primary chronic lymphocytic leukemia (CLL) patients treated with DIDS. CLL cells were treated with 0 uM (n=5, control), 150 uM (n=4), or 600 uM (n=2). DIDS with viable cell counts were determined by manual counting on a hemacytometer on days 2, 4, 6, and 8 of culture. Error bars indicate standard error of the mean.

Blood samples (8-16 mL) from patients were collected via peripheral bleed into BD Vacutainer CPT tubes (BD, Franklin Lakes, N.J.), centrifuged to sequester red blood cells below the separation gel according to manufacturer instructions, and transported within 24 hours to the Jackson Laboratory. Upon receipt, peripheral blood mononuclear cells (PBMC) were isolated from samples according to manufacturer specifications. White blood cell (WBC) counts from 14 primary chronic lymphocytic leukemia (CLL) samples from human patients were calculated from complete blood count (CBC) with differentials. Calculated values were compared with empirical cell counts following cell separation and overnight shipping. This reveals remarkably consistent efficiency of isolation. The primary CLL samples (WBC) were diluted to standard concentration and $3.0\times10^6$ cells were seeded in cultures. Replicate cultures were supplemented with 0 µM (n=5), 150 µM DIDS (n=4), or 600 µM DIDS (n=2). Viable cell counts were determined by manual counting using a hemacytometer on days 2, 4, 6, and 8 of culture. DIDS-treated cultures showed a significant decline in viable cell counts, relative to untreated control (FIG. 11).

Example 7: Effects of 4'-Bromo-3'-nitropropiophenone on Splenocytes

Figure 12:
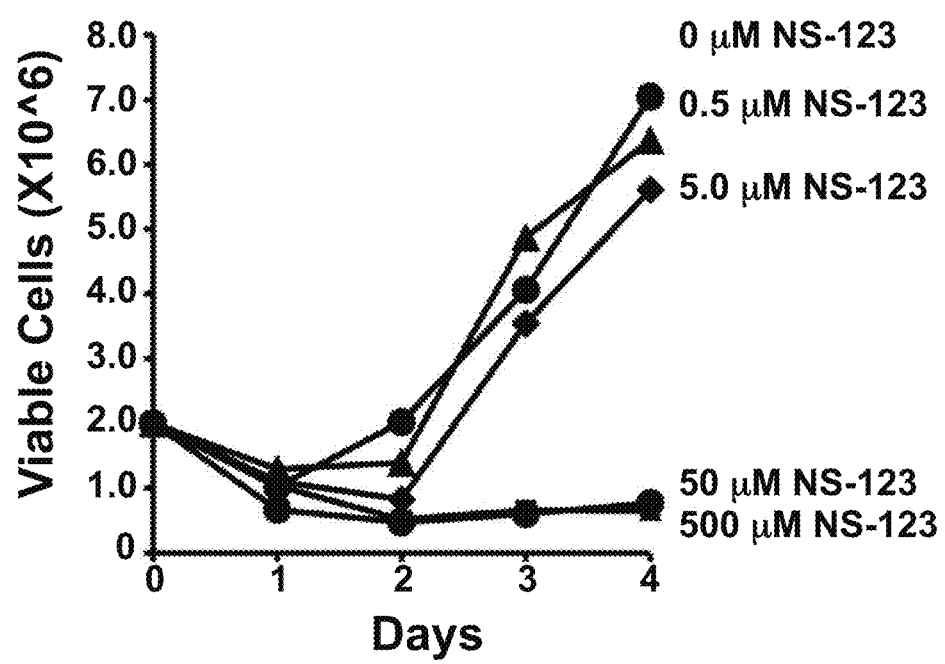
FIG. 12 shows a graph of primary AID-knockout mouse splenocytes seeded in cultures at day 0 at a concentration of 1×10^6 cells/ml in RPMI medium supplemented with aCD40+IL-4 to activate the B-cells. Individual cultures were supplemented with 0 (circle), 0.5 (triangle), 5 (diamond), 50 (square), or 500 uM (circle) NS-123, and viable cells were counted after Trypan blue staining on days 1, 2, 3, and 4.

Primary mouse B-cells were isolated from spleens of adult AID−/− mice as described in Example 1. Cultures were established at a concentration of $1\times10^6$ cells per ml in RPMI-1640 medium with 10% FBS. Cultures were activated with anti-CD40 antibody plus IL-4, and treated with 4'-Bromo-3' nitropropiophenone (NS-123) (purchased from Calbiochem; CAS No. 101860-83-7) at concentrations of 0.5, 5, 50, or 500 µM. Cells were re-activated by anti-CD40 plus IL-4 after two days in culture. Cell counts were determined after 1, 2, 3, and 4 days in culture by Trypan blue staining. At the concentration of 50 µM and 500 µM of NS-123 AID-null splenocytes were not viable. At the concentration of 5 µM of NS-123 the viability of the splenocytes is reduced when compared to untreated splenocytes (FIG. 12).

Figure 13:
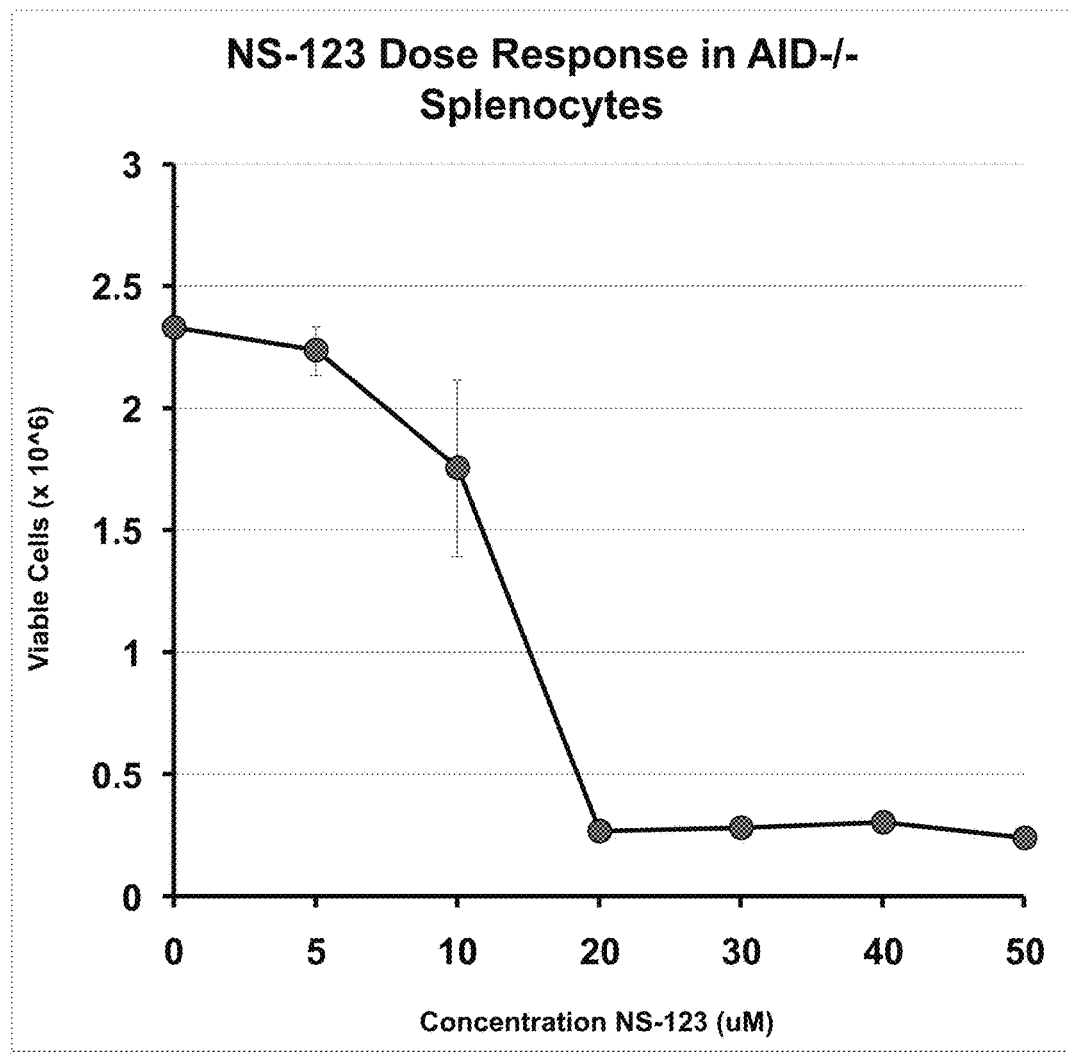
FIG. 13 shows a graph for a dose response of NS-123 on viability of primary AID-knockout mouse splenocytes seeded in cultures at day 0 at a concentration of 1×10^6 cells/ml in RPMI medium supplemented with aCD40+IL-4 to activate the B-cells. NS-123 concentration of 0, 5, 10, 20, 30 and 50 uM were tested.

Primary AID-knockout mouse splenocytes were seeded in cultures at day 0 at a concentration of $1\times10^6$ cells/ml in RPMI-1640 medium supplemented with anti-CD40 plus IL-4 to activate B-cells. Individual cultures were supplemented with 0, 5, 10, 20, 30, 40, or 50 µM NS-123 and viable cells were counted after Trypan blue staining on days 1, 2, 3, and 4 (FIG. 13). The LD50 for NS-123 in AID-null splenocytes was determined to be 14 µM. To demonstrate the effectiveness of NS-123 splenocytes isolated from wild type mice (expressing AID) and compared to the splenocytes from AID−/− mice, activated and non-activated can be tested.

Example 8: In Vivo Testing of DSB Inhibitors

Mice overexpressing AID ubiquitously or tissue-specific are treated with a DSB inhibitor. One such suitable mouse model is B6.Cg-Tg(Igk-Aicda)14Mnz/J where AID is overexpressed in B lymphocytes (B cells) or C57BL/6-Tg(CAG-Aicda)B1Hon/HonRbrc where AID is ubiquitously expressed using the CAG (chicken beta-actin promoter, rabbit beta-globin poly A, CMV-IE enhancer) promoter (Okazaki et al., J Exp Med. 2003, 197(9):1173-81). It has been reported that such mouse models do develop lymphomas and other cancerous lesions. The DSB inhibitor, (e.g. stilbene, DIDS, NS-123, or resveratrol) can be administered to the mice. Administration can be done by intravenous (i.v.), intraperitoneal (i.p.), intramuscular (i.m.) or subcutaneous (s.c.) injection, or using osmotic pumps for continuous treatment or via the drinking water.

In the case of C57BL/6-Tg(CAG-Aicda) mice it has been reported that these mice develop T cell lymphoma and die between 40 and 80 weeks depending on transgene insertion (Okazaki et al., J Exp Med. 2003, 197(9):1173-81). Treatment with DSB inhibitors can result in a decrease of the lymphomas and extension of lifespan.

Example 9: Xenograft Mouse Model

5×10^6 primary white blood cells (WBC) from primary chronic lymphocytic leukemia (CLL) patients with AID activity can be suspended in 0.1 mL of PBS and then injected i.v. or administered by osmotic pump into immunodeficient mice, e.g. NOD-scid or NOD-scid IL2Rgamma (NSG). After tumors formed flow on peripheral blood mice can be randomly assigned into one of four groups: vehicle control, 5 mg/kg DIDS, 25 mg/kg DIDS and 50 mg/kg DIDS is mixed in DMSO with 30% propylene glycol and injected i.v. at 1-week intervals for 4-8 weeks. Groups not receiving DIDS can be treated with the same volume of DMSO alone dissolved in 30% propylene glycol. Peripheral blood can be analyzed by flow in 1-week intervals. At the end of the study the mice can be sacrificed and histological analysis performed.

Example 10: Xenograft Mouse Model with AID+ or AID− Human Tumor Samples

NOD-scid IL2Rgamma (NSG mice) can be engrafted with AID+ and AID− human tumor samples to generate multiple, replicate in vivo models that as closely as possible reflect the patient disease. These can then be used to test in vivo efficacy of genetic chemotherapy, to relate efficacy to AID expression level, and to evaluate potential genetic chemotherapy side effects.

To generate multiple recipients (up to 15) from each patient sample, 1×10^6 peripheral blood mononuclear cells (PBMC) from each patient sample can be introduced into 6 week old male NSG mice by intravenous, intrasplenic, or if necessary intra-bone marrow, injection. Previous studies have indicated that B-lymphoid cancers have a successful rate of engrafting NSG mice of greater than 60% (Immunol, 2005, 174(10), 6477-89; Leukemia. 24(11), 1859-66; Ann NY Acad Sci, 2007. 1103: p. 90-3). Following engraftment each group of recipients can be subdivided divided into treatment subgroups of up to 5 mice each. Between one week and month after injection, mice (in groups of up to 5) can be treated with DIDS (using empirically determined concentrations), vehicle control, or remain untreated. As a starting regimen, mice can be treated with DIDS or other compounds by i.v. injection at 1 week intervals for 4 to 8 weeks, and can be monitored for human lymphoid cells in circulation by flow cytometry, collecting peripheral blood at 1 week intervals between drug injections. After 4-8 weeks of treatment, all recipient mice can be euthanized, and tumor development, burden, regression, and survival time can be subsequently be determined for all mice in each treatment group.

Tumor burden: At sacrifice, peripheral blood and lymphoid organ tissue will be analyzed for human leukemia cells by flow cytometry or immunofluorescence. To detect human cells, and distinguish them from mouse cells, co-stain for human leukemia diagnostic markers hCD19, hCD22, and hCD79a, as well as mouse markers, such as mCD19 can be performed. The number of human cells can be compared in untreated, vehicle-treated, and DIDS-treated recipients. If DIDS elicits a genetic chemotherapy response then fewer human leukemia cells would be expected in treated versus controls.

Apoptosis can be measured by staining with fluorescently labeled Annexin V, and counterstaining with the DNA binding dye 7-amino-actinomycin D (7-AAD). Human cells can be distinguished from mouse as above. The percentage of apoptotic cells can be determined by flow cytometry. Alternatively, apoptosis can be measured by immunofluorescence microscopy to detect AC3.

Post-treatment histopathology analysis. To evaluate response or resistance of patient derived xenograft mice to genetic chemotherapy all drug treated and control mice can be subjected to exhaustive histopathology analysis. Prior studies have suggested that leukemia cells in bone marrow microenvironments can survive otherwise cytotoxic chemotherapy. Thus analysis of bone marrow, other lymphoid niches, and potential sanctuary sites such as CNS for tumor cell occupancy, as well as staining for human B-cell markers such as CD5, CD19, CD22, CD23, or CD79a can be performed. The effects of drug treatment on the niche itself can be examined by performing parallel mouse histopathology using appropriate mouse tissue stains and markers. All tissues collected for histopathology (bone marrow, spleen, other tissues showing evidence of abnormality) can be fixed in formalin, trimmed, and paraffin embedded. All fixed, tissues can be stained with hematoxylin and eosin (H&E). For these analyses, the presence of human leukemia in the mice, and anatomical abnormalities caused by the drug treatment regimen can be sought. Formalin-fixed, paraffin embedded sections of femurs and spleens from xenograft mice can be specifically immunostained for human CD19, CD22, and CD79a (B-cell leukemia markers) as well as a panel of other lineage markers as negative controls (e.g. CD33, CD34 myeloid markers) to pinpoint human cell components of bone marrow and secondary hematopoietic organs. The goal of these analyses will be to measure residual human cells, and to identify the microenvironments they inhabit.

Example 11: AID Expression Analysis and Genotyping

For RNA and DNA preparation, between 1×10^6 cells and 5×10^7 cells, can be extracted using standard molecular biology protocols. AID mRNA expression can be measured in each sample by quantitative reverse transcription PCR (qRT-PCR). Oligonucleotide primer sequences to detect human AID transcript are: hAID fwd 5'-TCCTTTTCACTG-GACTTTGG-3' (SEQ ID NO:101); and hAID rev 5'-GACT-GAGGTTGGGGTTCC-3' (SEQ ID NO:102). RT-PCR with these primers produces a 196 bp reaction product specific for human AID. Primer sequences for human GAPDH transcript (on type of loading control) are: hGAPDH fwd 5'-GAGT-CAACGGATTTGGTCGT-3' (SEQ ID NO:103); and hGAPDH rev 5'-TTGATTTTGGAGGGATCTCG-3' (SEQ ID NO:104). RT-PCR with these primers produces a reaction product of 238 bp specific for the human GAPDH gene. Expression levels are quantified using a multiple normalization protocol according to Woo et al., Oncogene 2007, 26(41), 6010-20, ensuring the highest-level of confidence in sample-to-sample comparisons across the tumor cell collection. In each qRT-PCR assay, an AID-negative control can be included, such as normal human fibroblast (NHF). Tumors that show AID mRNA levels above the baseline level in negative controls can be classified as AID expressing (+); samples with AID mRNA levels at or below control levels can be classified as AID negative (−) categories. AID expression data can be integrated with clinical diagnostic information, especially the surface Ig and somatic hypermutation status. Within the AID+ category samples can be ranked according to AID mRNA expression level, and the presence or absence of somatic hypermutation in Ig loci, determined by standard clinical surrogate markers or by direct sequencing following sample collection.

Example 12: Sequencing to Measure AID Activity

The basis for genetic chemotherapy is AID activity in tumor cells. Therefore genome sequence analysis can be carried out to measure AID mutational activity. It is known that AID acts at Igh (the major physiological target), and at a host of non-Ig genes including Myc, Bcl6, Bcl11a (all frequently targeted oncogenes), CD93, and many others varying frequencies. A robotic capture system can be used to isolate genomic DNA flanking promoter elements (1-2 kb per gene) for all known human protein coding genes—approximately 26,000 genes. In this way, both known and unknown AID targets, as well as non-targeted (negative control) genes can be analyzed. All captured sequences can be bar-coded and multiplexed (2-4 samples per lane) for sequencing using a HiSeq instrument (Illumina, San Diego, Calif.). Because a standard HiSeq lane currently gives more than 20 billion nucleotides of sequence, 4× multiplexing can provide sufficient coverage to detect mutations occurring in any single gene at less than 2% frequency (see analytic strategy, below). The known AID targets (IGH (NCBI Gene ID 3492), BCL6 (NCBI Gene ID 604), MYC (NCBI Gene ID 4609), BCL11A (NCBI Gene ID 53335), CD93 (NCBI Gene ID 22918), PIM1 (NCBI Gene ID 5292) and/or PAX5) as well as MEF2B CD93 (NCBI Gene ID 100271849) and LTB (NCBI Gene ID 4050), two genes very rarely targeted by AID for either point mutations or DNA breaks (negative controls) can be analyzed. This is approach is ideal for detecting non-selected somatic mutations in heterogeneous cell populations containing a mix of tumor and non-tumor cells. After alignment of sequences to the human reference genome sequence using Burrows-Wheeler Aligner (BWA), spontaneously occurring somatic mutations can be identified as sequence differences that: (1) occur in at least two independent reads per sample, and are thus unlikely to be sequencing error; and (2) occur with a frequency of less than 50%, and thus are non-clonal somatic events, rather than germ-line polymorphisms (Bioinformatics 2009, 25(14): 1754-60). For most samples non-CLL cells can be sorted from the blood of many patients to use as an internal, patient-specific sample against which AID-dependent tumor mutation rates can be measured.

Example 13: DIDS Radiosensitizes Primary Mouse B

Figure 14:
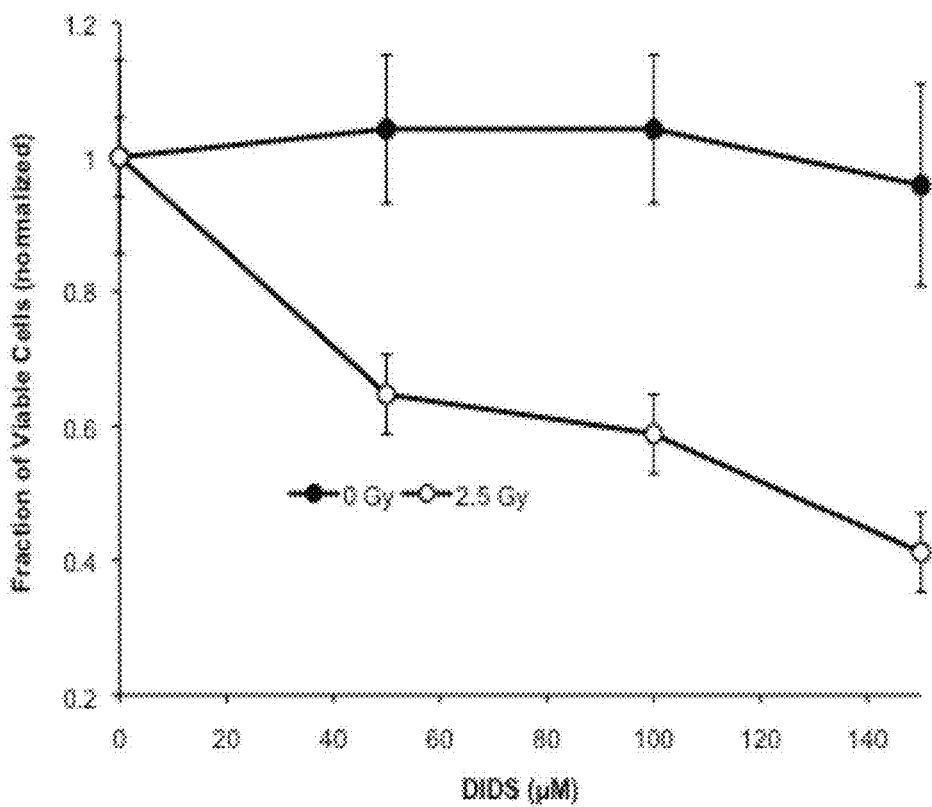
FIG. 14 shows a graph of primary mouse B-cells and their response to DIDS. Cells were then subjected to either 0 (filled circles) or 2.5 Gy (=250 rads; open circles). Error bars represent the standard error of the mean (S.E.M) from three independent experiments.

Primary mouse splenic B-cells were isolated from normal, wild-type C57BL/6J mice as described in Example 1 and sorted with magnetic beads (Miltenyi) to enrich B220+ IgM+ B-cells. Purified B-cells were cultured in complete RPMI-1640 medium with 10% FBS with 0, 50, 100, or 150 micromolar DIDS. Cells were then subjected to either 0 (FIG. 14, filled circles) or 2.5 Gy (=250 rads; FIG. 14, open circles) of gamma irradiation in a Cs137 irradiator. Cell viability was subsequently scored for each condition and plotted relative to the no DIDS condition by manual cytometry using a hemacytometer and Trypan blue dye exclusion 24 hours after irradiation. The fraction of viable cells is reported normalized to the corresponding 0 µM DIDS condition. Error bars represent the standard error of the mean (S.E.M) from three independent experiments. The data show that irradiation treatment combined with DIDS reduces viability significantly starting at a concentration of 50 micromolar DIDS.

Figure 15A:
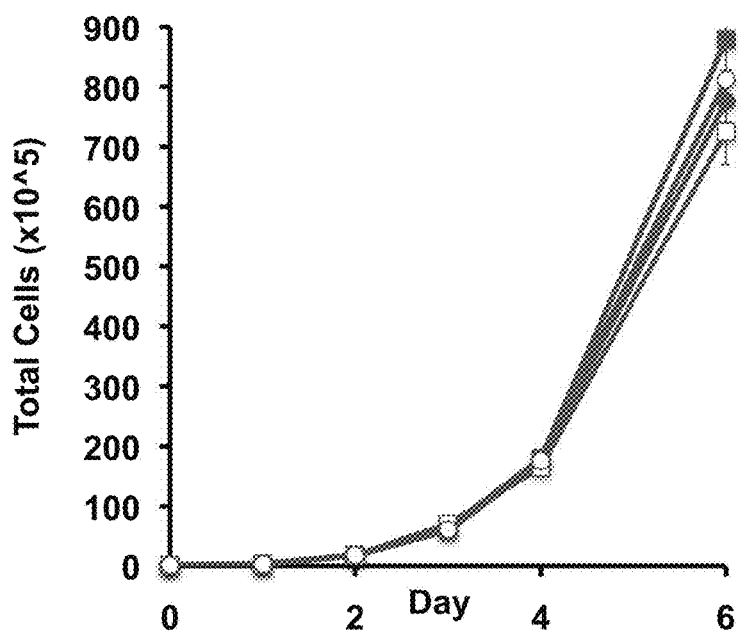
FIG. 15A shows total cell numbers of non-activated CH12-F3 cells treated with the various DIDS concentrations.
Figure 15B:
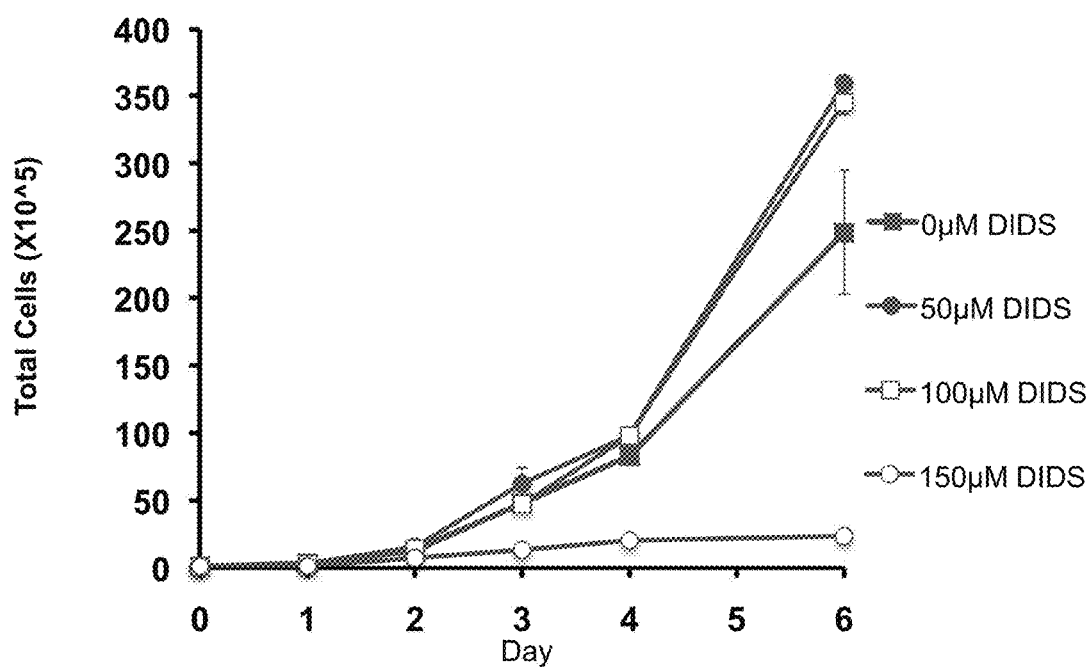
FIG. 15B shows total cell numbers of activated CH12-F3 cells treated with the various DIDS concentrations. Results for 0 μM DIDS are shown by filled squares, 50 μM DIDS by filled circles, 100 μM DIDS by open squares, and 150 μM DIDS by open circles.

Example 14: DIDS Synergizes with AID (AICDA) to Inhibit Growth and Impair Survival of Transformed B-Cells The mouse B-lymphoid leukemia cell line CH12-F3 was cultured in RPMI-1640 medium supplemented with 2-10 mM L-glutamine (Gibco), 10% (vol/vol) heat-inactivated fetal bovine serum (Omega Scientific) and 5% (vol/vol) NCTC 109 media (Gibco) (complete RPMI; non-activated) or complete RPMI-1640 medium containing 1 µg/ml anti-CD40 antibody, 25 ng/ml IL-4 and 1 ng/ml transforming growth factor beta 1 (TGF-beta1) (activated). Cultures were supplemented with 0, 50, 100, or 150 micromolar DIDS, and total cell counts were determined by manual cytometry after 0, 1, 2, 3, 4, or 6 days in culture. In FIG. 15A the non-activated cells treated with the various DIDS concentrations show no difference in cell viability or cell proliferation. In contrast, a strong decrease of total cell number was observed in activated CH12-F3 cells exposed to 150 micromolar DIDS (FIG. 15B).

Example 15: DIDS Treatment Prevents Repair of AID Generated DNA Damage

Mouse primary splenocytes isolated from 8-12 week old wild type (AID+/+) and AID-knockout (AID−/−) mice as

TABLE 1

Figure 16A:
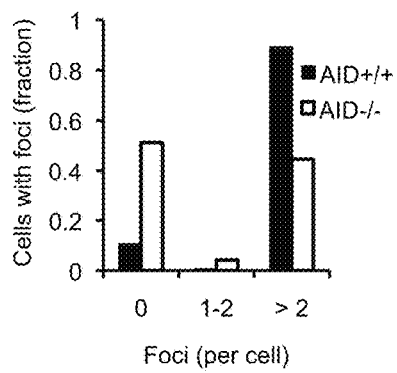
FIG. 16A shows number of foci detected in AID-null (AID−/−) and AID positive (AID+/+) splenocytes isolated from AID-knockout mice and B6 wild type mice, activated and treated with 150 μM DIDS.
Figure 16B:
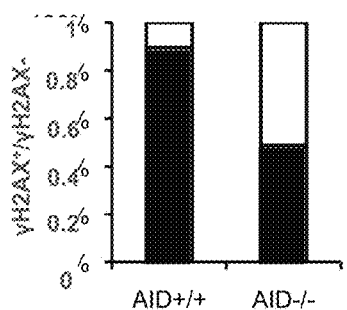
FIG. 16B shows the proportion of phospho-H2AX positive cells (filled bars) versus phospho-H2AX negative cells (open bars), quantified for AID+/+ in comparison to AID−/− cultures.
Figure 16C:
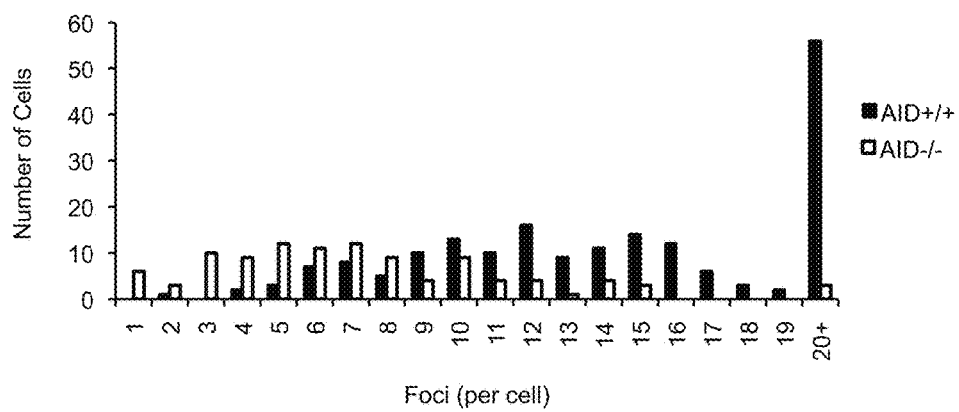
FIG. 16C shows the number of foci per cell was quantified for DIDS-treated AID+/+ (filled bars) versus AID−/− (open bars) cells.

Chromosomal damage in XKD cells. Karyotypes of CH12-F3 cells, a mouse lymphoma cell line, transduced with control shRNA (CH12-Ctrl) and CH12-XKD cells left untreated (no culture supplement) or cultured under non-activating conditions (anti-CD40) or activating conditions (anti-CD40 plus IL-4 plus TGF-β):

|  | CH12-Ctrl | | | CH12-XKD | | |
| --- | --- | --- | --- | --- | --- | --- |
|  | Untreated | Nonactivated | Activated | Untreated | Nonactivated | Activated |
| Cells with breaks (%) | 13 | 9 | 21 | 29 | 29 | 76 |
| Chromosomes (average) | 40 | 41 | 40 | 40 | 41 | 39 |
| Metaphases | 23 | 22 | 24 | 21 | 21 | 21 | described in Example 1 were exposed to 150 micromolar DIDS, and activated by anti-CD40 antibody plus interleukin-4, fixed and stained for the DNA break marker phospho-H2AX and for nuclear DNA using the fluorescent DNA staining dye 4',6-diamidino-2-phenylindole (DAPI). In FIG. 16A the fraction of cells containing 0, 1-2, or greater than 2 phospho-H2AX positive foci was quantified for AID+/+ (filled bars) and AID−/− (open bars) cells. A significant higher fraction of cells with greater than 2 foci was observed specifically in the DIDS-treated AID+/+ cells. In FIG. 16B the proportion of phospho-H2AX positive cells (filled bars) versus phospho-H2AX negative cells (open bars) was quantified for AID+/+ in comparison to AID−/− cultures. AID+/+ cells show a higher percentage of phospho-H2AX positive cells. In FIG. 16C the number of foci per cell was quantified for DIDS-treated AID+/+ (filled bars) versus AID−/− (open bars) cells. Data are expressed as the absolute number of cells (y-axis) harboring the indicated number of phosphor-H2AX foci (from 0 to >20; x-axis).

Example 16: AID (AICDA) Expression Status is a Biomarker that Identifies Candidate Patients for Genetic Chemotherapy AID (AICDA) expression status combined with IGVH hypermutation status is a biomarker that further stratifies candidate patients for genetic chemotherapy. In standard practice, IGVH mutation-positive (greater that 2% deviation from reference sequence) CLL is associated with generally better prognosis that IGVH mutation negative (less than 2% deviation from reference sequence). Genomic DNA was isolated from primary human chronic lymphocytic leukemia (CLL) cells, specific IGVH segments amplified by PCR, and sequenced using standard Sanger sequencing. Primer sequences for amplification of IGVH gene segments are:

```
                                           (SEQ ID NO: 107)
    VH1-FR1 5'-GGCCTCAGTGAAGGTCTCCTGCAAG-3';

(SEQ ID NO: 108)
    VH2-FR1 5'-GTCTGGTCCTACGCTGGTGAAACCC-3';

(SEQ ID NO: 109)
    VH3-FR1 5'-CTGGGGGGTCCCTGAGACTCTCCTG-3';

(SEQ ID NO: 110)
    VH4-FR1 5'-CTTCGGAGACCCTGTCCCTCACCTG-3';

(SEQ ID NO: 111)
    VH5-FR1 5'-CGGGGAGTCTCTGAAGATCTCCTGT-3';

(SEQ ID NO: 112)
    VH6-FR1 5'-TCGCAGACCCTCTCACTCACCTGTG-3';

(SEQ ID NO: 113)
    JH consensus 5'-CTTACCTGAGGAGACGGTGACC.
```

Mutations were identified as nucleotide differences relative to the reference genome sequence, and quantified as a percentage of total nucleotides. Mutation-positive samples were identified, per clinical diagnostic standards, as samples with greater than 2% deviation from reference. Mutation positive samples in Table 2 are JE1010, JE1014, JE1015, JE1021, JE1030, JE1048 and JE1061. The sample JE1050 shows no mutations. The samples JE1010, JE1014, JE1048 and JE1050 were also positive for AID expression.

TABLE 2

| IgVH Hypermutation Analysis | | |
|---|---|---|
| CDR2 (IGVH4-34) | | SEQ ID NO |
| Germline | GAAATCAATCATAGTGGAAGCACCAACTACAACCCGTCCCTCAAGAGT | 147 |
| JE1010(AID+) | GATATCAGTCATAGTGGCATCCCCAAGTACAACCCGTCCCTCAAGAGT | 148 |
| JE1014(AID+) | GAAATCAATCATGGTGGAAATCCCAACTACAACCCGTCTCTCAGGAGC | 149 |
| JE1015(AID−) | GAAATCAATCATGTTGGAAGTACCACCTACAACCCCTCCCTCAAGAGT | 150 |
| JE1021(AID−) | GCAATCAATAATAGTGGAAACACCTTGTTCACCCCATCCCTCACGAGT | 151 |
| JE1030(AID−) | GAAATCAATCACAGTGGAAGAACCAACCACAACCCGTCCCTCAGGAGT | 152 |
| JE1048(AID+) | GAAACCTATCATAGTGCATACACCAAGTACAGCCCGTCCCTCCAGGGT | 153 |
| JE1061(AID−) | GAGATCGATTATAGTGGAAACGCCAACTACAACCCGTCCCTCAAGAGT | 154 |
| JE1050(AID+) | GAAATCAATCATAGTGGAAGCACCAACTACAACCCGTCCCTCAAGAGT | 155 |

Figure 17:
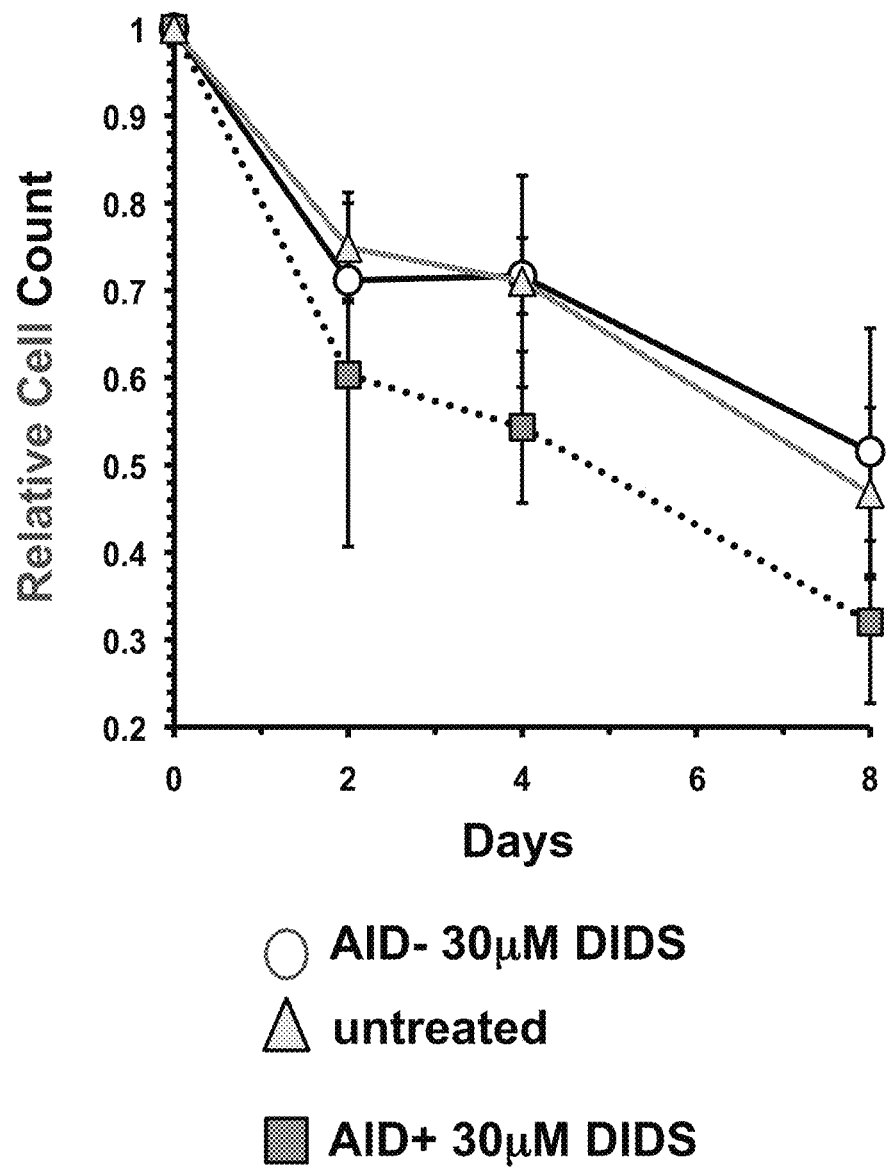
FIG. 17 shows cell viability of AID-expressing (AID+) or AID-negative (AID−) primary human CLL cells, untreated or treated with 30 μM DIDS.

Example 17: DIDS Synergizes with AID (AICDA) to Reduce Survival of CLL Cells AID-expressing (AID+) or AID-negative (AID−) primary human CLL cells were cultured as described in Example 4. Cells were cultured in basic RPMI-1640 medium without supplementation (untreated; triangle in FIG. 17) or with 30 micromolar DIDS. Open circles represent the data for AID-negative cells treated with 30 micromolar DIDS and filled boxes represent the data for AID-positive cells treated with 30 micromolar DIDS. The cell survival was scored by manual cytometry for viable cells after 2, 4, or 8 days of exposure. The untreated and the DIDS-treated AID− cells cultures were indistinguishable, whereas the DIDS-treated AID+ cultures showed reduced cell viability.

Example 18: Use of AID Expression as a Biomarker Identifies CLL Patients that Respond to Genetic Chemotherapy by DIDS Four individual AID-expressing (AID+) human CLL samples (JE1010, JE1036, JE1070, JE1075) and four individual AID-negative (AID−) human CLL samples (JE1015, JE1019, JE1031, JE1057) were identified using reverse-transcription (RT)-PCR with oligonucleotide primers specific to either human AID or human GAPDH (loading control). RT-PCR was done with the One-Step RT-PCR kit according to manufacturer's protocols (Qiagen). The oligonucleotide primers and PCR conditions used to detect Xrcc2 and GAPDH have been described (Deans et al., EMBO J 2000 19:6675-6685). As a specificity control for knockdown studies, the related gene Rad51 was detected by RT-PCR. Oligonucleotides to detect AID transcripts were hAID fwd 5'-TCCTTTTCACTGGACTTTGG-3' (SEQ ID NO:101); and hAID rev 5'-GACTGAGGTTGGGGTTCC-3' (SEQ ID NO:102). RT-PCR with these primers produces a 196 bp reaction product specific for human AID. Oligonucleotides to detect human GAPDH were 5'-ACCACAGTCCATGC-CATCAC-3' (SEQ ID NO:105) and 5'-TCCACCACCCT-GTGGCTGTA-3' (SEQ ID NO:106) producing a 238 bp reaction product. Reverse transcription and PCR conditions were Step 1. 50° C., 30 min; Step 2. 95° C., 15 min; Step 3. 94° C., 1 min; Step 4. 55° C., 30 sec; Step 5. ° C., 1 min; Step 6. Cycle steps 3-5, 35 times; Step 7. 72° C., 10 min; Step 8. 4° C., and hold indefinitely.

The RT-PCR products were separated by electrophoresis on a 1.0% agarose gel (with ethidium bromide) and were visualized with a Bio-Rad Gel Doc system.

Figure 18A:
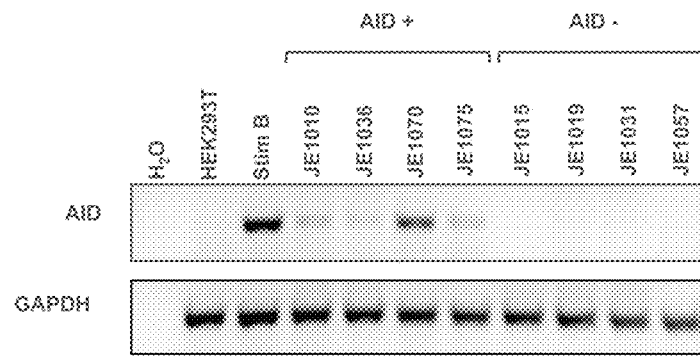
FIG. 18A shows RT-PCR expression of AID for primary human CLL cells.
Figure 18B:
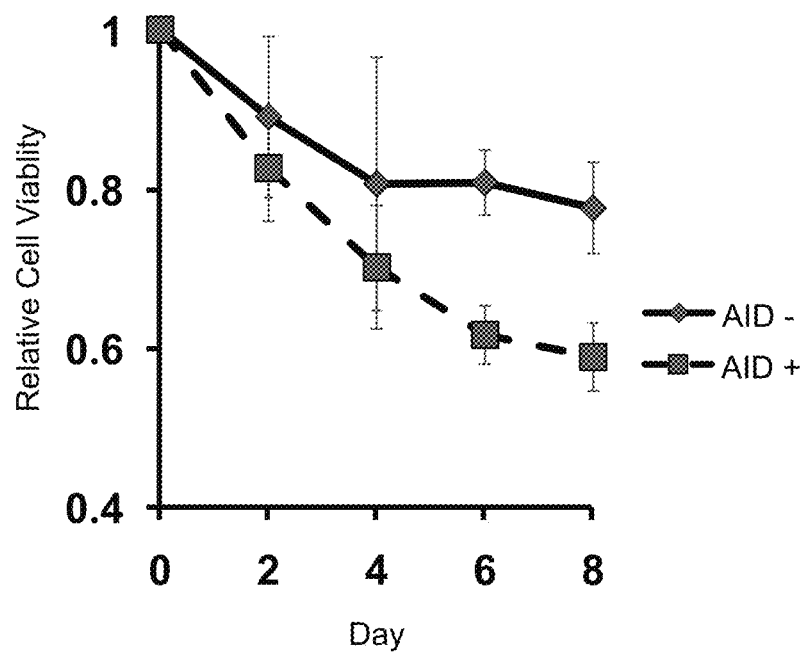
FIG. 18B shows the cell viability of primary human CLL cells in response to DIDS.

This assay rapidly and sensitively identifies AID+ and AID− patient samples as shown in FIG. 18A, where 8 representative samples are shown. Eight AID+ and eight AID− CLL samples were cultured in basic RPMI-1640 medium plus 30 micromolar DIDS, and survival was scored by manual cytometry for viable cells after 2, 4, 6, or 8 days. This analysis revealed that DIDS more strongly reduces cell viability in AID-positive than in AID-negative primary human CLL cells. This also reveals that AID expression, as a single marker, effectively identifies DIDS-responsive samples. When CLL cells expressing AID were treated with 10 μM DIDS significant effects on cell viability have been determined. A total of 117 lymphoma or leukemia patients were studies, of which 106 were CLL patients. In 47% AID expression was determined by RT-PCR.

Example 19: Effect of DIDS on Mouse Systemic Lupus Erythematosus (SLE) Model BXSB.Yaa Cd8/IL15−/− mice are an established model for SLE. These mice display many characteristics of human SLE including hypergammaglobulinemia, circulating anti-nuclear antibodies and immune complex medicated glomerulonephritis, and ultimately succumb to disease around 24 weeks of age (Andrews et al. 1978, *J Exp Med* 148: 1198-215; Dixon et al. 1978, *Arthritis Rheum* 21: S64-7; Izui et al. 2000, *Int Rev Immunol* 19: 447-72). Genetic deletion of Cd8a and IL15 from the model results in a similar clinical phenotype which appears much early with survival averaging 14 weeks of age (McPhee et al. 2011, *J Immunol* 187:4695-4704)

Figure 19A:
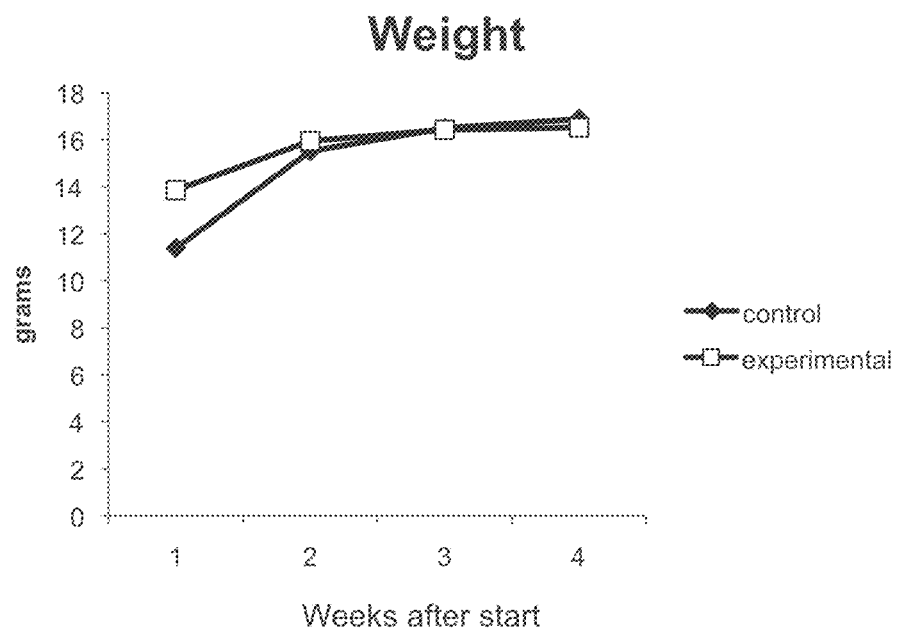
FIG. 19A shows the weight of BXSB.Yaa Cd8/IL15−/− mice treated with 25 mg/kg DIDS.
Figure 19B:
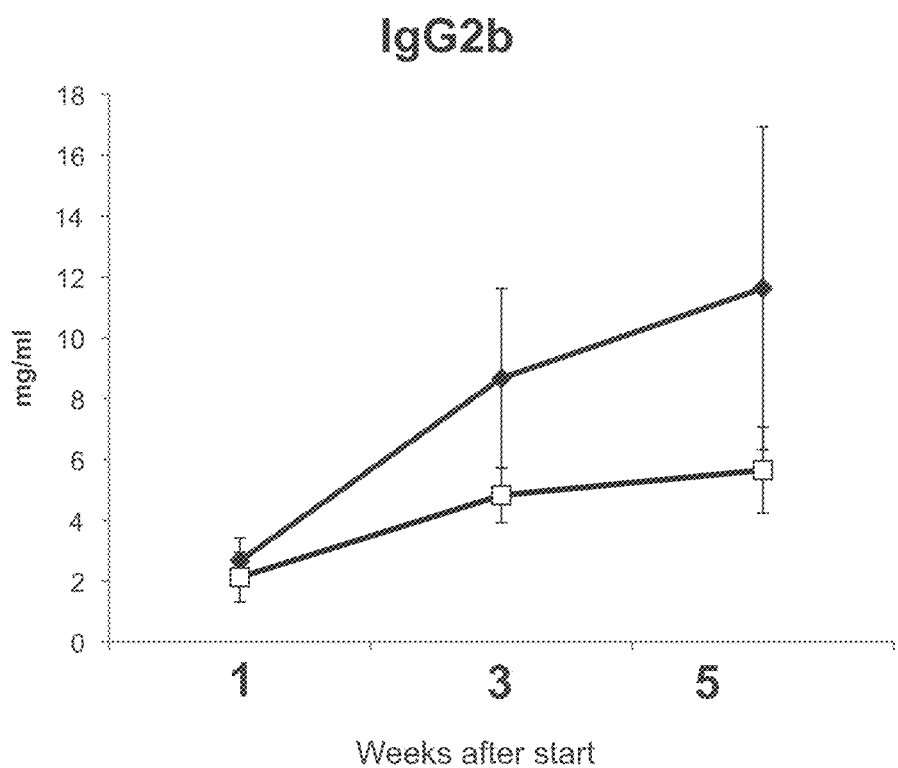
FIG. 19B shows the IgG2b serum content in of BXSB.Yaa Cd8/IL15−/− mice treated with 25 mg/kg DIDS.
Figure 20A:
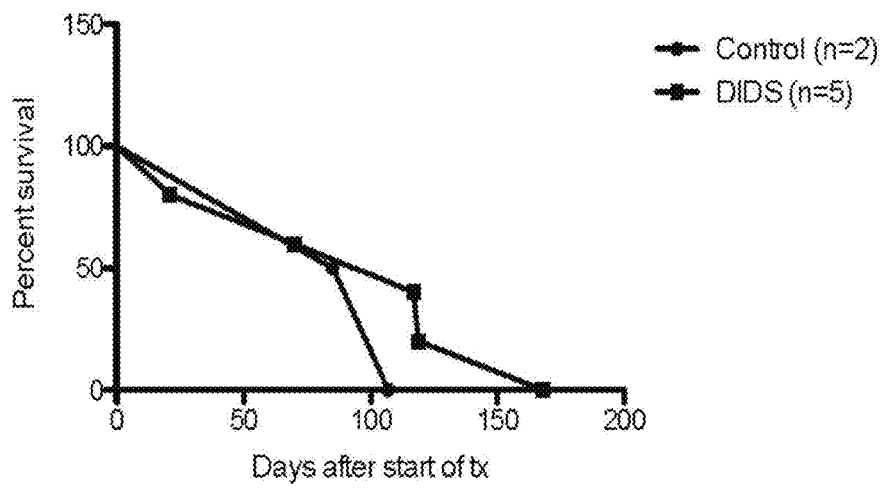
FIGS. 20A-20B show a log-rank Mantel Cox survival plots after treatment of BXSB.Yaa Cd8/I115−/− mice with either 25 mg/kg DIDS (20A) or 50 mg/kg DIDS (20B), shown as days after start of treatment.
Figure 20B:
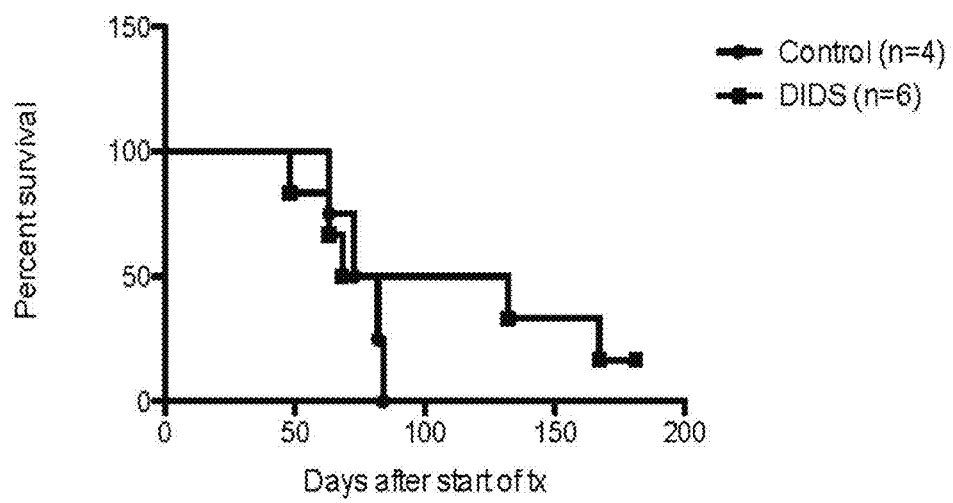
Figure 21A:
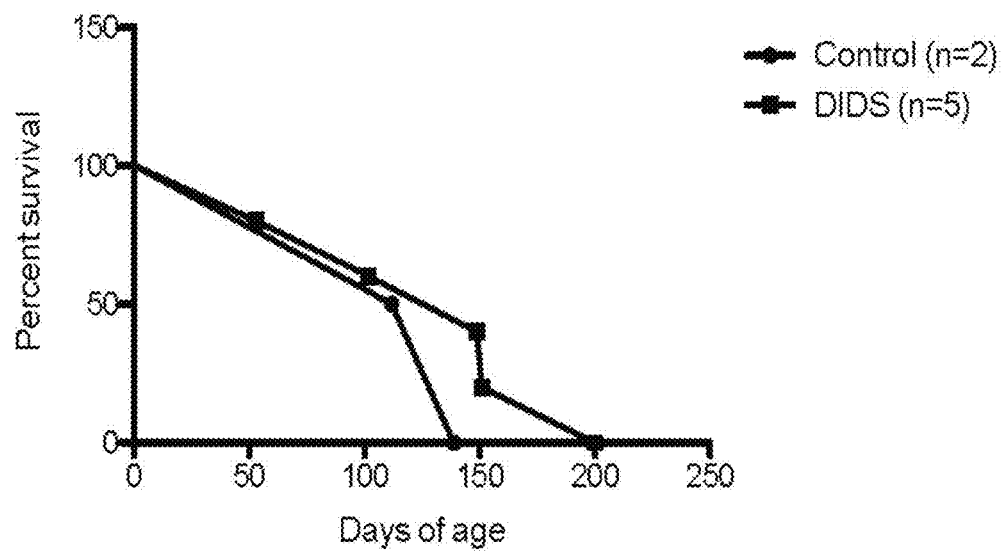
FIGS. 21A-21B show survival of BXSB.Yaa Cd8/IL15−/− mice treated with either 25 mg/kg DIDS (21A) or 50 mg/kg DIDS (21B), plotted as age of the mice in days applying the Gehan-Breslow-Wilcoxan test.
Figure 21B:
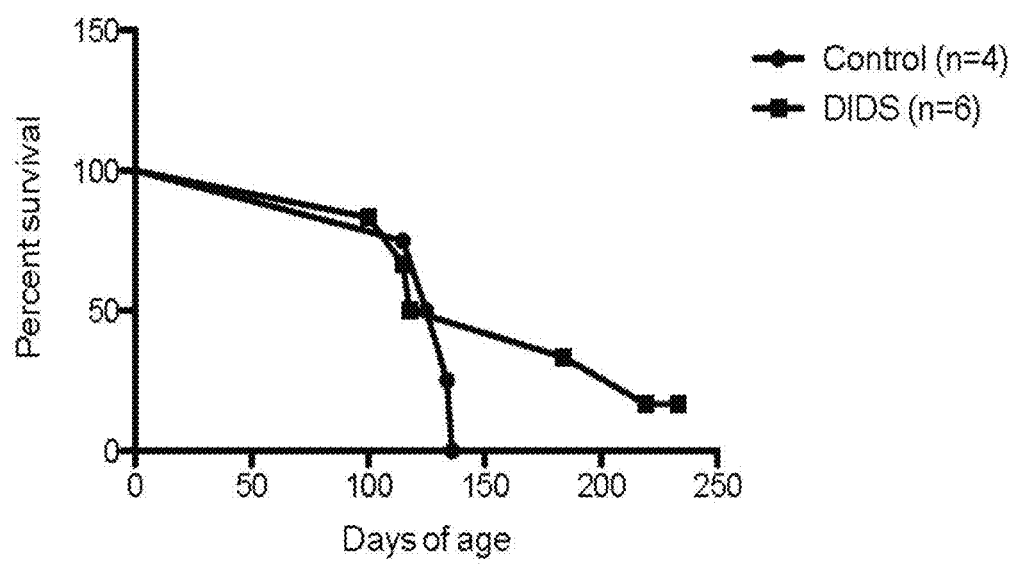

Six week old male BXSB.Cg-Cd8a<tm1Mak> IL15<tm1Imx>/Dcr (abbreviated as BXSB.Yaa Cd8/IL15−/−) mice were retro-orbitally bled into heparin primed tubes to collect serum. 25 mg/kg (n=5) or 50 mg/kg DIDS (n=6) in 4% potassium bicarbonate with PBS or an equivalent volume of 4% potassium bicarbonate (n=2 and n=4) was administered intraperitoneally on day 0, and every seven days for five weeks. Mice were weighed weekly and serum was collected at 14 day intervals for a 5-week period. These mice were then aged for survival. The serum was analyzed by ELISA for IgG1 and IgG2b content. For the ELISA plates were coated with goat anti-mouse Ig (IgG1 or IgG2b) and incubated overnight at 40° C. Plates were washed and serum samples were applied at appropriate dilutions along with mouse isotype standards and incubated for 1 hour at 37° C. Plates were washed three times and incubated with goat anti-mouse antibody conjugated to alkaline phosphatase for 1 hour. Plates were washed three times and P-nitrophenyl Phosphate (p-NPP, AMRESCO) was applied, incubated until standards developed adequately and read on a SpectraMax ELISA plate reader using SoftmaxPro software. Data are expressed as concentration of IgG (mg/ml) based on titration of isotype-specific purified mouse standards. FIG. 19A shows no weight difference between controls and treated animals. However, the analysis of IgG2b showed a striking decrease indicating being effective for lupus treatment (FIG. 20B). No significant difference was observed for IgG1 (data not shown). Survival data was analyzed using Graphpad Prism software and assessed for statistical significance using both the log-rank Mantel Cox with (FIG. 20A for the 25 mg/kg group with a p value of 0.4289 and FIG. 20B for the 50 mg/kg group with a p value of 0.3698) and Gehan-Breslow-Wilcoxan tests (FIG. 21A for the 25 mg/kg group with a p value of 0.7003 and FIG. 21B for the 50 mg/kg group with a p value of 0.7505).

Example 20: DIDS Disrupts RAD51 Focus Formation after DNA Damage

Figure 22:
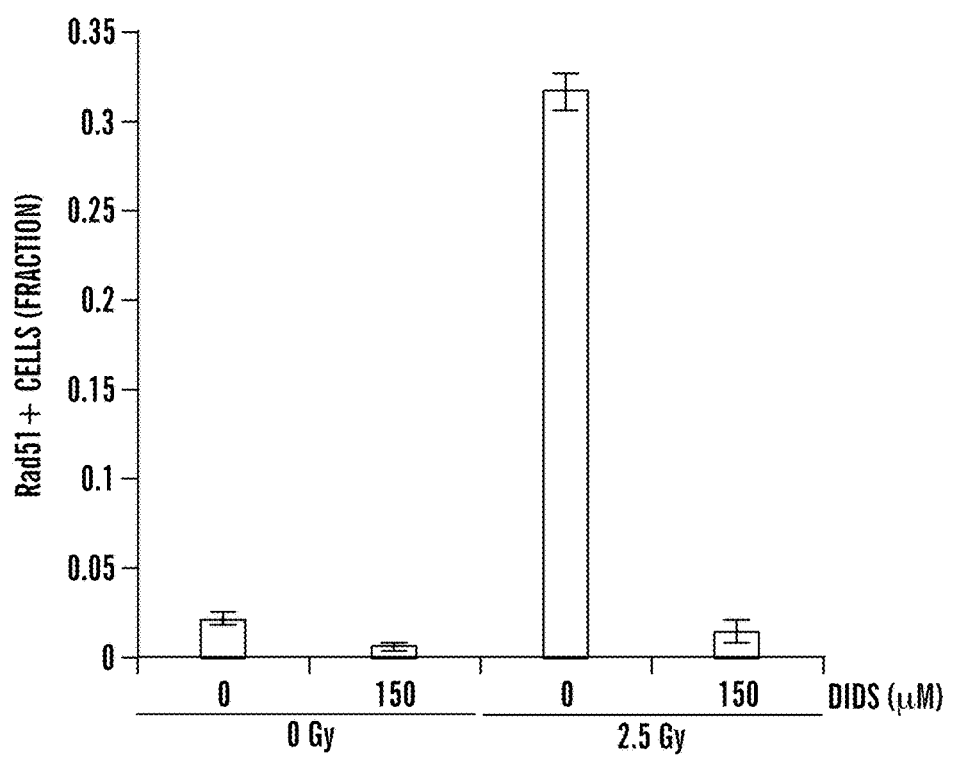
FIG. 22 shows that DIDS disrupts RAD51 focus formation after DNA damage. Irradiated cells not exposed to DIDS (0 mM) show efficient focus formation. DIDS exposure (150 mM) completely inhibits radiation-induced RAD51 focus formation, reducing the fraction of Rad51 focus+ cells to baseline levels (equivalent to those in the unirradiated, 0 Gy samples). Error bars show the standard error of the mean (S.E.M) from three independent experiments.

Primary mouse B-cells were isolated from spleen of wild type C57BL/6J mice by magnetic bead based sorting (Miltenyi) to purify B220+ IgM+ B-cells. B-cells were then cultured in standard RPMI-1640 medium supplemented with 10% FBS in the presence of either 0 or 150 μM DIDS, exposed to 0 or 2.5 Gy ionizing radiation in a Cs137 irradiator, and then stained by immunofluorescence for foci of the homologous recombination factor RAD51. The fraction of cells in each culture showing formation of RAD51 foci within the nucleus is reported. Irradiated cells not cultured with DIDS (0 μM) show efficient focus formation. DIDS exposure (150 μM) completely inhibits radiation-induced RAD51 focus formation, reducing the fraction of Rad51 focus+ cells to baseline levels (equivalent to those in the unirradiated, 0 Gy samples) as shown in FIG. 22. Error bars show the standard error of the mean (S.E.M) from three independent experiments.

Figure 23A:
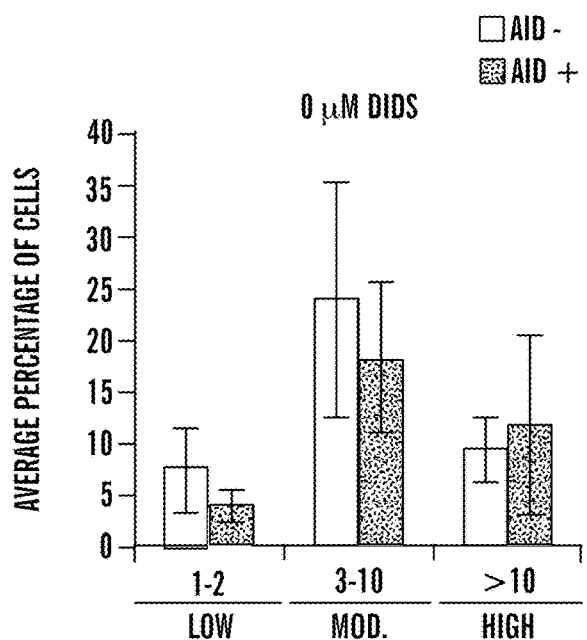
FIGS. 23A-23B show the number of phosphor-H2AX foci in AID-positive (AID+) and AID-negative (AID−) human cells depending on DIDS treatment. The number of foci are shown on the x-axis.
Figure 23B:
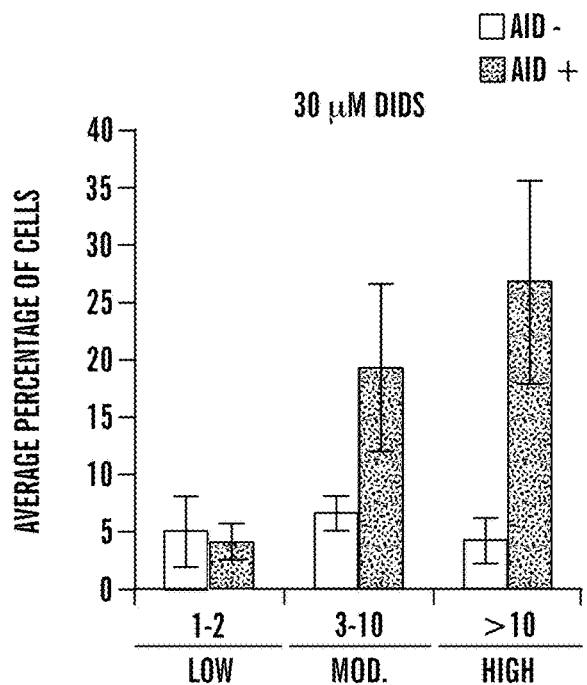

Example 21: DIDS Treatment Leads to Increased Levels of Phospho-H2AX Foci Preferentially in AID-Expressing Primary Human Chronic Lymphocytic Leukemia (CLL) Cells Primary human CLL patient derived cells were obtained from peripheral bleeds collected at the time of routine clinical monitoring. Primary peripheral blood samples were collected via routine venipuncture into BD Vacutainer CPT Cell Separation Tubes (Becton Dickinson). Samples were centrifuged to separate red blood cells (RBC) and then inverted to resuspend the monocuclear cells in their own plasma. Samples were stored overnight at the site of collection at room temperature then shipped via courier to the site of analysis. Each sample was tested for AID expression status by reverse transcription PCR (RT-PCR) to detect presence of the human AID mRNA (see Example 11). Samples were then divided into AID+ (those showing detectable levels of AID mRNA) and AID− (those showing no detectable AID mRNA above background) groups. Multiple independent cultures from different AID+ and AID− samples were initiated in standard RPMI-1640 medium containing 10% FBS plus either 0 or 30 µM DIDS. After 2 days in culture, cells from each culture/condition were fixed using paraformaldehyde, mounted on microscope coverslips, permeabilized by washing with weak detergent, and were processed for immunofluorescent detection of the DNA double strand break marker phosphor-H2AX (primary antibody: cat. No. A300-081A, Bethyl Laboratories; 1:400 dilution). After staining, cells were imaged using a Nikon 90i upright epifluorescence microscope and 100 individual nuclei were imaged for each sample. Nuclear DNA was counterstained with 4',6-diamidino-2-phenylindole (DAPI). The average percentage of cells showing 1-2 (Low), 3-10 (Mod.), or greater than 10 (High) phosphor-H2AX foci is shown in FIGS. 23 A and B. Error bars represent the standard error of the mean (S.E.M.) for 4 independent cultures of the AID− (open bars) samples and 5 independent cultures of the AID+ samples (filled bars). These data show that DIDS inhibits repair of AID-mediated genomic DNA double strand breaks (DSBs).

Figure 24:
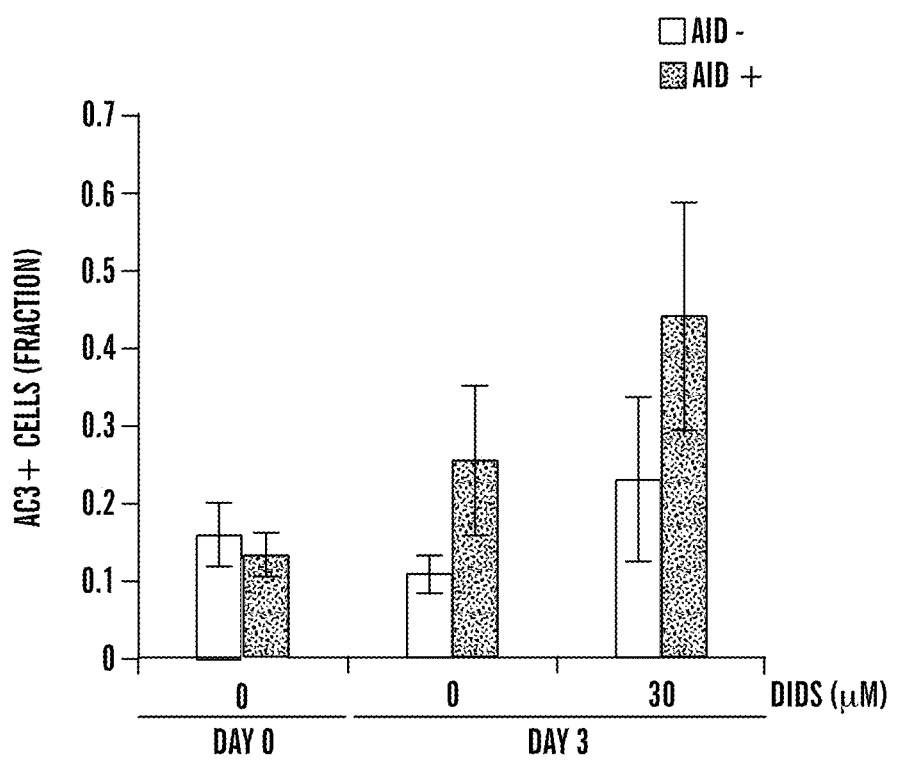
FIG. 24 shows activated caspase 3 (AC3) positive cells depending on DIDS treatment and AID expression. Error bars represent standard error of the mean (S.E.M.) for 4 independent cultures of the AID− samples −/− (open bars) and 5 independent cultures of the AID+ samples filled bars).

Example 22: DIDS Treatment Leads to Apoptosis Preferentially in AID+ Primary Human CLL Cells Primary human CLL patient derived cells were obtained from peripheral bleeds collected at the time of routine clinical monitoring. Primary peripheral blood samples were collected via routine venipuncture into BD Vacutainer CPT Cell Separation Tubes. Samples were centrifuged to separate red blood cells (RBC) and then inverted to resuspend the mononuclear cells in their own plasma. Samples were stored overnight at the site of collection at room temperature then shipped via courier to the site of analysis. Each sample was tested for AID expression status by reverse transcription PCR (RT-PCR) to detect presence of the human AID mRNA (see Example 11). Samples were then divided into AID+ (those showing detectable levels of AID mRNA) and AID− (those showing no detectable AID mRNA above background) groups. Multiple independent cultures from different AID+ and AID− samples were initiated in standard RPMI-1640 medium containing 10% FBS plus either 0 or 30 µM DIDS. After 3 days in culture, cells from were fixed with paraformaldehyde, mounted on microscope coverslips, permeabilized by washing with weak detergent, and processed for immunofluorescent detection of the apoptosis marker activated caspase 3 (AC3) (primary antibody: cat. No. ab13847, Abcam; 1:100 dilution). Nuclear DNA was counterstained with 4',6-diamidino-2-phenylindole (DAPI). After staining, cells were imaged using a Nikon 90i upright epifluorescence microscope. The fraction of cells showing positive staining for AC3 is shown for AID+(FIG. 24, filled bars) and AID− samples (FIG. 24, open bars). Error bars represent standard error of the mean (S.E.M.) for 4 independent cultures of the AID− samples and 5 independent cultures of the AID+ samples. AID positive cells treated with 30 µM DIDS show a higher fraction of AC3-positive cells.

Example 23: AID Expression and its Association with Primary Human Chronic Lymphocytic Leukemia Prognosis AID expression is associated with worse overall disease in primary human chronic lymphocytic leukemia. Eight individual AID+ and 8 individual AID− primary human CLL samples were selected on the basis of high white blood cell (WBC) count (greater than 58,000 per microliter). These were then analyzed for mean and median age at diagnosis (Age @ Dx) and for treatment. AID+ samples showed a lower mean age (63.75 versus 68 years) and median age (62.5 versus 68.5 years) at diagnosis (Table 3). Moreover, 4/8 AID+ patients received treatment whereas 1/8 AID− patients received treatment.

TABLE 3

Human CLL samples analyzed AID expression

| | ID | WBC | % lymph | sex | Age @ Dx | treatment |
|---|---|---|---|---|---|---|
| AID− | JE1015 (1) | 20.4 | 58.1 | M | 86 | None |
| | JE1019 (1, 2, 3) | 102.5 | 95.8 | M | 76 | None |
| | JE1031 (1) | 32.6 | 80.7 | F | 47 | None |
| | JE1056 (2, 3) | 68.1 | 91.1 | M | 70 | None |
| | JE1057 (1) | 31.3 | 81.3 | F | 64 | None |
| | JE1069 (2, 3) | 44.1 | 91.7 | M | 53 | Chloram. |
| | JE1088 (2, 3) | 135.4 | 93.5 | M | 67 | None |
| | JE1095 (2, 3) | 80.7 | 90.0 | M | 81 | None |
| | | | | | Mean 68 | |
| | | | | | Median 68.5 | |
| AID+ | JE1010 (1) | 43.6 | 83.2 | F | 51 | None |
| | JE1036 (1) | 22.6 | 65 | M | 63 | None |
| | JE1044 (2, 3) | 55.3 | 93.7 | F | 57 | IgG |
| | JE1045 (2, 3) | 17.1 | 68.7 | M | 62 | Flud. |
| | JE1046 (2, 3) | 47.8 | 89.5 | M | 79 | None |
| | JE1070 (1, 2, 3) | 78.3 | 91.0 | M | 53 | Chloram. |
| | JE1075 (1) | 39.3 | 87.6 | F | 72 | None |
| | JE1098 (2, 3) | 41.2 | 86.0 | F | 73 | Chloram. |
| | | | | | Mean 63.75 | |
| | | | | | Median 62.5 | |

Example 24: In Vivo Testing of AID in a Mouse Model

To test the in vivo effectiveness of DIDS, either AID+/+ (C57BL/6) or AID−/− mice (Muramatsu et al. et al., 2000 supra) were administered DIDS (10 mg/kg or 50 mg/kg) at weekly intervals, immunized at weeks 1 with dinitrophenol conjugated Keyhole limpet hemocyanin (DNP-KLH) in complete Freund's adjuvant (CFA) to stimulate lymphocyte activation, and boosted after 4 weeks with DNP-KLH (in incomplete Freund's adjuvant, IFA). After a total of 7 weeks (FIG. 25A) mice were euthanized. The group size was n=5. No animals in either the control or DIDS-treated groups showed overt signs of toxicity, relative to the untreated control groups. After 5 weeks, the AID+/+ mice showed slightly greater weight gain than the AID−/− mice, but this effect was independent of DIDS exposure, affecting the 0 mg/kg control and 50 mg/kg experimental cohorts equally (FIG. 25B). For this the mice were weighed weekly and the data represent the average fractional change in body mass for five animals, and error bars denote S.E.M.

Figure 26:
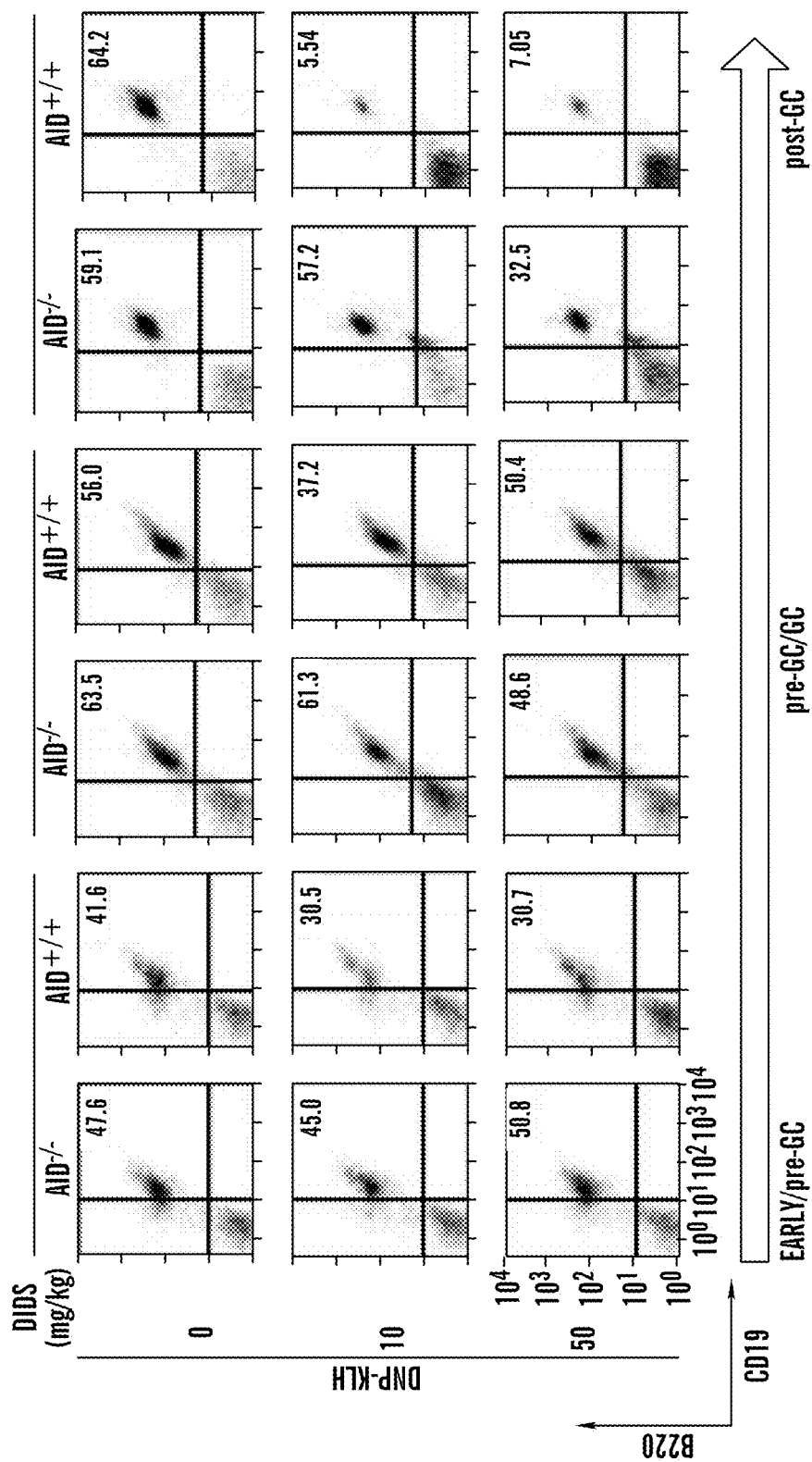
FIG. 26 shows endpoint flow cytometry dot plot analysis of bone marrow, spleen, and peripheral blood from AID−/− and AID+/+ mice immunized with DNP-KLH and treated with 0, 10, or 50 mg/kg DIDS. Plots represent the population of cells in the lymphocyte gate stained for expression of B220 (y-axis) and CD19 (x-axis). The numbers in the upper right corner of each plot provide the percentage of B220+/CD19+ cells for each analysis. The progression of B-cell maturation from early/pre-GC to post-GC is indicated below.

After the 7-week trial window, tissues from treated and control animals were fixed, sectioned, and analyzed after hematoxylin and eosin (H&E) staining. Analysis of spleen sections revealed no gross anatomical defects or differences in germinal center (GC) architecture between untreated and DIDS-treated animals, and no differences between AID+/+ mice and AID−/− controls. These data suggest that DIDS, at least up to 50 mg/kg, does not induce significant toxicity or general defects in splenic physiology in either AID+/+ or AID−/− mice. To determine whether DIDS induced a B-cell specific phenotype related to AID, bone marrow, spleen, and peripheral blood, from DIDS-treated AID+/+ versus AID−/− mice, were analyzed for the presence of B220+CD19+ B-cells, by flow cytometry (FIG. 26). A small (25%) reduction in B220+CD19+ B-cells was observed in the bone marrow of both 10 μM and 50 μM treated AID+/+ mice, but no consistent differences in the percentages of splenic B-cells in either AID+/+ or AID−/− mice. By contrast, both 10 μM and 50 μM DIDS induced a significant (9-11 fold) reduction in circulating B-lymphoid cells, specifically in AID+/+ but not AID−/− mice. In FIG. 26 the endpoint flow cytometry dot plot analysis of bone marrow, spleen, and peripheral blood from AID−/− and AID+/+ mice immunized with DNP-KLH and treated with 0, 10, or 50 mg/kg DIDS is shown. Plots represent the population of cells in the lymphocyte gate stained for expression of B220 (y-axis) and CD19 (x-axis). The numbers in the upper right corner of each plot provide the percentage of B220+/CD19+ cells for each analysis. The progression of B-cell maturation from early/pre-GC to post-GC is indicated below.

These data suggest that in vivo, systemic DIDS treatment selectively affected mature, post-germinal center B-cells, but had a negligible effect on early or pre-GC B-cells. This is consistent with the cell culture data described herein demonstrating a synergistic cytotoxicity induced by the combined effects of AID and DIDS. Significantly, none of the DIDS treated animals, in either the AID+/+ or AID−/− cohort, showed evidence of overt non-B-cell toxicity. Taken together, these data strongly imply that in vivo administration of DIDS specifically sensitizes AID-expressing B-cells—those undergoing germinal center reactions or ectopically expressing AID.

Figure 27:
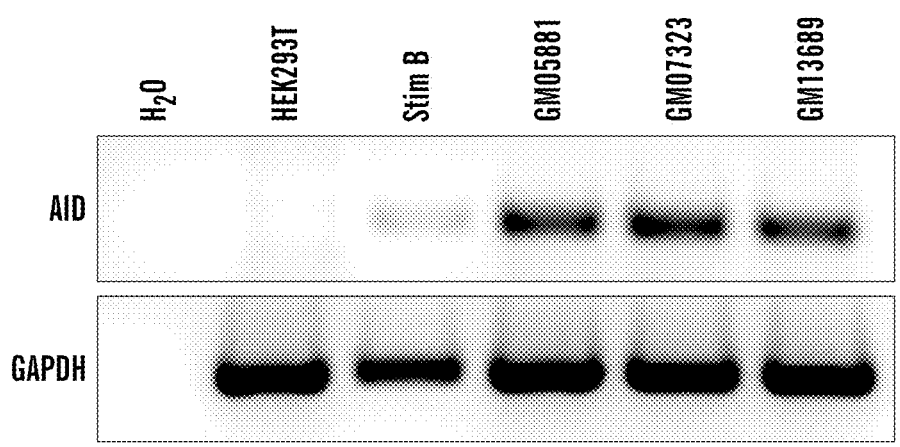
FIG. 27 shows RT-PCR expression analysis for AID and GAPDH (control) in Epstein-Ban virus transformed peripheral human B-lymphocytes.

Example 25: AID Expression Analysis in Epstein-Barr Virus Transformed Peripheral Human B-Lymphocytes Epstein-Ban virus transformed peripheral human B-lymphocytes derived cell lines GM05881, GM07323, and GM13689 (obtained from Corriell Institute, NIGMS Human Genetic Cell Repository) are a good representation of human non-Hodgkin's lymphoma. These cells were cultured in RPMI1640 medium supplemented with 2 mM glutamine and 15% fetal bovine serum. Total RNA was prepared from each of the cultured cell lines, or from human primary stimulated B-cells (Stim B), or from the human embryonic kidney cell line HEK293T by standard ribonucleic acid extraction methods (see Example 11). RNA was then analyzed by reverse-transcription (RT)-PCR for the AID transcript using the same primers as described in Example 11, and for the GAPDH transcript (loading control). These data show that AID is highly expressed in these transformed B-cell lines, at levels even higher than those in purified, activated primary B-cells (see FIG. 27).

Example 26: In Vivo Efficacy Testing of Genetic Chemotherapy in Mouse Models of Three B-Cell Leukemia/Lymphoma Types Human human patient-derived cell lines for chronic lymphocytic leukemia (CLL), acute lymphoblastic leukemia (ALL); and non-Hodgkin's lymphoma (NHL) will be engrafted into NRG (NOD.Rag1−/− Il2rγ−/−; NOD-Rag1<null> IL2rg<null>/WjI/SzJ) mice or NSG (NOD.scid Il2rγ−/−; NOD.Cg-Prkdc-scid<Il2rg>/WjI/SzJ) mice and xenografts will be established. The engrafted mice will be treated with the compound sodium (E)-5-acetamido-2-(4-(3-isopropylthioureido)-2-sulfonatostyryl)benzenesulfonate or sodium (E)-5-(3-isopropylureido)-2-(4-(2-methoxyacet-amido)-2-sulfonatostyryl)benzenesulfonate at doses ranging from 1 to 10 mg/kg. As control engrafted mice will be treated with fludarabine+cyclophosphamide or doxorubicin plus prednisone. The mice will be scored for tumor burden.

TABLE 4

SEQ ID NOs

| SEQ ID NO | Description |
| --- | --- |
| 001 | BCL6 mRNA; NM_001130845 |
| 002 | MYC mRNA; NM_002467 |
| 003 | BCL11A mRNA; NM_018014 |
| 004 | CD93 mRNA; NM_012072 |
| 005 | PIM1 mRNA; NM_002648 |
| 006 | PAX5 mRNA; NM_016734 |
| 007 | Rad51AP1 mRNA; NM_001130862 |
| 008 | Rad51B mRNA; NM_002877 |
| 009 | Rad51D mRNA; NM_002878 |
| 010 | XRCC2 mRNA; NM_005431 |
| 011 | XRCC3 mRNA; NM_001100119 |
| 012 | RAD54 mRNA; NM_000489 |
| 013 | RAD52 mRNA; NM_134424 |
| 014 | BRCA1 mRNA; NM_007300 |
| 015 | BRCA2 mRNA; NM_000059 |
| 016 | ATM mRNA; NM_000051 |
| 017 | ATR mRNA; NM_001184 |
| 018 | MRE11 mRNA; NM_005591 |
| 019 | RAD50 mRNA; NM_005732 |
| 020 | NBS1 mRNA; NM_002485 |
| 021 | WRN mRNA; NM_000553 |
| 022 | BLM mRNA; NM_000057 |
| 023 | RECQ4 mRNA; NM_004260 |
| 024 | LIG4 mRNA; NM_001098268 |
| 025 | XRCC4 mRNA; NM_003401 |
| 026 | PRKDC mRNA; NM_006904 |
| 027 | DCLRE1C mRNA; NM_001033855 |
| 028 | XRCC6 mRNA; NM_001469 |
| 029 | XRCC5 mRNA; NM_021141 |
| 030 | XLF mRNA; NM_024782 |
| 050 | XRCC2 inhibitory RNA |
| 051 | XRCC2 inhibitory RNA |
| 052 | XRCC2 inhibitory RNA |
| 053 | XRCC2 inhibitory RNA |
| 054 | XRCC2 inhibitory RNA |
| 055 | XRCC2 inhibitory RNA |
| 056 | XRCC2 inhibitory RNA |
| 057 | XRCC2 inhibitory RNA |
| 058 | XRCC2 inhibitory RNA |
| 059 | XRCC3 inhibitory RNA |
| 060 | XRCC3 inhibitory RNA |
| 061 | XRCC3 inhibitory RNA |
| 062 | XRCC3 inhibitory RNA |
| 063 | XRCC3 inhibitory RNA |

TABLE 4-continued

SEQ ID NOs

| SEQ ID NO | Description |
|---|---|
| 064 | RAD51 inhibitory RNA |
| 065 | RAD51 inhibitory RNA |
| 066 | RAD51 inhibitory RNA |
| 067 | RAD51 inhibitory RNA |
| 068 | RAD51 inhibitory RNA |
| 069 | RAD51 inhibitory RNA |
| 070 | RAD51 inhibitory RNA |
| 071 | RAD51 inhibitory RNA |
| 072 | RAD51 inhibitory RNA |
| 073 | RAD51B inhibitory RNA |
| 074 | RAD51B inhibitory RNA |
| 075 | RAD51B inhibitory RNA |
| 076 | RAD51B inhibitory RNA |
| 077 | RAD51B inhibitory RNA |
| 078 | RAD51B inhibitory RNA |
| 079 | RAD51B inhibitory RNA |
| 080 | RAD51B inhibitory RNA |
| 081 | RAD51C inhibitory RNA |
| 082 | RAD51C inhibitory RNA |
| 083 | RAD51C inhibitory RNA |
| 084 | RAD51C inhibitory RNA |
| 085 | RAD51C inhibitory RNA |
| 086 | RAD51C inhibitory RNA |
| 087 | RAD51C inhibitory RNA |
| 088 | RAD51C inhibitory RNA |
| 089 | RAD51C inhibitory RNA |
| 090 | RAD51D inhibitory RNA |
| 091 | RAD51D inhibitory RNA |
| 092 | RAD51D inhibitory RNA |
| 093 | RAD51D inhibitory RNA |
| 094 | RAD51D inhibitory RNA |
| 095 | RAD51D inhibitory RNA |
| 096 | RAD51D inhibitory RNA |
| 097 | RAD51D inhibitory RNA |
| 098 | RAD51D inhibitory RNA |
| 099 | AID amino acid sequence; NCBI Ref Seq: NP_065712 |
| 0100 | AID mRNA sequence; NCBI Ref Seq: NP_020661 |
| 0101 | hAID forward primer |
| 0102 | hAID rev primer |
| 0103 | hGAPDH fwd primer |
| 0104 | hGAPDH rev primer |
| 0105 | GAPDH primer |
| 0106 | GAPDH primer |
| 0107 | VH1-FR1 |
| 0108 | VH2-FR1 |
| 0109 | VH3-FR1 |
| 0110 | VH4-FR1 |
| 0111 | VH5-FR1 |
| 0112 | VH6-FR1 |
| 0113 | JH consensus |
| 0114 | Rad51AP1 amino acid sequence; NCBI Ref: NP_001124334 |
| 0115 | RAD51B amino acid sequence; NCBI Ref: NP_002868 |
| 0116 | RAD51D amino acid sequence; NCBI Ref: NP_001136043 |
| 0117 | XRCC2 amino acid sequence; NCBI Ref: NP_005422 |
| 0118 | XRCC3 amino acid sequence; NCBI Ref: NP_001093588 |
| 0119 | RAD54 amino acid sequence; NCBI Ref: NP_000480 |
| 0120 | RAD52 amino acid sequence; NCBI Ref: NP_602296 |
| 0121 | BRCA1 amino acid sequence; NCBI Ref: NP_009225 |
| 0122 | BRCA2 amino acid sequence; NCBI Ref: NP_000050 |
| 0123 | ATM amino acid sequence; NCBI Ref: NP_000042 |
| 0124 | ATR amino acid sequence; NCBI Ref: NP_001175 |
| 0125 | MRE11 amino acid sequence; NCBI Ref: NP_005582 |
| 0126 | RAD50 amino acid sequence; NCBI Ref: NP_005723 |
| 0127 | NBS1 amino acid sequence; NCBI Ref: NP_002476 |
| 0128 | WRN amino acid sequence; NCBI Ref: NP_000544 |
| 0129 | BLM amino acid sequence; NCBI Ref: NP_000048 |
| 0130 | RECQ4 amino acid sequence; NCBI Ref: NP_004251 |
| 0131 | LIG4 amino acid sequence; NCBI Ref: NP_001091738 |
| 0132 | XRCC4 amino acid sequence; NCBI Ref: NP_071801 |
| 0133 | PRKDC amino acid sequence; NCBI Ref: NP_008835 |
| 0134 | DCLRE1C amino acid sequence; NCBI Ref: NP_001029027 |
| 0135 | XRCC6 amino acid sequence; NCBI Ref: NP_001460 |
| 0136 | XRCC5 amino acid sequence; NCBI Ref: NP_066964 |
| 0137 | XLF amino acid sequence; NCBI Ref: NP_079058 |
| 0138 | APOBEC1 amino acid sequence; NCBI Ref: NP_001635 |
| 0139 | APOBEC2 amino acid sequence; NCBI Ref: NP_006780 |
| 0140 | APOBEC3A amino acid sequence; NCBI Ref: NNP_663745 |
| 0141 | APOBEC3C amino acid sequence; NCBI Ref: NP_055323 |
| 0142 | APOBEC3E amino acid sequence; NCBI Ref: NP_689639 |
| 0143 | APOBEC3F amino acid sequence; NCBI Ref: NP_660341 |
| 0144 | APOBEC3G amino acid sequence; NCBI Ref: NP_068594 |
| 0145 | APOBEC3H amino acid sequence; NCBI Ref: NP_001159475 |
| 0146 | APOBEC4 amino acid sequence; NCBI Ref: NP_982279 |
| 0157 | RAG1 mRNA sequence; NCBI Ref: NM_00448 |
| 0158 | RAG1 amino acid sequence; NCBI Ref: NP_000439 |
| 0159 | RAG2 mRNA sequence; NCBI Ref: NM_001243785 |
| 0160 | RAG2 amino acid sequence; NCBI Ref: NP_001230714 |
| 0161 | SPO11 mRNA sequence; NCBI Ref: NM_012444 |
| 0162 | SPO11 amino acid sequence; NCBI Ref: NP_036576 |
| 0163 | Rad51C isoform 1 mRNA sequence; NCBI Ref: NM_058216 |
| 0164 | Rad51C isoform 1 amino acid sequence; NCBI Ref: NP_478123 |
| 0165 | Rad51C isoform 2 mRNA sequence; NCBI Ref: NM_002876 |
| 0166 | Rad51C isoform 2 amino acid sequence; NCBI Ref: NP_002867 |

What is claimed herein is:

1. A method of reducing viability of a cancerous B cell, a chronic lymphoblastic leukemia (CLL) cell, or a B-cell lymphoma/leukemia cell, wherein the cell is determined to have a detectable level of activation-induced cytidine deaminase (AID), the method comprising;
    contacting the cell with an inhibitor of DNA double strand break repair, and
    wherein the inhibitor of DNA double strand break repair is selected from the group consisting of:
    (E)-4,4'-(ethene-1,2-diyl)bis(N-methylbenzamide);
    (E)-N-(4-(4-(dimethylamino)styryl)phenyl)cyclopropanesulfonamide;
    (E)-N-(4-(4-(dimethylamino)styryl)phenyl)propane-2-sulfonamide;
    (E)-N,N'-(ethene-1,2-diylbis(4,1-phenylene))bis(propane-2-sulfonamide);
    (E)-N,N'-(ethene-1,2-diylbis(4,1-phenylene))bis(dimethylamino-sulfonamide);
    sodium 6,6'-(ethane-1,2-diyl)bis(3-(3-isopropylureido)benzenesulfonate);
    sodium (E)-5-(3-cyclopropylthioureido)-2-(4-(1-methylethylsulfonamido)-2-sulfonatostyryl)benzenesulfonate;
    sodium (E)-5-(3-ethylureido)-2-(4-(2-methoxyacetamido)-2-sulfonatostyryl)benzenesulfonate;
    sodium (E)-5-acetamido-2-(4-(cyclopropanesulfonamido)-2-sulfonatostyryl)benzenesulfonate; and
    sodium (E)-5-acetamido-2-(4-((N,N-dimethylsulfamoyl)amino)-2-sulfonatostyryl)benzenesulfonate.

* * * * *

SEQUENCE LISTING

```
<160> NUMBER OF SEQ ID NOS: 166

<210> SEQ ID NO 1
<211> LENGTH: 3662
<212> TYPE: DNA
<213> ORGANISM: Homo sapiens

<400> SEQUENCE: 1
gcgagctggt ggttgaagct ggttaaagaa cagcctaggt attccagaag tgtttgagga      60
tcccttccat gaaggaagag aggaaagttt ttaagtaaac ctcccactcc catgtgtctt     120
cagctttctt ttgcaaagga gaaatccctt gaagtttggt aaagaccgag ttagtctatc     180
tctctttgcc tatctcgagt tgggctgggg agaggaggag ataggttctt ttgtcttttt     240
ctgtcttctc ccttccccac ttccttccct ccagtcccca ctcactcaca tgcacacact     300
aaccttggag ccgatgggat tgagtgactg gcacttggga ccacagagaa atgtcagagt     360
```

```
gtttggttac agactcaagg aaacctctca ttttagagtg ctcatttggt tttgagcaaa    420
attttggact gtgaagcaag gcattggtga agacaaaatg gcctcgccgg ctgacagctg    480
tatccagttc acccgccatg ccagtgatgt tcttctcaac cttaatcgtc tccggagtcg    540
agacatcttg actgatgttg tcattgttgt gagccgtgag cagtttagag cccataaaac    600
ggtcctcatg gcctgcagtg gcctgttcta tagcatcttt acagaccagt tgaaatgcaa    660
ccttagtgtg atcaatctag atcctgagat caaccctgag ggattctgca tcctcctgga    720
cttcatgtac acatctcggc tcaatttgcg ggagggcaac atcatggctg tgatggccac    780
ggctatgtac ctgcagatgg agcatgttgt ggacacttgc cggaagttta ttaaggccag    840
tgaagcagag atggtttctg ccatcaagcc tcctcgtgaa gagttcctca acagccggat    900
gctgatgccc aagacatca tggcctatcg gggtcgtgag gtggtggaga caacctgcc     960
actgaggagc gcccctgggt gtgagagcag agcctttgcc cccagcctgt acagtggcct   1020
gtccacaccg ccagcctctt attccatgta cagccacctc cctgtcagca gcctcctctt   1080
ctccgatgag gagtttcggg atgtccggat gcctgtggcc aacccttcc ccaaggagcg    1140
ggcactccca tgtgatagtg ccaggccagt ccctggtgag tacagccggc cgactttgga   1200
ggtgtccccc aatgtgtgcc acagcaatat ctattcaccc aaggaaacaa tcccagaaga   1260
ggcacgaagt gatatgcact acagtgtggc tgagggcctc aaacctgctg cccccctcagc   1320
ccgaaatgcc ccctacttcc cttgtgacaa ggccagcaaa aagaagagaa gaccctcctc   1380
ggaagatgag attgccctgc atttcgagcc ccccaatgca cccctgaacc ggaagggtct   1440
ggttagtcca cagagccccc agaaatctga ctgccagccc aactcgccca cagagtcctg   1500
cagcagtaag aatgcctgca tcctccaggc ttctggctcc cctccagcca agagccccac   1560
tgaccccaaa gcctgcaact ggaagaaata caagttcatc gtgctcaaca gcctcaacca   1620
gaatgccaaa ccagagggggc ctgagcaggc tgagctgggc cgccttttccc cacgagccta   1680
cacggcccca cctgcctgcc agccacccat ggagcctgag aaccttgacc tccagtcccc   1740
aaccaagctg agtgccagcg gggaggactc caccatccca caagccagcc ggctcaataa   1800
catcgttaac aggtccatga cgggctctcc ccgcagcagc agcgagagcc actcaccact   1860
ctacatgcac ccccgaagt gcacgtcctg cggctctcag tccccacagc atgcagagat   1920
gtgcctccac accgctggcc ccacgttccc tgaggagatg ggagagaccc agtctgagta   1980
ctcagattct agctgtgaga acggggcctt cttctgcaat gagtgtgact gccgcttctc   2040
tgaggaggcc tcactcaaga ggcacacgct gcagacccac agtgacaaac cctacaagtg   2100
tgaccgctgc caggcctcct ccgctacaa gggcaacctc gccagccaca agaccgtcca   2160
taccggtgag aaaccctatc gttgcaacat ctgtggggcc cagttcaacc ggccagccaa   2220
cctgaaaacc cacactcgaa ttcactctgg agagaagccc tacaaatgcg aaacctgcgg   2280
agccagattt gtacaggtgg cccacctccg tgcccatgtg cttatccaca ctggtgagaa   2340
gccctatccc tgtgaaatct gtggcacccg tttccggcac cttcagactc tgaagagcca   2400
cctgcgaatc cacacaggag agaaaccta ccattgtgag aagtgtaacc tgcatttccg   2460
tcacaaaagc cagctgcgac ttcacttgcg ccagaagcat ggcgccatca ccaacaccaa   2520
ggtgcaatac cgcgtgtcag ccactgacct gcctccggag ctccccaaag cctgctgaag   2580
catggagtgt tgatgctttc gtctccagcc ccttctcaga atctacccaa aggatactgt   2640
aacactttac aatgttcatc ccatgatgta gtgcctcttt catccactag tgcaaatcat   2700
agctgggggt tgggggtggt gggggtcggg gcctggggga ctgggagccg cagcagctcc   2760
```

-continued

| | |
|---|---|
| ccctccccca ctgccataaa acattaagaa aatcatattg cttcttctcc tatgtgtaag | 2820 |
| gtgaaccatg tcagcaaaaa gcaaaatcat tttatatgtc aaagcagggg agtatgcaaa | 2880 |
| agttctgact tgactttagt ctgcaaaatg aggaatgtat atgttttgtg ggaacagatg | 2940 |
| tttcttttgt atgtaaatgt gcattctttt aaaagacaag acttcagtat gttgtcaaag | 3000 |
| agagggcttt aattttttta accaaggtg aaggaatata tggcagagtt gtaaatatat | 3060 |
| aaatatatat atatataaaa taatatata taaacctaaa aaagatatat taaaaatata | 3120 |
| aaactgcgtt aaaggctcga ttttgtatct gcaggcagac acggatctga aatctttat | 3180 |
| tgagaaagag cacttaagag aatattttaa gtattgcatc tgtataagta agaaaatatt | 3240 |
| ttgtctaaaa tgcctcagtg tatttgtatt tttttgcaag tgaaggttta caatttacaa | 3300 |
| agtgtgtatt aaaaaaaaca aaaagaacaa aaaatctgc agaaggaaaa atgtgtaatt | 3360 |
| ttgttctagt tttcagtttg tatatacccg tacaacgtgt cctcacggtg cctttttca | 3420 |
| cggaagtttt caatgatggg cgagcgtgca ccatcccttt ttgaagtgta ggcagacaca | 3480 |
| gggacttgaa gttgttacta actaaactct ctttgggaat gtttgtctca tcccattctg | 3540 |
| cgtcatgctt gtgttataac tactccggag acagggtttg gctgtgtcta aactgcatta | 3600 |
| ccgcgttgta aaatatagct gtacaaatat aagaataaaa tgttgaaaag tcaaactgga | 3660 |
| aa | 3662 |

<210> SEQ ID NO 2
<211> LENGTH: 2379
<212> TYPE: DNA
<213> ORGANISM: Homo sapiens

<400> SEQUENCE: 2

| | |
|---|---|
| gaccccgag ctgtgctgct cgcggccgcc accgcgggc cccggccgtc cctggctccc | 60 |
| ctcctgcctc gagaagggca gggcttctca gaggcttggc gggaaaaaga acggagggag | 120 |
| ggatcgcgct gagtataaaa gccggttttc ggggctttat ctaactcgct gtagtaattc | 180 |
| cagcgagagg cagagggagc gagcgggcgg ccggctaggg tggaagagcc gggcgagcag | 240 |
| agctgcgctg cgggcgtcct gggaaggag atccggagcg aataggggc ttcgcctctg | 300 |
| gcccagccct cccgctgatc ccccagccag cggtccgcaa cccttgccgc atccacgaaa | 360 |
| ctttgcccat agcagcgggc gggcactttg cactggaact acaacaccc gagcaaggac | 420 |
| gcgactctcc cgacgcgggg aggctattct gcccatttgg ggacacttcc ccgccgctgc | 480 |
| caggacccgc ttctctgaaa ggctctcctt gcagctgctt agacgctgga ttttttcgg | 540 |
| gtagtggaaa accagcagcc tcccgcgacg atgcccctca acgttagctt caccaacagg | 600 |
| aactatgacc tcgactacga ctcggtgcag ccgtatttct actgcgacga ggaggagaac | 660 |
| ttctaccagc agcagcagca gagcgagctg cagccccgg cgcccagcga ggatatctgg | 720 |
| aagaaattcg agctgctgcc cacccgccc ctgtccccta gccgccgctc gggctctgc | 780 |
| tcgccctcct acgttgcggt cacacccttc tcccttcggg gagacaacga cggcggtggc | 840 |
| gggagcttct ccacggccga ccagctggag atggtgaccg agctgctggg aggagacatg | 900 |
| gtgaaccaga gtttcatctg cgacccggac gacgagacct tcatcaaaaa catcatcatc | 960 |
| caggactgta tgtggagcgg cttctcggcc gccgcaagc tcgtctcaga gaagctggcc | 1020 |
| tcctaccagg ctgcgcgcaa agacagcggc agcccgaacc cgcccgcgg ccacagcgtc | 1080 |
| tgctccacct ccagcttgta cctgcaggat ctgagcgccg ccgcctcaga gtgcatcgac | 1140 |

```
cctcggtgg tcttcccta ccctctcaac gacagcagct cgcccaagtc ctgcgcctcg      1200
caagactcca gcgccttctc tccgtcctcg gattctctgc tctcctcgac ggagtcctcc      1260
ccgcagggca gccccgagcc cctggtgctc catgaggaga caccgccac caccagcagc      1320 gactctgagg aggaacaaga agatgaggaa gaaatcgatg ttgtttctgt ggaaaagagg      1380
caggctcctg gcaaaaggtc agagtctgga tcaccttctg ctggaggcca cagcaaacct      1440
cctcacagcc cactggtcct caagaggtgc acgtctcca cacatcagca caactacgca      1500
gcgcctccct ccactcggaa ggactatcct gctgccaaga gggtcaagtt ggacagtgtc      1560
agagtcctga cacagatcag caacaaccga aaatgcacca gccccaggtc ctcggacacc      1620
gaggagaatg tcaagaggcg aacacacaac gtcttggagc gccagaggag gaacgagcta      1680
aaacggagct ttttttgccct gcgtgaccag atcccggagt tggaaaacaa tgaaaaggcc      1740
cccaaggtag ttatccttaa aaaagccaca gcatacatcc tgtccgtcca agcagaggag      1800
caaaagctca tttctgaaga ggacttgttg cggaaacgac gagaacagtt gaaacacaaa      1860
cttgaacagc tacggaactc ttgtgcgtaa ggaaaagtaa ggaaaacgat tccttctaac      1920
agaaatgtcc tgagcaatca cctatgaact tgtttcaaat gcatgatcaa atgcaacctc      1980
acaaccttgg ctgagtcttg agactgaaag atttagccat aatgtaaact gcctcaaatt      2040
ggactttggg cataaaagaa cttttttatg cttaccatct tttttttttc tttaacagat      2100
ttgtatttaa gaattgtttt taaaaaattt taagatttac acaatgtttc tctgtaaata      2160
ttgccattaa atgtaaataa ctttaataaa acgtttatag cagttacaca gaatttcaat      2220
cctagtatat agtaccagtt attataggta ctataaaccc taatttttt tatttaagta      2280 cattttgctt tttaaagttg attttttttct attgttttta gaaaaataa aataactggc      2340 aaatatatca ttgagccaaa tcttaaaaaa aaaaaaaaa                            2379

<210> SEQ ID NO 3
<211> LENGTH: 3958
<212> TYPE: DNA
<213> ORGANISM: Homo sapiens

<400> SEQUENCE: 3
tttttttttt tttttgctt aaaaaaaagc catgacggct ctcccacaat tcatcttccc      60
tgcgccatct ttgtattatt tctaatttat tttggatgtc aaaaggcact gatgaagata     120
ttttctctgg agtctccttc tttctaaccc ggctctcccg atgtgaaccg agccgtcgtc     180
cgcccgccgc cgccgccgcc gccgccgccg cccgccccgc agcccaccat gtctcgccgc     240
aagcaaggca accccagca cttaagcaaa cgggaattct cgcccgagcc tcttgaagcc     300
attcttacag atgatgaacc agaccacggc ccgttgggag ctccagaagg ggatcatgac     360
ctcctcacct gtgggcagtg ccagatgaac ttcccattgg gggacattct tattttatc      420 gagcacaaac ggaaacaatg caatggcagc ctctgcttag aaaagctgt ggataagcca     480 ccttcccctt caccaatcga gatgaaaaaa gcatccaatc ccgtggaggt tggcatccag     540
gtcacgccag aggatgacga ttgtttatca acgtcatcta gaggaatttg cccaaacag      600 gaacacatag cagataaact tctgcactgg aggggcctct cctcccctcg ttctgcacat     660
ggagctctaa tccccacgcc tgggatgagt gcagaatatg ccccgcaggg tatttgtaaa     720
gatgagccca gcagctacac atgtacaact tgcaaacagc cattcaccag tgcatggttt     780
ctcttgcaac acgcacagaa cactcatgga ttaagaatct acttagaaag cgaacacgga     840 agtccctga ccccgcgggt tggtatccct tcaggactag gtgcagaatg tccttcccag     900
```

```
ccacctctcc atgggattca tattgcagac aataacccct ttaacctgct aagaatacca    960
ggatcagtat cgagagaggc ttccggcctg cagaagggc gctttccacc cactccccc    1020
ctgtttagtc caccaccgag acatcacttg accccacc gcatagagcg cctgggggcg    1080
gaagagatgg ccctggccac ccatcacccg agtgcctttg acagggtgct gcggttgaat    1140
ccaatggcta tggagcctcc cgccatggat ttctctagga gacttagaga gctggcaggg    1200
aacacgtcta gcccaccgct gtccccaggc cggcccagcc ctatgcaaag gttactgcaa    1260
ccattccagc caggtagcaa gccgcccttc ctggcgacgc ccccctccc tcctctgcaa    1320
tccgcccctc ctccctccca gccccgtc aagtccaagt catgcgagtt ctgcggcaag    1380
acgttcaaat ttcagagcaa cctggtggtg caccggcgca gccacacggg cgagaagccc    1440
tacaagtgca acctgtgcga ccacgcgtgc acccaggcca gcaagctgaa gcgccacatg    1500
aagacgcaca tgcacaaatc gtcccccatg acggtcaagt ccgacgacgg tctctccacc    1560
gccagctccc cggaacccgg caccagcgac ttggtgggca gcgccagcag cgcgctcaag    1620
tccgtggtgg ccaagttcaa gagcgagaac gaccccaacc tgatcccgga aacggggac    1680
gaggaggaag aggaggacga cgaggaagag aagaagagg aggaaggagga ggaggaggag    1740
ctgacggaga gcgagagggt ggactacggc ttcgggctga gcctggaggc ggcgcgccac    1800
cacgagaaca gctcgcgggg cgcggtcgtg ggcgtgggcg acgagagccg cgccctgccc    1860
gacgtcatgc agggcatggt gctcagctcc atgcagcact tcagcgaggc cttccaccag    1920
gtcctgggcg agaagcataa gcgcggccac ctggccgagg ccgagggcca cagggacact    1980
tgcgacgaag actcggtggc cggcgagtcg gaccgcatag acgatggcac tgttaatggc    2040
cgcggctgct cccgggcga gtcggcctcg gggggcctgt ccaaaaagct gctgctgggc    2100
agccccagct cgctgagccc cttctctaag cgcatcaagc tcgagaagga gttcgacctg    2160
cccccggccg cgatgcccaa cacggagaac gtgtactcgc agtggctcgc cggctacgcg    2220
gcctccaggc agctcaaaga tcccttcctt agcttcggag actccagaca atcgcctttt    2280
gcctcctcgt cggagcactc ctcggagaac gggagtttgc gcttctccac accgcccggg    2340
gagctggacg gagggatctc ggggcgcagc ggcacgggaa gtggagggag cacgcccat    2400
attagtggtc cgggcccggg caggcccagc tcaaagagg gcagacgcag cgacacttgt    2460
tcttcacaca cccccattcg gcgtagtacc cagagagctc aagatgtgtg gcagttttcg    2520
gatggaagct cgagagccct aagttctga gaaaatttga agcccccagg ggtggggtgg    2580
acgcgtgccc cccagtcgac gtcagcgtgg tctgtcatcc tgctagtttg tgatgttttc    2640
tgacagtagc ctccaagaag ccgttgtgcg aagacagagt cctgcagagt ccttccagcc    2700
taggcctgca gcgccatttt atttatattt tttaataaaa agtaaaaaca aaaaacaga    2760
cccacattgg aacagtgaat cagtcccata gagagggccc gtggaccatc gctgtcatga    2820
gtgatgccct ggcccttctg aaaccagcca acctaattac ctgtattgtg aaatgcgca    2880
tgagtcccca ccccttgtt tctatacatt ctatgttgtc ttttaaaaag tgtgcttaac    2940
attgacacaa taaatgttgg agctttaggt ggtgtttgct tgttctttaa tttttaatgc    3000
ttataagaca atgaggctgc ttatgatttt gtacttctgt acctgtttcc tacagacacc    3060
catcgggtgg gtaggaggaa cagatttgag aaatgggcag gagatgtagg aggggaacta    3120
ggttaccgct tatcagatgg cataaatttt caaggagaat caaaatgcaa aacttgggaa    3180
taaatcatag caatatcata attaatgtag tagtaatatt gctgtttatt aatgctgaag    3240
```

| | |
|---|---|
| tgtggttttc ctaactgtct gacttataat ttgcatacca ttaaataatg cataatatgg | 3300 |
| cacgccgaat cctgtttttc aaatatatgc ttttggtggc taccatgcag gatttgaatt | 3360 |
| tgtcttttaa tttagcttag gaaagaacat cactgggcga gcggtaaatc ctaaagaagg | 3420 |
| tgataaatgt cagtagtttc ttattaaata ttctaatttt aggttcccaa accttcagga | 3480 |
| aatatatctt aatgcagaca aacaaacata aaacttcttt agtacttaca tcaggaaatt | 3540 |
| tggggcagat tttagagggg ggaaattata ggaggaaaga agttcacatc agaacagaca | 3600 |
| atcacagcaa tgctctattc cttagaaatt agtgccacaa ataagttaca tctacaaaca | 3660 |
| ggtggtaaaa attctttctg gcccagttaa tttgcacaga acttttctca gtttggtatt | 3720 |
| ttttactgct tggagatcca aagagaatt agaaacaaca tagcaaatta aaataggttt | 3780 |
| gtcaataata gagctcagac acctgtgtgc tgtagattca catacaggcc gtgaacctaa | 3840 |
| gtggggaaaa tcctacctat ccaccttctg gctagattac ctagcttagt gaaaagatag | 3900 |
| ccaaataatt ggcatgtgaa ttatttcctg cttattcata ataaataatg actgtcta | 3958 |

<210> SEQ ID NO 4
<211> LENGTH: 6701
<212> TYPE: DNA
<213> ORGANISM: Homo sapiens

<400> SEQUENCE: 4

| | |
|---|---|
| aaagccctca gcctttgtgt ccttctctgc gccggagtgg ctgcagctca cccctcagct | 60 |
| cccccttgggg cccagctggg agccgagata gaagctcctg tcgccgctgg gcttctcgcc | 120 |
| tcccgcagag ggccacacag agaccgggat ggccacctcc atgggcctgc tgctgctgct | 180 |
| gctgctgctc ctgacccagc ccggggcggg gacgggagct gacacggagg cggtggtctg | 240 |
| cgtggggacc gcctgctaca cggcccactc gggcaagctg agcgctgccg aggcccagaa | 300 |
| ccactgcaac cagaacgggg gcaacctggc cactgtgaag agcaaggagg aggcccagca | 360 |
| cgtccagcga gtactggccc agctcctgag gcgggaggca gccctgacgg cgaggatgag | 420 |
| caagttctgg attgggctcc agcgagagaa gggcaagtgc ctggacccta gtctgccgct | 480 |
| gaagggcttc agctgggtgg gcggggggga ggacacgcct tactctaact ggcacaagga | 540 |
| gctccggaac tcgtgcatct ccaagcgctg tgtgtctctg ctgctggacc tgtcccagcc | 600 |
| gctccttccc agccgcctcc ccaagtggtc tgagggcccc tgtgggagcc caggctcccc | 660 |
| cggaagtaac attgagggct tcgtgtgcaa gttcagcttc aaaggcatgt gccggcctct | 720 |
| ggcccctggg ggcccaggtc aggtgaccta caccaccccc ttccagacca ccagttcctc | 780 |
| cttggaggct gtgcccttg cctctgcggc caatgtagcc tgtgggaag gtgacaagga | 840 |
| cgagactcag agtcattatt tcctgtgcaa ggagaaggcc cccgatgtgt tcgactgggg | 900 |
| cagctcgggc cccctctgtg tcagccccaa gtatggctgc aacttcaaca atgggggctg | 960 |
| ccaccaggac tgctttgaag ggggggatgg ctccttcctc tgcggctgcc gaccaggatt | 1020 |
| ccggctgctg gatgacctgg tgacctgtgc ctctcgaaac ccttgcagct ccagcccatg | 1080 |
| tcgtggggg gccacgtgcg tcctgggacc ccatgggaaa aactacacgt gccgctgccc | 1140 |
| ccaagggtac cagctggact cgagtcagct ggactgtgtg gacgtggatg aatgccagga | 1200 |
| ctccccctgt gcccaggagt gtgtcaacac ccctgggggc ttccgctgcg aatgctgggt | 1260 |
| tggctatgag ccggcggtc ctggagaggg ggcctgtcag gatgtggatg agtgtgctct | 1320 |
| gggtcgctcg ccttgcgccc agggctgcac caacacagat ggctcatttc actgctcctg | 1380 |
| tgaggagggc tacgtcctgg ccggggagga cgggactcag tgccaggacg tggatgagtg | 1440 |

```
tgtgggcccg gggggccccc tctgcgacag cttgtgcttc aacacacaag ggtccttcca    1500
ctgtggctgc ctgccaggct gggtgctggc cccaaatggg gtctcttgca ccatggggcc    1560
tgtgtctctg ggaccaccat ctgggccccc cgatgaggag gacaaaggag agaaagaagg    1620
gagcaccgtg ccccgtgctg caacagccag tcccacaagg ggccccgagg gcaccccaa     1680 ggctacaccc accacaagta gaccttcgct gtcatctgac gcccccatca catctgcccc    1740
actcaagatg ctggccccca gtgggtcccc aggcgtctgg agggagccca gcatccatca    1800
cgccacagct gcctctggcc cccaggagcc tgcaggtggg gactcctccg tggccacaca    1860
aaacaacgat ggcactgacg ggcaaaagct gcttttattc tacatcctag gcaccgtggt    1920
ggccatccta ctcctgctgg ccctggctct ggggctactg gtctatcgca agcggagagc    1980
gaagagggag gagaagaagg agaagaagcc ccagaatgcg gcagacagtt actcctgggt    2040
tccagagcga gctgagagca gggccatgga gaaccagtac agtccgacac ctgggacaga    2100
ctgctgaaag tgaggtggcc ctagagacac tagagtcacc agccaccatc ctcagagctt    2160
tgaactcccc attccaaagg ggcacccaca ttttttgaa agactggact ggaatcttag     2220
caaacaattg taagtctcct ccttaaaggc cccttggaac atgcaggtat tttctacggg    2280
tgtttgatgt tcctgaagtg gaagctgtgt gttggcgtgc cacggtgggg atttcgtgac    2340
tctataatga ttgttactcc ccctcccttt tcaaattcca atgtgaccaa ttccggatca    2400
gggtgtgagg aggccggggc taaggggctc ccctgaatat cttctctgct cacttccacc    2460
atctaagagg aaaaggtgag ttgctcatgc tgattaggat tgaaatgatt tgtttctctt    2520
cctaggatga aaactaaatc aattaattat tcaattaggt aagaagatct ggttttttgg    2580
tcaaagggaa catgttcgga ctggaaacat ttctttacat ttgcattcct ccatttcgcc    2640
agcacaagtc ttgctaaatg tgatactgtt gacatcctcc agaatggcca gaagtgcaat    2700
taacctctta ggtggcaagg aggcaggaag tgcctcttta gttcttacat ttctaatagc    2760
cttgggttta tttgcaaagg aagcttgaaa aatatgagaa aagttgcttg aagtgcatta    2820
caggtgtttg tgaagtcaca taatctacgg ggctagggcg agagaggcca gggatttgtt    2880
cacagatact tgaattaatt catccaaatg tactgaggtt accacacact tgactacgga    2940
tgtgatcaac actaacaagg aaacaaattc aaggacaacc tgtctttgag ccagggcagg    3000
cctcagacac cctgcctgtg gccccgcctc cacttcatcc tgcccggaat gccagtgctc    3060
cgagctcaga cagaggaagc cctgcagaaa gttccatcag gctgtttcct aaaggatgtg    3120
tgaacgggag atgatgcact gtgttttgaa agttgtcatt ttaaagcatt ttagcacagt    3180
tcatagtcca cagttgatgc agcatcctga gattttaaat cctgaagtgt gggtggcgca    3240
cacaccaagt agggagctag tcaggcagtt tgcttaagga acttttgttc tctgtctctt    3300
ttccttaaaa ttgggggtaa ggagggaagg aagagggaaa gagatgacta actaaaatca    3360
tttttacagc aaaaactgct caaagccatt taaattatat cctcatttta aaagttacat    3420
ttgcaaatat ttctccctat gataatgtag tcgatagtgt gcactctttc tctctctctc    3480
tctctctcac acacacacac acacacacac acacacacac agagacacgg caccattctg    3540
cctggggcac tggaacacat tcctgggggt caccgatggt cagagtcact agaagttacc    3600
tgagtatctc tgggaggcct catgtctcct gtgggctttt taccaccact gtgcaggaga    3660
acagacagag gaaatgtgtc tccctccaag gccccaaagc ctcagagaaa gggtgtttct    3720
ggttttgcct tagcaatgca tcggtctctg aggtgacact ctggagtggt tgaagggcca    3780
```

```
caaggtgcag ggttaatact cttgccagtt ttgaaatata gatgctatgg ttcagattgt    3840
ttttaataga aaactaaagg ggcaggggaa gtgaaaggaa agatggaggt tttgtgcggc    3900 tcgatgggc atttggaact tcttttaaaa gtcatctcat ggtctccagt tttcagttgg    3960
aactctggtg tttaacactt aagggagaca aaggctgtgt ccatttggca aaacttcctt    4020
ggccacgaga ctctaggtga tgtgtgaagc tgggcagtct gtggtgtgga gagcagccat    4080
ctgtctggcc attcagagga ttctaaagac atggctggat gcgctgctga ccaacatcag    4140
cacttaaata aatgcaaatg caacatttct ccctctgggc cttgaaaatc cttgcccta    4200 tcatttgggg tgaaggagac atttctgtcc ttggcttccc acagcccaa cgcagtctgt    4260 gtatgattcc tgggatccaa cgagccctcc tattttcaca gtgttctgat tgctctcaca    4320
gcccaggccc atcgtctgtt ctctgaatgc agccctgttc tcaacaacag ggaggtcatg    4380 gaaccctct gtggaaccca aaggggaga atgggtgat aaagaatcca gttcctcaaa    4440 accttcctg gcaggctggg tccctctcct gctgggtggt gctttctctt gcacaccact    4500
cccaccacgg ggggagagcc agcaacccaa ccagacagct caggttgtgc atctgatgga    4560
aaccactggg ctcaaaacac gtgctttattc tcctgtttat ttttgctgtt actttgaagc    4620
atggaaattc ttgtttgggg gatcttgggg ctacagtagt gggtaaacaa atgcccaccg    4680
gccaagaggc cattaacaaa tcgtccttgt cctgagggc cccagcttgc tcgggcgtgg    4740
cacagtgggg aatccaaggg tcacagtatg gggagaggtg caccctgcca cctgctaact    4800
tctcgctaga cacagtgttt ctgcccaggt gacctgttca gcagcagaac aagccagggc    4860
catggggacg ggggaagttt tcacttggag atggacacca agacaatgaa gatttgttgt    4920
ccaaataggt caataattct gggagactct tggaaaaaac tgaatatatt caggaccaac    4980
tctctccctc ccctcatccc acatctcaaa gcagacaatg taaagagaga acatctcaca    5040
cacccagctc gccatgccta ctcattcctg aatttcaggt gccatcactg ctctttctttt    5100 cttctttgtc atttgagaaa ggatgcagga ggacaattcc cacagataat ctgaggaatg    5160
cagaaaaacc agggcaggac agttatcgac aatgcattag aacttggtga gcatcctctg    5220
tagagggact ccacccctgc tcaacagctt ggcttccagg caagaccaac cacatctggt    5280
ctctgccttc ggtggcccac acacctaagc gtcatcgtca ttgccatagc atcatgatgc    5340
aacacatcta cgtgtagcac tacgacgtta tgtttgggta atgtgggat gaactgcatg    5400 aggctctgat taaggatgtg gggaagtggg ctgcggtcac tgtcggcctt gcaaggccac    5460
ctggaggcct gtctgttagc cagtggtgga ggagcaaggc ttcaggaagg gccagccaca    5520
tgccatcttc cctgcgatca ggcaaaaaag tggaattaaa aagtcaaacc tttatatgca    5580
tgtgttatgt ccattttgca ggatgaactg agtttaaaag aatttttttt tctcttcaag    5640
ttgctttgtc ttttccatcc tcatcacaag cccttgtttg agtgtcttat ccctgagcaa    5700
tctttcgatg gatggagatg atcattaggt acttttgttt caacctttat tcctgtaaat    5760
atttctgtga aaactaggag aacagagatg agatttgaca aaaaaaaatt gaattaaaaa    5820
taacacagtc ttttaaaac taacatagga aagcctttcc tattatttct cttcttagct    5880
tctccattgt ctaaatcagg aaaacaggaa aacacagctt tctagcagct gcaaaatggt    5940
ttaatgcccc ctacatattt ccatcacctt gaacaatagc tttagcttgg gaatctgaga    6000
tatgatccca gaaaacatct gtctctactt cggctgcaaa acccatggtt taaatctata    6060
tggtttgtgc atttttctcaa ctaaaaatag agatgataat ccgaattctc catatattca    6120
ctaatcaaag acactatttt catactagat tcctgagaca aatactcact gaagggcttg    6180
```

-continued

```
tttaaaaata aattgtgttt tggtctgttc ttgtagataa tgcccttcta ttttaggtag    6240
aagctctgga atcccttat tgtgctgttg ctcttatctg caaggtggca agcagttctt     6300
ttcagcagat tttgcccact attcctctga gctgaagttc tttgcataga tttggcttaa    6360
gcttgaatta gatccctgca aaggcttgct ctgtgatgtc agatgtaatt gtaaatgtca    6420
gtaatcactt catgaatgct aaatgagaat gtaagtattt ttaaatgtgt gtatttcaaa    6480
tttgtttgac taattctgga attacaagat ttctatgcag gatttacctt catcctgtgc    6540
atgtttccca aactgtgagg agggaaggct cagagatcga gcttctcctc tgagttctaa    6600
caaaatggtg ctttgagggt cagcctttag gaaggtgcag cttttgttgtc ctttgagctt   6660 tctgttatgt gcctatccta ataaactctt aaacacattg a                        6701
```

<210> SEQ ID NO 5
<211> LENGTH: 2751
<212> TYPE: DNA
<213> ORGANISM: Homo sapiens

<400> SEQUENCE: 5

```
ccctttactc ctggctgcgg ggcgagccgg gcgtctgctg cagcggccgc ggtggctgag      60
gaggcccgag aggagtcggt ggcagcggcg gcggcgggac cggcagcagc agcagcagca    120
gcagcagcag caaccactag cctcctgccc cgcggcgctg ccgcacgagc ccacgagcc     180 gctcaccccg ccgttctcag cgctgcccga ccccgctggc gcgccctccc gccgccagtc    240
ccggcagcgc cctcagttgt cctccgactc gccctcggcc ttccgcgcca gccgcagcca    300
cagccgcaac gccacccgca gccacagcca cagccacagc cccaggcata gccttcggca    360
cagccccggc tccggctcct gcggcagctc ctctgggcac cgtccctgcg ccgacatcct    420
ggaggttggg atgctcttgt ccaaaatcaa ctcgcttgcc cacctgcgcg ccgcgccctg    480
caacgacctg cacgccacca gctggcgcc cggcaaggag aaggagcccc tggagtcgca    540
gtaccaggtg ggcccgctac tgggcagcgg cggcttcggc tcggtctact caggcatccg    600
cgtctccgac aacttgccgg tggccatcaa acacgtggag aaggaccgga tttccgactg    660
gggagagctg cctaatggca ctcgagtgcc catggaagtg gtcctgctga agaaggtgag    720
ctcgggtttc tccggcgtca ttaggctcct ggactggttc gagaggcccg acagtttcgt    780
cctgatcctg gagaggcccg agccggtgca agatctcttc gacttcatca cggaaagggg    840
agccctgcaa gaggagctgg cccgcagctt cttctggcag gtgctggagg ccgtgcggca    900
ctgccacaac tgcggggtgc tccaccgcga catcaaggac gaaaacatcc ttatcgacct    960
caatcgcggc gagctcaagc tcatcgactt cgggtcgggg cgctgctca aggacaccgt    1020 ctacacggac ttcgatggga cccgagtgta tagccctcca gagtggatcc gctaccatcg   1080
ctaccatggc aggtcggcgg cagtctggtc cctggggatc ctgctgtatg atatggtgtg   1140
tggagatatt cctttcgagc atgacgaaga gatcatcagg ggccaggttt cttcaggca   1200 gagggtctct tcagaatgtc agcatctcat tagatggtgc ttggccctga gaccatcaga   1260
taggccaacc ttcgaagaaa tccagaacca tccatggatg caagatgttc tcctgcccca   1320
ggaaactgct gagatccacc tccacagcct gtcgccgggg cccagcaaat agcagccttt   1380
ctggcaggtc ctccctctc ttgtcagatg cccgagggag gggaagcttc tgtctccagc    1440
ttcccgagta ccagtgacac gtctcgccaa gcaggacagt gcttgataca ggaacaacat   1500
ttacaactca ttccagatcc caggcccctg gaggctgcct cccaacagtg gggaagagtg   1560
```

```
actctccagg ggtcctaggc ctcaactcct cccatagata ctctcttctt ctcataggtg    1620
tccagcattg ctggactctg aaatatcccg ggggtggggg gtgggggtgg gtcagaaccc    1680
tgccatggaa ctgtttcctt catcatgagt tctgctgaat gccgcgatgg gtcaggtagg    1740
ggggaaacag gttgggatgg gataggacta gcaccatttt aagtccctgt cacctcttcc    1800
gactctttct gagtgccttc tgtggggact ccggctgtgc tgggagaaat acttgaactt    1860
gcctctttta cctgctgctt ctccaaaaat ctgcctgggt tttgttccct attttctct    1920 cctgtcctcc ctcaccccct ccttcatatg aaaggtgcca tggaagaggc tacagggcca    1980
aacgctgagc cacctgccct ttttctgcc tcctttagta aaactccgag tgaactggtc     2040 ttccttttttg gttttactt aactgtttca aagccaagac ctcacacaca caaaaaatgc    2100
acaaacaatg caatcaacag aaagctgta atgtgtgta cagttggcat ggtagtatac      2160
aaaaagattg tagtggatct aattttaag aaattttgcc tttaagttat ttacctgtt     2220 tttgtttctt gttttgaaag atgcgcattc taacctggag gtcaatgtta tgtatttatt    2280
tatttattta tttggttccc ttcctattcc aagcttccat agctgctgcc ctagttttct    2340
ttcctccttt cctcctctga cttggggacc ttttggggga gggctgcgac gcttgctctg    2400
tttgtggggt gacgggactc aggcgggaca gtgctgcagc tccctggctt ctgtggggcc    2460
cctcacctac ttaccaggt gggtcccggc tctgtgggtg atgggagggg gcattgctga    2520
ctgtgtatat aggataatta tgaaaagcag ttctggatgg tgtgccttcc agatcctctc    2580
tggggctgtg ttttgagcag caggtagcct gctggtttta tctgagtgaa atactgtaca    2640
ggggaataaa agagatctta ttttttttt tatacttggc gttttttgaa taaaaaccttt    2700 ttgtcttaaa aaaaaaaaaa aaaaaaaaaa aaaaaaaaaa aaaaaaaaaa a             2751

<210> SEQ ID NO 6
<211> LENGTH: 3650
<212> TYPE: DNA
<213> ORGANISM: Homo sapiens

<400> SEQUENCE: 6
agcactgctg ctctcccggc ttcccgctct actccggccg ggccgggtcc gccacgtctg      60
gcgcgctgag caggcccggc cgcgcagcgc ctaccctttc ctcgctccgg gccggcagtg     120
tggggcggcg cgctggggc gcggcgtgtc tggggacatc ttgtgatgtt ggcgagaaca     180
ggacatgatc tcacatggcg agaagctctt tagttcctta atcatttcac ggtgccttcg     240 gacgctttt ttccacctaa aacgtttagt ttcagctcag tgatcagcta ccccagctcg      300 gcggggagc ggaaggcttg aattattccg acctgtgagc ggcccctggc accaaaaaaa      360 aaaaaaaaa aaaaaaaaa agaaaaaaaa aggcacaaaa aagtggaaac ttttccctgt      420
ccattccatc aagtcctgaa aaatcaaaat ggatttagag aaaaattatc cgactcctcg     480
gaccagcagg acaggacatg gaggagtgaa tcagcttggg ggggttttg tgaatggacg     540 gccactcccg gatgtagtcc gccagaggat agtggaactt gctcatcaag gtgtcaggcc     600
ctgcgacatc tccaggcagc ttcgggtcag ccatggttgt gtcagcaaaa ttcttggcag     660
gtattatgag acaggaagca tcaagcctgg ggtaattgga ggatccaaac caaaggtcgc     720
cacacccaaa gtggtggaaa aaatcgctga atataaacgc caaaatccca ccatgtttgc     780
ctgggagatc agggaccggc tgctggcaga gcgggtgtgt gacaatgaca ccgtgcctag     840
cgtcagttcc atcaacagga tcatccggac aaaagtacag cagccaccca accaaccagt     900
cccagcttcc agtcacagca tagtgtccac tggctccgtg acgcaggtgt cctcggtgag     960
```

```
cacggattcg gccggctcgt cgtactccat cagcggcatc ctgggcatca cgtccccag    1020 cgccgacacc aacaagcgca agagagacga aggtattcag gagtctccgg tgccgaacgg    1080
ccactcgctt ccgggcagag acttcctccg gaagcagatg cggggagact tgttcacaca    1140
gcagcagctg gaggtgctgg accgcgtgtt tgagaggcag cactactcag acatcttcac    1200
caccacagag cccatcaagc ccgagcagac acagagtat tcagccatgg cctcgctggc    1260
tggtgggctg gacgacatga aggccaatct ggccagcccc accctgctg acatcgggag    1320 cagtgtgcca ggcccgcagt cctaccccat tgtgacaggc cgtgacttgg cgagcacgac    1380
cctccccggg taccctccac acgtcccccc cgctggacag ggcagctact cagcaccgac    1440
gctgacaggg atggtgcctg ggagtgagtt ttccgggagt ccctacagcc accctcagta    1500
ttcctcgtac aacgactcct ggaggttccc caacccgggg ctgcttggct ccccctacta    1560
ttatagcgct gccgcccgag gagccgcccc acctgcagcc gccactgcct atgaccgtca    1620
ctgacccttg gagccaggcg ggcaccaaac actgatggca cctattgagg gtgacagcca    1680
cccagccctc ctgaagatag ccagagagcc catgagaccg tcccccagca tcccccactt    1740
gcctgaagct cccctcttcc tctcttcctc cagggactct ggggccctt ggtgggccg    1800 ttggacttct ggatgcttgt ctatttctaa aagccaatct atgagcttct cccgatggcc    1860
actgggtctc tgcaaaccaa tagactgtcc tgcaaataac cgcagcccca gcccagcctg    1920
cctgtcctcc agctgtctga ctatccatcc atcataacca ccccagcctg ggaaggagag    1980
cttgcttttg ttgcttcagc agcacccatg taaatacctt cttgcttttc tgtgggcctg    2040
aaggtccgac tgagaagact gctccaccca tgatgcatct cgcactcttg gtgcatcacc    2100
ggacatctta gacctatggc agagcatcct ctctgccctg ggtgaccctg gcaggtgcgc    2160
tcagagctgt cctcaagatg gaggatgctg cccttgggcc ccagcctcct gctcatccct    2220
ccttctttag tatctttacg aggagtctca ctgggctggt tgtgctgcag gctcccctg    2280 aggcccctct ccaagaggag cacactttgg ggagatgtcc tggtttcctg cctccattc    2340 tctgggaccg atgcagtatc agcagctctt ttcagatca aagaactcaa agaaaactgt    2400
ctgggagatt cctcagctac ttttccgaag cagaatgtca tccgaggtat tgattacatt    2460
gtggactttg aatgtgaggg ctggatggga cgcaggagat catctgatcc cagccaagga    2520
ggggcctgag gctctcccta ctccctcagc ccctggaacg tgttttctg aggcatgccc    2580 aggttcaggt cacttcggac acctgccatg gacacttcac ccaccctcca ggacccagc    2640 aagtggattc tgggcaagcc tgttccggtg atgtagacaa taattaacac agaggacttt    2700
cccccacacc cagatcacaa acagcctaca gccagaactt ctgagcatcc tctcggggca    2760 gacctccc gtcctcgtgg agcttagcag gcagctgggc atggaggtgc tgggctggg    2820 gcagatgcct aatttcgcac aatgcatgcc cacctgttga tctaaggggc cgcgatggtc    2880
agggccacgg ccaagggcca cgggaacttg agagggagc ttgagaact cactgtgggc    2940 tagggtggtc agaggaagcc agcagggaag atctggggga cagaggaagg cctcctgagg    3000 gagggggcagg agagcagtga ggagctgctg tgtgacctgg gagtgatttt gacatggggg    3060
tgccaggtgc catcatctct ttacctgggg ccttaattcc ttgcatagtc tctcttgtca    3120
agtcagaaca gccaggtaga gcccttgtcc aaacctgggc tgaatgacag tgatgagagg    3180
gggcttggcc ttcttaggtg acaatgtccc ccatatctgt atgtcaccag gatggcgag    3240 agccagggca gagagagact ggacttggga tcagcaggcc aggcaggtct tgtcctggtc    3300
```

| | |
|---|---|
| ctggccacat gtctttgctg tgggacctca gacaaaaccc tgcacctctt tgagccttgg | 3360 |
| ctgccttggt gcagcagggt catctgtagg gccaccccac agctctttcc ttcccctcct | 3420 |
| ctctccaggg agccggggct gtgagaggat catctggggc aggccctcca cttccaagca | 3480 |
| agcagatggg ggtgggcacc tgaggcccaa taatatttgg accaagtggg aaacaagaac | 3540 |
| actcggaggg gcgggaatca aagagcctg gaaaagacc tagcccaact tcccttgtgg | 3600 |
| gaaactgagg cccagcttgg ggaaggccag gaccatgcag ggagaaaaag | 3650 |

<210> SEQ ID NO 7
<211> LENGTH: 2269
<212> TYPE: DNA
<213> ORGANISM: Homo sapiens

<400> SEQUENCE: 7

| | |
|---|---|
| acagcgcgtg cgccgccgca agcatggctg gtgatgattg gacgactggt aacagggggc | 60 |
| ggagggctcc gaagtctggt tttgggcggg aattgaaacc gccgctgaag ccaacaagaa | 120 |
| tttgagaact gtaaatacca agccttgaaa gggaccatgg tgcggcctgt gagacataag | 180 |
| aaaccagtca attactcaca gtttgaccac tctgacagtg atgatgattt tgtttctgca | 240 |
| actgtacctt taaacaagaa atccagaaca gcaccaaagg agttaaaaca agataaacca | 300 |
| aaacctaact tgaacaatct ccggaaagaa gaaatcccag tacaagagaa aacccctaaa | 360 |
| aaaagactcc ctgaaggtac ttttagtatt ccagctagtg cagtgccttg tacaaagatg | 420 |
| gctttagatg acaagctcta ccagagagac ttagaagttg cactagcttt atcagtgaag | 480 |
| gaacttccaa cagtcaccac taatgtgcag aactctcaag ataaaagcat tgaaaaacat | 540 |
| ggcagtagta aaatagaaac aatgaataag tctcctcata tctctaattg cagtgtagcc | 600 |
| agtgattatt tagatttgga taagattact gtggaagatg atgttggtgg tgttcaaggg | 660 |
| aaaagaaaag cagcatctaa agctgcagca cagcagagga gattcttct ggaaggcagt | 720 |
| gatggtgata gtgctaatga cactgaacca gactttgcac ctggtgaaga ttctgaggat | 780 |
| gattctgatt tttgtgagag tgaggataat gacgaagact tctctatgag aaaaagtaaa | 840 |
| gttaaagaaa ttaaaagaa agaagtgaag gtaaaatccc cagtagaaaa gaaagagaag | 900 |
| aaatctaaat ccaaatgtaa tgctttggtg acttcggtgg actctgctcc agctgccgtc | 960 |
| aaatcagaat ctcagtcctt gccaaaaag gtttctctgt cttcagatac cactaggaaa | 1020 |
| ccattagaaa tacgcagtcc ttcagctgaa agcaagaaac ctaaatgggt cccaccagcg | 1080 |
| gcatctggag gtagcagaag tagcagcagc ccactggtgg tagtgtctgt gaagtctccc | 1140 |
| aatcagagtc tccgccttgg cttgtccaga ttagcacgag ttaaacctt gcatccaaat | 1200 |
| gccactagca cctgagtgtg gtacaggagg aatgttggt tgggagaatc acagctttac | 1260 |
| aagggtgttt atatttgatt tgtgtttata tttgaggcag gtattgtaat ataaaggaat | 1320 |
| ccattaccat gtcctataaa tgacctctag ccatttatg attatgttct ctgtaaaact | 1380 |
| cttcaagact tcaatgagaa gtttgtttat aagaattatc ttctcatacc tttccttgtg | 1440 |
| aagagcgtat tctgtttttc tatcagttcg acatgaagtc cacatcacat gctgttcttt | 1500 |
| tctagttaca tgatgtgcct ttctagcttt gtctagttta tagcacctta actttaactg | 1560 |
| ttcagttta tctggcagag gaaaacattc ttatttcttt cagaagacat ttctgaaatc | 1620 |
| ttataagcta cttaagctac gttgtcagtt ttatcgcaaa gatgttttgt attttagcca | 1680 |
| aatcttttta tagtacaaac ttagaattat tttacacact aaaatggttg cagttttatg | 1740 |
| gcatatgtct ccgatttaga tggttattct ctagaaaata gtatttaaag acattttatg | 1800 |

```
aaatcttcat tgtcaaaacc tttaataaaa gtggaaatat tttgaaatgc ccttttcctt    1860
gataccactc atccacgtgt tcctgattgt ccacatttca tgataaaatg agagctccgc    1920
agagaatgtt agcctttctg ttgtaaatgt aatcttcaag tagtcacttt ttgttaagtt    1980 cttagaaag tagttgtcaa gtacttagtc atccctatta tgatatgaga tagtacagct    2040
tttcaggaag cttagatctg aatttacttt gaaaacaat tgtaatgaat attttatatt    2100
tacattgaga atttcaacta gcttctgatc aattttaat aaaaattttt caaatcatgt    2160
tagctgttaa aaatgtata ataactcagt ttttcttggt ttatggaaat atctatatta    2220
atgtgaaaat aattaattta gaattgtgat taaagtgagc atttgtcta               2269
```

<210> SEQ ID NO 8
<211> LENGTH: 1888
<212> TYPE: DNA
<213> ORGANISM: Homo sapiens

<400> SEQUENCE: 8

```
gttgctttgc ggcgttttcc gcggggaaac tgtgtaaagg gtggggaaac ttgaaagttg      60
gatgctgcag acccggcatg ggtagcaaga aactaaaacg agtgggttta tcacaagagc     120
tgtgtgaccg tctgagtaga catcagatcc ttacctgtca ggactttta tgtctttccc     180 cactggagct tatgaaggtg actggtctga gttatcgagg tgtccatgaa cttctatgta     240
tggtcagcag ggcctgtgcc ccaaagatgc aaacggctta tgggataaaa gcacaaaggt     300
ctgctgattt ctcaccagca ttcttatcta ctacccttc tgctttggac gaagccctgc      360
atggtggtgt ggcttgtgga tccctcacag agattacagg tccaccaggt tgtggaaaaa     420
ctcagttttg tataatgatg agcattttgg ctacattacc caccaacatg ggaggattag     480
aaggagctgt ggtgtacatt gacacagagt ctgcatttag tgctgaaaga ctggttgaaa     540
tagcagaatc ccgtttttcc agatatttta acactgaaga aaagttactt ttgacaagta     600
gtaaagttca tctttatcgg gaactcacct gtgatgaagt tctacaaagg attgaatctt     660
tggaagaaga aattatctca aaaggaatta aacttgtgat tcttgactct gttgcttctg     720
tggtcagaaa ggagtttgat gcacaacttc aaggcaatct caaagaaaga aacaagttct     780 tgcaagaga ggcatcctcc ttgaagtatt tggctgagga gttttcaatc ccagttatct      840
tgacgaatca gattacaacc catctgagtg gagccctggc ttctcaggca gacctggtgt     900
ctccagctga tgatttgtcc ctgtctgaag gcacttctgg atccagctgt gtgatagccg     960
cactaggaaa tacctggagt cacagtgtga atacccggct gatcctccag taccttgatt    1020
cagagagaag acagattctt attgccaagt ccccctctggc tcccttcacc tcatttgtct    1080
acaccatcaa ggaggaaggc ctggttcttc aagcctatgg aaattcctag agacagataa    1140
atgtgcaaac ctgttcatct tgccaagaaa aatccgcttt tctgccacag aaacaaaata    1200
ttgggaaaga gtcttgtggt gaaacaccca tcgttctctg ctaaaacatt tggttgctac    1260
tgtgtagact cagcttaagt catggaattc tagaggatgt atctcacaag taggatcaag    1320
aacaagccca acagtaatct gcatcataag ctgatttgat accatggcac tgacaatggg    1380
cactgatttg ataccatggc actgacaatg ggcacacagg gaacaggaaa tgggaatgag    1440
agcaagggtt gggttgtgtt cgtggaacac ataggttttt ttttttttaac tttctctttc    1500 taaaatattt catttgatg gaggtgaaat ttatataaga tgaaattaac catttttaaag    1560 taaacaattc cgtggcaact agatatcatg atgtgcaacc agcatctctg tctagttcca    1620
```

| | |
|---|---|
| aatattttca tcacccccaaa agcaagaccc ataaccatta tgcaagtgtt cctatttccc | 1680 |
| cctcctccca gctcctggaa acccaccaat ctactttgtt gctatggctt tacctattct | 1740 |
| ggatatttca tataaatgga atcatatagt gtctgtcttc tttcactagt atgttttcaa | 1800 |
| gtctcctcca tggtgtagcg tgcatcagta cttcattctt tttatggctg aataatattg | 1860 |
| cattgtcagg aaaaaaaaaa aaaaaaaa | 1888 |

<210> SEQ ID NO 9
<211> LENGTH: 2418
<212> TYPE: DNA
<213> ORGANISM: Homo sapiens

<400> SEQUENCE: 9

| | |
|---|---|
| ctggaacccg gaagcggcag cgcggcgcga cccggcgggc gggctctggg cgcgggaatc | 60 |
| ccggcggatc ccgggcgggc ggatgacccc cagccctacc cttggtgccg cctcctcctc | 120 |
| tctcctttct cctccggcag ccagcgcgcc tgtgtcctct ctaggaaggg gtaggggagg | 180 |
| ggcgtctgga gaggaccccc cgcgaatgcc cacgtgacgt gcagtccccc tggggctgtt | 240 |
| ccggcctgcg gggaacatgg gcgtgctcag ggtcggactg tgccctggcc ttaccgagga | 300 |
| gatgatccag cttctcagga gccacaggat caagacagtg gtggacctgg tttctgcaga | 360 |
| cctggaagag gtagctcaga aatgtggctt gtcttacaag gccctggttg ccctgaggcg | 420 |
| ggtgctgctg gctcagttct cggctttccc cgtgaatggc gctgatctct acgaggaact | 480 |
| gaagacctcc actgccatcc tgtccactgg cattggcagt cttgataaac tgcttgatgc | 540 |
| tggtctctat actggagaag tgactgaaat tgtaggaggc ccaggtagcg gcaaaactca | 600 |
| ggtatgtctc tgtatggcag caaatgtggc ccatggcctg cagcaaaacg tcctatatgt | 660 |
| agattccaat ggagggctga cagcttcccg cctcctccag ctgcttcagg ctaaaaccca | 720 |
| ggatgaggag gaacaggcag aagctctccg gaggatccag gtggtgcatg catttgacat | 780 |
| cttccagatg ctggatgtgc tgcaggagct ccgaggcact gtggcccagc aggtgactgg | 840 |
| ttcttcagga actgtgaagg tggtggttgt ggactcggtc actgcggtgg tttccccact | 900 |
| tctgggaggt cagcagaggg aaggcttggc cttgatgatg cagctggccc gagagctgaa | 960 |
| gaccctggcc cggaccttg gcatggcagt ggtggtgacc aaccacataa ctcgagacag | 1020 |
| ggacagcggg aggctcaaac ctgccctcgg acgtcctgg agctttgtgc ccagcactcg | 1080 |
| gattctcctg gacaccatcg agggagcagg agcatcaggc ggccggcgca tggcgtgtct | 1140 |
| ggccaaatct tcccgacagc caacaggttt ccaggagatg gtagacattg ggaccctgggg | 1200 |
| gacctcagag cagagtgcca cattacaggg tgatcagaca tgacctgtgc tgttgtttgg | 1260 |
| gaaacaggga agcattgggg acccctccca acttttcttc ccagtaacgc ctgctgttta | 1320 |
| ctgccacctg gcactggtga ctacagacgt tctcaggctg gccagaagag acatcttggg | 1380 |
| ttccttggcc tcactctctg taagcatata aaccacaggc gaaagaggat gctgcattgc | 1440 |
| gaggacccag aaattcatac tggtgccacg tttccttccc ttatttctaa cgtgtatgtt | 1500 |
| tctggtggaa accaagttca ccctggctgg gagcatctct gatgaggcat gctggcgact | 1560 |
| ggatggataa tcctgtgcat caccattgtg tcctgtgctc cctcctagcg cagtggccaa | 1620 |
| gccgggaaag cctctaactt gcctttgctg ctgctgcctt ttttttcttt tgtctctgcc | 1680 |
| tttccatttg ttagatgggg gcccactctt ccttagctct gtctctgagt tactgggtgg | 1740 |
| aaataagctt ataaatgaaa tactcttctt catctctgtt ttgctcttaa aaatataaaa | 1800 |
| aggcaattcc ccgagcccta gagccacctg atttcccctt agaaggctgt ttttcagttt | 1860 |

| | |
|---|---:|
| cccccagtga ggcccaaaga acagtttatt cctcctttcc tcttgctgat ttggtttcag | 1920 |
| acctgcctgc atcaccatga ctaggtgaga acgtgtgggc tcgctgcagt tccagggata | 1980 |
| taatttaaca gaaagggagg gtatgacctg ctcctggtga atccagccac tcatttaata | 2040 |
| tgcatggtgc cctgtgggc ccctccacag tacagcataa ccagaggtgc tgaaccatgg | 2100 |
| ccttgcccat aaacagacag aggagaattt gcacagtaaa tagagccagc tgggaaaatt | 2160 |
| gatgctgacg taaataatac atggcaaatc tagtcctta tgcagaaatt cattgctggt | 2220 |
| ggctccaaga tgcaatataa ttacacctct cttcctgcca gctgtaccac agctagtgcc | 2280 |
| ctagtgtatg aaataatccc tctgtctttc accagcactg tggccatccg tctgagagcc | 2340 |
| atgaccctgg ctgggagggg acgaagacac cagggaatgg aaaataaaag gaaaagtaca | 2400 |
| gaaaaaaaaa aaaaaaaa | 2418 |

```
<210> SEQ ID NO 10
<211> LENGTH: 3094
<212> TYPE: DNA
<213> ORGANISM: Homo sapiens

<400> SEQUENCE: 10
```

| | |
|---|---:|
| tttgactggc cgtagagtct gcgcagttgg tgaatggcgt tggtggcggg aaagttgagt | 60 |
| ctctcctgcg ccgagccttc ggggcgatgt gtagtgcctt ccatagggct gagtctggga | 120 |
| ccgagctcct tgcccgactt gaaggtagaa gttccttgaa agaaatagaa ccaaatctgt | 180 |
| ttgctgatga agattcacct gtgcatggtg atattcttga atttcatggc ccagaaggaa | 240 |
| caggaaaaac agaaatgctt tatcacctaa cagcacgatg tatacttccc aaatcagaag | 300 |
| gtggcctgga agtagaagtc ttatttattg atacagatta ccactttgat atgctccggc | 360 |
| tagttacaat tcttgagcac agactatccc aaagctctga agaaataatc aaatactgcc | 420 |
| tgggaagatt ttttttggtg tactgcagta gtagcaccca cttacttctt acactttact | 480 |
| cactagaaag tatgttttgt agtcacccat ctctctgcct tttgattttg gatagcctgt | 540 |
| cagcttttta ctggatagac cgcgtcaatg gaggagaaag tgtgaactta caggagtcta | 600 |
| ctctgaggaa atgttctcag tgcttagaga agcttgtaaa tgactatcgc ctggttcttt | 660 |
| ttgcaacgac acaaactata atgcagaaag cctcgagctc atcagaagaa ccttctcatg | 720 |
| cctctcgacg actgtgtgat gtggacatag actacagacc ttatctctgt aaggcatggc | 780 |
| agcaactggt gaagcacagg atgttttttct ccaaacaaga tgattctcaa agcagcaacc | 840 |
| aattttcatt agtttcacgt tgtttaaaaa gtaacagttt aaaaaaacat ttttttatta | 900 |
| ttggagaaag tggggttgaa ttttgttgat atacatcata aaatagtctt ttgcagggta | 960 |
| ctacgcaagc cttaaaattt tcttaagac agagtcttgc tctgtctccc aggctggagt | 1020 |
| gcagtggcac aatcatggct cactgcagcc ttgaactcct ggcctcaagg gatcctccta | 1080 |
| tgtgtgcctc ctagagtgca gggattacag gcgtgagcca ctgctcgtgg ccaaaagttt | 1140 |
| tcttttttttt ttttttctt tttgaaacag tcttactctg tctcccaggc tgctggagtg | 1200 |
| cagtggcaca atctcggccc gctgcagcct ctgcctcttg ggttcaagtg attcttccac | 1260 |
| ctcagcctcc caggtagctg ggattacagg caccccaccac cacgcctggc taattttttgt | 1320 |
| atttttaata gagacggggt ttcaccatgt tggccaggct ggtctcgaac tcctgacctc | 1380 |
| aagtgatcca cccacctcgg cctcccaaag tgctaggatt acaggcccgt gcccagccct | 1440 |
| aaagttttaa actctagggg aattaacagt atttctttac agaatggatt tgttaaacta | 1500 |

```
gcacagtaaa agtaaagact attctgtttc taggctgttg aatcaaagtg attttagcaa    1560
ttaaactttg tattaattta ccaccaatat ttcttcacaa aggaactttt aaaagattat    1620
ctcagaaagt aaatctgaga ggtaagaagt aataatgagt aaatggtaag tacttgagta    1680
aatctaaaga aatattgata gtaaggcaat cctaagcaaa aagaacaaag ctggaggcat    1740
cacgctaccc agcttcaaac tatactacaa ggctacagta accaaaacag catagtactg    1800
gcacaaaaac acacgtagac tgatggaaca gaatagagaa tttagaaatg agaccacaca    1860
cctataattt ttttgatctt cgatgaacct gacaaaaaca agcaatgggc aatggattct    1920
ctattcaata aatcgtgctg ggataactgg ccagccatat ggaaaagatt gaaaatggac    1980
gccttcctta tgccatatac aaaaattaac tcaagatgga ttaaagactt aatgtaaaac    2040
ccaaaacagt aaaaatcctg gaagacaacc caggcagtac cattcaggac ataggcacag    2100
gcaaagattt catgacgaag acgccaaaaa caattgcaac agaagcaaaa attcacaaat    2160
gggatctaat taaactaaag agctgcacag caaagaaaac tatcaagaga gtaaacagac    2220
agcttacaga atgggagaaa attgttgcaa actatgcatc tgagaaaggt ctgaaatcca    2280
gcatctatac gtaatttaaa caaatttaga agaaaaaacc accccattaa aaagtgggca    2340
aaggacatga acagacactt ttcaaaagaa gacatctgtg ccaacaatc ctatggaaaa    2400 aagcccagca tcactgatca ttagagaaat gcaaatcgaa acaacaacga gataccatct    2460
cacaccagtc aaatggcta ttataaaaat gtcagaaaat aacagatgct ggtgaggttg    2520
tggagaaaaa gatatgctta tacactgttg gtggaaatgt aaattaaatt agttcagcca    2580
ttgtggaaga cagtgtgggg ataaagacag agataccatt caacccagca atctcattac    2640
tgggtatata cccaaaggaa tagaaatcat tgttataaag acacatgcac gcgtatgttc    2700
gttgcagcac tgcccatcag tgacagactg gattaaaaaa atgtggtaca tacacaccag    2760
ggaatactat acagccataa aaaggaacaa gactgactgg gcgtggtggc tcatgcctgt    2820
gatcctagca ctttgcgagg ccgaggtggg tggattgccc gcgctcagga ggtcaagacc    2880
agcctgggca acacggtgaa accccatctc tattaaaata caaaaaatta gctgggcatg    2940
gtggtgcgtg cctgtagtgc cagctactca ggaggccgag gcaggagaat tgctggaacc    3000
caggaggtgg aggttgcagt gagctgagat cgcgccattg cactcccgcc tgggcgactc    3060
catctctaaa aaaaaaaaaa aaaaaaaaaa aaaa                                3094
```

<210> SEQ ID NO 11
<211> LENGTH: 2657
<212> TYPE: DNA
<213> ORGANISM: Homo sapiens

<400> SEQUENCE: 11

```
ctattggagg agaaggccga gaggagcagg acggcgggaa gaggagtgcg gaacccgcgg     60
gagactttga gccaggcctg ttaaaccaag ttctcagcag gatgtgcaca gagggcccag    120
gaggagcctc aggagccgga ctgccgttgg ccaaccgagt ccccagggag acacttaagg    180
gaaattaaac tgcagagtgc aagagatgcc tcagtcaagt cagccaaaaa cacgcgggtc    240
atccccaagc cccagagagt gacagagccc cgatgacacg gacacctcgg ctgctgtcac    300
ttccctggtt cgggcctccc acaggctttg aattgaaggc gagtgcctca gaatttgcat    360
ccattgttct gtctttcctg ggaagttatt catcctggtg gccagcccac cgacaaaatg    420
gatttggatc tactggacct gaatcccaga attattgctg caattaagaa agccaaactg    480
aaatcggtaa aggaggtttt acactttttct ggaccagact tgaagagact gaccaacctc    540
```

```
tccagcccg aggtctggca cttgctgaga acggcctcct tacacttgcg gggaagcagc    600
atccttacag cactgcagct gcaccagcag aaggagcggt tccccacgca gcaccagcgc    660
ctgagcctgg gctgcccggt gctggacgcg ctgctccgcg gtggcctgcc cctggacggc    720
atcactgagc tggccggacg cagctcggca gggaagaccc agctggcgct gcagctctgc    780
ctggctgtgc agttcccgcg gcagcacgga ggcctggagg ctggagccgt ctacatctgc    840
acggaagacg ccttcccgca caagcgcctg cagcagctca tggcccagca gccgcggctg    900
cgcactgacg ttccaggaga gctgcttcag aagctccgat ttggcagcca gatcttcatc    960
gagcacgtgg ccgatgtgga caccttgttg gagtgtgtga ataagaaggt ccccgtactg   1020
ctgtctcggg gcatggctcg cctggtggtc atcgactcgg tggcagcccc attccgctgt   1080
gaatttgaca gccaggcctc cgcccccagg gccaggcatc tgcagtccct gggggccacg   1140
ctgcgtgagc tgagcagtgc cttccagagc cctgtgctgt gcatcaacca ggtgacagag   1200
gccatggagg agcagggcgc agcacacggg ccgctggggt tctgggacga acgtgtttcc   1260
ccagcccttg gcataacctg ggctaaccag ctcctggtga gactgctggc tgaccggctc   1320
cgcgaggaag aggctgccct cggctgccca gcccggaccc tgcgggtgct ctctgccccc   1380
cacctgcccc cctcctcctg ttcctacacg atcagtgccg aaggggtgcg agggacacct   1440
gggacccagt cccactgaca cggtggcggc tgcacaacag ccctgcctga gaagccccga   1500
cacacggggc tcgggccttt aaaacgcgtc tgcctgggcc gtggcacagc tgggagcctg   1560
gttcagacac agctcttcca gggcagcggc tccactttct catccgaaga tggtggccac   1620
agactgaccc ccatctgagc tgggggatg ttctgcctct ccctgggtct ggggacaggc   1680
ccgcttgctg ggtacctggt ccccactgct gagctggccc ttggggagag gtgattctca   1740
gggctggagc ctggggtgtc ctacagtgac tccctgggag ccgcctgctt cttctctcca   1800 catgaagcc caactggggt tgcgtctgag gcctgccccc tgggctgggg cctcagaccc   1860
cctcagcctt gggaccgtgc ccacgagggt ctcccctcct gcacacaggg cagtccttac   1920
tcccccacca ctcaggccac agtggggctg caggcaggcg gctcctcctc acccacctct   1980
gggtccttgg ctcccgggg ccccacctcg gcacacactg tgcccacaa aacttcagtg   2040 tggtacaagg tggagaaagc atatcccacc aacctccagt gtcagggtcc aggagagcct   2100
gggggtgggg ggactgcctt gtctctagta gtgtggcctg tgccagcacc acagccggtc   2160
agaggagcgc aggcagcgca gggctggcac gtgacaggct cgtcagccac ctgggaacac   2220
agttctgggc aaagaggatc cgaggttgag aggaaggagg gtcccggtgt atcctggccc   2280
tgggggtctg ggcgtccagc tcagccctgg cctggctggg tggtattctg gtagggatat   2340
ggcaggactc ctggcagggc cacctgcagg accctgtcct gcagtccac actgtgcaga   2400 cccagtccca cactgtggcc aggccttaca tctggctgga aagcagagcc tcctgggaac   2460
acatctggct gcacaggctg aaatatccac ccagcaggca gagtggcgtg gcctccccat   2520
gggcacagtg gtgacccctt gattcccac cgtacaaccc cctccacccc ccactcagtg   2580
cctccacatg ctgcctggca cagaccaggc ctttgacaaa taaatgttca atggatgcaa   2640
aaaaaaaaaa aaaaaaa                                                  2657
```

<210> SEQ ID NO 12
<211> LENGTH: 11202
<212> TYPE: DNA
<213> ORGANISM: Homo sapiens -continued

<400> SEQUENCE: 12

```
aattctcctg cctgagcctc ggcccaacaa aatggcggcg gcagcggtgt cgctttgttt      60
ccgcggctcc tgcggcggtg gcagtggtag cggcctttga gctgtgggga ggttccagca     120
gcagctacag tgacgactaa gactccagtg catttctatc gtaaccgggc gcggggagc      180
gcagatcggc gcccagcaat cacagaagcc gacaaggcgt tcaagcgaaa acatgaccgc     240
tgagcccatg agtgaaagca agttgaatac attggtgcag aagcttcatg acttccttgc     300
acactcatca gaagaatctg aagaaacaag ttctcctcca cgacttgcaa tgaatcaaaa     360
cacagataaa atcagtggtt ctggaagtaa ctctgtatat gatggaaaaca gcaaggaaga     420
gggaactagc tcttcagaaa atccaagtc ttcaggatcg tcacgatcaa agaggaaacc     480
ttcaattgta acaaagtatg tagaatcaga tgatgaaaaa cctttggatg atgaaactgt     540
aaatgaagat gcgtctaatg aaaattcaga aaatgatatt actatgcaga gcttgccaaa     600
aggtacagtg attgtacagc cagagccagt gctgaatgaa gacaaagatg atttttaaagg     660
gcctgaattt agaagcagaa gtaaaatgaa aactgaaaat ctcaaaaaac gcggagaaga     720
tgggcttcat gggattgtga gctgcactgc ttgtggacaa caggtcaatc attttcaaaa     780
agattccatt tatagacacc cttcattgca agttcttatt tgtaagaatt gctttaagta     840
ttacatgagt gatgatatta gccgtgactc agatggaatg gatgaacaat gtaggtggtg     900
tgcggaaggt ggaaacttga tttgttgtga cttttgccat aatgctttct gcaagaaatg     960
cattctacgc aaccttggtc gaaggagtt gtccacaata atggatgaaa caaccaatg    1020
gtattgctac atttgtcacc cagagccttt gttggacttg gtcactgcat gtaacagcgt    1080
atttgagaat ttagaacagt tgttgcagca aaataagaag aagataaaag ttgacagtga    1140
aaagagtaat aaagtatatg aacatacatc cagattttct ccaaagaaga ctagttcaaa    1200
ttgtaatgga gaagaaaga aattagatga ttcctgttct ggctctgtaa cctactctta    1260
ttccgcacta attgtgccca agagatgat taagaaggca aaaaaactga ttgagaccac    1320
agccaacatg aactccagtt atgttaaatt tttaaagcag gcaacagata attcagaaat    1380
cagttctgct acaaaattac gtcagcttaa ggcttttaag tctgtgttgg ctgatattaa    1440
gaaggctcat cttgcattgg aagaagactt aaattccgag tttcgagcga tggatgctgt    1500
aaacaaagag aaaaatacca aagagcataa agtcatagat gctaagtttg aaacaaaagc    1560
acgaaaagga gaaaaaacctt gtgctttgga aaagaaggat atttcaaagt cagaagctaa    1620
actttcaaga aaacaggtag atagtgagca catgcatcag aatgttccaa cagaggaaca    1680
aagaacaaat aaaagtaccg gtggtgaaca taagaaatct gatagaaaag aagaacctca    1740
atatgaacct gccaacactt ctgaagattt agacatggat attgtgtctg ttccttcctc    1800
agttccagaa gacatttttg agaatcttga gactgctatg gaagttcaga gttcagttga    1860
tcatcaaggg gatggcagca gtggaactga acaagaagtg gagagttcat ctgtaaaatt    1920
aaatatttct tcaaaagaca acagaggagg tattaaatca aaaactacag ctaaagtaac    1980
aaaagaatta tatgttaaac tcactcctgt ttcccctttct aattccccaa ttaaaggtgc    2040
tgattgtcag gaagttccac aagataaaga tggctataaa agttgtggtc tgaaccccaa    2100
gttagagaaa tgtggacttg acaggaaaa cagtgataat gagcatttgg ttgaaaatga    2160
agtttcatta cttttagagg aatctgatct tcgaagatcc ccacgtgtaa agactacacc    2220
cttgaggcga ccgacagaaa ctaaccctgt aacatctaat tcagatgaag aatgtaatga    2280
aacagttaag gagaaacaaa aactatcagt tccagtgaga aaaaaggata gcgtaattc     2340
```

-continued

```
ttctgacagt gctatagata atcctaagcc taataaattg ccaaaatcta agcaatcaga    2400
gactgtggat caaaattcag attctgatga aatgctagca atcctcaaag aggtgagcag    2460
gatgagtcac agttcttctt cagatactga tattaatgaa attcatacaa accataagac    2520
tttgtatgat ttaaagactc aggcggggaa agatgataaa ggaaaaagga aacgaaaaag    2580
ttctacatct ggctcagatt ttgatactaa aaagggcaaa tcagctaaga gctctataat    2640
ttctaaaaag aaacgacaaa cccagtctga gtcttctaat tatgactcag aattagaaaa    2700
agagataaag agcatgagta aaattggtgc tgccagaacc accaaaaaaa gaattccaaa    2760
tacaaaagat tttgactctt ctgaagatga aaacacagc aaaaaggaa tggataatca     2820
agggcacaaa aatttgaaga cctcacaaga aggatcatct gatgatgctg aaagaaaaca    2880
agagagagag actttctctt cagcagaagg cacagttgat aaagacacga ccatcatgga    2940
attaagagat cgacttccta agaagcagca agcaagtgct tccactgatg gtgtcgataa    3000
gctttctggg aaagagcaga gttttacttc tttggaagtt agaaaagttg ctgaaactaa    3060
agaaaagagc aagcatctca aaaccaaaac atgtaaaaaa gtacaggatg cttatctga    3120
tattgcagag aaattcctaa agaaagacca gagcgatgaa acttctgaag atgataaaaa    3180
gcagagcaaa aagggaactg aagaaaaaaa gaaaccttca gactttaaga aaaaagtaat    3240
taaaatggaa caacagtatg aatcttcatc tgatggcact gaaaagttac ctgagcgaga    3300
agaaatttgt cattttccta agggcataaa acaaattaag aatggaacaa ctgatggaga    3360
aaagaaaagt aaaaaaataa gagataaaac ttctaaaaag aaggatgaat tatctgatta    3420
tgctgagaag tcaacaggga aaggagatag ttgtgactct tcagaggata aaaagagtaa    3480
gaatggagca tatggtagag agaagaaaag gtgcaagttg cttggaaaga gttcaaggaa    3540
gagacaagat tgttcatcat ctgatactga aaatattcc atgaaagaag atggttgtaa    3600
ctcttctgat aagagactga aaagaataga attgagggaa agaagaaatt taagttcaaa    3660
gagaaatact aaggaaatac aaagtggctc atcatcatct gatgctgagg aaagttctga    3720
agataataaa aagaagaagc aaagaacttc atctaaaaag aaggcagtca ttgtcaagga    3780
gaaaaagaga aactccctaa gaacaagcac taaaaggaag caagctgaca ttacatcctc    3840
atcttcttct gatatagaag atgatgatca gaattctata ggtgagggaa gcagcgatga    3900
acagaaaatt aagcctgtga ctgaaaattt agtgctgtct tcacatactg attttgcca    3960
atcttcagga gatgaagcct tatctaaatc agtgcctgtc acagtggatg atgatgatga    4020
cgacaatgat cctgagaata gaattgccaa gaagatgctg ttagaagaaa ttaaagccaa    4080
tctttcctct gatgaggatg gatcttcaga tgatgagcca aagaaggga aaaaagaac     4140
tggaaaacaa aatgaagaaa acccaggaga tgaggaagca aaaaatcaag tcaattctga    4200
atcagattca gattctgaag aatctaagaa gccaagatac agacataggc ttttgcggca    4260
caaattgact gtgagtgacg gagaatctgg agaagaaaaa aagacaaagc taaagagca    4320
taaagaagtc aaaggcagaa acagaagaaa ggtgagcagt gaagattcag aagattctga    4380
ttttcaggaa tcaggagtta gtgaagaagt tagtgaatcc gaagatgaac agcggcccag    4440
aacaaggtct gcaagaaaag cagagttgga agaaaatcag cggagctata acagaaaaa     4500
gaaaaggcga cgtattaagg ttcaagaaga ttcatccagt gaaaacaaga gtaattctga    4560
ggaagagag gaggaaaaag aagaggagga ggaagaggag gaggaggagg aagaggagga    4620
ggaagatgaa aatgatgatt ccaagtctcc tggaaaaggc agaagaaaaa ttcggaagat    4680
```

```
tcttaaagat gataaactga gaacagaaac acaaaatgct cttaaggaag aggaagagag    4740
acgaaaacgt attgctgaga gggagcgtga gcgagaaaaa ttgagagagg tgatagaaat    4800
tgaagatgct tcacccacca agtgtccaat aacaaccaag ttggttttag atgaagatga    4860
agaaaccaaa gaacctttag tgcaggttca tagaaatatg gttatcaaat tgaaccccca    4920
tcaagtagat ggtgttcagt ttatgtggga ttgctgctgt gagtctgtga aaaaaacaaa    4980
gaaatctcca ggtcaggat gcattcttgc ccactgtatg ggccttggta agactttaca    5040
ggtggtaagt tttcttcata cagttctttt gtgtgacaaa ctggatttca gcacggcgtt    5100
agtggtttgt cctcttaata ctgctttgaa ttggatgaat gaatttgaga agtggcaaga    5160
gggattaaaa gatgatgaga agcttgaggt ttctgaatta gcaactgtga aacgtcctca    5220
ggagagaagc tacatgctgc agaggtggca agaagatggt ggtgttatga tcataggcta    5280
tgagatgtat agaaatcttg ctcaaggaag gaatgtgaag agtcggaaac ttaaagaaat    5340
atttaacaaa gctttggttg atccaggccc tgattttgtt gtttgtgatg aaggccatat    5400
tctaaaaaat gaagcatctg ctgtttctaa agctatgaat tctatacgat caaggaggag    5460
gattatttta acaggaacac cacttcaaaa taacctaatt gagtatcatt gtatggttaa    5520
ttttatcaag gaaaatttac ttggatccat taaggagttc aggaatagat ttataaatcc    5580
aattcaaaat ggtcagtgtg cagattctac catggtagat gtcagagtga tgaaaaaacg    5640
tgctcacatt ctctatgaga tgttagctgg atgtgttcag aggaaagatt atacagcatt    5700
aacaaaattc ttgcctccaa aacacgaata tgtgttagct gtgagaatga cttctattca    5760
gtgcaagctc tatcagtact acttagatca cttaacaggt gtgggcaata atagtgaagg    5820
tggaagagga aaggcaggtg caaagctttt ccaagatttt cagatgttaa gtagaatatg    5880
gactcatcct tggtgtttgc agctagacta cattagcaaa gaaaataagg ttatttga    5940
tgaagacagt atggatgaat ttatagcctc agattctgat gaaacctcca tgagtttaag    6000
ctccgatgat tatacaaaaa agaagaaaaa agggaaaaag gggaaaaaag atagtagctc    6060
aagtggaagt ggcagtgaca atgatgttga agtgattaag gtctggaatt caagatctcg    6120
gggaggtggt gaaggaaatg tggatgaaac aggaaacaat ccttctgttt ctttaaaact    6180
ggaagaaagt aaagctactt cttcttctaa tccaagcagc ccagctccag actggtacaa    6240
agattttgtt acagatgctg atgctgaggt tttagagcat tctggaaaaa tggtacttct    6300
ctttgaaatt cttcgaatgg cagaggaaat tggggataaa gtccttgttt tcagccagtc    6360
cctcatatct ctggacttga ttgaagattt tcttgaatta gctagtaggg agaagacaga    6420
agataaagat aaacccctta tttataaagg tgaggggaag tggcttcgaa acattgacta    6480
ttaccgttta gatggttcca ctactgcaca gtcaaggaag aagtgggctg aagaatttaa    6540
tgatgaaact aatgtgagag gacgattatt tatcatttct actaaagcag gatctctagg    6600
aattaatctg gtagctgcta atcgagtaat tatattcgac gcttcttgga atccatctta    6660
tgacatccag agtatattca gagtttatcg ctttggacaa actaagcctg tttatgtata    6720
taggttctta gctcagggaa ccatggaaga taagtttatt gatcggcaag taactaagca    6780
gtcactgtct tttcgagttg ttgatcagca gcaggtggag cgtcatttta ctatgaatga    6840
gcttactgaa cctttatactt tgagccaga cttattagat gaccctaatt cagaaaagaa    6900
gaagaagagg gatactccca tgctgccaaa ggataccata cttgcagagc tccttcagat    6960
acataaagaa cacattgtag ataccatgaa acatgattct ctttggacc acaaagaaga    7020
agaagagttg actgaagaag aaagaaaagc agcttgggct gagtatgaag cagagaagaa    7080
```

```
gggactgacc atgcgtttca acataccaac tgggaccaat ttaccccctg tcagtttcaa    7140
ctctcaaact ccttatattc ctttcaattt gggagccctg tcagcaatga gtaatcaaca    7200
gctggaggac ctcattaatc aaggaagaga aaaagttgta gaagcaacaa acagtgtgac    7260
agcagtgagg attcaacctc ttgaggatat aatttcagct gtatggaagg agaacatgaa    7320
tctctcagag gcccaagtac aggcgttagc attaagtaga caagccagcc aggagcttga    7380
tgttaaacga agagaagcaa tctacaatga tgtattgaca aaacaacaga tgttaatcag    7440
ctgtgttcag cgaatactta tgaacagaag gctccagcag cagtacaatc agcagcaaca    7500
gcaacaaatg acttatcaac aagcaacact gggtcacctc atgatgccaa agcccccaaa    7560
tttgatcatg aatccttcta actaccagca gattgatatg agaggaatgt atcagccagt    7620
ggctggtggt atgcagccac caccattaca gcgtgcacca cccccaatga gaagcaaaaa    7680
tccaggacct tcccaaggga atcaatgtg attttgcact aaaagcttaa tggattgtta    7740
aaatcataga aagatctttt attttttag gaatcaatga cttaacagaa ctcaactgta    7800
taaatagttt ggtcccctta aatgccaatc ttccatatta gttttacttt tttttttttt    7860
aaatagggca taccatttct tcctgacatt tgtcagtgat gttgcctaga atcttcttac    7920
acacgctgag tacagaagat atttcaaatt gttttcagtg aaaacaagtc cttccataat    7980
agtaacaact ccacagattt cctctctaaa tttttatgcc tgcttttagc aaccataaaa    8040
ttgtcataaa attaataaat ttaggaaaga ataaagattt atatattcat tctttacata    8100
taaaaacaca cagctgagtt cttagagttg attcctcaag ttatgaaata cttttgtact    8160
taatccattt cttgattaaa gtgattgaaa tggttttaat gttcttttga ctgaagtctg    8220
aaactgggct cctgctttat tgtctctgtg actgaaagtt agaaactgag ggttatcttt    8280
gacacagaat tgtgtgcaat attcttaaat actactgctc taaaagttgg agaagtcttg    8340
cagttatctt agcattgtat aaacagcctt aagtatagcc taagaagaga attccttttt    8400
cttctttagt ccttctgcca tttttttattt tcagttatat gtgctgaaat aattactggt    8460
aaaatttcag ggttgtggat tatcttccac acatgaattt tctctctcct ggcacgaata    8520
taaagcacat ctcttaactg catggtgcca gtgctaatgc ttcatcctgt tgctggcagt    8580
gggatgtgga cttagaaaat caagttctag catttagta ggttaacact gaagttgtgg     8640
ttgttaggtt cacaccctgt tttataaaca acatcaaaat ggcagaacca ttgctgactt    8700
taggttcaca tgaggaatgt acttttaaca attcccagta ctatcagtat tgtgaaataa    8760
ttcctctgaa agataagaat cactggcttc tatgcgcttc ttttctctca tcatcatgtt    8820
cttttacccc agtttcctta catttttta aattgtttca gagtttgttt tttttttagt     8880
ttagattgtg aggcaattat taaatcaaaa ttaattcatc caatacccct ttactagaag    8940
ttttactaga aaatgtatta cattttattt tttcttaatc cagttctgca aaaatgacct    9000
ataaatttat tcatgtacaa ttttggttac ttgaattgtt aaagaaaaca ttgttttga    9060
ctatgggagt caactcaaca tggcagaacc atttttgaga tgatgataca acaggtagtg    9120
aaacagctta agaattccaa aaaaaaaaaa aaaaaaaaa aaagaaaac tgggtttggg      9180
ctttgcttta ggtatcactg gattagaatg agtttaacat tagctaaaac tgctttgagt    9240
tgtttggatg attaagagat tgccattttt atcttggaag aactagtggt aaaacatcca    9300
agagcactag gattgtgata cagaatttgt gaggtttggt ggatccacgc ccctctcccc    9360
cactttccca tgatgaaata tcactaataa atcctgtata tttagatatt atgctagcca    9420
```

| | |
|---|---:|
| tgtaatcaga tttatttaat tgggtggggc aggtgtgtat ttactttaga aaaaatgaaa | 9480 |
| aagacaagat ttatgagaaa tatttgaagg cagtacactc tggccaactg ttaccagttg | 9540 |
| gtatttctac aagttcagaa tattttaaac ctgatttact agacctggga attttcaaca | 9600 |
| tggtctaatt atttactcaa agacatagat gtgaaaattt taggcaacct tctaaatctt | 9660 |
| tttcaccatg gatgaaacta aacttaaag aataatactt agaagggtta attggaaatc | 9720 |
| agagtttgaa ataaaacttg gaccactttg tatacactct tctcacttga cattttagct | 9780 |
| atataatatg tactttgagt ataacatcaa gctttaacaa atatttaaag acaaaaaaat | 9840 |
| cacgtcagta aaatactaaa aggctcattt ttatatttgt tttagatgtt ttaaatagtt | 9900 |
| gcaatggatt aaaaatgatg atttaaaatg ttgcttgtaa tacagttttg cctgctaaat | 9960 |
| tctccacatt ttgtaacctg ttttatttct ttgggtgtaa agcgttttg cttagtattg | 10020 |
| tgatattgta tatgttttgt cccagttgta tagtaatgtt tcagtccatc atccagcttt | 10080 |
| ggctgctgaa atcatacagc tgtgaagact tgcctttgtt tctgttagac tgcttttcag | 10140 |
| ttctgtattg agtatcttaa gtactgtaga aaagatgtca cttcttcctt taaggctgtt | 10200 |
| ttgtaatata tataaggact ggaattgtgt ttttaaagaa aagcattcaa gtatgacaat | 10260 |
| atactatctg tgttttcacc attcaaagtg ctgtttagta gttgaaactt aaactattta | 10320 |
| atgtcattta ataaagtgac caaaatgtgt tgtgctcttt attgtattttt cacagctttg | 10380 |
| aaaatctgtg cacatactgt ttcatagaaa atgtatagct tttgttgtcc tatataatgg | 10440 |
| tggttctttt gcacatttag ttatttaata ttgagaggtc acgaagtttg ttattgaat | 10500 |
| ctgttatata ctaaattctg taaagggaga tctctcatct caaaaagaat ttacatacca | 10560 |
| ggaagtccat gtgtgtttgt gttagttttg gatgtctttg tgtaatccag ccccatttcc | 10620 |
| tgtttcccaa cagctgtaac actcatttta agtcaagcag ggctaccaac ccacacttga | 10680 |
| tagaaaagct gcttaccatt cagaagcttc cttattacct ggcctccaaa tgagctgaat | 10740 |
| attttgtagc cttcccttag ctatgttcat tttccctcca ttatcataaa atcagatcga | 10800 |
| tatttatgtg ccccaaacaa aactttaaga gcagttacat tctgtcccag tagcccttgt | 10860 |
| ttcctttgag agtagcatgt tgtgaggcta tagagactta ttctaccagt aaaacaggtc | 10920 |
| aatcctttta catgtttatt atactaaaaa ttatgttcag ggtatttact actttatttc | 10980 |
| accagactca gtctcaagtg acttggctat ctccaaatca gatctaccct tagagaataa | 11040 |
| acatttttct accgttattt tttttcaagt ctataatctg agccagtccc aaaggagtga | 11100 |
| tcaagtttca gaaatgcttt catcttcaca acattttata tatactatta tatggggtga | 11160 |
| ataaagtttt aaatccgaaa tataaaaaaa aaaaaaaaa aa | 11202 |

<210> SEQ ID NO 13
<211> LENGTH: 2673
<212> TYPE: DNA
<213> ORGANISM: Homo sapiens

<400> SEQUENCE: 13

| | |
|---|---:|
| cccattctcc tctgcgcggc ctccatctaa gatctcttcc ccttgtccat agcctagatc | 60 |
| gagctccctg tgtgcaccgc gcgctgcccg aggcgcaggt caaccagaat caagatgtct | 120 |
| gggactgagg aagcaattct tggaggacgt gacagccatc ctgctgctgg cggcggctca | 180 |
| gtgttatgct ttggacagtg ccagtacaca gcagaagagt accaggccat ccagaaggcc | 240 |
| ctgaggcaga ggctgggccc agaatacata agtagccgca tggctggcgg aggccagaag | 300 |
| gtgtgctaca ttgagggtca tcgggtaatt aatctggcca atgagatgtt tggttacaat | 360 |

```
ggctgggcac actccatcac gcagcagaat gtggattttg ttgacctcaa caatggcaag      420
ttctacgtgg gagtctgtgc atttgtgagg gtccagctga aggatggttc atatcatgaa      480
gatgttggtt atggtgttag tgagggcctc aagtccaagg ctttatcttt ggagaaggca      540
aggaaggagg cggtgacaga cgggctgaag cgagccctca ggagttttgg gaatgcactt      600
ggaaactgta ttctggacaa agactacctg agatcactaa ataagcttcc acgccagttg      660
cctcttgaag tggatttaac taaagcgaag agacaagatc ttgaaccgtc tgtggaggag      720
gcaagataca acagctgccg accgaacatg gccctgggac acccacagct gcagcaggtg      780 acctccccctt ccagacccag ccatgctgtg ataccggcgg accaggactg cagctcccga      840
agcctgagct catccgccgt ggagagcgag gccacgcacc agcggaagct ccggcagaag      900
cagctgcagc agcagttccg ggagcggatg gagaagcagc aggttcgagt ctccacgccg      960
tcagctgaga gagtgaggc agcgcctccg gcccctcctg tgacgcacag cactcctgta     1020
actgtctcag aaccactcct ggagaaagac ttccttgcag gagtgactca agaattaatc     1080
aagactcttg aagacaactc tgaaaagtgg gctgtgactc ccgatgcagg ggatggtgtg     1140
gtcaagccct cgtctagagc agacccagcc cagacctctg acacattagc cttgaacaac     1200
cagatggtga cccagaacag gactccacac agcgtttgcc accagaaacc acaagcaaaa     1260
tctggatctt gggaccctcca aacttatagc gctgaccaac gcacaacagg aaactgggaa     1320
tctcatagga agagccagga catgaagaaa aggaaatatg atccatctta actgaggctc     1380
aggccacata attggactct gtcacaaagg gactttggaa aactacttttt tggtcatgaa     1440 attgttcatc gctgctggag aatgaacgtc attgcgattt atcttgcttc attctgaacc     1500
ttatcaagag gatctgactg agagcccact gcagttagag ctgagcactt ttgaaaagct     1560
tgtccatcac tctagtaggg agaggctctg gacagatgaa tacctttttct tcggcttgtg     1620 aggcttccca ctatttatta ctgaactatt atgttaatga agatggacat tttaggaatc     1680
accaatggct ccttgccctc aagcaatata ggccagactt ggtcctaagc acctgcctca     1740
gcaattgtct acattcagtt gttttgcata acgtctgcct tctttccttt acggtccatg     1800
cctttaatgt tgcccacatt aagcactgtg gatcacgaca ggaaaaaggt tggagcagtg     1860
cttttcacta ctttgtatca atccaggcta caatcttcat ttaatataaa taatttatgg     1920
atttatgaca ttacaatcct gcattgtttc aagactgaca ttttttccta aggaaggaaa     1980
taatcatcta agaccacgaa aaaggctgtt ttttgtttt ttttttttt tttttttttg     2040 agacggggtc tggctgtgtt gccctgactg gagttcagtg gtgcaaacac agctctctcc     2100
acaacctctt gggcccaagt gatactccca cctctgcctt acaaaataca gggattactg     2160
gtgtgagcca ctgtgtctgg ccagaaaagg cattttttgag aaagcaaatc gtataccttta     2220 ttaacaaaat agaatatata tatattgctt atctgaaatg cttgaaacca gaattgtttt     2280 gcatttttttg aatatttgta tacacataat gagaccttgg ggatgggacc caagtctgaa     2340
cgtggaattc acctgtgttt cgtgtatatg cctcatacac ataattttgt gcatgaaaca     2400 gagttttttgt ataagaagat acactgcagc tgaagagggc tgggtttttt tttctcttag     2460
ggtcgctgca taaactgttg tatgcctggt gctttgcgac ttgtcacacg aggtcacgtg     2520
tggaattttc cacttctggc atcacgtcag tgctcagaaa ttttctgatc tcagagcatt     2580
tcaattaggg atgctcaaac gcaactgttt ctacttcccc atttcaggtg tgagatgtaa     2640
cccaccttga ccataaattg gctttttcata gtg                                 2673
```

<210> SEQ ID NO 14
<211> LENGTH: 7287
<212> TYPE: DNA
<213> ORGANISM: Homo sapiens

<400> SEQUENCE: 14

| | | | | | |
|---|---|---|---|---|---|
| gtaccttgat | ttcgtattct | gagaggctgc | tgcttagcgg | tagccccttg | gtttccgtgg | 60 |
| caacggaaaa | gcgcgggaat | tacagataaa | ttaaaactgc | gactgcgcgg | cgtgagctcg | 120 |
| ctgagacttc | ctggacgggg | gacaggctgt | ggggtttctc | agataactgg | gcccctgcgc | 180 |
| tcaggaggcc | ttcaccctct | gctctgggta | aagttcattg | gaacagaaag | aaatggattt | 240 |
| atctgctctt | cgcgttgaag | aagtacaaaa | tgtcattaat | gctatgcaga | aaatcttaga | 300 |
| gtgtcccatc | tgtctggagt | tgatcaagga | acctgtctcc | acaaagtgtg | accacatatt | 360 |
| ttgcaaattt | tgcatgctga | aacttctcaa | ccagaagaaa | gggccttcac | agtgtccttt | 420 |
| atgtaagaat | gatataacca | aaaggagcct | acaagaaagt | acgagattta | gtcaacttgt | 480 |
| tgaagagcta | ttgaaaatca | tttgtgcttt | tcagcttgac | acaggtttgg | agtatgcaaa | 540 |
| cagctataat | tttgcaaaaa | aggaaaataa | ctctcctgaa | catctaaaag | atgaagtttc | 600 |
| tatcatccaa | agtatgggct | acagaaaccg | tgccaaaaga | cttctacaga | gtgaacccga | 660 |
| aaatccttcc | ttgcaggaaa | ccagtctcag | tgtccaactc | tctaaccttg | gaactgtgag | 720 |
| aactctgagg | acaaagcagc | ggatacaacc | tcaaaagacg | tctgtctaca | ttgaattggg | 780 |
| atctgattct | tctgaagata | ccgttaataa | ggcaacttat | tgcagtgtgg | gagatcaaga | 840 |
| attgttacaa | atcaccccctc | aaggaaccag | ggatgaaatc | agtttggatt | ctgcaaaaaa | 900 |
| ggctgcttgt | gaattttctg | agacggatgt | aacaaatact | gaacatcatc | aacccagtaa | 960 |
| taatgatttg | aacaccactg | agaagcgtgc | agctgagagg | catccagaaa | agtatcaggg | 1020 |
| tagttctgtt | tcaaacttgc | atgtggagcc | atgtggcaca | aatactcatg | ccagctcatt | 1080 |
| acagcatgag | aacagcagtt | tattactcac | taaagacaga | atgaatgtag | aaaaggctga | 1140 |
| attctgtaat | aaaagcaaac | agcctggctt | agcaaggagc | caacataaca | gatgggctgg | 1200 |
| aagtaaggaa | acatgtaatg | ataggcggac | tcccagcaca | gaaaaaaagg | tagatctgaa | 1260 |
| tgctgatccc | ctgtgtgaga | gaaaagaatg | gaataagcag | aaactgccat | gctcagagaa | 1320 |
| tcctagagat | actgaagatg | ttccttggat | aacactaaat | agcagcattc | agaaagttaa | 1380 |
| tgagtggttt | tccagaagtg | atgaactgtt | aggttctgat | gactcacatg | atgggagtc | 1440 |
| tgaatcaaat | gccaaagtag | ctgatgtatt | ggacgttcta | aatgaggtag | atgaatattc | 1500 |
| tggttcttca | gagaaaatag | acttactggc | cagtgatcct | catgaggctt | taatatgtaa | 1560 |
| aagtgaaaga | gttcactcca | aatcagtaga | gagtaatatt | gaagacaaaa | tatttgggaa | 1620 |
| aacctatcgg | aagaaggcaa | gcctccccaa | cttaagccat | gtaactgaaa | atctaattat | 1680 |
| aggagcattt | gttactgagc | cacagataat | acaagagcgt | cccctcacaa | ataaattaaa | 1740 |
| gcgtaaaagg | agacctacat | caggccttca | tcctgaggat | tttatcaaga | aagcagattt | 1800 |
| ggcagttcaa | aagactcctg | aaatgataaa | tcagggaact | aaccaaacgg | agcagaatgg | 1860 |
| tcaagtgatg | aatattacta | atagtggtca | tgagaataaa | acaaaaggtg | attctattca | 1920 |
| gaatgagaaa | aatcctaacc | caatagaatc | actcgaaaaa | gaatctgctt | tcaaaacgaa | 1980 |
| agctgaacct | ataagcagca | gtataagcaa | tatggaactc | gaattaaata | tccacaattc | 2040 |
| aaaagcacct | aaaaagaata | ggctgaggag | gaagtcttct | accaggcata | ttcatgcgct | 2100 |
| tgaactagta | gtcagtagaa | atctaagccc | acctaattgt | actgaattgc | aaattgatag | 2160 |

```
ttgttctagc agtgaagaga taaagaaaaa aaagtacaac caaatgccag tcaggcacag    2220
cagaaaccta caactcatgg aaggtaaaga acctgcaact ggagccaaga agagtaacaa    2280
gccaaatgaa cagacaagta aaagacatga cagcgatact ttcccagagc tgaagttaac    2340
aaatgcacct ggttctttta ctaagtgttc aaataccagt gaacttaaag aatttgtcaa    2400
tcctagcctt ccaagagaag aaaaagaaga gaaactagaa acagttaaag tgtctaataa    2460
tgctgaagac cccaaagatc tcatgttaag tggagaaagg gttttgcaaa ctgaaagatc    2520
tgtagagagt agcagtattt cattggtacc tggtactgat tatggcactc aggaaagtat    2580
ctcgttactg gaagttagca ctctagggaa ggcaaaaaca gaaccaaata aatgtgtgag    2640
tcagtgtgca gcatttgaaa accccaaggg actaattcat ggttgttcca agataatag    2700 aaatgacaca gaaggcttta agtatccatt gggacatgaa gttaaccaca gtcgggaaac    2760
aagcatagaa atggaagaaa gtgaacttga tgctcagtat ttgcagaata cattcaaggt    2820
ttcaaagcgc cagtcatttg ctccgttttc aaatccagga aatgcagaag aggaatgtgc    2880
aacattctct gcccactctg ggtccttaaa gaaacaaagt ccaaaagtca cttttgaatg    2940
tgaacaaaag gaagaaaatc aaggaaagaa tgagtctaat atcaagcctg tacagacagt    3000
taatatcact gcaggctttc ctgtggttgg tcagaaagat aagccagttg ataatgccaa    3060
atgtagtatc aaaggaggct ctaggttttg tctatcatct cagttcagag gcaacgaaac    3120
tggactcatt actccaaata acatggact tttacaaaac ccatatcgta taccaccact    3180 tttttcccatc aagtcatttg ttaaaactaa atgtaagaaa aatctgctag aggaaaactt    3240
tgaggaacat tcaatgtcac ctgaaagaga aatgggaaat gagaacattc caagtacagt    3300
gagcacaatt agccgtaata acattagaga aaatgttttt aaagaagcca gctcaagcaa    3360
tattaatgaa gtaggttcca gtactaatga agtgggctcc agtattaatg aaataggttc    3420
cagtgatgaa acacattcaag cagaactagg tagaaacaga gggccaaaat tgaatgctat    3480
gcttagatta ggggttttgc aacctgaggt ctataaacaa agtcttcctg gaagtaattg    3540
taagcatcct gaaataaaaa agcaagaata tgaagaagta gttcagactg ttaatacaga    3600
tttctctcca tatctgattt cagataactt agaacagcct atgggaagta gtcatgcatc    3660
tcaggtttgt tctgagacac ctgatgacct gttagatgat ggtgaaataa aggaagatac    3720
tagttttgct gaaaatgaca ttaaggaaag ttctgctgtt tttagcaaaa gcgtccagaa    3780
aggagagctt agcaggagtc ctagcccttt caccatata catttggctc agggttaccg    3840
aagaggggcc aagaaattag agtcctcaga agagaactta tctagtgagg atgaagagct    3900
tcccctgctt caacacttgt tatttggtaa agtaaacaat atccttctc agtctactag    3960 gcatagcacc gttgctaccg agtgtctgtc taagaacaca gaggagaatt tattatcatt    4020
gaagaatagc ttaaatgact gcagtaacca ggtaatattg gcaaaggcat ctcaggaaca    4080
tcaccttagt gaggaaacaa aatgttctgc tagcttgttt tcttcacagt gcagtgaatt    4140
ggaagacttg actgcaaata caaacaccca ggatccttc ttgattggtt cttccaaaca    4200
aatgaggcat cagtctgaaa gccagggagt tggtctgagt gacaaggaat tggtttcaga    4260
tgatgaagaa agaggaacgg gcttggaaga aaataatcaa gaagagcaaa gcatggatc    4320 aaacttaggt gaagcagcat ctgggtgtga gagtgaaaca agcgtctctg aagactgctc    4380
agggctatcc tctcagagtg acatttaac cactcagcag agggatacca tgcaacataa    4440
cctgataaag ctccagcagg aaatggctga actagaagct gtgttagaac agcatgggag    4500
```

```
ccagccttct aacagctacc cttccatcat aagtgactct tctgcccttg aggacctgcg    4560
aaatccagaa caaagcacat cagaaaaaga ttcgcatata catggccaaa ggaacaactc    4620
catgttttct aaaaggccta gagaacatat atcagtatta acttcacaga aaagtagtga    4680 atacccctata agccagaatc cagaaggcct ttctgctgac aagtttgagg tgtctgcaga    4740
tagttctacc agtaaaaata aagaaccagg agtggaaagg tcatcccctt ctaaatgccc    4800
atcattagat gataggtggt acatgcacag ttgctctggg agtcttcaga atagaaacta    4860
cccatctcaa gaggagctca ttaaggttgt tgatgtggag gagcaacagc tggaagagtc    4920
tgggccacac gatttgacgg aaacatctta cttgccaagg caagatctag agggaacccc    4980
ttacctggaa tctggaatca gcctcttctc tgatgaccct gaatctgatc cttctgaaga    5040
cagagcccca gagtcagctc gtgttggcaa cataccatct tcaacctctg cattgaaagt    5100
tccccaattg aaagttgcag aatctgccca gagtccagct gctgctcata ctactgatac    5160
tgctgggtat aatgcaatgg aagaaagtgt gagcagggag aagccagaat tgacagcttc    5220
aacagaaagg gtcaacaaaa gaatgtccat ggtggtgtct ggcctgaccc cagaagaatt    5280
tatgctcgtg tacaagtttg ccagaaaaca ccacatcact ttaactaatc taattactga    5340
agagactact catgttgtta tgaaaacaga tgctgagttt gtgtgtgaac ggacactgaa    5400
atattttcta ggaattgcgg gaggaaaatg ggtagttagc tatttctggg tgacccagtc    5460
tattaaagaa agaaaaatgc tgaatgagca tgattttgaa gtcagaggag atgtggtcaa    5520
tggaagaaac caccaaggtc caaagcgagc aagagaatcc caggacagaa agatcttcag    5580
ggggctagaa atctgttgct atgggccctt caccaacatg cccacagatc aactggaatg    5640
gatggtacag ctgtgtggtg cttctgtggt gaaggagctt tcatcattca cccttggcac    5700
aggtgtccac ccaattgtgg ttgtgcagcc agatgcctgg acagaggaca atggcttcca    5760
tgcaattggg cagatgtgtg aggcacctgt ggtgacccga gagtgggtgt tggacagtgt    5820
agcactctac cagtgccagg agctggacac ctacctgata ccccagatcc cccacagcca    5880
ctactgactg cagccagcca caggtacaga gccacaggac cccaagaatg agcttacaaa    5940
gtggcctttc caggccctgg gagctcctct cactcttcag tccttctact gtcctggcta    6000
ctaaatattt tatgtacatc agcctgaaaa ggacttctgg ctatgcaagg gtcccttaaa    6060 gatttctgc ttgaagtctc ccttggaaat ctgccatgag cacaaaatta tggtaatttt    6120
tcacctgaga agatttttaaa accatttaaa cgccaccaat tgagcaagat gctgattcat    6180
tatttatcag ccctattctt tctattcagg ctgttgttgg cttagggctg gaagcacaga    6240
gtggcttggc ctcaagagaa tagctggttt ccctaagttt acttctctaa aaccctgtgt    6300
tcacaaaggc agagagtcag acccttcaat ggaaggagag tgcttgggat cgattatgtg    6360
acttaaagtc agaatagtcc ttgggcagtt ctcaaatgtt ggagtggaac attggggagg    6420
aaattctgag gcaggtatta gaaatgaaaa ggaaacttga aacctgggca tggtggctca    6480
cgcctgtaat cccagcactt tgggaggcca aggtgggcag atcactggag gtcaggagtt    6540
cgaaaccagc ctggccaaca tggtgaaacc ccatctctac taaaaataca gaaattagcc    6600
ggtcatggtg gtggacacct gtaatcccag ctactcaggt ggctaaggca ggagaatcac    6660
ttcagcccgg gaggtggagg ttgcagtgag ccaagatcat accacggcac tccagcctgg    6720
gtgacagtga gactgtggct caaaaaaaaa aaaaaaaaaa ggaaaatgaa actagaagag    6780
atttctaaaa gtctgagata tatttgctag atttctaaag aatgtgttct aaaacagcag    6840
aagattttca agaaccggtt tccaaagaca gtcttctaat tcctcattag taataagtaa    6900
```

```
aatgtttatt gttgtagctc tggtatataa tccattcctc ttaaaatata agacctctgg    6960
catgaatatt tcatatctat aaaatgacag atcccaccag gaaggaagct gttgctttct    7020
ttgaggtgat tttttccctt tgctccctgt tgctgaaacc atacagcttc ataaataatt    7080
ttgcttgctg aaggaagaaa aagtgttttt cataaaccca ttatccagga ctgtttatag    7140
ctgttggaag gactaggtct tccctagccc ccccagtgtg caagggcagt gaagacttga    7200
ttgtacaaaa tacgttttgt aaatgttgtg ctgttaacac tgcaaataaa cttggtagca    7260
aacacttcca aaaaaaaaaa aaaaaaa                                         7287

<210> SEQ ID NO 15
<211> LENGTH: 11386
<212> TYPE: DNA
<213> ORGANISM: Homo sapiens

<400> SEQUENCE: 15
gtggcgcgag cttctgaaac taggcggcag aggcggagcc gctgtggcac tgctgcgcct      60
ctgctgcgcc tcgggtgtct tttgcggcgg tgggtcgccg ccgggagaag cgtgagggga     120
cagatttgtg accggcgcgg ttttgtcag cttactccgg ccaaaaaaga actgcacctc      180
tggagcggac ttatttacca agcattggag gaatatcgta ggtaaaaatg cctattggat     240
ccaaagagag gccaacattt tttgaaattt ttaagcacg ctgcaacaaa gcagatttag      300
gaccaataag tcttaattgg tttgaagaac tttcttcaga agctccaccc tataattctg     360
aacctgcaga agaatctgaa cataaaaaca acaattacga accaaaccta tttaaaactc     420
cacaaaggaa accatcttat aatcagctgg cttcaactcc aataatattc aaagagcaag     480
ggctgactct gccgctgtac caatctcctg taaaagaatt agataaattc aaattagact     540
taggaaggaa tgttcccaat agtagacata aaagtcttcg cacagtgaaa actaaaatgg     600
atcaagcaga tgatgtttcc tgtccacttc taaattcttg tcttagtgaa agtcctgttg     660
ttctacaatg tacacatgta acaccacaaa gagataagtc agtggtatgt gggagtttgt     720
ttcatacacc aaagttttgtg aagggtcgtc agacaccaaa acatatttct gaaagtctag     780
gagctgaggt ggatcctgat atgtcttggt caagttcttt agctacacca cccaccctta     840
gttctactgt gctcatagtc agaaatgaag aagcatctga aactgtattt cctcatgata    900
ctactgctaa tgtgaaaagc tattttttcca atcatgatga aagtctgaag aaaaatgata     960
gatttatcgc ttctgtgaca gacagtgaaa acacaaatca aagagaagct gcaagtcatg    1020
gatttggaaa aacatcaggg aattcattta agtaaatag ctgcaaagac cacattggaa      1080
agtcaatgcc aaatgtccta gaagatgaag tatatgaaac agttgtagat acctctgaag    1140
aagatagttt ttcattatgt ttttctaaat gtagaacaaa aaatctacaa aaagtaagaa    1200
ctagcaagac taggaaaaaa attttccatg aagcaaacgc tgatgaatgt gaaaaatcta    1260
aaaaccaagt gaaagaaaaa tactcatttg tatctgaagt ggaaccaaat gatactgatc    1320
cattagattc aaatgtagca aatcagaagc cctttgagag tggaagtgac aaaatctcca    1380
aggaagttgt accgtctttg gcctgtgaat ggtctcaact aacccttcca ggtctaaatg    1440
gagcccagat ggaaaaata cccctattgc atatttcttc atgtgaccaa atatttcag      1500 aaaaagacct attagacaca gagaacaaaa gaaagaaaga ttttcttact tcagagaatt    1560
ctttgccacg tatttctagc ctaccaaaat cagagaagcc attaaatgag gaaacagtgg    1620
taaataagag agatgaagag cagcatcttg aatctcatac agactgcatt cttgcagtaa    1680
```

```
agcaggcaat atctggaact tctccagtgg cttcttcatt tcagggtatc aaaaagtcta   1740
tattcagaat aagagaatca cctaaagaga ctttcaatgc aagtttttca ggtcatatga   1800
ctgatccaaa ctttaaaaaa gaaactgaag cctctgaaag tggactggaa atacatactg   1860
tttgctcaca gaaggaggac tccttatgtc caaatttaat tgataatgga agctggccag   1920
ccaccaccac acagaattct gtagctttga agaatgcagg tttaatatcc actttgaaaa   1980
agaaaacaaa taagtttatt tatgctatac atgatgaaac atcttataaa ggaaaaaaaa   2040
taccgaaaga ccaaaaatca gaactaatta actgttcagc ccagtttgaa gcaaatgctt   2100
ttgaagcacc acttacattt gcaaatgctg attcaggttt attgcattct tctgtgaaaa   2160
gaagctgttc acagaatgat tctgaagaac caactttgtc cttaactagc tcttttggga   2220
caattctgag gaaatgttct agaaatgaaa catgttctaa taatacagta atctctcagg   2280
atcttgatta taagaagca aaatgtaata aggaaaaact acagttattt attaccccag    2340
aagctgattc tctgtcatgc ctgcaggaag gacagtgtga aaatgatcca aaaagcaaaa   2400
aagtttcaga tataaaagaa gaggtcttgg ctgcagcatg tcacccagta caacattcaa   2460
aagtggaata cagtgatact gactttcaat cccagaaaag tcttttatat gatcatgaaa   2520
atgccagcac tcttattta actcctactt ccaaggatgt tctgtcaaac ctagtcatga    2580
tttctagagg caaagaatca tacaaaatgt cagacaagct caaaggtaac aattatgaat   2640
ctgatgttga attaaccaaa atattccca tggaaaagaa tcaagatgta tgtgctttaa    2700
atgaaaatta taaaaacgtt gagctgttgc cacctgaaaa atacatgaga gtagcatcac   2760
cttcaagaaa ggtacaattc aaccaaaaca caaatctaag agtaatccaa aaaaatcaag   2820
aagaaactac ttcaatttca aaaataactg tcaatccaga ctctgaagaa cttttctcag   2880
acaatgagaa taatttgtc ttccaagtag ctaatgaaag gaataatctt gctttaggaa    2940
atactaagga acttcatgaa acagacttga cttgtgtaaa cgaacccatt ttcaagaact   3000
ctaccatggt tttatatgga gacacagtg ataaacaagc aacccaagtg tcaattaaaa    3060
aagatttggt ttatgttctt gcagaggaga acaaaaatag tgtaaagcag catataaaaa   3120
tgactctagg tcaagattta aaatcggaca tctccttgaa tatagataaa ataccagaaa   3180
aaaataatga ttacatgaac aaatgggcag gactcttagg tccaatttca aatcacagtt   3240
ttggaggtag cttcagaaca gcttcaaata aggaaatcaa gctctctgaa cataacatta   3300
agaagagcaa aatgttcttc aaagatattg aagaacaata tcctactagt ttagcttgtg   3360
ttgaaattgt aaataccttg gcattagata tcaaaagaa actgagcaag cctcagtcaa    3420
ttaatactgt atctgcacat ttacagagta gtgtagttgt ttctgattgt aaaaatagtc   3480 atataaccc tcagatgtta ttttccaagc aggattttaa ttcaaccat aatttaacac     3540 ctagccaaaa ggcagaaatt acagaacttt ctactatatt agaagaatca ggaagtcagt   3600
ttgaatttac tcagtttaga aaaccaagct acatattgca gaagagtaca tttgaagtgc   3660
ctgaaaacca gatgactatc ttaaagacca cttctgagga atgcagagat gctgatcttc   3720
atgtcataat gaatgcccca tcgattggtc aggtagacag cagcaagcaa tttgaaggta   3780
cagttgaaat taaacggaag tttgctggcc tgttgaaaaa tgactgtaac aaaagtgctt   3840
ctggttattt aacagatgaa aatgaagtgg ggtttagggg cttttattct gctcatggca   3900
caaaactgaa tgtttctact gaagctctgc aaaaagctgt gaaactgttt agtgatattg   3960
agaatattag tgaggaaact tctgcagagg tacatccaat aagtttatct tcaagtaaat   4020
gtcatgattc tgttgtttca atgtttaaga tagaaaatca taatgataaa actgtaagtg   4080
```

```
aaaaaaataa taaatgccaa ctgatattac aaaataatat tgaaatgact actggcactt   4140
ttgttgaaga aattactgaa aattacaaga gaaatactga aaatgaagat aacaaatata   4200
ctgctgccag tagaaattct cataacttag aatttgatgg cagtgattca agtaaaaatg   4260
atactgtttg tattcataaa gatgaaacgg acttgctatt tactgatcag cacaacatat   4320
gtcttaaatt atctggccag tttatgaagg agggaaacac tcagattaaa gaagatttgt   4380
cagatttaac tttttggaa gttgcgaaag ctcaagaagc atgtcatggt aatacttcaa   4440
ataaagaaca gttaactgct actaaaacgg agcaaaatat aaaagatttt gagacttctg   4500
atacatttt tcagactgca agtggggaaaa atattagtgt cgccaaagag tcatttaata   4560
aaattgtaaa tttctttgat cagaaaccag aagaattgca taacttttcc ttaaattctg   4620
aattacattc tgacataaga aagaacaaaa tggacattct aagttatgag gaaacagaca   4680
tagttaaaca caaaatactg aaagaaagtg tcccagttgg tactggaaat caactagtga   4740
ccttccaggg acaacccgaa cgtgatgaaa agatcaaaga acctactcta ttgggttttc   4800
atacagctag cgggaaaaaa gttaaaattg caaaggaatc tttggacaaa gtgaaaaacc   4860
tttttgatga aaaagagcaa ggtactagtg aaatcaccag tttagccat caatgggcaa   4920
agaccctaaa gtacagagag gcctgtaaag accttgaatt agcatgtgag accattgaga   4980
tcacagctgc cccaaagtgt aaagaaatgc agaattctct caataatgat aaaaaccttg   5040
tttctattga gactgtggtg ccacctaagc tcttaagtga taatttatgt agacaaactg   5100
aaaatctcaa aacatcaaaa agtatcttt tgaaagttaa agtacatgaa aatgtagaaa   5160
aagaaacagc aaaaagtcct gcaacttgtt acacaaatca gtccccttat tcagtcattg   5220
aaaattcagc cttagctttt tacacaagtt gtagtagaaaa aacttctgtg agtcagactt   5280
cattacttga agcaaaaaaa tggcttagag aaggaatatt tgatggtcaa ccagaaagaa   5340
taaatactgc agattatgta ggaaattatt tgtatgaaaa taattcaaac agtactatag   5400
ctgaaaatga caaaaatcat ctctccgaaa aacaagatac ttatttaagt aacagtagca   5460
tgtctaacag ctattcctac cattctgatg aggtatataa tgattcagga tatctctcaa   5520
aaaataaact tgattctggt attgagccag tattgaagaa tgttgaagat caaaaaaaca   5580
ctagttttc caaagtaata tccaatgtaa aagatgcaaa tgcataccca caaactgtaa   5640
atgaagatat ttgcgttgag gaacttgtga ctagctcttc accctgcaaa aataaaaatg   5700
cagccattaa attgtccata tctaatagta ataattttga ggtagggcca cctgcattta   5760
ggatagccag tggtaaaatc gtttgtgttt cacatgaaac aattaaaaaa gtgaaagaca   5820
tatttacaga cagtttcagt aaagtaatta aggaaaacaa cgagaataaa tcaaaaattt   5880
gccaaacgaa aattatggca ggttgttacg aggcattgga tgattcagag gatattcttc   5940
ataactctct agataatgat gaatgtagca cgcattcaca taggttttt gctgacattc   6000
agagtgaaga aattttacaa cataaccaaa atatgtctgg attggagaaa gtttctaaaa   6060
tatcaccttg tgatgttagt ttggaaactt cagatatatg taaatgtagt atagggaagc   6120
ttcataagtc agtctcatct gcaaatactt gtgggatttt tagcacagca agtgaaaaat   6180
ctgtccaggt atcagatgct tcattacaaa acgcaagaca agtgttttct gaaatagaag   6240
atagtaccaa gcaagtcttt tccaaagtat tgtttaaaag taacgaacat tcagaccagc   6300
tcacaagaga agaaaatact gctatacgta ctccagaaca tttaatatcc caaaaaggct   6360
tttcatataa tgtggtaaat tcatctgctt tctctggatt tagtacagca agtggaaagc   6420
```

```
aagtttccat tttagaaagt tccttacaca aagttaaggg agtgttagag gaatttgatt    6480
taatcagaac tgagcatagt cttcactatt cacctacgtc tagacaaaat gtatcaaaaa    6540
tacttcctcg tgttgataag agaaacccag agcactgtgt aaactcagaa atggaaaaaa    6600
cctgcagtaa agaatttaaa ttatcaaata acttaaatgt tgaaggtggt tcttcagaaa    6660
ataatcactc tattaaagtt tctccatatc tctctcaatt tcaacaagac aaacaacagt    6720
tggtattagg aaccaaagtg tcacttgttg agaacattca tgttttggga aaagaacagg    6780
cttcacctaa aaacgtaaaa atggaaattg gtaaaactga aacttttttct gatgttcctg    6840 tgaaaacaaa tatagaagtt tgttctactt actccaaaga ttcagaaaac tactttgaaa    6900
cagaagcagt agaaattgct aaagctttta tggaagatga tgaactgaca gattctaaac    6960
tgccaagtca tgccacacat tctctttttta catgtcccga aaatgaggaa atggttttgt    7020
caaattcaag aattggaaaa agaagaggag agccccttat cttagtggga gaaccctcaa    7080 tcaaagaaa cttattaaat gaatttgaca ggataataga aaatcaagaa aaatccttaa    7140
aggcttcaaa aagcactcca gatggcacaa taaaagatcg aagattgttt atgcatcatg    7200
tttctttaga gccgattacc tgtgtaccct ttcgcacaac taaggaacgt caagagatac    7260
agaatccaaa ttttaccgca cctggtcaag aatttctgtc taaatctcat ttgtatgaac    7320
atctgacttt ggaaaaatct tcaagcaatt tagcagtttc aggacatcca ttttatcaag    7380
tttctgctac aagaaatgaa aaaatgagac acttgattac tacaggcaga ccaaccaaag    7440
tctttgttcc accttttaaa actaaatcac attttcacag agttgaacag tgtgttagga    7500
atattaactt ggaggaaaac agacaaaagc aaaacattga tggacatggc tctgatgata    7560
gtaaaaataa gattaatgac aatgagattc atcagtttaa caaaaacaac tccaatcaag    7620
cagcagctgt aactttcaca aagtgtgaag aagaaccttt agatttaatt acaagtcttc    7680
agaatgccag agatatacag gatatgcgaa ttaagaagaa acaaaggcaa cgcgtctttc    7740
cacagccagg cagtctgtat cttgcaaaaa catccactct gcctcgaatc tctctgaaag    7800
cagcagtagg aggccaagtt ccctctgcgt gttctcataa acagctgtat acgtatggcg    7860
tttctaaaca ttgcataaaa attaacagca aaaatgcaga gtcttttcag tttcacactg    7920
aagattattt tggtaaggaa agtttatgga ctggaaaagg aatacagttg gctgatggtg    7980
gatggctcat accctccaat gatggaaagg ctggaaaaga agaatttttat agggctctgt    8040 gtgacactcc aggtgtggat ccaaagctta tttctagaat ttgggtttat aatcactata    8100
gatggatcat atgaaactg gcagctatgg aatgtgcctt tcctaaggaa tttgctaata    8160
gatgcctaag cccagaaagg gtgcttcttc aactaaaata cagatatgat acggaaattg    8220
atagaagcag aagatcggct ataaaaagaa taatggaaag ggatgacaca gctgcaaaaa    8280
cacttgttct ctgtgtttct gacataattt cattgagcgc aaatatatct gaaacttcta    8340
gcaataaaac tagtagtgca gatacccaaa agtggccat tattgaactt acagatgggt    8400
ggtatgctgt taaggcccag ttagatcctc ccctcttagc tgtcttaaag aatggcagac    8460
tgacagttgg tcagaagatt attcttcatg gagcagaact ggtgggctct cctgatgcct    8520
gtacacctct tgaagcccca gaatctctta tgttaaagat ttctgctaac agtactcggc    8580
ctgctcgctg gtataccaaa cttggattct ttcctgaccc tagacctttt cctctgccct    8640
tatcatcgct tttcagtgat ggaggaaatg ttggttgtgt tgatgtaatt attcaaagag    8700 catacccta t acagtggatg gagaagacat catctggatt atacatattt cgcaatgaaa    8760
gagaggaaga aaaggaagca gcaaaatatg tggaggccca acaaaagaga ctagaagcct    8820
```

```
tattcactaa aattcaggag gaatttgaag aacatgaaga aaacacaaca aaaccatatt   8880
taccatcacg tgcactaaca agacagcaag ttcgtgcttt gcaagatggt gcagagcttt   8940
atgaagcagt gaagaatgca gcagacccag cttaccttga gggttatttc agtgaagagc   9000
agttaagagc cttgaataat cacaggcaaa tgttgaatga taagaaacaa gctcagatcc   9060
agttggaaat taggaaggcc atggaatctg ctgaacaaaa ggaacaaggt ttatcaaggg   9120
atgtcacaac cgtgtggaag ttgcgtattg taagctattc aaaaaaagaa aaagattcag   9180
ttatactgag tatttggcgt ccatcatcag atttatattc tctgttaaca gaaggaaaga   9240
gatacagaat ttatcatctt gcaacttcaa aatctaaaag taaatctgaa agagctaaca   9300
tacagttagc agcgacaaaa aaaactcagt atcaacaact accggtttca gatgaaattt   9360
tatttcagat ttaccagcca cgggagcccc ttcacttcag caaattttta gatccagact   9420
ttcagccatc ttgttctgag gtggacctaa taggatttgt cgtttctgtt gtgaaaaaaa   9480
caggacttgc cccctttcgtc tatttgtcag acgaatgtta caatttactg gcaataaagt   9540
tttggataga ccttaatgag gacattatta agcctcatat gttaattgct gcaagcaacc   9600
tccagtggcg accagaatcc aaatcaggcc ttcttacttt atttgctgga gattttctg   9660 tgttttctgc tagtccaaaa gagggccact ttcaagagac attcaacaaa atgaaaaata   9720
ctgttgagaa tattgacata cttttgcaatg aagcagaaaa caagcttatg catatactgc   9780
atgcaaatga tcccaagtgg tccaccccaa ctaaagactg tacttcaggg ccgtacactg   9840
ctcaaatcat tcctggtaca ggaaacaagc ttctgatgtc ttctcctaat tgtgagatat   9900
attatcaaag tcctttatca ctttgtatgg ccaaaaggaa gtctgtttcc acacctgtct   9960
cagcccagat gacttcaaag tcttgtaaag gggagaaaga gattgatgac caaaagaact  10020
gcaaaaagag aagagccttg gatttcttga gtagactgcc tttacctcca cctgttagtc  10080
ccatttgtac atttgtttct ccggctgcac agaaggcatt tcagccacca aggagttgtg  10140
gcaccaaata cgaaacaccc ataaagaaaa aagaactgaa ttctcctcag atgactccat  10200
ttaaaaaatt caatgaaatt tctcttttgg aaagtaattc aatagctgac gaagaacttg  10260
cattgataaa tacccaagct cttttgtctg gttcaacagg agaaaaacaa tttatatctg  10320
tcagtgaatc cactaggact gctcccacca gttcagaaga ttatctcaga ctgaaacgac  10380
gttgtactac atctctgatc aaagaacagg agagttccca ggccagtacg gaagaatgtg  10440
agaaaaataa gcaggacaca attcaaacta aaaaatatat ctaagcattt gcaaaggcga  10500
caataaatta ttgacgctta acctttccag tttataagac tggaatataa tttcaaacca  10560
cacattagta cttatgttgc acaatgagaa aagaaattag tttcaaattt acctcagcgt  10620
ttgtgtatcg ggcaaaaatc gttttgcccg attccgtatt ggtatacttt tgcttcagtt  10680
gcatatctta aaactaaatg taatttatta actaatcaag aaaaacatct ttggctgagc  10740
tcggtggctc atgcctgtaa tcccaacact ttgagaagct gaggtgggag gagtgcttga  10800
ggccaggagt tcaagaccag cctgggcaac atagggagac ccccatcttt acaaagaaaa  10860
aaaaaagggg aaaagaaaat cttttaaatc tttggatttg atcactacaa gtattatttt  10920
acaagtgaaa taaacatacc attttctttt agattgtgtc attaaatgga atgaggtctc  10980
ttagtacagt tattttgatg cagataattc cttttagttt agctactatt ttagggatt  11040 tttttagag gtaactcact atgaaatagt tctccttaat gcaaatatgt tggttctgct  11100
atagttccat cctgttcaaa agtcaggatg aatatgaaga gtggtgtttc cttttgagca  11160
```

```
attcttcatc cttaagtcag catgattata agaaaaatag aaccctcagt gtaactctaa    11220
ttccttttta ctattccagt gtgatctctg aaattaaatt acttcaacta aaaattcaaa    11280
tactttaaat cagaagattt catagttaat ttattttttt tttcaacaaa atggtcatcc    11340
aaactcaaac ttgagaaaat atcttgcttt caaattggca ctgatt                  11386

<210> SEQ ID NO 16
<211> LENGTH: 13147
<212> TYPE: DNA
<213> ORGANISM: Homo sapiens

<400> SEQUENCE: 16
ccggagcccg agccgaaggg cgagccgcaa acgctaagtc gctggccatt ggtggacatg      60
gcgcaggcgc gtttgctccg acgggccgaa tgttttgggg cagtgttttg agcgcggaga     120
ccgcgtgata ctggatgcgc atgggcatac cgtgctctgc ggctgcttgg cgttgcttct     180
tcctccagaa gtgggcgctg gcagtcacg cagggtttga accggaagcg ggagtaggta      240
gctgcgtggc taacggagaa aagaagccgt ggccgcggga ggaggcgaga ggagtcggga     300
tctgcgctgc agccaccgcc gcggttgata ctactttgac cttccgagtg cagtgacagt     360
gatgtgtgtt ctgaaattgt gaaccatgag tctagtactt aatgatctgc ttatctgctg     420
ccgtcaacta gaacatgata gagctacaga acgaagaaa gaagttgaga aatttaagcg      480
cctgattcga gatcctgaaa caattaaaca tctagatcgg cattcagatt ccaaacaagg     540
aaaatatttg aattgggatg ctgtttttag attttttacag aaatatattc agaaagaaac    600
agaatgtctg agaatagcaa aaccaaatgt atcagcctca acacaagcct ccaggcagaa     660
aaagatgcag gaaatcagta gtttggtcaa atacttcatc aaatgtgcaa acagaagagc     720
acctaggcta aatgtcaag aactcttaaa ttatatcatg gatacagtga aagattcatc      780
taatggtgct atttacggag ctgattgtag caacatacta ctcaaagaca ttctttctgt     840
gagaaaatac tggtgtgaaa tatctcagca acagtggtta gaattgttct ctgtgtactt     900
caggctctat ctgaaacctt cacaagatgt tcatagagtt ttagtggcta gaataattca     960
tgctgttacc aaaggatgct gttctcagac tgacggatta aattccaaat ttttggactt    1020 ttttccaag gctattcagt gtgcgagaca agaaaagagc tcttcaggtc taaatcatat     1080
cttagcagct cttactatct tcctcaagac tttggctgtc aactttcgaa ttcgagtgtg    1140
tgaattagga gatgaaattc ttcccacttt gctttatatt tggactcaac ataggcttaa    1200
tgattcttta aaagaagtca ttattgaatt atttcaactg caaatttata tccatcatcc    1260
gaaaggagcc aaaacccaag aaaaaggtgc ttatgaatca acaaaatgga aagtatttt    1320 atacaactta tatgatctgc tagtgaatga gataagtcat ataggaagta gaggaaagta    1380
ttcttcagga tttcgtaata ttgccgtcaa agaaaatttg attgaattga tggcagatat    1440
ctgtcaccag gtttttaatg aagataccag atccttggag attctcaat cttacactac    1500 tacacaaaga gaatctagtg attacagtgt cccttgcaaa aggaagaaaa tagaactagg    1560
ctgggaagta ataaaagatc accttcagaa gtcacagaat gattttgatc ttgtgccttg    1620
gctacagatt gcaacccaat taatatcaaa gtatcctgca agtttaccta actgtgagct    1680
gtctccatta ctgatgatac tatctcagct tctaccccaa cagcgacatg ggaacgtac     1740 accatatgtg ttacgatgcc ttacggaagt tgcattgtgt caagacaaga ggtcaaacct    1800
agaaagctca caaagtcag atttattaaa actctggaat aaaatttggt gtattacctt     1860
tcgtggtata agttctgagc aaatacaagc tgaaaacttt ggcttacttg agccataat     1920
```

```
tcagggtagt ttagttgagg ttgacagaga attctggaag ttatttactg ggtcagcctg   1980
cagaccttca tgtcctgcag tatgctgttt gactttggca ctgaccacca gtatagttcc   2040
aggaacggta aaatgggaaa tagagcaaaa tatgtgtgaa gtaaatagaa gcttttcttt   2100
aaaggaatca ataatgaaat ggctcttatt ctatcagtta gagggtgact tagaaaatag   2160
cacagaagtg cctccaattc ttcacagtaa ttttcctcat cttgtactgg agaaaattct   2220
tgtgagtctc actatgaaaa actgtaaagc tgcaatgaat ttttccaaa gcgtgccaga    2280
atgtgaacac caccaaaaag ataaagaaga actttcattc tcagaagtag aagaactatt   2340
tcttcagaca acttttgaca agatggactt tttaaccatt gtgagagaat gtggtataga   2400
aaagcaccag tccagtattg gcttctctgt ccaccagaat ctcaaggaat cactggatcg   2460
ctgtcttctg ggattatcag aacagcttct gaataattac tcatctgaga ttacaaattc   2520
agaaactctt gtccggtgtt cacgtctttt ggtgggtgtc cttggctgct actgttacat   2580
gggtgtaata gctgaagagg aagcatataa gtcagaatta ttccagaaag ccaagtctct   2640
aatgcaatgt gcaggagaaa gtatcactct gtttaaaaat aagacaaatg aggaattcag   2700
aattggttcc ttgagaaata tgatgcagct atgtacacgt tgcttgagca actgtaccaa   2760
gaagagtcca ataagattg catctggctt tttcctgcga ttgttaacat caaagctaat    2820
gaatgacatt gcagatattt gtaaaagttt agcatccttc atcaaaaagc catttgaccg   2880
tggagaagta gaatcaatgg aagatgatac taatggaaat ctaatggagg tggaggatca   2940
gtcatccatg aatctatttta acgattaccc tgatagtagt gttagtgatg caaacgaacc   3000
tggagagagc caaagtacca taggtgccat taatcctttta gctgaagaat atctgtcaaa   3060
gcaagatcta cttttcttag acatgctcaa gttcttgtgt ttgtgtgtaa ctactgctca   3120
gaccaatact gtgtccttta gggcagctga tattcggagg aaattgttaa tgttaattga   3180
ttctagcacg ctagaaccta ccaaatccct ccacctgcat atgtatctaa tgctttttaaa  3240
ggagcttcct ggagaagagt accccttgcc aatggaagat gttcttgaac ttctgaaacc   3300
actatccaat gtgtgttctt tgtatcgtcg tgaccaagat gtttgtaaaa ctattttaaa   3360
ccatgtcctt catgtagtga aaaacctagg tcaaagcaat atggactctg agaacacaag   3420
ggatgctcaa ggacagtttc ttacagtaat tggagcattt tggcatctaa caaggagag    3480
gaaatatata ttctctgtaa gaatggcccct agtaaattgc cttaaaactt tgcttgaggc   3540
tgatccttat tcaaaatggg ccattcttaa tgtaatggga aaagactttc ctgtaaatga   3600
agtatttaca caatttcttg ctgacaatca tcaccaagtt cgcatgttgg ctgcagagtc   3660
aatcaataga ttgttccagg acacgaaggg agattcttcc aggttactga agcacttcc    3720
tttgaagctt cagcaaacag cttttgaaaa tgcatacttg aaagctcagg aaggaatgag   3780
agaaatgtcc catagtgctg agaaccctga aactttggat gaaatttata atagaaaatc   3840
tgttttactg acgttgatag ctgtggtttt atcctgtagc cctatctgcg aaaaacaggc   3900
tttgtttgcc ctgtgtaaat ctgtgaaaga gaatggatta gaacctcacc ttgtgaaaaa   3960
ggttttagag aaagtttctg aaactttttgg atatagacgt ttagaagact ttatggcatc   4020
tcatttagat tatctggttt tggaatggct aaatcttcaa gatactgaat acaacttatc   4080
ttcttttcct tttattttat taaactacac aaatattgag gatttctata gatcttgtta   4140
taaggttttg attccacatc tggtgattag aagtcatttt gatgaggtga agtccattgc   4200
taatcagatt caagaggact ggaaaagtct tctaacagac tgctttccaa agattcttgt   4260
```

```
aaatattctt ccttatttg cctatgaggg taccagagac agtgggatgg cacagcaaag    4320
agagactgct accaaggtct atgatatgct taaaagtgaa aacttattgg gaaaacagat    4380
tgatcactta ttcattagta atttaccaga gattgtggtg gagttattga tgacgttaca    4440
tgagccagca aattctagtg ccagtcagag cactgacctc tgtgactttt cagggatt     4500 ggatcctgct cctaatccac ctcatttcc atcgcatgtg attaaagcaa catttgccta    4560
tatcagcaat tgtcataaaa ccaagttaaa aagcatttta gaattctt ccaaaagccc     4620 tgattcctat cagaaaattc ttcttgccat atgtgagcaa gcagctgaaa caataatgt    4680 ttataagaag cacagaattc ttaaaatata tcacctgttt gttagtttat tactgaaaga   4740 tataaaagt ggcttaggag gagcttggc ctttgttctt cgagacgtta tttatacttt     4800
gattcactat atcaaccaaa ggccttcttg tatcatggat gtgtcattac gtagcttctc   4860
cctttgttgt gacttattaa gtcaggtttg ccagacagcc gtgacttact gtaaggatgc   4920
tctagaaaac catcttcatg ttattgttgg tacacttata ccccttgtgt atgagcaggt   4980
ggaggttcag aaacaggtat tggacttgtt gaaatactta gtgatagata acaaggataa   5040
tgaaaacctc tatatcacga ttaagctttt agatcctttt cctgaccatg ttgttttaa    5100 ggatttgcgt attactcagc aaaaaatcaa atacagtaga ggaccctttt cactcttgga   5160
ggaaattaac cattttctct cagtaagtgt ttatgatgca cttccattga caagacttga   5220
aggactaaag gatcttcgaa gacaactgga actacataaa gatcagatgg tggacattat   5280
gagagcttct caggataatc cgcaagatgg gattatggtg aaactagttg tcaatttgtt   5340
gcagttatcc aagatggcaa taaccacac tggtgaaaaa gaagttctag aggctgttgg    5400
aagctgcttg ggagaagtgg gtcctataga tttctctacc atagctatac aacatagtaa   5460
agatgcatct tataccaagg cccttaagtt atttgaagat aaagaacttc agtggacctt   5520
cataatgctg acctacctga ataacacact ggtagaagat tgtgtcaaag ttcgatcagc   5580
agctgttacc tgtttgaaaa acattttagc cacaaagact ggacatagtt tctgggagat   5640
ttataagatg acaacagatc caatgctggc ctatctacag cctttagaa catcaagaaa    5700 aaagttttta gaagtaccca gatttgacaa agaaaaccct tttgaaggcc tggatgatat   5760
aaatctgtgg attcctctaa gtgaaaatca tgacatttgg ataaagacac tgacttgtgc   5820 tttttggac agtggaggca caaaatgtga aattcttcaa ttattaaagc caatgtgtga    5880
agtgaaaact gacttttgtc agactgtact tccatacttg attcatgata ttttactcca   5940
agatacaaat gaatcatgga gaaatctgct ttctacacat gttcagggat ttttcaccag   6000
ctgtcttcga cacttctcgc aaacgagccg atccacaacc cctgcaaact tggattcaga   6060
gtcagagcac ttttccgat gctgtttgga taaaaatca caagaacaa tgcttgctgt      6120 tgtggactac atgagaagac aaaagagacc ttcttcagga acaatttta atgatgcttt    6180 ctggctggat ttaaattatc tagaagttgc caaggtagct cagtcttgtg ctgctcactt   6240
tacagcttta ctctatgcag aaatctatgc agataagaaa agtatggatg atcaagagaa   6300
aagaagtctt gcatttgaag aaggaagcca gagtacaact atttctagct tgagtgaaaa   6360
aagtaaagaa gaaactggaa taagtttaca ggatcttctc ttagaaatct acagaagtat   6420
aggggagcca gatagtttgt atggctgtgg tgagggaag atgttacaac ccattactag    6480
actacgaaca tatgaacacg aagcaatgtg gggcaaagcc ctagtaacat atgacctcga   6540
aacagcaatc ccctcatcaa cacgccaggc aggaatcatt caggccttgc agaatttggg   6600
actctgccat attctttccg tctatttaaa aggattggat tatgaaaata agactggtg    6660
```

```
tcctgaacta aagaacttc attaccaagc agcatggagg aatatgcagt gggaccattg    6720
cacttccgtc agcaaagaag tagaaggaac cagttaccat gaatcattgt acaatgctct    6780
acaatctcta agagacagag aattctctac attttatgaa agtctcaaat atgccagagt    6840
aaaagaagtg gaagagatgt gtaagcgcag ccttgagtct gtgtattcgc tctatcccac    6900
acttagcagg ttgcaggcca ttggagagct ggaaagcatt ggggagcttt tctcaagatc    6960
agtcacacat agacaactct ctgaagtata tattaagtgg cagaaacact cccagcttct    7020
caaggacagt gattttagtt ttcaggagcc tatcatggct ctacgcacag tcattttgga    7080
gatcctgatg gaaaggaaa tggacaactc acaaagagaa tgtattaagg acattctcac    7140
caaacacctt gtagaactct ctatactggc cagaactttc aagaacactc agctccctga    7200
aagggcaata tttcaaatta aacagtacaa ttcagttagc tgtggagtct ctgagtggca    7260
gctggaagaa gcacaagtat tctgggcaaa aaggagcag agtcttgccc tgagtattct    7320
caagcaaatg atcaagaagt tggatgccag ctgtgcagcg aacaatccca gcctaaaact    7380
tacatacaca gaatgtctga gggtttgtgg caactggtta gcagaaacgt gcttagaaaa    7440
tcctgcggtc atcatgcaga cctatctaga aaggcagta aagttgctg gaaattatga    7500 tggagaaagt agtgatgagc taagaaatgg aaaaatgaag gcatttctct cattagcccg    7560
gttttcagat actcaatacc aaagaattga aaactacatg aaatcatcgg aatttgaaaa    7620
caagcaagct ctcctgaaaa gagccaaaga ggaagtaggt ctccttaggg aacataaaat    7680
tcagacaaac agatacacag taaaggttca gcgagagctg gagttggatg aattagccct    7740
gcgtgcactg aaagaggatc gtaaacgctt cttatgtaaa gcagttgaaa attatatcaa    7800
ctgcttatta agtggagaag aacatgatat gtgggtattc cgactttgtt ccctctggct    7860
tgaaaattct ggagtttctg aagtcaatgg catgatgaag agagacggaa tgaagattcc    7920
aacatataaa ttttgcctc ttatgtacca attggctgct agaatgggga ccaagatgat    7980
gggaggccta ggatttcatg aagtcctcaa taatctaatc tctagaattt caatggatca    8040
cccccatcac actttgttta ttatactggc cttagcaaat gcaaacagag atgaatttct    8100
gactaaacca gaggtagcca aagaagcag aataactaaa aatgtgccta acaaagctc    8160 tcagcttgat gaggatcgaa cagaggctgc aaatagaata atatgtacta tcagaagtag    8220
gagacctcag atggtcagaa gtgttgaggc actttgtgat gcttatatta tattagcaaa    8280
cttagatgcc actcagtgga agactcagag aaaaggcata aatattccag cagaccagcc    8340
aattactaaa cttaagaatt tagaagatgt tgttgtccct actatggaaa ttaaggtgga    8400
ccacacagga gaatatggaa atctggtgac tatacagtca tttaaagcag aatttcgctt    8460
agcaggaggt gtaaatttac caaaaataat agattgtgta ggttccgatg caaggagag    8520 gagacagctt gttaagggcc gtgatgacct gagacaagat gctgtcatgc aacaggtctt    8580
ccagatgtgt aatacattac tgcagagaaa cacggaaact aggaagagga attaactat    8640 ctgtacttat aaggtggttc ccctctctca gcgaagtggt gttcttgaat ggtgcacagg    8700
aactgtcccc attggtgaat ttcttgttaa caatgaagat ggtgctcata aaagatacag    8760
gccaaatgat ttcagtgcct ttcagtgcca aagaaaatg atggaggtgc aaaaaaagtc    8820
ttttgaagag aaatatgaag tcttcatgga tgtttgccaa aattttcaac cagttttccg    8880
ttacttctgc atggaaaaat tcttggatcc agctatttgg tttgagaagc gattggctta    8940
tacgcgcagt gtagctactt cttctattgt tggttacata cttggacttg gtgatagaca    9000
```

```
tgtacagaat atcttgataa atgagcagtc agcagaactt gtacatatag atctaggtgt    9060
tgcttttgaa cagggcaaaa tccttcctac tcctgagaca gttcctttta gactcaccag    9120
agatattgtg gatggcatgg gcattacggg tgttgaaggt gtcttcagaa gatgctgtga    9180
gaaaaccatg gaagtgatga gaaactctca ggaaactctg ttaaccattg tagaggtcct    9240
tctatatgat ccactctttg actggaccat gaatcctttg aaagctttgt atttacagca    9300
gaggccggaa gatgaaactg agcttcaccc tactctgaat gcagatgacc aagaatgcaa    9360
acgaaatctc agtgatattg accagagttt caacaaagta gctgaacgtg tcttaatgag    9420
actacaagag aaactgaaag gagtggaaga aggcactgtg ctcagtgttg gtggacaagt    9480
gaatttgctc atacagcagg ccatagaccc caaaaatctc agccgacttt tcccaggatg    9540
gaaagcttgg gtgtgatctt cagtatatga attaccctttt cattcagcct ttagaaatta    9600
tattttagcc tttattttta acctgccaac atactttaag tagggattaa tatttaagtg    9660
aactattgtg ggttttttg aatgttggtt ttaatacttg atttaatcac cactcaaaaa    9720
tgttttgatg gtcttaagga acatctctgc tttcactctt tagaaataat ggtcattcgg    9780
gctgggcgca gcggctcacg cctgtaatcc cagcactttg ggaggccgag gtgagcggat    9840
cacaaggtca ggagttcgag accagcctgg ccaagagacc agcctggcca gtatggtgaa    9900
accctgtctc tactaaaaat acaaaaatta gccgagcatg gtggcgggca cctgtaatcc    9960
cagctactcg agaggctgag gcaggagaat ctcttgaacc tgggaggtga aggttgctgt   10020
gggccaaaat catgccattg cactccagcc tgggtgacaa gagcgaaact ccatctcaaa   10080
aaaaaaaaaa aaaaaacaga aacgtatttg gattttttcct agtaagatca ctcagtgtta   10140
ctaaataatg aagttgttat ggagaacaaa tttcaaagac acagttagtg tagttactat   10200
ttttttaagt gtgtattaaa acttctcatt ctattctctt tatcttttaa gcccttctgt   10260
actgtccatg tatgttatct ttctgtgata acttcataga ttgccttcta gttcatgaat   10320
tctcttgtca gatgtatata atctctttta ccctatccat tgggcttctt ctttcagaaa   10380
ttgttttca tttctaatta tgcatcattt ttcagatctc tgtttcttga tgtcattttt   10440
aatgttttt taatgttttt tatgtcacta attatttaa atgtctgtac ttgatagaca   10500
ctgtaatagt tctattaaat ttagttcctg ctgtttatat ctgttgatttt tgtatttga   10560
taggctgttc atccagtttt gtcttttga aaagtgagtt tattttcagc aaggctttat   10620
ctatgggaat cttgagtgtc tgtttatgtc atattcccag ggctgttgct gcacacaagc   10680
ccattcttat tttaatttct tggctttagg gtttccatac ctgaagtgta gcataaatac   10740
tgataggaga tttcccaggc caaggcaaac acacttcctc ctcatctcct tgtgctagtg   10800
ggcagaatat ttgattgatg ccttttttcac tgagagtata agcttccatg tgtcccacct   10860
ttatggcagg ggtggaagga ggtacattta attcccactg cctgccttg gcaagccctg   10920
ggttctttgc tccccatata gatgtctaag ctaaaagccg tgggttaatg agactggcaa   10980
attgttccag gacagctaca gcatcagctc acatattcac ctctctggtt tttcattccc   11040
ctcattttt tctgagacag agtcttgctc tgtcacccag gctggagtgc agtggcatga   11100
tctcagctca ctgaaacctc tgcctcctgg gttcaagcaa ttctcctgcc tcagcctccc   11160
gagtagctgg gactacaggc gtgtgccaac acgcccggct aatttttttgt attttttатта   11220
gagacggagt ttcaccgtgt tagccaggat ggtctcgatc gcttgacctc gtgatccacc   11280
ctcctcggcc tcccaaagtg ctgggattac aggtgtgagc caccgcgccc ggcctcattc   11340
ccctcatttt tgaccgtaag gatttcccct ttcttgtaag ttctgctatg tatttaaaag   11400
```

```
aatgttttct acattttatc cagcatttct ctgtgttctg ttggaaggga agggcttagg    11460
tatctagttt gatacatagg tagaagtgga acatttctct gtcccccagc tgtcatcata    11520
taagataaac atcagataaa aagccacctg aaagtaaaac tactgactcg tgtattagtg    11580
agtataatct cttctccatc cttaggaaaa tgttcatccc agctgcggag attaacaaat    11640
gggtgattga gctttctcct cgtatttgga ccttgaaggt tatataaatt ttttcttat     11700 gaagagttgg catttctttt tattgccaat ggcaggcact cattcatatt tgatctcctc    11760
accttcccct cccctaaaac caatctccag aacttttggg actataaatt tcttggtttg    11820
acttctggag aactgttcag aatattactt tgcatttcaa attacaaact taccttggtg    11880 tatcttttc  ttacaagctg cctaaatgaa tatttggtat atattggtag ttttattact    11940
atagtaaatc aaggaaatgc agtaaactta aaatgtcttt aagaaagccc tgaaatcttc    12000
atgggtgaaa ttagaaatta tcaactagat aatagtatag ataaatgaat ttgtagctaa    12060
ttcttgctag ttgttgcatc cagagagctt tgaataacat cattaatcta ctctttagcc    12120
ttgcatggta tgctatgagg ctcctgttct gttcaagtat tctaatcaat ggctttgaaa    12180
agtttatcaa atttacatac agatcacaag cctaggagaa ataactaatt cacagatgac    12240
agaattaaga ttataaaaga ttttttttt gtaatttag tagagacagg gttgccattg       12300
tattccagcc ttggcgacag agcaagactc tgcctcaaaa aaaaaaaaaa aaggttttg      12360 gcaagctgga actctttctg caaatgacta agatagaaaa ctgccaagga caaatgagga    12420
gtagttagat tttgaaaata ttaatcatag aatagttgtt gtatgctaag tcactgaccc    12480
atattatgta cagcatttct gatctttact ttgcaagatt agtgatacta tcccaataca    12540
ctgctggaga aatcagaatt tggagaaata agttgtccaa ggcaagaaga tagtaaatta    12600
taagtacaag tgtaatatgg acagtatcta acttgaaaag atttcaggcg aaaagaatct    12660 ggggttttgcc agtcagttgc tcaaaaggtc aatgaaaacc aaatagtgaa gctatcagag   12720
aagctaataa attatagact gcttgaacag ttgtgtccag attaagggag ataatagctt    12780
tcccacccta ctttgtgcag gtcataccctc cccaaagtgt ttacctaatc agtaggttca    12840
caaactcttg gtcattatag tatatgccta aatgtatgc acttaggaat gctaaaaatt       12900
taaatatggt ctaaagcaaa taaaagcaaa gaggaaaaac tttggacagc gtaaagacta    12960
gaatagtctt taaaagaa   agccagtata ttggtttgaa atatagagat gtgtcccaat    13020
ttcaagtatt ttaattgcac cttaatgaaa ttatctattt tctatagatt ttagtactat    13080
tgaatgtatt actttactgt tacctgaatt tattataaag tgttttttgaa taataattc     13140 taaaagc                                                              13147
```

<210> SEQ ID NO 17  
<211> LENGTH: 8258  
<212> TYPE: DNA  
<213> ORGANISM: Homo sapiens

<400> SEQUENCE: 17

```
ttccgggagg agttttggcc tccacacggc tccgtcgggc gccgcgctct tccggcagcg      60
gtagctttgg agacgccggg aacccgcgtt ggcgtggttg actagtgcct cgcagcctca    120
gcatggggga acatggcctg gagctggctt ccatgatccc cgccctgcgg gagctgggca    180
gtgccacacc agaggaatat aatacagttg tacagaagcc aagacaaatt ctgtgtcaat    240
tcattgaccg gatacttaca gatgtaaatg ttgttgctgt agaacttgta aagaaaactg    300
```

```
actctcagcc aacctccgtg atgttgcttg atttcatcca gcatatcatg aaatcctccc      360
cacttatgtt tgtaaatgtg agtggaagcc atgaggccaa aggcagttgt attgaattca      420
gtaattggat cataacgaga cttctgcgga ttgcagcaac tccctcctgt catttgttac      480
acaagaaaat ctgtgaagtc atctgttcat tattatttct ttttaaaagc aagagtcctg      540 ctattttttgg ggtactcaca aaagaattat tacaacttttt tgaagacttg gtttacctcc      600
atagaagaaa tgtgatgggt catgctgtgg aatggccagt ggtcatgagc cgattttttaa      660 gtcaattaga tgaacacatg ggatatttac aatcagctcc tttgcagttg atgagtatgc      720
aaaatttaga atttattgaa gtcactttat taatggttct tactcgtatt attgcaattg      780
tgttttttag aaggcaagaa ctcttacttt ggcagatagg ttgtgttctg ctagagtatg      840
gtagtccaaa aattaaatcc ctagcaatta gcttttttaac agaactttttt cagcttggag      900 gactaccagc acaaccagct agcactttttt tcagctcatt tttggaatta ttaaaacacc      960
ttgtagaaat ggatactgac caattgaaac tctatgaaga gccattatca aagctgataa     1020
agacactatt tccctttgaa gcagaagctt atagaaaatat tgaacctgtc tatttaaata     1080
tgctgctgga aaaactctgt gtcatgtttg aagacggtgt gctcatgcgg cttaagtctg     1140
atttgctaaa agcagcttttg tgccatttac tgcagtattt ccttaaattt gtgccagctg     1200
ggtatgaatc tgctttacaa gtcaggaagg tctatgtgag aaatatttgt aaagctcttt     1260
tggatgtgct tggaattgag gtagatgcag agtacttgtt gggcccactt tatgcagctt     1320
tgaaaatgga agtatggaa atcattgagg agattcaatg ccaaactcaa caggaaaacc     1380
tcagcagtaa tagtgatgga atatcaccca aaaggcgtcg tctcagctcg tctctaaacc     1440
cttctaaaag agcaccaaaa cagactgagg aaattaaaca tgtggacatg aaccaaaaga     1500
gcatattatg gagtgcactg aaacagaaag ctgaatccct tcagatttcc cttgaataca     1560
gtggcctaaa gaatcctgtt attgagatgt tagaaggaat tgctgttgtc ttacaactga     1620
ctgctctgtg tactgttcat tgttctcatc aaaacatgaa ctgccgtact ttcaaggact     1680
gtcaacataa atccaagaag aaaccttctg tagtgataac ttggatgtca ttggattttt     1740
acacaaaagt gcttaagagc tgtagaagtt tgttagaatc tgttcagaaa ctggacctgg     1800
aggcaaccat tgataaggtg gtgaaaattt atgatgcttt gatttatatg caagtaaaca     1860
gttcatttga agatcatatc ctggaagatt tatgtggtat gctctcactt ccatggatt     1920 attcccattc tgatgatggc tgtttaaagt tgaccacatt tgccgctaat cttctaacat     1980
taagctgtag gatttcagat agctattcac cacaggcaca atcacgatgt gtgtttcttc     2040
tgactctgtt tccaagaaga atattccttg agtggagaac agcagtttac aactgggccc     2100
tgcagagctc ccatgaagta atccgggcta gttgtgttag tggatttttt atcttattgc     2160
agcagcagaa ttcttgtaac agagttccca agattcttat agataaagtc aaagatgatt     2220
ctgacattgt caagaaagaa tttgcttcta tacttggtca acttgtctgt actcttcacg     2280
gcatgtttta tctgacaagt tctttaacag aaccttctc tgaacacgga catgtggacc     2340
tcttctgtag gaacttgaaa gccacttctc aacatgaatg ttcatcttct caactaaaag     2400
cttctgtctg caagccattc cttttcctac tgaaaaaaaa aatacctagt ccagtaaaac     2460
ttgctttcat agataatcta catcatcttt gtaagcatct tgattttaga gaagatgaaa     2520
cagatgtaaa agcagttctt ggaacttttat taaatttaat ggaagatcca gacaaagatg     2580
ttagagtggc ttttagtgga aatatcaagc acatattgga atccttggac tctgaagatg     2640
gatttataaa ggagcttttt gtcttaagaa tgaaggaagc atatacacat gcccaaatat     2700
```

```
caagaaataa tgagctgaag gataccttga ttcttacaac aggggatatt ggaagggccg    2760
caaaaggaga tttggtacca tttgcactct tacacttatt gcattgtttg ttatccaagt    2820
cagcatctgt ctctggagca gcatacacag aaattagagc tctggttgca gctaaaagtg    2880
ttaaactgca aagttttttc agccagtata agaaacccat ctgtcagttt ttggtagaat    2940
cccttcactc tagtcagatg acagcacttc cgaatactcc atgccagaat gctgacgtgc    3000
gaaaacaaga tgtggctcac cagagagaaa tggctttaaa tacgttgtct gaaattgcca    3060
acgttttcga ctttcctgat cttaatcgtt ttcttactag gacattacaa gttctactac    3120
ctgatcttgc tgccaaagca agccctgcag cttctgctct cattcgaact ttaggaaaac    3180
aattaaatgt caatcgtaga gagattttaa taaacaactt caaatatatt ttttctcatt    3240
tggtctgttc ttgttccaaa gatgaattag aacgtgccct tcattatctg aagaatgaaa    3300
cagaaattga actggggagc ctgttgagac aagatttcca aggattgcat aatgaattat    3360
tgctgcgtat tggagaacac tatcaacagg ttttttaatgg tttgtcaata cttgcctcat    3420
ttgcatccag tgatgatcca tatcagggcc cgagagatat catatcacct gaactgatgg    3480
ctgattattt acaacccaaa ttgttgggca ttttggcttt ttttaacatg cagttactga    3540
gctctagtgt tggcattgaa gataagaaaa tggccttgaa cagtttgatg tctttgatga    3600
agttaatggg acccaaacat gtcagttctg tgagggtgaa gatgatgacc acactgagaa    3660
ctggccttcg attcaaggat gattttcctg aattgtgttg cagagcttgg gactgctttg    3720
ttcgctgcct ggatcatgct tgtctgggct cccttctcag tcatgtaata gtagctttgt    3780
tacctcttat acacatccag cctaaagaaa ctgcagctat cttccactac ctcataattg    3840
aaaacaggga tgctgtgcaa gattttcttc atgaaatata ttttttacct gatcatccag    3900
aattaaaaaa gataaaagcc gttctccagg aatacagaaa ggagacctct gagagcactg    3960
atcttcagac aactcttcag ctctctatga aggccattca acatgaaaat gtcgatgttc    4020
gtattcatgc tcttacaagc ttgaaggaaa ccttgtataa aaatcaggaa aaactgataa    4080
agtatgcaac agacagtgaa acagtagaac ctattatctc acagttggtg acagtgcttt    4140
tgaaaggttg ccaagatgca aactctcaag ctcggttgct ctgtggggaa tgtttagggg    4200 aattggggc gatagatcca ggtcgattag atttctcaac aactgaaact caaggaaaag    4260
attttacatt tgtgactgga gtagaagatt caagctttgc ctatggatta ttgatggagc    4320
taacaagagc ttaccttgcg tatgctgata atagccgagc tcaagattca gctgcctatg    4380
ccattcagga gttgctttct atttatgact gtagagagat ggagaccaac ggcccaggtc    4440
accaattgtg gaggagattt cctgagcatg ttcgggaaat actagaacct catctaaata    4500
ccagatacaa gagttctcag aagtcaaccg attggtctgg agtaaagaag ccaatttact    4560
taagtaaatt gggtagtaac tttgcagaat ggtcagcatc ttgggcaggt tatcttatta    4620
caaaggttcg acatgatctt gccagtaaaa ttttcacctg ctgtagcatt atgatgaagc    4680
atgatttcaa agtgaccatc tatcttcttc cacatattct ggtgtatgtc ttactgggtt    4740
gtaatcaaga agatcagcag gaggtttatg cagaaattat ggcagttcta aagcatgacg    4800
atcagcatac cataaatacc caagacattg catctgatct gtgtcaactc agtacacaga    4860
ctgtgttctc catgcttgac catctcacac agtgggcaag gcacaaattt caggcactga    4920
aagctgagaa atgccacac agcaaatcaa acagaaataa ggtagactca atggtatcta    4980
ctgtggatta tgaagactat cagagtgtaa cccgttttct agacctcata ccccaggata    5040
```

```
ctctggcagt agcttccttt cgctccaaag catacacacg agctgtaatg cactttgaat    5100
catttattac agaaaagaag caaaatattc aggaacatct tggatttta cagaaattgt     5160
atgctgctat gcatgaacct gatggagtgg ccggagtcag tgcaattaga aaggcagaac    5220
catctctaaa agaacagatc cttgaacatg aaagccttgg cttgctgagg gatgccactg    5280
cttgttatga cagggctatt cagctagaac cagaccagat cattcattat catggtgtag    5340
taaagtccat gttaggtctt ggtcagctgt ctactgttat cactcaggtg aatggagtgc    5400
atgctaacag gtccgagtgg acagatgaat taaacacgta cagagtggaa gcagcttgga    5460
aattgtcaca gtgggatttg gtggaaaact atttggcagc agatggaaaa tctacaacat    5520
ggagtgtcag actgggacag ctattattat cagccaaaaa aagagatatc acagcttttt    5580
atgactcact gaaactagtg agagcagaac aaattgtacc tctttcagct gcaagctttg    5640
aaagaggctc ctaccaacga ggatatgaat atattgtgag attgcacatg ttatgtgagt    5700
tggagcatag catcaaacca cttttccagc attctccagg tgacagttct caagaagatt    5760
ctctaaactg ggtagctcga ctagaaatga cccagaattc ctacagagcc aaggagccta    5820
tcctggctct ccggagggct ttactaagcc tcaacaaaag accagattac aatgaaatgg    5880
ttggagaatg ctggctgcag agtgccaggg tagctagaaa ggctggtcac caccagacag    5940
cctacaatgc tctccttaat gcaggggaat cacgactcgc tgaactgtac gtggaaaggg    6000
caaagtggct ctggtccaag ggtgatgttc accaggcact aattgttctt caaaaaggtg    6060
ttgaattatg ttttcctgaa aatgaaaccc cacctgaggg taagaacatg ttaatccatg    6120
gtcgagctat gctactagtg ggccgattta tggaagaaac agctaacttt gaaagcaatg    6180
caattatgaa aaatataag gatgtgaccg cgtgcctgcc agaatgggag gatgggcatt      6240
tttaccttgc caagtactat gacaaattga tgcccatggt cacagacaac aaaatggaaa    6300
agcaaggtga tctcatccgg tatatagttc ttcattttgg cagatctcta caatatggaa    6360
atcagttcat atatcagtca atgccacgaa tgttaactct atggcttgat tatggtacaa    6420
aggcatatga atgggaaaaa gctggccgct ccgatcgtgt acaaatgagg aatgatttgg    6480
gtaaaataaa caaggttatc acagagcata caaactattt agctccatat caattttga     6540
ctgcttttc acaattgatc tctcgaattt gtcattctca cgatgaagtt tttgttgtct     6600
tgatggaaat aatagccaaa gtatttctag cctatcctca acaagcaatg tggatgatga    6660
cagctgtgtc aaagtcatct tatcccatgc gtgtgaacag atgcaaggaa tcctcaata      6720
aagctattca tatgaaaaaa tccttagaga gtttgttgg agatgcaact cgcctaacag      6780
ataagcttct agaattgtgc aataaaccgg ttgatggaag tagttccaca ttaagcatga    6840
gcactcattt taaaatgctt aaaaagctgg tagaagaagc aacatttagt gaaatcctca    6900
ttcctctaca atcagtcatg atacctacac ttccatcaat tctgggtacc catgctaacc    6960
atgctagcca tgaaccattt cctggacatt gggcctatat tgcagggttt gatgatatgg    7020
tggaaattct tgcttctctt cagaaaccaa agaagatttc tttaaaaggc tcagatggaa    7080
agttctacat catgatgtgt aagccaaaag atgacctgag aaaggattgt agactaatgg    7140
aattcaattc cttgattaat aagtgcttaa gaaaagatgc agagtctcgt agaagagaac    7200
ttcatattcg aacatatgca gttattccac taaatgatga atgtgggatt attgaatggg    7260
tgaacaacac tgctggtttg agacctattc tgaccaaact atataagaa aagggagtgt     7320
atatgacagg aaaagaactt cgccagtgta tgctaccaaa gtcagcagct ttatctgaaa    7380
aactcaaagt attccgagaa tttctcctgc ccaggcatcc tcctatttt catgagtggt      7440
```

```
ttctgagaac attccctgat cctacatcat ggtacagtag tagatcagct tactgccgtt    7500
ccactgcagt aatgtcaatg gttggttata ttctggggct tggagaccgt catggtgaaa    7560
atattctctt tgattctttg actggtgaat gcgtacatgt agatttcaat tgtcttttca    7620
ataagggaga aacctttgaa gttccagaaa ttgtgccatt tcgcctgact cataatatgg    7680
ttaatggaat gggtcctatg gaacagagg gtcttttcg aagagcatgt gaagttacaa      7740
tgaggctgat gcgtgatcag cgagagcctt aatgagtgt cttaaagact tttctacatg     7800
atcctcttgt ggaatggagt aaaccagtga agggcattc caaagcgcca ctgaatgaaa     7860
ctggagaagt tgtcaatgaa aaggccaaga cccatgttct tgacattgag cagcgactac    7920
aaggtgtaat caagactcga aatagagtga caggactgcc gttatctatt gaaggacatg    7980
tgcattacct tatacaggaa gctactgatg aaaacttact atgccagatg tatcttggtt    8040
ggactccata tatgtgaaat gaaattatgt aaaagaatat gttaataatc taaaagtaat    8100
gcatttggta tgaatctgtg gttgtatctg ttcaattcta aagtacaaca taaatttacg    8160
ttctcagcaa ctgttatttc tctctgatca ttaattatat gtaaaataat atacattcag    8220
ttattaagaa ataaactgct ttcttaatac aaaaaaaa                            8258

<210> SEQ ID NO 18
<211> LENGTH: 5141
<212> TYPE: DNA
<213> ORGANISM: Homo sapiens

<400> SEQUENCE: 18
acgttatcca tgaagtgtcg cgagagaaac ggacgccgtt ctctcccgcg gaattcaggt      60
ttacggccct gcgggttctc agagaatttc tagaatttgg aatcgagtgc attttctgac     120
atttgagtac agtacccagg ggttcttgga gaagaacctg gtcccagagg agcttgactg     180
accataaaaa tgagtactgc agatgcactt gatgatgaaa acacatttaa aatattagtt     240
gcaacagata ttcatcttgg atttatggag aaagatgcag tcagaggaaa tgatacgttt     300
gtaacactcg atgaaatttt aagacttgcc caggaaaatg aagtggattt tattttgtta     360
ggtggtgatc ttttcatga aaataagccc tcaaggaaaa cattacatac ctgcctcgag      420
ttattaagaa atattgtat gggtgatcgg cctgtccagt ttgaaattct cagtgatcag      480
tcagtcaact ttggttttag taagtttcca tgggtgaact atcaagatgg caacctcaac     540
atttcaattc cagtgtttag tattcatggc aatcatgacg atcccacagg ggcagatgca     600
ctttgtgcct tggacatttt aagttgtgct ggatttgtaa atcactttgg acgttcaatg     660
tctgtggaga agatagacat tagtccggtt ttgcttcaaa aaggaagcac aaagattgcg     720
ctatatggtt taggatccat tccagatgaa aggctctatc gaatgtttgt caataaaaaa    780
gtaacaatgt tgagaccaaa ggaagatgag aactcttggt ttaacttatt tgtgattcat     840
cagaacagga gtaaacatgg aagtactaac ttcattccag aacaattttt ggatgacttc    900
attgatcttg ttatctgggg ccatgaacat gagtgtaaaa tagctccaac caaaaatgaa    960
caacagctgt tttatatctc acaacctgga agctcagtgg ttacttctct ttccccagga   1020
gaagctgtaa agaaacatgt tggtttgctg cgtattaaag gaggaagat gaatatgcat    1080 aaaattcctc ttcacacagt gcggcagttt ttcatggagg atattgttct agctaatcat   1140
ccagacattt ttaacccaga taatcctaaa gtaacccaag ccatacaaag cttctgtttg   1200
gagaagattg aagaaatgct tgaaaatgct gaacgggaac gtctgggtaa ttctcaccag   1260
```

```
ccagagaagc ctcttgtacg actgcgagtg gactatagtg gaggttttga acctttcagt   1320
gttcttcgct ttagccagaa atttgtggat cgggtagcta atccaaaaga cattatccat   1380
tttttcaggc atagagaaca aaaggaaaaa acaggagaag agatcaactt tgggaaactt   1440
atcacaaagc cttcagaagg aacaacttta agggtagaaa atcttgtaaa acagtacttt   1500
caaaccgcag agaagaatgt gcagctctca ctgctaacag aaagagggat gggtgaagca   1560
gtacaagaat ttgtggacaa ggaggagaaa gatgccattg aggaattagt gaaataccag   1620
ttggaaaaaa cacagcgatt tcttaaagaa cgtcatattg atgccctcga agacaaaatc   1680
gatgaggagg tacgtcgttt cagagaaacc agacaaaaaa atactaatga agaagatgat   1740
gaagtccgtg aggctatgac cagggccaga gcactcagat ctcagtcaga ggagtctgct   1800
tctgccttta gtgctgatga ccttatgagt atagatttag cagaacagat ggctaatgac   1860
tctgatgata gcatctcagc agcaaccaac aaaggaagag gccgaggaag aggtcgaaga   1920
ggtggaagag gcagaattc agcatcgaga ggagggtctc aaagaggaag agcagacact   1980
ggtctggaga cttctacccg tagcaggaac tcaaagactc tgtgtcagc atctagaaat   2040
atgtctatta tagatgcctt taaatctaca agacagcagc cttcccgaaa tgtcactact   2100
aagaattatt cagaggtgat tgaggtagat gaatcagatg tggaagaaga cattttcct   2160
accacttcaa agacagatca aaggtggtcc agcacatcat ccagcaaaat catgtcccag   2220
agtcaagtat cgaaagggt tgattttgaa tcaagtgagg atgatgatga tgatcctttt   2280
atgaacacta gttctttaag aagaaataga agataatata tttaatggca ctgagaaaca   2340
tgcaagatac aggaaaaatg aaaatgttac aagctaagag tttacagttt aagattttaa   2400
gtattgtttc ctgagcataa ctccataagt aagaaatttc tagttcacag acatacaata   2460
gcattgattc accttgtttt tttaacctgg ttgttgtagt aagagctttg tttcaatatc   2520
actcttgagt aaagattaaa ataaagctac cattttacat ttctatttca taatgaaaaa   2580
ctatgtcagt attttaatat ggttacattt agccaaagtt gagggaaaga gcttataaaa   2640
tttaacttct tcataatttt agtaatttcc tagaggttct gggttttctg aaagtaaaac   2700
aatttatgcg aacctatgtc taaattcact gtttgttact atgtatgttt ttttccaatg   2760
cttcttataa gactaaatga ttagaagtac ctaatagttt gaacagatat gtttttattt   2820
aaaagagtag aataacccttt cagaattact gagtttttta ttccagttgt agcaaagatt   2880
tcaaaagatt gtgttcccat taagtggtag taatttcctt tattattctg tatccttaat   2940
ggtgttctct ctctctctct ctctctctct ctctccctct ccccccgtt ccccactctt   3000
cctttctcct ttgcttttc ttctctttca tacatatatg cgtgcctagt tctaggagga   3060
aacgggttaa aaattgtttt aaactacatc ttgaaaatat tgaagaattt gttttaggta   3120
gagtggtcag ttgaacctta cagtaaagta tagaaatata tttaatgtgg aatgtcaatg   3180
ccaggatttc tcattaacaa tattttatct caactttggt tcctgtgata catttctgaa   3240
tgggcaattc cagaaatctt agtagcccat gttaagcttc tattttttac ttgttttcgg   3300
ggagaaataa gaattagaca tcttcagatt taagttaaat aatcccattc tttataatcc   3360
tctgtaaaaa gatccctgag attattcctt cttctagtttt tatgcgacag ctttacttta   3420
aaattcaagt tatacatctt gggagtacaa tggcccgaca tttcttcata ggtagaaaca   3480
aatacttgac tcagtgatac tcatgaccat tagaatagtc atacctggaa tgtgtcaaat   3540
tataagagac agacacttgg ttagtggctg cctcatatag cacttttgaa gaggcctaag   3600
tcaaaacttg caatataaca ttctattgac tttcttaaaa atattttttc tgtacctaac   3660
```

```
ttgagcataa gggttatttg agcaagtaac attaactcag tggaaggcat tgtcctgtga    3720
aatattctta ggcagatctg cccacatctt tattgaactt gaaatctaat atttctagta    3780
tttgaacaaa gcagaaggtt aagtcaggga agagcagtgc tgtccatgat gtaatggaag    3840
ctaccagggg aggcagtgtc tggatgatgc tgtgctacct accctgcac aagccatgct     3900 ggctcagtct gagctgtggg ccacatcagc tagtggctct tctcatgcat cagttaggtg    3960
ggtctgggtg agagttatag tgagggaatg gtcactaaag tatcctgaca agttcctagg    4020
aaaaaaggaa taaagttttt ttccttaaaa aaaaaaaat tgctcttggc tgtgaaaaga     4080
ggtactaaat gcgattcagt tcaccgctaa ggaaagtgat gacatagcag ttacagaggg    4140
tgataaatct ctccagctaa ttcaggtcat tttgtgaata ctatgtatca agccctgaaa    4200
atatggtaaa taaaacgtga cagggaaacc ttttttttgat tgaatattgt tacatagtta   4260
aatgtgctat atatccttaa tattttatat tgatcctgca aaatctgttg gttttagggg    4320
agttttgttt tttgtttcta acaatttttca gacctgttgg tataggaatg tagaagtctt   4380
tcagatgatt tgaaagcagc tgcatttgct cttggaggct ttgggagagc aggaatgaaa    4440
acattcagag gaagacatct gtagggaatt cttctgttac ttaccaaaga ataagtgtct    4500
ttctggtgtt ttatttccta tcataaaaat acaacagtgc atttacaagg ttaaagattc    4560
ctcgaagttc taggaaattc ttgaaaatat aagtggtgct tagaaaattc aagcatttag    4620
gaatgtgacc tttaattcag gtatgtaaaa gacttttttc ccaaactttt aaaagtagga    4680
aatacaataa atacagaaaa gtcatatggt tgaataaata attataaatt gagcactgat    4740
ggaatccctc tacaggtcaa gaaatagcgc agtgtcctgg atgcccatta tattgttttc    4800
tcctttctgg gtaacaagcc ctaacttctg taatttaaaa gctcctactt ttgccacaag    4860
gtggtgcttc tgccattaga cgcagttagg aggatgcaac tgcaaatcta aaattacgaa    4920
gttagtgtag ttgcaataaa cttagaacat atgcattaat actaaaccta tgcagtaata   4980
ccataattag ccttctaatc atgtaatttg ctttacttag gtatttcatt tggttcagcc    5040
tgttatggaa tttaccagct tgataaattt gcctataaag ttttataaag aaaaggaata    5100
ttttgttttc ataagagga aaatccattc ttagaaaaaa a                         5141
```

<210> SEQ ID NO 19
<211> LENGTH: 6597
<212> TYPE: DNA
<213> ORGANISM: Homo sapiens

<400> SEQUENCE: 19

```
tttcccggcg tgccccagga gagcggcgtg gacgcgtgcg ggcctagagg cccacgtgat     60
ccgcagggcg gccgaggcag gaagctgtga gtgcgcggtt gcggggtcgc attgtggcta    120 cggcttttgcg tccccggcgg gcagcccag gctggtcccc gcctccgctc tccccaccgg    180
cggggaaagc agctggtgtg ggaggaaagg ctccatcccc cgcccctct ctcccgctgt    240 tggctggcag gatcttttgg cagtcctgtg gcctcgctcc ccgcccggat cctcctgacc    300
ctgagattcg cgggtctcac gtcccgtgca cgccttgctt cggcctcagt taagcctttg    360
tggactccag gtccctggtg agattagaaa cgtttgcaaa catgtcccgg atcgaaaaga    420
tgagcattct gggcgtgcgg agttttggaa tagaggacaa agataagcaa attatcactt    480
tcttcagccc ccttacaatt ttggttggac ccaatggggc gggaaagacg accatcattg    540
aatgtctaaa atatatttgt actggagatt tccctcctgg aaccaaagga atacatttg     600
```

```
tacacgatcc caaggttgct caagaaacag atgtgagagc ccagattcgt ctgcaatttc      660
gtgatgtcaa tggagaactt atagctgtgc aaagatctat ggtgtgtact cagaaaagca      720
aaaagacaga atttaaaact ctggaaggag tcattactag aacaaagcat ggtgaaaagg      780
tcagtctgag ctctaagtgt gcagaaattg accgagaaat gatcagttct cttggggttt      840
ccaaggctgt gctaaataat gtcattttct gtcatcaaga agattctaat tggcctttaa      900
gtgaaggaaa ggcttttgaag caaaagtttg atgagatttt ttcagcaaca agatacatta      960
aagccttaga aacacttcgg caggtacgtc agacacaagg tcagaaagta aagaatatc     1020
aaatggaact aaaatatctg aagcaatata aggaaaaagc ttgtgagatt cgtgatcaga     1080
ttacaagtaa ggaagcccag ttaacatctt caaaggaaat tgtcaaatcc tatgagaatg     1140
aacttgatcc attgaagaat cgtctaaaag aaattgaaca taatctctct aaaataatga     1200
aacttgacaa tgaaattaaa gccttggata gccgaaagaa gcaaatggag aaagataata     1260
gtgaactgga agagaaaatg gaaaaggttt tcaagggac tgatgagcaa ctaaatgact     1320
tatatcacaa tcaccagaga acagtaaggg agaaagaaag gaaattggta gactgtcatc     1380
gtgaactgga aaaactaaat aaagaatcta ggcttctcaa tcaggaaaaa tcagaactgc     1440
ttgttgaaca gggtcgtcta cagctgcaag cagatcgcca tcaagaacat atccgagcta     1500
gagattcatt aattcagtct ttggcaacac agctagaatt ggatggcttt gagcgtggac     1560
cattcagtga aagacagatt aaaaattttc acaaacttgt gagagagaga caagaagggg     1620
aagcaaaaac tgccaaccaa ctgatgaatg actttgcaga aaagagact ctgaaacaaa      1680
aacagataga tgagataaga gataagaaaa ctggactggg aagaataatt gagttaaaat     1740
cagaaatcct aagtaagaag cagaatgagc tgaaaaatgt gaagtatgaa ttacagcagt     1800
tggaaggatc ttcagacagg attcttgaac tggaccagga gctcataaaa gctgaacgtg     1860
agttaagcaa ggctgagaaa aacagcaatg tagaaacctt aaaaatggaa gtaataagtc     1920
tccaaaatga aaaagcagac ttagacagga ccctgcgtaa acttgaccag agatgggagc     1980
agttaaaacca tcatacaaca acacgtaccc aaatggagat gctgaccaaa gacaaagctg     2040
acaaagatga acaaatcaga aaaataaaat ctaggcacag tgatgaatta acctcactgt     2100
tgggatattt tcccaacaaa aaacagcttg aagactggct acatagtaaa tcaaaagaaa     2160
ttaatcagac cagggacaga cttgccaaat tgaacaagga actagcttca tctgagcaga     2220
ataaaaatca tataaataat gaactaaaaa gaaaggaaga gcagttgtcc agttacgaag     2280
acaagctgtt tgatgtttgt ggtagccagg attttgaaag tgatttagac aggcttaaag     2340
aggaaattga aaaatcatca aaacagcgag ccatgctggc tggagccaca gcagtttact     2400
cccagttcat tactcagcta acagacgaaa accagtcatg ttgccccgtt tgtcagagag     2460
ttttttcagac agaggctgag ttacaagaag tcatcagtga tttgcagtct aaactgcgac     2520
ttgctccaga taaactcaag tcaacagaat cagagctaaa aaaaaaggaa aagcggcgtg     2580
atgaaatgct gggacttgtg cccatgaggc aaagcataat tgatttgaag gagaaggaaa     2640
taccagaatt aagaaacaaa ctgcagaatg tcaatagaga catacagcgc ctaaagaacg     2700
acatagaaga acaagaaaca ctcttgggta caataatgcc tgaagaagaa gtgccaaag     2760
tatgcctgac agatgttaca attatggaga ggttccagat ggaacttaaa gatgttgaaa     2820
gaaaaattgc acaacaagca gctaagctac aaggaataga cttagatcga actgtccaac     2880
aagtcaacca ggagaaacaa gagaaacagc acaagttaga cacagtttct agtaagattg     2940
aattgaatcg taagcttata caggaccagc aggaacagat tcaacatcta aaaagtacaa     3000
```

```
caaatgagct aaaatctgag aaacttcaga tatccactaa tttgcaacgt cgtcagcaac   3060
tggaggagca gactgtggaa ttatccactg aagttcagtc tttgtacaga gagataaagg   3120
atgctaaaga gcaggtaagc cctttggaaa caacattgga aaagttccag caagaaaaag   3180
aagaattaat caacaaaaaa aatacaagca acaaaatagc acaggataaa ctgaatgata   3240
ttaaagagaa ggttaaaaat attcatggct atatgaaaga cattgagaat tatattcaag   3300
atgggaaaga cgactataag aagcaaaaag aaactgaact taataaagta atagctcaac   3360
taagtgaatg cgagaaacac aaagaaaaga taaatgaaga tatgagactc atgagacaag   3420
atattgatac acagaagata caagaaaggt ggctacaaga taaccttact ttaagaaaaa   3480
gaaatgagga actaaaagaa gttgaagaag aaagaaaaca acatttgaag gaaatgggtc   3540
aaatgcaggt tttgcaaatg aaaagtgaac atcagaagtt ggaagagaac atagacaata   3600 taaaagaaa tcataatttg gcattagggc gacagaaagg ttatgaagaa gaaattattc   3660
attttaagaa agaacttcga gaaccacaat ttcgggatgc tgaggaaaag tatagagaaa   3720
tgatgattgt tatgaggaca acagaacttg tgaacaagga tctggatatt tattataaga   3780
ctcttgacca agcaataatg aaatttcaca gtatgaaaat ggaagaaatc aataaaatta   3840
tacgtgacct gtggcgaagt acctatcgtg acaagatat tgaatacata gaaatacggt   3900
ctgatgccga tgaaaatgta tcagcttctg ataaaaggcg gaattataac taccgagtgg   3960
tgatgctgaa gggagacaca gccttggata tgcgaggacg atgcagtgct ggacaaaagg   4020
tattagcctc actcatcatt cgcctggccc tggctgaaac gttctgcctc aactgtggca   4080
tcattgcctt ggatgagcca acaacaaatc ttgaccgaga aaacattgaa tctcttgcac   4140
atgctctggt tgagataata aaaagtcgct cacagcagcg taacttccag cttctggtaa   4200
tcactcatga tgaagatttt gtggagcttt taggacgttc tgaatatgtg gagaaattct   4260
acaggattaa aaagaacatc gatcagtgct cagagattgt gaaatgcagt gttagctccc   4320
tgggattcaa tgttcattaa aaatatccaa gatttaaatg ccatagaaat gtaggtcctc   4380
agaaagtgta taataagaaa cttatttctc atatcaactt agtcaataag aaaatatatt   4440
ctttcaaagg aacattgtgt ctaggatttt ggatgttgag aggttctaaa atcatgaaac   4500
ttgtttcact gaaaattgga cagattgcct gtttctgatt tgctgctctt catcccattc   4560
caggcagcct ctgtcaggcc ttcagggttc agcagtacag ccgagactcg actctgtgcc   4620
tccctcccca gtgcaaatgc atgcttcttc tcaaagcact gttgagaagg agataattac   4680
tgccttgaaa atttatggtt ttggtatttt tttaaatcat agttaaatgt tacctctgaa   4740
tttacttcct tgcatgtggt ttgaaaaact gagtattaat atctgaggat gaccagaaat   4800
ggtgagatgt atgtttggct ctgcttttaa ctttataaat ccagtgacct ctctctctgg   4860
gacttggttt ccccaactaa aatttgaagt agttgaatgg ggtctcaaag tttgacagga   4920 acctaagta atcatctaag tcagtaccca ccaccttctt ctcctacata tcccttccag   4980
atggtcatcc agactcagag ctctctctac agagaggaaa ttctccactg tgcacaccca   5040
cctttggaaa gctctgacca cttgaggcct gatctgccca tcgtgaagaa gcctgtaaca   5100
ctcctctgcg tctatcctgt gtagcatact ggcttcacca tcaatcctga ttcctctcta   5160
agtgggcatt gccatgtgga aggcaagcca ggctcactca cagagtcaag gcctgctccc   5220
tgtagggtcc aaccagacct ggaagaacag gcctctccat ttgctcttca gatgccactt   5280
ctaagaaaag cctaatcaca gttttcctg gaattgccag ctgacatctt gaatccttcc   5340
```

-continued

| | |
|---|---|
| attccacaca gaatgcaacc aagtcacacg cttttgaatt atgctttgta gagttttgtc | 5400 |
| attcagagtc agccaggacc ataccgggtc ttgattcagt cacatggcat ggttttgtgc | 5460 |
| catctgtagc tataatgagc atgtttgcct agacagcttt tctcaactgg gtccagaaga | 5520 |
| gaattaagcc ctaaggtcct aaggcatcta tctgtgctag gttaaatggt tggcccccaa | 5580 |
| agatagacag gtcctgattt ctagaacccg tgactgttac tttatacagc aaaggaaact | 5640 |
| ttgcagatgt gattaaagct aaggaccttag acagagta tcctgggggt ggtggtgggg | 5700 |
| tgggggggggg tcctaaatgt aatcacgagt aagattaaga gcaaatcaat tctagtcata | 5760 |
| tattaaacat ccacaataac caagatattt ttatcccaag aatgcaagat ttcagaaaat | 5820 |
| gaaaaatctg ttgataaatc catcactata ataaaccga aggtgaaaaa aattctgaaa | 5880 |
| aaattctagc agctatattt gataaaattc aacatctcct agctttagca aactcacagt | 5940 |
| tttgcaaata atattttctt aatgttatct gttgctaaat caaaattaaa cagtcatctt | 6000 |
| aactgcaaaa taaaacattt ctcagtaaat attaaagcca gttaccttct atcaacatgt | 6060 |
| taatgaaagt gctagttgtt gcagcaaaga ataacaaagg caatacacga tcaatatagg | 6120 |
| cagtgaaaca aaagtatcat ttgcaagtta aaacagactt cccaattta aatctggttt | 6180 |
| cccctgaat atgtggcatc cttggcagca cttctgagag tggctgcttt cattccaaga | 6240 |
| agcccatggg tttggaggtg ggataggtgc cttctggct tctcattgct gcttctagat | 6300 |
| cagtctccaa atatccccct tccccacatt ggaatgaata gccatcacag catggatgga | 6360 |
| ggttagaatg agccagactg cctgggctca atcctagca caccactcac tagctgggga | 6420 |
| ccttgagcaa gttatttgtc ctgttttctg tttccttata tgtaaaagtg ggtaaaatgg | 6480 |
| tacatatttt gtagggttgt tatgaagatt gaatgacatt atttacaaac tgcttagaac | 6540 |
| tgcttgccac ctactaaata ctgtgtaagt gttcaagaaa aagctgtctt catttca | 6597 |

<210> SEQ ID NO 20
<211> LENGTH: 4639
<212> TYPE: DNA
<213> ORGANISM: Homo sapiens

<400> SEQUENCE: 20

| | |
|---|---|
| gagcgcgcac gtcccggagc ccatgccgac cgcaggcgcc gtatccgcgc tcgtctagca | 60 |
| gccccggtta cgcggttgca cgtcggcccc agccctgagg agccggaccg atgtggaaac | 120 |
| tgctgcccgc cgcgggcccg gcaggaggag aaccatacag acttttgact ggcgttgagt | 180 |
| acgttgttgg aaggaaaaac tgtgccattc tgattgaaaa tgatcagtcg atcagccgaa | 240 |
| atcatgctgt gttaactgct aacttttctg taaccaacct gagtcaaaca gatgaaatcc | 300 |
| ctgtattgac attaaaagat aattctaagt atggtacctt tgttaatgag gaaaaaatgc | 360 |
| agaatggctt ttcccgaact ttgaagtcgg gggatggtat tactttggga gtgtttggaa | 420 |
| gtaaattcag aatagagtat gagcctttgg ttgcatgctc ttcttgttta gatgtctctg | 480 |
| ggaaaactgc tttaaatcaa gctatattgc aacttggagg atttactgta aacaattgga | 540 |
| cagaagaatg cactcacctt gtcatggtat cagtgaaagt taccattaaa acaatatgtg | 600 |
| cactcatttg tggacgtcca attgtaaagc cagaatattt tactgaattc ctgaaagcag | 660 |
| ttgagtccaa gaagcagcct ccacaaattg aaagttttta cccacctctt gatgaaccat | 720 |
| ctattggaag taaaaatgtt gatctgtcag gacggcagga agaaaacaa atcttcaaag | 780 |
| ggaaaacatt tatattttg aatgccaaac agcataagaa attgagttcc gcagttgtct | 840 |
| ttggaggtgg ggaagctagg ttgataacag aagagaatga agaagaacat aatttctttt | 900 |

```
tggctccggg aacgtgtgtt gttgatacag gaataacaaa ctcacagacc ttaattcctg    960
actgtcagaa gaaatggatt cagtcaataa tggatatgct ccaaaggcaa ggtcttagac   1020
ctattcctga agcagaaatt ggattggcgg tgattttcat gactacaaag aattactgtg   1080
atcctcaggg ccatcccagt acaggattaa agacaacaac tccaggacca agcctttcac   1140
aaggcgtgtc agttgatgaa aaactaatgc caagcgcccc agtgaacact acaacatacg   1200
tagctgacac agaatcagag caagcagata catgggattt gagtgaaagg ccaaaagaaa   1260
tcaaagtctc caaaatggaa caaaaattca gaatgctttc acaagatgca cccactgtaa   1320
aggagtcctg caaacaagc tctaataata atagtatggt atcaaatact ttggctaaga   1380
tgagaatccc aaactatcag cttctcaccaa ctaaattgcc aagtataaat aaaagtaaag   1440 ataggcttc tcagcagcag cagaccaact ccatcagaaa ctactttcag ccgtctacca   1500
aaaaaaggga aagggatgaa gaaaatcaag aaatgtcttc atgcaaatca gcaagaatag   1560
aaacgtcttg ttctcttta gaacaaacac aacctgctac accctcattg tggaaaaata   1620
aggagcagca tctatctgag aatgagcctg tggacacaaa ctcagacaat aacttattta   1680
cagatacaga tttaaaatct attgtgaaaa attctgccag taatctcat gctgcagaaa   1740 agctaagatc aaataaaaaa agggaaatgg atgatgtggc catagaagat gaagtattgg   1800
aacagttatt caaggacaca aaaccagagt tagaaattga tgtgaaagtt caaaacagg   1860 aggaagatgt caatgttaga aaaaggccaa ggatggatat agaaacaaat gacactttca   1920
gtgatgaagc agtaccagaa agtagcaaaa tatctcaaga aaatgaaatt gggaagaaac   1980
gtgaactcaa ggaagactca ctatggtcag ctaaagaaat atctaacaat gacaaacttc   2040
aggatgatag tgagatgctt ccaaaaaagc tgttattgac tgaatttaga tcactggtga   2100
ttaaaaactc tacttccaga aatccatctg gcataaatga tgattatggt caactaaaaa   2160
atttcaagaa attcaaaaag gtcacatatc ctggagcagg aaaacttcca cacatcattg   2220
gaggatcaga tctaatagct catcatgctc gaaagaatac agaactagaa gagtggctaa   2280
ggcaggaaat ggaggtacaa aatcaacatg caaagaaga gtctcttgct gatgatcttt   2340
ttagatacaa tccttattta aaaaggagaa gataactgag gatttaaaa agaagccatg   2400 gaaaaacttc ctagtaagca tctacttcag gccaacaagg ttatatgaat atatagtgta   2460
tagaagcgat ttaagttaca atgttttatg gcctaaattt attaaataaa atgcacaaaa   2520
ctttgattct tttgtatgta acaattgttt gttctgtttt caggctttgt cattgcatct   2580
ttttttcatt tttaaatgtg ttttgtttat taaatagtta atatagtcac agttcaaaat   2640
tctaaatgta cgtaaggtaa agactaaagt caccccttcca ccattgtcct agctacttgg   2700
ttcccctcag aaaaaaattc atgatactca tttcttatga atctttccag ggattttga   2760 gtcctattca aattcctatt tttaaataat ttcctacaca aatgatagca taacatatgc   2820
agtgttctac accttgcttt tttacttagt agattaaaaa ttataggaat atcaatataa   2880 tgttttaat atttttctt ttccattatg ctgtagtctt acctaaactc tggtgatcca   2940
aacaaaatgg cttcagtggt gcagatgtca cctacatgtt attctagtac tagaaactga   3000
agaccatgtg gagacttcat caaacatggg tttagttttc accagaatgg aaagacctgt   3060
accccttttt ggtggtctta ctgagctggg tgggtgtctg ttttgagctt atttagagtc   3120
ctagttttcc tacttataaa gtagaaatgg tgagattgtt ttcttttct accttaaagg   3180 gagatggtaa gaaacaatga atgtcttttt tcaaacttta ttgacaagtg attttcaagt   3240
```

| | |
|---|---|
| ctgtgttcaa aaatatattc atgtacctgt gatccagcaa aagggagtt ccagtcaaga | 3300 |
| gtcactacaa ctgattagtt gtttagagaa tgagaaatgg aacagtgagg aatggaggcc | 3360 |
| atatttccat gacttcccct gtaaacagaa gcaacagaag ggacaagagg ctggcctcta | 3420 |
| catcactctc accttccaaa tcttgtggaa gtgcatctac ttgccagaac caaattaact | 3480 |
| tacttccaag ttctggctgc ttgcaggtgg aactccagct gcaagggagt tagggaaatg | 3540 |
| aaggtctttt tttaaaagct tctcagcctt cctagggaac agaaattggg tgagccaatc | 3600 |
| tgcaatttct actacaggca ttgagaccag ttagattatt gaaatattat agagagttat | 3660 |
| gaacacttaa attatgatag tggtatgaca ttggatagaa catgggatac tttagaagta | 3720 |
| gaattgacag ggcatattag ttgatgaaat ggagtcattt gagtctctta atagccatgt | 3780 |
| atcataatta ccaagtgaag ctggtggaac atatggtctc cattttacag ttaaggaata | 3840 |
| taatggacag attaatattg ttctctgtca tgcccacaat ccctttctaa ggaagactgc | 3900 |
| cctactatag cagttttat atttgtcaat ttatgaatat aatgaatgag agttctggta | 3960 |
| cctcctgtct ttacaaatat tggtgttgtc agtatttttc cttttaacc attccaatcg | 4020 |
| gtgtgtagtg atgtttcatt ttggttttaa tttgtatatc cctgatagct ataattgggt | 4080 |
| catagaaatt ctttatacat tctagatgca agtctcttgt cggatatatg tattgagata | 4140 |
| ttacacctag tctgtggctt gactgttttc tttatgtctt ttgatgaata aagttttaa | 4200 |
| attttgacaa ggtcaaattt attttttct tttgtttgat atttttctc tccaatttaa | 4260 |
| ccccaagatt tcagatattc tgctctatta tataaacttt atattttat atttgtgatc | 4320 |
| taccttgaat tgatatgtat gttgtgaatt atggatcagg gttcttttt tccccatac | 4380 |
| aagtatccag tcattgtaac actgtttatt gaaagaatta cctttcctc attaaattac | 4440 |
| cttgccaatt agtaaaaaat caattaacca taatggtgga tctgtttctg gactttctgt | 4500 |
| ttggttacac tgaaatgttt gtccatcctt gcactcactc ataccatact gccttgaatt | 4560 |
| actgtagctg catagatgct ccttaagttg ggattacatt gtaataaacg caatgtaagt | 4620 |
| taaaaaaaaa aaaaaaaa | 4639 |

<210> SEQ ID NO 21
<211> LENGTH: 5765
<212> TYPE: DNA
<213> ORGANISM: Homo sapiens

<400> SEQUENCE: 21

| | |
|---|---|
| cagccgcccc tcctgcggcc gctgcggggg ccgccgcctg acttcggaca ccggccccgc | 60 |
| acccgccagg aggggaggga aggggaggcg gggagagcga cggcgggggg cgggcggtgg | 120 |
| accccgcctc ccccggcaca gcctgctgag gggaagaggg ggtctccgct cttcctcagt | 180 |
| gcactctctg actgaagccc ggcgcgtggg gtgcagcggg agtgcgaggg gactggacag | 240 |
| gtgggaagat gggaatgagg accggccggc gggaatgttc tcacttctcc ggattccacc | 300 |
| gggatgcagg actctagctg cccagccgca cctgcgaaga gactacactt cccgaggtgc | 360 |
| tcagcggcag cgagggcctc cacgcatgcg caccgcggcg cgctgggcgg ggctggatgg | 420 |
| gctgtggtgg gagggttgca gcgccgcgag aaaggcgagc cggccggggg gcggggaaag | 480 |
| gggtggggca ggaacggggg cggggacggc gctgaggggg cgggtcgggt aggtctcccg | 540 |
| gagctgatgt gtactgtgtg cgccggggag gcgccggctt gtactcggca gcgcgggaat | 600 |
| aaagtttgct gatttggtgt ctagcctgga tgcctgggtt gcaggccctg cttgtggtgg | 660 |
| cgctccacag tcatccggct gaagaagacc tgttggactg gatcttctcg ggttttcttt | 720 |

```
cagatattgt tttgtattta cccatgaaga cattgttttt tggactctgc aaataggaca      780
tttcaaagat gagtgaaaaa aaattggaaa caactgcaca gcagcggaaa tgtcctgaat      840
ggatgaatgt gcagaataaa agatgtgctg tagaagaaag aaaggcatgt gttcggaaga      900
gtgttttga agatgacctc cccttcttag aattcactgg atccattgtg tatagttacg       960
atgctagtga ttgctctttc ctgtcagaag atattagcat gagtctatca gatggggatg     1020
tggtgggatt tgacatggag tggccaccat tatacaatag agggaaactt ggcaaagttg     1080
cactaattca gttgtgtgtt tctgagagca atgttactt gttccacgtt tcttccatgt      1140
cagttttcc ccagggatta aaatgttgc ttgaaataa agcagttaaa aaggcaggtg        1200
taggaattga aggagatcag tggaaacttc tacgtgactt tgatatcaaa ttgaagaatt     1260
ttgtggagtt gacagatgtt gccaataaaa agctgaaatg cacagagacc tggagcctta    1320
acagtctggt taaacaccctc ttaggtaaac agctcctgaa agacaagtct atccgctgta   1380
gcaattggag taaatttcct ctcactgagg accagaaact gtatgcagcc actgatgctt    1440
atgctggttt tattatttac cgaaatttag agattttgga tgatactgtg caaaggtttg    1500
ctataaataa agaggaagaa atcctactta gcgacatgaa caaacagttg acttcaatct    1560
ctgaggaagt gatggatctg gctaagcatc ttcctcatgc tttcagtaaa ttggaaaacc    1620
cacggagggt ttctatctta ctaaaggata ttttcagaaaa tctatattca ctgaggagga   1680
tgataattgg gtctactaac attgagactg aactgaggcc cagcaataat ttaaacttat    1740
tatcctttga agattcaact actgggggag tacaacagaa acaaattaga gaacatgaag    1800
ttttaattca cgttgaagat gaaacatggg acccaacact tgatcattta gctaaacatg    1860
atggagaaga tgtacttgga aataaagtgg aacgaaaaga gatggatttt gaagatggag    1920
tagaagacaa caaattgaaa gagaatatgg aaagagcttg tttgatgtcg ttagatatta    1980
cagaacatga actccaaatt ttggaacagc agtctcagga agaatatctt agtgatattg    2040
cttataaatc tactgagcat ttatctccca atgataatga aaacgatacg tcctatgtaa    2100
ttgagagtga tgaagattta gaaatggaga tgcttaagca tttatctccc aatgataatg    2160
aaaacgatac gtcctatgta attgagagtg atgaagattt agaaatggag atgcttaagt    2220
ctttagaaaa cctcaatagt ggcacggtag aaccaactca ttctaaatgc ttaaaaatgg    2280
aaagaaatct gggtcttcct actaaagaag aagaagaaga tgatgaaaat gaagctaatg    2340
aagggggaaga agatgatgat aaggacttt tgtggccagc acccaatgaa gagcaagtta    2400
cttgcctcaa gatgtacttt ggccattcca gtttaaacc agttcagtgg aaagtgattc     2460
attcagtatt agaagaaaga agagataatg ttgctgtcat ggcaactgga tatggaaaga    2520
gtttgtgctt ccagtatcca cctgtttatg taggcaagat tggccttgtt atctctcccc    2580
ttatttctct gatggaagac caagtgctac agcttaaaat gtccaacatc ccagcttgct    2640
tccttggatc agcacagtca gaaaatgttc taacagatat taaattaggt aaataccgga    2700
ttgtatacgt aactccagaa tactgttcag gtaacatggg cctgctccag caacttgagg    2760
ctgatattgg tatcacgctc attgctgtgg atgaggctca ctgtatttct gagtgggggc    2820
atgattttag ggattcattc aggaagttgg gctccctaaa gacagcactg ccaatggttc    2880
caatcgttgc acttactgct actgcaagtt cttcaatccg ggaagacatt gtacgttgct    2940
taaatctgag aaatcctcag atcacctgta ctggttttga tcgaccaaac ctgtatttag    3000
aagttaggcg aaaaacaggg aatatccttc aggatctgca gccatttctt gtcaaaacaa    3060
```

```
gttcccactg ggaatttgaa ggtccaacaa tcatctactg tccttctaga aaaatgacac    3120
aacaagttac aggtgaactt aggaaactga atctatcctg tggaacatac catgcgggca    3180
tgagttttag cacaaggaaa gacattcatc ataggtttgt aagagatgaa attcagtgtg    3240
tcatagctac catagctttt ggaatgggca ttaataaagc tgacattcgc caagtcattc    3300
attacggtgc tcctaaggac atggaatcat attatcagga gattggtaga gctggtcgtg    3360
atggacttca aagttcttgt cacgtcctct gggctcctgc agacattaac ttaaataggc    3420
accttcttac tgagatacgt aatgagaagt ttcgattata caaattaaag atgatggcaa    3480
agatggaaaa atatcttcat tctagcagat gtaggagaca atcatccttg tctcattttg    3540
aggacaaaca agtacaaaaa gcctccttgg gaattatggg aactgaaaaa tgctgtgata    3600
attgcaggtc cagattggat cattgctatt ccatggatga ctcagaggat acatcctggg    3660
actttggtcc acaagcattt aagcttttgt ctgctgtgga catcttaggc gaaaaatttg    3720
gaattgggct tccaattttta tttctccgag gatctaattc tcagcgtctt gccgatcaat    3780
atcgcaggca cagtttattt ggcactggca aggatcaaac agagagttgg tggaaggctt    3840
tttcccgtca gctgatcact gagggattct tggtagaagt ttctcggtat aacaaattta    3900
tgaagatttg cgcccttacg aaaaagggta gaaattggct tcataaagct aatacagaat    3960
ctcagagcct catccttcaa gctaatgaag aattgtgtcc aaagaagttg cttctgccta    4020
gttcgaaaac tgtatcttcg ggcaccaaag agcattgtta taatcaagta ccagttgaat    4080
taagtacaga gaagaagtct aacttggaga gttatattc ttataaacca tgtgataaga    4140
tttcttctgg gagtaacatt tctaaaaaaa gtatcatggt acagtcacca gaaaaagctt    4200
acagttcctc acagcctgtt atttcggcac aagagcagga gactcagatt gtgttatatg    4260
gcaaattggt agaagctagg cagaaacatg ccaataaaat ggatgttccc ccagctattc    4320
tggcaacaaa caagatactg gtggatatgg ccaaaatgag accaactacg gttgaaaacg    4380
taaaaaggat tgatggtgtt tctgaaggca agctgccat gttggcccct ctgttggaag    4440
tcatcaaaca tttctgccaa acaaatagtg ttcagacaga cctcttttca agtacaaaac    4500
ctcaagaaga acagaagacg agtctggtag caaaaaataa aatatgcaca cttttcacagt    4560 ctatggccat cacatactct ttattccaag aaaagaagat gcctttgaag agcatagctg    4620
agagcaggat tctgcctctc atgacaattg gcatgcactt atcccaagcg gtgaaagctg    4680 gctgcccct tgatttggag cgagcaggcc tgactccaga ggttcagaag attattgctg    4740
atgttatccg aaaccctccc gtcaactcag atatgagtaa aattagccta atcagaatgt    4800
tagttcctga aaacattgac acgtaccctta tccacatggc aattgagatc cttaaacatg    4860
gtcctgacag cggacttcaa ccttcatgtg atgtcaacaa aaggagatgt tttcccggtt    4920
ctgaagagat ctgttcaagt tctaagagaa gcaaggaaga agtaggcatc aatactgaga    4980
cttcatctgc agagagaaag agacgattac ctgtgtggtt tgccaaagga agtgatacca    5040
gcaagaaatt aatggacaaa acgaaaaggg gaggtctttt tagttaagct ggcaattacc    5100
agaacaatta tgtttcttgc tgtattataa aggatagct atattttatt tctgaagagt    5160
aaggagtagt attttggctt aaaaatcatt ctaattacaa agttcactgt ttattgaaga    5220
actggcatct taaatcagcc ttccgcaatt catgtagttt ctgggtcttc tgggagccta    5280
cgtgagtaca tcacctaaca gaatattaaa ttagacttcc tgtaagattg ctttaagaaa    5340
ctgttactgt cctgtttct aatctctttta ttaaaacagt gtatttggaa aatgttatgt    5400
gctctgattt gatatagata acagattagt agttacatgg taattatgtg atataaaata    5460
```

-continued

```
ttcatatatt atcaaaattc tgttttgtaa atgtaagaaa gcatagttat tttacaaatt    5520
gttttactg tcttttgaag aagttcttaa atacgttgtt aaatggtatt agttgaccag     5580
ggcagtgaaa atgaaaccgc attttgggtg ccattaaata gggaaaaaac atgtaaaaaa    5640
tgtaaaatgg agaccaattg cactaggcaa gtgtatattt tgtattttat atacaatttc    5700
tattattttt caagtaataa aacaatgttt ttcatactga atattaaaaa aaaaaaaaa     5760
aaaaa                                                                5765
```

<210> SEQ ID NO 22
<211> LENGTH: 4528
<212> TYPE: DNA
<213> ORGANISM: Homo sapiens

<400> SEQUENCE: 22

```
ggcgggaagt gagccagggc ttggcgcggc ggccgtggtt gcggcgcggg aagtttggat      60
cctggttccg tccgctagga gtctgcgtgc gaggattatg gctgctgttc ctcaaaataa    120
tctacaggag caactagaac gtcactcagc cagaacactt aataataaat taagtctttc    180
aaaaccaaaa ttttcaggtt tcacttttaa aagaaaaaca tcttcagata acaatgtatc    240
tgtaactaat gtgtcagtag caaaaacacc tgtattaaga aataaagatg ttaatgttac    300
cgaagacttt tccttcagtg aacctctacc caacaccaca aatcagcaaa gggtcaagga    360
cttctttaaa aatgctccag caggacagga aacacagaga ggtggatcaa atcattatt     420
gccagatttc ttgcagactc cgaaggaagt tgtatgcact acccaaaaca caccaactgt    480
aaagaaatcc cgggatactg ctctcaagaa attagaattt agttcttcac cagattcttt    540
aagtaccatc aatgattggg atgatatgga tgactttgat acttctgaga cttcaaaatc    600
atttgttaca ccaccccaaa gtcactttgt aagagtaagc actgctcaga aatcaaaaaa    660
gggtaagaga aacttttta aagcacagct ttatacaaca aacacagtaa agactgattt     720
gcctccaccc tcctctgaaa gcgagcaaat agatttgact gaggaacaga aggatgactc    780
agaatggtta agcagcgatg tgatttgcat cgatgatggc cccattgctg aagtgcatat    840
aaaatgaagat gctcaggaaa gtgactctct gaaaactcat ttggaagatg aaagagataa    900
tagcgaaaag aagaagaatt tggaagaagc tgaattacat tcaactgaga aagttccatg    960
tattgaattt gatgatgatg attatgatac ggattttgtt ccaccttctc cagaagaaat   1020
tatttctgct tcttcttcct cttcaaaatg ccttagtacg ttaaaggacc ttgacacctc   1080
tgacagaaaa gaggatgttc ttagcacatc aaaagatctt ttgtcaaaac ctgagaaaat   1140
gagtatgcag gagctgaatc cagaaaccag cacagactgt gacgctagac agataagttt   1200
acagcagcag ttattcatg tgatggagca catctgtaaa ttaattgata ctattcctga    1260
tgataaactg aaacttttgg attgtgggaa cgaactgctt cagcagcgga acataagaag   1320
gaaacttcta cggaagtag atttttaataa aagtgatgcc agtcttcttg gctcattgtg    1380
gagatacagg cctgattcac ttgatggccc tatggagggt gattcctgcc ctacagggaa   1440
ttctatgaag gagttaaatt tttcacacct tccctcaaat tctgtttctc ctggggactg   1500
tttactgact accaccctag gaagacagg attctctgcc accaggaaga atctttttga    1560
aaggccttta ttcaataccc atttacagaa gtcctttgta agtagcaact gggctgaaac   1620
accaagacta ggaaaaaaaa atgaaagctc ttatttccca ggaaatgttc tcacaagcac   1680
tgctgtgaaa gatcagaata acatactgc ttcaataaat gacttagaaa gagaaaccca    1740
```

```
accttcctat gatattgata attttgacat agatgacttt gatgatgatg atgactggga    1800
agacataatg cataatttag cagccagcaa atcttccaca gctgcctatc aacccatcaa    1860
ggaaggtcgg ccaattaaat cagtatcaga aagactttcc tcagccaaga cagactgtct    1920
tccagtgtca tctactgctc aaaatataaa cttctcagag tcaattcaga attatactga    1980
caagtcagca caaaatttag catccagaaa tctgaaacat gagcgtttcc aaagtcttag    2040
ttttcctcat acaaaggaaa tgatgaagat ttttcataaa aaatttggcc tgcataattt    2100
tagaactaat cagctagagg cgatcaatgc tgcactgctt ggtgaagact gttttatcct    2160
gatgccgact ggaggtggta agagtttgtg ttaccagctc cctgcctgtg tttctcctgg    2220
ggtcactgtt gtcatttctc ccttgagatc acttatcgta gatcaagtcc aaaagctgac    2280
ttccttggat attccagcta catatctgac aggtgataag actgactcag aagctacaaa    2340
tatttacctc cagttatcaa aaaaagaccc aatcataaaa cttctatatg tcactccaga    2400
aaagatctgt gcaagtaaca gactcatttc tactctggag aatctctatg agaggaagct    2460
cttggcacgt tttgttattg atgaagcaca ttgtgtcagt cagtggggac atgattttcg    2520
tcaagattac aaaagaatga atatgcttcg ccagaagttt ccttctgttc cggtgatggc    2580
tcttacggcc acagctaatc ccagggtaca gaaggacatc ctgactcagc tgaagattct    2640
cagacctcag gtgtttagca tgagctttaa cagacataat ctgaaatact atgtattacc    2700
gaaaaagcct aaaaaggtgg catttgattg cctagaatgg atcagaaagc accacccata    2760
tgattcaggg ataatttact gcctctccag gcgagaatgt gacaccatgg ctgacacgtt    2820
acagagagat gggctcgctg ctcttgctta ccatgctggc ctcagtgatt ctgccagaga    2880
tgaagtgcag cagaagtgga ttaatcagga tggctgtcag gttatctgtg ctacaattgc    2940
atttggaatg gggattgaca aaccggacgt gcgatttgtg attcatgcat ctctccctaa    3000
atctgtggag ggttactacc aagaatctgg cagagctgga agagatgggg aaatatctca    3060
ctgcctgctt ttctatacct atcatgatgt gaccagactg aaaagactta taatgatgga    3120
aaaagatgga aaccatcata caagagaaac tcacttcaat aatttgtata gcatggtaca    3180
ttactgtgaa aatataacgg aatgcaggag aatacagctt ttggcctact ttggtgaaaa    3240
tggatttaat cctgattttt gtaagaaaca cccagatgtt tcttgtgata attgctgtaa    3300
aacaaaggat tataaaacaa gagatgtgac tgacgatgtg aaaagtattg taagatttgt    3360
tcaagaacat agttcatcac aaggaatgag aaatataaaa catgtaggtc cttctggaag    3420
atttactatg aatatgctgg tcgacatttt cttggggagt aagagtgcaa aaatccagtc    3480
aggtatattt ggaaaaggat ctgcttattc acgacacaat gccgaaagac ttttaaaaa    3540
gctgatactt gacaagattt tggatgaaga cttatatatc aatgccaatg accaggcgat    3600
cgcttatgtg atgctcggaa ataaagccca aactgtacta aatggcaatt taaaggtaga    3660
ctttatggaa acagaaaatt ccagcagtgt gaaaaaacaa aaagcgttag tagcaaaagt    3720
gtctcagagg gaagagatgg ttaaaaaatg tcttggagaa cttacagaag tctgcaaatc    3780
tctggggaaa gttttggtg tccattactt caatatttt aataccgtca ctctcaagaa    3840
gcttgcagaa tctttatctt ctgatcctga ggttttgctt caaattgatg gtgttactga    3900
agacaaactg gaaaaatatg gtgcggaagt gatttcagta ttacagaaat actctgaatg    3960
gacatcgcca gctgaagaca gttccccagg gataagcctg tccagcagca gaggccccgg    4020
aagaagtgcc gctgaggagc tcgacgagga aatacccgta tcttcccact actttgcaag    4080
taaaaccaga aatgaaagga agaggaaaaa gatgccagcc tcccaaaggt ctaagaggag    4140
```

| | |
|---|---|
| aaaaactgct tccagtggtt ccaaggcaaa ggggggtct gccacatgta gaaagatatc | 4200 |
| ttccaaaacg aaatcctcca gcatcattgg atccagttca gcctcacata cttctcaagc | 4260 |
| gacatcagga gccaatagca aattggggat tatggctcca ccgaagccta taaatagacc | 4320 |
| gtttcttaag ccttcatatg cattctcata acaaccgaat ctcaatgtac atagaccctc | 4380 |
| tttcttgttt gtcagcatct gaccatctgt gactataaag ctgttattct tgttatacca | 4440 |
| tttgaagttt ttactcgtct ctattaatat ttaaataaat gctgggggt gatagttctt | 4500 |
| cttttaaaa taaacatttt cttttgaa | 4528 |

<210> SEQ ID NO 23
<211> LENGTH: 3840
<212> TYPE: DNA
<213> ORGANISM: Homo sapiens

<400> SEQUENCE: 23

| | |
|---|---|
| ctggacgatc gcaagcgcgg aggccgggcg ggcgcgcgcg ccatggagcg gctgcgggac | 60 |
| gtgcgggagc ggctgcaggc gtgggagcgc gcgttccgac ggcagcgcgg gcggcgaccg | 120 |
| agccaggacg acgtggaggc ggcgccggag gagacccgcg cgctctaccg ggaataccgc | 180 |
| actctgaagc gtaccacggg ccaggccggc ggcgggctcc gcagctccga gtcgctcccc | 240 |
| gcggcggccg aagaggcgcc agagcccgc tgctgggggc cccatctgaa tcgggctgcg | 300 |
| accaagagtc cacagcctac gccagggcgg agccgccagg gctcggtgcc ggactacggg | 360 |
| cagcggctca aggccaatct gaaaggcacc ctgcaggccg accagccct gggccgcaga | 420 |
| ccgtggcctc taggaagagc ctcatctaag gcatccaccc caaagccccc aggtacaggg | 480 |
| cctgtcccct cctttgcaga aaagtcagt gatgagcctc cacagctccc tgagccccag | 540 |
| ccaaggccag gccggctcca gcatctgcag gcatccctga ccagcggct gggctcccta | 600 |
| gatcctggct ggttacagcg atgtcacagt gaggtcccag attttctggg ggccccaaa | 660 |
| gcctgcaggc ctgatctagg ctcagaggaa tcacaacttc tgatccctgg tgagtcggct | 720 |
| gtccttggtc ctggtgctgg ctcccagggc ccagaggctt cagccttcca agaagtcagc | 780 |
| atccgtgtgg ggagccccca gcccagcagc agtggaggcg agaagcggag atggaacgag | 840 |
| gagccctggg agagccccgc acaggtccag caggagagca gccaagctgg accccatcg | 900 |
| gagggggctg ggctgtagc agttgaggaa gaccctccag gggaacctgt acaggcacag | 960 |
| ccacctcagc cctgcagcag cccatcgaac cccaggtacc acggactcag cccctccagt | 1020 |
| caagctaggg ctgggaaggc tgagggcaca gcccccctgc acatcttccc tcggctggcc | 1080 |
| cgccatgaca ggggcaatta cgtacggctc aacatgaagc agaaacacta cgtgcgggc | 1140 |
| cgggcactcc gtagcaggct cctccgcaag caggcatgga agcagaagtg gcggaagaaa | 1200 |
| ggggagtgtt ttgggggtgg tggtgccaca gtcacaacca aggagtcttg tttcctgaac | 1260 |
| gagcagttcg atcactgggc agcccagtgt ccccggccag caagtgagga agacacagat | 1320 |
| gctgttgggc ctgagccact ggttccttca ccacaacctg tacctgaggt gcccagcctg | 1380 |
| gaccccaccg tgctgccact ctactccctg ggccctcag gcagttggc agagacgccg | 1440 |
| gctgaggtgt tccaggccct ggagcagctg ggcaccaag cctttcgccc tgggcaggag | 1500 |
| cgtgcagtca tgcggatcct gtctggcatc tccacgctgc tggtgctgcc tacaggtgcc | 1560 |
| ggcaagtccc tgtgctacca gctcccagcg ctgctctaca gccggcgcag ccctgcctc | 1620 |
| acgttggtcg tctctccct gctgtcactc atggatgacc aggtgtctgg cctgccaccg | 1680 |

| | |
|---|---|
| tgtctcaagg cggcctgcat acactcgggc atgaccagga agcaacggga atctgtcctg | 1740 |
| cagaagattc gggcagccca ggtacacgtg ctgatgctga cacctgaggc actggtgggg | 1800 |
| gcgggaggcc tccctccagc cgcacagctg cctccagttg cttttgcctg cattgatgag | 1860 |
| gcccactgcc tctcccagtg gtcccacaac ttcggccct gctacctgcg cgtctgcaag | 1920 |
| gtgcttcggg agcgcatggg cgtgcactgc ttcctgggcc tcacagccac agccacacgc | 1980 |
| cgcactgcca gtgacgtggc acagcacctg gctgtggctg aagagcctga cctccacggg | 2040 |
| ccagccccag ttcccaccaa cctgcacctt tccgtgtcca tggacaggga cacagaccag | 2100 |
| gcactgttga cgctgctgca aggcaaacgt tttcaaaacc tcgattccat tatcatttac | 2160 |
| tgcaaccggc gcgaggacac agagcggatc gctgcgctcc tccgaacctg cctgcacgca | 2220 |
| gcctgggtcc cagggtctgg aggtcgtgcc cccaaaacca cagccgaggc ctaccacgcg | 2280 |
| ggcatgtgca gccgggaacg gcggcgggta cagcgagcct tcatgcaggg ccagttgcgg | 2340 |
| gtggtggtgg ccacggtggc ctttgggatg gggctggacc ggccagatgt gcgggctgtg | 2400 |
| ctgcatctgg ggctgccccc aagcttcgag agctacgtgc aggccgtggg ccgggccggg | 2460 |
| cgtgacgggc agcctgccca ctgccacctc ttcctgcagc cccagggcga agacctgcga | 2520 |
| gagctgcgca gacatgtgca cgccgacagc acggacttcc tggctgtgaa gaggctggta | 2580 |
| cagcgcgtgt tcccagcctg cacctgcacc tgcaccaggc cgccctcgga gcaggaaggg | 2640 |
| gccgtgggtg gggagaggcc tgtgcccaag tacccccctc aagaggctga gcagcttagc | 2700 |
| caccaagcag cccaggacc cagaagggtc tgcatgggcc atgagcgggc actcccaata | 2760 |
| cagcttaccg tacaggcttt ggacatgccg gaggaggcca tcgagacttt gctgtgctac | 2820 |
| ctggagctgc acccacacca ctggctggag ctgctggcga ccacctatac ccattgccgt | 2880 |
| ctgaactgcc ctgggggccc tgcccagctc caggccctgg cccacaggtg tccccctttg | 2940 |
| gctgtgtgct ggcccagca gctgcctgag gacccagggc aaggcagcag ctccgtggag | 3000 |
| tttgacatgt caagctggt ggactccatg ggctgggagc tggcctctgt gcggcgggct | 3060 |
| ctctgccagc tgcagtggga ccacgagccc aggacaggtg tgcggcgtgg acagggggtg | 3120 |
| cttgtgggagt tcagtgagct ggccttccac cttcgcagcc cggggaccct gaccgctgag | 3180 |
| gagaaggacc agatatgtga cttcctctat ggccgtgtgc aggcccggga gcgccaggcc | 3240 |
| ctggcccgtc tgcgcagaac cttccaggcc tttcacagcg tagccttccc cagctgcggg | 3300 |
| ccctgcctgg agcagcagga tgaggagcgc agcaccaggc tcaaggacct gctcggccgc | 3360 |
| tactttgagg aagaggaagg gcaggagccg ggaggcatgg aggacgcaca gggccccgag | 3420 |
| ccagggcagg ccagactcca ggattgggag gaccaggtcc gctgcgacat ccgccagttc | 3480 |
| ctgtccctga ggcagagga gaagttctcc agcaggctg tggcccgcat cttccacggc | 3540 |
| atcggaagcc cctgctaccc ggcccaggtg tacgggcagg accgacgctt ctggagaaaa | 3600 |
| tacctgcacc tgagcttcca tgccctggtg gcctggcca cggaagagct cctgcaggtg | 3660 |
| gcccgctgac tgcactgcat tgggggatgt cgggtagagc tggggttgtc agaggctagg | 3720 |
| gcagtgactg aggacctggg caaaacctgc cacagggtgt gggaacgagg aggctccaaa | 3780 |
| atgcagaata aaaatgctc actttgtttt tatgggaaaa aaaaaaaaa aaaaaaaaa | 3840 |

<210> SEQ ID NO 24
<211> LENGTH: 4077
<212> TYPE: DNA
<213> ORGANISM: Homo sapiens

<400> SEQUENCE: 24

-continued

```
gccagtgagc ccccgcgacg gtggcccgga cggaaaagat acctcggcgg cgtgggcccg      60
gctccctgct ccaggaccta gggatcttgg ccttccaccc tcctccgagc accaggactc     120
cctccagttc cgtacccgag gcctccgtgg tgaagaggtg ccggacccga tgagctcggg     180
agtccaccat cgctctgcaa gccgcagtta acgagaaga ttcatcaccg ctttgatggc      240
tgcctcacaa acttcacaaa ctgttgcatc tcacgttcct tttgcagatt tgtgttcaac     300
tttagaacga atacagaaaa gtaaaggacg tgcagaaaaa atcagacact tcagggaatt     360
tttagattct tggagaaaat ttcatgatgc tcttcataag aaccacaaag atgtcacaga     420 ctcttttat ccagcaatga gactaattct tcctcagcta aaagagaga gaatggccta       480 tggaattaaa gaaactatgc ttgctaagct ttatattgag ttgcttaatt tacctagaga     540
tggaaaagat gccctcaaac ttttaaacta cagaacaccc actggaactc atggagatgc     600
tggagacttt gcaatgattg catattttgt gttgaagcca agatgtttac agaaaggaag     660
tttaaccata cagcaagtaa acgaccttt agactcaatt gccagcaata attctgctaa      720
aagaaaagac ctaataaaaa agagccttct tcaacttata actcagagtt cagcacttga     780
gcaaaagtgg cttatacgga tgatcataaa ggatttaaag cttggtgtta gtcagcaaac     840
tatcttttct gttttcata atgatgctgc tgagttgcat aatgtcacta cagatctgga     900
aaaagtctgt aggcaactgc atgatccttc tgtaggactc agtgatattt ctatcacttt     960 atttctgca tttaaaccaa tgctagctgc tattgcagat attgagcaca ttgagaagga     1020
tatgaaacat cagagttct acatagaaac caagctagat ggtgaacgta tgcaaatgca     1080
caaagatgga gatgtatata aatacttctc tcgaaatgga tataactaca ctgatcagtt     1140
tggtgcttct cctactgaag gttctcttac cccattcatt cataatgcat caaagcaga     1200 tatacaaatc tgtattcttg atggtgagat gatggcctat aatcctaata cacaaacttt     1260
catgcaaaag ggaactaagt ttgatattaa aagaatggta gaggattctg atctgcaaac     1320
ttgttattgt gttttgatg tattgatggt taataataaa aagctagggc atgagactct     1380
gagaaagagg tatgagattc ttagtagtat ttttacacca attccaggta gaatagaaat     1440
agtgcagaaa acacaagctc atactaagaa tgaagtaatt gatgcattga atgaagcaat     1500
agataaaaga gaagagggaa ttatggtaaa acaacctcta tccatctaca agccagacaa     1560
aagaggtgaa gggtggttaa aaattaaacc agagtatgtc agtggactaa tggatgaatt     1620
ggacatttta attgttggag gatattgggg taaaggatca cggggtggaa tgatgtctca     1680
ttttctgtgt gcagtagcag agaagccccc tcctggtgag aagccatctg tgtttcatac     1740
tctctctcgt gttgggtctg gctgcaccat gaaagaactg tatgatctgg gtttgaaatt     1800
ggccaagtat tggaagcctt ttcatagaaa agctccacca agcagcattt tatgtggaac     1860
agagaagcca gaagtataca ttgaaccttg taattctgtc attgttcaga ttaaagcagc     1920
agagatcgta cccagtgata tgtataaaac tggctgcacc ttgcgttttc cacgaattga     1980
aaagataaga gatgacaagg agtggcatga gtgcatgacc ctggacgacc tagaacaact     2040 taggggaag gcatctggta agctcgcatc taaacacctt tatataggtg gtgatgatga     2100
accacaagaa aaaagcgga aagctgcccc aaagatgaag aaagttattg gaattattga     2160
gcacttaaaa gcacctaacc ttactaacgt taacaaaatt tctaatatat ttgaagatgt     2220
agagttttgt gttatgagtg gaacagatag ccagccaaag cctgacctgg agaacagaat     2280
tgcagaattt ggtggttata tagtacaaaa tccaggccca gacacgtact gtgtaattgc     2340
```

```
agggtctgag aacatcagag tgaaaaacat aattttgtca aataaacatg atgttgtcaa      2400
gcctgcatgg cttttagaat gttttaagac caaaagcttt gtaccatggc agcctcgctt      2460
tatgattcat atgtgcccat caaccaaaga acattttgcc cgtgaatatg attgctatgg      2520
tgatagttat ttcattgata cagacttgaa ccaactgaag gaagtattct caggaattaa      2580
aaattctaac gagcagactc ctgaagaaat ggcttctctg attgctgatt tagaatatcg      2640
gtattcctgg gattgctctc ctctcagtat gtttcgacgc cacaccgttt atttggactc      2700
gtatgctgtt attaatgacc tgagtaccaa aaatgagggg acaaggttag ctattaaagc      2760
cttggagctt cggtttcatg gagcaaaagt agtttcttgt ttagctgagg gagtgtctca      2820
tgtaataatt ggggaagatc atagtcgtgt tgcagatttt aaagctttta gaagaacttt      2880
taagagaaag tttaaaatcc taaagaaag ttgggtaact gattcaatag acaagtgtga      2940
attacaagaa gaaaaccagt atttgattta aagctaggtt tcctagtgag gaaagcctct      3000
gatctggcag actcattgca gcaggtggta atgataaaat actaaactac attttatttt      3060
tgtatcttaa aaatctatgc ctaaaagta tcattacata taggaaaaca ataattttaa      3120
cttttaaggt tgaaaagaca atagcccaaa gccaagaaag aaaaattatc ttgaatgtag      3180
tattcaatga ttttttatga tcaaggtgaa ataaacagtc taaagaagag gtgttttat      3240 aatatccata tagaaatcta gaattttac ttagatacta ataaaataca tttagaaact      3300
tttaaagtca tgaaaagca ttaaccttct aaacagtata ttctaaaaag tcaaaacgtt      3360
aacaatagtt tttatctaat aaaagcactg caagaaaata gggtagaatt gttacagctg      3420
gacttgtaaa aatatgtctt tttactcagg gtttaaaatg tcccatttaa atatgaaatg      3480
taaacaaatt tgttttttaa ggttaaggcc aaatgtaaca ataaaaccct gtcgatggtt      3540
ttagctaaat tagaggaagt tgtatgagac ttaatgatct aaaaacttaa aattgaattg      3600
gtttgattaa aaataaagct tgcaatttta aaagtagctc acatttaatt tcttgtgtga      3660
aatagaacat gcttttaaagg aagtattttt atgtgaattt gcattccagt ataaatagta      3720
ttcacaaaaa agattttcct agattttatc tattgaatag gtgtcaatat ggcatgcata      3780
ttgtaacttt cattagaaat aagttgcttt gacttttaaa aatgacatag ttagattatt      3840
taaagtcaat gtatatagta tatattatgt atggatttat ataccaaatt ttggaataca      3900
gcctatctca tgaccatatt gaatgtacg gaatttgatc catgcgatac tatgtgtgca      3960
ttatttgaaa gttattggaa attttattca aaccgtggaa caaatgtatg tgattttgtt      4020
atacttctta atttaaataa aatatttaat gcactattaa aaaaaaaaaa aaaaaa        4077
```

<210> SEQ ID NO 25
<211> LENGTH: 1688
<212> TYPE: DNA
<213> ORGANISM: Homo sapiens

<400> SEQUENCE: 25

```
cgggatttag atcacgtccc gcaggccggc ggaagtagct gatactctca ttggttgcaa        60
aaccttgatc tgtgaaagcg ggcgttttgg aagataccgg aagtagagtc acggagaggt       120
attaagaaat ggagagaaaa ataagcagaa tccaccttgt ttctgaaccc agtataactc       180
attttctaca agtatcttgg gagaaaacac tggaatctgg ttttgttatt acacttactg       240
atggtcattc agcatggact gggacagttt ctgaatcaga gatttcccaa gaagctgatg       300
acatggcaat ggaaaaaggg aaatatgttg gtgaactgag aaaagcattg ttgtcaggag       360
caggaccagc tgatgtatac acgtttaatt tttctaaaga gtcttgttat tcttctcttg       420
```

```
agaaaaacct gaaagatgtc tcattcagac ttggttcctt caacctagag aaagttgaaa    480
acccagctga agtcattaga gaacttattt gttattgctt ggacaccatt gcagaaaatc    540 aagcccaaaaa tgagcacctg cagaaagaaa atgaaaggct tctgagagat tggaatgatg   600
ttcaaggacg atttgaaaaa tgtgtgagtg ctaaggaagc tttggagact gatctttata    660
agcggtttat tctggtgttg aatgagaaga aacaaaaat cagaagtttg cataataaat     720
tattaaatgc agctcaagaa cgagaaaagg acatcaaaca agaagggaa actgcaatct     780 gttctgaaat gactgctgac cgagatccag tctatgatga gagtactgat gaggaaagtg    840
aaaaccaaac tgatctctct gggttggctt cagctgctgt aagtaaagat gattccatta    900
tttcaagtct tgatgtcact gatattgcac caagtagaaa aaggagacag cgaatgcaaa    960
gaaatcttgg gacagaacct aaaatggctc tcaggagaa tcagcttcaa gaaaaggaaa    1020
agcctgattc ttcactacct gagacgtcta aaaaggagca catctcagct gaaaacatgt    1080
ctttagaaac tctgagaaac agcagcccag aagacctctt tgatgagatt taacagtctc    1140
aaaaaatact ttgatgttca ctagactatg ttttctattc atttctttaa aatgaaaaag    1200
gagaatttca agtcagcagc cgctattacc gtatcttaca atttaattac atacacagtg    1260
aattgaaacc attgtgcaaa atggattaca catgtataca aagatacgat ttgatgatga    1320
cactggcaca ttattctaaa ctattcattc agcatgccta taattacata aattgtatga    1380 gacttttgt tgcaaaggac acatttatca tattcattca cacatattat atgtgatagc    1440
tgtccaacat cctgtctggg aagattttga aaacaggaca agaaaacat cattttaaaa    1500 tgtcttcagc ttttttgaa tagacgtatt caaacatatt ctgaacattg atgtttgaac    1560 atttttaattt gtgtgatgat gtagaaaata taatttagt ttgtacataa acattgtgaa    1620
aatctgataa taaaattttt gatacattga aaaaaaaaaa aaaaaaaaaa aaaaaaaaa    1680 aaaaaaaa                                                             1688
```

<210> SEQ ID NO 26
<211> LENGTH: 13509
<212> TYPE: DNA
<213> ORGANISM: Homo sapiens

<400> SEQUENCE: 26

```
ggggcatttc cgggtccggg ccgagcgggc gcacgcgcgg gagcgggact cggcggcatg    60
gcgggctccg gagccggtgt gcgttgctcc ctgctgcggc tgcaggagac cttgtccgct   120
gcggaccgct gcggtgctgc cctggccggt catcaactga tccgcggcct ggggcaggaa   180
tgcgtcctga gcagcagccc cgcggtgctg gcattacaga catctttagt tttttccaga   240
gatttcggtt tgcttgtatt tgtccggaag tcactcaaca gtattgaatt tcgtgaatgt   300
agagaagaaa tcctaaagtt tttatgtatt ttcttagaaa aaatgggcca gaagatcgca   360
ccttactctg ttgaaattaa gaacacttgt accagtgttt atacaaaaga tagagctgct   420
aaatgtaaaa ttccagcccct ggaccttctt attaagttac ttcagacttt tagaagttct   480
agactcatgg atgaatttaa aattggagaa ttatttagta aattctatgg agaacttgca   540
ttgaaaaaaa aaataccaga tacagtttta gaaaagtat atgagctcct aggattattg   600
ggtgaagttc atcctagtga gatgataaat aatgcagaaa acctgttccg cgcttttctg   660
ggtgaactta agacccagat gacatcagca gtaagagagc ccaaactacc tgttctggca   720
ggatgtctga aggggttgtc ctcacttctg tgcaacttca ctaagtccat ggaagaagat   780
```

| | |
|---|---|
| ccccagactt caagggagat ttttaattttt gtactaaagg caattcgtcc tcagattgat | 840 |
| ctgaagagat atgctgtgcc ctcagctggc ttgcgcctat ttgccctgca tgcatctcag | 900 |
| tttagcacct gccttctgga caactacgtg tctctatttg aagtcttgtt aaagtggtgt | 960 |
| gcccacacaa atgtagaatt gaaaaaagct gcactttcag ccctggaatc ctttctgaaa | 1020 |
| caggtttcta atatggtggc gaaaaatgca gaaatgcata aaaataaact gcagtacttt | 1080 |
| atggagcagt tttatggaat catcagaaat gtggattcga acaacaagga gttatctatt | 1140 |
| gctatccgtg gatatggact ttttgcagga ccgtgcaagg ttataaacgc aaaagatgtt | 1200 |
| gacttcatgt acgttgagct cattcagcgc tgcaagcaga tgttcctcac ccagacagac | 1260 |
| actggtgacg accgtgttta tcagatgcca agcttcctcc agtctgttgc aagcgtcttg | 1320 |
| ctgtaccttg acacagttcc tgaggtgtat actccagttc tggagcacct cgtggtgatg | 1380 |
| cagatagaca gtttcccaca gtacagtcca aaaatgcagc tggtgtgttg cagagccata | 1440 |
| gtgaaggtgt tcctagcttt ggcagcaaaa gggccagttc tcaggaattg cattagtact | 1500 |
| gtggtgcatc agggtttaat cagaatatgt tctaaaccag tggtccttcc aaagggccct | 1560 |
| gagtctgaat ctgaagacca ccgtgcttca ggggaagtca gaactggcaa atggaaggtg | 1620 |
| cccacataca aagactacgt ggatctcttc agacatctcc tgagctctga ccagatgatg | 1680 |
| gattctattt tagcagatga agcatttttc tctgtgaatt cctccagtga aagtctgaat | 1740 |
| catttacttt atgatgaatt tgtaaaatcc gttttgaaga ttgttgagaa attggatctt | 1800 |
| acacttgaaa tacagactgt tggggaacaa gagaatggag atgaggcgcc tggtgtttgg | 1860 |
| atgatcccaa cttcagatcc agcggctaac ttgcatccag ctaaacctaa agattttcg | 1920 |
| gctttcatta acctggtgga attttgcaga gagattctcc ctgagaaaca agcagaattt | 1980 |
| tttgaaccat gggtgtactc attttcatat gaattaattt tgcaatctac aaggttgccc | 2040 |
| ctcatcagtg gtttctacaa attgctttct attacagtaa gaaatgccaa gaaaataaaa | 2100 |
| tatttcgagg gagttagtcc aaagagtctg aaacactctc ctgaagaccc agaaaagtat | 2160 |
| tcttgctttg ctttatttgt gaaatttggc aaagaggtgg cagttaaaat gaagcagtac | 2220 |
| aaagatgaac ttttggcctc ttgtttgacc tttcttctgt ccttgccaca caacatcatt | 2280 |
| gaactcgatg ttagagccta cgttcctgca ctgcagatgg ctttcaaact gggcctgagc | 2340 |
| tatacccct tggcagaagt aggcctgaat gctctagaag aatggtcaat ttatattgac | 2400 |
| agacatgtaa tgcagcctta ttacaaagac attctcccct gcctggatgg atacctgaag | 2460 |
| acttcagcct tgtcagatga gaccaagaat aactgggaag tgtcagctct ttctcgggct | 2520 |
| gcccagaaag gatttaataa agtggtgtta agcatctga agaagacaaa gaacctttca | 2580 |
| tcaaacgaag caatatcctt agaagaaata agaattagag tagtacaaat gcttggatct | 2640 |
| ctaggaggac aaataaacaa aaatcttctg acagtcacgt cctcagatga gatgatgaag | 2700 |
| agctatgtgg cctgggacag agagaagcgg ctgagctttg cagtgccctt tagagagatg | 2760 |
| aaacctgtca ttttcctgga tgtgttcctg cctcgagtca cagaattagc gctcacagcc | 2820 |
| agtgacagac aaactaaagt tgcagcctgt gaacttttac atagcatggt tatgtttatg | 2880 |
| ttgggcaaag ccacgcagat gccagaaggg ggacagggag ccccacccat gtaccagctc | 2940 |
| tataagcgga cgtttcctgt gctgcttcga cttgcgtgtg atgttgatca ggtgacaagg | 3000 |
| caactgtatg agccactagt tatgcagctg attcactggt tcactaacaa caagaaattt | 3060 |
| gaaagtcagg atactgttgc cttactagaa gctatattgg atggaattgt ggaccctgtt | 3120 |
| gacagtactt taagagattt ttgtggtcgg tgtattcgag aattccttaa atggtccatt | 3180 |

```
aagcaaataa caccacagca gcaggagaag agtccagtaa acaccaaatc gcttttcaag    3240
cgactttata gccttgcgct tcaccccaat gctttcaaga ggctgggagc atcacttgcc    3300
tttaataata tctacaggga attcaggaa gaagagtctc tggtggaaca gtttgtgttt    3360
gaagccttgg tgatatacat ggagagtctg gccttagcac atgcagatga aagtccttta    3420
ggtacaattc aacagtgttg tgatgccatt gatcacctat gccgcatcat tgaaaagaag    3480 catgttttctt taaataaagc aaagaaacga cgtttgccgc gaggatttcc accttccgca    3540
tcattgtgtt tattggatct ggtcaagtgg cttttagctc attgtgggag ccccagaca    3600 gaatgtcgac acaaatccat tgaactcttt tataaattcg ttcctttatt gccaggcaac    3660 agatcccta atttgtggct gaaagatgtt ctcaaggaag aaggtgtctc tttctcatc    3720 aacacctttg aggggggtgg ctgtggccag ccctcgggca tcctggccca gcccaccctc    3780
ttgtaccttc ggggccatt cagcctgcag ccacgctat gctggctgga cctgctcctg    3840
gccgcgttgg agtgctacaa cacgttcatt ggcgagagaa ctgtaggagc gctccaggtc    3900
ctaggtactg aagcccagtc ttcacttttg aaagcagtgg ctttcttctt agaaagcatt    3960
gccatgcatg acattatagc agcagaaaag tgctttggca ctggggcagc aggtaacaga    4020
acaagcccac aagagggaga aaggtacaac tacagcaaat gcaccgttgt ggtccggatt    4080
atggagttta ccacgactct gctaaacacc tccccggaag gatggaagct cctgaagaag    4140
gacttgtgta atacacacct gatgagagtc ctggtgcaga cgctgtgtga gcccgcaagc    4200
ataggtttca acatcggaga cgtccaggtt atggctcatc ttcctgatgt ttgtgtgaat    4260
ctgatgaaag ctctaaagat gtccccatac aaagatatcc tagagaccca tctgagagag    4320
aaaataacag cacagagcat tgaggagctt tgtgccgtca acttgtatgg ccctgacgcg    4380
caagtggaca ggagcaggct ggctgctgtt gtgtctgcct gtaaacagct tcacagagct    4440
gggcttctgc ataatatatt accgtctcag tccacagatt tgcatcattc tgttggcaca    4500
gaacttcttt ccctggttta taaggcatt gcccctggag atgagagaca gtgtctgcct    4560
tctctagacc tcagttgtaa gcagctggcc agcggacttc tggagttagc cttgctttt    4620 ggaggactgt gtgagcgcct tgtgagtctt ctcctgaacc cagcggtgct gtccacggcg    4680
tccttgggca gctcacaggg cagcgtcatc cacttctccc atggggagta tttctatagc    4740
ttgttctcag aaacgatcaa cacggaatta ttgaaaaatc tggatcttgc tgtattggag    4800
ctcatgcagt cttcagtgga taataccaaa atggtgagtg ccgttttgaa cggcatgtta    4860
gaccagagct caggagcg agcaaaccag aaacaccaag gactgaaact tgcgactaca    4920
attctgcaac actggaagaa gtgtgattca tggtgggcca agattcccc tctcgaaact    4980 aaaatggcag tgctggcctt actggcaaaa attttacaga ttgattcatc tgtatcttt    5040 aatacaagtc atggttcatt ccctgaagtc tttacaacat atattagtct acttgctgac    5100
acaaagctgg atctacattt aaaggccaa gctgtcactc ttcttccatt cttccaccagc    5160 ctcactggag gcagtctgga ggaacttaga cgtgttctgg agcagctcat cgttgctcac    5220
ttccccatgc agtccaggga atttcctcca ggaactccgc ggttcaataa ttatgtggac    5280
tgcatgaaaa agtttctaga tgcattggaa ttatctcaaa gccctatgtt gttggaattg    5340
atgacagaag ttctttgtcg ggaacagcag catgtcatgg aagaattatt tcaatccagt    5400
ttcaggagga ttgccagaag gggttcatgt gtcacacaag taggccttct ggaaagcgtg    5460
tatgaaatgt tcaggaagga tgaccccgc ctaagtttca cacgccagtc ctttgtggac    5520
```

```
cgctccctcc tcactctgct gtggcactgt agcctggatg ctttgagaga attcttcagc    5580
acaattgtgg tggatgccat tgatgtgttg aagtccaggt ttacaaagct aaatgaatct    5640
acctttgata ctcaaatcac caagaagatg gctactata agattctaga cgtgatgtat     5700
tctcgccttc ccaaagatga tgttcatgct aaggaatcaa aaattaatca agttttccat    5760
ggctcgtgta ttacagaagg aaatgaactt acaaagacat tgattaaatt gtgctacgat    5820
gcatttacag agaacatggc aggagagaat cagctgctgg agaggagaag actttaccat    5880
tgtgcagcat acaactgcgc catatctgtc atctgctgtg tcttcaatga gttaaaattt    5940
taccaaggtt ttctgtttag tgaaaaacca gaaaagaact tgcttatttt tgaaaatctg    6000
atcgacctga agcgccgcta taattttcct gtagaagttg aggttcctat ggaaagaaag    6060
aaaaagtaca ttgaaattag gaagaagcc agagaagcag caaatgggga ttcagatggt      6120
ccttcctata tgtcttccct gtcatatttg gcagacagta ccctgagtga ggaaatgagt    6180
caatttgatt tctcaaccgg agttcagagc tattcataca gctcccaaga ccctagacct    6240
gccactggtc gttttcggag acgggagcag cgggacccca cggtgcatga tgatgtgctg    6300
gagctggaga tggacgagct caatcggcat gagtgcatgg cgcccctgac ggccctggtc    6360
aagcacatgc acagaagcct gggcccgcct caaggagaag aggattcagt gccaagagat    6420
cttccttctt ggatgaaatt cctccatggc aaactgggaa atccaatagt accattaaat    6480
atccgtctct tcttagccaa gcttgttatt aatacagaag aggtctttcg cccttacgcg    6540
aagcactggc ttagcccctt gctgcagctg gctgcttctg aaaacaatgg aggagaagga    6600
attcactaca tggtggttga gatagtggcc actattcttt catggacagg cttggccact    6660
ccaacagggg tccctaaaga tgaagtgtta gcaaatcgat tgcttaattt cctaatgaaa    6720
catgtctttc atccaaaaag agctgtgttt agacacaacc ttgaaattat aaagacccct    6780
gtcgagtgct ggaaggattg tttatccatc ccttataggt taatatttga aagttttcc      6840 ggtaaagatc ctaattctaa agacaactca gtagggattc aattgctagg catcgtgatg    6900
gccaatgacc tgcctcccta tgacccacag tgtggcatcc agagtagcga atacttccag    6960
gctttggtga ataatatgtc ctttgtaaga tataaagaag tgtatgccgc tgcagcagaa    7020
gttctaggac ttatacttcg atatgttatg gagagaaaaa acatactgga ggagtctctg    7080
tgtgaactgg ttgcgaaaca attgaagcaa catcagaata ctatggagga caagtttatt    7140
gtgtgcttga caaagtgac caagagcttc cctcctcttg cagacaggtt catgaatgct     7200
gtgttctttc tgctgccaaa atttcatgga gtgttgaaaa cactctgtct ggaggtggta    7260
ctttgtcgtg tggagggaat gacagagctg tacttccagt aaagagcaa ggacttcgtt     7320 caagtcatga gacatagaga tgatgaaaga caaaaagtat gtttggacat aatttataag    7380
atgatgccaa agttaaaacc agtagaactc cgagaacttc tgaaccccgt tgtggaattc    7440
gtttcccatc cttctacaac atgtagggaa caaatgtata atattctcat gtggattcat    7500
gataattaca gagatccaga aagtgagaca gataatgact cccaggaaat atttaagttg    7560
gcaaaagatg tgctgattca aggattgatc gatgagaacc ctggacttca attaattatt    7620
cgaaatttct ggagccatga aactaggtta ccttcaaata ccttggaccg gttgctggca    7680
ctaaattcct tatattctcc taagatagaa gtgcactttt taagtttagc aacaaatttt    7740
ctgctcgaaa tgaccagcat gagcccagat tatccaaacc ccatgttcga gcatcctctg    7800
tcagaatgcg aatttcagga atataccatt gattctgatt ggcgtttccg aagtactgtt    7860
ctcactccga tgtttgtgga gacccaggcc tcccagggca ctctccagac ccgtacccag    7920
```

```
gaagggtccc tctcagctcg ctggccagtg gcagggcaga taaggggccac ccagcagcag    7980
catgacttca cactgacaca gactgcagat ggaagaagct catttgattg gctgaccggg    8040
agcagcactg acccgctggt cgaccacacc agtccctcat ctgactcctt gctgtttgcc    8100
cacaagagga gtgaaaggtt acagagagca cccttgaagt cagtgggggcc tgattttggg   8160
aaaaaaaggc tgggccttcc aggggacgag gtggataaca aagtgaaagg tgcggccggc    8220
cggacggacc tactacgact gcgcagacgg tttatgaggg accaggagaa gctcagtttg    8280
atgtatgcca gaaaaggcgt tgctgagcaa aaacgagaga aggaaatcaa gagtgagtta    8340
aaaatgaagc aggatgccca ggtcgttctg tacagaagct accggcacgg agaccttcct    8400
gacattcaga tcaagcacag cagcctcatc accccgttac aggccgtggc ccagagggac    8460
ccaataattg caaacagct ctttagcagc ttgttttctg gaattttgaa agagatggat     8520
aaatttaaga cactgtctga aaaaaacaac atcactcaaa agttgcttca agacttcaat    8580
cgttttctta ataccacctt ctctttcttt ccacccttttg tctcttgtat tcaggacatt   8640
agctgtcagc acgcagccct gctgagcctc gacccagcgg ctgttagcgc tggttgcctg   8700
gccagcctac agcagcccgt gggcatccgc ctgctagagg aggctctgct ccgcctgctg   8760
cctgctgagc tgcctgccaa gcgagtccgt gggaaggccc gcctccctcc tgatgtcctc   8820
agatgggtgg agcttgctaa gctgtataga tcaattggag aatacgacgt cctccgtggg   8880
attttacca gtgagatagg aacaaagcaa atcactcaga gtgcattatt agcagaagcc    8940
agaagtgatt attctgaagc tgctaagcag tatgatgagg ctctcaataa acaagactgg   9000
gtagatggtg agcccacaga agccgagaag gattttttggg aacttgcatc ccttgactgt  9060
tacaaccacc ttgctgagtg gaaatcactt gaatactgtt ctacagccag tatagacagt   9120
gagaaccccc cagacctaaa taaaatctgg agtgaaccat tttatcagga aacatatcta   9180
ccttacatga tccgcagcaa gctgaagctg ctgctccagg gagaggctga ccagtccctg   9240
ctgacattta ttgacaaagc tatgcacggg gagctccaga aggcgattct agagcttcat   9300
tacagtcaag agctgagtct gctttacctc ctgcaagatg atgttgacag agccaaaatat 9360
tacattcaaa atggcattca gagttttatg cagaattatt ctagtattga tgtcctctta   9420
caccaaagta gactcaccaa attgcagtct gtacaggctt taacagaaat tcaggagttc   9480
atcagctttta taagcaaaca aggcaattta tcatctcaag ttcccttaa gagacttctg    9540
aacacctgga caaacagata tccagatgct aaaatggacc caatgaacat ctgggatgac   9600
atcatcacaa atcgatgttt ctttctcagc aaaatagagg agaagcttac ccctcttcca   9660
gaagataata gtatgaatgt ggatcaagat ggagaccccca gtgacaggat ggaagtgcaa   9720
gagcaggaag aagatatcag ctccctgatc aggagttgca agttttccat gaaaatgaag   9780
atgatagaca gtgcccggaa gcagaacaat ttctcacttg ctatgaaact actgaaggag   9840
ctgcataaag agtcaaaaac cagagacgat tggctggtga gctgggtgca gagctactgc   9900
cgcctgagcc actgccggag ccggtcccag ggctgctctg agcaggtgct cactgtgctg   9960
aaaacagtct ctttgttgga tgagaacaac gtgtcaagct acttaagcaa aaatattctg  10020
gctttccgtg accagaacat tctcttgggt acaacttaca ggatcatagc gaatgctctc  10080
agcagtgagc cagcctgcct tgctgaaatc gaggaggaca aggctagaag aatcttagag  10140
ctttctggat ccagttcaga ggattcagag aaggtgatcg cgggtctgta ccagagagca  10200
ttccagcacc tctctgaggc tgtgcaggcg gctgaggagg aggcccagcc tccctcctgg  10260
```

```
agctgtgggc ctgcagctgg ggtgattgat gcttacatga cgctggcaga tttctgtgac    10320
caacagctgc gcaaggagga agagaatgca tcagttattg attctgcaga actgcaggcg    10380
tatccagcac ttgtggtgga gaaaatgttg aaagctttaa aattaaattc caatgaagcc    10440
agattgaagt ttcctagatt acttcagatt atagaacggt atccagagga gactttgagc    10500
ctcatgacaa aagagatctc ttccgttccc tgctggcagt tcatcagctg gatcagccac    10560
atggtggcct tactgacaa agaccaagcc gttgctgttc agcactctgt ggaagaaatc    10620
actgataact acccgcaggc tattgtttat cccttcatca taagcagcga aagctattcc    10680
ttcaaggata cttctactgg tcataagaat aaggagtttg tggcaaggat taaaagtaag    10740
ttggatcaag gaggagtgat tcaagatttt attaatgcct tagatcagct ctctaatcct    10800
gaactgctct ttaaggattg gagcaatgat gtaagagctg aactagcaaa accccctgta    10860
aataaaaaaa acattgaaaa aatgtatgaa agaatgtatg cagccttggg tgacccaaag    10920
gctccaggcc tgggggcctt tagaaggaag tttattcaga cttttggaaa agaatttgat    10980
aaacattttg ggaaaggagg ttctaaacta ctgagaatga agctcagtga cttcaacgac    11040
attaccaaca tgctactttt aaaaatgaac aaagactcaa agcccctgg gaatctgaaa    11100 gaatgttcac cctggatgag cgacttcaaa gtggagttcc tgagaaatga gctggagatt    11160
cccggtcagt atgacggtag gggaaagcca ttgccagagt accacgtgcg aatcgccggg    11220
tttgatgagc gggtgacagt catggcgtct ctgcgaaggc ccaagcgcat catcatccgt    11280
ggccatgacg agagggaaca cccttttcctg gtgaagggtg gcgaggacct gcggcaggac    11340
cagcgcgtgg agcagctctt ccaggtcatg aatgggatcc tggcccaaga ctccgcctgc    11400
agccagaggg ccctgcagct gaggacctat agcgttgtgc ccatgacctc caggttagga    11460
ttaattgagt ggcttgaaaa tactgttacc ttgaaggacc ttctttgaa caccatgtcc    11520 caagaggaga aggcggctta cctgagtgat cccagggcac cgccgtgtga atataaagat    11580
tggctgacaa aaatgtcagg aaaacatgat gttggagctt acatgctaat gtataaggc    11640 gctaatcgta ctgaaacagt cacgtctttt agaaaacgag aaagtaaagt gcctgctgat    11700
ctcttaaagc gggccttcgt gaggatgagt acaagccctg aggctttcct ggcgctccgc    11760
tcccacttcg ccagctctca cgctctgata tgcatcagcc actggatcct cgggattgga    11820
gacagacatc tgaacaactt tatggtggcc atggagactg gcggcgtgat cgggatcgac    11880
tttgggcatg cgtttggatc cgctacacag tttctgccag tccctgagtt gatgcctttt    11940
cggctaactc gccagtttat caatctgatg ttaccaatga agaaacggg ccttatgtac    12000 agcatcatgg tacacgcact ccgggccttc cgctcagacc ctggcctgct caccaacacc    12060
atggatgtgt ttgtcaagga gccctccttt gattggaaaa attttgaaca gaaaatgctg    12120 aaaaaggag ggtcatggat tcaagaaata aatgttgctg aaaaaaattg gtaccccga    12180 cagaaaatat gttacgctaa gagaaagtta gcaggtgcca atccagcagt cattacttgt    12240
gatgagctac tcctgggtca tgagaaggcc cctgccttca gagactatgt ggctgtggca    12300
cgaggaagca agatcacaa cattcgtgcc caagaaccag agagtgggct ttcagaagag    12360
actcaagtga agtgcctgat ggaccaggca acagacccca acatccttgg cagaacctgg    12420
gaaggatggg agccctggat gtgaggtctg tgggagtctg cagatagaaa gcattacatt    12480
gtttaaagaa tctactatac tttggttggc agcattccat gagctgattt tcctgaaaca    12540 ctaaagaaa atgtcttttg tgctacagtt tcgtagcatg agtttaaatc aagattatga    12600
tgagtaaatg tgtatgggtt aaatcaaaga taaggttata gtaacatcaa agattaggtg    12660
```

-continued

```
aggtttatag aaagatagat atccaggctt accaaagtat taagtcaaga atataatatg   12720
tgatcagctt tcaaagcatt tacaagtgct gcaagttagt gaaacagctg tctccgtaaa   12780
tggaggaaat gtggggaagc cttggaatgc ccttctggtt ctggcacatt ggaaagcaca   12840
ctcagaaggc ttcatcacca agattttggg agagtaaagc taagtatagt tgatgtaaca   12900
ttgtagaagc agcataggaa caataagaac aataggtaaa gctataatta tggcttatat   12960
ttagaaatga ctgcatttga tattttagga tattttccta ggttttttcc tttcattta    13020
ttctcttcta gttttgacat tttatgatag atttgctctc tagaaggaaa cgtctttatt   13080
taggagggca aaaattttgg tcatagcatt cacttttgct attccaatct acaactggaa   13140
gatacataaa agtgctttgc attgaatttg ggataacttc aaaaatccca tggttgttgt   13200
tagggatagt actaagcatt tcagttccag gagaataaaa gaaattccta tttgaaatga   13260
attcctcatt tggaggaaaa aaagcatgca ttctagcaca acaagatgaa attatggaat   13320
acaaaagtgg ctccttccca tgtgcagtcc ctgtccccc ccgccagtcc tccacaccca   13380
aactgtttct gattggcttt tagcttttg ttgtttttt ttttccttct aacacttgta    13440
tttggaggct cttctgtgat tttgagaagt atactcttga gtgtttaata aagttttttt   13500
ccaaaagta                                                           13509
```

<210> SEQ ID NO 27
<211> LENGTH: 3701
<212> TYPE: DNA
<213> ORGANISM: Homo sapiens

<400> SEQUENCE: 27

```
gcttcccgga agtggcggcg cggtcagggc tggccttggc ttcagctgcg gttttggggt     60
cccggactct gggatcggcg gcgctatgag ttctttcgag gggcagatgg ccgagtatcc    120
aactatctcc atagaccgct tcgatagggg aaacctgagg gccgcgcct acttcctgtc    180
ccactgccac aaagatcaca tgaaaggatt aagagcccct accttgaaaa gaaggttgga    240
gtgcagcttg aaggtttatc tatactgttc acctgtgact aaggagttgt tgttaacgag    300
cccgaaatac agatttggga agaaacgaat tatatctatt gaaatcgaga ctcctaccca    360
gatatcttta gtggatgaag catcaggaga gaaggaagag attgttgtga ctctcttacc    420
agctggtcac tgtccgggat cagttatgtt tttatttcag ggcaataatg gaactgtcct    480
gtacacagga gacttcagat tggcgcaagg agaagctgct agaatggagc ttctgcactc    540
cggggggcaga gtcaaagaca tccaaagtgt atatttggat actacgttct gtgatccaag    600
attttaccaa attccaagtc gggaggagtg tttaagtgga gtcttagagc tggtccgaag    660
ctggatcact cggagcccgt accatgttgt gtggctgaac tgcaaagcgg cttatggcta    720
tgaatatctg ttcaccaacc ttagtgaaga attaggagtc caggttcatg tgaataagct    780
agacatgttt aggaacatgc ctgagatcct tcatcatctc acaacagacc gcaacactca    840
gatccatgca tgccggcatc ccaaggcaga ggaatatttt cagtggagca aattaccctg    900
tggaattact tccagaaata gaattccact ccacataatc agcattaagc catccaccat    960
gtggtttgga gaaaggagca gaaaaacaaa tgtaattgtg aggactggag agagttcata   1020
cagagcttgt ttttcttttc actcctccta cagtgagatt aaagatttct tgagctacct   1080
ctgtcctgtg aacgcatatc caaatgtcat tccagttggc acaactatgg ataaagttgt   1140
cgaaatctta aagcctttat gccggtcttc ccaaagtacg gagccaaagt ataaaccact   1200
```

```
gggaaaactg aagagagcta gaacagttca ccgagactca gaggaggaag atgactatct    1260
ctttgatgat cctctgccaa tacctttaag gcacaaagtt ccatacccgg aaacttttca    1320
ccctgaggta ttttcaatga ctgcagtatc agaaaagcag cctgaaaaac tgagacaaac    1380
cccaggatgc tgcagagcag agtgtatgca gagctctcgt ttcacaaact ttgtagattg    1440
tgaagaatcc aacagtgaaa gtgaagaaga agtaggaatc ccagcttcac tgcaaggaga    1500
tctgggctct gtacttcacc tgcaaaaggc tgatggggat gtaccccagt gggaagtatt    1560
ctttaaaaga aatgatgaaa tcacagatga gagtttggaa aacttccctt cctccacagt    1620
ggcaggggga tctcagtcac caaagctttt cagtgactct gatggagaat caactcacat    1680
ctcctcccag aattcttccc agtcaacaca cataacagaa caaggaagtc aaggctggga    1740
cagccaatct gatactgttt tgttatcttc ccaagagaga aacagtgggg atattacttc    1800
cttggacaaa gctgactaca gaccaacaat caaagagaat attcctgcct ctctcatgga    1860
acaaaatgta atttgcccaa aggatactta ctctgatttg aaaagcagag ataaagatgt    1920
gacaatagtt cctagtactg agaaccaac tactctaagc agtgagacac atatacccga    1980 ggaaaaagt ttgctaaatc ttagcacaaa tgcagattcc cagagctctt ctgattttga    2040
agttccctca actccagaag ctgagttacc taaacgagag catttacaat atttatatga    2100
gaagctggca actggtgaga gtatagcagt caaaaaaaga aaatgctcac tcttagatac    2160
ctaagaattc aaagcgtttc aacctagagc aaccactaaa aaacctgcac agagatgaca    2220
gtcaatatta caatagagaa atacagtac ttaaaaatgt tcaaataacc tggttgggtg    2280
tggtggctca cacttgtaat cccagcactt tgaggtgggc aatggcttga gcccaggagt    2340
tcgacaccag cctggccaac acagtgaaat gtgtctctac ttacaaaaaa aaaaaaaaaa    2400
aaaaaagcca ggcatggtgg tgggctactc tggaggccct tgaggatcac ttgagcccag    2460
gagattgagg ctgcagtgag ccatgactgt gccactgcac ctctagtctg ggtgacagag    2520
caagaccctg tttaaaaaag aaaaaggcca ggcacggtgg ctcatgcctg taatcccagc    2580
tacgcaggag gccaaggcag gagaatcact tgaacctggg aggtggtggt tgcagtgagc    2640
tgagattgtg tcattgcact ccagcctggg caacaagagc aaaactctgt ctcaaaaaaa    2700
aaaaaaaaaa aaagaaaaa aaaatggtag aactaaaccc atacgtatca atgattacat    2760
taaatgtaaa tggtctaagt gcatcaatga caagagacac ggaaaaaacc aacataaccc    2820
agtgatctgc tgtctataaa gaaagtcaat tcaagtgatt gataggttaa aaggatggaa    2880
aaaccatgta aacaattaaa aatggagtgg ttatatggac agtttcctaa tgataaaagg    2940
tctagttcac caagaagaca aaataatcct aaacgtatat gcacctaaca gctccaaaaa    3000
tttatgaagc tagaacagct gaaaagagac aaactaatgc acaattacag ctagggatta    3060
atttaacatc cctccttagt aacagaacta gtatatacac attaatcagt aagaatatag    3120
aactgaaaat cataagccga ctggattaaa ttgacattta tagaacacac caccccaaac    3180
tagcagaatg tatctcctga agtacacatg gaacattcag catgatcata tctttgctca    3240
taaacacacc tgatttaaat tgacaaactt ggatctagta tgataaactg atggctatag    3300
acaaaatcag cacctatttt atccccaaag atgttaagtc acttaacctt gatgtgaata    3360
cggtggccaa attagaagcg gacaattaga atataaaaga aaatgctcaa gaattaaatg    3420
gtggccaggc acagtaactc ctgcctgcaa tcccagtact ttgggaggct cgcttgagct    3480
cagggttttg agtccagcct gggcaacaca cagggagacc ctgtctccac aaaatgttag    3540
ccagacatgg tggtgtgcac ctgtagtcct cgctacttgg aaggcttagg tggcaggatg    3600
```

-continued

| | |
|---|---|
| gattgagccc aggaggttga aactgcagtg agctgattgt gcccagcctg ggcaacaaag | 3660 |
| caagacccca tctcaagaaa aataaattaa aaaaaactaa a | 3701 |

<210> SEQ ID NO 28
<211> LENGTH: 2156
<212> TYPE: DNA
<213> ORGANISM: Homo sapiens

<400> SEQUENCE: 28

| | |
|---|---|
| gcgcatgcgt ggattgtcgt cttctgtcca agttggtcgc ttccctgcgc caaagtgagc | 60 |
| agtagccaac atgtcagggt gggagtcata ttacaaaacc gagggcgatg aagaagcaga | 120 |
| ggaagaacaa gaagagaacc ttgaagcaag tggagactat aaatattcag gaagagatag | 180 |
| tttgattttt ttggttgatg cctccaaggc tatgtttgaa tctcagagtg aagatgagtt | 240 |
| gacacctttt gacatgagca tccagtgtat ccaaagtgtg tacatcagta agatcataag | 300 |
| cagtgatcga gatctcttgg ctgtggtgtt ctatggtacc gagaaagaca aaaattcagt | 360 |
| gaatttttaaa aatatttacg tcttacagga gctggataat ccaggtgcaa aacgaattct | 420 |
| agagcttgac cagtttaagg ggcagcaggg acaaaaacgt ttccaagaca tgatgggcca | 480 |
| cggatctgac tactcactca gtgaagtgct gtgggtctgt gccaacctct ttagtgatgt | 540 |
| ccaattcaag atgagtcata agaggatcat gctgttcacc aatgaagaca ccccccatgg | 600 |
| caatgacagt gccaaagcca gccgggccag gaccaaagcc ggtgatctcc gagatacagg | 660 |
| catcttcctt gacttgatgc acctgaagaa acctgggggc tttgacatat ccttgttcta | 720 |
| cagagatatc atcagcatag cagaggatga ggaccctcagg gttcactttg aggaatccag | 780 |
| caagctagaa gacctgttgc ggaaggttcg cgccaaggag accaggaagc gagcactcag | 840 |
| caggttaaag ctgaagctca acaaagatat agtgatctct gtgggcattt ataatctggt | 900 |
| ccagaaggct ctcaagcctc ctccaataaa gctctatcgg gaaacaaatg aaccagtgaa | 960 |
| aaccaagacc cggacctta atacaagtac aggcggtttg cttctgccta gcgataccaa | 1020 |
| gaggtctcag atctatggga gtcgtcagat tatactggag aaagaggaaa cagaagagct | 1080 |
| aaaacggttt gatgatccag gtttgatgct catgggtttc aagccgttgg tactgctgaa | 1140 |
| gaaacaccat tacctgaggc cctccctgtt cgtgtaccca gaggagtcgc tggtgattgg | 1200 |
| gagctcaacc ctgttcagtg ctctgctcat caagtgtctg gagaaggagg ttgcagcatt | 1260 |
| gtgcagatac acaccccgca ggaacatccc tccttatttt gtggctttgg tgccacagga | 1320 |
| agaagagttg gatgaccaga aaattcaggt gactcctcca ggcttccagc tggtctttt | 1380 |
| acccttttgct gatgataaaa ggaagatgcc ctttactgaa aaaatcatgg caactccaga | 1440 |
| gcaggtgggc aagatgaagg ctatcgttga gaagcttcgc ttcacataca gaagtgacag | 1500 |
| ctttgagaac cccgtgctgc agcagcactt caggaacctg gaggccttgg ccttggattt | 1560 |
| gatggagccg gaacaagcag tggacctgac attgccaag gttgaagcaa tgaataaaag | 1620 |
| actgggctcc ttggtggatg agtttaagga gcttgtttac ccaccagatt acaatcctga | 1680 |
| agggaaagtt accaagagaa aacacgataa tgaaggttct ggaagcaaaa ggcccaaggt | 1740 |
| ggagtattca gaagaggagc tgaagaccca catcagcaag ggtacgctgg gcaagttcac | 1800 |
| tgtgcccatg ctgaaagagg cctgccgggc ttacgggctg aagagtgggc tgaagaagca | 1860 |
| ggagctgctg gaagccctca ccaagcactt ccaggactga ccagaggccg cgcgtccagc | 1920 |
| tgcccttccg cagtgtggcc aggctgcctg gccttgtcct cagccagtta aaatgtgttt | 1980 |

```
ctcctgagct aggaagagtc tacccgacat aagtcgaggg actttatgtt tttgaggctt    2040
tctgttgcca tggtgatggt gtagccctcc cactttgctg ttccttactt tactgcctga    2100
ataaagagcc ctaagtttgt actatatact gttaaaaaaa aaaaaaaaa aaaaaa         2156

<210> SEQ ID NO 29
<211> LENGTH: 3448
<212> TYPE: DNA
<213> ORGANISM: Homo sapiens

<400> SEQUENCE: 29
acggtttccc cgccccttc aggcctagca ggaaacgaag cggctctttc cgctatctgc      60
cgcttgtcca ccggaagcga gttgcgacac ggcaggttcc cgcccggaag aagcgaccaa   120
agcgcctgag gaccggcaac atggtgcggt cggggaataa ggcagctgtt gtgctgtgta   180
tggacgtggg ctttaccatg agtaactcca ttcctggtat agaatcccca tttgaacaag   240
caaagaaggt gataaccatg tttgtacagc gacaggtgtt tgctgagaac aaggatgaga   300
ttgctttagt cctgttggt acagatggca ctgacaatcc cctttctggt ggggatcagt    360
atcagaacat cacagtgcac agacatctga tgctaccaga ttttgatttg ctggaggaca   420
ttgaaagcaa aatccaacca ggttctcaac aggctgactt cctggatgca ctaatcgtga   480
gcatggatgt gattcaacat gaaacaatag gaaagaagtt tgagaagagg catattgaaa   540
tattcactga cctcagcagc cgattcagca aaagtcagct ggatattata attcatagct   600
tgaagaaatg tgacatctcc ctgcaattct tcttgccttt ctcacttggc aaggaagatg   660
gaagtgggga cagaggagat ggccccttc gcttaggtgg ccatgggcct tcctttccac    720
taaaaggaat taccgaacag caaaagaag gtcttgagat agtgaaaatg gtgatgatat   780
ctttagaagg tgaagatggg ttggatgaaa tttattcatt cagtgagagt ctgagaaaac   840
tgtgcgtctt caagaaaatt gagaggcatt ccattcactg gccctgccga ctgaccattg   900
gctccaattt gtctataagg attgcagcct ataaatcgat tctacaggag agagttaaaa   960
agacttggac agttgtggat gcaaaaaccc taaaaaaaga agatatacaa aaagaaacag  1020
tttattgctt aaatgatgat gatgaaactg aagttttaaa agaggatatt attcaagggt  1080
tccgctatgg aagtgatata gttcctttct ctaaagtgga tgaggaacaa atgaaatata  1140
aatcggaggg gaagtgcttc tctgttttgg gattttgtaa atcttctcag gttcagagaa  1200
gattcttcat gggaaatcaa gttctaaagg tctttgcagc aagagatgat gaggcagctg  1260
cagttgcact ttcctcctg attcatgctt tggatgactt agacatggtg gccatagttc  1320
gatatgctta tgacaaaaga gctaatcctc aagtcggcgt ggcttttcct catatcaagc  1380
ataactatga gtgtttagtg tatgtgcagc tgccttcat ggaagacttg cggcaataca   1440
tgttttcatc cttgaaaaac agtaagaaat atgctcccac cgaggcacag ttgaatgctg  1500
ttgatgcttt gattgactcc atgagcttgg caaagaaaga tgaagacaga cacccttg    1560 aagacttgtt tccaaccacc aaaatcccaa atcctcgatt tcagagatta tttcagtgtc  1620
tgctgcacag agctttacat ccccgggagc tctaccccc aattcagcag catatttgga  1680
atatgctgaa tcctcccgct gaggtgacaa caaaagtca gattcctctc tctaaaataa   1740
agaccctttt tcctctgatt gaagccaaga aaaggatca agtgactgct caggaaattt   1800
tccaagacaa ccatgaagat ggacctacag ctaaaaaatt aaagactgag caaggggag    1860 cccacttcag cgtctccagt ctggctgaag gcagtgtcac ctctgttgga agtgtgaatc   1920
ctgctgaaaa cttccgtgtt ctagtgaaac agaagaaggc cagctttgag gaagcgagta   1980
```

| | |
|---|---|
| accagctcat aaatcacatc gaacagtttt tggatactaa tgaaacaccg tattttatga | 2040 |
| agagcataga ctgcatccga gccttccggg aagaagccat taagtttca gaagagcagc | 2100 |
| gctttaacaa cttcctgaaa gcccttcaag agaaagtgga aattaaacaa ttaaatcatt | 2160 |
| tctgggaaat tgttgtccag gatgaatta ctctgatcac caaagaggaa gcctctggaa | 2220 |
| gttctgtcac agctgaggaa gccaaaaagt ttctggcccc caaagacaaa ccaagtggag | 2280 |
| acacagcagc tgtatttgaa gaaggtggtg atgtggacga tttattggac atgatatagg | 2340 |
| tcgtggatgt atggggaatc taagagagct gccatcgctg tgatgctggg agttctaaca | 2400 |
| aaacaagttg gatgcggcca ttcaagggga gccaaaatct caagaaattc ccagcaggtt | 2460 |
| acctggaggc ggatcatcta attctctgtg gaatgaatac acacatatat attacaaggg | 2520 |
| ataatttaga ccccatacaa gtttataaag agtcattgtt attttctggt tggtgtatta | 2580 |
| ttttttctgt ggtcttactg atctttgtat attacataca tgctttgaag tttctggaaa | 2640 |
| gtagatcttt tcttgaccta gtatatcagt gacagttgca gcccttgtga tgtgattagt | 2700 |
| gtctcatgtg gaaccatggc atggttattg atgagtttct taaccctttc cagagtcctc | 2760 |
| ctttgcctga tcctccaaca gctgtcacaa cttgtgttga gcaagcagta gcatttgctt | 2820 |
| cctcccaaca agcagctggg ttaggaaaac catgggtaag gacggactca cttctcttt | 2880 |
| tagttgaggc cttctagtta ccacattact ctgcctctgt ataggtgg ttttctttaa | 2940 |
| gtggggtggg aaggggagca caatttccct tcatactcct tttaagcagt gagttatggt | 3000 |
| ggtggtctca tgaagaaaag acctttggc ccaatctctg ccatatcagt gaacctttag | 3060 |
| aaactcaaaa actgagaaat ttactacagt agttagaatt atatcacttc actgttctct | 3120 |
| acttgcaagc ctcaaagaga gaaagtttcg ttatattaaa acacttaggt aacttttcgg | 3180 |
| tctttcccat ttctacctaa gtcagctttc atctttgtgg atggtgtctc ctttactaaa | 3240 |
| taagaaaata acaaagccct tattctcttt ttttcttgtc ctcattcttg ccttgagttc | 3300 |
| cagttcctct ttggtgtaca gacttcttgg tacccagtca cctctgtctt cagcaccctc | 3360 |
| ataagtcgtc actaatacac agttttgtac atgtaacatt aaaggcataa atgactcatc | 3420 |
| tctctgtgaa aaaaaaaaaa aaaaaaaa | 3448 |

<210> SEQ ID NO 30
<211> LENGTH: 2119
<212> TYPE: DNA
<213> ORGANISM: Homo sapiens

<400> SEQUENCE: 30

| | |
|---|---|
| ataggccccg ccctgtatc ccaagaccct gcctcctctt gcggtggggg gaaagcggcc | 60 |
| tcttactcta ggccttttcgg tttgcgcgag cgggcaggaa agcgtgcgtg cggctaagag | 120 |
| agtgggcgct ctcgcggccg ctgacgatgg aagaactgga gcaaggcctg ttgatgcagc | 180 |
| catgggcgtg gctacagctt gcagagaact ccctcttggc caaggttttt atcaccaagc | 240 |
| agggctatgc cttgttggtt tcagatcttc aacaggtgtg gcatgaacag gtggacacta | 300 |
| gtgtggtcag ccagcgagcc aaggagctga acagcggct cactgctcct cctgcagctt | 360 |
| tcctctgtca tttggataat ctccttcgcc cattgttgaa ggacgctgct caccctagcg | 420 |
| aagctacctt ctcctgtgat tgtgtggcag atgcactgat tctacgggtg cgaagtgagc | 480 |
| tctctggcct ccccttctat tggaatttcc actgcatgct agctagtcct tccctggtct | 540 |
| cccaacattt gattcgtcct ctgatgggca tgagtctggc attacagtgc caagtgaggg | 600 |

```
agctagcaac gttacttcat atgaaagacc tagagatcca agactaccag gagagtgggg    660
ctacgctgat tcgagatcga ttgaagacag aaccatttga agaaaattcc ttcttggaac    720
aatttatgat agagaaactg ccagaggcat gcagcattgg tgatggaaag ccctttgtca    780
tgaatctgca ggatctgtat atggcagtca ccacacaaga ggtccaagtg ggacagaagc    840
atcaaggcgc tggagatcct catacctcaa acagtgcttc cctgcaagga atcgatagcc    900
aatgtgtaaa ccagccagaa caactggtct cctcagcccc aaccctctca gcacctgaga    960
aagagtccac gggtacttca ggccctctgc agagacctca gctgtcaaag gtcaagagga   1020
agaagccaag gggtctcttc agttaatctg ttgtggcctc agctgctgag gatggacttg   1080
gagaacagct tccaagcttc accttgaaag aagcttacat ggcagcaata tttctaaaat   1140
agtgatacag tcagaggcct cctgtaaggg cgagagaact gaagttgatg ttgacaggcc   1200
cacagggaat tggccttccc tgttcaagtg gaagccagtc tctgagaatc ccgtgctctc   1260
ctctcttttg gtggaggttc tgtaggttca ggtttctacc atggacttta ggtatatagg   1320
gcaagtcagc aagaaagcac cacacactca ggaagccttg tctacctttc cctagcgtct   1380
ctagccagcc agcccagat actcctcaga gacccacttc tctcttttgc atggaataaa   1440
aagcactcac agtccctgct tttgggatta cttatgctgt ggaactcata acccaattca   1500
cttccttcac tgggtcccac cccattgttg tctctggatg aagtctagcc atcagtctgg   1560
tccttcagat tcttcgtaaa cttttctgca gttgccagag ctaagtctcc atttggaaac   1620
tttgatctca agaactctct tgatggtggg cacaagacag ataggtgatt gctgcттttcc   1680
tttgccaaac ttggatgcat ttttctcttt gtttccaaag tataggcaac aggttaaact   1740
accacgtggg gtagtttatc aatcctcccg cctcatcctt ctgcataact gggactaaag   1800
gcacacacca ccacacctag ctaatttttg tatttttttg tgtgtggaga caaggctttg   1860
ccatgttgcc caggctggtc ttgaactcct ggactctagt gatctgccca cctcaacctc   1920
ccaaagtgct gggattacag gcatgagcta ccacgcctat ccaatttctg tttattttac   1980
ttcgatggt taaatgcctc ttatt caaa tatcctgtat atatactggc gtttctgtcc   2040
tgatgtcaag tctcgagaga agatgatcaa acaataataa aатaатттата ataagaacaa   2100
caaaaaaaaa aaaaaaaaa                                                 2119

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000
```

```
<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000
```

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
ccggccagtc caaatggcta ttatactcga gtataatagc catttggact ggttttttg        58

<210> SEQ ID NO 51
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ccggcccact tacttcttac actttctcga gaaagtgtaa gaagtaagtg ggttttttg        58

<210> SEQ ID NO 52
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ccggcccgac ttgaaggtag aagttctcga gaacttctac cttcaagtcg ggttttttg        58

<210> SEQ ID NO 53
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
ccggacccac ttacttctta cacttctcga gaagtgtaag aagtaagtgg gtttttg    58

<210> SEQ ID NO 54
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
ccggtgatat gctccggcta gttacctcga ggtaactagc cggagcatat cattttg    58

<210> SEQ ID NO 55
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
ccggatgaga ccacacacct ataatctcga gattataggt gtgtggtctc attttttg    58

<210> SEQ ID NO 56
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
ccggtcatta gtttcacgtt gtttactcga gtaaacaacg tgaaactaat gattttg    58

<210> SEQ ID NO 57
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
ccggtgcaac gacacaaact ataatctcga gattatagtt tgtgtcgttg cattttg    58

<210> SEQ ID NO 58
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
ccggcaccta acagcacgat gtatactcga gtatacatcg tgctgttagg tgttttg    58

<210> SEQ ID NO 59
<211> LENGTH: 58
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 59
ccgggcctgc ttcttctctc catatctcga gatatggaga gaagaagcag gcttttttg       58

<210> SEQ ID NO 60
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
ccggcccaga attattgctg caattctcga gaattgcagc ataattctg ggttttttg        58

<210> SEQ ID NO 61
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
ccgggctgca attaagaaag ccaaactcga gtttggcttt cttaattgca gcttttttg       58

<210> SEQ ID NO 62
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ccggctgctt cagaagctcc gatttctcga gaaatcggag cttctgaagc agttttttg      58

<210> SEQ ID NO 63
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
ccggcttgtt ggagtgtgtg ataaactcga gttattcaca cactccaaca agttttttg      58

<210> SEQ ID NO 64
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
ccgggctgaa gctatgttcg ccattctcga gaatggcgaa catagcttca gcttttt         57
```

<210> SEQ ID NO 65
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
ccggcggtca gagatcatac agattctcga gaatctgtat gatctctgac cgttttt        57

<210> SEQ ID NO 66
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
ccgggctaag actaactcaa gataactcga gttatcttga gttagtctta gctttt        57

<210> SEQ ID NO 67
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
ccggcgccct ttacagaaca gactactcga gtagtctgtt ctgtaaaggg cgttttt        57

<210> SEQ ID NO 68
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
ccggccacaa cccatttcac ggttactcga gtaaccgtga atgggttgt ggttttt        57

<210> SEQ ID NO 69
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
ccggcggtca gagatcatac agattctcga gaatctgtat gatctctgac cgttttg        58

<210> SEQ ID NO 70
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
ccggcgccct tacagaaca gactactcga gtagtctgtt ctgtaaaggg cgtttttg            58

<210> SEQ ID NO 71
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ccggttagag cagtgtggca taaatctcga gatttatgcc acactgctct aattttg            58

<210> SEQ ID NO 72
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
ccgggctgaa gctatgttcg ccattctcga gaatggcgaa catagcttca gcttttg            58

<210> SEQ ID NO 73
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
ccggcctgtg atgaagttct acaaactcga gtttgtagaa cttcatcaca ggttttttg           59

<210> SEQ ID NO 74
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
ccggccatta tgcaagtgtt cctatctcga gataggaaca cttgcataat ggttttttg           59

<210> SEQ ID NO 75
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
ccgggcaaac ggcttatggg ataaactcga gtttatccca taagccgttt gcttttttg           59

<210> SEQ ID NO 76
<211> LENGTH: 59
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
ccggcccagt tatcttgacg aatcactcga gtgattcgtc aagataactg ggttttttg    59

<210> SEQ ID NO 77
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77 ccgcccaaa gatgcaaacg gcttactcga gtaagccgtt tgcatctttg ggttttttg    59

<210> SEQ ID NO 78
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
ccggccaaag atgcaaacgg cttatctcga gataagccgt ttgcatcttt ggttttg    58

<210> SEQ ID NO 79
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
ccggggcatc ctccttgaag tatttctcga gaaatacttc aaggaggatg cctttttg    58

<210> SEQ ID NO 80
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
ccggttgaca cagagtctgc atttactcga gtaaatgcag actctgtgtc aattttg    58

<210> SEQ ID NO 81
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
ccggcagaag agaatgtctc acaaactcga gtttgtgaga cattctcttc tgttttttg    59

<210> SEQ ID NO 82
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 82
ccgggttggg atatctaaag cagaactcga gttctgcttt agatatccca acttttttg     59

<210> SEQ ID NO 83
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 83
ccgggcttca taatcacctt ctgttctcga gaacagaagg tgattatgaa gcttttttg     59

<210> SEQ ID NO 84
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 84
ccgggcaaag aagttgggat atctactcga gtagatatcc caacttcttt gcttttttg     59

<210> SEQ ID NO 85
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 85
ccgggaagcc ttagaaactc tgcaactcga gttgcagagt ttctaaggct tcttttttg     59

<210> SEQ ID NO 86
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 86
ccgggttggg atatctaaag cagaactcga gttctgcttt agatatccca actttttg     58

<210> SEQ ID NO 87
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 87
ccggcagaag agaatgtctc acaaactcga gtttgtgaga cattctcttc tgtttttg    58

<210> SEQ ID NO 88
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
ccggagcata cccagggctt cataactcga gttatgaagc cctgggtatg cttttttg    58

<210> SEQ ID NO 89
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
ccgggcaaag aagttgggat atctactcga gtagatatcc caacttcttt gctttttg    58

<210> SEQ ID NO 90
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
ccgggaaatg tggcttgtct tacaactcga gttgtaagac aagccacatt tctttttg    59

<210> SEQ ID NO 91
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
ccgggtctct atactggaga agtgactcga gtcacttctc cagtatagag actttttg    59

<210> SEQ ID NO 92
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
ccggccacgt ttccttccct tatttctcga gaaataaggg aaggaaacgt ggtttttg    59

<210> SEQ ID NO 93
<211> LENGTH: 59

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
ccggcgtgta tgtttctggt ggaaactcga gtttccacca gaaacataca cgttttttg      59

<210> SEQ ID NO 94
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
ccgggctggt ctctatactg gagaactcga gttctccagt atagagacca gcttttttg      59

<210> SEQ ID NO 95
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
ccgggctcag aaatgtggct tgtctctcga gagacaagcc acatttctga gcttttttg      59

<210> SEQ ID NO 96
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
ccggcctgtg ctgttgtttg ggaaactcga gtttcccaaa caacagcaca ggttttttg      59

<210> SEQ ID NO 97
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
ccggctggaa gaggtagctc agaaactcga gtttctgagc tacctcttcc agttttttg      59

<210> SEQ ID NO 98
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
```
ccggcaggta tgtctctgta tggcactcga gtgccataca gagacatacc tgttttttg    59

<210> SEQ ID NO 99
<211> LENGTH: 198
<212> TYPE: PRT
<213> ORGANISM: Homo sapiens

<400> SEQUENCE: 99

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 100
<211> LENGTH: 2794
<212> TYPE: DNA
<213> ORGANISM: Homo sapiens

<400> SEQUENCE: 100
agagaaccat cattaattga agtgagattt ttctggcctg agacttgcag ggaggcaaga    60
agacactctg acaccacta tggacagcct cttgatgaac cggaggaagt ttctttacca   120
attcaaaaat gtccgctggg ctaagggtcg gcgtgagacc tacctgtgct acgtagtgaa   180
gaggcgtgac agtgctacat cctttcact ggactttggt tatcttcgca ataagaacgg   240
ctgccacgtg gaattgctct tcctccgcta catctcggac tgggacctag accctggccg   300
ctgctaccgc gtcacctggt tcacctcctg gagcccctgc tacgactgtg cccgacatgt   360
ggccgacttt ctgcgaggga accccaacct cagtctgagg atcttcaccg cgcgcctcta   420
cttctgtgag gaccgcaagg ctgagcccga ggggctgcgg cggctgcacc gcgcgggggt   480
gcaaatagcc atcatgacct tcaaagatta ttttactgc tggaatactt ttgtagaaaa   540
ccacgaaaga acttcaaag cctgggaagg gctgcatgaa aattcagttc gtctctccag   600
acagcttcgg cgcatccttt tgcccctgta tgaggttgat gacttacgag acgcatttcg   660

```
tactttggga ctttgatagc aacttccagg aatgtcacac acgatgaaat atctctgctg    720
aagacagtgg ataaaaaaca gtccttcaag tcttctctgt ttttattctt caactctcac    780
tttcttagag tttacagaaa aaatatttat atacgactct ttaaaaagat ctatgtcttg    840
aaaatagaga aggaacacag gtctggccag ggacgtgctg caattggtgc agttttgaat    900
gcaacattgt cccctactgg gaataacaga actgcaggac ctgggagcat cctaaagtgt    960
caacgttttt ctatgacttt taggtaggat gagagcagaa ggtagatcct aaaaagcatg   1020
gtgagaggat caaatgtttt tatatcaaca tcctttatta tttgattcat ttgagttaac   1080
agtggtgtta gtgatagatt tttctattct tttcccttga cgtttacttt caagtaacac   1140
aaactcttcc atcaggccat gatctatagg acctcctaat gagagtatct gggtgattgt   1200
gaccccaaac catctctcca aagcattaat atccaatcat gcgctgtatg ttttaatcag   1260
cagaagcatg tttttatgtt tgtacaaaag aagattgtta tgggtgggga tggaggtata   1320
gaccatgcat ggtcaccttc aagctacttt aataaaggat cttaaaatgg gcaggaggac   1380
tgtgaacaag acaccctaat aatgggttga tgtctgaagt agcaaatctt ctggaaacgc   1440
aaactctttt aaggaagtcc ctaatttaga aacacccaca aacttcacat atcataatta   1500
gcaaacaatt ggaaggaagt tgcttgaatg ttggggagag gaaaatctat tggctctcgt   1560
gggtctcttc atctcagaaa tgccaatcag gtcaaggttt gctacatttt gtatgtgtgt   1620
gatgcttctc ccaaaggtat attaactata aagagagtt gtgacaaaac agaatgataa   1680
agctgcgaac cgtggcacac gctcatagtt ctagctgctt gggaggttga ggagggagga   1740
tggcttgaac acaggtgttc aaggccagcc tgggcaacat aacaagatcc tgtctctcaa   1800 aaaaaaaaa aaaaaaaga aagagagagg gccgggcgtg gtggctcacg cctgtaatcc   1860
cagcactttg ggaggccgag ccgggcggat cacctgtggt caggagtttg agaccagcct   1920
ggccaacatg gcaaaacccc gtctgtactc aaaatgcaaa aattagccag gcgtggtagc   1980
aggcacctgt aatcccagct acttgggagg ctgaggcagg agaatcgctt gaacccagga   2040
ggtggaggtt gcagtaagct gagatcgtgc cgttgcactc cagcctgggc gacaagagca   2100
agactctgtc tcagaaaaaa aaaaaaaaa gagagagaga gagaaagaga acaatatttg   2160
ggagagaagg atggggaagc attgcaagga aattgtgctt tatccaacaa aatgtaagga   2220
gccaataagg gatccctatt tgtctctttt ggtgtctatt tgtccctaac aactgtcttt   2280
gacagtgaga aaaatattca gaataaccat atccctgtgc cgttattacc tagcaaccct   2340
tgcaatgaag atgagcagat ccacaggaaa acttgaatgc acaactgtct tattttaatc   2400
ttattgtaca taagtttgta aaagagttaa aaattgttac ttcatgtatt catttatatt   2460
ttatattatt ttgcgtctaa tgatttttta ttaacatgat ttccttttct gatatattga   2520
aatggagtct caaagcttca taaatttata actttagaaa tgattctaat aacaacgtat   2580
gtaattgtaa cattgcagta atggtgctac gaagccattt ctcttgattt ttagtaaact   2640
tttatgacag caaatttgct tctggctcac tttcaatcag ttaaataaat gataaataat   2700
tttggaagct gtgaagataa ataccaaat aaaataatat aaaagtgatt tatatgaagt   2760
taaaataaaa aatcagtatg atggaataaa cttg                               2794
```

<210> SEQ ID NO 101
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 101
tccttttcac tggactttgg                                                   20

<210> SEQ ID NO 102
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
gactgaggtt ggggttcc                                                     18

<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
gagtcaacgg atttggtcgt                                                   20

<210> SEQ ID NO 104
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
ttgattttgg agggatctcg                                                   20

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
accacagtcc atgccatcac                                                   20

<210> SEQ ID NO 106
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
tccaccaccc tgtggctgta                                                   20

<210> SEQ ID NO 107
```

```
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
ggcctcagtg aaggtctcct gcaag                                         25

<210> SEQ ID NO 108
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
gtctggtcct acgctggtga aaccc                                         25

<210> SEQ ID NO 109
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109 ctgggggtc cctgagactc tcctg                                          25

<210> SEQ ID NO 110
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
cttcggagac cctgtccctc acctg                                         25

<210> SEQ ID NO 111
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
cggggagtct ctgaagatct cctgt                                         25

<210> SEQ ID NO 112
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
```
tcgcagaccc tctcactcac ctgtg                                      25

<210> SEQ ID NO 113
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic consensus sequence"

<400> SEQUENCE: 113
cttacctgag gagacggtga cc                                         22

<210> SEQ ID NO 114
<211> LENGTH: 352
<212> TYPE: PRT
<213> ORGANISM: Homo sapiens

<400> SEQUENCE: 114

Met Val Arg Pro Val Arg His Lys Lys Pro Val Asn Tyr Ser Gln Phe
1               5                   10                  15

Asp His Ser Asp Ser Asp Asp Phe Val Ser Ala Thr Val Pro Leu
            20                  25                  30

Asn Lys Lys Ser Arg Thr Ala Pro Lys Glu Leu Lys Gln Asp Lys Pro
        35                  40                  45

Lys Pro Asn Leu Asn Asn Leu Arg Lys Glu Glu Ile Pro Val Gln Glu
    50                  55                  60

Lys Thr Pro Lys Lys Arg Leu Pro Glu Gly Thr Phe Ser Ile Pro Ala
65                  70                  75                  80

Ser Ala Val Pro Cys Thr Lys Met Ala Leu Asp Asp Lys Leu Tyr Gln
                85                  90                  95

Arg Asp Leu Glu Val Ala Leu Ala Leu Ser Val Lys Glu Leu Pro Thr
            100                 105                 110

Val Thr Thr Asn Val Gln Asn Ser Gln Asp Lys Ser Ile Glu Lys His
        115                 120                 125

Gly Ser Ser Lys Ile Glu Thr Met Asn Lys Ser Pro His Ile Ser Asn
    130                 135                 140

Cys Ser Val Ala Ser Asp Tyr Leu Asp Leu Asp Lys Ile Thr Val Glu
145                 150                 155                 160

Asp Asp Val Gly Gly Val Gln Gly Lys Arg Lys Ala Ala Ser Lys Ala
                165                 170                 175

Ala Ala Gln Gln Arg Lys Ile Leu Leu Glu Gly Ser Asp Gly Asp Ser
            180                 185                 190

Ala Asn Asp Thr Glu Pro Asp Phe Ala Pro Gly Glu Asp Ser Glu Asp
        195                 200                 205

Asp Ser Asp Phe Cys Glu Ser Glu Asp Asn Asp Glu Asp Phe Ser Met
    210                 215                 220

Arg Lys Ser Lys Val Lys Glu Ile Lys Lys Lys Glu Val Lys Val Lys
225                 230                 235                 240

Ser Pro Val Glu Lys Lys Glu Lys Lys Ser Lys Ser Lys Cys Asn Ala
                245                 250                 255

Leu Val Thr Ser Val Asp Ser Ala Pro Ala Ala Val Lys Ser Glu Ser
            260                 265                 270

Gln Ser Leu Pro Lys Lys Val Ser Leu Ser Ser Asp Thr Thr Arg Lys
        275                 280                 285

```
Pro Leu Glu Ile Arg Ser Pro Ser Ala Glu Ser Lys Lys Pro Lys Trp
    290                 295                 300

Val Pro Ala Ala Ser Gly Gly Ser Arg Ser Ser Ser Pro Leu
305                 310                 315                 320

Val Val Val Ser Val Lys Ser Pro Asn Gln Ser Leu Arg Leu Gly Leu
                325                 330                 335

Ser Arg Leu Ala Arg Val Lys Pro Leu His Pro Asn Ala Thr Ser Thr
                340                 345                 350

<210> SEQ ID NO 115
<211> LENGTH: 350
<212> TYPE: PRT
<213> ORGANISM: Homo sapiens

<400> SEQUENCE: 115

Met Gly Ser Lys Lys Leu Lys Arg Val Gly Leu Ser Gln Glu Leu Cys
1               5                   10                  15

Asp Arg Leu Ser Arg His Gln Ile Leu Thr Cys Gln Asp Phe Leu Cys
                20                  25                  30

Leu Ser Pro Leu Glu Leu Met Lys Val Thr Gly Leu Ser Tyr Arg Gly
                35                  40                  45

Val His Glu Leu Leu Cys Met Val Ser Arg Ala Cys Ala Pro Lys Met
        50                  55                  60

Gln Thr Ala Tyr Gly Ile Lys Ala Gln Arg Ser Ala Asp Phe Ser Pro
65                  70                  75                  80

Ala Phe Leu Ser Thr Thr Leu Ser Ala Leu Asp Glu Ala Leu His Gly
                85                  90                  95

Gly Val Ala Cys Gly Ser Leu Thr Glu Ile Thr Gly Pro Pro Gly Cys
                100                 105                 110

Gly Lys Thr Gln Phe Cys Ile Met Met Ser Ile Leu Ala Thr Leu Pro
                115                 120                 125

Thr Asn Met Gly Gly Leu Glu Gly Ala Val Val Tyr Ile Asp Thr Glu
130                 135                 140

Ser Ala Phe Ser Ala Glu Arg Leu Val Glu Ile Ala Glu Ser Arg Phe
145                 150                 155                 160

Pro Arg Tyr Phe Asn Thr Glu Glu Lys Leu Leu Leu Thr Ser Ser Lys
                165                 170                 175

Val His Leu Tyr Arg Glu Leu Thr Cys Asp Glu Val Leu Gln Arg Ile
                180                 185                 190

Glu Ser Leu Glu Glu Glu Ile Ile Ser Lys Gly Ile Lys Leu Val Ile
                195                 200                 205

Leu Asp Ser Val Ala Ser Val Val Arg Lys Glu Phe Asp Ala Gln Leu
                210                 215                 220

Gln Gly Asn Leu Lys Glu Arg Asn Lys Phe Leu Ala Arg Glu Ala Ser
225                 230                 235                 240

Ser Leu Lys Tyr Leu Ala Glu Glu Phe Ser Ile Pro Val Ile Leu Thr
                245                 250                 255

Asn Gln Ile Thr Thr His Leu Ser Gly Ala Leu Ala Ser Gln Ala Asp
                260                 265                 270

Leu Val Ser Pro Ala Asp Asp Leu Ser Leu Ser Glu Gly Thr Ser Gly
                275                 280                 285

Ser Ser Cys Val Ile Ala Ala Leu Gly Asn Thr Trp Ser His Ser Val
                290                 295                 300

Asn Thr Arg Leu Ile Leu Gln Tyr Leu Asp Ser Glu Arg Arg Gln Ile
305                 310                 315                 320
```

Leu Ile Ala Lys Ser Pro Leu Ala Pro Phe Thr Ser Phe Val Tyr Thr
                325                 330                 335

Ile Lys Glu Glu Gly Leu Val Leu Gln Ala Tyr Gly Asn Ser
            340                 345                 350

<210> SEQ ID NO 116
<211> LENGTH: 348
<212> TYPE: PRT
<213> ORGANISM: Homo sapiens

<400> SEQUENCE: 116

Met Gly Val Leu Arg Val Gly Leu Cys Pro Gly Leu Thr Glu Met
1               5                   10                  15

Ile Gln Leu Leu Arg Ser His Arg Ile Lys Thr Val Val Asp Leu Val
                20                  25                  30

Ser Ala Asp Leu Glu Glu Val Ala Gln Lys Cys Gly Leu Ser Tyr Lys
            35                  40                  45

Thr Trp Arg Ala His Ser Ser Gly Asn Leu Gly Gly Leu Gln Leu Pro
        50                  55                  60

Gln Val Pro Ala Gly Arg Ser Trp Ser Gly Val Arg Asn Ala Leu Lys
65                  70                  75                  80

Lys Ala Gly Leu Gly His Gly Gly Thr Asp Gly Leu Ser Leu Asn Ala
                85                  90                  95

Phe Asp Glu Arg Gly Thr Ala Val Ser Thr Ser Arg Leu Asp Lys Leu
            100                 105                 110

Leu Asp Ala Gly Leu Tyr Thr Gly Glu Val Thr Glu Ile Val Gly Gly
        115                 120                 125

Pro Gly Ser Gly Lys Thr Gln Val Cys Leu Cys Met Ala Ala Asn Val
130                 135                 140

Ala His Gly Leu Gln Gln Asn Val Leu Tyr Val Asp Ser Asn Gly Gly
145                 150                 155                 160

Leu Thr Ala Ser Arg Leu Leu Gln Leu Leu Gln Ala Lys Thr Gln Asp
                165                 170                 175

Glu Glu Glu Gln Ala Glu Ala Leu Arg Arg Ile Gln Val Val His Ala
            180                 185                 190

Phe Asp Ile Phe Gln Met Leu Asp Val Leu Gln Glu Leu Arg Gly Thr
        195                 200                 205

Val Ala Gln Gln Val Thr Gly Ser Ser Gly Thr Val Lys Val Val Val
    210                 215                 220

Val Asp Ser Val Thr Ala Val Val Ser Pro Leu Leu Gly Gly Gln Gln
225                 230                 235                 240

Arg Glu Gly Leu Ala Leu Met Met Gln Leu Ala Arg Glu Leu Lys Thr
                245                 250                 255

Leu Ala Arg Asp Leu Gly Met Ala Val Val Val Thr Asn His Ile Thr
            260                 265                 270

Arg Asp Arg Asp Ser Gly Arg Leu Lys Pro Ala Leu Gly Arg Ser Trp
        275                 280                 285

Ser Phe Val Pro Ser Thr Arg Ile Leu Leu Asp Thr Ile Glu Gly Ala
    290                 295                 300

Gly Ala Ser Gly Gly Arg Arg Met Ala Cys Leu Ala Lys Ser Ser Arg
305                 310                 315                 320

Gln Pro Thr Gly Phe Gln Glu Met Val Asp Ile Gly Thr Trp Gly Thr
                325                 330                 335

Ser Glu Gln Ser Ala Thr Leu Gln Gly Asp Gln Thr
            340                 345

<210> SEQ ID NO 117
<211> LENGTH: 280
<212> TYPE: PRT
<213> ORGANISM: Homo sapiens

<400> SEQUENCE: 117

Met Cys Ser Ala Phe His Arg Ala Glu Ser Gly Thr Glu Leu Leu Ala
1               5                   10                  15

Arg Leu Glu Gly Arg Ser Ser Leu Lys Glu Ile Glu Pro Asn Leu Phe
            20                  25                  30

Ala Asp Glu Asp Ser Pro Val His Gly Asp Ile Leu Glu Phe His Gly
        35                  40                  45

Pro Glu Gly Thr Gly Lys Thr Glu Met Leu Tyr His Leu Thr Ala Arg
    50                  55                  60

Cys Ile Leu Pro Lys Ser Glu Gly Gly Leu Glu Val Glu Val Leu Phe
65                  70                  75                  80

Ile Asp Thr Asp Tyr His Phe Asp Met Leu Arg Leu Val Thr Ile Leu
                85                  90                  95

Glu His Arg Leu Ser Gln Ser Ser Glu Glu Ile Ile Lys Tyr Cys Leu
            100                 105                 110

Gly Arg Phe Phe Leu Val Tyr Cys Ser Ser Ser Thr His Leu Leu Leu
        115                 120                 125

Thr Leu Tyr Ser Leu Glu Ser Met Phe Cys Ser His Pro Ser Leu Cys
130                 135                 140

Leu Leu Ile Leu Asp Ser Leu Ser Ala Phe Tyr Trp Ile Asp Arg Val
145                 150                 155                 160

Asn Gly Gly Glu Ser Val Asn Leu Gln Glu Ser Thr Leu Arg Lys Cys
                165                 170                 175

Ser Gln Cys Leu Glu Lys Leu Val Asn Asp Tyr Arg Leu Val Leu Phe
            180                 185                 190

Ala Thr Thr Gln Thr Ile Met Gln Lys Ala Ser Ser Ser Glu Glu
        195                 200                 205

Pro Ser His Ala Ser Arg Arg Leu Cys Asp Val Asp Ile Asp Tyr Arg
    210                 215                 220

Pro Tyr Leu Cys Lys Ala Trp Gln Gln Leu Val Lys His Arg Met Phe
225                 230                 235                 240

Phe Ser Lys Gln Asp Asp Ser Gln Ser Ser Asn Gln Phe Ser Leu Val
                245                 250                 255

Ser Arg Cys Leu Lys Ser Asn Ser Leu Lys Lys His Phe Phe Ile Ile
            260                 265                 270

Gly Glu Ser Gly Val Glu Phe Cys
        275                 280

<210> SEQ ID NO 118
<211> LENGTH: 346
<212> TYPE: PRT
<213> ORGANISM: Homo sapiens

<400> SEQUENCE: 118

Met Asp Leu Asp Leu Leu Asp Leu Asn Pro Arg Ile Ile Ala Ala Ile
1               5                   10                  15

Lys Lys Ala Lys Leu Lys Ser Val Lys Glu Val Leu His Phe Ser Gly
            20                  25                  30

Pro Asp Leu Lys Arg Leu Thr Asn Leu Ser Ser Pro Glu Val Trp His

```
            35                  40                  45
Leu Leu Arg Thr Ala Ser Leu His Leu Arg Gly Ser Ser Ile Leu Thr
 50                  55                  60

Ala Leu Gln Leu His Gln Gln Lys Glu Arg Phe Pro Thr Gln His Gln
 65                  70                  75                  80

Arg Leu Ser Leu Gly Cys Pro Val Leu Asp Ala Leu Leu Arg Gly Gly
                 85                  90                  95

Leu Pro Leu Asp Gly Ile Thr Glu Leu Ala Gly Arg Ser Ser Ala Gly
                100                 105                 110

Lys Thr Gln Leu Ala Leu Gln Leu Cys Leu Ala Val Gln Phe Pro Arg
            115                 120                 125

Gln His Gly Gly Leu Glu Ala Gly Ala Val Tyr Ile Cys Thr Glu Asp
        130                 135                 140

Ala Phe Pro His Lys Arg Leu Gln Gln Leu Met Ala Gln Pro Arg
145                 150                 155                 160

Leu Arg Thr Asp Val Pro Gly Glu Leu Leu Gln Lys Leu Arg Phe Gly
                165                 170                 175

Ser Gln Ile Phe Ile Glu His Val Ala Asp Val Asp Thr Leu Leu Glu
                180                 185                 190

Cys Val Asn Lys Lys Val Pro Val Leu Leu Ser Arg Gly Met Ala Arg
            195                 200                 205

Leu Val Val Ile Asp Ser Val Ala Ala Pro Phe Arg Cys Glu Phe Asp
        210                 215                 220

Ser Gln Ala Ser Ala Pro Arg Ala Arg His Leu Gln Ser Leu Gly Ala
225                 230                 235                 240

Thr Leu Arg Glu Leu Ser Ser Ala Phe Gln Ser Pro Val Leu Cys Ile
                245                 250                 255

Asn Gln Val Thr Glu Ala Met Glu Glu Gln Gly Ala Ala His Gly Pro
                260                 265                 270

Leu Gly Phe Trp Asp Glu Arg Val Ser Pro Ala Leu Gly Ile Thr Trp
            275                 280                 285

Ala Asn Gln Leu Leu Val Arg Leu Leu Ala Asp Arg Leu Arg Glu Glu
        290                 295                 300

Glu Ala Ala Leu Gly Cys Pro Ala Arg Thr Leu Arg Val Leu Ser Ala
305                 310                 315                 320

Pro His Leu Pro Pro Ser Ser Cys Ser Tyr Thr Ile Ser Ala Glu Gly
                325                 330                 335

Val Arg Gly Thr Pro Gly Thr Gln Ser His
                340                 345

<210> SEQ ID NO 119
<211> LENGTH: 2492
<212> TYPE: PRT
<213> ORGANISM: Homo sapiens

<400> SEQUENCE: 119

Met Thr Ala Glu Pro Met Ser Glu Ser Lys Leu Asn Thr Leu Val Gln
  1               5                  10                  15

Lys Leu His Asp Phe Leu Ala His Ser Ser Glu Glu Ser Glu Thr
             20                  25                  30

Ser Ser Pro Pro Arg Leu Ala Met Asn Gln Asn Thr Asp Lys Ile Ser
             35                  40                  45

Gly Ser Gly Ser Asn Ser Asp Met Met Glu Asn Ser Lys Glu Glu Gly
         50                  55                  60
```

```
Thr Ser Ser Ser Glu Lys Ser Lys Ser Ser Gly Ser Ser Arg Ser Lys
 65                  70                  75                  80

Arg Lys Pro Ser Ile Val Thr Lys Tyr Val Glu Ser Asp Asp Glu Lys
                 85                  90                  95

Pro Leu Asp Asp Glu Thr Val Asn Glu Asp Ala Ser Asn Glu Asn Ser
            100                 105                 110

Glu Asn Asp Ile Thr Met Gln Ser Leu Pro Lys Gly Thr Val Ile Val
        115                 120                 125

Gln Pro Glu Pro Val Leu Asn Glu Asp Lys Asp Phe Lys Gly Pro
    130                 135                 140

Glu Phe Arg Ser Arg Ser Lys Met Lys Thr Glu Asn Leu Lys Lys Arg
145                 150                 155                 160

Gly Glu Asp Gly Leu His Gly Ile Val Ser Cys Thr Ala Cys Gly Gln
                165                 170                 175

Gln Val Asn His Phe Gln Lys Asp Ser Ile Tyr Arg His Pro Ser Leu
            180                 185                 190

Gln Val Leu Ile Cys Lys Asn Cys Phe Lys Tyr Tyr Met Ser Asp Asp
        195                 200                 205

Ile Ser Arg Asp Ser Asp Gly Met Asp Glu Gln Cys Arg Trp Cys Ala
    210                 215                 220

Glu Gly Gly Asn Leu Ile Cys Cys Asp Phe Cys His Asn Ala Phe Cys
225                 230                 235                 240

Lys Lys Cys Ile Leu Arg Asn Leu Gly Arg Lys Glu Leu Ser Thr Ile
                245                 250                 255

Met Asp Glu Asn Asn Gln Trp Tyr Cys Tyr Ile Cys His Pro Glu Pro
            260                 265                 270

Leu Leu Asp Leu Val Thr Ala Cys Asn Ser Val Phe Glu Asn Leu Glu
        275                 280                 285

Gln Leu Leu Gln Gln Asn Lys Lys Ile Lys Val Asp Ser Glu Lys
    290                 295                 300

Ser Asn Lys Val Tyr Glu His Thr Ser Arg Phe Ser Pro Lys Lys Thr
305                 310                 315                 320

Ser Ser Asn Cys Asn Gly Glu Glu Lys Lys Leu Asp Asp Ser Cys Ser
                325                 330                 335

Gly Ser Val Thr Tyr Ser Tyr Ser Ala Leu Ile Val Pro Lys Glu Met
            340                 345                 350

Ile Lys Lys Ala Lys Lys Leu Ile Glu Thr Thr Ala Asn Met Asn Ser
        355                 360                 365

Ser Tyr Val Lys Phe Leu Lys Gln Ala Thr Asp Asn Ser Glu Ile Ser
    370                 375                 380

Ser Ala Thr Lys Leu Arg Gln Leu Lys Ala Phe Lys Ser Val Leu Ala
385                 390                 395                 400

Asp Ile Lys Lys Ala His Leu Ala Leu Glu Glu Asp Leu Asn Ser Glu
                405                 410                 415

Phe Arg Ala Met Asp Ala Val Asn Lys Glu Lys Asn Thr Lys Glu His
            420                 425                 430

Lys Val Ile Asp Ala Lys Phe Glu Thr Lys Ala Arg Lys Gly Glu Lys
        435                 440                 445

Pro Cys Ala Leu Glu Lys Lys Asp Ile Ser Lys Ser Glu Ala Lys Leu
    450                 455                 460

Ser Arg Lys Gln Val Asp Ser Glu His Met His Gln Asn Val Pro Thr
465                 470                 475                 480

Glu Glu Gln Arg Thr Asn Lys Ser Thr Gly Gly Glu His Lys Lys Ser
```

```
                485                 490                 495
Asp Arg Lys Glu Glu Pro Gln Tyr Glu Pro Ala Asn Thr Ser Glu Asp
            500                 505                 510

Leu Asp Met Asp Ile Val Ser Val Pro Ser Ser Val Pro Glu Asp Ile
        515                 520                 525

Phe Glu Asn Leu Glu Thr Ala Met Glu Val Gln Ser Ser Val Asp His
        530                 535                 540

Gln Gly Asp Gly Ser Ser Gly Thr Glu Gln Glu Val Glu Ser Ser
545                 550                 555                 560

Val Lys Leu Asn Ile Ser Ser Lys Asp Asn Arg Gly Gly Ile Lys Ser
                565                 570                 575

Lys Thr Thr Ala Lys Val Thr Lys Glu Leu Tyr Val Lys Leu Thr Pro
            580                 585                 590

Val Ser Leu Ser Asn Ser Pro Ile Lys Gly Ala Asp Cys Gln Glu Val
        595                 600                 605

Pro Gln Asp Lys Asp Gly Tyr Lys Ser Cys Gly Leu Asn Pro Lys Leu
        610                 615                 620

Glu Lys Cys Gly Leu Gly Gln Glu Asn Ser Asp Asn Glu His Leu Val
625                 630                 635                 640

Glu Asn Glu Val Ser Leu Leu Leu Glu Ser Asp Leu Arg Arg Ser
                645                 650                 655

Pro Arg Val Lys Thr Thr Pro Leu Arg Arg Pro Thr Glu Thr Asn Pro
            660                 665                 670

Val Thr Ser Asn Ser Asp Glu Glu Cys Asn Glu Thr Val Lys Glu Lys
        675                 680                 685

Gln Lys Leu Ser Val Pro Val Arg Lys Asp Lys Arg Asn Ser Ser
        690                 695                 700

Asp Ser Ala Ile Asp Asn Pro Lys Pro Asn Lys Leu Pro Lys Ser Lys
705                 710                 715                 720

Gln Ser Glu Thr Val Asp Gln Asn Ser Asp Ser Asp Glu Met Leu Ala
                725                 730                 735

Ile Leu Lys Glu Val Ser Arg Met Ser His Ser Ser Ser Ser Asp Thr
            740                 745                 750

Asp Ile Asn Glu Ile His Thr Asn His Lys Thr Leu Tyr Asp Leu Lys
        755                 760                 765

Thr Gln Ala Gly Lys Asp Asp Lys Gly Lys Arg Lys Arg Lys Ser Ser
        770                 775                 780

Thr Ser Gly Ser Asp Phe Asp Thr Lys Lys Gly Lys Ser Ala Lys Ser
785                 790                 795                 800

Ser Ile Ile Ser Lys Lys Lys Arg Gln Thr Gln Ser Glu Ser Ser Asn
                805                 810                 815

Tyr Asp Ser Glu Leu Glu Lys Glu Ile Lys Ser Met Ser Lys Ile Gly
            820                 825                 830

Ala Ala Arg Thr Thr Lys Lys Arg Ile Pro Asn Thr Lys Asp Phe Asp
        835                 840                 845

Ser Ser Glu Asp Glu Lys His Ser Lys Lys Gly Met Asp Asn Gln Gly
        850                 855                 860

His Lys Asn Leu Lys Thr Ser Gln Glu Gly Ser Ser Asp Ala Glu
865                 870                 875                 880

Arg Lys Gln Glu Arg Glu Thr Phe Ser Ser Ala Glu Gly Thr Val Asp
                885                 890                 895

Lys Asp Thr Thr Ile Met Glu Leu Arg Asp Arg Leu Pro Lys Lys Gln
            900                 905                 910
```

-continued

```
Gln Ala Ser Ala Ser Thr Asp Gly Val Asp Lys Leu Ser Gly Lys Glu
                915                 920                 925
Gln Ser Phe Thr Ser Leu Glu Val Arg Lys Val Ala Glu Thr Lys Glu
        930                 935                 940
Lys Ser Lys His Leu Lys Thr Lys Thr Cys Lys Lys Val Gln Asp Gly
945                 950                 955                 960
Leu Ser Asp Ile Ala Glu Lys Phe Leu Lys Asp Gln Ser Asp Glu
                965                 970                 975
Thr Ser Glu Asp Asp Lys Lys Gln Ser Lys Lys Gly Thr Glu Glu Lys
                980                 985                 990
Lys Lys Pro Ser Asp Phe Lys Lys Lys Val Ile Lys Met Glu Gln Gln
                995                 1000                1005
Tyr Glu Ser Ser Ser Asp Gly Thr Glu Lys Leu Pro Glu Arg Glu
        1010                1015                1020
Glu Ile Cys His Phe Pro Lys Gly Ile Lys Gln Ile Lys Asn Gly
        1025                1030                1035
Thr Thr Asp Gly Glu Lys Lys Ser Lys Lys Ile Arg Asp Lys Thr
        1040                1045                1050
Ser Lys Lys Lys Asp Glu Leu Ser Asp Tyr Ala Glu Lys Ser Thr
        1055                1060                1065
Gly Lys Gly Asp Ser Cys Asp Ser Ser Glu Asp Lys Lys Ser Lys
        1070                1075                1080
Asn Gly Ala Tyr Gly Arg Glu Lys Lys Arg Cys Lys Leu Leu Gly
        1085                1090                1095
Lys Ser Ser Arg Lys Arg Gln Asp Cys Ser Ser Ser Asp Thr Glu
        1100                1105                1110
Lys Tyr Ser Met Lys Glu Asp Gly Cys Asn Ser Ser Asp Lys Arg
        1115                1120                1125
Leu Lys Arg Ile Glu Leu Arg Glu Arg Arg Asn Leu Ser Ser Lys
        1130                1135                1140
Arg Asn Thr Lys Glu Ile Gln Ser Gly Ser Ser Ser Ser Asp Ala
        1145                1150                1155
Glu Glu Ser Ser Glu Asp Asn Lys Lys Lys Lys Gln Arg Thr Ser
        1160                1165                1170
Ser Lys Lys Lys Ala Val Ile Val Lys Glu Lys Lys Arg Asn Ser
        1175                1180                1185
Leu Arg Thr Ser Thr Lys Arg Lys Gln Ala Asp Ile Thr Ser Ser
        1190                1195                1200
Ser Ser Asp Ile Glu Asp Asp Gln Asn Ser Ile Gly Glu
        1205                1210                1215
Gly Ser Ser Asp Glu Gln Lys Ile Lys Pro Val Thr Glu Asn Leu
        1220                1225                1230
Val Leu Ser Ser His Thr Gly Phe Cys Gln Ser Ser Gly Asp Glu
        1235                1240                1245
Ala Leu Ser Lys Ser Val Pro Val Thr Val Asp Asp Asp Asp Asp
        1250                1255                1260
Asp Asn Asp Pro Glu Asn Arg Ile Ala Lys Lys Met Leu Leu Glu
        1265                1270                1275
Glu Ile Lys Ala Asn Leu Ser Ser Asp Glu Asp Gly Ser Ser Asp
        1280                1285                1290
Asp Glu Pro Glu Glu Gly Lys Lys Arg Thr Gly Lys Gln Asn Glu
        1295                1300                1305
```

```
Glu Asn Pro Gly Asp Glu Glu Ala Lys Asn Gln Val  Asn Ser Glu
    1310                1315                     1320

Ser Asp Ser Asp Ser Glu Glu Ser Lys Lys Pro Arg  Tyr Arg His
    1325                1330                     1335

Arg Leu Leu Arg His Lys Leu Thr Val Ser Asp Gly  Glu Ser Gly
    1340                1345                     1350

Glu Glu Lys Lys Thr Lys Pro Lys Glu His Lys Glu  Val Lys Gly
    1355                1360                     1365

Arg Asn Arg Arg Lys Val Ser Ser Glu Asp Ser Glu  Asp Ser Asp
    1370                1375                     1380

Phe Gln Glu Ser Gly Val Ser Glu Glu Val Ser Glu  Ser Glu Asp
    1385                1390                     1395

Glu Gln Arg Pro Arg Thr Arg Ser Ala Lys Lys Ala  Glu Leu Glu
    1400                1405                     1410

Glu Asn Gln Arg Ser Tyr Lys Gln Lys Lys Arg  Arg Arg Ile
    1415                1420                    1425

Lys Val Gln Glu Asp Ser Ser Ser Glu Asn Lys Ser  Asn Ser Glu
    1430                1435                     1440

Glu Glu Glu Glu Glu Lys Glu Glu Glu Glu Glu  Glu Glu Glu
    1445                1450                   1455

Glu Glu Glu Glu Glu Glu Asp Glu Asn Asp Asp Ser  Lys Ser Pro
    1460                1465                     1470

Gly Lys Gly Arg Lys Lys Ile Arg Lys Ile Leu Lys  Asp Asp Lys
    1475                1480                     1485

Leu Arg Thr Glu Thr Gln Asn Ala Leu Lys Glu Glu  Glu Glu Arg
    1490                1495                     1500

Arg Lys Arg Ile Ala Glu Arg Glu Arg Glu Arg Glu  Lys Leu Arg
    1505                1510                     1515

Glu Val Ile Glu Ile Glu Asp Ala Ser Pro Thr Lys  Cys Pro Ile
    1520                1525                     1530

Thr Thr Lys Leu Val Leu Asp Glu Asp Glu Glu Thr  Lys Glu Pro
    1535                1540                     1545

Leu Val Gln Val His Arg Asn Met Val Ile Lys Leu  Lys Pro His
    1550                1555                     1560

Gln Val Asp Gly Val Gln Phe Met Trp Asp Cys Cys  Cys Glu Ser
    1565                1570                     1575

Val Lys Lys Thr Lys Lys Ser Pro Gly Ser Gly Cys  Ile Leu Ala
    1580                1585                     1590

His Cys Met Gly Leu Gly Lys Thr Leu Gln Val Val  Ser Phe Leu
    1595                1600                     1605

His Thr Val Leu Leu Cys Asp Lys Leu Asp Phe Ser  Thr Ala Leu
    1610                1615                     1620

Val Val Cys Pro Leu Asn Thr Ala Leu Asn Trp Met  Asn Glu Phe
    1625                1630                     1635

Glu Lys Trp Gln Glu Gly Leu Lys Asp Asp Glu Lys  Leu Glu Val
    1640                1645                     1650

Ser Glu Leu Ala Thr Val Lys Arg Pro Gln Glu Arg  Ser Tyr Met
    1655                1660                     1665

Leu Gln Arg Trp Gln Glu Asp Gly Gly Val Met Ile  Ile Gly Tyr
    1670                1675                     1680

Glu Met Tyr Arg Asn Leu Ala Gln Gly Arg Asn Val  Lys Ser Arg
    1685                1690                     1695

Lys Leu Lys Glu Ile Phe Asn Lys Ala Leu Val Asp Pro Gly Pro
```

-continued

|     |     |     |     |     |     |     |     |     |     |
|-----|-----|-----|-----|-----|-----|-----|-----|-----|-----|
|     | 1700 |     |     | 1705 |     |     | 1710 |     |     |
| Asp | Phe | Val | Val | Cys | Asp | Glu | Gly | His | Ile | Leu | Lys | Asn | Glu | Ala |
|     | 1715 |     |     | 1720 |     |     | 1725 |     |     |
| Ser | Ala | Val | Ser | Lys | Ala | Met | Asn | Ser | Ile | Arg | Ser | Arg | Arg | Arg |
|     | 1730 |     |     | 1735 |     |     | 1740 |     |     |
| Ile | Ile | Leu | Thr | Gly | Thr | Pro | Leu | Gln | Asn | Asn | Leu | Ile | Glu | Tyr |
|     | 1745 |     |     | 1750 |     |     | 1755 |     |     |
| His | Cys | Met | Val | Asn | Phe | Ile | Lys | Glu | Asn | Leu | Leu | Gly | Ser | Ile |
|     | 1760 |     |     | 1765 |     |     | 1770 |     |     |
| Lys | Glu | Phe | Arg | Asn | Arg | Phe | Ile | Asn | Pro | Ile | Gln | Asn | Gly | Gln |
|     | 1775 |     |     | 1780 |     |     | 1785 |     |     |
| Cys | Ala | Asp | Ser | Thr | Met | Val | Asp | Val | Arg | Val | Met | Lys | Lys | Arg |
|     | 1790 |     |     | 1795 |     |     | 1800 |     |     |
| Ala | His | Ile | Leu | Tyr | Glu | Met | Leu | Ala | Gly | Cys | Val | Gln | Arg | Lys |
|     | 1805 |     |     | 1810 |     |     | 1815 |     |     |
| Asp | Tyr | Thr | Ala | Leu | Thr | Lys | Phe | Leu | Pro | Pro | Lys | His | Glu | Tyr |
|     | 1820 |     |     | 1825 |     |     | 1830 |     |     |
| Val | Leu | Ala | Val | Arg | Met | Thr | Ser | Ile | Gln | Cys | Lys | Leu | Tyr | Gln |
|     | 1835 |     |     | 1840 |     |     | 1845 |     |     |
| Tyr | Tyr | Leu | Asp | His | Leu | Thr | Gly | Val | Gly | Asn | Asn | Ser | Glu | Gly |
|     | 1850 |     |     | 1855 |     |     | 1860 |     |     |
| Gly | Arg | Gly | Lys | Ala | Gly | Ala | Lys | Leu | Phe | Gln | Asp | Phe | Gln | Met |
|     | 1865 |     |     | 1870 |     |     | 1875 |     |     |
| Leu | Ser | Arg | Ile | Trp | Thr | His | Pro | Trp | Cys | Leu | Gln | Leu | Asp | Tyr |
|     | 1880 |     |     | 1885 |     |     | 1890 |     |     |
| Ile | Ser | Lys | Glu | Asn | Lys | Gly | Tyr | Phe | Asp | Glu | Asp | Ser | Met | Asp |
|     | 1895 |     |     | 1900 |     |     | 1905 |     |     |
| Glu | Phe | Ile | Ala | Ser | Asp | Ser | Asp | Glu | Thr | Ser | Met | Ser | Leu | Ser |
|     | 1910 |     |     | 1915 |     |     | 1920 |     |     |
| Ser | Asp | Asp | Tyr | Thr | Lys | Lys | Lys | Lys | Gly | Lys | Lys | Gly | Lys |
|     | 1925 |     |     | 1930 |     |     | 1935 |     |     |
| Lys | Asp | Ser | Ser | Ser | Ser | Gly | Ser | Gly | Ser | Asp | Asn | Asp | Val | Glu |
|     | 1940 |     |     | 1945 |     |     | 1950 |     |     |
| Val | Ile | Lys | Val | Trp | Asn | Ser | Arg | Ser | Arg | Gly | Gly | Gly | Glu | Gly |
|     | 1955 |     |     | 1960 |     |     | 1965 |     |     |
| Asn | Val | Asp | Glu | Thr | Gly | Asn | Asn | Pro | Ser | Val | Ser | Leu | Lys | Leu |
|     | 1970 |     |     | 1975 |     |     | 1980 |     |     |
| Glu | Glu | Ser | Lys | Ala | Thr | Ser | Ser | Ser | Asn | Pro | Ser | Ser | Pro | Ala |
|     | 1985 |     |     | 1990 |     |     | 1995 |     |     |
| Pro | Asp | Trp | Tyr | Lys | Asp | Phe | Val | Thr | Asp | Ala | Asp | Ala | Glu | Val |
|     | 2000 |     |     | 2005 |     |     | 2010 |     |     |
| Leu | Glu | His | Ser | Gly | Lys | Met | Val | Leu | Leu | Phe | Glu | Ile | Leu | Arg |
|     | 2015 |     |     | 2020 |     |     | 2025 |     |     |
| Met | Ala | Glu | Glu | Ile | Gly | Asp | Lys | Val | Leu | Val | Phe | Ser | Gln | Ser |
|     | 2030 |     |     | 2035 |     |     | 2040 |     |     |
| Leu | Ile | Ser | Leu | Asp | Leu | Ile | Glu | Asp | Phe | Leu | Glu | Leu | Ala | Ser |
|     | 2045 |     |     | 2050 |     |     | 2055 |     |     |
| Arg | Glu | Lys | Thr | Glu | Asp | Lys | Asp | Lys | Pro | Leu | Ile | Tyr | Lys | Gly |
|     | 2060 |     |     | 2065 |     |     | 2070 |     |     |
| Glu | Gly | Lys | Trp | Leu | Arg | Asn | Ile | Asp | Tyr | Tyr | Arg | Leu | Asp | Gly |
|     | 2075 |     |     | 2080 |     |     | 2085 |     |     |
| Ser | Thr | Thr | Ala | Gln | Ser | Arg | Lys | Lys | Trp | Ala | Glu | Glu | Phe | Asn |
|     | 2090 |     |     | 2095 |     |     | 2100 |     |     |

Asp Glu Thr Asn Val Arg Gly Arg Leu Phe Ile Ile Ser Thr Lys
2105                2110                2115

Ala Gly Ser Leu Gly Ile Asn Leu Val Ala Ala Asn Arg Val Ile
2120                2125                2130

Ile Phe Asp Ala Ser Trp Asn Pro Ser Tyr Asp Ile Gln Ser Ile
2135                2140                2145

Phe Arg Val Tyr Arg Phe Gly Gln Thr Lys Pro Val Tyr Val Tyr
2150                2155                2160

Arg Phe Leu Ala Gln Gly Thr Met Glu Asp Lys Ile Tyr Asp Arg
2165                2170                2175

Gln Val Thr Lys Gln Ser Leu Ser Phe Arg Val Val Asp Gln Gln
2180                2185                2190

Gln Val Glu Arg His Phe Thr Met Asn Glu Leu Thr Glu Leu Tyr
2195                2200                2205

Thr Phe Glu Pro Asp Leu Leu Asp Asp Pro Asn Ser Glu Lys Lys
2210                2215                2220

Lys Lys Arg Asp Thr Pro Met Leu Pro Lys Asp Thr Ile Leu Ala
2225                2230                2235

Glu Leu Leu Gln Ile His Lys Glu His Ile Val Gly Tyr His Glu
2240                2245                2250

His Asp Ser Leu Leu Asp His Lys Glu Glu Glu Leu Thr Glu
2255                2260                2265

Glu Glu Arg Lys Ala Ala Trp Ala Glu Tyr Glu Ala Glu Lys Lys
2270                2275                2280

Gly Leu Thr Met Arg Phe Asn Ile Pro Thr Gly Thr Asn Leu Pro
2285                2290                2295

Pro Val Ser Phe Asn Ser Gln Thr Pro Tyr Ile Pro Phe Asn Leu
2300                2305                2310

Gly Ala Leu Ser Ala Met Ser Asn Gln Gln Leu Glu Asp Leu Ile
2315                2320                2325

Asn Gln Gly Arg Glu Lys Val Val Glu Ala Thr Asn Ser Val Thr
2330                2335                2340

Ala Val Arg Ile Gln Pro Leu Glu Asp Ile Ile Ser Ala Val Trp
2345                2350                2355

Lys Glu Asn Met Asn Leu Ser Glu Ala Gln Val Gln Ala Leu Ala
2360                2365                2370

Leu Ser Arg Gln Ala Ser Gln Glu Leu Asp Val Lys Arg Arg Glu
2375                2380                2385

Ala Ile Tyr Asn Asp Val Leu Thr Lys Gln Gln Met Leu Ile Ser
2390                2395                2400

Cys Val Gln Arg Ile Leu Met Asn Arg Arg Leu Gln Gln Gln Tyr
2405                2410                2415

Asn Gln Gln Gln Gln Gln Met Thr Tyr Gln Gln Ala Thr Leu
2420                2425                2430

Gly His Leu Met Met Pro Lys Pro Pro Asn Leu Ile Met Asn Pro
2435                2440                2445

Ser Asn Tyr Gln Gln Ile Asp Met Arg Gly Met Tyr Gln Pro Val
2450                2455                2460

Ala Gly Gly Met Gln Pro Pro Leu Gln Arg Ala Pro Pro Pro
2465                2470                2475

Met Arg Ser Lys Asn Pro Gly Pro Ser Gln Gly Lys Ser Met
2480                2485                2490

<210> SEQ ID NO 120
<211> LENGTH: 418
<212> TYPE: PRT
<213> ORGANISM: Homo sapiens

<400> SEQUENCE: 120

```
Met Ser Gly Thr Glu Glu Ala Ile Leu Gly Gly Arg Asp Ser His Pro
1               5                   10                  15

Ala Ala Gly Gly Gly Ser Val Leu Cys Phe Gln Cys Gln Tyr Thr
            20                  25                  30

Ala Glu Glu Tyr Gln Ala Ile Gln Lys Ala Leu Arg Gln Arg Leu Gly
        35                  40                  45

Pro Glu Tyr Ile Ser Ser Arg Met Ala Gly Gly Gln Lys Val Cys
50                  55                  60

Tyr Ile Glu Gly His Arg Val Ile Asn Leu Ala Asn Glu Met Phe Gly
65                  70                  75                  80

Tyr Asn Gly Trp Ala His Ser Ile Thr Gln Gln Asn Val Asp Phe Val
                85                  90                  95

Asp Leu Asn Asn Gly Lys Phe Tyr Val Gly Val Cys Ala Phe Val Arg
                100                 105                 110

Val Gln Leu Lys Asp Gly Ser Tyr His Glu Asp Val Gly Tyr Gly Val
            115                 120                 125

Ser Glu Gly Leu Lys Ser Lys Ala Leu Ser Leu Glu Lys Ala Arg Lys
130                 135                 140

Glu Ala Val Thr Asp Gly Leu Lys Arg Ala Leu Arg Ser Phe Gly Asn
145                 150                 155                 160

Ala Leu Gly Asn Cys Ile Leu Asp Lys Asp Tyr Leu Arg Ser Leu Asn
                165                 170                 175

Lys Leu Pro Arg Gln Leu Pro Leu Glu Val Asp Leu Thr Lys Ala Lys
            180                 185                 190

Arg Gln Asp Leu Glu Pro Ser Val Glu Glu Ala Arg Tyr Asn Ser Cys
        195                 200                 205

Arg Pro Asn Met Ala Leu Gly His Pro Gln Leu Gln Gln Val Thr Ser
210                 215                 220

Pro Ser Arg Pro Ser His Ala Val Ile Pro Ala Asp Gln Asp Cys Ser
225                 230                 235                 240

Ser Arg Ser Leu Ser Ser Ala Val Glu Ser Glu Ala Thr His Gln
                245                 250                 255

Arg Lys Leu Arg Gln Lys Gln Leu Gln Gln Phe Arg Glu Arg Met
            260                 265                 270

Glu Lys Gln Gln Val Arg Val Ser Thr Pro Ser Ala Glu Lys Ser Glu
        275                 280                 285

Ala Ala Pro Pro Ala Pro Val Thr His Ser Pro Val Thr Val
        290                 295                 300

Ser Glu Pro Leu Leu Glu Lys Asp Phe Leu Ala Gly Val Thr Gln Glu
305                 310                 315                 320

Leu Ile Lys Thr Leu Glu Asp Asn Ser Glu Lys Trp Ala Val Thr Pro
                325                 330                 335

Asp Ala Gly Asp Gly Val Val Pro Ser Ser Arg Ala Asp Pro Ala
            340                 345                 350

Gln Thr Ser Asp Thr Leu Ala Leu Asn Asn Gln Met Val Thr Gln Asn
        355                 360                 365

Arg Thr Pro His Ser Val Cys His Gln Lys Pro Gln Ala Lys Ser Gly
370                 375                 380
```

-continued

Ser Trp Asp Leu Gln Thr Tyr Ser Ala Asp Gln Arg Thr Thr Gly Asn
385                 390                 395                 400

Trp Glu Ser His Arg Lys Ser Gln Asp Met Lys Lys Arg Lys Tyr Asp
            405                 410                 415

Pro Ser

<210> SEQ ID NO 121
<211> LENGTH: 1863
<212> TYPE: PRT
<213> ORGANISM: Homo sapiens

<400> SEQUENCE: 121

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

-continued

```
Glu Lys Lys Val Asp Leu Asn Ala Asp Pro Leu Cys Glu Arg Lys Glu
                340                 345                 350

Trp Asn Lys Gln Lys Leu Pro Cys Ser Glu Asn Pro Arg Asp Thr Glu
                355                 360                 365

Asp Val Pro Trp Ile Thr Leu Asn Ser Ser Ile Gln Lys Val Asn Glu
        370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Lys Ile Asp Leu Leu
                420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
        450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
        530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
        610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
        690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
                740                 745                 750
```

```
Ser Gly Glu Arg Val Leu Gln Thr Glu Arg Ser Val Glu Ser Ser
            755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
            930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
            995                 1000                1005

Ser Pro Glu Arg Glu Met Gly Asn Glu Asn Ile Pro Ser Thr Val
    1010                1015                1020

Ser Thr Ile Ser Arg Asn Asn Ile Arg Glu Asn Val Phe Lys Glu
    1025                1030                1035

Ala Ser Ser Ser Asn Ile Asn Glu Val Gly Ser Ser Thr Asn Glu
    1040                1045                1050

Val Gly Ser Ser Ile Asn Glu Ile Gly Ser Ser Asp Glu Asn Ile
    1055                1060                1065

Gln Ala Glu Leu Gly Arg Asn Arg Gly Pro Lys Leu Asn Ala Met
    1070                1075                1080

Leu Arg Leu Gly Val Leu Gln Pro Glu Val Tyr Lys Gln Ser Leu
    1085                1090                1095

Pro Gly Ser Asn Cys Lys His Pro Glu Ile Lys Lys Gln Glu Tyr
    1100                1105                1110

Glu Glu Val Val Gln Thr Val Asn Thr Asp Phe Ser Pro Tyr Leu
    1115                1120                1125

Ile Ser Asp Asn Leu Glu Gln Pro Met Gly Ser Ser His Ala Ser
    1130                1135                1140

Gln Val Cys Ser Glu Thr Pro Asp Asp Leu Leu Asp Asp Gly Glu
    1145                1150                1155

Ile Lys Glu Asp Thr Ser Phe Ala Glu Asn Asp Ile Lys Glu Ser
```

```
              1160                1165                1170

Ser  Ala  Val  Phe  Ser  Lys  Ser  Val  Gln  Lys  Gly  Glu  Leu  Ser  Arg
         1175                1180                1185

Ser  Pro  Ser  Pro  Phe  Thr  His  Thr  His  Leu  Ala  Gln  Gly  Tyr  Arg
         1190                1195                1200

Arg  Gly  Ala  Lys  Lys  Leu  Glu  Ser  Ser  Glu  Glu  Asn  Leu  Ser  Ser
         1205                1210                1215

Glu  Asp  Glu  Glu  Leu  Pro  Cys  Phe  Gln  His  Leu  Leu  Phe  Gly  Lys
         1220                1225                1230

Val  Asn  Asn  Ile  Pro  Ser  Gln  Ser  Thr  Arg  His  Ser  Thr  Val  Ala
         1235                1240                1245

Thr  Glu  Cys  Leu  Ser  Lys  Asn  Thr  Glu  Asn  Leu  Leu  Ser  Leu
         1250                1255                1260

Lys  Asn  Ser  Leu  Asn  Asp  Cys  Ser  Asn  Gln  Val  Ile  Leu  Ala  Lys
         1265                1270                1275

Ala  Ser  Gln  Glu  His  His  Leu  Ser  Glu  Glu  Thr  Lys  Cys  Ser  Ala
         1280                1285                1290

Ser  Leu  Phe  Ser  Ser  Gln  Cys  Ser  Glu  Leu  Glu  Asp  Leu  Thr  Ala
         1295                1300                1305

Asn  Thr  Asn  Thr  Gln  Asp  Pro  Phe  Leu  Ile  Gly  Ser  Ser  Lys  Gln
         1310                1315                1320

Met  Arg  His  Gln  Ser  Glu  Ser  Gln  Gly  Val  Gly  Leu  Ser  Asp  Lys
         1325                1330                1335

Glu  Leu  Val  Ser  Asp  Asp  Glu  Glu  Arg  Gly  Thr  Gly  Leu  Glu  Glu
         1340                1345                1350

Asn  Asn  Gln  Glu  Glu  Gln  Ser  Met  Asp  Ser  Asn  Leu  Gly  Glu  Ala
         1355                1360                1365

Ala  Ser  Gly  Cys  Glu  Ser  Glu  Thr  Ser  Val  Ser  Glu  Asp  Cys  Ser
         1370                1375                1380

Gly  Leu  Ser  Ser  Gln  Ser  Asp  Ile  Leu  Thr  Thr  Gln  Gln  Arg  Asp
         1385                1390                1395

Thr  Met  Gln  His  Asn  Leu  Ile  Lys  Leu  Gln  Gln  Glu  Met  Ala  Glu
         1400                1405                1410

Leu  Glu  Ala  Val  Leu  Glu  Gln  His  Gly  Ser  Gln  Pro  Ser  Asn  Ser
         1415                1420                1425

Tyr  Pro  Ser  Ile  Ile  Ser  Asp  Ser  Ser  Ala  Leu  Glu  Asp  Leu  Arg
         1430                1435                1440

Asn  Pro  Glu  Gln  Ser  Thr  Ser  Glu  Lys  Ala  Val  Leu  Thr  Ser  Gln
         1445                1450                1455

Lys  Ser  Ser  Glu  Tyr  Pro  Ile  Ser  Gln  Asn  Pro  Glu  Gly  Leu  Ser
         1460                1465                1470

Ala  Asp  Lys  Phe  Glu  Val  Ser  Ala  Asp  Ser  Ser  Thr  Ser  Lys  Asn
         1475                1480                1485

Lys  Glu  Pro  Gly  Val  Glu  Arg  Ser  Ser  Pro  Ser  Lys  Cys  Pro  Ser
         1490                1495                1500

Leu  Asp  Asp  Arg  Trp  Tyr  Met  His  Ser  Cys  Ser  Gly  Ser  Leu  Gln
         1505                1510                1515

Asn  Arg  Asn  Tyr  Pro  Ser  Gln  Glu  Glu  Leu  Ile  Lys  Val  Val  Asp
         1520                1525                1530

Val  Glu  Glu  Gln  Gln  Leu  Glu  Glu  Ser  Gly  Pro  His  Asp  Leu  Thr
         1535                1540                1545

Glu  Thr  Ser  Tyr  Leu  Pro  Arg  Gln  Asp  Leu  Glu  Gly  Thr  Pro  Tyr
         1550                1555                1560
```

```
Leu Glu Ser Gly Ile Ser Leu Phe Ser Asp Pro Glu Ser Asp
    1565            1570            1575

Pro Ser Glu Asp Arg Ala Pro Glu Ser Ala Arg Val Gly Asn Ile
1580            1585            1590

Pro Ser Ser Thr Ser Ala Leu Lys Val Pro Gln Leu Lys Val Ala
1595            1600            1605

Glu Ser Ala Gln Ser Pro Ala Ala His Thr Thr Asp Thr Ala
1610            1615            1620

Gly Tyr Asn Ala Met Glu Glu Ser Val Ser Arg Glu Lys Pro Glu
1625            1630            1635

Leu Thr Ala Ser Thr Glu Arg Val Asn Lys Arg Met Ser Met Val
1640            1645            1650

Val Ser Gly Leu Thr Pro Glu Glu Phe Met Leu Val Tyr Lys Phe
1655            1660            1665

Ala Arg Lys His His Ile Thr Leu Thr Asn Leu Ile Thr Glu Glu
1670            1675            1680

Thr Thr His Val Val Met Lys Thr Asp Ala Glu Phe Val Cys Glu
1685            1690            1695

Arg Thr Leu Lys Tyr Phe Leu Gly Ile Ala Gly Gly Lys Trp Val
1700            1705            1710

Val Ser Tyr Phe Trp Val Thr Gln Ser Ile Lys Glu Arg Lys Met
1715            1720            1725

Leu Asn Glu His Asp Phe Glu Val Arg Gly Asp Val Val Asn Gly
1730            1735            1740

Arg Asn His Gln Gly Pro Lys Arg Ala Arg Glu Ser Gln Asp Arg
1745            1750            1755

Lys Ile Phe Arg Gly Leu Glu Ile Cys Cys Tyr Gly Pro Phe Thr
1760            1765            1770

Asn Met Pro Thr Asp Gln Leu Glu Trp Met Val Gln Leu Cys Gly
1775            1780            1785

Ala Ser Val Val Lys Glu Leu Ser Ser Phe Thr Leu Gly Thr Gly
1790            1795            1800

Val His Pro Ile Val Val Val Gln Pro Asp Ala Trp Thr Glu Asp
1805            1810            1815

Asn Gly Phe His Ala Ile Gly Gln Met Cys Glu Ala Pro Val Val
1820            1825            1830

Thr Arg Glu Trp Val Leu Asp Ser Val Ala Leu Tyr Gln Cys Gln
1835            1840            1845

Glu Leu Asp Thr Tyr Leu Ile Pro Gln Ile Pro His Ser His Tyr
1850            1855            1860
```

<210> SEQ ID NO 122
<211> LENGTH: 3418
<212> TYPE: PRT
<213> ORGANISM: Homo sapiens

<400> SEQUENCE: 122

```
Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
                20                  25                  30

Glu Glu Leu Ser Ser Glu Ala Pro Pro Tyr Asn Ser Glu Pro Ala Glu
            35                  40                  45

Glu Ser Glu His Lys Asn Asn Asn Tyr Glu Pro Asn Leu Phe Lys Thr
```

-continued

```
            50                  55                  60
Pro Gln Arg Lys Pro Ser Tyr Asn Gln Leu Ala Ser Thr Pro Ile Ile
 65                  70                  75                  80

Phe Lys Glu Gln Gly Leu Thr Leu Pro Leu Tyr Gln Ser Pro Val Lys
                     85                  90                  95

Glu Leu Asp Lys Phe Lys Leu Asp Leu Gly Arg Asn Val Pro Asn Ser
                100                 105                 110

Arg His Lys Ser Leu Arg Thr Val Lys Thr Lys Met Asp Gln Ala Asp
                115                 120                 125

Asp Val Ser Cys Pro Leu Leu Asn Ser Cys Leu Ser Glu Ser Pro Val
                130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                    165                 170                 175

Pro Lys His Ile Ser Glu Ser Leu Gly Ala Glu Val Asp Pro Asp Met
                    180                 185                 190

Ser Trp Ser Ser Ser Leu Ala Thr Pro Pro Thr Leu Ser Ser Thr Val
                    195                 200                 205

Leu Ile Val Arg Asn Glu Glu Ala Ser Glu Thr Val Phe Pro His Asp
                    210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                    245                 250                 255

Asn Gln Arg Glu Ala Ala Ser His Gly Phe Gly Lys Thr Ser Gly Asn
                    260                 265                 270

Ser Phe Lys Val Asn Ser Cys Lys Asp His Ile Gly Lys Ser Met Pro
                    275                 280                 285

Asn Val Leu Glu Asp Glu Val Tyr Glu Thr Val Val Asp Thr Ser Glu
                    290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Ile Phe His Glu Ala
                    325                 330                 335

Asn Ala Asp Glu Cys Glu Lys Ser Lys Asn Gln Val Lys Glu Lys Tyr
                    340                 345                 350

Ser Phe Val Ser Glu Val Glu Pro Asn Asp Thr Asp Pro Leu Asp Ser
                    355                 360                 365

Asn Val Ala Asn Gln Lys Pro Phe Glu Ser Gly Ser Asp Lys Ile Ser
                    370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                    405                 410                 415

Ser Ser Cys Asp Gln Asn Ile Ser Glu Lys Asp Leu Leu Asp Thr Glu
                    420                 425                 430

Asn Lys Arg Lys Lys Asp Phe Leu Thr Ser Glu Asn Ser Leu Pro Arg
                    435                 440                 445

Ile Ser Ser Leu Pro Lys Ser Glu Lys Pro Leu Asn Glu Glu Thr Val
                    450                 455                 460

Val Asn Lys Arg Asp Glu Glu Gln His Leu Glu Ser His Thr Asp Cys
465                 470                 475                 480
```

-continued

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
                500                 505                 510

Lys Glu Thr Phe Asn Ala Ser Phe Ser Gly His Met Thr Asp Pro Asn
                515                 520                 525

Phe Lys Lys Glu Thr Glu Ala Ser Glu Ser Gly Leu Glu Ile His Thr
                530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
                580                 585                 590

Ala Ile His Asp Glu Thr Ser Tyr Lys Gly Lys Lys Ile Pro Lys Asp
                595                 600                 605

Gln Lys Ser Glu Leu Ile Asn Cys Ser Ala Gln Phe Glu Ala Asn Ala
                610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
                660                 665                 670

Asn Glu Thr Cys Ser Asn Asn Thr Val Ile Ser Gln Asp Leu Asp Tyr
                675                 680                 685

Lys Glu Ala Lys Cys Asn Lys Glu Lys Leu Gln Leu Phe Ile Thr Pro
                690                 695                 700

Glu Ala Asp Ser Leu Ser Cys Leu Gln Glu Gly Gln Cys Glu Asn Asp
705                 710                 715                 720

Pro Lys Ser Lys Lys Val Ser Asp Ile Lys Glu Glu Val Leu Ala Ala
                725                 730                 735

Ala Cys His Pro Val Gln His Ser Lys Val Glu Tyr Ser Asp Thr Asp
                740                 745                 750

Phe Gln Ser Gln Lys Ser Leu Leu Tyr Asp His Glu Asn Ala Ser Thr
                755                 760                 765

Leu Ile Leu Thr Pro Thr Ser Lys Asp Val Leu Ser Asn Leu Val Met
                770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
                820                 825                 830

Leu Leu Pro Pro Glu Lys Tyr Met Arg Val Ala Ser Pro Ser Arg Lys
                835                 840                 845

Val Gln Phe Asn Gln Asn Thr Asn Leu Arg Val Ile Gln Lys Asn Gln
850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

```
Glu Arg Asn Asn Leu Ala Leu Gly Asn Thr Lys Glu Leu His Thr
                900                 905                 910

Asp Leu Thr Cys Val Asn Glu Pro Ile Phe Lys Asn Ser Thr Met Val
            915                 920                 925

Leu Tyr Gly Asp Thr Gly Asp Lys Gln Ala Thr Gln Val Ser Ile Lys
        930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile Ser Asn His Ser Phe Gly Gly Ser
        995                 1000                1005

Phe Arg Thr Ala Ser Asn Lys Glu Ile Lys Leu Ser Glu His Asn
    1010                1015                1020

Ile Lys Lys Ser Lys Met Phe Phe Lys Asp Ile Glu Glu Gln Tyr
    1025                1030                1035

Pro Thr Ser Leu Ala Cys Val Glu Ile Val Asn Thr Leu Ala Leu
    1040                1045                1050

Asp Asn Gln Lys Lys Leu Ser Lys Pro Gln Ser Ile Asn Thr Val
    1055                1060                1065

Ser Ala His Leu Gln Ser Ser Val Val Val Ser Asp Cys Lys Asn
    1070                1075                1080

Ser His Ile Thr Pro Gln Met Leu Phe Ser Lys Gln Asp Phe Asn
    1085                1090                1095

Ser Asn His Asn Leu Thr Pro Ser Gln Lys Ala Glu Ile Thr Glu
    1100                1105                1110

Leu Ser Thr Ile Leu Glu Glu Ser Gly Ser Gln Phe Glu Phe Thr
    1115                1120                1125

Gln Phe Arg Lys Pro Ser Tyr Ile Leu Gln Lys Ser Thr Phe Glu
    1130                1135                1140

Val Pro Glu Asn Gln Met Thr Ile Leu Lys Thr Thr Ser Glu Glu
    1145                1150                1155

Cys Arg Asp Ala Asp Leu His Val Ile Met Asn Ala Pro Ser Ile
    1160                1165                1170

Gly Gln Val Asp Ser Ser Lys Gln Phe Glu Gly Thr Val Glu Ile
    1175                1180                1185

Lys Arg Lys Phe Ala Gly Leu Leu Lys Asn Asp Cys Asn Lys Ser
    1190                1195                1200

Ala Ser Gly Tyr Leu Thr Asp Glu Asn Glu Val Gly Phe Arg Gly
    1205                1210                1215

Phe Tyr Ser Ala His Gly Thr Lys Leu Asn Val Ser Thr Glu Ala
    1220                1225                1230

Leu Gln Lys Ala Val Lys Leu Phe Ser Asp Ile Glu Asn Ile Ser
    1235                1240                1245

Glu Glu Thr Ser Ala Glu Val His Pro Ile Ser Leu Ser Ser Ser
    1250                1255                1260

Lys Cys His Asp Ser Val Val Ser Met Phe Lys Ile Glu Asn His
    1265                1270                1275

Asn Asp Lys Thr Val Ser Glu Lys Asn Asn Lys Cys Gln Leu Ile
    1280                1285                1290

Leu Gln Asn Asn Ile Glu Met Thr Thr Gly Thr Phe Val Glu Glu
```

-continued

```
            1295                1300                1305

Ile Thr Glu Asn Tyr Lys Arg Asn Thr Glu Asn Glu Asp Asn Lys
    1310                1315                1320

Tyr Thr Ala Ala Ser Arg Asn Ser His Asn Leu Glu Phe Asp Gly
    1325                1330                1335

Ser Asp Ser Ser Lys Asn Asp Thr Val Cys Ile His Lys Asp Glu
    1340                1345                1350

Thr Asp Leu Leu Phe Thr Asp Gln His Asn Ile Cys Leu Lys Leu
    1355                1360                1365

Ser Gly Gln Phe Met Lys Glu Gly Asn Thr Gln Ile Lys Glu Asp
    1370                1375                1380

Leu Ser Asp Leu Thr Phe Leu Glu Val Ala Lys Ala Gln Glu Ala
    1385                1390                1395

Cys His Gly Asn Thr Ser Asn Lys Glu Gln Leu Thr Ala Thr Lys
    1400                1405                1410

Thr Glu Gln Asn Ile Lys Asp Phe Glu Thr Ser Asp Thr Phe Phe
    1415                1420                1425

Gln Thr Ala Ser Gly Lys Asn Ile Ser Val Ala Lys Glu Ser Phe
    1430                1435                1440

Asn Lys Ile Val Asn Phe Phe Asp Gln Lys Pro Glu Glu Leu His
    1445                1450                1455

Asn Phe Ser Leu Asn Ser Glu Leu His Ser Asp Ile Arg Lys Asn
    1460                1465                1470

Lys Met Asp Ile Leu Ser Tyr Glu Glu Thr Asp Ile Val Lys His
    1475                1480                1485

Lys Ile Leu Lys Glu Ser Val Pro Val Gly Thr Gly Asn Gln Leu
    1490                1495                1500

Val Thr Phe Gln Gly Gln Pro Glu Arg Asp Glu Lys Ile Lys Glu
    1505                1510                1515

Pro Thr Leu Leu Gly Phe His Thr Ala Ser Gly Lys Lys Val Lys
    1520                1525                1530

Ile Ala Lys Glu Ser Leu Asp Lys Val Lys Asn Leu Phe Asp Glu
    1535                1540                1545

Lys Glu Gln Gly Thr Ser Glu Ile Thr Ser Phe Ser His Gln Trp
    1550                1555                1560

Ala Lys Thr Leu Lys Tyr Arg Glu Ala Cys Lys Asp Leu Glu Leu
    1565                1570                1575

Ala Cys Glu Thr Ile Glu Ile Thr Ala Ala Pro Lys Cys Lys Glu
    1580                1585                1590

Met Gln Asn Ser Leu Asn Asn Asp Lys Asn Leu Val Ser Ile Glu
    1595                1600                1605

Thr Val Val Pro Pro Lys Leu Leu Ser Asp Asn Leu Cys Arg Gln
    1610                1615                1620

Thr Glu Asn Leu Lys Thr Ser Lys Ser Ile Phe Leu Lys Val Lys
    1625                1630                1635

Val His Glu Asn Val Glu Lys Glu Thr Ala Lys Ser Pro Ala Thr
    1640                1645                1650

Cys Tyr Thr Asn Gln Ser Pro Tyr Ser Val Ile Glu Asn Ser Ala
    1655                1660                1665

Leu Ala Phe Tyr Thr Ser Cys Ser Arg Lys Thr Ser Val Ser Gln
    1670                1675                1680

Thr Ser Leu Leu Glu Ala Lys Lys Trp Leu Arg Glu Gly Ile Phe
    1685                1690                1695
```

```
Asp Gly Gln Pro Glu Arg Ile Asn Thr Ala Asp Tyr Val Gly Asn
    1700                1705                1710

Tyr Leu Tyr Glu Asn Asn Ser Asn Ser Thr Ile Ala Glu Asn Asp
    1715                1720                1725

Lys Asn His Leu Ser Glu Lys Gln Asp Thr Tyr Leu Ser Asn Ser
    1730                1735                1740

Ser Met Ser Asn Ser Tyr Ser Tyr His Ser Asp Glu Val Tyr Asn
    1745                1750                1755

Asp Ser Gly Tyr Leu Ser Lys Asn Lys Leu Asp Ser Gly Ile Glu
    1760                1765                1770

Pro Val Leu Lys Asn Val Glu Asp Gln Lys Asn Thr Ser Phe Ser
    1775                1780                1785

Lys Val Ile Ser Asn Val Lys Asp Ala Asn Ala Tyr Pro Gln Thr
    1790                1795                1800

Val Asn Glu Asp Ile Cys Val Glu Glu Leu Val Thr Ser Ser Ser
    1805                1810                1815

Pro Cys Lys Asn Lys Asn Ala Ala Ile Lys Leu Ser Ile Ser Asn
    1820                1825                1830

Ser Asn Asn Phe Glu Val Gly Pro Pro Ala Phe Arg Ile Ala Ser
    1835                1840                1845

Gly Lys Ile Val Cys Val Ser His Glu Thr Ile Lys Lys Val Lys
    1850                1855                1860

Asp Ile Phe Thr Asp Ser Phe Ser Lys Val Ile Lys Glu Asn Asn
    1865                1870                1875

Glu Asn Lys Ser Lys Ile Cys Gln Thr Lys Ile Met Ala Gly Cys
    1880                1885                1890

Tyr Glu Ala Leu Asp Asp Ser Glu Asp Ile Leu His Asn Ser Leu
    1895                1900                1905

Asp Asn Asp Glu Cys Ser Thr His Ser His Lys Val Phe Ala Asp
    1910                1915                1920

Ile Gln Ser Glu Glu Ile Leu Gln His Asn Gln Asn Met Ser Gly
    1925                1930                1935

Leu Glu Lys Val Ser Lys Ile Ser Pro Cys Asp Val Ser Leu Glu
    1940                1945                1950

Thr Ser Asp Ile Cys Lys Cys Ser Ile Gly Lys Leu His Lys Ser
    1955                1960                1965

Val Ser Ser Ala Asn Thr Cys Gly Ile Phe Ser Thr Ala Ser Gly
    1970                1975                1980

Lys Ser Val Gln Val Ser Asp Ala Ser Leu Gln Asn Ala Arg Gln
    1985                1990                1995

Val Phe Ser Glu Ile Glu Asp Ser Thr Lys Gln Val Phe Ser Lys
    2000                2005                2010

Val Leu Phe Lys Ser Asn Glu His Ser Asp Gln Leu Thr Arg Glu
    2015                2020                2025

Glu Asn Thr Ala Ile Arg Thr Pro Glu His Leu Ile Ser Gln Lys
    2030                2035                2040

Gly Phe Ser Tyr Asn Val Val Asn Ser Ser Ala Phe Ser Gly Phe
    2045                2050                2055

Ser Thr Ala Ser Gly Lys Gln Val Ser Ile Leu Glu Ser Ser Leu
    2060                2065                2070

His Lys Val Lys Gly Val Leu Glu Glu Phe Asp Leu Ile Arg Thr
    2075                2080                2085
```

```
Glu His Ser Leu His Tyr Ser Pro Thr Ser Arg Gln Asn Val Ser
    2090                2095                2100

Lys Ile Leu Pro Arg Val Asp Lys Arg Asn Pro Glu His Cys Val
    2105                2110                2115

Asn Ser Glu Met Glu Lys Thr Cys Ser Lys Glu Phe Lys Leu Ser
    2120                2125                2130

Asn Asn Leu Asn Val Glu Gly Gly Ser Ser Glu Asn Asn His Ser
    2135                2140                2145

Ile Lys Val Ser Pro Tyr Leu Ser Gln Phe Gln Gln Asp Lys Gln
    2150                2155                2160

Gln Leu Val Leu Gly Thr Lys Val Ser Leu Val Glu Asn Ile His
    2165                2170                2175

Val Leu Gly Lys Glu Gln Ala Ser Pro Lys Asn Val Lys Met Glu
    2180                2185                2190

Ile Gly Lys Thr Glu Thr Phe Ser Asp Val Pro Val Lys Thr Asn
    2195                2200                2205

Ile Glu Val Cys Ser Thr Tyr Ser Lys Asp Ser Glu Asn Tyr Phe
    2210                2215                2220

Glu Thr Glu Ala Val Glu Ile Ala Lys Ala Phe Met Glu Asp Asp
    2225                2230                2235

Glu Leu Thr Asp Ser Lys Leu Pro Ser His Ala Thr His Ser Leu
    2240                2245                2250

Phe Thr Cys Pro Glu Asn Glu Glu Met Val Leu Ser Asn Ser Arg
    2255                2260                2265

Ile Gly Lys Arg Arg Gly Glu Pro Leu Ile Leu Val Gly Glu Pro
    2270                2275                2280

Ser Ile Lys Arg Asn Leu Leu Asn Glu Phe Asp Arg Ile Ile Glu
    2285                2290                2295

Asn Gln Glu Lys Ser Leu Lys Ala Ser Lys Ser Thr Pro Asp Gly
    2300                2305                2310

Thr Ile Lys Asp Arg Arg Leu Phe Met His His Val Ser Leu Glu
    2315                2320                2325

Pro Ile Thr Cys Val Pro Phe Arg Thr Thr Lys Glu Arg Gln Glu
    2330                2335                2340

Ile Gln Asn Pro Asn Phe Thr Ala Pro Gly Gln Glu Phe Leu Ser
    2345                2350                2355

Lys Ser His Leu Tyr Glu His Leu Thr Leu Glu Lys Ser Ser Ser
    2360                2365                2370

Asn Leu Ala Val Ser Gly His Pro Phe Tyr Gln Val Ser Ala Thr
    2375                2380                2385

Arg Asn Glu Lys Met Arg His Leu Ile Thr Thr Gly Arg Pro Thr
    2390                2395                2400

Lys Val Phe Val Pro Pro Phe Lys Thr Lys Ser His Phe His Arg
    2405                2410                2415

Val Glu Gln Cys Val Arg Asn Ile Asn Leu Glu Glu Asn Arg Gln
    2420                2425                2430

Lys Gln Asn Ile Asp Gly His Gly Ser Asp Asp Ser Lys Asn Lys
    2435                2440                2445

Ile Asn Asp Asn Glu Ile His Gln Phe Asn Lys Asn Asn Ser Asn
    2450                2455                2460

Gln Ala Ala Ala Val Thr Phe Thr Lys Cys Glu Glu Glu Pro Leu
    2465                2470                2475

Asp Leu Ile Thr Ser Leu Gln Asn Ala Arg Asp Ile Gln Asp Met
```

```
                2480                 2485                 2490

Arg Ile Lys Lys Lys Gln Arg Gln Arg Val Phe Pro Gln Pro Gly
    2495                2500                2505

Ser Leu Tyr Leu Ala Lys Thr Ser Thr Leu Pro Arg Ile Ser Leu
    2510                2515                2520

Lys Ala Ala Val Gly Gly Gln Val Pro Ser Ala Cys Ser His Lys
    2525                2530                2535

Gln Leu Tyr Thr Tyr Gly Val Ser Lys His Cys Ile Lys Ile Asn
    2540                2545                2550

Ser Lys Asn Ala Glu Ser Phe Gln Phe His Thr Glu Asp Tyr Phe
    2555                2560                2565

Gly Lys Glu Ser Leu Trp Thr Gly Lys Gly Ile Gln Leu Ala Asp
    2570                2575                2580

Gly Gly Trp Leu Ile Pro Ser Asn Asp Gly Lys Ala Gly Lys Glu
    2585                2590                2595

Glu Phe Tyr Arg Ala Leu Cys Asp Thr Pro Gly Val Asp Pro Lys
    2600                2605                2610

Leu Ile Ser Arg Ile Trp Val Tyr Asn His Tyr Arg Trp Ile Ile
    2615                2620                2625

Trp Lys Leu Ala Ala Met Glu Cys Ala Phe Pro Lys Glu Phe Ala
    2630                2635                2640

Asn Arg Cys Leu Ser Pro Glu Arg Val Leu Leu Gln Leu Lys Tyr
    2645                2650                2655

Arg Tyr Asp Thr Glu Ile Asp Arg Ser Arg Arg Ser Ala Ile Lys
    2660                2665                2670

Lys Ile Met Glu Arg Asp Asp Thr Ala Ala Lys Thr Leu Val Leu
    2675                2680                2685

Cys Val Ser Asp Ile Ile Ser Leu Ser Ala Asn Ile Ser Glu Thr
    2690                2695                2700

Ser Ser Asn Lys Thr Ser Ser Ala Asp Thr Gln Lys Val Ala Ile
    2705                2710                2715

Ile Glu Leu Thr Asp Gly Trp Tyr Ala Val Lys Ala Gln Leu Asp
    2720                2725                2730

Pro Pro Leu Leu Ala Val Leu Lys Asn Gly Arg Leu Thr Val Gly
    2735                2740                2745

Gln Lys Ile Ile Leu His Gly Ala Glu Leu Val Gly Ser Pro Asp
    2750                2755                2760

Ala Cys Thr Pro Leu Glu Ala Pro Glu Ser Leu Met Leu Lys Ile
    2765                2770                2775

Ser Ala Asn Ser Thr Arg Pro Ala Arg Trp Tyr Thr Lys Leu Gly
    2780                2785                2790

Phe Phe Pro Asp Pro Arg Pro Phe Pro Leu Pro Leu Ser Ser Leu
    2795                2800                2805

Phe Ser Asp Gly Gly Asn Val Gly Cys Val Asp Val Ile Ile Gln
    2810                2815                2820

Arg Ala Tyr Pro Ile Gln Trp Met Glu Lys Thr Ser Ser Gly Leu
    2825                2830                2835

Tyr Ile Phe Arg Asn Glu Arg Glu Glu Lys Glu Ala Ala Lys
    2840                2845                2850

Tyr Val Glu Ala Gln Gln Lys Arg Leu Glu Ala Leu Phe Thr Lys
    2855                2860                2865

Ile Gln Glu Glu Phe Glu Glu His Glu Glu Asn Thr Thr Lys Pro
    2870                2875                2880
```

-continued

```
Tyr Leu Pro Ser Arg Ala Leu Thr Arg Gln Gln Val Arg Ala Leu
        2885            2890                2895

Gln Asp Gly Ala Glu Leu Tyr Glu Ala Val Lys Asn Ala Ala Asp
2900                2905                2910

Pro Ala Tyr Leu Glu Gly Tyr Phe Ser Glu Glu Gln Leu Arg Ala
2915                2920                2925

Leu Asn Asn His Arg Gln Met Leu Asn Asp Lys Gln Ala Gln
2930                2935                2940

Ile Gln Leu Glu Ile Arg Lys Ala Met Glu Ser Ala Glu Gln Lys
        2945            2950                2955

Glu Gln Gly Leu Ser Arg Asp Val Thr Thr Val Trp Lys Leu Arg
2960                2965                2970

Ile Val Ser Tyr Ser Lys Lys Glu Lys Asp Ser Val Ile Leu Ser
        2975            2980                2985

Ile Trp Arg Pro Ser Ser Asp Leu Tyr Ser Leu Leu Thr Glu Gly
        2990            2995                3000

Lys Arg Tyr Arg Ile Tyr His Leu Ala Thr Ser Lys Ser Lys Ser
        3005            3010                3015

Lys Ser Glu Arg Ala Asn Ile Gln Leu Ala Ala Thr Lys Lys Thr
        3020            3025                3030

Gln Tyr Gln Gln Leu Pro Val Ser Asp Glu Ile Leu Phe Gln Ile
        3035            3040                3045

Tyr Gln Pro Arg Glu Pro Leu His Phe Ser Lys Phe Leu Asp Pro
        3050            3055                3060

Asp Phe Gln Pro Ser Cys Ser Glu Val Asp Leu Ile Gly Phe Val
        3065            3070                3075

Val Ser Val Val Lys Lys Thr Gly Leu Ala Pro Phe Val Tyr Leu
        3080            3085                3090

Ser Asp Glu Cys Tyr Asn Leu Leu Ala Ile Lys Phe Trp Ile Asp
        3095            3100                3105

Leu Asn Glu Asp Ile Ile Lys Pro His Met Leu Ile Ala Ala Ser
        3110            3115                3120

Asn Leu Gln Trp Arg Pro Glu Ser Lys Ser Gly Leu Leu Thr Leu
        3125            3130                3135

Phe Ala Gly Asp Phe Ser Val Phe Ser Ala Ser Pro Lys Glu Gly
        3140            3145                3150

His Phe Gln Glu Thr Phe Asn Lys Met Lys Asn Thr Val Glu Asn
        3155            3160                3165

Ile Asp Ile Leu Cys Asn Glu Ala Glu Asn Lys Leu Met His Ile
        3170            3175                3180

Leu His Ala Asn Asp Pro Lys Trp Ser Thr Pro Thr Lys Asp Cys
        3185            3190                3195

Thr Ser Gly Pro Tyr Thr Ala Gln Ile Ile Pro Gly Thr Gly Asn
        3200            3205                3210

Lys Leu Leu Met Ser Ser Pro Asn Cys Glu Ile Tyr Tyr Gln Ser
        3215            3220                3225

Pro Leu Ser Leu Cys Met Ala Lys Arg Lys Ser Val Ser Thr Pro
        3230            3235                3240

Val Ser Ala Gln Met Thr Ser Lys Ser Cys Lys Gly Glu Lys Glu
        3245            3250                3255

Ile Asp Asp Gln Lys Asn Cys Lys Lys Arg Arg Ala Leu Asp Phe
        3260            3265                3270
```

```
Leu Ser Arg Leu Pro Leu Pro Pro Val Ser Pro Ile Cys Thr
3275             3280             3285

Phe Val Ser Pro Ala Ala Gln Lys Ala Phe Gln Pro Pro Arg Ser
3290             3295             3300

Cys Gly Thr Lys Tyr Glu Thr Pro Ile Lys Lys Lys Glu Leu Asn
3305             3310             3315

Ser Pro Gln Met Thr Pro Phe Lys Lys Phe Asn Glu Ile Ser Leu
3320             3325             3330

Leu Glu Ser Asn Ser Ile Ala Asp Glu Glu Leu Ala Leu Ile Asn
3335             3340             3345

Thr Gln Ala Leu Leu Ser Gly Ser Thr Gly Glu Lys Gln Phe Ile
3350             3355             3360

Ser Val Ser Glu Ser Thr Arg Thr Ala Pro Thr Ser Ser Glu Asp
3365             3370             3375

Tyr Leu Arg Leu Lys Arg Arg Cys Thr Thr Ser Leu Ile Lys Glu
3380             3385             3390

Gln Glu Ser Ser Gln Ala Ser Thr Glu Glu Cys Glu Lys Asn Lys
3395             3400             3405

Gln Asp Thr Ile Thr Thr Lys Lys Tyr Ile
3410             3415

<210> SEQ ID NO 123
<211> LENGTH: 3056
<212> TYPE: PRT
<213> ORGANISM: Homo sapiens

<400> SEQUENCE: 123

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
                20                  25                  30

Leu Ile Arg Asp Pro Glu Thr Ile Lys His Leu Asp Arg His Ser Asp
            35                  40                  45

Ser Lys Gln Gly Lys Tyr Leu Asn Trp Asp Ala Val Phe Arg Phe Leu
        50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220
```

```
Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
            245                 250                 255

Glu Ile Leu Pro Thr Leu Leu Tyr Ile Trp Thr Gln His Arg Leu Asn
            260                 265                 270

Asp Ser Leu Lys Glu Val Ile Ile Glu Leu Phe Gln Leu Gln Ile Tyr
            275                 280                 285

Ile His His Pro Lys Gly Ala Lys Thr Gln Glu Lys Gly Ala Tyr Glu
            290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
            340                 345                 350

Cys His Gln Val Phe Asn Glu Asp Thr Arg Ser Leu Glu Ile Ser Gln
        355                 360                 365

Ser Tyr Thr Thr Thr Gln Arg Glu Ser Ser Asp Tyr Ser Val Pro Cys
370                 375                 380

Lys Arg Lys Lys Ile Glu Leu Gly Trp Glu Val Ile Lys Asp His Leu
385                 390                 395                 400

Gln Lys Ser Gln Asn Asp Phe Asp Leu Val Pro Trp Leu Gln Ile Ala
            405                 410                 415

Thr Gln Leu Ile Ser Lys Tyr Pro Ala Ser Leu Pro Asn Cys Glu Leu
            420                 425                 430

Ser Pro Leu Leu Met Ile Leu Ser Gln Leu Leu Pro Gln Gln Arg His
            435                 440                 445

Gly Glu Arg Thr Pro Tyr Val Leu Arg Cys Leu Thr Glu Val Ala Leu
450                 455                 460

Cys Gln Asp Lys Arg Ser Asn Leu Glu Ser Ser Gln Lys Ser Asp Leu
465                 470                 475                 480

Leu Lys Leu Trp Asn Lys Ile Trp Cys Ile Thr Phe Arg Gly Ile Ser
                485                 490                 495

Ser Glu Gln Ile Gln Ala Glu Asn Phe Gly Leu Leu Gly Ala Ile Ile
            500                 505                 510

Gln Gly Ser Leu Val Glu Val Asp Arg Glu Phe Trp Lys Leu Phe Thr
            515                 520                 525

Gly Ser Ala Cys Arg Pro Ser Cys Pro Ala Val Cys Cys Leu Thr Leu
530                 535                 540

Ala Leu Thr Thr Ser Ile Val Pro Gly Thr Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
            580                 585                 590

Thr Glu Val Pro Pro Ile Leu His Ser Asn Phe Pro His Leu Val Leu
            595                 600                 605

Glu Lys Ile Leu Val Ser Leu Thr Met Lys Asn Cys Lys Ala Ala Met
        610                 615                 620

Asn Phe Phe Gln Ser Val Pro Glu Cys Glu His His Gln Lys Asp Lys
625                 630                 635                 640
```

-continued

```
Glu Glu Leu Ser Phe Ser Glu Val Glu Leu Phe Leu Gln Thr Thr
                645                 650                 655
Phe Asp Lys Met Asp Phe Leu Thr Ile Val Arg Glu Cys Gly Ile Glu
        660                 665                 670
Lys His Gln Ser Ser Ile Gly Phe Ser Val His Gln Asn Leu Lys Glu
            675                 680                 685
Ser Leu Asp Arg Cys Leu Leu Gly Leu Ser Glu Gln Leu Leu Asn Asn
        690                 695                 700
Tyr Ser Ser Glu Ile Thr Asn Ser Glu Thr Leu Val Arg Cys Ser Arg
705                 710                 715                 720
Leu Leu Val Gly Val Leu Gly Cys Tyr Cys Tyr Met Gly Val Ile Ala
                725                 730                 735
Glu Glu Glu Ala Tyr Lys Ser Glu Leu Phe Gln Lys Ala Lys Ser Leu
            740                 745                 750
Met Gln Cys Ala Gly Glu Ser Ile Thr Leu Phe Lys Asn Lys Thr Asn
        755                 760                 765
Glu Glu Phe Arg Ile Gly Ser Leu Arg Asn Met Met Gln Leu Cys Thr
        770                 775                 780
Arg Cys Leu Ser Asn Cys Thr Lys Lys Ser Pro Asn Lys Ile Ala Ser
785                 790                 795                 800
Gly Phe Phe Leu Arg Leu Leu Thr Ser Lys Leu Met Asn Asp Ile Ala
                805                 810                 815
Asp Ile Cys Lys Ser Leu Ala Ser Phe Ile Lys Lys Pro Phe Asp Arg
            820                 825                 830
Gly Glu Val Glu Ser Met Glu Asp Asp Thr Asn Gly Asn Leu Met Glu
        835                 840                 845
Val Glu Asp Gln Ser Ser Met Asn Leu Phe Asn Asp Tyr Pro Asp Ser
850                 855                 860
Ser Val Ser Asp Ala Asn Glu Pro Gly Glu Ser Gln Ser Thr Ile Gly
865                 870                 875                 880
Ala Ile Asn Pro Leu Ala Glu Glu Tyr Leu Ser Lys Gln Asp Leu Leu
                885                 890                 895
Phe Leu Asp Met Leu Lys Phe Leu Cys Leu Cys Val Thr Thr Ala Gln
            900                 905                 910
Thr Asn Thr Val Ser Phe Arg Ala Ala Asp Ile Arg Arg Lys Leu Leu
        915                 920                 925
Met Leu Ile Asp Ser Ser Thr Leu Glu Pro Thr Lys Ser Leu His Leu
        930                 935                 940
His Met Tyr Leu Met Leu Leu Lys Glu Leu Pro Gly Glu Glu Tyr Pro
945                 950                 955                 960
Leu Pro Met Glu Asp Val Leu Glu Leu Leu Lys Pro Leu Ser Asn Val
                965                 970                 975
Cys Ser Leu Tyr Arg Arg Asp Gln Asp Val Cys Lys Thr Ile Leu Asn
            980                 985                 990
His Val Leu His Val Val Lys Asn Leu Gly Gln Ser Asn Met Asp Ser
        995                 1000                1005
Glu Asn Thr Arg Asp Ala Gln Gly Gln Phe Leu Thr Val Ile Gly
        1010                1015                1020
Ala Phe Trp His Leu Thr Lys Glu Arg Lys Tyr Ile Phe Ser Val
        1025                1030                1035
Arg Met Ala Leu Val Asn Cys Leu Lys Thr Leu Leu Glu Ala Asp
        1040                1045                1050
Pro Tyr Ser Lys Trp Ala Ile Leu Asn Val Met Gly Lys Asp Phe
```

-continued

```
            1055              1060              1065
Pro Val Asn Glu Val Phe Thr Gln Phe Leu Ala Asp Asn His His
            1070              1075              1080
Gln Val Arg Met Leu Ala Ala Glu Ser Ile Asn Arg Leu Phe Gln
            1085              1090              1095
Asp Thr Lys Gly Asp Ser Ser Arg Leu Leu Lys Ala Leu Pro Leu
            1100              1105              1110
Lys Leu Gln Gln Thr Ala Phe Glu Asn Ala Tyr Leu Lys Ala Gln
            1115              1120              1125
Glu Gly Met Arg Glu Met Ser His Ser Ala Glu Asn Pro Glu Thr
            1130              1135              1140
Leu Asp Glu Ile Tyr Asn Arg Lys Ser Val Leu Leu Thr Leu Ile
            1145              1150              1155
Ala Val Val Leu Ser Cys Ser Pro Ile Cys Glu Lys Gln Ala Leu
            1160              1165              1170
Phe Ala Leu Cys Lys Ser Val Lys Glu Asn Gly Leu Glu Pro His
            1175              1180              1185
Leu Val Lys Lys Val Leu Glu Lys Val Ser Glu Thr Phe Gly Tyr
            1190              1195              1200
Arg Arg Leu Glu Asp Phe Met Ala Ser His Leu Asp Tyr Leu Val
            1205              1210              1215
Leu Glu Trp Leu Asn Leu Gln Asp Thr Glu Tyr Asn Leu Ser Ser
            1220              1225              1230
Phe Pro Phe Ile Leu Leu Asn Tyr Thr Asn Ile Glu Asp Phe Tyr
            1235              1240              1245
Arg Ser Cys Tyr Lys Val Leu Ile Pro His Leu Val Ile Arg Ser
            1250              1255              1260
His Phe Asp Glu Val Lys Ser Ile Ala Asn Gln Ile Gln Glu Asp
            1265              1270              1275
Trp Lys Ser Leu Leu Thr Asp Cys Phe Pro Lys Ile Leu Val Asn
            1280              1285              1290
Ile Leu Pro Tyr Phe Ala Tyr Glu Gly Thr Arg Asp Ser Gly Met
            1295              1300              1305
Ala Gln Gln Arg Glu Thr Ala Thr Lys Val Tyr Asp Met Leu Lys
            1310              1315              1320
Ser Glu Asn Leu Leu Gly Lys Gln Ile Asp His Leu Phe Ile Ser
            1325              1330              1335
Asn Leu Pro Glu Ile Val Val Glu Leu Leu Met Thr Leu His Glu
            1340              1345              1350
Pro Ala Asn Ser Ser Ala Ser Gln Ser Thr Asp Leu Cys Asp Phe
            1355              1360              1365
Ser Gly Asp Leu Asp Pro Ala Pro Asn Pro Pro His Phe Pro Ser
            1370              1375              1380
His Val Ile Lys Ala Thr Phe Ala Tyr Ile Ser Asn Cys His Lys
            1385              1390              1395
Thr Lys Leu Lys Ser Ile Leu Glu Ile Leu Ser Lys Ser Pro Asp
            1400              1405              1410
Ser Tyr Gln Lys Ile Leu Leu Ala Ile Cys Glu Gln Ala Ala Glu
            1415              1420              1425
Thr Asn Asn Val Tyr Lys Lys His Arg Ile Leu Lys Ile Tyr His
            1430              1435              1440
Leu Phe Val Ser Leu Leu Leu Lys Asp Ile Lys Ser Gly Leu Gly
            1445              1450              1455
```

```
Gly Ala Trp Ala Phe Val Leu Arg Asp Val Ile Tyr Thr Leu Ile
1460                1465                1470

His Tyr Ile Asn Gln Arg Pro Ser Cys Ile Met Asp Val Ser Leu
1475                1480                1485

Arg Ser Phe Ser Leu Cys Cys Asp Leu Leu Ser Gln Val Cys Gln
1490                1495                1500

Thr Ala Val Thr Tyr Cys Lys Asp Ala Leu Glu Asn His Leu His
1505                1510                1515

Val Ile Val Gly Thr Leu Ile Pro Leu Val Tyr Glu Gln Val Glu
1520                1525                1530

Val Gln Lys Gln Val Leu Asp Leu Leu Lys Tyr Leu Val Ile Asp
1535                1540                1545

Asn Lys Asp Asn Glu Asn Leu Tyr Ile Thr Ile Lys Leu Leu Asp
1550                1555                1560

Pro Phe Pro Asp His Val Val Phe Lys Asp Leu Arg Ile Thr Gln
1565                1570                1575

Gln Lys Ile Lys Tyr Ser Arg Gly Pro Phe Ser Leu Leu Glu Glu
1580                1585                1590

Ile Asn His Phe Leu Ser Val Ser Val Tyr Asp Ala Leu Pro Leu
1595                1600                1605

Thr Arg Leu Glu Gly Leu Lys Asp Leu Arg Arg Gln Leu Glu Leu
1610                1615                1620

His Lys Asp Gln Met Val Asp Ile Met Arg Ala Ser Gln Asp Asn
1625                1630                1635

Pro Gln Asp Gly Ile Met Val Lys Leu Val Val Asn Leu Leu Gln
1640                1645                1650

Leu Ser Lys Met Ala Ile Asn His Thr Gly Glu Lys Glu Val Leu
1655                1660                1665

Glu Ala Val Gly Ser Cys Leu Gly Glu Val Gly Pro Ile Asp Phe
1670                1675                1680

Ser Thr Ile Ala Ile Gln His Ser Lys Asp Ala Ser Tyr Thr Lys
1685                1690                1695

Ala Leu Lys Leu Phe Glu Asp Lys Glu Leu Gln Trp Thr Phe Ile
1700                1705                1710

Met Leu Thr Tyr Leu Asn Asn Thr Leu Val Glu Asp Cys Val Lys
1715                1720                1725

Val Arg Ser Ala Ala Val Thr Cys Leu Lys Asn Ile Leu Ala Thr
1730                1735                1740

Lys Thr Gly His Ser Phe Trp Glu Ile Tyr Lys Met Thr Thr Asp
1745                1750                1755

Pro Met Leu Ala Tyr Leu Gln Pro Phe Arg Thr Ser Arg Lys Lys
1760                1765                1770

Phe Leu Glu Val Pro Arg Phe Asp Lys Glu Asn Pro Phe Glu Gly
1775                1780                1785

Leu Asp Asp Ile Asn Leu Trp Ile Pro Leu Ser Glu Asn His Asp
1790                1795                1800

Ile Trp Ile Lys Thr Leu Thr Cys Ala Phe Leu Asp Ser Gly Gly
1805                1810                1815

Thr Lys Cys Glu Ile Leu Gln Leu Leu Lys Pro Met Cys Glu Val
1820                1825                1830

Lys Thr Asp Phe Cys Gln Thr Val Leu Pro Tyr Leu Ile His Asp
1835                1840                1845
```

-continued

Ile Leu Leu Gln Asp Thr Asn Glu Ser Trp Arg Asn Leu Leu Ser
1850                1855                1860

Thr His Val Gln Gly Phe Phe Thr Ser Cys Leu Arg His Phe Ser
1865                1870                1875

Gln Thr Ser Arg Ser Thr Thr Pro Ala Asn Leu Asp Ser Glu Ser
1880                1885                1890

Glu His Phe Phe Arg Cys Cys Leu Asp Lys Lys Ser Gln Arg Thr
1895                1900                1905

Met Leu Ala Val Val Asp Tyr Met Arg Gln Lys Arg Pro Ser
1910                1915                1920

Ser Gly Thr Ile Phe Asn Asp Ala Phe Trp Leu Asp Leu Asn Tyr
1925                1930                1935

Leu Glu Val Ala Lys Val Ala Gln Ser Cys Ala Ala His Phe Thr
1940                1945                1950

Ala Leu Leu Tyr Ala Glu Ile Tyr Ala Asp Lys Lys Ser Met Asp
1955                1960                1965

Asp Gln Glu Lys Arg Ser Leu Ala Phe Glu Glu Gly Ser Gln Ser
1970                1975                1980

Thr Thr Ile Ser Ser Leu Ser Glu Lys Ser Lys Glu Glu Thr Gly
1985                1990                1995

Ile Ser Leu Gln Asp Leu Leu Leu Glu Ile Tyr Arg Ser Ile Gly
2000                2005                2010

Glu Pro Asp Ser Leu Tyr Gly Cys Gly Gly Gly Lys Met Leu Gln
2015                2020                2025

Pro Ile Thr Arg Leu Arg Thr Tyr Glu His Glu Ala Met Trp Gly
2030                2035                2040

Lys Ala Leu Val Thr Tyr Asp Leu Glu Thr Ala Ile Pro Ser Ser
2045                2050                2055

Thr Arg Gln Ala Gly Ile Ile Gln Ala Leu Gln Asn Leu Gly Leu
2060                2065                2070

Cys His Ile Leu Ser Val Tyr Leu Lys Gly Leu Asp Tyr Glu Asn
2075                2080                2085

Lys Asp Trp Cys Pro Glu Leu Glu Glu Leu His Tyr Gln Ala Ala
2090                2095                2100

Trp Arg Asn Met Gln Trp Asp His Cys Thr Ser Val Ser Lys Glu
2105                2110                2115

Val Glu Gly Thr Ser Tyr His Glu Ser Leu Tyr Asn Ala Leu Gln
2120                2125                2130

Ser Leu Arg Asp Arg Glu Phe Ser Thr Phe Tyr Glu Ser Leu Lys
2135                2140                2145

Tyr Ala Arg Val Lys Glu Val Glu Glu Met Cys Lys Arg Ser Leu
2150                2155                2160

Glu Ser Val Tyr Ser Leu Tyr Pro Thr Leu Ser Arg Leu Gln Ala
2165                2170                2175

Ile Gly Glu Leu Glu Ser Ile Gly Glu Leu Phe Ser Arg Ser Val
2180                2185                2190

Thr His Arg Gln Leu Ser Glu Val Tyr Ile Lys Trp Gln Lys His
2195                2200                2205

Ser Gln Leu Leu Lys Asp Ser Asp Phe Ser Phe Gln Glu Pro Ile
2210                2215                2220

Met Ala Leu Arg Thr Val Ile Leu Glu Ile Leu Met Glu Lys Glu
2225                2230                2235

Met Asp Asn Ser Gln Arg Glu Cys Ile Lys Asp Ile Leu Thr Lys

```
                    2240                   2245                    2250

His  Leu  Val  Glu  Leu  Ser  Ile  Leu  Ala  Arg  Thr  Phe  Lys  Asn  Thr
     2255                   2260                   2265

Gln  Leu  Pro  Glu  Arg  Ala  Ile  Phe  Gln  Ile  Lys  Gln  Tyr  Asn  Ser
     2270                   2275                   2280

Val  Ser  Cys  Gly  Val  Ser  Glu  Trp  Gln  Leu  Glu  Glu  Ala  Gln  Val
     2285                   2290                   2295

Phe  Trp  Ala  Lys  Lys  Glu  Gln  Ser  Leu  Ala  Leu  Ser  Ile  Leu  Lys
     2300                   2305                   2310

Gln  Met  Ile  Lys  Lys  Leu  Asp  Ala  Ser  Cys  Ala  Ala  Asn  Asn  Pro
     2315                   2320                   2325

Ser  Leu  Lys  Leu  Thr  Tyr  Thr  Glu  Cys  Leu  Arg  Val  Cys  Gly  Asn
     2330                   2335                   2340

Trp  Leu  Ala  Glu  Thr  Cys  Leu  Glu  Asn  Pro  Ala  Val  Ile  Met  Gln
     2345                   2350                   2355

Thr  Tyr  Leu  Glu  Lys  Ala  Val  Glu  Val  Ala  Gly  Asn  Tyr  Asp  Gly
     2360                   2365                   2370

Glu  Ser  Ser  Asp  Glu  Leu  Arg  Asn  Gly  Lys  Met  Lys  Ala  Phe  Leu
     2375                   2380                   2385

Ser  Leu  Ala  Arg  Phe  Ser  Asp  Thr  Gln  Tyr  Gln  Arg  Ile  Glu  Asn
     2390                   2395                   2400

Tyr  Met  Lys  Ser  Ser  Glu  Phe  Glu  Asn  Lys  Gln  Ala  Leu  Leu  Lys
     2405                   2410                   2415

Arg  Ala  Lys  Glu  Glu  Val  Gly  Leu  Leu  Arg  Glu  His  Lys  Ile  Gln
     2420                   2425                   2430

Thr  Asn  Arg  Tyr  Thr  Val  Lys  Val  Gln  Arg  Glu  Leu  Glu  Leu  Asp
     2435                   2440                   2445

Glu  Leu  Ala  Leu  Arg  Ala  Leu  Lys  Glu  Asp  Arg  Lys  Arg  Phe  Leu
     2450                   2455                   2460

Cys  Lys  Ala  Val  Glu  Asn  Tyr  Ile  Asn  Cys  Leu  Leu  Ser  Gly  Glu
     2465                   2470                   2475

Glu  His  Asp  Met  Trp  Val  Phe  Arg  Leu  Cys  Ser  Leu  Trp  Leu  Glu
     2480                   2485                   2490

Asn  Ser  Gly  Val  Ser  Glu  Val  Asn  Gly  Met  Met  Lys  Arg  Asp  Gly
     2495                   2500                   2505

Met  Lys  Ile  Pro  Thr  Tyr  Lys  Phe  Leu  Pro  Leu  Met  Tyr  Gln  Leu
     2510                   2515                   2520

Ala  Ala  Arg  Met  Gly  Thr  Lys  Met  Met  Gly  Gly  Leu  Gly  Phe  His
     2525                   2530                   2535

Glu  Val  Leu  Asn  Asn  Leu  Ile  Ser  Arg  Ile  Ser  Met  Asp  His  Pro
     2540                   2545                   2550

His  His  Thr  Leu  Phe  Ile  Ile  Leu  Ala  Leu  Ala  Asn  Ala  Asn  Arg
     2555                   2560                   2565

Asp  Glu  Phe  Leu  Thr  Lys  Pro  Glu  Val  Ala  Arg  Arg  Ser  Arg  Ile
     2570                   2575                   2580

Thr  Lys  Asn  Val  Pro  Lys  Gln  Ser  Ser  Gln  Leu  Asp  Glu  Asp  Arg
     2585                   2590                   2595

Thr  Glu  Ala  Ala  Asn  Arg  Ile  Ile  Cys  Thr  Ile  Arg  Ser  Arg  Arg
     2600                   2605                   2610

Pro  Gln  Met  Val  Arg  Ser  Val  Glu  Ala  Leu  Cys  Asp  Ala  Tyr  Ile
     2615                   2620                   2625

Ile  Leu  Ala  Asn  Leu  Asp  Ala  Thr  Gln  Trp  Lys  Thr  Gln  Arg  Lys
     2630                   2635                   2640
```

-continued

Gly Ile Asn Ile Pro Ala Asp Gln Pro Ile Thr Lys Leu Lys Asn
2645                2650                2655

Leu Glu Asp Val Val Val Pro Thr Met Glu Ile Lys Val Asp His
2660                2665                2670

Thr Gly Glu Tyr Gly Asn Leu Val Thr Ile Gln Ser Phe Lys Ala
2675                2680                2685

Glu Phe Arg Leu Ala Gly Gly Val Asn Leu Pro Lys Ile Ile Asp
2690                2695                2700

Cys Val Gly Ser Asp Gly Lys Glu Arg Arg Gln Leu Val Lys Gly
2705                2710                2715

Arg Asp Asp Leu Arg Gln Asp Ala Val Met Gln Gln Val Phe Gln
2720                2725                2730

Met Cys Asn Thr Leu Leu Gln Arg Asn Thr Glu Thr Arg Lys Arg
2735                2740                2745

Lys Leu Thr Ile Cys Thr Tyr Lys Val Val Pro Leu Ser Gln Arg
2750                2755                2760

Ser Gly Val Leu Glu Trp Cys Thr Gly Thr Val Pro Ile Gly Glu
2765                2770                2775

Phe Leu Val Asn Asn Glu Asp Gly Ala His Lys Arg Tyr Arg Pro
2780                2785                2790

Asn Asp Phe Ser Ala Phe Gln Cys Gln Lys Lys Met Met Glu Val
2795                2800                2805

Gln Lys Lys Ser Phe Glu Glu Lys Tyr Glu Val Phe Met Asp Val
2810                2815                2820

Cys Gln Asn Phe Gln Pro Val Phe Arg Tyr Phe Cys Met Glu Lys
2825                2830                2835

Phe Leu Asp Pro Ala Ile Trp Phe Glu Lys Arg Leu Ala Tyr Thr
2840                2845                2850

Arg Ser Val Ala Thr Ser Ser Ile Val Gly Tyr Ile Leu Gly Leu
2855                2860                2865

Gly Asp Arg His Val Gln Asn Ile Leu Ile Asn Glu Gln Ser Ala
2870                2875                2880

Glu Leu Val His Ile Asp Leu Gly Val Ala Phe Glu Gln Gly Lys
2885                2890                2895

Ile Leu Pro Thr Pro Glu Thr Val Pro Phe Arg Leu Thr Arg Asp
2900                2905                2910

Ile Val Asp Gly Met Gly Ile Thr Gly Val Glu Gly Val Phe Arg
2915                2920                2925

Arg Cys Cys Glu Lys Thr Met Glu Val Met Arg Asn Ser Gln Glu
2930                2935                2940

Thr Leu Leu Thr Ile Val Glu Val Leu Leu Tyr Asp Pro Leu Phe
2945                2950                2955

Asp Trp Thr Met Asn Pro Leu Lys Ala Leu Tyr Leu Gln Gln Arg
2960                2965                2970

Pro Glu Asp Glu Thr Glu Leu His Pro Thr Leu Asn Ala Asp Asp
2975                2980                2985

Gln Glu Cys Lys Arg Asn Leu Ser Asp Ile Asp Gln Ser Phe Asn
2990                2995                3000

Lys Val Ala Glu Arg Val Leu Met Arg Leu Gln Glu Lys Leu Lys
3005                3010                3015

Gly Val Glu Glu Gly Thr Val Leu Ser Val Gly Gly Gln Val Asn
3020                3025                3030

```
Leu Leu Ile Gln Gln Ala Ile Asp Pro Lys Asn Leu Ser Arg Leu
    3035                3040                3045

Phe Pro Gly Trp Lys Ala Trp Val
    3050                3055
```

<210> SEQ ID NO 124
<211> LENGTH: 2644
<212> TYPE: PRT
<213> ORGANISM: Homo sapiens

<400> SEQUENCE: 124

```
Met Gly Glu His Gly Leu Glu Leu Ala Ser Met Ile Pro Ala Leu Arg
1               5                   10                  15

Glu Leu Gly Ser Ala Thr Pro Glu Glu Tyr Asn Thr Val Val Gln Lys
            20                  25                  30

Pro Arg Gln Ile Leu Cys Gln Phe Ile Asp Arg Ile Leu Thr Asp Val
        35                  40                  45

Asn Val Val Ala Val Glu Leu Val Lys Lys Thr Asp Ser Gln Pro Thr
    50                  55                  60

Ser Val Met Leu Leu Asp Phe Ile Gln His Ile Met Lys Ser Ser Pro
65                  70                  75                  80

Leu Met Phe Val Asn Val Ser Gly Ser His Glu Ala Lys Gly Ser Cys
                85                  90                  95

Ile Glu Phe Ser Asn Trp Ile Ile Thr Arg Leu Leu Arg Ile Ala Ala
            100                 105                 110

Thr Pro Ser Cys His Leu Leu His Lys Lys Ile Cys Glu Val Ile Cys
        115                 120                 125

Ser Leu Leu Phe Leu Phe Lys Ser Lys Ser Pro Ala Ile Phe Gly Val
    130                 135                 140

Leu Thr Lys Glu Leu Leu Gln Leu Phe Glu Asp Leu Val Tyr Leu His
145                 150                 155                 160

Arg Arg Asn Val Met Gly His Ala Val Glu Trp Pro Val Val Met Ser
                165                 170                 175

Arg Phe Leu Ser Gln Leu Asp Glu His Met Gly Tyr Leu Gln Ser Ala
            180                 185                 190

Pro Leu Gln Leu Met Ser Met Gln Asn Leu Glu Phe Ile Glu Val Thr
        195                 200                 205

Leu Leu Met Val Leu Thr Arg Ile Ile Ala Ile Val Phe Phe Arg Arg
    210                 215                 220

Gln Glu Leu Leu Leu Trp Gln Ile Gly Cys Val Leu Leu Glu Tyr Gly
225                 230                 235                 240

Ser Pro Lys Ile Lys Ser Leu Ala Ile Ser Phe Leu Thr Glu Leu Phe
                245                 250                 255

Gln Leu Gly Gly Leu Pro Ala Gln Pro Ala Ser Thr Phe Phe Ser Ser
            260                 265                 270

Phe Leu Glu Leu Leu Lys His Leu Val Glu Met Asp Thr Asp Gln Leu
        275                 280                 285

Lys Leu Tyr Glu Glu Pro Leu Ser Lys Leu Ile Lys Thr Leu Phe Pro
    290                 295                 300

Phe Glu Ala Glu Ala Tyr Arg Asn Ile Glu Pro Val Tyr Leu Asn Met
305                 310                 315                 320

Leu Leu Glu Lys Leu Cys Val Met Phe Glu Asp Gly Val Leu Met Arg
                325                 330                 335

Leu Lys Ser Asp Leu Leu Lys Ala Ala Leu Cys His Leu Leu Gln Tyr
            340                 345                 350
```

```
Phe Leu Lys Phe Val Pro Ala Gly Tyr Glu Ser Ala Leu Gln Val Arg
            355                 360                 365

Lys Val Tyr Val Arg Asn Ile Cys Lys Ala Leu Leu Asp Val Leu Gly
    370                 375                 380

Ile Glu Val Asp Ala Glu Tyr Leu Leu Gly Pro Leu Tyr Ala Ala Leu
385                 390                 395                 400

Lys Met Glu Ser Met Glu Ile Ile Glu Ile Gln Cys Gln Thr Gln
                405                 410                 415

Gln Glu Asn Leu Ser Ser Asn Ser Asp Gly Ile Ser Pro Lys Arg Arg
                420                 425                 430

Arg Leu Ser Ser Leu Asn Pro Ser Lys Arg Ala Pro Lys Gln Thr
            435                 440                 445

Glu Glu Ile Lys His Val Asp Met Asn Gln Lys Ser Ile Leu Trp Ser
            450                 455                 460

Ala Leu Lys Gln Lys Ala Glu Ser Leu Gln Ile Ser Leu Glu Tyr Ser
465                 470                 475                 480

Gly Leu Lys Asn Pro Val Ile Glu Met Leu Glu Gly Ile Ala Val Val
                485                 490                 495

Leu Gln Leu Thr Ala Leu Cys Thr Val His Cys Ser His Gln Asn Met
            500                 505                 510

Asn Cys Arg Thr Phe Lys Asp Cys Gln His Lys Ser Lys Lys Lys Pro
            515                 520                 525

Ser Val Val Ile Thr Trp Met Ser Leu Asp Phe Tyr Thr Lys Val Leu
    530                 535                 540

Lys Ser Cys Arg Ser Leu Leu Glu Ser Val Gln Lys Leu Asp Leu Glu
545                 550                 555                 560

Ala Thr Ile Asp Lys Val Val Lys Ile Tyr Asp Ala Leu Ile Tyr Met
                565                 570                 575

Gln Val Asn Ser Ser Phe Glu Asp His Ile Leu Glu Asp Leu Cys Gly
            580                 585                 590

Met Leu Ser Leu Pro Trp Ile Tyr Ser His Ser Asp Asp Gly Cys Leu
            595                 600                 605

Lys Leu Thr Thr Phe Ala Ala Asn Leu Leu Thr Leu Ser Cys Arg Ile
    610                 615                 620

Ser Asp Ser Tyr Ser Pro Gln Ala Gln Ser Arg Cys Val Phe Leu Leu
625                 630                 635                 640

Thr Leu Phe Pro Arg Arg Ile Phe Leu Glu Trp Arg Thr Ala Val Tyr
                645                 650                 655

Asn Trp Ala Leu Gln Ser Ser His Glu Val Ile Arg Ala Ser Cys Val
            660                 665                 670

Ser Gly Phe Phe Ile Leu Leu Gln Gln Asn Ser Cys Asn Arg Val
    675                 680                 685

Pro Lys Ile Leu Ile Asp Lys Val Lys Asp Asp Ser Asp Ile Val Lys
            690                 695                 700

Lys Glu Phe Ala Ser Ile Leu Gly Gln Leu Val Cys Thr Leu His Gly
705                 710                 715                 720

Met Phe Tyr Leu Thr Ser Ser Leu Thr Glu Pro Phe Ser Glu His Gly
                725                 730                 735

His Val Asp Leu Phe Cys Arg Asn Leu Lys Ala Thr Ser Gln His Glu
            740                 745                 750

Cys Ser Ser Ser Gln Leu Lys Ala Ser Val Cys Lys Pro Phe Leu Phe
    755                 760                 765
```

```
Leu Leu Lys Lys Lys Ile Pro Ser Pro Val Lys Leu Ala Phe Ile Asp
770                 775                 780

Asn Leu His His Leu Cys Lys His Leu Asp Phe Arg Glu Asp Glu Thr
785                 790                 795                 800

Asp Val Lys Ala Val Leu Gly Thr Leu Leu Asn Leu Met Glu Asp Pro
                805                 810                 815

Asp Lys Asp Val Arg Val Ala Phe Ser Gly Asn Ile Lys His Ile Leu
                820                 825                 830

Glu Ser Leu Asp Ser Glu Asp Gly Phe Ile Lys Glu Leu Phe Val Leu
                835                 840                 845

Arg Met Lys Glu Ala Tyr Thr His Ala Gln Ile Ser Arg Asn Asn Glu
850                 855                 860

Leu Lys Asp Thr Leu Ile Leu Thr Thr Gly Asp Ile Gly Arg Ala Ala
865                 870                 875                 880

Lys Gly Asp Leu Val Pro Phe Ala Leu Leu His Leu His Cys Leu
                885                 890                 895

Leu Ser Lys Ser Ala Ser Val Ser Gly Ala Ala Tyr Thr Glu Ile Arg
                900                 905                 910

Ala Leu Val Ala Ala Lys Ser Val Lys Leu Gln Ser Phe Phe Ser Gln
                915                 920                 925

Tyr Lys Lys Pro Ile Cys Gln Phe Leu Val Glu Ser Leu His Ser Ser
930                 935                 940

Gln Met Thr Ala Leu Pro Asn Thr Pro Cys Gln Asn Ala Asp Val Arg
945                 950                 955                 960

Lys Gln Asp Val Ala His Gln Arg Glu Met Ala Leu Asn Thr Leu Ser
                965                 970                 975

Glu Ile Ala Asn Val Phe Asp Phe Pro Asp Leu Asn Arg Phe Leu Thr
                980                 985                 990

Arg Thr Leu Gln Val Leu Leu Pro  Asp Leu Ala Ala Lys Ala Ser Pro
        995                 1000                1005

Ala Ala  Ser Ala Leu Ile Arg  Thr Leu Gly Lys Gln  Leu Asn Val
    1010                 1015                 1020

Asn Arg  Arg Glu Ile Leu Ile  Asn Asn Phe Lys Tyr  Ile Phe Ser
    1025                 1030                 1035

His Leu  Val Cys Ser Cys Ser  Lys Asp Glu Leu Glu  Arg Ala Leu
    1040                 1045                 1050

His Tyr  Leu Lys Asn Glu Thr  Glu Ile Glu Leu Gly  Ser Leu Leu
    1055                 1060                 1065

Arg Gln  Asp Phe Gln Gly Leu  His Asn Glu Leu Leu  Leu Arg Ile
    1070                 1075                 1080

Gly Glu  His Tyr Gln Gln Val  Phe Asn Gly Leu Ser  Ile Leu Ala
    1085                 1090                 1095

Ser Phe  Ala Ser Ser Asp Asp  Pro Tyr Gln Gly Pro  Arg Asp Ile
    1100                 1105                 1110

Ile Ser  Pro Glu Leu Met Ala  Asp Tyr Leu Gln Pro  Lys Leu Leu
    1115                 1120                 1125

Gly Ile  Leu Ala Phe Phe Asn  Met Gln Leu Leu Ser  Ser Ser Val
    1130                 1135                 1140

Gly Ile  Glu Asp Lys Lys Met  Ala Leu Asn Ser Leu  Met Ser Leu
    1145                 1150                 1155

Met Lys  Leu Met Gly Pro Lys  His Val Ser Ser Val  Arg Val Lys
    1160                 1165                 1170

Met Met  Thr Thr Leu Arg Thr  Gly Leu Arg Phe Lys  Asp Asp Phe
```

```
                1175                1180                1185
Pro Glu Leu Cys Cys Arg Ala Trp Asp Cys Phe Val Arg Cys Leu
                1190                1195                1200
Asp His Ala Cys Leu Gly Ser Leu Leu Ser His Val Ile Val Ala
                1205                1210                1215
Leu Leu Pro Leu Ile His Ile Gln Pro Lys Glu Thr Ala Ala Ile
                1220                1225                1230
Phe His Tyr Leu Ile Ile Glu Asn Arg Asp Ala Val Gln Asp Phe
                1235                1240                1245
Leu His Glu Ile Tyr Phe Leu Pro Asp His Pro Glu Leu Lys Lys
                1250                1255                1260
Ile Lys Ala Val Leu Gln Glu Tyr Arg Lys Glu Thr Ser Glu Ser
                1265                1270                1275
Thr Asp Leu Gln Thr Thr Leu Gln Leu Ser Met Lys Ala Ile Gln
                1280                1285                1290
His Glu Asn Val Asp Val Arg Ile His Ala Leu Thr Ser Leu Lys
                1295                1300                1305
Glu Thr Leu Tyr Lys Asn Gln Glu Lys Leu Ile Lys Tyr Ala Thr
                1310                1315                1320
Asp Ser Glu Thr Val Glu Pro Ile Ile Ser Gln Leu Val Thr Val
                1325                1330                1335
Leu Leu Lys Gly Cys Gln Asp Ala Asn Ser Gln Ala Arg Leu Leu
                1340                1345                1350
Cys Gly Glu Cys Leu Gly Glu Leu Gly Ala Ile Asp Pro Gly Arg
                1355                1360                1365
Leu Asp Phe Ser Thr Thr Glu Thr Gln Gly Lys Asp Phe Thr Phe
                1370                1375                1380
Val Thr Gly Val Glu Asp Ser Ser Phe Ala Tyr Gly Leu Leu Met
                1385                1390                1395
Glu Leu Thr Arg Ala Tyr Leu Ala Tyr Ala Asp Asn Ser Arg Ala
                1400                1405                1410
Gln Asp Ser Ala Ala Tyr Ala Ile Gln Glu Leu Leu Ser Ile Tyr
                1415                1420                1425
Asp Cys Arg Glu Met Glu Thr Asn Gly Pro Gly His Gln Leu Trp
                1430                1435                1440
Arg Arg Phe Pro Glu His Val Arg Glu Ile Leu Glu Pro His Leu
                1445                1450                1455
Asn Thr Arg Tyr Lys Ser Ser Gln Lys Ser Thr Asp Trp Ser Gly
                1460                1465                1470
Val Lys Lys Pro Ile Tyr Leu Ser Lys Leu Gly Ser Asn Phe Ala
                1475                1480                1485
Glu Trp Ser Ala Ser Trp Ala Gly Tyr Leu Ile Thr Lys Val Arg
                1490                1495                1500
His Asp Leu Ala Ser Lys Ile Phe Thr Cys Cys Ser Ile Met Met
                1505                1510                1515
Lys His Asp Phe Lys Val Thr Ile Tyr Leu Leu Pro His Ile Leu
                1520                1525                1530
Val Tyr Val Leu Leu Gly Cys Asn Gln Glu Asp Gln Gln Glu Val
                1535                1540                1545
Tyr Ala Glu Ile Met Ala Val Leu Lys His Asp Asp Gln His Thr
                1550                1555                1560
Ile Asn Thr Gln Asp Ile Ala Ser Asp Leu Cys Gln Leu Ser Thr
                1565                1570                1575
```

```
Gln Thr Val Phe Ser Met Leu Asp His Leu Thr Gln Trp Ala Arg
1580                1585                1590

His Lys Phe Gln Ala Leu Lys Ala Glu Lys Cys Pro His Ser Lys
1595                1600                1605

Ser Asn Arg Asn Lys Val Asp Ser Met Val Ser Thr Val Asp Tyr
1610                1615                1620

Glu Asp Tyr Gln Ser Val Thr Arg Phe Leu Asp Leu Ile Pro Gln
1625                1630                1635

Asp Thr Leu Ala Val Ala Ser Phe Arg Ser Lys Ala Tyr Thr Arg
1640                1645                1650

Ala Val Met His Phe Glu Ser Phe Ile Thr Glu Lys Lys Gln Asn
1655                1660                1665

Ile Gln Glu His Leu Gly Phe Leu Gln Lys Leu Tyr Ala Ala Met
1670                1675                1680

His Glu Pro Asp Gly Val Ala Gly Val Ser Ala Ile Arg Lys Ala
1685                1690                1695

Glu Pro Ser Leu Lys Glu Gln Ile Leu Glu His Glu Ser Leu Gly
1700                1705                1710

Leu Leu Arg Asp Ala Thr Ala Cys Tyr Asp Arg Ala Ile Gln Leu
1715                1720                1725

Glu Pro Asp Gln Ile Ile His Tyr His Gly Val Val Lys Ser Met
1730                1735                1740

Leu Gly Leu Gly Gln Leu Ser Thr Val Ile Thr Gln Val Asn Gly
1745                1750                1755

Val His Ala Asn Arg Ser Glu Trp Thr Asp Glu Leu Asn Thr Tyr
1760                1765                1770

Arg Val Glu Ala Ala Trp Lys Leu Ser Gln Trp Asp Leu Val Glu
1775                1780                1785

Asn Tyr Leu Ala Ala Asp Gly Lys Ser Thr Thr Trp Ser Val Arg
1790                1795                1800

Leu Gly Gln Leu Leu Leu Ser Ala Lys Lys Arg Asp Ile Thr Ala
1805                1810                1815

Phe Tyr Asp Ser Leu Lys Leu Val Arg Ala Glu Gln Ile Val Pro
1820                1825                1830

Leu Ser Ala Ala Ser Phe Glu Arg Gly Ser Tyr Gln Arg Gly Tyr
1835                1840                1845

Glu Tyr Ile Val Arg Leu His Met Leu Cys Glu Leu Glu His Ser
1850                1855                1860

Ile Lys Pro Leu Phe Gln His Ser Pro Gly Asp Ser Ser Gln Glu
1865                1870                1875

Asp Ser Leu Asn Trp Val Ala Arg Leu Glu Met Thr Gln Asn Ser
1880                1885                1890

Tyr Arg Ala Lys Glu Pro Ile Leu Ala Leu Arg Arg Ala Leu Leu
1895                1900                1905

Ser Leu Asn Lys Arg Pro Asp Tyr Asn Glu Met Val Gly Glu Cys
1910                1915                1920

Trp Leu Gln Ser Ala Arg Val Ala Arg Lys Ala Gly His His Gln
1925                1930                1935

Thr Ala Tyr Asn Ala Leu Leu Asn Ala Gly Glu Ser Arg Leu Ala
1940                1945                1950

Glu Leu Tyr Val Glu Arg Ala Lys Trp Leu Trp Ser Lys Gly Asp
1955                1960                1965
```

```
Val His Gln Ala Leu Ile Val Leu Gln Lys Gly Val Glu Leu Cys
1970                1975                1980

Phe Pro Glu Asn Glu Thr Pro Pro Glu Gly Lys Asn Met Leu Ile
1985                1990                1995

His Gly Arg Ala Met Leu Leu Val Gly Arg Phe Met Glu Glu Thr
2000                2005                2010

Ala Asn Phe Glu Ser Asn Ala Ile Met Lys Lys Tyr Lys Asp Val
2015                2020                2025

Thr Ala Cys Leu Pro Glu Trp Glu Asp Gly His Phe Tyr Leu Ala
2030                2035                2040

Lys Tyr Tyr Asp Lys Leu Met Pro Met Val Thr Asp Asn Lys Met
2045                2050                2055

Glu Lys Gln Gly Asp Leu Ile Arg Tyr Ile Val Leu His Phe Gly
2060                2065                2070

Arg Ser Leu Gln Tyr Gly Asn Gln Phe Ile Tyr Gln Ser Met Pro
2075                2080                2085

Arg Met Leu Thr Leu Trp Leu Asp Tyr Gly Thr Lys Ala Tyr Glu
2090                2095                2100

Trp Glu Lys Ala Gly Arg Ser Asp Arg Val Gln Met Arg Asn Asp
2105                2110                2115

Leu Gly Lys Ile Asn Lys Val Ile Thr Glu His Thr Asn Tyr Leu
2120                2125                2130

Ala Pro Tyr Gln Phe Leu Thr Ala Phe Ser Gln Leu Ile Ser Arg
2135                2140                2145

Ile Cys His Ser His Asp Glu Val Phe Val Val Leu Met Glu Ile
2150                2155                2160

Ile Ala Lys Val Phe Leu Ala Tyr Pro Gln Gln Ala Met Trp Met
2165                2170                2175

Met Thr Ala Val Ser Lys Ser Ser Tyr Pro Met Arg Val Asn Arg
2180                2185                2190

Cys Lys Glu Ile Leu Asn Lys Ala Ile His Met Lys Lys Ser Leu
2195                2200                2205

Glu Lys Phe Val Gly Asp Ala Thr Arg Leu Thr Asp Lys Leu Leu
2210                2215                2220

Glu Leu Cys Asn Lys Pro Val Asp Gly Ser Ser Thr Leu Ser
2225                2230                2235

Met Ser Thr His Phe Lys Met Leu Lys Lys Leu Val Glu Glu Ala
2240                2245                2250

Thr Phe Ser Glu Ile Leu Ile Pro Leu Gln Ser Val Met Ile Pro
2255                2260                2265

Thr Leu Pro Ser Ile Leu Gly Thr His Ala Asn His Ala Ser His
2270                2275                2280

Glu Pro Phe Pro Gly His Trp Ala Tyr Ile Ala Gly Phe Asp Asp
2285                2290                2295

Met Val Glu Ile Leu Ala Ser Leu Gln Lys Pro Lys Lys Ile Ser
2300                2305                2310

Leu Lys Gly Ser Asp Gly Lys Phe Tyr Ile Met Met Cys Lys Pro
2315                2320                2325

Lys Asp Asp Leu Arg Lys Asp Cys Arg Leu Met Glu Phe Asn Ser
2330                2335                2340

Leu Ile Asn Lys Cys Leu Arg Lys Asp Ala Glu Ser Arg Arg Arg
2345                2350                2355

Glu Leu His Ile Arg Thr Tyr Ala Val Ile Pro Leu Asn Asp Glu
```

```
                2360                2365                2370

Cys Gly Ile Ile Glu Trp Val Asn Asn Thr Ala Gly Leu Arg Pro
    2375                2380                2385

Ile Leu Thr Lys Leu Tyr Lys Glu Lys Gly Val Tyr Met Thr Gly
    2390                2395                2400

Lys Glu Leu Arg Gln Cys Met Leu Pro Lys Ser Ala Ala Leu Ser
    2405                2410                2415

Glu Lys Leu Lys Val Phe Arg Glu Phe Leu Pro Arg His Pro
    2420                2425                2430

Pro Ile Phe His Glu Trp Phe Leu Arg Thr Phe Pro Asp Pro Thr
    2435                2440                2445

Ser Trp Tyr Ser Ser Arg Ser Ala Tyr Cys Arg Ser Thr Ala Val
    2450                2455                2460

Met Ser Met Val Gly Tyr Ile Leu Gly Leu Gly Asp Arg His Gly
    2465                2470                2475

Glu Asn Ile Leu Phe Asp Ser Leu Thr Gly Glu Cys Val His Val
    2480                2485                2490

Asp Phe Asn Cys Leu Phe Asn Lys Gly Glu Thr Phe Glu Val Pro
    2495                2500                2505

Glu Ile Val Pro Phe Arg Leu Thr His Asn Met Val Asn Gly Met
    2510                2515                2520

Gly Pro Met Gly Thr Glu Gly Leu Phe Arg Arg Ala Cys Glu Val
    2525                2530                2535

Thr Met Arg Leu Met Arg Asp Gln Arg Glu Pro Leu Met Ser Val
    2540                2545                2550

Leu Lys Thr Phe Leu His Asp Pro Leu Val Glu Trp Ser Lys Pro
    2555                2560                2565

Val Lys Gly His Ser Lys Ala Pro Leu Asn Glu Thr Gly Glu Val
    2570                2575                2580

Val Asn Glu Lys Ala Lys Thr His Val Leu Asp Ile Glu Gln Arg
    2585                2590                2595

Leu Gln Gly Val Ile Lys Thr Arg Asn Arg Val Thr Gly Leu Pro
    2600                2605                2610

Leu Ser Ile Glu Gly His Val His Tyr Leu Ile Gln Glu Ala Thr
    2615                2620                2625

Asp Glu Asn Leu Leu Cys Gln Met Tyr Leu Gly Trp Thr Pro Tyr
    2630                2635                2640

Met
```

<210> SEQ ID NO 125
<211> LENGTH: 708
<212> TYPE: PRT
<213> ORGANISM: Homo sapiens

<400> SEQUENCE: 125

```
Met Ser Thr Ala Asp Ala Leu Asp Asp Glu Asn Thr Phe Lys Ile Leu
1               5                   10                  15

Val Ala Thr Asp Ile His Leu Gly Phe Met Glu Lys Asp Ala Val Arg
            20                  25                  30

Gly Asn Asp Thr Phe Val Thr Leu Asp Glu Ile Leu Arg Leu Ala Gln
        35                  40                  45

Glu Asn Glu Val Asp Phe Ile Leu Leu Gly Gly Asp Leu Phe His Glu
    50                  55                  60

Asn Lys Pro Ser Arg Lys Thr Leu His Thr Cys Leu Glu Leu Leu Arg
```

```
                65                  70                  75                  80
Lys Tyr Cys Met Gly Asp Arg Pro Val Gln Phe Glu Ile Leu Ser Asp
                    85                  90                  95
Gln Ser Val Asn Phe Gly Phe Ser Lys Phe Pro Trp Val Asn Tyr Gln
                    100                 105                 110
Asp Gly Asn Leu Asn Ile Ser Ile Pro Val Phe Ser Ile His Gly Asn
                    115                 120                 125
His Asp Asp Pro Thr Gly Ala Asp Ala Leu Cys Ala Leu Asp Ile Leu
130                 135                 140
Ser Cys Ala Gly Phe Val Asn His Phe Gly Arg Ser Met Ser Val Glu
145                 150                 155                 160
Lys Ile Asp Ile Ser Pro Val Leu Leu Gln Lys Gly Ser Thr Lys Ile
                    165                 170                 175
Ala Leu Tyr Gly Leu Gly Ser Ile Pro Asp Glu Arg Leu Tyr Arg Met
                    180                 185                 190
Phe Val Asn Lys Lys Val Thr Met Leu Arg Pro Lys Glu Asp Glu Asn
                    195                 200                 205
Ser Trp Phe Asn Leu Phe Val Ile His Gln Asn Arg Ser Lys His Gly
                    210                 215                 220
Ser Thr Asn Phe Ile Pro Glu Gln Phe Leu Asp Asp Phe Ile Asp Leu
225                 230                 235                 240
Val Ile Trp Gly His Glu His Glu Cys Lys Ile Ala Pro Thr Lys Asn
                    245                 250                 255
Glu Gln Gln Leu Phe Tyr Ile Ser Gln Pro Gly Ser Ser Val Val Thr
                    260                 265                 270
Ser Leu Ser Pro Gly Glu Ala Val Lys Lys His Val Gly Leu Leu Arg
                    275                 280                 285
Ile Lys Gly Arg Lys Met Asn Met His Lys Ile Pro Leu His Thr Val
                    290                 295                 300
Arg Gln Phe Phe Met Glu Asp Ile Val Leu Ala Asn His Pro Asp Ile
305                 310                 315                 320
Phe Asn Pro Asp Asn Pro Lys Val Thr Gln Ala Ile Gln Ser Phe Cys
                    325                 330                 335
Leu Glu Lys Ile Glu Glu Met Leu Glu Asn Ala Glu Arg Glu Arg Leu
                    340                 345                 350
Gly Asn Ser His Gln Pro Glu Lys Pro Leu Val Arg Leu Arg Val Asp
                    355                 360                 365
Tyr Ser Gly Gly Phe Glu Pro Phe Ser Val Leu Arg Phe Ser Gln Lys
                    370                 375                 380
Phe Val Asp Arg Val Ala Asn Pro Lys Asp Ile Ile His Phe Phe Arg
385                 390                 395                 400
His Arg Glu Gln Lys Glu Lys Thr Gly Glu Glu Ile Asn Phe Gly Lys
                    405                 410                 415
Leu Ile Thr Lys Pro Ser Glu Gly Thr Thr Leu Arg Val Glu Asp Leu
                    420                 425                 430
Val Lys Gln Tyr Phe Gln Thr Ala Glu Lys Asn Val Gln Leu Ser Leu
                    435                 440                 445
Leu Thr Glu Arg Gly Met Gly Glu Ala Val Gln Glu Phe Val Asp Lys
                    450                 455                 460
Glu Glu Lys Asp Ala Ile Glu Glu Leu Val Lys Tyr Gln Leu Glu Lys
465                 470                 475                 480
Thr Gln Arg Phe Leu Lys Glu Arg His Ile Asp Ala Leu Glu Asp Lys
                    485                 490                 495
```

```
Ile Asp Glu Glu Val Arg Arg Phe Arg Glu Thr Arg Gln Lys Asn Thr
            500                 505                 510

Asn Glu Glu Asp Asp Glu Val Arg Glu Ala Met Thr Arg Ala Arg Ala
            515                 520                 525

Leu Arg Ser Gln Ser Glu Ser Ala Ser Ala Phe Ser Ala Asp Asp
530                 535                 540

Leu Met Ser Ile Asp Leu Ala Glu Gln Met Ala Asn Asp Ser Asp Asp
545                 550                 555                 560

Ser Ile Ser Ala Ala Thr Asn Lys Gly Arg Gly Arg Gly Arg Gly Arg
                565                 570                 575

Arg Gly Gly Arg Gly Gln Asn Ser Ala Ser Arg Gly Gly Ser Gln Arg
            580                 585                 590

Gly Arg Ala Asp Thr Gly Leu Glu Thr Ser Thr Arg Ser Arg Asn Ser
            595                 600                 605

Lys Thr Ala Val Ser Ala Ser Arg Asn Met Ser Ile Ile Asp Ala Phe
610                 615                 620

Lys Ser Thr Arg Gln Gln Pro Ser Arg Asn Val Thr Thr Lys Asn Tyr
625                 630                 635                 640

Ser Glu Val Ile Glu Val Asp Glu Ser Asp Val Glu Glu Asp Ile Phe
            645                 650                 655

Pro Thr Thr Ser Lys Thr Asp Gln Arg Trp Ser Ser Thr Ser Ser Ser
            660                 665                 670

Lys Ile Met Ser Gln Ser Gln Val Ser Lys Gly Val Asp Phe Glu Ser
            675                 680                 685

Ser Glu Asp Asp Asp Asp Pro Phe Met Asn Thr Ser Ser Leu Arg
            690                 695                 700

Arg Asn Arg Arg
705

<210> SEQ ID NO 126
<211> LENGTH: 1312
<212> TYPE: PRT
<213> ORGANISM: Homo sapiens

<400> SEQUENCE: 126

Met Ser Arg Ile Glu Lys Met Ser Ile Leu Gly Val Arg Ser Phe Gly
1               5                   10                  15

Ile Glu Asp Lys Asp Lys Gln Ile Ile Thr Phe Phe Ser Pro Leu Thr
            20                  25                  30

Ile Leu Val Gly Pro Asn Gly Ala Gly Lys Thr Thr Ile Ile Glu Cys
        35                  40                  45

Leu Lys Tyr Ile Cys Thr Gly Asp Phe Pro Pro Gly Thr Lys Gly Asn
    50                  55                  60

Thr Phe Val His Asp Pro Lys Val Ala Gln Glu Thr Asp Val Arg Ala
65                  70                  75                  80

Gln Ile Arg Leu Gln Phe Arg Asp Val Asn Gly Glu Leu Ile Ala Val
                85                  90                  95

Gln Arg Ser Met Val Cys Thr Gln Lys Ser Lys Lys Thr Glu Phe Lys
            100                 105                 110

Thr Leu Glu Gly Val Ile Thr Arg Thr Lys His Gly Glu Lys Val Ser
            115                 120                 125

Leu Ser Ser Lys Cys Ala Glu Ile Asp Arg Glu Met Ile Ser Ser Leu
    130                 135                 140

Gly Val Ser Lys Ala Val Leu Asn Asn Val Ile Phe Cys His Gln Glu
```

-continued

```
            145                 150                 155                 160
Asp Ser Asn Trp Pro Leu Ser Glu Gly Lys Ala Leu Lys Gln Lys Phe
                    165                 170                 175

Asp Glu Ile Phe Ser Ala Thr Arg Tyr Ile Lys Ala Leu Glu Thr Leu
                    180                 185                 190

Arg Gln Val Arg Gln Thr Gln Gly Gln Lys Val Lys Glu Tyr Gln Met
                    195                 200                 205

Glu Leu Lys Tyr Leu Lys Gln Tyr Lys Glu Lys Ala Cys Glu Ile Arg
            210                 215                 220

Asp Gln Ile Thr Ser Lys Glu Ala Gln Leu Thr Ser Ser Lys Glu Ile
225                 230                 235                 240

Val Lys Ser Tyr Glu Asn Glu Leu Asp Pro Leu Lys Asn Arg Leu Lys
                    245                 250                 255

Glu Ile Glu His Asn Leu Ser Lys Ile Met Lys Leu Asp Asn Glu Ile
                    260                 265                 270

Lys Ala Leu Asp Ser Arg Lys Lys Gln Met Glu Lys Asp Asn Ser Glu
                    275                 280                 285

Leu Glu Glu Lys Met Glu Lys Val Phe Gln Gly Thr Asp Glu Gln Leu
            290                 295                 300

Asn Asp Leu Tyr His Asn His Gln Arg Thr Val Arg Glu Lys Glu Arg
305                 310                 315                 320

Lys Leu Val Asp Cys His Arg Glu Leu Glu Lys Leu Asn Lys Glu Ser
                    325                 330                 335

Arg Leu Leu Asn Gln Glu Lys Ser Glu Leu Leu Val Glu Gln Gly Arg
                    340                 345                 350

Leu Gln Leu Gln Ala Asp Arg His Gln Glu His Ile Arg Ala Arg Asp
            355                 360                 365

Ser Leu Ile Gln Ser Leu Ala Thr Gln Leu Glu Leu Asp Gly Phe Glu
                    370                 375                 380

Arg Gly Pro Phe Ser Glu Arg Gln Ile Lys Asn Phe His Lys Leu Val
385                 390                 395                 400

Arg Glu Arg Gln Glu Gly Glu Ala Lys Thr Ala Asn Gln Leu Met Asn
                    405                 410                 415

Asp Phe Ala Glu Lys Glu Thr Leu Lys Gln Lys Gln Ile Asp Glu Ile
                    420                 425                 430

Arg Asp Lys Lys Thr Gly Leu Gly Arg Ile Ile Glu Leu Lys Ser Glu
            435                 440                 445

Ile Leu Ser Lys Lys Gln Asn Glu Leu Lys Asn Val Lys Tyr Glu Leu
            450                 455                 460

Gln Gln Leu Glu Gly Ser Ser Asp Arg Ile Leu Glu Leu Asp Gln Glu
465                 470                 475                 480

Leu Ile Lys Ala Glu Arg Glu Leu Ser Lys Ala Glu Lys Asn Ser Asn
                    485                 490                 495

Val Glu Thr Leu Lys Met Glu Val Ile Ser Leu Gln Asn Glu Lys Ala
                    500                 505                 510

Asp Leu Asp Arg Thr Leu Arg Lys Leu Asp Gln Glu Met Glu Gln Leu
            515                 520                 525

Asn His His Thr Thr Arg Thr Gln Met Glu Met Leu Thr Lys Asp
                    530                 535                 540

Lys Ala Asp Lys Asp Glu Gln Ile Arg Lys Ile Lys Ser Arg His Ser
545                 550                 555                 560

Asp Glu Leu Thr Ser Leu Leu Gly Tyr Phe Pro Asn Lys Lys Gln Leu
                    565                 570                 575
```

```
Glu Asp Trp Leu His Ser Lys Ser Lys Glu Ile Asn Gln Thr Arg Asp
            580                 585                 590

Arg Leu Ala Lys Leu Asn Lys Glu Leu Ala Ser Ser Glu Gln Asn Lys
            595                 600                 605

Asn His Ile Asn Asn Glu Leu Lys Arg Lys Glu Glu Gln Leu Ser Ser
            610                 615                 620

Tyr Glu Asp Lys Leu Phe Asp Val Cys Gly Ser Gln Asp Phe Glu Ser
625                 630                 635                 640

Asp Leu Asp Arg Leu Lys Glu Glu Ile Glu Lys Ser Ser Lys Gln Arg
            645                 650                 655

Ala Met Leu Ala Gly Ala Thr Ala Val Tyr Ser Gln Phe Ile Thr Gln
            660                 665                 670

Leu Thr Asp Glu Asn Gln Ser Cys Cys Pro Val Cys Gln Arg Val Phe
            675                 680                 685

Gln Thr Glu Ala Glu Leu Gln Glu Val Ile Ser Asp Leu Gln Ser Lys
            690                 695                 700

Leu Arg Leu Ala Pro Asp Lys Leu Lys Ser Thr Glu Ser Glu Leu Lys
705                 710                 715                 720

Lys Lys Glu Lys Arg Arg Asp Glu Met Leu Gly Leu Val Pro Met Arg
            725                 730                 735

Gln Ser Ile Ile Asp Leu Lys Glu Lys Glu Ile Pro Glu Leu Arg Asn
            740                 745                 750

Lys Leu Gln Asn Val Asn Arg Asp Ile Gln Arg Leu Lys Asn Asp Ile
            755                 760                 765

Glu Glu Gln Glu Thr Leu Leu Gly Thr Ile Met Pro Glu Glu Glu Ser
            770                 775                 780

Ala Lys Val Cys Leu Thr Asp Val Thr Ile Met Glu Arg Phe Gln Met
785                 790                 795                 800

Glu Leu Lys Asp Val Glu Arg Lys Ile Ala Gln Gln Ala Ala Lys Leu
            805                 810                 815

Gln Gly Ile Asp Leu Asp Arg Thr Val Gln Gln Val Asn Gln Glu Lys
            820                 825                 830

Gln Glu Lys Gln His Lys Leu Asp Thr Val Ser Ser Lys Ile Glu Leu
            835                 840                 845

Asn Arg Lys Leu Ile Gln Asp Gln Gln Glu Gln Ile Gln His Leu Lys
850                 855                 860

Ser Thr Thr Asn Glu Leu Lys Ser Glu Lys Leu Gln Ile Ser Thr Asn
865                 870                 875                 880

Leu Gln Arg Arg Gln Gln Leu Glu Glu Gln Thr Val Glu Leu Ser Thr
            885                 890                 895

Glu Val Gln Ser Leu Tyr Arg Glu Ile Lys Asp Ala Lys Glu Gln Val
            900                 905                 910

Ser Pro Leu Glu Thr Thr Leu Glu Lys Phe Gln Gln Glu Lys Glu Glu
            915                 920                 925

Leu Ile Asn Lys Lys Asn Thr Ser Asn Lys Ile Ala Gln Asp Lys Leu
            930                 935                 940

Asn Asp Ile Lys Glu Lys Val Lys Asn Ile His Gly Tyr Met Lys Asp
945                 950                 955                 960

Ile Glu Asn Tyr Ile Gln Asp Gly Lys Asp Asp Tyr Lys Lys Gln Lys
            965                 970                 975

Glu Thr Glu Leu Asn Lys Val Ile Ala Gln Leu Ser Glu Cys Glu Lys
            980                 985                 990
```

His Lys Glu Lys Ile Asn Glu Asp Met Arg Leu Met Arg Gln Asp Ile
            995                 1000                1005

Asp Thr Gln Lys Ile Gln Glu Arg Trp Leu Gln Asp Asn Leu Thr
            1010                1015                1020

Leu Arg Lys Arg Asn Glu Glu Leu Lys Glu Val Glu Glu Glu Arg
            1025                1030                1035

Lys Gln His Leu Lys Glu Met Gly Gln Met Gln Val Leu Gln Met
            1040                1045                1050

Lys Ser Glu His Gln Lys Leu Glu Glu Asn Ile Asp Asn Ile Lys
            1055                1060                1065

Arg Asn His Asn Leu Ala Leu Gly Arg Gln Lys Gly Tyr Glu Glu
            1070                1075                1080

Glu Ile Ile His Phe Lys Lys Glu Leu Arg Glu Pro Gln Phe Arg
            1085                1090                1095

Asp Ala Glu Glu Lys Tyr Arg Glu Met Met Ile Val Met Arg Thr
            1100                1105                1110

Thr Glu Leu Val Asn Lys Asp Leu Asp Ile Tyr Tyr Lys Thr Leu
            1115                1120                1125

Asp Gln Ala Ile Met Lys Phe His Ser Met Lys Met Glu Glu Ile
            1130                1135                1140

Asn Lys Ile Ile Arg Asp Leu Trp Arg Ser Thr Tyr Arg Gly Gln
            1145                1150                1155

Asp Ile Glu Tyr Ile Glu Ile Arg Ser Asp Ala Asp Glu Asn Val
            1160                1165                1170

Ser Ala Ser Asp Lys Arg Arg Asn Tyr Asn Tyr Arg Val Val Met
            1175                1180                1185

Leu Lys Gly Asp Thr Ala Leu Asp Met Arg Gly Arg Cys Ser Ala
            1190                1195                1200

Gly Gln Lys Val Leu Ala Ser Leu Ile Ile Arg Leu Ala Leu Ala
            1205                1210                1215

Glu Thr Phe Cys Leu Asn Cys Gly Ile Ile Ala Leu Asp Glu Pro
            1220                1225                1230

Thr Thr Asn Leu Asp Arg Glu Asn Ile Glu Ser Leu Ala His Ala
            1235                1240                1245

Leu Val Glu Ile Ile Lys Ser Arg Ser Gln Gln Arg Asn Phe Gln
            1250                1255                1260

Leu Leu Val Ile Thr His Asp Glu Asp Phe Val Glu Leu Leu Gly
            1265                1270                1275

Arg Ser Glu Tyr Val Glu Lys Phe Tyr Arg Ile Lys Lys Asn Ile
            1280                1285                1290

Asp Gln Cys Ser Glu Ile Val Lys Cys Ser Val Ser Ser Leu Gly
            1295                1300                1305

Phe Asn Val His
            1310

<210> SEQ ID NO 127
<211> LENGTH: 754
<212> TYPE: PRT
<213> ORGANISM: Homo sapiens

<400> SEQUENCE: 127

Met Trp Lys Leu Leu Pro Ala Ala Gly Pro Ala Gly Gly Glu Pro Tyr
1               5                   10                  15

Arg Leu Leu Thr Gly Val Glu Tyr Val Val Gly Arg Lys Asn Cys Ala
            20                  25                  30

```
Ile Leu Ile Glu Asn Asp Gln Ser Ile Ser Arg Asn His Ala Val Leu
         35                  40                  45

Thr Ala Asn Phe Ser Val Thr Asn Leu Ser Gln Thr Asp Glu Ile Pro
 50                  55                  60

Val Leu Thr Leu Lys Asp Asn Ser Lys Tyr Gly Thr Phe Val Asn Glu
 65                  70                  75                  80

Glu Lys Met Gln Asn Gly Phe Ser Arg Thr Leu Lys Ser Gly Asp Gly
                 85                  90                  95

Ile Thr Phe Gly Val Phe Gly Ser Lys Phe Arg Ile Glu Tyr Glu Pro
                100                 105                 110

Leu Val Ala Cys Ser Ser Cys Leu Asp Val Ser Gly Lys Thr Ala Leu
                115                 120                 125

Asn Gln Ala Ile Leu Gln Leu Gly Gly Phe Thr Val Asn Asn Trp Thr
        130                 135                 140

Glu Glu Cys Thr His Leu Val Met Val Ser Val Lys Val Thr Ile Lys
145                 150                 155                 160

Thr Ile Cys Ala Leu Ile Cys Gly Arg Pro Ile Val Lys Pro Glu Tyr
                165                 170                 175

Phe Thr Glu Phe Leu Lys Ala Val Glu Ser Lys Lys Gln Pro Pro Gln
                180                 185                 190

Ile Glu Ser Phe Tyr Pro Pro Leu Asp Glu Pro Ser Ile Gly Ser Lys
        195                 200                 205

Asn Val Asp Leu Ser Gly Arg Gln Glu Arg Lys Gln Ile Phe Lys Gly
        210                 215                 220

Lys Thr Phe Ile Phe Leu Asn Ala Lys Gln His Lys Lys Leu Ser Ser
225                 230                 235                 240

Ala Val Val Phe Gly Gly Gly Glu Ala Arg Leu Ile Thr Glu Glu Asn
                245                 250                 255

Glu Glu Glu His Asn Phe Phe Leu Ala Pro Gly Thr Cys Val Val Asp
                260                 265                 270

Thr Gly Ile Thr Asn Ser Gln Thr Leu Ile Pro Asp Cys Gln Lys Lys
        275                 280                 285

Trp Ile Gln Ser Ile Met Asp Met Leu Gln Arg Gln Gly Leu Arg Pro
        290                 295                 300

Ile Pro Glu Ala Glu Ile Gly Leu Ala Val Ile Phe Met Thr Thr Lys
305                 310                 315                 320

Asn Tyr Cys Asp Pro Gln Gly His Pro Ser Thr Gly Leu Lys Thr Thr
                325                 330                 335

Thr Pro Gly Pro Ser Leu Ser Gln Gly Val Ser Val Asp Glu Lys Leu
                340                 345                 350

Met Pro Ser Ala Pro Val Asn Thr Thr Thr Tyr Val Ala Asp Thr Glu
        355                 360                 365

Ser Glu Gln Ala Asp Thr Trp Asp Leu Ser Glu Arg Pro Lys Glu Ile
        370                 375                 380

Lys Val Ser Lys Met Glu Gln Lys Phe Arg Met Leu Ser Gln Asp Ala
385                 390                 395                 400

Pro Thr Val Lys Glu Ser Cys Lys Thr Ser Ser Asn Asn Ser Met
                405                 410                 415

Val Ser Asn Thr Leu Ala Lys Met Arg Ile Pro Asn Tyr Gln Leu Ser
                420                 425                 430

Pro Thr Lys Leu Pro Ser Ile Asn Lys Ser Lys Asp Arg Ala Ser Gln
        435                 440                 445
```

```
Gln Gln Gln Thr Asn Ser Ile Arg Asn Tyr Phe Gln Pro Ser Thr Lys
    450                 455                 460
Lys Arg Glu Arg Asp Glu Glu Asn Gln Glu Met Ser Ser Cys Lys Ser
465                 470                 475                 480
Ala Arg Ile Glu Thr Ser Cys Ser Leu Leu Glu Gln Thr Gln Pro Ala
                485                 490                 495
Thr Pro Ser Leu Trp Lys Asn Lys Glu Gln His Leu Ser Glu Asn Glu
            500                 505                 510
Pro Val Asp Thr Asn Ser Asp Asn Asn Leu Phe Thr Asp Thr Asp Leu
        515                 520                 525
Lys Ser Ile Val Lys Asn Ser Ala Ser Lys Ser His Ala Ala Glu Lys
    530                 535                 540
Leu Arg Ser Asn Lys Lys Arg Glu Met Asp Asp Val Ala Ile Glu Asp
545                 550                 555                 560
Glu Val Leu Glu Gln Leu Phe Lys Asp Thr Lys Pro Glu Leu Glu Ile
                565                 570                 575
Asp Val Lys Val Gln Lys Gln Glu Glu Asp Val Asn Val Arg Lys Arg
            580                 585                 590
Pro Arg Met Asp Ile Glu Thr Asn Asp Thr Phe Ser Asp Glu Ala Val
        595                 600                 605
Pro Glu Ser Ser Lys Ile Ser Gln Glu Asn Glu Ile Gly Lys Lys Arg
    610                 615                 620
Glu Leu Lys Glu Asp Ser Leu Trp Ser Ala Lys Glu Ile Ser Asn Asn
625                 630                 635                 640
Asp Lys Leu Gln Asp Asp Ser Glu Met Leu Pro Lys Lys Leu Leu Leu
                645                 650                 655
Thr Glu Phe Arg Ser Leu Val Ile Lys Asn Ser Thr Ser Arg Asn Pro
            660                 665                 670
Ser Gly Ile Asn Asp Asp Tyr Gly Gln Leu Lys Asn Phe Lys Lys Phe
        675                 680                 685
Lys Lys Val Thr Tyr Pro Gly Ala Gly Lys Leu Pro His Ile Ile Gly
    690                 695                 700
Gly Ser Asp Leu Ile Ala His His Ala Arg Lys Asn Thr Glu Leu Glu
705                 710                 715                 720
Glu Trp Leu Arg Gln Glu Met Glu Val Gln Asn Gln His Ala Lys Glu
                725                 730                 735
Glu Ser Leu Ala Asp Asp Leu Phe Arg Tyr Asn Pro Tyr Leu Lys Arg
            740                 745                 750
Arg Arg

<210> SEQ ID NO 128
<211> LENGTH: 1432
<212> TYPE: PRT
<213> ORGANISM: Homo sapiens

<400> SEQUENCE: 128

Met Ser Glu Lys Lys Leu Glu Thr Thr Ala Gln Gln Arg Lys Cys Pro
1               5                   10                  15
Glu Trp Met Asn Val Gln Asn Lys Arg Cys Ala Val Glu Glu Arg Lys
                20                  25                  30
Ala Cys Val Arg Lys Ser Val Phe Glu Asp Asp Leu Pro Phe Leu Glu
            35                  40                  45
Phe Thr Gly Ser Ile Val Tyr Ser Tyr Asp Ala Ser Asp Cys Ser Phe
        50                  55                  60
```

```
Leu Ser Glu Asp Ile Ser Met Ser Leu Ser Asp Gly Asp Val Val Gly
 65                  70                  75                  80

Phe Asp Met Glu Trp Pro Pro Leu Tyr Asn Arg Gly Lys Leu Gly Lys
                 85                  90                  95

Val Ala Leu Ile Gln Leu Cys Val Ser Glu Ser Lys Cys Tyr Leu Phe
            100                 105                 110

His Val Ser Ser Met Ser Val Phe Pro Gln Gly Leu Lys Met Leu Leu
        115                 120                 125

Glu Asn Lys Ala Val Lys Ala Gly Val Gly Ile Glu Gly Asp Gln
    130                 135                 140

Trp Lys Leu Leu Arg Asp Phe Asp Ile Lys Leu Lys Asn Phe Val Glu
145                 150                 155                 160

Leu Thr Asp Val Ala Asn Lys Lys Leu Lys Cys Thr Glu Thr Trp Ser
                165                 170                 175

Leu Asn Ser Leu Val Lys His Leu Leu Gly Lys Gln Leu Leu Lys Asp
            180                 185                 190

Lys Ser Ile Arg Cys Ser Asn Trp Ser Lys Phe Pro Leu Thr Glu Asp
        195                 200                 205

Gln Lys Leu Tyr Ala Ala Thr Asp Ala Tyr Ala Gly Phe Ile Ile Tyr
    210                 215                 220

Arg Asn Leu Glu Ile Leu Asp Asp Thr Val Gln Arg Phe Ala Ile Asn
225                 230                 235                 240

Lys Glu Glu Glu Ile Leu Leu Ser Asp Met Asn Lys Gln Leu Thr Ser
                245                 250                 255

Ile Ser Glu Glu Val Met Asp Leu Ala Lys His Leu Pro His Ala Phe
            260                 265                 270

Ser Lys Leu Glu Asn Pro Arg Arg Val Ser Ile Leu Leu Lys Asp Ile
        275                 280                 285

Ser Glu Asn Leu Tyr Ser Leu Arg Arg Met Ile Ile Gly Ser Thr Asn
    290                 295                 300

Ile Glu Thr Glu Leu Arg Pro Ser Asn Asn Leu Asn Leu Leu Ser Phe
305                 310                 315                 320

Glu Asp Ser Thr Thr Gly Gly Val Gln Gln Lys Gln Ile Arg Glu His
                325                 330                 335

Glu Val Leu Ile His Val Glu Asp Glu Thr Trp Asp Pro Thr Leu Asp
            340                 345                 350

His Leu Ala Lys His Asp Gly Glu Asp Val Leu Gly Asn Lys Val Glu
        355                 360                 365

Arg Lys Glu Asp Gly Phe Glu Asp Gly Val Glu Asp Asn Lys Leu Lys
    370                 375                 380

Glu Asn Met Glu Arg Ala Cys Leu Met Ser Leu Asp Ile Thr Glu His
385                 390                 395                 400

Glu Leu Gln Ile Leu Glu Gln Ser Gln Glu Glu Tyr Leu Ser Asp
                405                 410                 415

Ile Ala Tyr Lys Ser Thr Glu His Leu Ser Pro Asn Asp Asn Glu Asn
            420                 425                 430

Asp Thr Ser Tyr Val Ile Glu Ser Asp Glu Asp Leu Glu Met Glu Met
        435                 440                 445

Leu Lys His Leu Ser Pro Asn Asp Asn Glu Asn Asp Thr Ser Tyr Val
    450                 455                 460

Ile Glu Ser Asp Glu Asp Leu Glu Met Glu Met Leu Lys Ser Leu Glu
465                 470                 475                 480

Asn Leu Asn Ser Gly Thr Val Glu Pro Thr His Ser Lys Cys Leu Lys
```

-continued

```
                485                 490                 495
Met Glu Arg Asn Leu Gly Leu Pro Thr Lys Glu Glu Glu Asp Asp
                500                 505                 510

Glu Asn Glu Ala Asn Glu Gly Glu Glu Asp Asp Asp Lys Asp Phe Leu
            515                 520                 525

Trp Pro Ala Pro Asn Glu Glu Gln Val Thr Cys Leu Lys Met Tyr Phe
530                 535                 540

Gly His Ser Ser Phe Lys Pro Val Gln Trp Lys Val Ile His Ser Val
545                 550                 555                 560

Leu Glu Glu Arg Arg Asp Asn Val Ala Val Met Ala Thr Gly Tyr Gly
                565                 570                 575

Lys Ser Leu Cys Phe Gln Tyr Pro Val Tyr Val Gly Lys Ile Gly
            580                 585                 590

Leu Val Ile Ser Pro Leu Ile Ser Leu Met Glu Asp Gln Val Leu Gln
                595                 600                 605

Leu Lys Met Ser Asn Ile Pro Ala Cys Phe Leu Gly Ser Ala Gln Ser
            610                 615                 620

Glu Asn Val Leu Thr Asp Ile Lys Leu Gly Lys Tyr Arg Ile Val Tyr
625                 630                 635                 640

Val Thr Pro Glu Tyr Cys Ser Gly Asn Met Gly Leu Leu Gln Gln Leu
                645                 650                 655

Glu Ala Asp Ile Gly Ile Thr Leu Ile Ala Val Asp Glu Ala His Cys
            660                 665                 670

Ile Ser Glu Trp Gly His Asp Phe Arg Asp Ser Phe Arg Lys Leu Gly
                675                 680                 685

Ser Leu Lys Thr Ala Leu Pro Met Val Pro Ile Val Ala Leu Thr Ala
690                 695                 700

Thr Ala Ser Ser Ser Ile Arg Glu Asp Ile Val Arg Cys Leu Asn Leu
705                 710                 715                 720

Arg Asn Pro Gln Ile Thr Cys Thr Gly Phe Asp Arg Pro Asn Leu Tyr
                725                 730                 735

Leu Glu Val Arg Arg Lys Thr Gly Asn Ile Leu Gln Asp Leu Gln Pro
            740                 745                 750

Phe Leu Val Lys Thr Ser Ser His Trp Glu Phe Glu Gly Pro Thr Ile
            755                 760                 765

Ile Tyr Cys Pro Ser Arg Lys Met Thr Gln Gln Val Thr Gly Glu Leu
770                 775                 780

Arg Lys Leu Asn Leu Ser Cys Gly Thr Tyr His Ala Gly Met Ser Phe
785                 790                 795                 800

Ser Thr Arg Lys Asp Ile His His Arg Phe Val Arg Asp Glu Ile Gln
                805                 810                 815

Cys Val Ile Ala Thr Ile Ala Phe Gly Met Gly Ile Asn Lys Ala Asp
            820                 825                 830

Ile Arg Gln Val Ile His Tyr Gly Ala Pro Lys Asp Met Glu Ser Tyr
                835                 840                 845

Tyr Gln Glu Ile Gly Arg Ala Gly Arg Asp Gly Leu Gln Ser Ser Cys
            850                 855                 860

His Val Leu Trp Ala Pro Ala Asp Ile Asn Leu Asn Arg His Leu Leu
865                 870                 875                 880

Thr Glu Ile Arg Asn Glu Lys Phe Arg Leu Tyr Lys Leu Lys Met Met
                885                 890                 895

Ala Lys Met Glu Lys Tyr Leu His Ser Ser Arg Cys Arg Arg Gln Ile
                900                 905                 910
```

```
Ile Leu Ser His Phe Glu Asp Lys Gln Val Gln Lys Ala Ser Leu Gly
        915                 920                 925

Ile Met Gly Thr Glu Lys Cys Cys Asp Asn Cys Arg Ser Arg Leu Asp
    930                 935                 940

His Cys Tyr Ser Met Asp Asp Ser Glu Asp Thr Ser Trp Asp Phe Gly
945                 950                 955                 960

Pro Gln Ala Phe Lys Leu Leu Ser Ala Val Asp Ile Leu Gly Glu Lys
                965                 970                 975

Phe Gly Ile Gly Leu Pro Ile Leu Phe Leu Arg Gly Ser Asn Ser Gln
            980                 985                 990

Arg Leu Ala Asp Gln Tyr Arg Arg His Ser Leu Phe Gly Thr Gly Lys
                995                 1000                1005

Asp Gln Thr Glu Ser Trp Trp Lys Ala Phe Ser Arg Gln Leu Ile
    1010                1015                1020

Thr Glu Gly Phe Leu Val Glu Val Ser Arg Tyr Asn Lys Phe Met
    1025                1030                1035

Lys Ile Cys Ala Leu Thr Lys Lys Gly Arg Asn Trp Leu His Lys
    1040                1045                1050

Ala Asn Thr Glu Ser Gln Ser Leu Ile Leu Gln Ala Asn Glu Glu
    1055                1060                1065

Leu Cys Pro Lys Lys Leu Leu Pro Ser Ser Lys Thr Val Ser
    1070                1075                1080

Ser Gly Thr Lys Glu His Cys Tyr Asn Gln Val Pro Val Glu Leu
    1085                1090                1095

Ser Thr Glu Lys Lys Ser Asn Leu Glu Lys Leu Tyr Ser Tyr Lys
    1100                1105                1110

Pro Cys Asp Lys Ile Ser Ser Gly Ser Asn Ile Ser Lys Lys Ser
    1115                1120                1125

Ile Met Val Gln Ser Pro Glu Lys Ala Tyr Ser Ser Ser Gln Pro
    1130                1135                1140

Val Ile Ser Ala Gln Glu Gln Glu Thr Gln Ile Val Leu Tyr Gly
    1145                1150                1155

Lys Leu Val Glu Ala Arg Gln Lys His Ala Asn Lys Met Asp Val
    1160                1165                1170

Pro Pro Ala Ile Leu Ala Thr Asn Lys Ile Leu Val Asp Met Ala
    1175                1180                1185

Lys Met Arg Pro Thr Thr Val Glu Asn Val Lys Arg Ile Asp Gly
    1190                1195                1200

Val Ser Glu Gly Lys Ala Ala Met Leu Ala Pro Leu Leu Glu Val
    1205                1210                1215

Ile Lys His Phe Cys Gln Thr Asn Ser Val Gln Thr Asp Leu Phe
    1220                1225                1230

Ser Ser Thr Lys Pro Gln Glu Gln Lys Thr Ser Leu Val Ala
    1235                1240                1245

Lys Asn Lys Ile Cys Thr Leu Ser Gln Ser Met Ala Ile Thr Tyr
    1250                1255                1260

Ser Leu Phe Gln Glu Lys Lys Met Pro Leu Lys Ser Ile Ala Glu
    1265                1270                1275

Ser Arg Ile Leu Pro Leu Met Thr Ile Gly Met His Leu Ser Gln
    1280                1285                1290

Ala Val Lys Ala Gly Cys Pro Leu Asp Leu Glu Arg Ala Gly Leu
    1295                1300                1305
```

```
Thr Pro Glu Val Gln Lys Ile Ile Ala Asp Val Ile Arg Asn Pro
    1310                1315                1320

Pro Val Asn Ser Asp Met Ser Lys Ile Ser Leu Ile Arg Met Leu
    1325                1330                1335

Val Pro Glu Asn Ile Asp Thr Tyr Leu Ile His Met Ala Ile Glu
    1340                1345                1350

Ile Leu Lys His Gly Pro Asp Ser Gly Leu Gln Pro Ser Cys Asp
    1355                1360                1365

Val Asn Lys Arg Arg Cys Phe Pro Gly Ser Glu Glu Ile Cys Ser
    1370                1375                1380

Ser Ser Lys Arg Ser Lys Glu Glu Val Gly Ile Asn Thr Glu Thr
    1385                1390                1395

Ser Ser Ala Glu Arg Lys Arg Arg Leu Pro Val Trp Phe Ala Lys
    1400                1405                1410

Gly Ser Asp Thr Ser Lys Lys Leu Met Asp Lys Thr Lys Arg Gly
    1415                1420                1425

Gly Leu Phe Ser
    1430

<210> SEQ ID NO 129
<211> LENGTH: 1417
<212> TYPE: PRT
<213> ORGANISM: Homo sapiens

<400> SEQUENCE: 129

Met Ala Ala Val Pro Gln Asn Asn Leu Gln Glu Gln Leu Glu Arg His
1               5                   10                  15

Ser Ala Arg Thr Leu Asn Asn Lys Leu Ser Leu Ser Lys Pro Lys Phe
                20                  25                  30

Ser Gly Phe Thr Phe Lys Lys Lys Thr Ser Ser Asp Asn Asn Val Ser
            35                  40                  45

Val Thr Asn Val Ser Val Ala Lys Thr Pro Val Leu Arg Asn Lys Asp
        50                  55                  60

Val Asn Val Thr Glu Asp Phe Ser Phe Ser Glu Pro Leu Pro Asn Thr
65                  70                  75                  80

Thr Asn Gln Gln Arg Val Lys Asp Phe Phe Lys Asn Ala Pro Ala Gly
                85                  90                  95

Gln Glu Thr Gln Arg Gly Gly Ser Lys Ser Leu Leu Pro Asp Phe Leu
            100                 105                 110

Gln Thr Pro Lys Glu Val Val Cys Thr Thr Gln Asn Thr Pro Thr Val
        115                 120                 125

Lys Lys Ser Arg Asp Thr Ala Leu Lys Lys Leu Glu Phe Ser Ser Ser
    130                 135                 140

Pro Asp Ser Leu Ser Thr Ile Asn Asp Trp Asp Asp Met Asp Asp Phe
145                 150                 155                 160

Asp Thr Ser Glu Thr Ser Lys Ser Phe Val Thr Pro Pro Gln Ser His
                165                 170                 175

Phe Val Arg Val Ser Thr Ala Gln Lys Ser Lys Lys Gly Lys Arg Asn
            180                 185                 190

Phe Phe Lys Ala Gln Leu Tyr Thr Thr Asn Thr Val Lys Thr Asp Leu
        195                 200                 205

Pro Pro Pro Ser Ser Glu Ser Glu Gln Ile Asp Leu Thr Glu Glu Gln
    210                 215                 220

Lys Asp Asp Ser Glu Trp Leu Ser Ser Asp Val Ile Cys Ile Asp Asp
225                 230                 235                 240
```

-continued

```
Gly Pro Ile Ala Glu Val His Ile Asn Glu Asp Ala Gln Glu Ser Asp
            245                 250                 255

Ser Leu Lys Thr His Leu Glu Asp Glu Arg Asp Asn Ser Glu Lys Lys
            260                 265                 270

Lys Asn Leu Glu Glu Ala Glu Leu His Ser Thr Glu Lys Val Pro Cys
            275                 280                 285

Ile Glu Phe Asp Asp Asp Asp Tyr Asp Thr Asp Phe Val Pro Pro Ser
            290                 295                 300

Pro Glu Glu Ile Ile Ser Ala Ser Ser Ser Ser Lys Cys Leu Ser
305                 310                 315                 320

Thr Leu Lys Asp Leu Asp Thr Ser Asp Arg Lys Glu Asp Val Leu Ser
            325                 330                 335

Thr Ser Lys Asp Leu Leu Ser Lys Pro Glu Lys Met Ser Met Gln Glu
            340                 345                 350

Leu Asn Pro Glu Thr Ser Thr Asp Cys Asp Ala Arg Gln Ile Ser Leu
            355                 360                 365

Gln Gln Gln Leu Ile His Val Met Glu His Ile Cys Lys Leu Ile Asp
            370                 375                 380

Thr Ile Pro Asp Asp Lys Leu Lys Leu Leu Asp Cys Gly Asn Glu Leu
385                 390                 395                 400

Leu Gln Gln Arg Asn Ile Arg Arg Lys Leu Leu Thr Glu Val Asp Phe
            405                 410                 415

Asn Lys Ser Asp Ala Ser Leu Leu Gly Ser Leu Trp Arg Tyr Arg Pro
            420                 425                 430

Asp Ser Leu Asp Gly Pro Met Glu Gly Asp Ser Cys Pro Thr Gly Asn
            435                 440                 445

Ser Met Lys Glu Leu Asn Phe Ser His Leu Pro Ser Asn Ser Val Ser
            450                 455                 460

Pro Gly Asp Cys Leu Leu Thr Thr Thr Leu Gly Lys Thr Gly Phe Ser
465                 470                 475                 480

Ala Thr Arg Lys Asn Leu Phe Glu Arg Pro Leu Phe Asn Thr His Leu
            485                 490                 495

Gln Lys Ser Phe Val Ser Ser Asn Trp Ala Glu Thr Pro Arg Leu Gly
            500                 505                 510

Lys Lys Asn Glu Ser Ser Tyr Phe Pro Gly Asn Val Leu Thr Ser Thr
            515                 520                 525

Ala Val Lys Asp Gln Asn Lys His Thr Ala Ser Ile Asn Asp Leu Glu
            530                 535                 540

Arg Glu Thr Gln Pro Ser Tyr Asp Ile Asp Asn Phe Asp Ile Asp Asp
545                 550                 555                 560

Phe Asp Asp Asp Asp Trp Glu Asp Ile Met His Asn Leu Ala Ala
            565                 570                 575

Ser Lys Ser Ser Thr Ala Ala Tyr Gln Pro Ile Lys Glu Gly Arg Pro
            580                 585                 590

Ile Lys Ser Val Ser Glu Arg Leu Ser Ser Ala Lys Thr Asp Cys Leu
            595                 600                 605

Pro Val Ser Ser Thr Ala Gln Asn Ile Asn Phe Ser Glu Ser Ile Gln
            610                 615                 620

Asn Tyr Thr Asp Lys Ser Ala Gln Asn Leu Ala Ser Arg Asn Leu Lys
625                 630                 635                 640

His Glu Arg Phe Gln Ser Leu Ser Phe Pro His Thr Lys Glu Met Met
            645                 650                 655
```

```
Lys Ile Phe His Lys Lys Phe Gly Leu His Asn Phe Arg Thr Asn Gln
                660                 665                 670

Leu Glu Ala Ile Asn Ala Ala Leu Leu Gly Glu Asp Cys Phe Ile Leu
            675                 680                 685

Met Pro Thr Gly Gly Lys Ser Leu Cys Tyr Gln Leu Pro Ala Cys
    690                 695                 700

Val Ser Pro Gly Val Thr Val Ile Ser Pro Leu Arg Ser Leu Ile
705                 710                 715                 720

Val Asp Gln Val Gln Lys Leu Thr Ser Leu Asp Ile Pro Ala Thr Tyr
                725                 730                 735

Leu Thr Gly Asp Lys Thr Asp Ser Glu Ala Thr Asn Ile Tyr Leu Gln
            740                 745                 750

Leu Ser Lys Lys Asp Pro Ile Ile Lys Leu Leu Tyr Val Thr Pro Glu
            755                 760                 765

Lys Ile Cys Ala Ser Asn Arg Leu Ile Ser Thr Leu Glu Asn Leu Tyr
770                 775                 780

Glu Arg Lys Leu Leu Ala Arg Phe Val Ile Asp Glu Ala His Cys Val
785                 790                 795                 800

Ser Gln Trp Gly His Asp Phe Arg Gln Asp Tyr Lys Arg Met Asn Met
                805                 810                 815

Leu Arg Gln Lys Phe Pro Ser Val Pro Val Met Ala Leu Thr Ala Thr
            820                 825                 830

Ala Asn Pro Arg Val Gln Lys Asp Ile Leu Thr Gln Leu Lys Ile Leu
            835                 840                 845

Arg Pro Gln Val Phe Ser Met Ser Phe Asn Arg His Asn Leu Lys Tyr
850                 855                 860

Tyr Val Leu Pro Lys Lys Pro Lys Lys Val Ala Phe Asp Cys Leu Glu
865                 870                 875                 880

Trp Ile Arg Lys His His Pro Tyr Asp Ser Gly Ile Ile Tyr Cys Leu
                885                 890                 895

Ser Arg Arg Glu Cys Asp Thr Met Ala Asp Thr Leu Gln Arg Asp Gly
            900                 905                 910

Leu Ala Ala Leu Ala Tyr His Ala Gly Leu Ser Asp Ser Ala Arg Asp
            915                 920                 925

Glu Val Gln Gln Lys Trp Ile Asn Gln Asp Gly Cys Gln Val Ile Cys
930                 935                 940

Ala Thr Ile Ala Phe Gly Met Gly Ile Asp Lys Pro Asp Val Arg Phe
945                 950                 955                 960

Val Ile His Ala Ser Leu Pro Lys Ser Val Glu Gly Tyr Tyr Gln Glu
                965                 970                 975

Ser Gly Arg Ala Gly Arg Asp Gly Glu Ile Ser His Cys Leu Leu Phe
            980                 985                 990

Tyr Thr Tyr His Asp Val Thr Arg Leu Lys Arg Leu Ile Met Met Glu
            995                 1000                1005

Lys Asp Gly Asn His His Thr Arg Glu Thr His Phe Asn Asn Leu
    1010                1015                1020

Tyr Ser Met Val His Tyr Cys Glu Asn Ile Thr Glu Cys Arg Arg
    1025                1030                1035

Ile Gln Leu Leu Ala Tyr Phe Gly Glu Asn Gly Phe Asn Pro Asp
    1040                1045                1050

Phe Cys Lys Lys His Pro Val Ser Cys Asp Asn Cys Cys Lys
    1055                1060                1065

Thr Lys Asp Tyr Lys Thr Arg Asp Val Thr Asp Asp Val Lys Ser
```

```
                1070                1075                1080
Ile Val Arg Phe Val Gln Glu His Ser Ser Gln Gly Met Arg
    1085                1090                1095

Asn Ile Lys His Val Gly Pro Ser Gly Arg Phe Thr Met Asn Met
    1100                1105                1110

Leu Val Asp Ile Phe Leu Gly Ser Lys Ser Ala Lys Ile Gln Ser
    1115                1120                1125

Gly Ile Phe Gly Lys Gly Ser Ala Tyr Ser Arg His Asn Ala Glu
    1130                1135                1140

Arg Leu Phe Lys Lys Leu Ile Leu Asp Lys Ile Leu Asp Glu Asp
    1145                1150                1155

Leu Tyr Ile Asn Ala Asn Asp Gln Ala Ile Ala Tyr Val Met Leu
    1160                1165                1170

Gly Asn Lys Ala Gln Thr Val Leu Asn Gly Asn Leu Lys Val Asp
    1175                1180                1185

Phe Met Glu Thr Glu Asn Ser Ser Ser Val Lys Lys Gln Lys Ala
    1190                1195                1200

Leu Val Ala Lys Val Ser Gln Arg Glu Glu Met Val Lys Lys Cys
    1205                1210                1215

Leu Gly Glu Leu Thr Glu Val Cys Lys Ser Leu Gly Lys Val Phe
    1220                1225                1230

Gly Val His Tyr Phe Asn Ile Phe Asn Thr Val Thr Leu Lys Lys
    1235                1240                1245

Leu Ala Glu Ser Leu Ser Ser Asp Pro Glu Val Leu Leu Gln Ile
    1250                1255                1260

Asp Gly Val Thr Glu Asp Lys Leu Glu Lys Tyr Gly Ala Glu Val
    1265                1270                1275

Ile Ser Val Leu Gln Lys Tyr Ser Glu Trp Thr Ser Pro Ala Glu
    1280                1285                1290

Asp Ser Ser Pro Gly Ile Ser Leu Ser Ser Ser Arg Gly Pro Gly
    1295                1300                1305

Arg Ser Ala Ala Glu Glu Leu Asp Glu Glu Ile Pro Val Ser Ser
    1310                1315                1320

His Tyr Phe Ala Ser Lys Thr Arg Asn Glu Arg Lys Arg Lys Lys
    1325                1330                1335

Met Pro Ala Ser Gln Arg Ser Lys Arg Arg Lys Thr Ala Ser Ser
    1340                1345                1350

Gly Ser Lys Ala Lys Gly Gly Ser Ala Thr Cys Arg Lys Ile Ser
    1355                1360                1365

Ser Lys Thr Lys Ser Ser Ser Ile Ile Gly Ser Ser Ser Ala Ser
    1370                1375                1380

His Thr Ser Gln Ala Thr Ser Gly Ala Asn Ser Lys Leu Gly Ile
    1385                1390                1395

Met Ala Pro Pro Lys Pro Ile Asn Arg Pro Phe Leu Lys Pro Ser
    1400                1405                1410

Tyr Ala Phe Ser
    1415

<210> SEQ ID NO 130
<211> LENGTH: 1208
<212> TYPE: PRT
<213> ORGANISM: Homo sapiens

<400> SEQUENCE: 130
```

```
Met Glu Arg Leu Arg Asp Val Arg Glu Arg Leu Gln Ala Trp Glu Arg
1               5                   10                  15

Ala Phe Arg Arg Gln Arg Gly Arg Pro Ser Gln Asp Asp Val Glu
            20                  25                  30

Ala Ala Pro Glu Glu Thr Arg Ala Leu Tyr Arg Glu Tyr Arg Thr Leu
                35                  40                  45

Lys Arg Thr Thr Gly Gln Ala Gly Gly Leu Arg Ser Ser Glu Ser
    50                  55                  60

Leu Pro Ala Ala Ala Glu Ala Pro Glu Arg Cys Trp Gly Pro
65                  70                  75                  80

His Leu Asn Arg Ala Ala Thr Lys Ser Pro Gln Pro Thr Pro Gly Arg
                85                  90                  95

Ser Arg Gln Gly Ser Val Pro Asp Tyr Gly Gln Arg Leu Lys Ala Asn
                100                 105                 110

Leu Lys Gly Thr Leu Gln Ala Gly Pro Ala Leu Gly Arg Arg Pro Trp
            115                 120                 125

Pro Leu Gly Arg Ala Ser Ser Lys Ala Ser Thr Pro Lys Pro Pro Gly
    130                 135                 140

Thr Gly Pro Val Pro Ser Phe Ala Glu Lys Val Ser Asp Glu Pro Pro
145                 150                 155                 160

Gln Leu Pro Glu Pro Gln Pro Arg Pro Gly Arg Leu Gln His Leu Gln
                165                 170                 175

Ala Ser Leu Ser Gln Arg Leu Gly Ser Leu Asp Pro Gly Trp Leu Gln
                180                 185                 190

Arg Cys His Ser Glu Val Pro Asp Phe Leu Gly Ala Pro Lys Ala Cys
            195                 200                 205

Arg Pro Asp Leu Gly Ser Glu Glu Ser Gln Leu Leu Ile Pro Gly Glu
    210                 215                 220

Ser Ala Val Leu Gly Pro Gly Ala Gly Ser Gln Gly Pro Glu Ala Ser
225                 230                 235                 240

Ala Phe Gln Glu Val Ser Ile Arg Val Gly Ser Pro Gln Pro Ser Ser
                245                 250                 255

Ser Gly Gly Glu Lys Arg Arg Trp Asn Glu Glu Pro Trp Glu Ser Pro
            260                 265                 270

Ala Gln Val Gln Gln Glu Ser Ser Gln Ala Gly Pro Pro Ser Glu Gly
    275                 280                 285

Ala Gly Ala Val Ala Val Glu Glu Asp Pro Pro Gly Glu Pro Val Gln
    290                 295                 300

Ala Gln Pro Pro Gln Pro Cys Ser Ser Pro Ser Asn Pro Arg Tyr His
305                 310                 315                 320

Gly Leu Ser Pro Ser Ser Gln Ala Arg Ala Gly Lys Ala Glu Gly Thr
                325                 330                 335

Ala Pro Leu His Ile Phe Pro Arg Leu Ala Arg His Asp Arg Gly Asn
                340                 345                 350

Tyr Val Arg Leu Asn Met Lys Gln Lys His Tyr Val Arg Gly Arg Ala
            355                 360                 365

Leu Arg Ser Arg Leu Leu Arg Lys Gln Ala Trp Lys Gln Lys Trp Arg
    370                 375                 380

Lys Lys Gly Glu Cys Phe Gly Gly Gly Ala Thr Val Thr Thr Lys
385                 390                 395                 400

Glu Ser Cys Phe Leu Asn Glu Gln Phe Asp His Trp Ala Ala Gln Cys
                405                 410                 415

Pro Arg Pro Ala Ser Glu Glu Asp Thr Asp Ala Val Gly Pro Glu Pro
```

-continued

```
            420                 425                 430
Leu Val Pro Ser Pro Gln Pro Val Pro Glu Val Pro Ser Leu Asp Pro
            435                 440                 445

Thr Val Leu Pro Leu Tyr Ser Leu Gly Pro Ser Gly Gln Leu Ala Glu
450                 455                 460

Thr Pro Ala Glu Val Phe Gln Ala Leu Glu Gln Leu Gly His Gln Ala
465                 470                 475                 480

Phe Arg Pro Gly Gln Glu Arg Ala Val Met Arg Ile Leu Ser Gly Ile
                485                 490                 495

Ser Thr Leu Leu Val Leu Pro Thr Gly Ala Gly Lys Ser Leu Cys Tyr
            500                 505                 510

Gln Leu Pro Ala Leu Leu Tyr Ser Arg Arg Ser Pro Cys Leu Thr Leu
            515                 520                 525

Val Val Ser Pro Leu Leu Ser Leu Met Asp Asp Gln Val Ser Gly Leu
            530                 535                 540

Pro Pro Cys Leu Lys Ala Ala Cys Ile His Ser Gly Met Thr Arg Lys
545                 550                 555                 560

Gln Arg Glu Ser Val Leu Gln Lys Ile Arg Ala Ala Gln Val His Val
                565                 570                 575

Leu Met Leu Thr Pro Glu Ala Leu Val Gly Ala Gly Leu Pro Pro
            580                 585                 590

Ala Ala Gln Leu Pro Pro Val Ala Phe Ala Cys Ile Asp Glu Ala His
            595                 600                 605

Cys Leu Ser Gln Trp Ser His Asn Phe Arg Pro Cys Tyr Leu Arg Val
            610                 615                 620

Cys Lys Val Leu Arg Glu Arg Met Gly Val His Cys Phe Leu Gly Leu
625                 630                 635                 640

Thr Ala Thr Ala Thr Arg Arg Thr Ala Ser Asp Val Ala Gln His Leu
                645                 650                 655

Ala Val Ala Glu Glu Pro Asp Leu His Gly Pro Ala Pro Val Pro Thr
            660                 665                 670

Asn Leu His Leu Ser Val Ser Met Asp Arg Asp Thr Asp Gln Ala Leu
            675                 680                 685

Leu Thr Leu Leu Gln Gly Lys Arg Phe Gln Asn Leu Asp Ser Ile Ile
            690                 695                 700

Ile Tyr Cys Asn Arg Arg Glu Asp Thr Glu Arg Ile Ala Ala Leu Leu
705                 710                 715                 720

Arg Thr Cys Leu His Ala Ala Trp Val Pro Gly Ser Gly Gly Arg Ala
                725                 730                 735

Pro Lys Thr Thr Ala Glu Ala Tyr His Ala Gly Met Cys Ser Arg Glu
            740                 745                 750

Arg Arg Arg Val Gln Arg Ala Phe Met Gln Gly Gln Leu Arg Val Val
                755                 760                 765

Val Ala Thr Val Ala Phe Gly Met Gly Leu Asp Arg Pro Asp Val Arg
            770                 775                 780

Ala Val Leu His Leu Gly Leu Pro Pro Ser Phe Glu Ser Tyr Val Gln
785                 790                 795                 800

Ala Val Gly Arg Ala Gly Arg Asp Gly Gln Pro Ala His Cys His Leu
                805                 810                 815

Phe Leu Gln Pro Gln Gly Glu Asp Leu Arg Glu Leu Arg Arg His Val
            820                 825                 830

His Ala Asp Ser Thr Asp Phe Leu Ala Val Lys Arg Leu Val Gln Arg
            835                 840                 845
```

Val Phe Pro Ala Cys Thr Cys Thr Cys Thr Arg Pro Ser Glu Gln
    850                 855                 860

Glu Gly Ala Val Gly Gly Glu Arg Pro Val Pro Lys Tyr Pro Pro Gln
865                 870                 875                 880

Glu Ala Glu Gln Leu Ser His Gln Ala Ala Pro Gly Pro Arg Arg Val
                885                 890                 895

Cys Met Gly His Glu Arg Ala Leu Pro Ile Gln Leu Thr Val Gln Ala
                900                 905                 910

Leu Asp Met Pro Glu Glu Ala Ile Glu Thr Leu Leu Cys Tyr Leu Glu
            915                 920                 925

Leu His Pro His His Trp Leu Glu Leu Leu Ala Thr Thr Tyr Thr His
    930                 935                 940

Cys Arg Leu Asn Cys Pro Gly Pro Ala Gln Leu Gln Ala Leu Ala
945                 950                 955                 960

His Arg Cys Pro Pro Leu Ala Val Cys Leu Ala Gln Gln Leu Pro Glu
                965                 970                 975

Asp Pro Gly Gln Gly Ser Ser Val Glu Phe Asp Met Val Lys Leu
            980                 985                 990

Val Asp Ser Met Gly Trp Glu Leu Ala Ser Val Arg Ala Leu Cys
    995                 1000                1005

Gln Leu Gln Trp Asp His Glu Pro Arg Thr Gly Val Arg Arg Gly
    1010                1015                1020

Thr Gly Val Leu Val Glu Phe Ser Glu Leu Ala Phe His Leu Arg
    1025                1030                1035

Ser Pro Gly Asp Leu Thr Ala Glu Glu Lys Asp Gln Ile Cys Asp
    1040                1045                1050

Phe Leu Tyr Gly Arg Val Gln Ala Arg Glu Arg Gln Ala Leu Ala
    1055                1060                1065

Arg Leu Arg Arg Thr Phe Gln Ala Phe His Ser Val Ala Phe Pro
    1070                1075                1080

Ser Cys Gly Pro Cys Leu Glu Gln Gln Asp Glu Glu Arg Ser Thr
    1085                1090                1095

Arg Leu Lys Asp Leu Leu Gly Arg Tyr Phe Glu Glu Glu Glu Gly
    1100                1105                1110

Gln Glu Pro Gly Gly Met Glu Asp Ala Gln Gly Pro Glu Pro Gly
    1115                1120                1125

Gln Ala Arg Leu Gln Asp Trp Glu Asp Gln Val Arg Cys Asp Ile
    1130                1135                1140

Arg Gln Phe Leu Ser Leu Arg Pro Glu Lys Phe Ser Ser Arg
    1145                1150                1155

Ala Val Ala Arg Ile Phe His Gly Ile Gly Ser Pro Cys Tyr Pro
    1160                1165                1170

Ala Gln Val Tyr Gly Gln Asp Arg Arg Phe Trp Arg Lys Tyr Leu
    1175                1180                1185

His Leu Ser Phe His Ala Leu Val Gly Leu Ala Thr Glu Glu Leu
    1190                1195                1200

Leu Gln Val Ala Arg
    1205

<210> SEQ ID NO 131
<211> LENGTH: 911
<212> TYPE: PRT
<213> ORGANISM: Homo sapiens

<400> SEQUENCE: 131

Met Ala Ala Ser Gln Thr Ser Gln Thr Val Ala Ser His Val Pro Phe
1               5                   10                  15

Ala Asp Leu Cys Ser Thr Leu Glu Arg Ile Gln Lys Ser Lys Gly Arg
            20                  25                  30

Ala Glu Lys Ile Arg His Phe Arg Glu Phe Leu Asp Ser Trp Arg Lys
        35                  40                  45

Phe His Asp Ala Leu His Lys Asn His Lys Asp Val Thr Asp Ser Phe
    50                  55                  60

Tyr Pro Ala Met Arg Leu Ile Leu Pro Gln Leu Glu Arg Glu Arg Met
65                  70                  75                  80

Ala Tyr Gly Ile Lys Glu Thr Met Leu Ala Lys Leu Tyr Ile Glu Leu
                85                  90                  95

Leu Asn Leu Pro Arg Asp Gly Lys Asp Ala Leu Lys Leu Leu Asn Tyr
            100                 105                 110

Arg Thr Pro Thr Gly Thr His Gly Asp Ala Gly Asp Phe Ala Met Ile
        115                 120                 125

Ala Tyr Phe Val Leu Lys Pro Arg Cys Leu Gln Lys Gly Ser Leu Thr
    130                 135                 140

Ile Gln Gln Val Asn Asp Leu Leu Asp Ser Ile Ala Ser Asn Asn Ser
145                 150                 155                 160

Ala Lys Arg Lys Asp Leu Ile Lys Lys Ser Leu Leu Gln Leu Ile Thr
                165                 170                 175

Gln Ser Ser Ala Leu Glu Gln Lys Trp Leu Ile Arg Met Ile Ile Lys
            180                 185                 190

Asp Leu Lys Leu Gly Val Ser Gln Gln Thr Ile Phe Ser Val Phe His
        195                 200                 205

Asn Asp Ala Ala Glu Leu His Asn Val Thr Thr Asp Leu Glu Lys Val
    210                 215                 220

Cys Arg Gln Leu His Asp Pro Ser Val Gly Leu Ser Asp Ile Ser Ile
225                 230                 235                 240

Thr Leu Phe Ser Ala Phe Lys Pro Met Leu Ala Ala Ile Ala Asp Ile
                245                 250                 255

Glu His Ile Glu Lys Asp Met Lys His Gln Ser Phe Tyr Ile Glu Thr
            260                 265                 270

Lys Leu Asp Gly Glu Arg Met Gln Met His Lys Asp Gly Asp Val Tyr
        275                 280                 285

Lys Tyr Phe Ser Arg Asn Gly Tyr Asn Tyr Thr Asp Gln Phe Gly Ala
    290                 295                 300

Ser Pro Thr Glu Gly Ser Leu Thr Pro Phe Ile His Asn Ala Phe Lys
305                 310                 315                 320

Ala Asp Ile Gln Ile Cys Ile Leu Asp Gly Glu Met Met Ala Tyr Asn
                325                 330                 335

Pro Asn Thr Gln Thr Phe Met Gln Lys Gly Thr Lys Phe Asp Ile Lys
            340                 345                 350

Arg Met Val Glu Asp Ser Asp Leu Gln Thr Cys Tyr Cys Val Phe Asp
        355                 360                 365

Val Leu Met Val Asn Asn Lys Lys Leu Gly His Glu Thr Leu Arg Lys
    370                 375                 380

Arg Tyr Glu Ile Leu Ser Ser Ile Phe Thr Pro Ile Pro Gly Arg Ile
385                 390                 395                 400

Glu Ile Val Gln Lys Thr Gln Ala His Thr Lys Asn Glu Val Ile Asp
                405                 410                 415

```
Ala Leu Asn Glu Ala Ile Asp Lys Arg Glu Glu Gly Ile Met Val Lys
            420                 425                 430

Gln Pro Leu Ser Ile Tyr Lys Pro Asp Lys Arg Gly Glu Gly Trp Leu
            435                 440                 445

Lys Ile Lys Pro Glu Tyr Val Ser Gly Leu Met Asp Glu Leu Asp Ile
450                 455                 460

Leu Ile Val Gly Gly Tyr Trp Gly Lys Gly Ser Arg Gly Gly Met Met
465                 470                 475                 480

Ser His Phe Leu Cys Ala Val Ala Glu Lys Pro Pro Gly Glu Lys
                485                 490                 495

Pro Ser Val Phe His Thr Leu Ser Arg Val Gly Ser Gly Cys Thr Met
            500                 505                 510

Lys Glu Leu Tyr Asp Leu Gly Leu Lys Leu Ala Lys Tyr Trp Lys Pro
            515                 520                 525

Phe His Arg Lys Ala Pro Pro Ser Ser Ile Leu Cys Gly Thr Glu Lys
            530                 535                 540

Pro Glu Val Tyr Ile Glu Pro Cys Asn Ser Val Ile Val Gln Ile Lys
545                 550                 555                 560

Ala Ala Glu Ile Val Pro Ser Asp Met Tyr Lys Thr Gly Cys Thr Leu
                565                 570                 575

Arg Phe Pro Arg Ile Glu Lys Ile Arg Asp Asp Lys Glu Trp His Glu
            580                 585                 590

Cys Met Thr Leu Asp Asp Leu Glu Gln Leu Arg Gly Lys Ala Ser Gly
            595                 600                 605

Lys Leu Ala Ser Lys His Leu Tyr Ile Gly Gly Asp Asp Glu Pro Gln
610                 615                 620

Glu Lys Lys Arg Lys Ala Ala Pro Lys Met Lys Lys Val Ile Gly Ile
625                 630                 635                 640

Ile Glu His Leu Lys Ala Pro Asn Leu Thr Asn Val Asn Lys Ile Ser
                645                 650                 655

Asn Ile Phe Glu Asp Val Glu Phe Cys Val Met Ser Gly Thr Asp Ser
            660                 665                 670

Gln Pro Lys Pro Asp Leu Glu Asn Arg Ile Ala Glu Phe Gly Gly Tyr
            675                 680                 685

Ile Val Gln Asn Pro Gly Pro Asp Thr Tyr Cys Val Ile Ala Gly Ser
            690                 695                 700

Glu Asn Ile Arg Val Lys Asn Ile Ile Leu Ser Asn Lys His Asp Val
705                 710                 715                 720

Val Lys Pro Ala Trp Leu Leu Glu Cys Phe Lys Thr Lys Ser Phe Val
                725                 730                 735

Pro Trp Gln Pro Arg Phe Met Ile His Met Cys Pro Ser Thr Lys Glu
            740                 745                 750

His Phe Ala Arg Glu Tyr Asp Cys Tyr Gly Asp Ser Tyr Phe Ile Asp
            755                 760                 765

Thr Asp Leu Asn Gln Leu Lys Glu Val Phe Ser Gly Ile Lys Asn Ser
            770                 775                 780

Asn Glu Gln Thr Pro Glu Glu Met Ala Ser Leu Ile Ala Asp Leu Glu
785                 790                 795                 800

Tyr Arg Tyr Ser Trp Asp Cys Ser Pro Leu Ser Met Phe Arg Arg His
                805                 810                 815

Thr Val Tyr Leu Asp Ser Tyr Ala Val Ile Asn Asp Leu Ser Thr Lys
            820                 825                 830
```

```
Asn Glu Gly Thr Arg Leu Ala Ile Lys Ala Leu Glu Leu Arg Phe His
                835                 840                 845

Gly Ala Lys Val Val Ser Cys Leu Ala Glu Gly Val Ser His Val Ile
850                 855                 860

Ile Gly Glu Asp His Ser Arg Val Ala Asp Phe Lys Ala Phe Arg Arg
865                 870                 875                 880

Thr Phe Lys Arg Lys Phe Lys Ile Leu Lys Glu Ser Trp Val Thr Asp
                885                 890                 895

Ser Ile Asp Lys Cys Glu Leu Gln Glu Glu Asn Gln Tyr Leu Ile
                900                 905                 910

<210> SEQ ID NO 132
<211> LENGTH: 336
<212> TYPE: PRT
<213> ORGANISM: Homo sapiens

<400> SEQUENCE: 132

Met Glu Arg Lys Ile Ser Arg Ile His Leu Val Ser Glu Pro Ser Ile
1               5                   10                  15

Thr His Phe Leu Gln Val Ser Trp Glu Lys Thr Leu Glu Ser Gly Phe
                20                  25                  30

Val Ile Thr Leu Thr Asp Gly His Ser Ala Trp Thr Gly Thr Val Ser
                35                  40                  45

Glu Ser Glu Ile Ser Gln Glu Ala Asp Asp Met Ala Met Glu Lys Gly
50                  55                  60

Lys Tyr Val Gly Glu Leu Arg Lys Ala Leu Leu Ser Gly Ala Gly Pro
65                  70                  75                  80

Ala Asp Val Tyr Thr Phe Asn Phe Ser Lys Glu Ser Cys Tyr Phe Phe
                85                  90                  95

Phe Glu Lys Asn Leu Lys Asp Val Ser Phe Arg Leu Gly Ser Phe Asn
                100                 105                 110

Leu Glu Lys Val Glu Asn Pro Ala Glu Val Ile Arg Glu Leu Ile Cys
                115                 120                 125

Tyr Cys Leu Asp Thr Ile Ala Glu Asn Gln Ala Lys Asn Glu His Leu
130                 135                 140

Gln Lys Glu Asn Glu Arg Leu Leu Arg Asp Trp Asn Asp Val Gln Gly
145                 150                 155                 160

Arg Phe Glu Lys Cys Val Ser Ala Lys Glu Ala Leu Glu Thr Asp Leu
                165                 170                 175

Tyr Lys Arg Phe Ile Leu Val Leu Asn Glu Lys Lys Thr Lys Ile Arg
                180                 185                 190

Ser Leu His Asn Lys Leu Leu Asn Ala Ala Gln Glu Arg Glu Lys Asp
                195                 200                 205

Ile Lys Gln Glu Gly Glu Thr Ala Ile Cys Ser Glu Met Thr Ala Asp
210                 215                 220

Arg Asp Pro Val Tyr Asp Glu Ser Thr Asp Glu Glu Ser Glu Asn Gln
225                 230                 235                 240

Thr Asp Leu Ser Gly Leu Ala Ser Ala Val Ser Lys Asp Asp Ser
                245                 250                 255

Ile Ile Ser Ser Leu Asp Val Thr Asp Ile Ala Pro Ser Arg Lys Arg
                260                 265                 270

Arg Gln Arg Met Gln Arg Asn Leu Gly Thr Glu Pro Lys Met Ala Pro
                275                 280                 285

Gln Glu Asn Gln Leu Gln Glu Lys Glu Asn Ser Arg Pro Asp Ser Ser
                290                 295                 300
```

Leu Pro Glu Thr Ser Lys Lys Glu His Ile Ser Ala Glu Asn Met Ser
305                 310                 315                 320

Leu Glu Thr Leu Arg Asn Ser Ser Pro Glu Asp Leu Phe Asp Glu Ile
            325                 330                 335

<210> SEQ ID NO 133
<211> LENGTH: 4128
<212> TYPE: PRT
<213> ORGANISM: Homo sapiens

<400> SEQUENCE: 133

Met Ala Gly Ser Ala Gly Val Arg Cys Ser Leu Leu Arg Leu Gln
1               5                   10                  15

Glu Thr Leu Ser Ala Ala Asp Arg Cys Gly Ala Ala Leu Ala Gly His
                20                  25                  30

Gln Leu Ile Arg Gly Leu Gly Gln Glu Cys Val Leu Ser Ser Ser Pro
            35                  40                  45

Ala Val Leu Ala Leu Gln Thr Ser Leu Val Phe Ser Arg Asp Phe Gly
        50                  55                  60

Leu Leu Val Phe Val Arg Lys Ser Leu Asn Ser Ile Glu Phe Arg Glu
65                  70                  75                  80

Cys Arg Glu Glu Ile Leu Lys Phe Leu Cys Ile Phe Leu Glu Lys Met
                85                  90                  95

Gly Gln Lys Ile Ala Pro Tyr Ser Val Glu Ile Lys Asn Thr Cys Thr
            100                 105                 110

Ser Val Tyr Thr Lys Asp Arg Ala Ala Lys Cys Lys Ile Pro Ala Leu
        115                 120                 125

Asp Leu Leu Ile Lys Leu Leu Gln Thr Phe Arg Ser Ser Arg Leu Met
    130                 135                 140

Asp Glu Phe Lys Ile Gly Glu Leu Phe Ser Lys Phe Tyr Gly Glu Leu
145                 150                 155                 160

Ala Leu Lys Lys Lys Ile Pro Asp Thr Val Leu Glu Lys Val Tyr Glu
                165                 170                 175

Leu Leu Gly Leu Leu Gly Glu Val His Pro Ser Glu Met Ile Asn Asn
            180                 185                 190

Ala Glu Asn Leu Phe Arg Ala Phe Leu Gly Glu Leu Lys Thr Gln Met
        195                 200                 205

Thr Ser Ala Val Arg Glu Pro Lys Leu Pro Val Leu Ala Gly Cys Leu
    210                 215                 220

Lys Gly Leu Ser Ser Leu Leu Cys Asn Phe Thr Lys Ser Met Glu Glu
225                 230                 235                 240

Asp Pro Gln Thr Ser Arg Glu Ile Phe Asn Phe Val Leu Lys Ala Ile
                245                 250                 255

Arg Pro Gln Ile Asp Leu Lys Arg Tyr Ala Val Pro Ser Ala Gly Leu
            260                 265                 270

Arg Leu Phe Ala Leu His Ala Ser Gln Phe Ser Thr Cys Leu Leu Asp
        275                 280                 285

Asn Tyr Val Ser Leu Phe Glu Val Leu Leu Lys Trp Cys Ala His Thr
    290                 295                 300

Asn Val Glu Leu Lys Lys Ala Ala Leu Ser Ala Leu Glu Ser Phe Leu
305                 310                 315                 320

Lys Gln Val Ser Asn Met Val Ala Lys Asn Ala Glu Met His Lys Asn
                325                 330                 335

Lys Leu Gln Tyr Phe Met Glu Gln Phe Tyr Gly Ile Ile Arg Asn Val

```
            340                 345                 350
Asp Ser Asn Asn Lys Glu Leu Ser Ile Ala Ile Arg Gly Tyr Gly Leu
            355                 360                 365

Phe Ala Gly Pro Cys Lys Val Ile Asn Ala Lys Asp Val Asp Phe Met
            370                 375             380

Tyr Val Glu Leu Ile Gln Arg Cys Lys Gln Met Phe Leu Thr Gln Thr
385                 390                 395                 400

Asp Thr Gly Asp Asp Arg Val Tyr Gln Met Pro Ser Phe Leu Gln Ser
                405                 410                 415

Val Ala Ser Val Leu Leu Tyr Leu Asp Thr Val Pro Glu Val Tyr Thr
            420                 425                 430

Pro Val Leu Glu His Leu Val Val Met Gln Ile Asp Ser Phe Pro Gln
            435                 440                 445

Tyr Ser Pro Lys Met Gln Leu Val Cys Cys Arg Ala Ile Val Lys Val
            450                 455                 460

Phe Leu Ala Leu Ala Ala Lys Gly Pro Val Leu Arg Asn Cys Ile Ser
465                 470                 475                 480

Thr Val Val His Gln Gly Leu Ile Arg Ile Cys Ser Lys Pro Val Val
                485                 490                 495

Leu Pro Lys Gly Pro Glu Ser Glu Ser Glu Asp His Arg Ala Ser Gly
                500                 505                 510

Glu Val Arg Thr Gly Lys Trp Lys Val Pro Thr Tyr Lys Asp Tyr Val
            515                 520                 525

Asp Leu Phe Arg His Leu Leu Ser Ser Asp Gln Met Met Asp Ser Ile
            530                 535                 540

Leu Ala Asp Glu Ala Phe Phe Ser Val Asn Ser Ser Glu Ser Leu
545                 550                 555                 560

Asn His Leu Leu Tyr Asp Glu Phe Val Lys Ser Val Leu Lys Ile Val
                565                 570                 575

Glu Lys Leu Asp Leu Thr Leu Glu Ile Gln Thr Val Gly Glu Gln Glu
                580                 585                 590

Asn Gly Asp Glu Ala Pro Gly Val Trp Met Ile Pro Thr Ser Asp Pro
            595                 600                 605

Ala Ala Asn Leu His Pro Ala Lys Pro Lys Asp Phe Ser Ala Phe Ile
            610                 615                 620

Asn Leu Val Glu Phe Cys Arg Glu Ile Leu Pro Glu Lys Gln Ala Glu
625                 630                 635                 640

Phe Phe Glu Pro Trp Val Tyr Ser Phe Ser Tyr Glu Leu Ile Leu Gln
                645                 650                 655

Ser Thr Arg Leu Pro Leu Ile Ser Gly Phe Tyr Lys Leu Leu Ser Ile
                660                 665                 670

Thr Val Arg Asn Ala Lys Lys Ile Lys Tyr Phe Glu Gly Val Ser Pro
            675                 680                 685

Lys Ser Leu Lys His Ser Pro Glu Asp Pro Lys Tyr Ser Cys Phe
            690                 695                 700

Ala Leu Phe Val Lys Phe Gly Lys Glu Val Ala Val Lys Met Lys Gln
705                 710                 715                 720

Tyr Lys Asp Glu Leu Leu Ala Ser Cys Leu Thr Phe Leu Leu Ser Leu
                725                 730                 735

Pro His Asn Ile Ile Glu Leu Asp Val Arg Ala Tyr Val Pro Ala Leu
                740                 745                 750

Gln Met Ala Phe Lys Leu Gly Leu Ser Tyr Thr Pro Leu Ala Glu Val
            755                 760                 765
```

```
Gly Leu Asn Ala Leu Glu Glu Trp Ser Ile Tyr Ile Asp Arg His Val
    770                 775                 780

Met Gln Pro Tyr Tyr Lys Asp Ile Leu Pro Cys Leu Asp Gly Tyr Leu
785                 790                 795                 800

Lys Thr Ser Ala Leu Ser Asp Glu Thr Lys Asn Asn Trp Glu Val Ser
                805                 810                 815

Ala Leu Ser Arg Ala Ala Gln Lys Gly Phe Asn Lys Val Val Leu Lys
                820                 825                 830

His Leu Lys Lys Thr Lys Asn Leu Ser Ser Asn Glu Ala Ile Ser Leu
                835                 840                 845

Glu Glu Ile Arg Ile Arg Val Val Gln Met Leu Gly Ser Leu Gly Gly
    850                 855                 860

Gln Ile Asn Lys Asn Leu Leu Thr Val Thr Ser Ser Asp Glu Met Met
865                 870                 875                 880

Lys Ser Tyr Val Ala Trp Asp Arg Glu Lys Arg Leu Ser Phe Ala Val
                885                 890                 895

Pro Phe Arg Glu Met Lys Pro Val Ile Phe Leu Asp Val Phe Leu Pro
                900                 905                 910

Arg Val Thr Glu Leu Ala Leu Thr Ala Ser Asp Arg Gln Thr Lys Val
                915                 920                 925

Ala Ala Cys Glu Leu Leu His Ser Met Val Met Phe Met Leu Gly Lys
                930                 935                 940

Ala Thr Gln Met Pro Glu Gly Gly Gln Gly Ala Pro Pro Met Tyr Gln
945                 950                 955                 960

Leu Tyr Lys Arg Thr Phe Pro Val Leu Leu Arg Leu Ala Cys Asp Val
                965                 970                 975

Asp Gln Val Thr Arg Gln Leu Tyr Glu Pro Leu Val Met Gln Leu Ile
                980                 985                 990

His Trp Phe Thr Asn Asn Lys Lys Phe Glu Ser Gln Asp Thr Val Ala
                995                 1000                1005

Leu Leu Glu Ala Ile Leu Asp Gly Ile Val Asp Pro Val Asp Ser
    1010            1015            1020

Thr Leu Arg Asp Phe Cys Gly Arg Cys Ile Arg Glu Phe Leu Lys
    1025            1030            1035

Trp Ser Ile Lys Gln Ile Thr Pro Gln Gln Glu Lys Ser Pro
    1040            1045            1050

Val Asn Thr Lys Ser Leu Phe Lys Arg Leu Tyr Ser Leu Ala Leu
    1055            1060            1065

His Pro Asn Ala Phe Lys Arg Leu Gly Ala Ser Leu Ala Phe Asn
    1070            1075            1080

Asn Ile Tyr Arg Glu Phe Arg Glu Glu Glu Ser Leu Val Glu Gln
    1085            1090            1095

Phe Val Phe Glu Ala Leu Val Ile Tyr Met Glu Ser Leu Ala Leu
    1100            1105            1110

Ala His Ala Asp Glu Lys Ser Leu Gly Thr Ile Gln Gln Cys Cys
    1115            1120            1125

Asp Ala Ile Asp His Leu Cys Arg Ile Ile Glu Lys Lys His Val
    1130            1135            1140

Ser Leu Asn Lys Ala Lys Lys Arg Arg Leu Pro Arg Gly Phe Pro
    1145            1150            1155

Pro Ser Ala Ser Leu Cys Leu Leu Asp Leu Val Lys Trp Leu Leu
    1160            1165            1170
```

-continued

Ala His Cys Gly Arg Pro Gln Thr Glu Cys Arg His Lys Ser Ile
1175                1180                1185

Glu Leu Phe Tyr Lys Phe Val Pro Leu Leu Pro Gly Asn Arg Ser
1190                1195                1200

Pro Asn Leu Trp Leu Lys Asp Val Leu Lys Glu Glu Gly Val Ser
1205                1210                1215

Phe Leu Ile Asn Thr Phe Glu Gly Gly Cys Gly Gln Pro Ser
1220                1225                1230

Gly Ile Leu Ala Gln Pro Thr Leu Leu Tyr Leu Arg Gly Pro Phe
1235                1240                1245

Ser Leu Gln Ala Thr Leu Cys Trp Leu Asp Leu Leu Ala Ala
1250                1255                1260

Leu Glu Cys Tyr Asn Thr Phe Ile Gly Glu Arg Thr Val Gly Ala
1265                1270                1275

Leu Gln Val Leu Gly Thr Glu Ala Gln Ser Ser Leu Leu Lys Ala
1280                1285                1290

Val Ala Phe Phe Leu Glu Ser Ile Ala Met His Asp Ile Ile Ala
1295                1300                1305

Ala Glu Lys Cys Phe Gly Thr Gly Ala Ala Gly Asn Arg Thr Ser
1310                1315                1320

Pro Gln Glu Gly Glu Arg Tyr Asn Tyr Ser Lys Cys Thr Val Val
1325                1330                1335

Val Arg Ile Met Glu Phe Thr Thr Thr Leu Leu Asn Thr Ser Pro
1340                1345                1350

Glu Gly Trp Lys Leu Leu Lys Lys Asp Leu Cys Asn Thr His Leu
1355                1360                1365

Met Arg Val Leu Val Gln Thr Leu Cys Glu Pro Ala Ser Ile Gly
1370                1375                1380

Phe Asn Ile Gly Asp Val Gln Val Met Ala His Leu Pro Asp Val
1385                1390                1395

Cys Val Asn Leu Met Lys Ala Leu Lys Met Ser Pro Tyr Lys Asp
1400                1405                1410

Ile Leu Glu Thr His Leu Arg Glu Lys Ile Thr Ala Gln Ser Ile
1415                1420                1425

Glu Glu Leu Cys Ala Val Asn Leu Tyr Gly Pro Asp Ala Gln Val
1430                1435                1440

Asp Arg Ser Arg Leu Ala Ala Val Val Ser Ala Cys Lys Gln Leu
1445                1450                1455

His Arg Ala Gly Leu Leu His Asn Ile Leu Pro Ser Gln Ser Thr
1460                1465                1470

Asp Leu His His Ser Val Gly Thr Glu Leu Leu Ser Leu Val Tyr
1475                1480                1485

Lys Gly Ile Ala Pro Gly Asp Glu Arg Gln Cys Leu Pro Ser Leu
1490                1495                1500

Asp Leu Ser Cys Lys Gln Leu Ala Ser Gly Leu Leu Glu Leu Ala
1505                1510                1515

Phe Ala Phe Gly Gly Leu Cys Glu Arg Leu Val Ser Leu Leu Leu
1520                1525                1530

Asn Pro Ala Val Leu Ser Thr Ala Ser Leu Gly Ser Ser Gln Gly
1535                1540                1545

Ser Val Ile His Phe Ser His Gly Glu Tyr Phe Tyr Ser Leu Phe
1550                1555                1560

Ser Glu Thr Ile Asn Thr Glu Leu Leu Lys Asn Leu Asp Leu Ala

```
              1565                1570                1575

Val Leu Glu Leu Met Gln Ser  Ser Val Asp Asn Thr  Lys Met Val
        1580                1585                1590

Ser Ala Val Leu Asn Gly Met  Leu Asp Gln Ser Phe  Arg Glu Arg
        1595                1600                1605

Ala Asn Gln Lys His Gln Gly  Leu Lys Leu Ala Thr  Thr Ile Leu
        1610                1615                1620

Gln His Trp Lys Lys Cys Asp  Ser Trp Trp Ala Lys  Asp Ser Pro
        1625                1630                1635

Leu Glu Thr Lys Met Ala Val  Leu Ala Leu Leu Ala  Lys Ile Leu
        1640                1645                1650

Gln Ile Asp Ser Ser Val Ser  Phe Asn Thr Ser His  Gly Ser Phe
        1655                1660                1665

Pro Glu Val Phe Thr Thr Tyr  Ile Ser Leu Leu Ala  Asp Thr Lys
        1670                1675                1680

Leu Asp Leu His Leu Lys Gly  Gln Ala Val Thr Leu  Leu Pro Phe
        1685                1690                1695

Phe Thr Ser Leu Thr Gly Gly  Ser Leu Glu Glu Leu  Arg Arg Val
        1700                1705                1710

Leu Glu Gln Leu Ile Val Ala  His Phe Pro Met Gln  Ser Arg Glu
        1715                1720                1725

Phe Pro Pro Gly Thr Pro Arg  Phe Asn Asn Tyr Val  Asp Cys Met
        1730                1735                1740

Lys Lys Phe Leu Asp Ala Leu  Glu Leu Ser Gln Ser  Pro Met Leu
        1745                1750                1755

Leu Glu Leu Met Thr Glu Val  Leu Cys Arg Glu Gln  Gln His Val
        1760                1765                1770

Met Glu Glu Leu Phe Gln Ser  Ser Phe Arg Arg Ile  Ala Arg Arg
        1775                1780                1785

Gly Ser Cys Val Thr Gln Val  Gly Leu Leu Glu Ser  Val Tyr Glu
        1790                1795                1800

Met Phe Arg Lys Asp Asp Pro  Arg Leu Ser Phe Thr  Arg Gln Ser
        1805                1810                1815

Phe Val Asp Arg Ser Leu Leu  Thr Leu Leu Trp His  Cys Ser Leu
        1820                1825                1830

Asp Ala Leu Arg Glu Phe Phe  Ser Thr Ile Val Val  Asp Ala Ile
        1835                1840                1845

Asp Val Leu Lys Ser Arg Phe  Thr Lys Leu Asn Glu  Ser Thr Phe
        1850                1855                1860

Asp Thr Gln Ile Thr Lys Lys  Met Gly Tyr Tyr Lys  Ile Leu Asp
        1865                1870                1875

Val Met Tyr Ser Arg Leu Pro  Lys Asp Asp Val His  Ala Lys Glu
        1880                1885                1890

Ser Lys Ile Asn Gln Val Phe  His Gly Ser Cys Ile  Thr Glu Gly
        1895                1900                1905

Asn Glu Leu Thr Lys Thr Leu  Ile Lys Leu Cys Tyr  Asp Ala Phe
        1910                1915                1920

Thr Glu Asn Met Ala Gly Glu  Asn Gln Leu Leu Glu  Arg Arg Arg
        1925                1930                1935

Leu Tyr His Cys Ala Ala Tyr  Asn Cys Ala Ile Ser  Val Ile Cys
        1940                1945                1950

Cys Val Phe Asn Glu Leu Lys  Phe Tyr Gln Gly Phe  Leu Phe Ser
        1955                1960                1965
```

-continued

Glu Lys Pro Glu Lys Asn Leu Leu Ile Phe Glu Asn Leu Ile Asp
    1970            1975                1980

Leu Lys Arg Arg Tyr Asn Phe Pro Val Glu Val Glu Val Pro Met
    1985            1990                1995

Glu Arg Lys Lys Lys Tyr Ile Glu Ile Arg Lys Glu Ala Arg Glu
    2000            2005                2010

Ala Ala Asn Gly Asp Ser Asp Gly Pro Ser Tyr Met Ser Ser Leu
    2015            2020                2025

Ser Tyr Leu Ala Asp Ser Thr Leu Ser Glu Glu Met Ser Gln Phe
    2030            2035                2040

Asp Phe Ser Thr Gly Val Gln Ser Tyr Tyr Ser Ser Gln Asp
    2045            2050                2055

Pro Arg Pro Ala Thr Gly Arg Phe Arg Arg Glu Gln Arg Asp
    2060            2065                2070

Pro Thr Val His Asp Asp Val Leu Glu Leu Glu Met Asp Glu Leu
    2075            2080                2085

Asn Arg His Glu Cys Met Ala Pro Leu Thr Ala Leu Val Lys His
    2090            2095                2100

Met His Arg Ser Leu Gly Pro Pro Gln Gly Glu Glu Asp Ser Val
    2105            2110                2115

Pro Arg Asp Leu Pro Ser Trp Met Lys Phe Leu His Gly Lys Leu
    2120            2125                2130

Gly Asn Pro Ile Val Pro Leu Asn Ile Arg Leu Phe Leu Ala Lys
    2135            2140                2145

Leu Val Ile Asn Thr Glu Glu Val Phe Arg Pro Tyr Ala Lys His
    2150            2155                2160

Trp Leu Ser Pro Leu Leu Gln Leu Ala Ala Ser Glu Asn Asn Gly
    2165            2170                2175

Gly Glu Gly Ile His Tyr Met Val Val Glu Ile Val Ala Thr Ile
    2180            2185                2190

Leu Ser Trp Thr Gly Leu Ala Thr Pro Thr Gly Val Pro Lys Asp
    2195            2200                2205

Glu Val Leu Ala Asn Arg Leu Leu Asn Phe Leu Met Lys His Val
    2210            2215                2220

Phe His Pro Lys Arg Ala Val Phe Arg His Asn Leu Glu Ile Ile
    2225            2230                2235

Lys Thr Leu Val Glu Cys Trp Lys Asp Cys Leu Ser Ile Pro Tyr
    2240            2245                2250

Arg Leu Ile Phe Glu Lys Phe Ser Gly Lys Asp Pro Asn Ser Lys
    2255            2260                2265

Asp Asn Ser Val Gly Ile Gln Leu Leu Gly Ile Val Met Ala Asn
    2270            2275                2280

Asp Leu Pro Pro Tyr Asp Pro Gln Cys Gly Ile Gln Ser Ser Glu
    2285            2290                2295

Tyr Phe Gln Ala Leu Val Asn Asn Met Ser Phe Val Arg Tyr Lys
    2300            2305                2310

Glu Val Tyr Ala Ala Ala Glu Val Leu Gly Leu Ile Leu Arg
    2315            2320                2325

Tyr Val Met Glu Arg Lys Asn Ile Leu Glu Glu Ser Leu Cys Glu
    2330            2335                2340

Leu Val Ala Lys Gln Leu Lys Gln His Gln Asn Thr Met Glu Asp
    2345            2350                2355

```
Lys Phe Ile Val Cys Leu Asn Lys Val Thr Lys Ser Phe Pro Pro
    2360                2365                2370

Leu Ala Asp Arg Phe Met Asn Ala Val Phe Phe Leu Leu Pro Lys
    2375                2380                2385

Phe His Gly Val Leu Lys Thr Leu Cys Leu Glu Val Val Leu Cys
    2390                2395                2400

Arg Val Glu Gly Met Thr Glu Leu Tyr Phe Gln Leu Lys Ser Lys
    2405                2410                2415

Asp Phe Val Gln Val Met Arg His Arg Asp Asp Glu Arg Gln Lys
    2420                2425                2430

Val Cys Leu Asp Ile Ile Tyr Lys Met Met Pro Lys Leu Lys Pro
    2435                2440                2445

Val Glu Leu Arg Glu Leu Leu Asn Pro Val Val Glu Phe Val Ser
    2450                2455                2460

His Pro Ser Thr Thr Cys Arg Glu Gln Met Tyr Asn Ile Leu Met
    2465                2470                2475

Trp Ile His Asp Asn Tyr Arg Asp Pro Glu Ser Glu Thr Asp Asn
    2480                2485                2490

Asp Ser Gln Glu Ile Phe Lys Leu Ala Lys Asp Val Leu Ile Gln
    2495                2500                2505

Gly Leu Ile Asp Glu Asn Pro Gly Leu Gln Leu Ile Ile Arg Asn
    2510                2515                2520

Phe Trp Ser His Glu Thr Arg Leu Pro Ser Asn Thr Leu Asp Arg
    2525                2530                2535

Leu Leu Ala Leu Asn Ser Leu Tyr Ser Pro Lys Ile Glu Val His
    2540                2545                2550

Phe Leu Ser Leu Ala Thr Asn Phe Leu Leu Glu Met Thr Ser Met
    2555                2560                2565

Ser Pro Asp Tyr Pro Asn Pro Met Phe Glu His Pro Leu Ser Glu
    2570                2575                2580

Cys Glu Phe Gln Glu Tyr Thr Ile Asp Ser Asp Trp Arg Phe Arg
    2585                2590                2595

Ser Thr Val Leu Thr Pro Met Phe Val Glu Thr Gln Ala Ser Gln
    2600                2605                2610

Gly Thr Leu Gln Thr Arg Thr Gln Glu Gly Ser Leu Ser Ala Arg
    2615                2620                2625

Trp Pro Val Ala Gly Gln Ile Arg Ala Thr Gln Gln Gln His Asp
    2630                2635                2640

Phe Thr Leu Thr Gln Thr Ala Asp Gly Arg Ser Ser Phe Asp Trp
    2645                2650                2655

Leu Thr Gly Ser Ser Thr Asp Pro Leu Val Asp His Thr Ser Pro
    2660                2665                2670

Ser Ser Asp Ser Leu Leu Phe Ala His Lys Arg Ser Glu Arg Leu
    2675                2680                2685

Gln Arg Ala Pro Leu Lys Ser Val Gly Pro Asp Phe Gly Lys Lys
    2690                2695                2700

Arg Leu Gly Leu Pro Gly Asp Glu Val Asp Asn Lys Val Lys Gly
    2705                2710                2715

Ala Ala Gly Arg Thr Asp Leu Leu Arg Leu Arg Arg Arg Phe Met
    2720                2725                2730

Arg Asp Gln Glu Lys Leu Ser Leu Met Tyr Ala Arg Lys Gly Val
    2735                2740                2745

Ala Glu Gln Lys Arg Glu Lys Glu Ile Lys Ser Glu Leu Lys Met
```

```
              2750                2755                2760
Lys  Gln  Asp  Ala  Gln  Val  Val  Leu  Tyr  Arg  Ser  Tyr  Arg  His  Gly
          2765                2770                2775

Asp  Leu  Pro  Asp  Ile  Gln  Ile  Lys  His  Ser  Ser  Leu  Ile  Thr  Pro
          2780                2785                2790

Leu  Gln  Ala  Val  Ala  Gln  Arg  Asp  Pro  Ile  Ile  Ala  Lys  Gln  Leu
          2795                2800                2805

Phe  Ser  Ser  Leu  Phe  Ser  Gly  Ile  Leu  Lys  Glu  Met  Asp  Lys  Phe
          2810                2815                2820

Lys  Thr  Leu  Ser  Glu  Lys  Asn  Asn  Ile  Thr  Gln  Lys  Leu  Leu  Gln
          2825                2830                2835

Asp  Phe  Asn  Arg  Phe  Leu  Asn  Thr  Thr  Phe  Ser  Phe  Phe  Pro  Pro
          2840                2845                2850

Phe  Val  Ser  Cys  Ile  Gln  Asp  Ile  Ser  Cys  Gln  His  Ala  Ala  Leu
          2855                2860                2865

Leu  Ser  Leu  Asp  Pro  Ala  Ala  Val  Ser  Ala  Gly  Cys  Leu  Ala  Ser
          2870                2875                2880

Leu  Gln  Gln  Pro  Val  Gly  Ile  Arg  Leu  Leu  Glu  Glu  Ala  Leu  Leu
          2885                2890                2895

Arg  Leu  Leu  Pro  Ala  Glu  Leu  Pro  Ala  Lys  Arg  Val  Arg  Gly  Lys
          2900                2905                2910

Ala  Arg  Leu  Pro  Pro  Asp  Val  Leu  Arg  Trp  Val  Glu  Leu  Ala  Lys
          2915                2920                2925

Leu  Tyr  Arg  Ser  Ile  Gly  Glu  Tyr  Asp  Val  Leu  Arg  Gly  Ile  Phe
          2930                2935                2940

Thr  Ser  Glu  Ile  Gly  Thr  Lys  Gln  Ile  Thr  Gln  Ser  Ala  Leu  Leu
          2945                2950                2955

Ala  Glu  Ala  Arg  Ser  Asp  Tyr  Ser  Glu  Ala  Ala  Lys  Gln  Tyr  Asp
          2960                2965                2970

Glu  Ala  Leu  Asn  Lys  Gln  Asp  Trp  Val  Asp  Gly  Glu  Pro  Thr  Glu
          2975                2980                2985

Ala  Glu  Lys  Asp  Phe  Trp  Glu  Leu  Ala  Ser  Leu  Asp  Cys  Tyr  Asn
          2990                2995                3000

His  Leu  Ala  Glu  Trp  Lys  Ser  Leu  Glu  Tyr  Cys  Ser  Thr  Ala  Ser
          3005                3010                3015

Ile  Asp  Ser  Glu  Asn  Pro  Pro  Asp  Leu  Asn  Lys  Ile  Trp  Ser  Glu
          3020                3025                3030

Pro  Phe  Tyr  Gln  Glu  Thr  Tyr  Leu  Pro  Tyr  Met  Ile  Arg  Ser  Lys
          3035                3040                3045

Leu  Lys  Leu  Leu  Leu  Gln  Gly  Glu  Ala  Asp  Gln  Ser  Leu  Leu  Thr
          3050                3055                3060

Phe  Ile  Asp  Lys  Ala  Met  His  Gly  Glu  Leu  Gln  Lys  Ala  Ile  Leu
          3065                3070                3075

Glu  Leu  His  Tyr  Ser  Gln  Glu  Leu  Ser  Leu  Leu  Tyr  Leu  Leu  Gln
          3080                3085                3090

Asp  Asp  Val  Asp  Arg  Ala  Lys  Tyr  Tyr  Ile  Gln  Asn  Gly  Ile  Gln
          3095                3100                3105

Ser  Phe  Met  Gln  Asn  Tyr  Ser  Ser  Ile  Asp  Val  Leu  Leu  His  Gln
          3110                3115                3120

Ser  Arg  Leu  Thr  Lys  Leu  Gln  Ser  Val  Gln  Ala  Leu  Thr  Glu  Ile
          3125                3130                3135

Gln  Glu  Phe  Ile  Ser  Phe  Ile  Ser  Lys  Gln  Gly  Asn  Leu  Ser  Ser
          3140                3145                3150
```

-continued

```
Gln Val Pro Leu Lys Arg Leu Leu Asn Thr Trp Thr Asn Arg Tyr
3155                3160                3165

Pro Asp Ala Lys Met Asp Pro Met Asn Ile Trp Asp Asp Ile Ile
3170                3175                3180

Thr Asn Arg Cys Phe Phe Leu Ser Lys Ile Glu Glu Lys Leu Thr
3185                3190                3195

Pro Leu Pro Glu Asp Asn Ser Met Asn Val Asp Gln Asp Gly Asp
3200                3205                3210

Pro Ser Asp Arg Met Glu Val Gln Glu Gln Glu Glu Asp Ile Ser
3215                3220                3225

Ser Leu Ile Arg Ser Cys Lys Phe Ser Met Lys Met Lys Met Ile
3230                3235                3240

Asp Ser Ala Arg Lys Gln Asn Asn Phe Ser Leu Ala Met Lys Leu
3245                3250                3255

Leu Lys Glu Leu His Lys Glu Ser Lys Thr Arg Asp Asp Trp Leu
3260                3265                3270

Val Ser Trp Val Gln Ser Tyr Cys Arg Leu Ser His Cys Arg Ser
3275                3280                3285

Arg Ser Gln Gly Cys Ser Glu Gln Val Leu Thr Val Leu Lys Thr
3290                3295                3300

Val Ser Leu Leu Asp Glu Asn Asn Val Ser Ser Tyr Leu Ser Lys
3305                3310                3315

Asn Ile Leu Ala Phe Arg Asp Gln Asn Ile Leu Leu Gly Thr Thr
3320                3325                3330

Tyr Arg Ile Ile Ala Asn Ala Leu Ser Ser Glu Pro Ala Cys Leu
3335                3340                3345

Ala Glu Ile Glu Glu Asp Lys Ala Arg Arg Ile Leu Glu Leu Ser
3350                3355                3360

Gly Ser Ser Ser Glu Asp Ser Glu Lys Val Ile Ala Gly Leu Tyr
3365                3370                3375

Gln Arg Ala Phe Gln His Leu Ser Glu Ala Val Gln Ala Ala Glu
3380                3385                3390

Glu Glu Ala Gln Pro Pro Ser Trp Ser Cys Gly Pro Ala Ala Gly
3395                3400                3405

Val Ile Asp Ala Tyr Met Thr Leu Ala Asp Phe Cys Asp Gln Gln
3410                3415                3420

Leu Arg Lys Glu Glu Glu Asn Ala Ser Val Ile Asp Ser Ala Glu
3425                3430                3435

Leu Gln Ala Tyr Pro Ala Leu Val Val Glu Lys Met Leu Lys Ala
3440                3445                3450

Leu Lys Leu Asn Ser Asn Glu Ala Arg Leu Lys Phe Pro Arg Leu
3455                3460                3465

Leu Gln Ile Ile Glu Arg Tyr Pro Glu Glu Thr Leu Ser Leu Met
3470                3475                3480

Thr Lys Glu Ile Ser Ser Val Pro Cys Trp Gln Phe Ile Ser Trp
3485                3490                3495

Ile Ser His Met Val Ala Leu Leu Asp Lys Asp Gln Ala Val Ala
3500                3505                3510

Val Gln His Ser Val Glu Glu Ile Thr Asp Asn Tyr Pro Gln Ala
3515                3520                3525

Ile Val Tyr Pro Phe Ile Ile Ser Ser Glu Ser Tyr Ser Phe Lys
3530                3535                3540
```

-continued

| | | | | | | | | | | | |
|---|---|---|---|---|---|---|---|---|---|---|---|
|Asp|Thr|Ser|Thr|Gly|His|Lys|Asn|Lys|Glu|Phe|Val|Ala|Arg|Ile|
|3545| | | | |3550| | | | |3555| | | | |

Lys Ser Lys Leu Asp Gln Gly Gly Val Ile Gln Asp Phe Ile Asn
3560                    3565                    3570

Ala Leu Asp Gln Leu Ser Asn Pro Glu Leu Leu Phe Lys Asp Trp
3575                    3580                    3585

Ser Asn Asp Val Arg Ala Glu Leu Ala Lys Thr Pro Val Asn Lys
3590                    3595                    3600

Lys Asn Ile Glu Lys Met Tyr Glu Arg Met Tyr Ala Ala Leu Gly
3605                    3610                    3615

Asp Pro Lys Ala Pro Gly Leu Gly Ala Phe Arg Arg Lys Phe Ile
3620                    3625                    3630

Gln Thr Phe Gly Lys Glu Phe Asp Lys His Phe Gly Lys Gly Gly
3635                    3640                    3645

Ser Lys Leu Leu Arg Met Lys Leu Ser Asp Phe Asn Asp Ile Thr
3650                    3655                    3660

Asn Met Leu Leu Leu Lys Met Asn Lys Asp Ser Lys Pro Pro Gly
3665                    3670                    3675

Asn Leu Lys Glu Cys Ser Pro Trp Met Ser Asp Phe Lys Val Glu
3680                    3685                    3690

Phe Leu Arg Asn Glu Leu Glu Ile Pro Gly Gln Tyr Asp Gly Arg
3695                    3700                    3705

Gly Lys Pro Leu Pro Glu Tyr His Val Arg Ile Ala Gly Phe Asp
3710                    3715                    3720

Glu Arg Val Thr Val Met Ala Ser Leu Arg Arg Pro Lys Arg Ile
3725                    3730                    3735

Ile Ile Arg Gly His Asp Glu Arg Glu His Pro Phe Leu Val Lys
3740                    3745                    3750

Gly Gly Glu Asp Leu Arg Gln Asp Gln Arg Val Glu Gln Leu Phe
3755                    3760                    3765

Gln Val Met Asn Gly Ile Leu Ala Gln Asp Ser Ala Cys Ser Gln
3770                    3775                    3780

Arg Ala Leu Gln Leu Arg Thr Tyr Ser Val Val Pro Met Thr Ser
3785                    3790                    3795

Arg Leu Gly Leu Ile Glu Trp Leu Glu Asn Thr Val Thr Leu Lys
3800                    3805                    3810

Asp Leu Leu Leu Asn Thr Met Ser Gln Glu Glu Lys Ala Ala Tyr
3815                    3820                    3825

Leu Ser Asp Pro Arg Ala Pro Pro Cys Glu Tyr Lys Asp Trp Leu
3830                    3835                    3840

Thr Lys Met Ser Gly Lys His Asp Val Gly Ala Tyr Met Leu Met
3845                    3850                    3855

Tyr Lys Gly Ala Asn Arg Thr Glu Thr Val Thr Ser Phe Arg Lys
3860                    3865                    3870

Arg Glu Ser Lys Val Pro Ala Asp Leu Leu Lys Arg Ala Phe Val
3875                    3880                    3885

Arg Met Ser Thr Ser Pro Glu Ala Phe Leu Ala Leu Arg Ser His
3890                    3895                    3900

Phe Ala Ser Ser His Ala Leu Ile Cys Ile Ser His Trp Ile Leu
3905                    3910                    3915

Gly Ile Gly Asp Arg His Leu Asn Asn Phe Met Val Ala Met Glu
3920                    3925                    3930

Thr Gly Gly Val Ile Gly Ile Asp Phe Gly His Ala Phe Gly Ser

```
                 3935                3940                3945

Ala Thr Gln Phe Leu Pro Val Pro Glu Leu Met Pro Phe Arg Leu
    3950                3955                3960

Thr Arg Gln Phe Ile Asn Leu Met Leu Pro Met Lys Glu Thr Gly
    3965                3970                3975

Leu Met Tyr Ser Ile Met Val His Ala Leu Arg Ala Phe Arg Ser
    3980                3985                3990

Asp Pro Gly Leu Leu Thr Asn Thr Met Asp Val Phe Val Lys Glu
    3995                4000                4005

Pro Ser Phe Asp Trp Lys Asn Phe Glu Gln Lys Met Leu Lys Lys
    4010                4015                4020

Gly Gly Ser Trp Ile Gln Glu Ile Asn Val Ala Glu Lys Asn Trp
    4025                4030                4035

Tyr Pro Arg Gln Lys Ile Cys Tyr Ala Lys Arg Lys Leu Ala Gly
    4040                4045                4050

Ala Asn Pro Ala Val Ile Thr Cys Asp Glu Leu Leu Leu Gly His
    4055                4060                4065

Glu Lys Ala Pro Ala Phe Arg Asp Tyr Val Ala Val Ala Arg Gly
    4070                4075                4080

Ser Lys Asp His Asn Ile Arg Ala Gln Glu Pro Glu Ser Gly Leu
    4085                4090                4095

Ser Glu Glu Thr Gln Val Lys Cys Leu Met Asp Gln Ala Thr Asp
    4100                4105                4110

Pro Asn Ile Leu Gly Arg Thr Trp Glu Gly Trp Glu Pro Trp Met
    4115                4120                4125

<210> SEQ ID NO 134
<211> LENGTH: 692
<212> TYPE: PRT
<213> ORGANISM: Homo sapiens

<400> SEQUENCE: 134

Met Ser Ser Phe Glu Gly Gln Met Ala Glu Tyr Pro Thr Ile Ser Ile
1               5                  10                  15

Asp Arg Phe Asp Arg Glu Asn Leu Arg Ala Arg Ala Tyr Phe Leu Ser
            20                  25                  30

His Cys His Lys Asp His Met Lys Gly Leu Arg Ala Pro Thr Leu Lys
        35                  40                  45

Arg Arg Leu Glu Cys Ser Leu Lys Val Tyr Leu Tyr Cys Ser Pro Val
    50                  55                  60

Thr Lys Glu Leu Leu Leu Thr Ser Pro Lys Tyr Arg Phe Trp Lys Lys
65                  70                  75                  80

Arg Ile Ile Ser Ile Glu Ile Glu Thr Pro Thr Gln Ile Ser Leu Val
                85                  90                  95

Asp Glu Ala Ser Gly Glu Lys Glu Glu Ile Val Val Thr Leu Leu Pro
            100                 105                 110

Ala Gly His Cys Pro Gly Ser Val Met Phe Leu Phe Gln Gly Asn Asn
        115                 120                 125

Gly Thr Val Leu Tyr Thr Gly Asp Phe Arg Leu Ala Gln Gly Glu Ala
    130                 135                 140

Ala Arg Met Glu Leu Leu His Ser Gly Gly Arg Val Lys Asp Ile Gln
145                 150                 155                 160

Ser Val Tyr Leu Asp Thr Thr Phe Cys Asp Pro Arg Phe Tyr Gln Ile
                165                 170                 175
```

```
Pro Ser Arg Glu Glu Cys Leu Ser Gly Val Leu Glu Leu Val Arg Ser
            180                 185                 190

Trp Ile Thr Arg Ser Pro Tyr His Val Val Trp Leu Asn Cys Lys Ala
        195                 200                 205

Ala Tyr Gly Tyr Glu Tyr Leu Phe Thr Asn Leu Ser Glu Glu Leu Gly
    210                 215                 220

Val Gln Val His Val Asn Lys Leu Asp Met Phe Arg Asn Met Pro Glu
225                 230                 235                 240

Ile Leu His His Leu Thr Thr Asp Arg Asn Thr Gln Ile His Ala Cys
                245                 250                 255

Arg His Pro Lys Ala Glu Glu Tyr Phe Gln Trp Ser Lys Leu Pro Cys
            260                 265                 270

Gly Ile Thr Ser Arg Asn Arg Ile Pro Leu His Ile Ile Ser Ile Lys
        275                 280                 285

Pro Ser Thr Met Trp Phe Gly Glu Arg Ser Arg Lys Thr Asn Val Ile
    290                 295                 300

Val Arg Thr Gly Glu Ser Ser Tyr Arg Ala Cys Phe Ser Phe His Ser
305                 310                 315                 320

Ser Tyr Ser Glu Ile Lys Asp Phe Leu Ser Tyr Leu Cys Pro Val Asn
                325                 330                 335

Ala Tyr Pro Asn Val Ile Pro Val Gly Thr Thr Met Asp Lys Val Val
            340                 345                 350

Glu Ile Leu Lys Pro Leu Cys Arg Ser Ser Gln Ser Thr Glu Pro Lys
        355                 360                 365

Tyr Lys Pro Leu Gly Lys Leu Lys Arg Ala Arg Thr Val His Arg Asp
    370                 375                 380

Ser Glu Glu Asp Asp Tyr Leu Phe Asp Asp Pro Leu Pro Ile Pro
385                 390                 395                 400

Leu Arg His Lys Val Pro Tyr Pro Glu Thr Phe His Pro Glu Val Phe
                405                 410                 415

Ser Met Thr Ala Val Ser Glu Lys Gln Pro Glu Lys Leu Arg Gln Thr
            420                 425                 430

Pro Gly Cys Cys Arg Ala Glu Cys Met Gln Ser Ser Arg Phe Thr Asn
        435                 440                 445

Phe Val Asp Cys Glu Glu Ser Asn Ser Glu Ser Glu Glu Val Gly
    450                 455                 460

Ile Pro Ala Ser Leu Gln Gly Asp Leu Gly Ser Val Leu His Leu Gln
465                 470                 475                 480

Lys Ala Asp Gly Asp Val Pro Gln Trp Glu Val Phe Phe Lys Arg Asn
                485                 490                 495

Asp Glu Ile Thr Asp Glu Ser Leu Glu Asn Phe Pro Ser Ser Thr Val
            500                 505                 510

Ala Gly Gly Ser Gln Ser Pro Lys Leu Phe Ser Asp Ser Asp Gly Glu
        515                 520                 525

Ser Thr His Ile Ser Ser Gln Asn Ser Ser Gln Ser Thr His Ile Thr
    530                 535                 540

Glu Gln Gly Ser Gln Gly Trp Asp Ser Gln Ser Asp Thr Val Leu Leu
545                 550                 555                 560

Ser Ser Gln Glu Arg Asn Ser Gly Asp Ile Thr Ser Leu Asp Lys Ala
                565                 570                 575

Asp Tyr Arg Pro Thr Ile Lys Glu Asn Ile Pro Ala Ser Leu Met Glu
            580                 585                 590

Gln Asn Val Ile Cys Pro Lys Asp Thr Tyr Ser Asp Leu Lys Ser Arg
```

-continued

```
                595                 600                 605
Asp Lys Asp Val Thr Ile Val Pro Ser Thr Gly Glu Pro Thr Thr Leu
    610                 615                 620

Ser Ser Glu Thr His Ile Pro Glu Glu Lys Ser Leu Leu Asn Leu Ser
625                 630                 635                 640

Thr Asn Ala Asp Ser Gln Ser Ser Asp Phe Glu Val Pro Ser Thr
                645                 650                 655

Pro Glu Ala Glu Leu Pro Lys Arg Glu His Leu Gln Tyr Leu Tyr Glu
                660                 665                 670

Lys Leu Ala Thr Gly Glu Ser Ile Ala Val Lys Lys Arg Lys Cys Ser
                675                 680                 685

Leu Leu Asp Thr
        690

<210> SEQ ID NO 135
<211> LENGTH: 609
<212> TYPE: PRT
<213> ORGANISM: Homo sapiens

<400> SEQUENCE: 135

Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
                20                  25                  30

Ser Gly Arg Asp Ser Leu Ile Phe Leu Val Asp Ala Ser Lys Ala Met
            35                  40                  45

Phe Glu Ser Gln Ser Glu Asp Glu Leu Thr Pro Phe Asp Met Ser Ile
    50                  55                  60

Gln Cys Ile Gln Ser Val Tyr Ile Ser Lys Ile Ile Ser Ser Asp Arg
65                  70                  75                  80

Asp Leu Leu Ala Val Val Phe Tyr Gly Thr Glu Lys Asp Lys Asn Ser
                85                  90                  95

Val Asn Phe Lys Asn Ile Tyr Val Leu Gln Glu Leu Asp Asn Pro Gly
                100                 105                 110

Ala Lys Arg Ile Leu Glu Leu Asp Gln Phe Lys Gly Gln Gln Gly Gln
            115                 120                 125

Lys Arg Phe Gln Asp Met Met Gly His Gly Ser Asp Tyr Ser Leu Ser
130                 135                 140

Glu Val Leu Trp Val Cys Ala Asn Leu Phe Ser Asp Val Gln Phe Lys
145                 150                 155                 160

Met Ser His Lys Arg Ile Met Leu Phe Thr Asn Glu Asp Asn Pro His
                165                 170                 175

Gly Asn Asp Ser Ala Lys Ala Ser Arg Ala Arg Thr Lys Ala Gly Asp
                180                 185                 190

Leu Arg Asp Thr Gly Ile Phe Leu Asp Leu Met His Leu Lys Lys Pro
            195                 200                 205

Gly Gly Phe Asp Ile Ser Leu Phe Tyr Arg Asp Ile Ile Ser Ile Ala
    210                 215                 220

Glu Asp Glu Asp Leu Arg Val His Phe Glu Glu Ser Ser Lys Leu Glu
225                 230                 235                 240

Asp Leu Leu Arg Lys Val Arg Ala Lys Glu Thr Arg Lys Arg Ala Leu
                245                 250                 255

Ser Arg Leu Lys Leu Lys Leu Asn Lys Asp Ile Val Ile Ser Val Gly
                260                 265                 270
```

```
Ile Tyr Asn Leu Val Gln Lys Ala Leu Lys Pro Pro Ile Lys Leu
        275                 280                 285

Tyr Arg Glu Thr Asn Glu Pro Val Lys Thr Lys Thr Arg Thr Phe Asn
290                 295                 300

Thr Ser Thr Gly Gly Leu Leu Leu Pro Ser Asp Thr Lys Arg Ser Gln
305                 310                 315                 320

Ile Tyr Gly Ser Arg Gln Ile Ile Leu Glu Lys Glu Thr Glu Glu
        325                 330                 335

Leu Lys Arg Phe Asp Asp Pro Gly Leu Met Leu Met Gly Phe Lys Pro
        340                 345                 350

Leu Val Leu Leu Lys Lys His His Tyr Leu Arg Pro Ser Leu Phe Val
        355                 360                 365

Tyr Pro Glu Glu Ser Leu Val Ile Gly Ser Ser Thr Leu Phe Ser Ala
370                 375                 380

Leu Leu Ile Lys Cys Leu Glu Lys Glu Val Ala Ala Leu Cys Arg Tyr
385                 390                 395                 400

Thr Pro Arg Arg Asn Ile Pro Pro Tyr Phe Val Ala Leu Val Pro Gln
                405                 410                 415

Glu Glu Glu Leu Asp Asp Gln Lys Ile Gln Val Thr Pro Pro Gly Phe
        420                 425                 430

Gln Leu Val Phe Leu Pro Phe Ala Asp Asp Lys Arg Lys Met Pro Phe
        435                 440                 445

Thr Glu Lys Ile Met Ala Thr Pro Glu Gln Val Gly Lys Met Lys Ala
        450                 455                 460

Ile Val Glu Lys Leu Arg Phe Thr Tyr Arg Ser Asp Ser Phe Glu Asn
465                 470                 475                 480

Pro Val Leu Gln Gln His Phe Arg Asn Leu Glu Ala Leu Ala Leu Asp
                485                 490                 495

Leu Met Glu Pro Glu Gln Ala Val Asp Leu Thr Leu Pro Lys Val Glu
        500                 505                 510

Ala Met Asn Lys Arg Leu Gly Ser Leu Val Asp Glu Phe Lys Glu Leu
        515                 520                 525

Val Tyr Pro Pro Asp Tyr Asn Pro Glu Gly Lys Val Thr Lys Arg Lys
530                 535                 540

His Asp Asn Glu Gly Ser Gly Ser Lys Arg Pro Lys Val Glu Tyr Ser
545                 550                 555                 560

Glu Glu Glu Leu Lys Thr His Ile Ser Lys Gly Thr Leu Gly Lys Phe
                565                 570                 575

Thr Val Pro Met Leu Lys Glu Ala Cys Arg Ala Tyr Gly Leu Lys Ser
        580                 585                 590

Gly Leu Lys Lys Gln Glu Leu Leu Glu Ala Leu Thr Lys His Phe Gln
        595                 600                 605

Asp

<210> SEQ ID NO 136
<211> LENGTH: 732
<212> TYPE: PRT
<213> ORGANISM: Homo sapiens

<400> SEQUENCE: 136

Met Val Arg Ser Gly Asn Lys Ala Ala Val Val Leu Cys Met Asp Val
1               5                   10                  15

Gly Phe Thr Met Ser Asn Ser Ile Pro Gly Ile Glu Ser Pro Phe Glu
                20                  25                  30
```

```
Gln Ala Lys Lys Val Ile Thr Met Phe Val Gln Arg Gln Val Phe Ala
             35                  40                  45
Glu Asn Lys Asp Glu Ile Ala Leu Val Leu Phe Gly Thr Asp Gly Thr
 50                  55                  60
Asp Asn Pro Leu Ser Gly Gly Asp Gln Tyr Gln Asn Ile Thr Val His
 65                  70                  75                  80
Arg His Leu Met Leu Pro Asp Phe Asp Leu Leu Glu Asp Ile Glu Ser
                 85                  90                  95
Lys Ile Gln Pro Gly Ser Gln Gln Ala Asp Phe Leu Asp Ala Leu Ile
                100                 105                 110
Val Ser Met Asp Val Ile Gln His Glu Thr Ile Gly Lys Lys Phe Glu
             115                 120                 125
Lys Arg His Ile Glu Ile Phe Thr Asp Leu Ser Ser Arg Phe Ser Lys
 130                 135                 140
Ser Gln Leu Asp Ile Ile Ile His Ser Leu Lys Lys Cys Asp Ile Ser
145                 150                 155                 160
Leu Gln Phe Phe Leu Pro Phe Ser Leu Gly Lys Glu Asp Gly Ser Gly
                165                 170                 175
Asp Arg Gly Asp Gly Pro Phe Arg Leu Gly Gly His Gly Pro Ser Phe
             180                 185                 190
Pro Leu Lys Gly Ile Thr Glu Gln Gln Lys Glu Gly Leu Glu Ile Val
                195                 200                 205
Lys Met Val Met Ile Ser Leu Glu Gly Glu Asp Gly Leu Asp Glu Ile
             210                 215                 220
Tyr Ser Phe Ser Glu Ser Leu Arg Lys Leu Cys Val Phe Lys Lys Ile
225                 230                 235                 240
Glu Arg His Ser Ile His Trp Pro Cys Arg Leu Thr Ile Gly Ser Asn
                245                 250                 255
Leu Ser Ile Arg Ile Ala Ala Tyr Lys Ser Ile Leu Gln Glu Arg Val
             260                 265                 270
Lys Lys Thr Trp Thr Val Val Asp Ala Lys Thr Leu Lys Lys Glu Asp
                275                 280                 285
Ile Gln Lys Glu Thr Val Tyr Cys Leu Asn Asp Asp Asp Glu Thr Glu
 290                 295                 300
Val Leu Lys Glu Asp Ile Ile Gln Gly Phe Arg Tyr Gly Ser Asp Ile
305                 310                 315                 320
Val Pro Phe Ser Lys Val Asp Glu Glu Gln Met Lys Tyr Lys Ser Glu
                325                 330                 335
Gly Lys Cys Phe Ser Val Leu Gly Phe Cys Lys Ser Ser Gln Val Gln
             340                 345                 350
Arg Arg Phe Phe Met Gly Asn Gln Val Leu Lys Val Phe Ala Ala Arg
             355                 360                 365
Asp Asp Glu Ala Ala Val Ala Leu Ser Ser Leu Ile His Ala Leu
 370                 375                 380
Asp Asp Leu Asp Met Val Ala Ile Val Arg Tyr Ala Tyr Asp Lys Arg
385                 390                 395                 400
Ala Asn Pro Gln Val Gly Val Ala Phe Pro His Ile Lys His Asn Tyr
                405                 410                 415
Glu Cys Leu Val Tyr Val Gln Leu Pro Phe Met Glu Asp Leu Arg Gln
             420                 425                 430
Tyr Met Phe Ser Ser Leu Lys Asn Ser Lys Lys Tyr Ala Pro Thr Glu
             435                 440                 445
Ala Gln Leu Asn Ala Val Asp Ala Leu Ile Asp Ser Met Ser Leu Ala
```

```
                450                 455                 460
Lys Lys Asp Glu Lys Thr Asp Thr Leu Glu Asp Leu Phe Pro Thr Thr
465                 470                 475                 480

Lys Ile Pro Asn Pro Arg Phe Gln Arg Leu Phe Gln Cys Leu Leu His
                485                 490                 495

Arg Ala Leu His Pro Arg Glu Pro Leu Pro Pro Ile Gln Gln His Ile
                500                 505                 510

Trp Asn Met Leu Asn Pro Pro Ala Glu Val Thr Thr Lys Ser Gln Ile
                515                 520                 525

Pro Leu Ser Lys Ile Lys Thr Leu Phe Pro Leu Ile Glu Ala Lys Lys
                530                 535                 540

Lys Asp Gln Val Thr Ala Gln Glu Ile Phe Gln Asp Asn His Glu Asp
545                 550                 555                 560

Gly Pro Thr Ala Lys Lys Leu Lys Thr Glu Gln Gly Gly Ala His Phe
                565                 570                 575

Ser Val Ser Ser Leu Ala Glu Gly Ser Val Thr Ser Val Gly Ser Val
                580                 585                 590

Asn Pro Ala Glu Asn Phe Arg Val Leu Val Lys Gln Lys Lys Ala Ser
                595                 600                 605

Phe Glu Glu Ala Ser Asn Gln Leu Ile Asn His Ile Glu Gln Phe Leu
                610                 615                 620

Asp Thr Asn Glu Thr Pro Tyr Phe Met Lys Ser Ile Asp Cys Ile Arg
625                 630                 635                 640

Ala Phe Arg Glu Glu Ala Ile Lys Phe Ser Glu Glu Gln Arg Phe Asn
                645                 650                 655

Asn Phe Leu Lys Ala Leu Gln Glu Lys Val Glu Ile Lys Gln Leu Asn
                660                 665                 670

His Phe Trp Glu Ile Val Val Gln Asp Gly Ile Thr Leu Ile Thr Lys
                675                 680                 685

Glu Glu Ala Ser Gly Ser Ser Val Thr Ala Glu Ala Lys Lys Phe
                690                 695                 700

Leu Ala Pro Lys Asp Lys Pro Ser Gly Asp Thr Ala Ala Val Phe Glu
705                 710                 715                 720

Glu Gly Gly Asp Val Asp Asp Leu Leu Asp Met Ile
                725                 730

<210> SEQ ID NO 137
<211> LENGTH: 299
<212> TYPE: PRT
<213> ORGANISM: Homo sapiens

<400> SEQUENCE: 137

Met Glu Glu Leu Glu Gln Gly Leu Leu Met Gln Pro Trp Ala Trp Leu
1               5                   10                  15

Gln Leu Ala Glu Asn Ser Leu Leu Ala Lys Val Phe Ile Thr Lys Gln
                20                  25                  30

Gly Tyr Ala Leu Leu Val Ser Asp Leu Gln Gln Val Trp His Glu Gln
                35                  40                  45

Val Asp Thr Ser Val Val Ser Gln Arg Ala Lys Glu Leu Asn Lys Arg
                50                  55                  60

Leu Thr Ala Pro Pro Ala Ala Phe Leu Cys His Leu Asp Asn Leu Leu
65                  70                  75                  80

Arg Pro Leu Leu Lys Asp Ala Ala His Pro Ser Glu Ala Thr Phe Ser
                85                  90                  95
```

```
Cys Asp Cys Val Ala Asp Ala Leu Ile Leu Arg Val Arg Ser Glu Leu
                100                 105                 110

Ser Gly Leu Pro Phe Tyr Trp Asn Phe His Cys Met Leu Ala Ser Pro
            115                 120                 125

Ser Leu Val Ser Gln His Leu Ile Arg Pro Leu Met Gly Met Ser Leu
        130                 135                 140

Ala Leu Gln Cys Gln Val Arg Glu Leu Ala Thr Leu Leu His Met Lys
145                 150                 155                 160

Asp Leu Glu Ile Gln Asp Tyr Gln Glu Ser Gly Ala Thr Leu Ile Arg
                165                 170                 175

Asp Arg Leu Lys Thr Glu Pro Phe Glu Asn Ser Phe Leu Glu Gln
            180                 185                 190

Phe Met Ile Glu Lys Leu Pro Glu Ala Cys Ser Ile Gly Asp Gly Lys
            195                 200                 205

Pro Phe Val Met Asn Leu Gln Asp Leu Tyr Met Ala Val Thr Thr Gln
        210                 215                 220

Glu Val Gln Val Gly Gln Lys His Gln Gly Ala Gly Asp Pro His Thr
225                 230                 235                 240

Ser Asn Ser Ala Ser Leu Gln Gly Ile Asp Ser Gln Cys Val Asn Gln
                245                 250                 255

Pro Glu Gln Leu Val Ser Ser Ala Pro Thr Leu Ser Ala Pro Glu Lys
            260                 265                 270

Glu Ser Thr Gly Thr Ser Gly Pro Leu Gln Arg Pro Gln Leu Ser Lys
            275                 280                 285

Val Lys Arg Lys Lys Pro Arg Gly Leu Phe Ser
290                 295

<210> SEQ ID NO 138
<211> LENGTH: 236
<212> TYPE: PRT
<213> ORGANISM: Homo sapiens

<400> SEQUENCE: 138

Met Thr Ser Glu Lys Gly Pro Ser Thr Gly Asp Pro Thr Leu Arg Arg
1               5                   10                  15

Arg Ile Glu Pro Trp Glu Phe Asp Val Phe Tyr Asp Pro Arg Glu Leu
                20                  25                  30

Arg Lys Glu Ala Cys Leu Leu Tyr Glu Ile Lys Trp Gly Met Ser Arg
            35                  40                  45

Lys Ile Trp Arg Ser Ser Gly Lys Asn Thr Thr Asn His Val Glu Val
        50                  55                  60

Asn Phe Ile Lys Lys Phe Thr Ser Glu Arg Asp Phe His Pro Ser Met
65                  70                  75                  80

Ser Cys Ser Ile Thr Trp Phe Leu Ser Trp Ser Pro Cys Trp Glu Cys
                85                  90                  95

Ser Gln Ala Ile Arg Glu Phe Leu Ser Arg His Pro Gly Val Thr Leu
            100                 105                 110

Val Ile Tyr Val Ala Arg Leu Phe Trp His Met Asp Gln Gln Asn Arg
        115                 120                 125

Gln Gly Leu Arg Asp Leu Val Asn Ser Gly Val Thr Ile Gln Ile Met
    130                 135                 140

Arg Ala Ser Glu Tyr Tyr His Cys Trp Arg Asn Phe Val Asn Tyr Pro
145                 150                 155                 160

Pro Gly Asp Glu Ala His Trp Pro Gln Tyr Pro Pro Leu Trp Met Met
                165                 170                 175
```

```
Leu Tyr Ala Leu Glu Leu His Cys Ile Ile Leu Ser Leu Pro Pro Cys
            180                 185                 190

Leu Lys Ile Ser Arg Arg Trp Gln Asn His Leu Thr Phe Phe Arg Leu
            195                 200                 205

His Leu Gln Asn Cys His Tyr Gln Thr Ile Pro Pro His Ile Leu Leu
210                 215                 220

Ala Thr Gly Leu Ile His Pro Ser Val Ala Trp Arg
225                 230                 235

<210> SEQ ID NO 139
<211> LENGTH: 224
<212> TYPE: PRT
<213> ORGANISM: Homo sapiens

<400> SEQUENCE: 139

Met Ala Gln Lys Glu Ala Val Ala Thr Glu Ala Ala Ser Gln
1               5                   10                  15

Asn Gly Glu Asp Leu Glu Asn Leu Asp Asp Pro Glu Lys Leu Lys Glu
            20                  25                  30

Leu Ile Glu Leu Pro Pro Phe Glu Ile Val Thr Gly Glu Arg Leu Pro
        35                  40                  45

Ala Asn Phe Phe Lys Phe Gln Phe Arg Asn Val Glu Tyr Ser Ser Gly
    50                  55                  60

Arg Asn Lys Thr Phe Leu Cys Tyr Val Val Glu Ala Gln Gly Lys Gly
65                  70                  75                  80

Gly Gln Val Gln Ala Ser Arg Gly Tyr Leu Glu Asp Glu His Ala Ala
                85                  90                  95

Ala His Ala Glu Glu Ala Phe Phe Asn Thr Ile Leu Pro Ala Phe Asp
            100                 105                 110

Pro Ala Leu Arg Tyr Asn Val Thr Trp Tyr Val Ser Ser Ser Pro Cys
        115                 120                 125

Ala Ala Cys Ala Asp Arg Ile Ile Lys Thr Leu Ser Lys Thr Lys Asn
    130                 135                 140

Leu Arg Leu Leu Ile Leu Val Gly Arg Leu Phe Met Trp Glu Glu Pro
145                 150                 155                 160

Glu Ile Gln Ala Ala Leu Lys Lys Leu Lys Glu Ala Gly Cys Lys Leu
                165                 170                 175

Arg Ile Met Lys Pro Gln Asp Phe Glu Tyr Val Trp Gln Asn Phe Val
            180                 185                 190

Glu Gln Glu Gly Gly Ser Lys Ala Phe Gln Pro Trp Glu Asp Ile
        195                 200                 205

Gln Glu Asn Phe Leu Tyr Tyr Glu Glu Lys Leu Ala Asp Ile Leu Lys
    210                 215                 220

<210> SEQ ID NO 140
<211> LENGTH: 199
<212> TYPE: PRT
<213> ORGANISM: Homo sapiens

<400> SEQUENCE: 140

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45
```

```
Asp Gln His Arg Gly Phe Leu His Asn Gln Ala Lys Asn Leu Leu Cys
         50                  55                  60

Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                 85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
            115                 120                 125

Ile Tyr Asp Tyr Asp Pro Leu Tyr Lys Glu Ala Leu Gln Met Leu Arg
        130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
                180                 185                 190

Ile Leu Gln Asn Gln Gly Asn
        195
```

<210> SEQ ID NO 141
<211> LENGTH: 190
<212> TYPE: PRT
<213> ORGANISM: Homo sapiens

<400> SEQUENCE: 141

```
Met Asn Pro Gln Ile Arg Asn Pro Met Lys Ala Met Tyr Pro Gly Thr
  1               5                  10                  15

Phe Tyr Phe Gln Phe Lys Asn Leu Trp Glu Ala Asn Asp Arg Asn Glu
                 20                  25                  30

Thr Trp Leu Cys Phe Thr Val Glu Gly Ile Lys Arg Arg Ser Val Val
             35                  40                  45

Ser Trp Lys Thr Gly Val Phe Arg Asn Gln Val Asp Ser Glu Thr His
 50                  55                  60

Cys His Ala Glu Arg Cys Phe Leu Ser Trp Phe Cys Asp Asp Ile Leu
 65                  70                  75                  80

Ser Pro Asn Thr Lys Tyr Gln Val Thr Trp Tyr Thr Ser Trp Ser Pro
                 85                  90                  95

Cys Pro Asp Cys Ala Gly Glu Val Ala Glu Phe Leu Ala Arg His Ser
                100                 105                 110

Asn Val Asn Leu Thr Ile Phe Thr Ala Arg Leu Tyr Tyr Phe Gln Tyr
            115                 120                 125

Pro Cys Tyr Gln Glu Gly Leu Arg Ser Leu Ser Gln Glu Gly Val Ala
        130                 135                 140

Val Glu Ile Met Asp Tyr Glu Asp Phe Lys Tyr Cys Trp Glu Asn Phe
145                 150                 155                 160

Val Tyr Asn Asp Asn Glu Pro Phe Lys Pro Trp Lys Gly Leu Lys Thr
                165                 170                 175

Asn Phe Arg Leu Leu Lys Arg Arg Leu Arg Glu Ser Leu Gln
            180                 185                 190
```

<210> SEQ ID NO 142
<211> LENGTH: 386
<212> TYPE: PRT

<213> ORGANISM: Homo sapiens

<400> SEQUENCE: 142

```
Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Pro Val Leu Pro Lys Arg Gln
    50                  55                  60

Ser Asn His Arg Gln Glu Val Tyr Phe Arg Phe Glu Asn His Ala Glu
65                  70                  75                  80

Met Cys Phe Leu Ser Trp Phe Cys Gly Asn Arg Leu Pro Ala Asn Arg
                85                  90                  95

Arg Phe Gln Ile Thr Trp Phe Val Ser Trp Asn Pro Cys Leu Pro Cys
            100                 105                 110

Val Val Lys Val Thr Lys Phe Leu Ala Glu His Pro Asn Val Thr Leu
        115                 120                 125

Thr Ile Ser Ala Ala Arg Leu Tyr Tyr Tyr Arg Asp Arg Asp Trp Arg
130                 135                 140

Trp Val Leu Leu Arg Leu His Lys Ala Gly Ala Arg Val Lys Ile Met
145                 150                 155                 160

Asp Tyr Glu Asp Phe Ala Tyr Cys Trp Glu Asn Phe Val Cys Asn Glu
                165                 170                 175

Gly Gln Pro Phe Met Pro Trp Tyr Lys Phe Asp Asp Asn Tyr Ala Ser
            180                 185                 190

Leu His Arg Thr Leu Lys Glu Ile Leu Arg Asn Pro Met Glu Ala Met
        195                 200                 205

Tyr Pro His Ile Phe Tyr Phe His Phe Lys Asn Leu Leu Lys Ala Cys
    210                 215                 220

Gly Arg Asn Glu Ser Trp Leu Cys Phe Thr Met Glu Val Thr Lys His
225                 230                 235                 240

His Ser Ala Val Phe Arg Lys Arg Gly Val Phe Arg Asn Gln Val Asp
                245                 250                 255

Pro Glu Thr His Cys His Ala Glu Arg Cys Phe Leu Ser Trp Phe Cys
            260                 265                 270

Asp Asp Ile Leu Ser Pro Asn Thr Asn Tyr Glu Val Thr Trp Tyr Thr
        275                 280                 285

Ser Trp Ser Pro Cys Pro Glu Cys Ala Gly Glu Val Ala Glu Phe Leu
    290                 295                 300

Ala Arg His Ser Asn Val Asn Leu Thr Ile Phe Thr Ala Arg Leu Cys
305                 310                 315                 320

Tyr Phe Trp Asp Thr Asp Tyr Gln Glu Gly Leu Cys Ser Leu Ser Gln
                325                 330                 335

Glu Gly Ala Ser Val Lys Ile Met Gly Tyr Lys Asp Phe Val Ser Cys
            340                 345                 350

Trp Lys Asn Phe Val Tyr Ser Asp Asp Glu Pro Phe Lys Pro Trp Lys
        355                 360                 365

Gly Leu Gln Thr Asn Phe Arg Leu Leu Lys Arg Arg Leu Arg Glu Ile
    370                 375                 380

Leu Gln
385
```

<210> SEQ ID NO 143
<211> LENGTH: 373
<212> TYPE: PRT
<213> ORGANISM: Homo sapiens

<400> SEQUENCE: 143

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Arg
        35                  40                  45

Leu Asp Ala Lys Ile Phe Arg Gly Gln Val Tyr Ser Gln Pro Glu His
    50                  55                  60

His Ala Glu Met Cys Phe Leu Ser Trp Phe Cys Gly Asn Gln Leu Pro
65                  70                  75                  80

Ala Tyr Lys Cys Phe Gln Ile Thr Trp Phe Val Ser Trp Thr Pro Cys
                85                  90                  95

Pro Asp Cys Val Ala Lys Leu Ala Glu Phe Leu Ala Glu His Pro Asn
            100                 105                 110

Val Thr Leu Thr Ile Ser Ala Ala Arg Leu Tyr Tyr Tyr Trp Glu Arg
        115                 120                 125

Asp Tyr Arg Arg Ala Leu Cys Arg Leu Ser Gln Ala Gly Ala Arg Val
    130                 135                 140

Lys Ile Met Asp Asp Glu Glu Phe Ala Tyr Cys Trp Glu Asn Phe Val
145                 150                 155                 160

Tyr Ser Glu Gly Gln Pro Phe Met Pro Trp Tyr Lys Phe Asp Asp Asn
                165                 170                 175

Tyr Ala Phe Leu His Arg Thr Leu Lys Glu Ile Leu Arg Asn Pro Met
            180                 185                 190

Glu Ala Met Tyr Pro His Ile Phe Tyr Phe His Phe Lys Asn Leu Arg
        195                 200                 205

Lys Ala Tyr Gly Arg Asn Glu Ser Trp Leu Cys Phe Thr Met Glu Val
    210                 215                 220

Val Lys His His Ser Pro Val Ser Trp Lys Arg Gly Val Phe Arg Asn
225                 230                 235                 240

Gln Val Asp Pro Glu Thr His Cys His Ala Glu Arg Cys Phe Leu Ser
                245                 250                 255

Trp Phe Cys Asp Asp Ile Leu Ser Pro Asn Thr Asn Tyr Glu Val Thr
            260                 265                 270

Trp Tyr Thr Ser Trp Ser Pro Cys Pro Glu Cys Ala Gly Glu Val Ala
        275                 280                 285

Glu Phe Leu Ala Arg His Ser Asn Val Asn Leu Thr Ile Phe Thr Ala
    290                 295                 300

Arg Leu Tyr Tyr Phe Trp Asp Thr Asp Tyr Gln Glu Gly Leu Arg Ser
305                 310                 315                 320

Leu Ser Gln Glu Gly Ala Ser Val Glu Ile Met Gly Tyr Lys Asp Phe
                325                 330                 335

Lys Tyr Cys Trp Glu Asn Phe Val Tyr Asn Asp Asp Glu Pro Phe Lys
            340                 345                 350

Pro Trp Lys Gly Leu Lys Tyr Asn Phe Leu Phe Leu Asp Ser Lys Leu
        355                 360                 365

Gln Glu Ile Leu Glu
    370

<210> SEQ ID NO 144
<211> LENGTH: 384
<212> TYPE: PRT
<213> ORGANISM: Homo sapiens

<400> SEQUENCE: 144

```
Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Pro
        35                  40                  45

Leu Asp Ala Lys Ile Phe Arg Gly Gln Val Tyr Ser Glu Leu Lys Tyr
    50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
    130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
        195                 200                 205

Glu Pro Trp Val Arg Gly Arg His Glu Thr Tyr Leu Cys Tyr Glu Val
    210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
        275                 280                 285

Phe Ser Cys Ala Gln Glu Met Ala Lys Phe Ile Ser Lys Asn Lys His
    290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Asp Glu His Ser
        355                 360                 365

Gln Asp Leu Ser Gly Arg Leu Arg Ala Ile Leu Gln Asn Gln Glu Asn
```

<210> SEQ ID NO 145
<211> LENGTH: 200
<212> TYPE: PRT
<213> ORGANISM: Homo sapiens

<400> SEQUENCE: 145

Met Ala Leu Leu Thr Ala Glu Thr Phe Arg Leu Gln Phe Asn Asn Lys
1               5                   10                  15

Arg Arg Leu Arg Arg Pro Tyr Tyr Pro Arg Lys Ala Leu Leu Cys Tyr
                20                  25                  30

Gln Leu Thr Pro Gln Asn Gly Ser Thr Pro Thr Arg Gly Tyr Phe Glu
            35                  40                  45

Asn Lys Lys Cys His Ala Glu Ile Cys Phe Ile Asn Glu Ile Lys
        50                  55                  60

Ser Met Gly Leu Asp Glu Thr Gln Cys Tyr Gln Val Thr Cys Tyr Leu
65                  70                  75                  80

Thr Trp Ser Pro Cys Ser Ser Cys Ala Trp Glu Leu Val Asp Phe Ile
                85                  90                  95

Lys Ala His Asp His Leu Asn Leu Gly Ile Phe Ala Ser Arg Leu Tyr
            100                 105                 110

Tyr His Trp Cys Lys Pro Gln Gln Lys Gly Leu Arg Leu Leu Cys Gly
        115                 120                 125

Ser Gln Val Pro Val Glu Val Met Gly Phe Pro Lys Phe Ala Asp Cys
130                 135                 140

Trp Glu Asn Phe Val Asp His Glu Lys Pro Leu Ser Phe Asn Pro Tyr
145                 150                 155                 160

Lys Met Leu Glu Glu Leu Asp Lys Asn Ser Arg Ala Ile Lys Arg Arg
                165                 170                 175

Leu Glu Arg Ile Lys Ile Pro Gly Val Arg Ala Gln Gly Arg Tyr Met
            180                 185                 190

Asp Ile Leu Cys Asp Ala Glu Val
        195                 200

<210> SEQ ID NO 146
<211> LENGTH: 367
<212> TYPE: PRT
<213> ORGANISM: Homo sapiens

<400> SEQUENCE: 146

Met Glu Pro Ile Tyr Glu Glu Tyr Leu Ala Asn His Gly Thr Ile Val
1               5                   10                  15

Lys Pro Tyr Tyr Trp Leu Ser Phe Ser Leu Asp Cys Ser Asn Cys Pro
                20                  25                  30

Tyr His Ile Arg Thr Gly Glu Glu Ala Arg Val Ser Leu Thr Glu Phe
            35                  40                  45

Cys Gln Ile Phe Gly Phe Pro Tyr Gly Thr Thr Phe Pro Gln Thr Lys
        50                  55                  60

His Leu Thr Phe Tyr Glu Leu Lys Thr Ser Ser Gly Ser Leu Val Gln
65                  70                  75                  80

Lys Gly His Ala Ser Ser Cys Thr Gly Asn Tyr Ile His Pro Glu Ser
                85                  90                  95

Met Leu Phe Glu Met Asn Gly Tyr Leu Asp Ser Ala Ile Tyr Asn Asn
            100                 105                 110

Asp Ser Ile Arg His Ile Ile Leu Tyr Ser Asn Asn Ser Pro Cys Asn

```
              115                 120                 125
Glu Ala Asn His Cys Cys Ile Ser Lys Met Tyr Asn Phe Leu Ile Thr
            130                 135                 140
Tyr Pro Gly Ile Thr Leu Ser Ile Tyr Phe Ser Gln Leu Tyr His Thr
145                 150                 155                 160
Glu Met Asp Phe Pro Ala Ser Ala Trp Asn Arg Glu Ala Leu Arg Ser
                165                 170                 175
Leu Ala Ser Leu Trp Pro Arg Val Val Leu Ser Pro Ile Ser Gly Gly
            180                 185                 190
Ile Trp His Ser Val Leu His Ser Phe Ile Ser Gly Val Gly Ser
        195                 200                 205
His Val Phe Gln Pro Ile Leu Thr Gly Arg Ala Leu Ala Asp Arg His
    210                 215                 220
Asn Ala Tyr Glu Ile Asn Ala Ile Thr Gly Val Lys Pro Tyr Phe Thr
225                 230                 235                 240
Asp Val Leu Leu Gln Thr Lys Arg Asn Pro Asn Thr Lys Ala Gln Glu
                245                 250                 255
Ala Leu Glu Ser Tyr Pro Leu Asn Asn Ala Phe Pro Gly Gln Phe Phe
            260                 265                 270
Gln Met Pro Ser Gly Gln Leu Gln Pro Asn Leu Pro Asp Leu Arg
        275                 280                 285
Ala Pro Val Val Phe Val Leu Val Pro Leu Arg Asp Leu Pro Pro Met
    290                 295                 300
His Met Gly Gln Asn Pro Asn Lys Pro Arg Asn Ile Val Arg His Leu
305                 310                 315                 320
Asn Met Pro Gln Met Ser Phe Gln Glu Thr Lys Asp Leu Gly Arg Leu
                325                 330                 335
Pro Thr Gly Arg Ser Val Glu Ile Val Glu Ile Thr Glu Gln Phe Ala
            340                 345                 350
Ser Ser Lys Glu Ala Asp Glu Lys Lys Lys Lys Gly Lys Lys
        355                 360                 365

<210> SEQ ID NO 147
<211> LENGTH: 48
<212> TYPE: DNA
<213> ORGANISM: Homo sapiens

<400> SEQUENCE: 147
gaaatcaatc atagtggaag caccaactac aacccgtccc tcaagagt            48

<210> SEQ ID NO 148
<211> LENGTH: 48
<212> TYPE: DNA
<213> ORGANISM: Homo sapiens

<400> SEQUENCE: 148
gatatcagtc atagtggcat ccccaagtac aacccgtccc tcaagagt            48

<210> SEQ ID NO 149
<211> LENGTH: 48
<212> TYPE: DNA
<213> ORGANISM: Homo sapiens

<400> SEQUENCE: 149
gaaatcaatc atggtggaaa tcccaactac aacccgtctc tcaggagc            48

<210> SEQ ID NO 150
```

```
<211> LENGTH: 48
<212> TYPE: DNA
<213> ORGANISM: Homo sapiens

<400> SEQUENCE: 150
gaaatcaatc atgttggaag taccacctac aaccctccc tcaagagt           48

<210> SEQ ID NO 151
<211> LENGTH: 48
<212> TYPE: DNA
<213> ORGANISM: Homo sapiens

<400> SEQUENCE: 151
gcaatcaata atagtggaaa caccttgttc accccatccc tcacgagt           48

<210> SEQ ID NO 152
<211> LENGTH: 48
<212> TYPE: DNA
<213> ORGANISM: Homo sapiens

<400> SEQUENCE: 152
gaaatcaatc acagtggaag aaccaaccac aacccgtccc tcaggagt           48

<210> SEQ ID NO 153
<211> LENGTH: 48
<212> TYPE: DNA
<213> ORGANISM: Homo sapiens

<400> SEQUENCE: 153
gaaacctatc atagtgcata caccaagtac agcccgtccc tccagggt           48

<210> SEQ ID NO 154
<211> LENGTH: 48
<212> TYPE: DNA
<213> ORGANISM: Homo sapiens

<400> SEQUENCE: 154
gagatcgatt atagtggaaa cgccaactac aacccgtccc tcaagagt           48

<210> SEQ ID NO 155
<211> LENGTH: 48
<212> TYPE: DNA
<213> ORGANISM: Homo sapiens

<400> SEQUENCE: 155
gaaatcaatc atagtggaag caccaactac aacccgtccc tcaagagt           48

<210> SEQ ID NO 156
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(21)
<223> OTHER INFORMATION: a, c, t, g, unknown or other

<400> SEQUENCE: 156
aannnnnnnn nnnnnnnnnn ntt                                      23

<210> SEQ ID NO 157
<211> LENGTH: 6582
```

<212> TYPE: DNA
<213> ORGANISM: Homo sapiens

<400> SEQUENCE: 157

| | | | | | |
|---|---|---|---|---|---|
| agagggcaag | gagagagcag | agaacacact | ttgccttctc | tttggtattg | agtaatatca | 60 |
| accaaattgc | agacatctca | acactttggc | caggcagcct | gctgagcaag | gtacctcagc | 120 |
| cagcatggca | gcctctttcc | cacccacctt | gggactcagt | tctgccccag | atgaaattca | 180 |
| gcacccacat | attaaatttt | cagaatggaa | atttaagctg | ttccgggtga | gatcctttga | 240 |
| aaagacacct | gaagaagctc | aaaaggaaaa | gaaggattcc | tttgagggga | accctctct | 300 |
| ggagcaatct | ccagcagtcc | tggacaaggc | tgatggtcag | aagccagtcc | caactcagcc | 360 |
| attgttaaaa | gcccacccta | agttttcaaa | gaaatttcac | gacaacgaga | agcaagagg | 420 |
| caaagcgatc | catcaagcca | accttcgaca | tctctgccgc | atctgtggga | attcttttag | 480 |
| agctgatgag | cacaacagga | gatatccagt | ccatggtcct | gtggatggta | aaaccctagg | 540 |
| cctttttacga | aagaaggaaa | agagagctac | ttcctggccg | gacctcattg | ccaaggtttt | 600 |
| ccggatcgat | gtgaaggcag | atgttgactc | gatccacccc | actgagttct | gccataactg | 660 |
| ctggagcatc | atgcacagga | agtttagcag | tgccccatgt | gaggtttact | tcccgaggaa | 720 |
| cgtgaccatg | gagtggcacc | cccacacacc | atcctgtgac | atctgcaaca | ctgcccgtcg | 780 |
| gggactcaag | aggaagagtc | ttcagccaaa | cttgcagctc | agcaaaaaac | tcaaaactgt | 840 |
| gcttgaccaa | gcaagacaag | cccgtcagcg | caagagaaga | gctcaggcaa | ggatcagcag | 900 |
| caaggatgtc | atgaagaaga | tcgccaactg | cagtaagata | catcttagta | ccaagctcct | 960 |
| tgcagtggac | ttcccagagc | actttgtgaa | atccatctcc | tgccagatct | gtgaacacat | 1020 |
| tctggctgac | cctgtggaga | ccaactgtaa | gcatgtcttt | tgccgggtct | gcattctcag | 1080 |
| atgcctcaaa | gtcatgggca | gctattgtcc | ctcttgccga | tatccatgct | ccctactga | 1140 |
| cctggagagt | ccagtgaagt | cctttctgag | cgtcttgaat | tccctgatgg | tgaaatgtcc | 1200 |
| agcaaaagag | tgcaatgagg | aggtcagttt | ggaaaaatat | aatcaccaca | tctcaagtca | 1260 |
| caaggaatca | aaagagattt | ttgtgcacat | taataaaggg | ggccggcccc | gccaacatct | 1320 |
| tctgtcgctg | actcggagag | ctcagaagca | ccggctgagg | gagctcaagc | tgcaagtcaa | 1380 |
| agcctttgct | gacaaagaag | aaggtggaga | tgtgaagtcc | gtgtgcatga | ccttgttcct | 1440 |
| gctggctctg | agggcgagga | atgagcacag | gcaagctgat | gagctggagg | ccatcatgca | 1500 |
| gggaaagggc | tctggcctgc | agccagctgt | ttgcttggcc | atccgtgtca | acaccttcct | 1560 |
| cagctgcagt | cagtaccaca | agatgtacag | gactgtgaaa | gccatcacag | ggagacagat | 1620 |
| ttttcagcct | ttgcatgccc | ttcggaatgc | tgagaaggta | cttctgccag | gctaccacca | 1680 |
| ctttgagtgg | cagccaccctc | tgaagaatgt | gtcttccagc | actgatgttg | gcattattga | 1740 |
| tgggctgtct | ggactatcat | cctctgtgga | tgattaccca | gtggacacca | ttgcaaagag | 1800 |
| gttccgctat | gattcagctt | tggtgtctgc | tttgatggac | atggaagaag | acatcttgga | 1860 |
| aggcatgaga | tcccaagacc | ttgatgatta | cctgaatggc | cccttcactg | tggtggtgaa | 1920 |
| ggagtcttgt | gatggaatgg | agacgtgag | tgagaagcat | gggagtgggc | ctgtagttcc | 1980 |
| agaaaaggca | gtccgttttt | cattcacaat | catgaaaatt | actattgccc | acagctctca | 2040 |
| gaatgtgaaa | gtatttgaag | aagccaaacc | taactctgaa | ctgtgttgca | agccattgtg | 2100 |
| ccttatgctg | gcagatgagt | ctgaccacga | gacgctgact | gccatcctga | gtcctctcat | 2160 |
| tgctgagagg | gaggccatga | agagcagtga | attaatgctt | gagctgggag | gcattctccg | 2220 |

```
gactttcaag ttcatcttca ggggcaccgg ctatgatgaa aaacttgtgc gggaagtgga      2280
aggcctcgag gcttctggct cagtctacat ttgtactctt tgtgatgcca cccgtctgga      2340
agcctctcaa aatcttgtct tccactctat aaccagaagc catgctgaga acctggaacg      2400
ttatgaggtc tggcgttcca acccttacca tgagtctgtg aagaactgc gggatcgggt       2460 gaaaggggtc tcagctaaac ctttcattga dacagtccct tccatagatg cactccactg      2520
tgacattggc aatgcagctg agttctacaa gatcttccag ctagagatag gggaagtgta      2580
taagaatccc aatgcttcca agaggaaag gaaaaggtgg caggccacac tggacaagca      2640
tctccggaag aagatgaacc tcaaaccaat catgaggatg aatggcaact ttgccaggaa      2700
gctcatgacc aaagagactg tggatgcagt ttgtgagtta attccttccg aggagaggca      2760
cgaggctctg agggagctga tggatcttta cctgaagatg aaaccagtat ggcgatcatc      2820
atgccctgct aaagagtgcc cagaatccct ctgccagtac agtttcaatt cacagcgttt      2880
tgctgagctc ctttctacga agttcaagta taggtatgag ggaaaaatca ccaattattt      2940
tcacaaaacc ctggcccatg ttcctgaaat tattgagagg gatggctcca ttggggcatg      3000
ggcaagtgag ggaaatgagt ctggtaacaa actgtttagg cgcttccgga aaatgaatgc      3060
caggcagtcc aaatgctatg agatggaaga tgtcctgaaa caccactggt tgtacacctc      3120
caaatacctc cagaagttta tgaatgctca taatgcatta aaaacctctg ggtttaccat      3180
gaaccctcag gcaagcttag gggacccatt aggcatagag gactctctgg aaagccaaga      3240
ttcaatggaa ttttaagtag ggcaaccact tatgagttgg ttttgcaat tgagtttccc       3300 tctgggttgc attgagggct tctcctagca cccttttactg ctgtgtatgg ggcttcacca     3360
tccaagaggt ggtaggttgg agtaagatgc tacagatgct ctcaagtcag gaatagaaac      3420
tgatgagctg attgcttgag gcttttagtg agttccgaaa agcaacagga aaaatcagtt      3480
atctgaaagc tcagtaactc agaacaggag taactgcagg ggaccagaga tgagcaaaga      3540
tctgtgtgtg ttggggagct gtcatgtaaa tcaaagccaa ggttgtcaaa gaacagccag      3600
tgaggccagg aaagaaattg gtcttgtggt tttcattttt ttccccttg attgattata       3660 ttttgtattg agatatgata agtgccttct atttcatttt tgaataattc ttcatttta       3720 taatttttaca tatcttggct tgctatataa gattcaaaag agcttttttaa attttttctaa   3780 taatatctta catttgtaca gcatgatgac ctttacaaag tgctctcaat gcatttaccc      3840
attcgttata taaatatgtt acatcaggac aactttgaga aaatcagtcc tttttatgt       3900 ttaaattatg tatctattgt aaccttcaga gtttaggagg tcatctgctg tcatggattt      3960
ttcaataatg aatttagaat acacctgtta gctacagtta gttattaaat cttctgataa      4020
tatatgttta cttagctatc agaagccaag tatgattctt tattttact tttcatttc        4080 aagaaattta gagtttccaa atttagagct tctgcataca gtcttaaagc cacagaggct      4140
tgtaaaaata taggttagct tgatgtctaa aaatatattt catgtcttac tgaaacattt      4200
tgccagactt tctccaaatg aaacctgaat caattttttct aaatctaggt ttcatagagt     4260
cctctcctct gcaatgtgtt attctttcta taatgatcag tttactttca gtggattcag      4320
aattgtgtag caggataacc ttgtattttt ccatccgcta gtttagatg gagtccaaac       4380 gcagtacagc agaagagtta acatttacac agtgcttttt accactgtgg aatgttttca      4440
cactcatttt tccttacaac aattctgagg agtaggtgtt gttattatct ccatttgatg      4500
ggggtttaaa tgatttgctc aaagtcattt aggggtaata aatacttggc ttggaaattt      4560
aacacagtcc ttttgtctcc aaagcccttc ttctttccac cacaaattaa tcactatgtt      4620
```

```
tataaggtag tatcagaatt tttttaggat tcacaactaa tcactatagc acatgacctt    4680
gggattacat ttttatgggg caggggtaag caagttttta atcatttgt gtgctctggc     4740 tcttttgata gaagaaagca acacaaaagc tccaaagggc cccctaaccc tcttgtggct    4800
ccagttattt ggaaactatg atctgcatcc ttaggaatct gggatttgcc agttgctggc    4860
aatgtagagc aggcatggaa ttttatatgc tagtgagtca taatgatatg ttagtgttaa    4920 ttagttttt cttcctttga ttttattggc cataattgct actcttcata cacagtatat     4980
caaagagctt gataatttag ttgtcaaaag tgcatcggcg acattatctt taattgtatg    5040
tatttggtgc ttcttcaggg attgaactca gtatctttca ttaaaaaaca cagcagtttt    5100
ccttgctttt tatatgcaga atatcaaagt catttctaat ttagttgtca aaaacatata    5160
catattttaa cattagtttt tttgaaaact cttggttttg ttttttttgga aatgagtggg   5220 ccactaagcc cactttccc ttcatcctgc ttaatccttc cagcatgtct ctgcactaat     5280
aaacagctaa attcacataa tcatcctatt tactgaagca tggtcatgct ggtttataga   5340 tttttttaccc atttctactc ttttttctcta ttggtggcac tgtaaatact tccagtatt   5400 aaattatcct tttctaacac tgtaggaact attttgaatg catgtgacta agagcatgat   5460
ttatagcaca acctttccaa taatccctta atcagatcac attttgataa accctgggaa   5520
catctggctg caggaatttc aatatgtaga acgctgcct atggtttttt gcccttactg     5580
ttgagactgc aatatcctag accctagttt tatactagag ttttatttt agcaatgcct    5640 attgcaagtg caattatata ctccagggaa attcaccaca ctgaatcgag catttgtgtg   5700
tgtatgtgtg aagtatatac tgggacttca gaagtgcaat gtattttttct cctgtgaaac  5760 ctgaatctac aagttttcct gccaagccac tcaggtgcat tgcagggacc agtgataatg   5820
gctgatgaaa attgatgatt ggtcagtgag gtcaaaagga gccttgggat taataaacat   5880
gcactgagaa gcaagaggag gagaaaaaga tgtcttttc ttccaggtga actggaattt     5940
agttttgcct cagattttt tcccacaaga tacagaagaa gataaagatt ttttggttg     6000 agagtgtggg tcttgcatta catcaaacag agttcaaatt ccacacagat aagaggcagg   6060
atatataagc gccagtggta gttgggagga ataaaccatt atttggatgc aggtggtttt   6120
tgattgcaaa tatgtgtgtg tcttcagtga ttgtatgaca gatgatgtat tcttttgatg   6180
ttaaaagatt ttaagtaaga gtagatacat tgtacccatt ttacattttc ttatttaac    6240 tacagtaatc tacataaata tacctcagaa atcattttg gtgattattt tttgttttgt   6300
agaattgcac ttcagtttat tttcttacaa ataaccttac attttgttta atggcttcca   6360
agagcctttt tttttttttgt atttcagaga aaattcaggt accaggatgc aatggattta   6420
tttgattcag gggacctgtg tttccatgtc aaatgttttc aaataaaatg aaatatgagt   6480
ttcaatactt tttatatttt aatatttcca ttcattaata ttatggttat tgtcagcaat    6540
tttatgtttg aatatttgaa ataaaagttt aagatttgaa aa                       6582
```

<210> SEQ ID NO 158
<211> LENGTH: 1043
<212> TYPE: PRT
<213> ORGANISM: Homo sapiens

<400> SEQUENCE: 158

Met Ala Ala Ser Phe Pro Pro Thr Leu Gly Leu Ser Ser Ala Pro Asp
1               5                   10                  15

Glu Ile Gln His Pro His Ile Lys Phe Ser Glu Trp Lys Phe Lys Leu

-continued

```
                20                  25                  30
Phe Arg Val Arg Ser Phe Glu Lys Thr Pro Glu Glu Ala Gln Lys Glu
            35                  40                  45
Lys Lys Asp Ser Phe Glu Gly Lys Pro Ser Leu Glu Gln Ser Pro Ala
 50                  55                  60
Val Leu Asp Lys Ala Asp Gly Gln Lys Pro Val Pro Thr Gln Pro Leu
 65                  70                  75                  80
Leu Lys Ala His Pro Lys Phe Ser Lys Phe His Asp Asn Glu Lys
                85                  90                  95
Ala Arg Gly Lys Ala Ile His Gln Ala Asn Leu Arg His Leu Cys Arg
            100                 105                 110
Ile Cys Gly Asn Ser Phe Arg Ala Asp Glu His Asn Arg Arg Tyr Pro
            115                 120                 125
Val His Gly Pro Val Asp Gly Lys Thr Leu Gly Leu Leu Arg Lys Lys
            130                 135                 140
Glu Lys Arg Ala Thr Ser Trp Pro Asp Leu Ile Ala Lys Val Phe Arg
145                 150                 155                 160
Ile Asp Val Lys Ala Asp Val Asp Ser Ile His Pro Thr Glu Phe Cys
                165                 170                 175
His Asn Cys Trp Ser Ile Met His Arg Lys Phe Ser Ser Ala Pro Cys
            180                 185                 190
Glu Val Tyr Phe Pro Arg Asn Val Thr Met Glu Trp His Pro His Thr
            195                 200                 205
Pro Ser Cys Asp Ile Cys Asn Thr Ala Arg Arg Gly Leu Lys Arg Lys
            210                 215                 220
Ser Leu Gln Pro Asn Leu Gln Leu Ser Lys Lys Leu Lys Thr Val Leu
225                 230                 235                 240
Asp Gln Ala Arg Gln Ala Arg Gln Arg Lys Arg Ala Gln Ala Arg
                245                 250                 255
Ile Ser Ser Lys Asp Val Met Lys Lys Ile Ala Asn Cys Ser Lys Ile
            260                 265                 270
His Leu Ser Thr Lys Leu Leu Ala Val Asp Phe Pro Glu His Phe Val
            275                 280                 285
Lys Ser Ile Ser Cys Gln Ile Cys Glu His Ile Leu Ala Asp Pro Val
            290                 295                 300
Glu Thr Asn Cys Lys His Val Phe Cys Arg Val Cys Ile Leu Arg Cys
305                 310                 315                 320
Leu Lys Val Met Gly Ser Tyr Cys Pro Ser Cys Arg Tyr Pro Cys Phe
            325                 330                 335
Pro Thr Asp Leu Glu Ser Pro Val Lys Ser Phe Leu Ser Val Leu Asn
            340                 345                 350
Ser Leu Met Val Lys Cys Pro Ala Lys Glu Cys Asn Glu Glu Val Ser
            355                 360                 365
Leu Glu Lys Tyr Asn His His Ile Ser Ser His Lys Glu Ser Lys Glu
            370                 375                 380
Ile Phe Val His Ile Asn Lys Gly Gly Arg Pro Arg Gln His Leu Leu
385                 390                 395                 400
Ser Leu Thr Arg Arg Ala Gln Lys His Arg Leu Arg Glu Leu Lys Leu
                405                 410                 415
Gln Val Lys Ala Phe Ala Asp Lys Glu Glu Gly Gly Asp Val Lys Ser
            420                 425                 430
Val Cys Met Thr Leu Phe Leu Leu Ala Leu Arg Ala Arg Asn Glu His
            435                 440                 445
```

-continued

Arg Gln Ala Asp Glu Leu Glu Ala Ile Met Gln Gly Lys Gly Ser Gly
    450                 455                 460

Leu Gln Pro Ala Val Cys Leu Ala Ile Arg Val Asn Thr Phe Leu Ser
465                 470                 475                 480

Cys Ser Gln Tyr His Lys Met Tyr Arg Thr Val Lys Ala Ile Thr Gly
                485                 490                 495

Arg Gln Ile Phe Gln Pro Leu His Ala Leu Arg Asn Ala Glu Lys Val
            500                 505                 510

Leu Leu Pro Gly Tyr His His Phe Glu Trp Gln Pro Pro Leu Lys Asn
        515                 520                 525

Val Ser Ser Thr Asp Val Gly Ile Ile Asp Gly Leu Ser Gly Leu
    530                 535                 540

Ser Ser Ser Val Asp Asp Tyr Pro Val Asp Thr Ile Ala Lys Arg Phe
545                 550                 555                 560

Arg Tyr Asp Ser Ala Leu Val Ser Ala Leu Met Asp Met Glu Glu Asp
                565                 570                 575

Ile Leu Glu Gly Met Arg Ser Gln Asp Leu Asp Asp Tyr Leu Asn Gly
            580                 585                 590

Pro Phe Thr Val Val Lys Glu Ser Cys Asp Gly Met Gly Asp Val
        595                 600                 605

Ser Glu Lys His Gly Ser Gly Pro Val Pro Glu Lys Ala Val Arg
    610                 615                 620

Phe Ser Phe Thr Ile Met Lys Ile Thr Ile Ala His Ser Ser Gln Asn
625                 630                 635                 640

Val Lys Val Phe Glu Glu Ala Lys Pro Asn Ser Glu Leu Cys Cys Lys
                645                 650                 655

Pro Leu Cys Leu Met Leu Ala Asp Glu Ser Asp His Glu Thr Leu Thr
            660                 665                 670

Ala Ile Leu Ser Pro Leu Ile Ala Glu Arg Glu Ala Met Lys Ser Ser
        675                 680                 685

Glu Leu Met Leu Glu Leu Gly Gly Ile Leu Arg Thr Phe Lys Phe Ile
    690                 695                 700

Phe Arg Gly Thr Gly Tyr Asp Glu Lys Leu Val Arg Glu Val Glu Gly
705                 710                 715                 720

Leu Glu Ala Ser Gly Ser Val Tyr Ile Cys Thr Leu Cys Asp Ala Thr
                725                 730                 735

Arg Leu Glu Ala Ser Gln Asn Leu Val Phe His Ser Ile Thr Arg Ser
            740                 745                 750

His Ala Glu Asn Leu Glu Arg Tyr Glu Val Trp Arg Ser Asn Pro Tyr
        755                 760                 765

His Glu Ser Val Glu Glu Leu Arg Asp Arg Val Lys Gly Val Ser Ala
    770                 775                 780

Lys Pro Phe Ile Glu Thr Val Pro Ser Ile Asp Ala Leu His Cys Asp
785                 790                 795                 800

Ile Gly Asn Ala Ala Glu Phe Tyr Lys Ile Phe Gln Leu Glu Ile Gly
                805                 810                 815

Glu Val Tyr Lys Asn Pro Asn Ala Ser Lys Glu Glu Arg Lys Arg Trp
            820                 825                 830

Gln Ala Thr Leu Asp Lys His Leu Arg Lys Lys Met Asn Leu Lys Pro
        835                 840                 845

Ile Met Arg Met Asn Gly Asn Phe Ala Arg Lys Leu Met Thr Lys Glu
    850                 855                 860

```
Thr Val Asp Ala Val Cys Glu Leu Ile Pro Ser Glu Glu Arg His Glu
865                 870                 875                 880

Ala Leu Arg Glu Leu Met Asp Leu Tyr Leu Lys Met Lys Pro Val Trp
                885                 890                 895

Arg Ser Ser Cys Pro Ala Lys Glu Cys Pro Glu Ser Leu Cys Gln Tyr
                900                 905                 910

Ser Phe Asn Ser Gln Arg Phe Ala Glu Leu Leu Ser Thr Lys Phe Lys
                915                 920                 925

Tyr Arg Tyr Glu Gly Lys Ile Thr Asn Tyr Phe His Lys Thr Leu Ala
                930                 935                 940

His Val Pro Glu Ile Ile Glu Arg Asp Gly Ser Ile Gly Ala Trp Ala
945                 950                 955                 960

Ser Glu Gly Asn Glu Ser Gly Asn Lys Leu Phe Arg Arg Phe Arg Lys
                965                 970                 975

Met Asn Ala Arg Gln Ser Lys Cys Tyr Glu Met Glu Asp Val Leu Lys
                980                 985                 990

His His Trp Leu Tyr Thr Ser Lys  Tyr Leu Gln Lys Phe  Met Asn Ala
                995                 1000                1005

His Asn  Ala Leu Lys Thr Ser  Gly Phe Thr Met Asn  Pro Gln Ala
    1010                1015                1020

Ser Leu  Gly Asp Pro Leu Gly  Ile Glu Asp Ser Leu   Glu Ser Gln
    1025                1030                1035

Asp Ser  Met Glu Phe
    1040

<210> SEQ ID NO 159
<211> LENGTH: 2652
<212> TYPE: DNA
<213> ORGANISM: Homo sapiens

<400> SEQUENCE: 159
attagatcag tgttcataag aacatctgta ggcacacata cacactctct ttacagtcag     60
ccttctgctt gccacagtca tagtgggcag tcagtgaatc ttccccaagt gctgacaatt    120
aatacctggt ttagcggcaa agattcagag aggcgtgagc agcccctctg ccttcaggg     180 attcaaagat ccatctttcg gttctgtaag acagtcacgg cttttgtaac ctcggtgccc    240
ccttcaacct cccgcccaa gcacctccag ggtcgtcagg ggtgtagttt tgagtcgcgc    300
tcctaagcat ccagacaggc aggacaccgt aacgacatct ctgccgggag tcccttcaga    360
ctgcggtctc cagacaaaaa tctacgtacc atcagaaact atgtctctgc agatggtaac    420
agtcagtaat aacatagcct taattcagcc aggcttctca ctgatgaatt ttgatggaca    480
agttttcttc tttggacaaa aaggctggcc caaaagatcc tgccccactg gagttttcca    540
tctggatgta aagcataacc atgtcaaact gaagcctaca attttctcta aggattcctg    600
ctacctccct cctcttcgct acccagccac ttgcacattc aaaggcagct tggagtctga    660
aaagcatcaa tacatcatcc atggagggaa acaccaaac aatgaggttt cagataagat    720
ttatgtcatg tctattgttt gcaagaacaa caaaaaggtt acttttcgct gcacagagaa    780
agacttggta ggagatgttc ctgaagccag atatggtcat ccattaatg tggtgtacag    840 ccgagggaaa agtatgggtg ttctctttgg aggacgctca tacatgcctt ctacccacag    900
aaccacagaa aaatggaata gtgtagctga ctgcctgccc tgtgttttcc tggtggattt    960
tgaatttggg tgtgctacat catacattct tccagaactt caggatgggc tatcttttca   1020
tgtctctatt gccaaaaatg acaccatcta tatttagga ggacattcac ttgccaataa   1080
```

```
tatccggcct gccaacctgt acagaataag ggttgatctt ccctgggta gcccagctgt   1140 gaattgcaca gtcttgccag gaggaatctc tgtctccagt gcaatcctga ctcaaactaa   1200
caatgatgaa tttgttattg ttggtggcta tcagcttgaa atcaaaaaa gaatgatctg    1260 caacatcatc tctttagagg acaacaagat agaaattcgt gagatggaga ccccagattg   1320
gaccccagac attaagcaca gcaagatatg gtttggaagc aacatgggaa atggaactgt   1380
ttttcttggc ataccaggag acaataaaca agttgtttca gaaggattct atttctatat   1440
gttgaaatgt gctgaagatg atactaatga agagcagaca acattcacaa acagtcaaac   1500
atcaacagaa gatccagggg attccactcc ctttgaagac tctgaagaat tttgtttcag   1560
tgcagaagca aatagttttg atggtgatga tgaatttgac acctataatg aagatgatga   1620
agaagatgag tctgagacag gctactggat tacatgctgc cctacttgtg atgtggatat   1680
caacacttgg gtaccattct attcaactga gctcaacaaa cccgccatga tctactgctc   1740
tcatggggat gggcactggg tccatgctca gtgcatggat ctggcagaac gcacactcat   1800
ccatctgtca gcaggaagca acaagtatta ctgcaatgag catgtggaga tagcaagagc   1860
tctacacact ccccaaagag tcctacccct aaaaaagcct ccaatgaaat ccctccgtaa   1920
aaaaggttct ggaaaaatct tgactcctgc caagaaatcc tttcttagaa ggttgtttga   1980 ttagtttttgc aaaagccttt cagattcagg tgtatgaat ttttgaatct atttttaaaa    2040
tcataacatt gattttaaaa atacatttt gtttatttaa aatgcctatg ttttctttta    2100
gttacatgaa ttaagggcca gaaaaagtg tttataatgc aatgataaat aaagtcattc    2160
tagaccctat acattttgaa aatattttac ccaaatactc aatttactaa tttattcttc   2220
actgaggatt tctgatctga ttttttattc aacaaacctt aaacacccag aagcagtaat    2280
aatcatcgag gtatgtttat attattata taagtcttgg taacaaataa cctataaagt    2340
gtttatgaca aatttagcca ataaagaaat taacacccaa aagaattaaa ttgattattt   2400
tgtgcaacat aacaattcgg cagttggcca aaacttaaaa gcaagatcta ctacatccca   2460
cattagtgtt ctttatatac cttcaagcaa ccctttggat tatgcccatg aacaagttag   2520
tttctcatag ctttacagat gtagatataa atataaatat atgtatacat atagatagat   2580
aatgttctcc actgacacaa aagaagaaat aaataatcta catcaaaaaa aaaaaaaaa    2640 aaaaaaaaaa aa                                                      2652
```

<210> SEQ ID NO 160
<211> LENGTH: 527
<212> TYPE: PRT
<213> ORGANISM: Homo sapiens

<400> SEQUENCE: 160

```
Met Ser Leu Gln Met Val Thr Val Ser Asn Asn Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Leu
        35                  40                  45

Asp Val Lys His Asn His Val Lys Leu Lys Pro Thr Ile Phe Ser Lys
    50                  55                  60

Asp Ser Cys Tyr Leu Pro Pro Leu Arg Tyr Pro Ala Thr Cys Thr Phe
65                  70                  75                  80

Lys Gly Ser Leu Glu Ser Glu Lys His Gln Tyr Ile Ile His Gly Gly
```

```
                     85                  90                  95
Lys Thr Pro Asn Asn Glu Val Ser Asp Lys Ile Tyr Val Met Ser Ile
                100                 105                 110

Val Cys Lys Asn Asn Lys Lys Val Thr Phe Arg Cys Thr Glu Lys Asp
                115                 120                 125

Leu Val Gly Asp Val Pro Glu Ala Arg Tyr Gly His Ser Ile Asn Val
                130                 135                 140

Val Tyr Ser Arg Gly Lys Ser Met Gly Val Leu Phe Gly Gly Arg Ser
145                 150                 155                 160

Tyr Met Pro Ser Thr His Arg Thr Thr Glu Lys Trp Asn Ser Val Ala
                165                 170                 175

Asp Cys Leu Pro Cys Val Phe Leu Val Asp Phe Glu Phe Gly Cys Ala
                180                 185                 190

Thr Ser Tyr Ile Leu Pro Glu Leu Gln Asp Gly Leu Ser Phe His Val
                195                 200                 205

Ser Ile Ala Lys Asn Asp Thr Ile Tyr Ile Leu Gly Gly His Ser Leu
                210                 215                 220

Ala Asn Asn Ile Arg Pro Ala Asn Leu Tyr Arg Ile Arg Val Asp Leu
225                 230                 235                 240

Pro Leu Gly Ser Pro Ala Val Asn Cys Thr Val Leu Pro Gly Gly Ile
                245                 250                 255

Ser Val Ser Ala Ile Leu Thr Gln Thr Asn Asn Asp Glu Phe Val
                260                 265                 270

Ile Val Gly Gly Tyr Gln Leu Glu Asn Gln Lys Arg Met Ile Cys Asn
                275                 280                 285

Ile Ile Ser Leu Glu Asp Asn Lys Ile Glu Ile Arg Glu Met Glu Thr
                290                 295                 300

Pro Asp Trp Thr Pro Asp Ile Lys His Ser Lys Ile Trp Phe Gly Ser
305                 310                 315                 320

Asn Met Gly Asn Gly Thr Val Phe Leu Gly Ile Pro Gly Asp Asn Lys
                325                 330                 335

Gln Val Val Ser Glu Gly Phe Tyr Phe Tyr Met Leu Lys Cys Ala Glu
                340                 345                 350

Asp Asp Thr Asn Glu Glu Gln Thr Thr Phe Thr Asn Ser Gln Thr Ser
                355                 360                 365

Thr Glu Asp Pro Gly Asp Ser Thr Pro Phe Glu Asp Ser Glu Glu Phe
                370                 375                 380

Cys Phe Ser Ala Glu Ala Asn Ser Phe Asp Gly Asp Asp Glu Phe Asp
385                 390                 395                 400

Thr Tyr Asn Glu Asp Asp Glu Asp Glu Ser Glu Thr Gly Tyr Trp
                405                 410                 415

Ile Thr Cys Cys Pro Thr Cys Asp Val Asp Ile Asn Thr Trp Val Pro
                420                 425                 430

Phe Tyr Ser Thr Glu Leu Asn Lys Pro Ala Met Ile Tyr Cys Ser His
                435                 440                 445

Gly Asp Gly His Trp Val His Ala Gln Cys Met Asp Leu Ala Glu Arg
                450                 455                 460

Thr Leu Ile His Leu Ser Ala Gly Ser Asn Lys Tyr Tyr Cys Asn Glu
465                 470                 475                 480

His Val Glu Ile Ala Arg Ala Leu His Thr Pro Gln Arg Val Leu Pro
                485                 490                 495

Leu Lys Lys Pro Pro Met Lys Ser Leu Arg Lys Lys Gly Ser Gly Lys
                500                 505                 510
```

Ile Leu Thr Pro Ala Lys Lys Ser Phe Leu Arg Arg Leu Phe Asp
    515                 520                 525

<210> SEQ ID NO 161
<211> LENGTH: 1826
<212> TYPE: DNA
<213> ORGANISM: Homo sapiens

<400> SEQUENCE: 161

| | | | | |
|---|---|---|---|---|
| ccgctcagaa | agcgcgggaa | aggcacgcag | ccacgcccca | agggcgcagc ctaggacagg | 60 |
| ggcttctgga | gcttctggca | gccgtctgcc | ctcatggcct | ttgcacctat ggggcccgag | 120 |
| gcctcgttct | tcgacgtttt | ggaccgacac | agggagtccc | tgctggctgc cctgaggaga | 180 |
| ggtggcaggg | agcccccaac | tgggggaagc | cgcctggcct | ccagttctga ggttcttgca | 240 |
| tctatagaaa | atattatcca | agacataatc | acaagcttgg | caagaaatga agcacctgca | 300 |
| ttcacgatag | acaacagatc | aagctgggaa | aacataaagt | ttgaagattc tgtgggtctt | 360 |
| cagatggtat | cccattgcac | caccagaaag | atcaaaagtg | attcaccaaa atcagctcaa | 420 |
| aaatttctc | taatccttaa | atattgtcc | atgatttata | aattagtaca gagcaacact | 480 |
| tatgcaacca | aaagggacat | atattacact | gacagtcaac | tctttggtaa ccagactgtc | 540 |
| gtcgacaata | ttatcaatga | catttcttgc | atgttaaaag | tgtcaaggag gagtctacat | 600 |
| atattatcta | catcaaaagg | tttaattgct | ggcaacttaa | gatacatcga ggaagatggc | 660 |
| accaaagtga | attgtacctg | tggtgcaacg | gctgttgctg | tgccatcgaa tattcaagga | 720 |
| attcggaatt | tagttacaga | tgcaaagttt | gtattaattg | tagaaaaaga tgcaacattt | 780 |
| cagcggctcc | tagatgacaa | cttttgcaac | aaattgtctc | cttgcatcat gattacggga | 840 |
| aagggagttc | ctgatctaaa | cacaagactt | ttagtcaaga | aactgtggga tacatttcat | 900 |
| gttcctgttt | tcactcttgt | agatgctgat | ccacatggca | tagaaataat gtgcatctat | 960 |
| aagtatggat | ctatgtctat | gtcttttgaa | gctcatcatc | tcacagttcc agctattaga | 1020 |
| tggcttggtc | ttctcccttc | tgatcttaaa | agattaaatg | tacctaaaga tagtttgatt | 1080 |
| ccactgacaa | aaagggacca | aatgaaactt | gacagtatcc | tgaggagacc ttatgttacc | 1140 |
| tgccaaccat | tttggagaaa | agaaatggaa | ataatggcag | actctaaaat gaaggcagaa | 1200 |
| attcaagctt | tgactttcct | atcatcagat | tatctttcca | gagtgtactt acctaacaaa | 1260 |
| ttaaaatttg | gaggatggat | ataaaaataa | atcagaagaa | cttctgattg ccagaggctt | 1320 |
| ttcattagtt | tgttttgat | tggcaaatac | tattgtggaa | agaacatata ttatattctt | 1380 |
| aattctgtaa | aagtgaaata | aaataacttt | ccgttaatta | tatattttg tcaaaacaaa | 1440 |
| tgctgtactc | caattttctt | tgcaaggcct | tattcttgcc | tctatagaga cagatttctg | 1500 |
| tcctatcttc | taaagcaaat | tataaaagaa | tatgttattt | tgacctttaa attattttg | 1560 |
| aaaaaataat | attttataca | tgtcatcaaa | gtctacaaaa | tatttaccttc ctacgataca | 1620 |
| actaatgtta | acgcataaag | tatcttactg | gtaacaaaaa | tcataatgat ctgaatttga | 1680 |
| gatgttgcaa | atgaattgtg | gtgtccggta | gtttcttctt | acatttttcct ttgccttat | 1740 |
| actttagggg | tcttactcca | ttaattcatt | tgttacatta | gtaaaattca gtatgaataa | 1800 |
| atatttggat | tgatgtaaaa | aaaaaa | | | 1826 |

<210> SEQ ID NO 162
<211> LENGTH: 396
<212> TYPE: PRT
<213> ORGANISM: Homo sapiens

<400> SEQUENCE: 162

```
Met Ala Phe Ala Pro Met Gly Pro Glu Ala Ser Phe Phe Asp Val Leu
1               5                   10                  15

Asp Arg His Arg Glu Ser Leu Leu Ala Ala Leu Arg Arg Gly Gly Arg
            20                  25                  30

Glu Pro Pro Thr Gly Gly Ser Arg Leu Ala Ser Ser Ser Glu Val Leu
        35                  40                  45

Ala Ser Ile Glu Asn Ile Ile Gln Asp Ile Ile Thr Ser Leu Ala Arg
    50                  55                  60

Asn Glu Ala Pro Ala Phe Thr Ile Asp Asn Arg Ser Ser Trp Glu Asn
65                  70                  75                  80

Ile Lys Phe Glu Asp Ser Val Gly Leu Gln Met Val Ser His Cys Thr
                85                  90                  95

Thr Arg Lys Ile Lys Ser Asp Ser Pro Lys Ser Ala Gln Lys Phe Ser
            100                 105                 110

Leu Ile Leu Lys Ile Leu Ser Met Ile Tyr Lys Leu Val Gln Ser Asn
        115                 120                 125

Thr Tyr Ala Thr Lys Arg Asp Ile Tyr Tyr Thr Asp Ser Gln Leu Phe
    130                 135                 140

Gly Asn Gln Thr Val Val Asp Asn Ile Ile Asn Asp Ile Ser Cys Met
145                 150                 155                 160

Leu Lys Val Ser Arg Arg Ser Leu His Ile Leu Ser Thr Ser Lys Gly
                165                 170                 175

Leu Ile Ala Gly Asn Leu Arg Tyr Ile Glu Glu Asp Gly Thr Lys Val
            180                 185                 190

Asn Cys Thr Cys Gly Ala Thr Ala Val Ala Val Pro Ser Asn Ile Gln
        195                 200                 205

Gly Ile Arg Asn Leu Val Thr Asp Ala Lys Phe Val Leu Ile Val Glu
    210                 215                 220

Lys Asp Ala Thr Phe Gln Arg Leu Leu Asp Asp Asn Phe Cys Asn Lys
225                 230                 235                 240

Leu Ser Pro Cys Ile Met Ile Thr Gly Lys Gly Val Pro Asp Leu Asn
                245                 250                 255

Thr Arg Leu Leu Val Lys Lys Leu Trp Asp Thr Phe His Val Pro Val
            260                 265                 270

Phe Thr Leu Val Asp Ala Asp Pro His Gly Ile Glu Ile Met Cys Ile
        275                 280                 285

Tyr Lys Tyr Gly Ser Met Ser Met Ser Phe Glu Ala His His Leu Thr
    290                 295                 300

Val Pro Ala Ile Arg Trp Leu Gly Leu Leu Pro Ser Asp Leu Lys Arg
305                 310                 315                 320

Leu Asn Val Pro Lys Asp Ser Leu Ile Pro Leu Thr Lys Arg Asp Gln
                325                 330                 335

Met Lys Leu Asp Ser Ile Leu Arg Arg Pro Tyr Val Thr Cys Gln Pro
            340                 345                 350

Phe Trp Arg Lys Glu Met Glu Ile Met Ala Asp Ser Lys Met Lys Ala
        355                 360                 365

Glu Ile Gln Ala Leu Thr Phe Leu Ser Ser Asp Tyr Leu Ser Arg Val
    370                 375                 380

Tyr Leu Pro Asn Lys Leu Lys Phe Gly Gly Trp Ile
385                 390                 395
```

<210> SEQ ID NO 163
<211> LENGTH: 1295
<212> TYPE: DNA
<213> ORGANISM: Homo sapiens

<400> SEQUENCE: 163

```
gtgcggagtt tggctgctcc ggggttagca ggtgagcctg cgatgcgcgg gaagacgttc      60
cgctttgaaa tgcagcggga tttggtgagt ttcccgctgt ctccagcggt gcgggtgaag     120
ctggtgtctg cggggttcca gactgctgag gaactcctag aggtgaaacc ctccgagctt     180
agcaaagaag ttgggatatc taaagcagaa gccttagaaa ctctgcaaat tatcagaaga     240
gaatgtctca caaataaacc aagatatgct ggtacatctg agtcacacaa gaagtgtaca     300
gcactggaac ttcttgagca ggagcatacc cagggcttca taatcacctt ctgttcagca     360
ctagatgata ttcttggggg tggagtgccc ttaatgaaaa caacagaaat ttgtggtgca     420
ccaggtgttg gaaaaacaca attatgtatg cagttggcag tagatgtgca gataccagaa     480
tgttttggag gagtggcagg tgaagcagtt tttattgata cagagggaag ttttatggtt     540
gatagagtgg tagaccttgc tactgcctgc attcagcacc ttcagcttat agcagaaaaa     600
cacaagggag aggaacaccg aaaagctttg gaggatttca ctcttgataa tattctttct     660
catatttatt attttcgctg tcgtgactac acagagttac tggcacaagt ttatcttctt     720
ccagatttcc tttcagaaca ctcaaaggtt cgactagtga tagtggatgg tattgctttt     780
ccatttcgtc atgacctaga tgcctgtct cttcgtactc ggttattaaa tggcctagcc     840
cagcaaatga tcagccttgc aaataatcac agattagctg taattttaac caatcagatg     900
acaacaaaga ttgatagaaa tcaggccttg cttgttcctg cattagggga agttgggga      960
catgctgcta caatacggct aatctttcat tgggaccgaa agcaaaggtt ggcaacattg    1020
tacaagtcac ccagccagaa ggaatgcaca gtactgtttc aaatcaaacc tcagggattt    1080
agagatactg ttgttacttc tgcatgttca ttgcaaacag aaggttcctt gagcacccgg    1140
aaacggtcac gagacccaga ggaagaatta taacccagaa acaaatctca aagtgtacaa    1200
atttattgat gttgtgaaat caatgtgtac aagtggactt gttaccttaa agtataaata    1260
aacacactat ggcatgaatg aaaaaaaaaa aaaaa                               1295
```

<210> SEQ ID NO 164
<211> LENGTH: 376
<212> TYPE: PRT
<213> ORGANISM: Homo sapiens

<400> SEQUENCE: 164

Met Arg Gly Lys Thr Phe Arg Phe Glu Met Gln Arg Asp Leu Val Ser
1               5                   10                  15

Phe Pro Leu Ser Pro Ala Val Arg Val Lys Leu Val Ser Ala Gly Phe
            20                  25                  30

Gln Thr Ala Glu Glu Leu Leu Glu Val Lys Pro Ser Glu Leu Ser Lys
        35                  40                  45

Glu Val Gly Ile Ser Lys Ala Glu Ala Leu Glu Thr Leu Gln Ile Ile
    50                  55                  60

Arg Arg Glu Cys Leu Thr Asn Lys Pro Arg Tyr Ala Gly Thr Ser Glu
65                  70                  75                  80

Ser His Lys Lys Cys Thr Ala Leu Glu Leu Leu Glu Gln Glu His Thr
                85                  90                  95

Gln Gly Phe Ile Ile Thr Phe Cys Ser Ala Leu Asp Asp Ile Leu Gly
            100                 105                 110

Gly Gly Val Pro Leu Met Lys Thr Glu Ile Cys Gly Ala Pro Gly
            115                 120                 125

Val Gly Lys Thr Gln Leu Cys Met Gln Leu Ala Val Asp Val Gln Ile
    130                 135                 140

Pro Glu Cys Phe Gly Gly Val Ala Gly Glu Ala Val Phe Ile Asp Thr
145                 150                 155                 160

Glu Gly Ser Phe Met Val Asp Arg Val Val Asp Leu Ala Thr Ala Cys
                165                 170                 175

Ile Gln His Leu Gln Leu Ile Ala Glu Lys His Lys Gly Glu Glu His
                180                 185                 190

Arg Lys Ala Leu Glu Asp Phe Thr Leu Asp Asn Ile Leu Ser His Ile
                195                 200                 205

Tyr Tyr Phe Arg Cys Arg Asp Tyr Thr Glu Leu Leu Ala Gln Val Tyr
    210                 215                 220

Leu Leu Pro Asp Phe Leu Ser Glu His Ser Lys Val Arg Leu Val Ile
225                 230                 235                 240

Val Asp Gly Ile Ala Phe Pro Phe Arg His Asp Leu Asp Asp Leu Ser
                245                 250                 255

Leu Arg Thr Arg Leu Leu Asn Gly Leu Ala Gln Gln Met Ile Ser Leu
                260                 265                 270

Ala Asn Asn His Arg Leu Ala Val Ile Leu Thr Asn Gln Met Thr Thr
                275                 280                 285

Lys Ile Asp Arg Asn Gln Ala Leu Leu Val Pro Ala Leu Gly Glu Ser
            290                 295                 300

Trp Gly His Ala Ala Thr Ile Arg Leu Ile Phe His Trp Asp Arg Lys
305                 310                 315                 320

Gln Arg Leu Ala Thr Leu Tyr Lys Ser Pro Ser Gln Lys Glu Cys Thr
                325                 330                 335

Val Leu Phe Gln Ile Lys Pro Gln Gly Phe Arg Asp Thr Val Val Thr
                340                 345                 350

Ser Ala Cys Ser Leu Gln Thr Glu Gly Ser Leu Ser Thr Arg Lys Arg
            355                 360                 365

Ser Arg Asp Pro Glu Glu Glu Leu
    370                 375

<210> SEQ ID NO 165
<211> LENGTH: 607
<212> TYPE: DNA
<213> ORGANISM: Homo sapiens

<400> SEQUENCE: 165
gtgcggagtt tggctgctcc ggggttagca ggtgagcctg cgatgcgcgg gaagacgttc      60
cgctttgaaa tgcagcggga tttggtgagt ttcccgctgt ctccagcggt gcgggtgaag     120
ctggtgtctg cggggttcca gactgctgag gaactcctag aggtgaaacc ctccgagctt     180
agcaaagaag ttgggatatc taaagcagaa gccttagaaa ctctgcaaat tatcagaaga     240
gaatgtctca caaataaacc aagatatgct ggtacatctg agtcacacaa gaagtgtaca     300
gcactggaac ttcttgagca ggagcatacc cagggcttca taatcacctt ctgttcagca     360
ctagatgata ttcttggggg tggagtgccc ttaatgaaaa caacagaaat ttgtggtgca     420
ccaggtgttg gaaaaacaca attatggtaa aataaagtgt tctcctttta agggtgggtt     480
taataacata ttatgaaagt agtattttgt actatcgtca ggaaaccaaa taagatatat     540

```
atgtgctctt aattttaagt gtgtatgtgc attaaacaaa aattagctta caaaaaaaaa    600
aaaaaaa                                                              607
```

<210> SEQ ID NO 166
<211> LENGTH: 135
<212> TYPE: PRT
<213> ORGANISM: Homo sapiens

<400> SEQUENCE: 166

```
Met Arg Gly Lys Thr Phe Arg Phe Glu Met Gln Arg Asp Leu Val Ser
1               5                   10                  15

Phe Pro Leu Ser Pro Ala Val Arg Val Lys Leu Val Ser Ala Gly Phe
            20                  25                  30

Gln Thr Ala Glu Glu Leu Leu Glu Val Lys Pro Ser Glu Leu Ser Lys
        35                  40                  45

Glu Val Gly Ile Ser Lys Ala Glu Ala Leu Glu Thr Leu Gln Ile Ile
    50                  55                  60

Arg Arg Glu Cys Leu Thr Asn Lys Pro Arg Tyr Ala Gly Thr Ser Glu
65                  70                  75                  80

Ser His Lys Lys Cys Thr Ala Leu Glu Leu Leu Glu Gln Glu His Thr
                85                  90                  95

Gln Gly Phe Ile Ile Thr Phe Cys Ser Ala Leu Asp Asp Ile Leu Gly
            100                 105                 110

Gly Gly Val Pro Leu Met Lys Thr Thr Glu Ile Cys Gly Ala Pro Gly
        115                 120                 125

Val Gly Lys Thr Gln Leu Trp
    130                 135
```